(12) United States Patent
Heckel et al.

(10) Patent No.: US 7,514,468 B2
(45) Date of Patent: *Apr. 7, 2009

(54) INDOLINONE DERIVATIVES SUBSTITUTED IN THE 6 POSITION, THE PREPARATION THEREOF AND THEIR USE AS PHARMACEUTICAL COMPOSITIONS

(75) Inventors: Armin Heckel, Biberach (DE); Frank Hilberg, Vienna (AT); Thorsten Lehmann-Lintz, Ochsenhausen (DE); Guenter Linz, Mittelbiberach (DE); Joerg Kley, Mittelbiberach (DE); Jacobus C. A. Van Meel, Moedling (AT); Werner Rall, Mittelbiberach (DE); Gerald Juergen Roth, Biberach (DE); Peter Sieger, Mittelbiberach (DE); Ulrike Tontsch-Grunt, Baden (AT)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 729 days.

This patent is subject to a terminal disclaimer.

(21) Appl. No.: 10/624,983

(22) Filed: Jul. 22, 2003

(65) Prior Publication Data
US 2006/0194813 A1 Aug. 31, 2006

Related U.S. Application Data

(60) Provisional application No. 60/403,106, filed on Aug. 13, 2002.

(30) Foreign Application Priority Data

Jul. 23, 2002 (DE) ............................ 102 33 366

(51) Int. Cl.
A61K 31/404 (2006.01)
C07D 209/34 (2006.01)
(52) U.S. Cl. ...................... 514/421; 548/512
(58) Field of Classification Search ................ 514/421; 548/512
See application file for complete search history.

(56) References Cited

U.S. PATENT DOCUMENTS

| 6,762,180 | B1 | 7/2004 | Roth et al. | |
|---|---|---|---|---|
| 6,855,710 | B2 * | 2/2005 | Walter et al. | 514/228.2 |
| 7,169,936 | B2 * | 1/2007 | Roth et al. | 548/491 |
| 2005/0043389 | A1 | 2/2005 | Roth et al. | |
| 2006/0148883 | A1 | 7/2006 | Park et al. | |
| 2006/0194813 | A1 | 8/2006 | Heckel et al. | |
| 2007/0004757 | A1 * | 1/2007 | Roth et al. | 514/254.09 |

FOREIGN PATENT DOCUMENTS

| CA | 2342622 A1 | 4/2000 |
|---|---|---|
| CA | 2381821 A1 | 3/2001 |
| CA | 2342662 A1 | 10/2002 |
| CA | 2493436 A1 | 1/2004 |
| WO | 9220642 A1 | 11/1992 |
| WO | 9910325 A1 | 3/1999 |
| WO | 9915500 A1 | 4/1999 |
| WO | WO 00/18734 | 4/2000 |
| WO | WO0056710 | 9/2000 |
| WO | 0116130 A1 | 3/2001 |
| WO | 0127080 A2 | 4/2001 |
| WO | 0127081 A1 | 4/2001 |
| WO | WO03026650 | 4/2003 |
| WO | WO03027102 | 4/2003 |
| WO | WO2004009547 | 1/2004 |

OTHER PUBLICATIONS

International Search Report for Reference #PCT/EP 03/07960.
Kuhn et al.; The Roles of Myofibroblast in Idiopathic Pulmonary Fibrosis; American Journal of Pathology; vol. 138; No. 5; May 1991; pp. 1257-1265.
Suzuki et al.; Epidermal Growth Factor Receptor Tyrosine Kinase Inhibition Augments a Murine Model of Pulmonary Fibrosis; Cander Research; Aug. 2003; vol. 63; No. 16; pp. 5054-5059.
Lebensztejn; Reversibility of Advanced Liver Fibrosis -- Therapeutic Possibility and Biochemical Monitoring of the Disease; Przegl Epidemiol.; 2005; vol. 59; No. 2; pp. 535-540.
International Search Report, Form PCT/ISA/210, for corresponding PCT/EP03/07961 Oct. 14, 2003.
International Search Report, From PCT/ISA/210, for corresponding PCT/EP2005/057013 Feb. 9, 2006.

* cited by examiner

*Primary Examiner*—Rebecca L Anderson
*Assistant Examiner*—Jason M. Nolan
(74) *Attorney, Agent, or Firm*—Michael P. Morris; Mary-Ellen M. Devlin; Timothy X. Witkowski

(57) ABSTRACT

The present invention relates to indolinone derivatives substituted in the 6 position of general formula

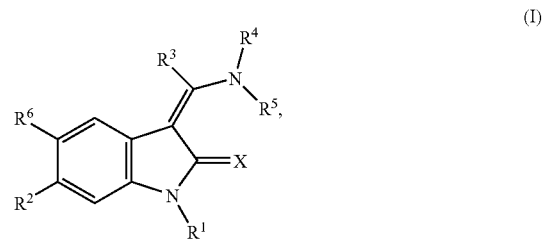

(I)

wherein
$R_1$ to $R_6$ and X are defined as in claim 1, the tautomers, enantiomers, diastereomers, mixtures thereof and the salts thereof, particularly the physiologically acceptable salts thereof, which have valuable pharmacological properties, in particular an inhibiting effect on various receptor tyrosine kinases and on the proliferation of endothelial cells and various tumour cells, pharmaceutical compositions containing these compounds, their use and processes for preparing them.

18 Claims, No Drawings

INDOLINONE DERIVATIVES SUBSTITUTED IN THE 6 POSITION, THE PREPARATION THEREOF AND THEIR USE AS PHARMACEUTICAL COMPOSITIONS

The present invention relates to indolinone derivatives substituted in the 6position of general formula

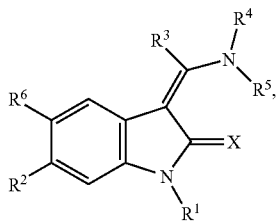

(I)

the tautomers, enantiomers, diastereomers, mixtures thereof and the salts thereof, particularly the physiologically acceptable salts thereof which have valuable pharmacological properties, pharmaceutical compositions containing these compounds, the use thereof and processes for the preparation thereof.

The above compounds of general formula I have valuable pharmacological properties, particularly an inhibiting effect on various kinases, especially receptor tyrosine kinases such as VEGFR1, VEGFR2, VEGFR3, PDGFRα, PDGFRβ, FGFR1, FGFR3, EGFR, HER2, c-Kit, IGF1R and HGFR, Flt-3, as well as on the proliferation of cultivated human cells, particularly endothelial cells, e.g. in angiogenesis, but also on the proliferation of other cells, particularly tumour cells.

The present invention thus relates to the above compounds of general formula I which have valuable pharmacological properties, pharmaceutical compositions containing these pharmacologically active compounds, the use thereof and processes for the preparation thereof.

In the above general formula I

X denotes an oxygen or sulphur atom, $R^1$ denotes a hydrogen atom, a $C_{1-4}$-alkoxy-carbonyl, $C_{1-3}$-alkyl-carbonyl, aminomethyl, $C_{1-3}$-alkylaminomethyl, di-($C_{1-3}$-alkyl)-aminomethyl or a 5- to 7-membered cycloalkyleneiminomethyl group, $R^2$ denotes a fluorine, chlorine or bromine atom or a cyano group, $R^3$ denotes a phenyl or naphthyl group or a phenyl or naphthyl group mono- or disubstituted by a fluorine, chlorine, bromine or iodine atom, by a trifluoromethyl, $C_{1-3}$-alkyl or $C_{1-3}$-alkoxy group, while in the case of disubstitution the substituents may be identical or different and the above mentioned unsubstituted as well as the mono- and disubstituted phenyl and naphthyl groups may additionally be substituted by a fluorine, chlorine, bromine or iodine atom, by a $C_{1-3}$-alkyl, $C_{1-4}$-alkoxy, $C_{1-4}$-alkoxy-carbonyl, $C_{1-4}$-alkoxy-carbonyl-$C_{1-3}$-alkoxy, $C_{1-4}$-alkyloxy-carbonylamino-$C_{1-4}$-alkoxy-carbonyl-$C_{1-3}$-alkylamino, $C_{1-4}$-alkoxy-carbonyl-$C_{1-3}$-alkyl-N—($C_{1-3}$-alkyl)-amino, aminocarbonyl, $C_{1-3}$-alkylamino-carbonyl, di-($C_{1-3}$-alkyl)-aminocarbonyl, benzyloxy, carboxy, carboxy-$C_{1-3}$-alkoxy, carboxy-$C_{1-3}$-alkylamino, carboxy-$C_{1-3}$-alkyl-N—($C_{1-3}$-alkyl)-amino, cyano, trifluoromethyl, nitro, amino, $C_{4-7}$-cycloalkylamino, $C_{1-3}$-alkyl-carbonyl-amino, N—($C_{1-3}$-alkyl)-N-($C_{1-3}$-alkyl-carbonyl)-amino, phenyl-carbonylamino, N—($C_{1-3}$-alkyl)-N-(phenyl-carbonyl)-amino, benzyl-carbonylamino, N—($C_{1-3}$-alkyl)-N-(benzyl-carbonyl)-amino, hydroxy, $C_{1-3}$-alkylsulphonylamino, N—($C_{1-3}$-alkyl)-$C_{1-3}$-alkyl-sulphonylamino, phenylsulphonylamino, N—($C_{1-3}$-alkyl)-phenylsulphonylamino, phenyl-$C_{1-3}$-alkyl-sulphonylamino, N—($C_{1-3}$-alkyl)-N-(phenyl-$C_{1-3}$-alkyl-sulphonyl)-amino, $C_{1-3}$-alkylamino or di-($C_{1-3}$-alkyl)-amino group, by a $C_{1-3}$- or $C_{4-6}$-alkyl group which is substituted by a hydroxy, cyano, carboxy, $C_{1-4}$-alkoxy, $C_{1-4}$-alkoxy-carbonyl, aminocarbonyl, ($C_{1-3}$-alkyl-amino)-carbonyl, di-($C_{1-3}$-alkyl)-aminocarbonyl, amino, $C_{1-3}$-alkylamino, [di-($C_{1-3}$-alkyl)-amino], N—($C_{1-4}$-alkoxy-carbonyl)-amino, N—($C_{1-4}$-alkoxy-carbonyl)-N—$C_{1-3}$-alkyl)-amino, phenylamino, diphenylamino, N-phenyl-N—$C_{1-3}$-alkyl)-amino, benzylamino, dibenzylamino, N-benzyl-N—($C_{1-3}$-alkyl)-amino, heteroarylamino, N-heteroaryl-N—($C_{1-3}$-alkyl)-amino, $C_{1-4}$-alkyl-sulphonylamino, N—($C_{1-3}$-alkyl)-$C_{1-4}$-alkylsulphonylamino, phenyl-sulphonylamino, N—($C_{1-3}$-alkyl)-phenylsulphonylamino, phenyl-$C_{1-3}$-alkyl-sulphonylamino, N—($C_{1-3}$-alkyl)-N-(phenyl-$C_{1-3}$-alkyl-sulphonyl)-amino, benzylcarbonylamino, N—($C_{1-3}$-alkyl)-N-(benzylcarbonyl)-amino, phenyl-carbonylamino, N—($C_{1-3}$-alkyl)-N-(phenylcarbonyl)-amino, 4-($C_{1-3}$-alkyl)-piperazin-1-yl-carbonyl, ($C_{1-6}$-alkyl-carbonyl)-amino, N—($C_{1-3}$-alkyl)-N—($C_{1-6}$-alkyl-carbonyl)-amino, ($C_{3-7}$-cycloalkyl-carbonyl)-amino, N—($C_{1-3}$-alkyl)-N—($C_{3-7}$-cycloalkyl-carbonyl)-amino, ($C_{3-7}$-cycloalkyl-$C_{1-3}$-alkyl-carbonyl)-amino, N—($C_{1-3}$-alkyl)-N—($C_{3-7}$-cycloalkyl-$C_{1-3}$-alkyl-carbonyl)-amino, ($C_{1-4}$-alkoxy-$C_{1-3}$-alkyl-carbonyl)-amino, N—($C_{1-3}$-alkyl)-N—$C_{1-4}$-alkoxy-$C_{1-3}$-alkyl-carbonyl)-amino, (heteroaryl-carbonyl)-amino, N—($C_{1-3}$-alkyl)-N-(heteroaryl-carbonyl)-amino, ($C_{3-7}$-cycloalkyl-sulphonyl)-amino, N—($C_{1-3}$-alkyl)-N—($C_{3-7}$-cycloalkyl-sulphonyl)-amino, ($C_{3-7}$-cycloalkyl-$C_{1-3}$-alkyl-sulphonyl)-amino, N—($C_{1-3}$-alkyl)-N—($C_{3-7}$-cycloalkyl-$C_{1-3}$-alkyl-sulphonyl)-amino, ($C_{1-4}$-alkoxy-$C_{1-3}$-alkyl-sulphonyl)-amino, N—($C_{1-3}$-alkyl)-N—($C_{1-4}$-alkoxy-$C_{1-3}$-alkyl-sulphonyl)-amino, (heteroaryl-sulphonyl)-amino, N—($C_{1-3}$-alkyl)-N-(heteroaryl-sulphonyl)-amino, tetrazolyl or heteroaryl group, by a carboxy-$C_{2-3}$-alkenyl, aminocarbonyl-$C_{2-3}$-alkenyl, ($C_{1-3}$-alkyl-amino)-carbonyl-$C_{2-3}$-alkenyl, di-($C_{1-3}$-alkyl)-amino-carbonyl-$C_{2-3}$-alkenyl or $C_{1-4}$-alkoxy-carbonyl-$C_{2-3}$-alkenyl group, by a heteroaryl group or by a cycloalkyleneimino or cycloalkyleneimino-$C_{1-3}$-alkyl group with in each case 5 to 7 ring members, wherein in each case a methylene group linked to the imino group is replaced by a carbonyl or sulphonyl group or the two methylene groups linked to the imino group are each replaced by a carbonyl group or a —$CH_2$—$CH_2$— group linked to the imino group is replaced by the group —O—CO—, while the carbonyl group of the —O—CO— group is linked to the imino group and a phenyl ring may be fused to the 5- to 7-membered cycloalkyleneimino group via two adjacent carbon atoms, or by a cycloalkyleneimino, cycloalkyleneiminocarbonyl, cycloalkyleneiminosulphonyl, cycloalkyleneimino-$C_{1-3}$-alkyl, cycloalkyleneiminocarbonyl-$C_{1-3}$-alkyl or cycloalkyleneiminosulphonyl-$C_{1-3}$-alkyl group with 4 to 7 ring members in each case, while in each case the methylene group in the 4 position of a 6- or 7-membered cycloalkyleneimino group may be substituted by a carboxy, $C_{1-4}$-alkoxy-carbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl)- group, while the substituents may be identical or different, $R^4$ denotes a benzopyrazolyl group, a $C_{3-7}$-cycloalkyl group which may be substituted by a N-[di-($C_{1-3}$-alkyl)-amino-$C_{1-3}$-alkyl-carbonyl]-amino or N-[di-($C_{1-3}$-alkyl)-amino-$C_{1-3}$-alkyl-carbonyl]-N—$C_{1-3}$-alkyl-amino group, while the methylene group in the 4 position of a 6- or 7-membered cycloalkyl group may be substituted by an amino, $C_{1-3}$-alkylamino or di-($C_{1-3}$-alkyl)-amino group or replaced by a —NH or —N($C_{1-3}$-alkyl) group, or a phenyl, naphthyl or heteroaryl group substituted by the group $R_9$ which may additionally be mono- or disubstituted by fluorine, chlorine, bromine or iodine atoms, by $C_{1-5}$-alkyl, trifluoromethyl, hydroxy, $C_{1-4}$-alkoxy, benzyloxy, carboxy, $C_{1-4}$-alkoxy-carbonyl, amino, $C_{1-3}$-alkylamino, di-($C_{1-3}$-alkyl)-amino, acetylamino, $C_{1-3}$-alkyl-sulphonylamino, aminocarbonyl, $C_{1-3}$-alkyl-aminocarbonyl, di-($C_{1-3}$-alkyl)-aminocarbonyl, aminosulphonyl, $C_{1-3}$-alkyl-aminosulphonyl, di-($C_{1-3}$-alkyl)-aminosulphonyl, nitro or cyano groups, while the substituents may be identical or different and wherein $R_9$ denotes a hydrogen, fluorine, chlorine, bromine or iodine atom, a cyano, nitro, amino, $C_{1-5}$-alkyl, $C_{3-7}$-cycloalkyl, trifluoromethyl, phenyl, tetrazolyl or heteroaryl group, a $C_{1-3}$-alkyl-sulphonyl, amino-$C_{1-3}$-alkyl-sulphonyl, ($C_{1-3}$-alkylamino)-$C_{1-3}$-alkyl-sulphonyl or di-($C_{1-3}$-alkyl)-amino-$C_{1-3}$-alkylsulphonyl group, a $C_{1-4}$-alkoxy group, a ω-$C_{1-3}$-alkoxy-$C_{2-3}$-alkoxy, phenyl-$C_{1-3}$-alkoxy, ω-amino-$C_{2-3}$-alkoxy, ω-($C_{1-3}$-alkylamino)-$C_{2-3}$-alkoxy, ω-[di-($C_{1-3}$-alkyl)-amino]-$C_{2-3}$-alkoxy, ω-(phenyl-$C_{1-3}$-alkylamino)-$C_{2-3}$-alkoxy, ω-[N—($C_{1-3}$-alkyl)-phenyl-$C_{1-3}$-alkylamino]-$C_{2-3}$-alkoxy, ω-($C_{5-7}$-cycloalkyleneimino)-$C_{2-3}$-alkoxy or $C_{1-3}$-alkylmercapto group, a carboxy or $C_{1-4}$-alkoxy-carbonyl group, aminocarbonyl, $C_{1-4}$-alkyl-amino-carbonyl, N—($C_{1-5}$-alkyl)-$C_{1-3}$-alkylaminocarbonyl, $C_{3-7}$-cycloalkyl-amino-carbonyl, N—($C_{1-5}$-alkyl)-$C_{3-7}$-cycloalkylaminocarbonyl, (phenyl-$C_{1-3}$-alkyl)-amino-carbonyl, N—($C_{1-3}$-alkyl)-phenyl-$C_{1-3}$-alkylaminocarbonyl group, a $C_{1-3}$-alkylaminocarbonyl or N—($C_{1-3}$-alkyl)-$C_{1-3}$-alkylaminocarbonyl group, wherein one or two alkyl moieties are substituted independently of one another by a nitro, cyano, carbamoyl, N—($C_{1-3}$-alkyl)-carbamoyl, di-N—$C_{1-3}$-alkyl)-carbamoyl, carboxy or $C_{1-4}$-alkoxy-carbonyl group or in the 2 or 3position by an amino, ($C_{1-3}$-alkyl)-amino, di-($C_{1-3}$-alkyl)-amino, ($C_{1-4}$-alkoxy-carbonyl)-amino, N—($C_{1-4}$-alkoxy-carbonyl)-N—($C_{1-3}$-alkyl)-amino, piperazino, N—($C_{1-3}$-alkyl)-piperazino, a 4- to 7-membered cycloalkyleneimino group, a hydroxy or methoxy group, a 4- to 7-membered cycloalkyleneiminocarbonyl group wherein the cycloalkylene moiety may be fused to a phenyl ring via two adjacent ring atoms or may be bridged to a methylene or ethylene group via two non-adjacent ring atoms or one or two hydrogen atoms in each case may be replaced by a $C_{1-3}$-alkyl group and/or in each case the methylene group in the 4 position of a 6- or 7-membered cycloalkyleneiminocarbonyl group may be substituted by a carboxy, $C_{1-4}$-alkoxy-carbonyl, aminocarbonyl, $C_{1-3}$-alkylaminocarbonyl, di-($C_{1-3}$-alkyl)-aminocarbonyl, di-($C_{1-3}$-alkyl)-amino-$C_{1-3}$-alkyl, di-($C_{1-3}$-alkyl)-amino, phenyl-$C_{1-3}$-alkylamino or N—($C_{1-3}$-alkyl)-phenyl-$C_{1-3}$-alkylamino group, a hydroxy or methoxy group or replaced by an oxygen or sulphur atom, by a sulphinyl, sulphonyl or —NH group or by a nitrogen atom, which is substituted by $C_{1-3}$-alkyl, phenyl, $C_{1-3}$-alkyl-carbonyl, $C_{1-4}$-alkoxy-carbonyl, di-($C_{1-3}$-alkyl)-amino-$C_{1-3}$-alkyl, ω-hydroxy-$C_{2-3}$-alkyl or benzoyl group, a 4- to 7-membered cycloalkyleneimino group wherein a methylene group linked to the imino group by a carbonyl or sulphonyl group may be replaced or the cycloalkylene moiety may be fused to a phenyl ring or one or two hydrogen atoms in each case may be replaced by a $C_{1-3}$-alkyl group and/or in each case the methylene group in the 4 position of a 6- or 7-membered cycloalkyleneimino group may be substituted by a carboxy, $C_{1-4}$-alkoxy-carbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{1-4}$-alkyl group substituted by the group $R_{10}$, where $R_{10}$ denotes a $C_{3-7}$-cycloalkyl group, while the methylene group in the 4 position of a 6- or 7-membered cycloalkyl group may be substituted by an amino, $C_{1-3}$-alkylamino or di-($C_{1-3}$-alkyl)-amino group or replaced by a —NH or —N($C_{1-3}$-alkyl) group or in a 5- to 7-membered cycloalkyl group a —(CH$_2$)$_2$ group may be replaced by a —CO—NH group, a —(CH$_2$)$_3$ group may be replaced by a —NH—CO—NH or —CO—NH—CO group or a —(CH$_2$)$_4$ group may be replaced by a —NH—CO—NH—CO group, while in each case a hydrogen atom bonded to a nitrogen atom may be replaced by a $C_{1-3}$-alkyl group, a phenyl, triazolyl or heteroaryl group, a hydroxy or $C_{1-4}$-alkoxy group, an amino, $C_{1-7}$-alkylamino, di-($C_{1-7}$-alkyl)-amino, phenylamino, N-phenyl-N—($C_{1-3}$-alkyl)-amino, N-(phenyl-$C_{1-3}$-alkyl)-amino, N—($C_{1-3}$-alkyl)-N-(phenyl-$C_{1-3}$-alkyl)-amino or di-(phenyl-$C_{1-3}$-alkyl)-amino group, a ω-hydroxy-$C_{2-3}$-alkyl-amino, N—($C_{1-3}$-alkyl)-(ω-hydroxy-$C_{2-3}$-alkyl)-amino, di-(ω-hydroxy-$C_{2-3}$-alkyl)-amino or di-(ω-($C_{1-3}$-alkoxy)-$C_{2-3}$-alkyl)-amino-group, a $C_{1-3}$-alkyl-carbonylamino-$C_{2-3}$-alkyl-amino or $C_{1-3}$-alkyl-carbonyl-amino-$C_{2-3}$-alkyl-N—($C_{1-3}$-alkyl)-amino group, a $C_{1-4}$-alkyloxy-carbonyl-amino, N—($C_{1-4}$-alkyloxy-carbonyl)-N—($C_{1-3}$-alkyl)-amino or N-{ω-[N—($C_{1-4}$-alkoxy-carbonyl)-amino]-($C_{1-4}$-alkyl)}-N—($C_{1-3}$-alkyl)-amino group, a $C_{1-3}$-alkylsulphonylamino, N—($C_{1-3}$-alkyl)-$C_{1-3}$-alkylsulphonylamino, $C_{1-3}$-alkylsulphonylamino-$C_{2-3}$-alkyl-amino or $C_{1-3}$-alkylsulphonyl-amino-$C_{2-3}$-alkyl-N—($C_{1-3}$-alkyl)-amino group, a hydroxycarbonyl-$C_{1-3}$-alkylamino or N—($C_{1-3}$-alkyl)-hydroxycarbonyl-$C_{1-3}$-alkyl-amino group, an N-(ω-amino-$C_{2-3}$-alkyl)-N—($C_{1-3}$-alkyl)-amino, N-(ω-$C_{1-3}$-alkylamino-$C_{2-3}$-alkyl)-N—($C_{1-3}$-alkyl)- amino, N-[ω-di-($C_{1-3}$-alkyl)-amino-$C_{2-3}$-alkyl]-N—$C_{1-3}$-alkyl)-amino, N-(ω-$C_{1-3}$-alkoxy-$C_{2-3}$-alkoxy-$C_{1-3}$-alkyl)-amino or N-(ω-$C_{1-3}$-alkoxy-$C_{2-3}$-alkoxy-$C_{1-3}$-alkyl)-N—($C_{1-3}$-alkyl)-amino group, a guanidino group wherein one or two hydrogen atoms may each be replaced by a $C_{1-3}$-alkyl group, a $C_{4-7}$-cycloalkylamino, $C_{4-7}$-cycloalkyl-$C_{1-3}$-alkylamino or $C_{4-7}$-cyclo-alkenylamino group wherein position 1 of the ring does not participate in the double bond and the above mentioned groups may each additionally be substituted at the aminonitrogen atom by a $C_{5-7}$-cycloalkyl, $C_{2-4}$-alkenyl or $C_{1-4}$-alkyl group, a 4- to 7-membered cycloalkyleneimino group wherein
the cycloalkylene moiety may be fused with a phenyl group or with an oxazolo, imidazolo, thiazolo, pyridino, pyrazino or pyrimidino group optionally substituted by a fluorine, chlorine, bromine or iodine atom or by a nitro, $C_{1-3}$-alkyl, $C_{1-3}$-alkoxy or amino group and/or one or two hydrogen atoms may each be replaced by a $C_{1-3}$-alkyl, $C_{1-4}$-alkoxy-carbonyl, amino, $C_{1-3}$-alkylamino or di-($C_{1-3}$-alkyl)-amino group, $C_{5-7}$-cycloalkyl or phenyl group and/or the methylene group in position 3 of a 5-membered cycloalkyleneimino group may be substituted by a hydroxy, hydroxy-$C_{1-3}$-alkyl, $C_{1-4}$-alkoxy or $C_{1-3}$-alkoxy-$C_{1-3}$-alkyl group, in each case the methylene group in position 3 or 4 of a 6- or 7-membered cycloalkyleneimino group may be substituted by a hydroxy, hydroxy-$C_{1-3}$-alkyl, $C_{1-4}$-alkoxy, $C_{1-4}$-alkoxy-$C_{1-3}$-alkyl, carboxy, $C_{1-4}$-alkoxy-carbonyl, aminocarbonyl, $C_{1-3}$-alkylaminocarbonyl, di-($C_{1-3}$-alkyl)-aminocarbonyl, $C_{1-3}$-alkylamino, di-($C_{1-3}$-alkyl)-amino, N-(phenyl-$C_{1-3}$-alkyl)-amino or N—($C_{1-3}$-alkyl)-N-(phenyl-$C_{1-3}$-alkyl)-amino group or may be replaced by an oxygen or sulphur atom, by a sulphinyl, sulphonyl, —NH, —N($C_{1-3}$-alkyl-), —N(phenyl), —N(phenyl-$C_{1-3}$-alkyl-), —N($C_{1-3}$-alkyl-carbonyl-), —N($C_{1-4}$-hydroxy-carbonyl-), —N($C_{1-4}$-alkoxy-carbonyl-), —N (benzoyl-) or —N(phenyl-$C_{1-3}$-alkyl-carbonyl-) group, while a methylene group linked to an imino-nitrogen atom of the cycloalkyleneimino group may be replaced by a carbonyl or sulphonyl group or in a 5- to 7-membered monocyclic cyclo-alkyleneimino group or a cycloalkyleneimino group fused to a phenyl group the two methylene groups linked to the imino-nitrogen atom may each be replaced by a carbonyl group, and all the dialkylamino groups contained in the group $R^{10}$ may also be present in quaternised form, for example as the N-methyl-(N,N-dialkyl)-ammonium group, the counter-ion preferably being selected from among iodide, chloride, bromide, methylsulphonate, para-toluenesulphonate, or trifluoroacetate, or $R_9$ denotes a $C_{1-4}$-alkyl group which is substituted by a carboxy, $C_{1-4}$-alkoxy-carbonyl, aminocarbonyl, $C_{1-3}$-alkylaminocarbonyl, di-($C_{1-3}$-alkyl)-aminocarbonyl, N-[amino-$C_{1-3}$-alkyl]-aminocarbonyl, N-[($C_{1-3}$-alkyl)-amino-$C_{1-3}$-alkyl]-aminocarbonyl, N-[di-($C_{1-3}$-alkyl)-amino-$C_{1-3}$-alkyl]-aminocarbonyl, N-[amino-$C_{1-3}$-alkyl]-N—($C_{1-3}$-alkyl)-aminocarbonyl, N-[($C_{1-3}$-alkyl)-amino-$C_{1-3}$-alkyl]-N—($C_{1-3}$-alkyl)-aminocarbonyl, N—($C_{3-7}$-cycloalkyl)-N—$C_{1-3}$-alkyl)-amino or N-[di-($C_{1-3}$-alkyl)-amino-$C_{1-3}$-alkyl]-N—($C_{1-3}$-alkyl)-aminocarbonyl group or by a 4- to 7-membered cycloalkyleneiminocarbonyl group, while in the above mentioned cycloalkyleneimino groups
one or two hydrogen atoms may each be replaced by a $C_{1-3}$-alkyl, carboxy, $C_{1-4}$-alkoxy-carbonyl, aminocarbonyl, $C_{1-3}$-alkylaminocarbonyl or di-($C_{1-3}$-alkyl)-aminocarbonyl group or one or two hydrogen atoms, which are bonded to a carbon atom not adjacent to the imino group, may be replaced by an amino, $C_{1-3}$-alkylamino, di-($C_{1-3}$-alkyl)-amino, phenyl-$C_{1-3}$-alkylamino or N—($C_{1-3}$-alkyl)-phenyl-$C_{1-3}$-alkylamino group and/or the methylene group in the 4 position of a 6- or 7-membered cyclo-alkyleneimino group may be replaced by one of the groups —S, —SO, —SO$_2$, —NH, —N($C_{1-3}$-alkyl), —N(phenyl), —N($C_{1-3}$-alkyl-carbonyl), —N($C_{1-4}$-alkoxy-carbonyl), —N(benzoyl) or —O—, an N—($C_{1-3}$-alkyl)-$C_{1-3}$-alkyl-carbonyl-amino group which is additionally substituted in the alkyl moiety by a carboxy or $C_{1-4}$-alkoxy-carbonyl group, or a group of formula

wherein
$R^7$ denotes a hydrogen atom, a $C_{1-4}$-alkyl or $C_{3-7}$-cycloalkyl group, a $C_{1-3}$-alkyl group terminally substituted by a phenyl, heteroaryl, trifluoromethyl, aminocarbonyl, $C_{1-4}$-alkylamino-carbonyl, di-($C_{1-4}$-alkyl)-amino-carbonyl, $C_{1-3}$-alkyl-carbonyl, $C_{1-3}$-alkyl-sulphonylamino, N—($C_{1-3}$-alkyl)-$C_{1-3}$-alkyl-sulphonylamino, $C_{1-3}$-alkyl-aminosulphonyl or di-($C_{1-3}$-alkyl)-aminosulphonyl group, a $C_{2-3}$-alkyl group terminally substituted by a hydroxy or $C_{1-3}$-alkoxy group, a $C_{1-4}$-alkyl-carbonyl, benzylcarbonyl, heteroarylcarbonyl, heteroaryl-$C_{1-3}$-alkyl-carbonyl, cycloalkyleneimino-$C_{1-3}$-alkyl-carbonyl with 5 to 7 ring atoms in the cycloalkyleneimino moiety, $C_{1-3}$-alkoxy-$C_{1-3}$-alkyl-carbonyl, amino-$C_{1-3}$-alkylcarbonyl, ($C_{1-3}$-alkyl)-amino-$C_{1-3}$-alkyl-carbonyl, di-($C_{1-3}$-alkyl)-amino-carbonyl-$C_{1-3}$-alkyl, $C_{1-4}$-alkylsulphonyl, phenylsulphonyl, heteroarylsulphonyl, heteroaryl-$C_{1-3}$-alkyl-sulphonyl or benzyl-sulphonyl group or a phenylcarbonyl group optionally substituted in the phenyl moiety by one or two methoxy groups and $R^8$ denotes a $C_{1-3}$-alkyl, di-($C_{1-3}$-alkyl)-amino-$C_{1-3}$-alkyl-amino-carbonyl or 1-($C_{1-3}$-alkyl)-piperidin-4-yl-aminocarbonyl group, a $C_{1-4}$-alkyl-carbonyl group terminally substituted by a (ω-alkoxy-$C_{2-3}$-alkyl)-amino, $C_{1-3}$-alkyl-carbonyl-amino or N-[di-($C_{1-3}$-alkyl)-amino-$C_{1-3}$-alkyl]-N—($C_{1-3}$-alkyl)-amino group or a $C_{2-4}$-alkyl, carbonyl, $C_{1-4}$-alkyl-carbonyl or carbonyl-$C_{1-3}$-alkyl group terminally substituted by one of the groups described under $R^{10}$, while $R^{10}$ additionally also denotes a $C_{5-7}$-cycloalkyloxy group wherein the methylene group may be substituted in the 4 position by a —NH or —N($C_{1-3}$-alkyl)-group, a 5- to 7-membered cycloalkyleneimino-amino group, while the methylene group in the 4 position of a 6- or 7-membered cycloalkyleneimino group may be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl)-group, or may denote an N-(heteroaryl-$C_{1-3}$-alkyl)-amino group, $R^5$ denotes a hydrogen atom or a $C_{1-3}$-alkyl group and
$R^6$ denotes a hydrogen atom or a nitro group, while the unsubstituted, mono- or disubstituted phenyl groups contained in the above definitions, whether singly bonded or fused on, may additionally be substituted by one or two fluorine, chlorine, bromine or iodine atoms or by one or two $C_{1-5}$-alkyl, $C_{1-4}$-alkoxy, benzyloxy, carboxy, cyano, $C_{1-4}$-alkoxy-carbonyl, aminocarbonyl, $C_{1-4}$-alkylamino-carbonyl, di-($C_{1-4}$-alkyl)-amino-carbonyl, aminosulphonyl, $C_{1-3}$-alkyl-aminosulphonyl, di-($C_{1-3}$-alkyl)-aminosulphonyl, trifluoromethyl, nitro, amino, hydroxy, $C_{1-3}$-alkylsulphonylamino, $C_{1-3}$-alkylamino or di-($C_{1-3}$-alkyl)-amino groups, while the substituents may be identical or different, the above mentioned alkyl groups including straight-chain and branched alkyl groups, wherein additionally one to 3 hydrogen atoms may be replaced by fluorine atoms, while, unless otherwise stated, the expression a heteroaryl group refers to a monocyclic 5- or 6-membered heteroaryl group optionally substituted in the carbon skeleton by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl or phenyl-$C_{1-3}$-alkyl group or an oxygen or sulphur atom and additionally contains a nitrogen atom or an imino group optionally substituted by a $C_{1-3}$-alkyl or phenyl-$C_{1-3}$-alkyl group and two nitrogen atoms, and moreover a phenyl ring may be fused to the above mentioned monocyclic heterocyclic groups via two adjacent carbon atoms and the bonding takes place via a nitrogen atom or via a carbon atom of the heterocyclic moiety or a fused-on phenyl ring, and additionally any carboxy, amino or imino group present may be substituted by a group which can be cleaved in vivo, or may be present in the form of a prodrug group, e.g. in the form of a group which may be converted in vivo into a carboxy group or in the form of a group which may be converted in vivo into an imino or amino group, the tautomers, enantiomers, diastereomers, mixtures thereof and the salts thereof, with the exception of the compounds (Z)-3-[1-(4-piperidinomethyl-phenylamino)-1-phenyl-methylidene]-6-chloro-2-indolinone and (Z)-3-[1-(4-piperidinomethyl-phenylamino)-1-phenyl-methylidene]-6-bromo-2-indolinone.

By a group which may be converted in-vivo into a carboxy group is meant for example a hydroxymethyl group, a carboxy group esterified with an alcohol wherein the alcoholic moiety preferably denotes a $C_{1-6}$-alkanol, a phenyl-$C_{1-3}$-alkanol, a $C_{3-9}$-cycloalkanol, while a $C_{5-8}$-cycloalkanol may additionally be substituted by one or two $C_{1-3}$-alkyl groups, a $C_{5-8}$-cycloalkanol, wherein a methylene group is replaced in the 3 or 4 position by an oxygen atom or by an imino group optionally substituted by a $C_{1-3}$-alkyl, phenyl-$C_{1-3}$-alkyl, phenyl-$C_{1-3}$-alkoxy-carbonyl or $C_{1-6}$-alkyl-carbonyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom which carries a double or triple bond, a $C_{3-8}$-cycloalkyl-$C_{1-3}$-alkanol, a bicycloalkanol with a total of 8 to 10 carbon atoms which may additionally be substituted in the bicycloalkyl moiety by one or two $C_{1-3}$-alkyl groups, a 1,3-dihydro-3-oxo-1-isobenzofuranol or an alcohol of formula

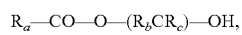

wherein $R_a$ denotes a $C_{1-8}$-alkyl, $C_{5-7}$-cycloalkyl, phenyl or phenyl-$C_{1-3}$-alkyl group, $R_b$ denotes a hydrogen atom, a $C_{1-3}$-alkyl, $C_{5-7}$-cycloalkyl or phenyl group and $R_c$ denotes a hydrogen atom or a $C_{1-3}$-alkyl group, and by a group which can be cleaved in vivo from an imino or amino group is meant for example a hydroxy group, an acyl group such as the benzoyl or pyridinoyl group or a $C_{1-16}$-alkyl-carbonyl group such as the formyl, acetyl, propionyl, butanoyl, pentanoyl or hexanoyl group, an allyloxycarbonyl group, a $C_{1-16}$-alkoxy-carbonyl group such as the methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxy-carbonyl group, a phenyl-$C_{1-6}$-alkoxy-carbonyl group such as the benzyloxycarbonyl, phenylethoxycarbonyl or phenylpropoxycarbonyl group, a $C_{1-3}$-alkylsulphonyl-$C_{1-4}$-alkoxy-carbonyl, $C_{1-3}$-alkoxy-$C_{2-4}$-alkoxy-$C_{2-4}$-alkoxy-carbonyl or $R_aCO$—O—($R_b$-$CR_c$)—O—CO— group wherein $R_a$ denotes a $C_{1-8}$-alkyl, $C_{5-7}$-cycloalkyl, phenyl or phenyl-$C_{1-3}$-alkyl group, $R_b$ denotes a hydrogen atom, a $C_{1-3}$-alkyl, $C_{5-7}$-cycloalkyl or phenyl group and $R_c$ denotes a hydrogen atom, a $C_{1-3}$-alkyl or $R_aCO$—O—($R_bCR_c$)—O— group wherein $R_a$ to $R_c$ are as hereinbefore defined, and additionally for an amino group the phthalimido group, while the above mentioned ester groups may also be used as a group which can be converted in vivo into a carboxy group.

Preferred prodrug groups for a carboxy group include a $C_{1-6}$-alkoxy-carbonyl group such as the methoxycarbonyl, ethoxycarbonyl, n-propyloycarbonyl, isopropyloxycarbonyl, n-butyloxycarbonyl, n-pentyloxycarbonyl, n-hexyloxy-carbonyl or cyclohexyloxycarbonyl group or phenyl-$C_{1-3}$-alkoxy-carbonyl group such as the benzyloxycarbonyl group and for an imino or amino group a $C_{1-9}$-alkoxy-carbonyl group such as the methoxycarbonyl, ethoxycarbonyl, n-propyloxycarbonyl, isopropyloxycarbonyl, n-butyloxycarbonyl, n-pentyloxycarbonyl, n-hexyloxycarbonyl, cyclohexyloxy-carbonyl, n-heptyloxycarbonyl, n-octyloxycarbonyl or n-nonyloxycarbonyl group, a phenyl-$C_{1-3}$-alkoxy-carbonyl group such as the benzyloxycarbonyl group, a phenylcarbonyl group optionally substituted by a $C_{1-3}$-alkyl group such as the benzoyl or 4-ethyl-benzoyl group, a pyridinoyl group such as the nicotinoyl group, a $C_{1-3}$-alkylsulphonyl-n-$C_{2-3}$-alkoxy-carbonyl or $C_{1-3}$-alkoxy-$C_{2-3}$-alkoxy-$C_{1-4}$-alkoxy-carbonyl group such as the 2-methylsulphonylethoxycarbonyl or 2-(2-ethoxy)-ethoxycarbonyl group.

Moreover, the saturated alkyl and alkoxy moieties containing more than 2 carbon atoms mentioned in the definitions above as well as the alkanoyl and unsaturated alkyl moieties which contain more than 3 carbon atoms also include the branched isomers thereof such as the isopropyl, tert.butyl, isobutyl group, etc.

One sub-group of compounds of general formula I deserving special mention are those wherein X denotes an oxygen or sulphur atom, $R^1$ denotes a hydrogen atom, a $C_{1-4}$-alkoxy-carbonyl, $C_{1-3}$-alkyl-carbonyl, aminomethyl, $C_{1-3}$-alkylaminomethyl, di-($C_{1-3}$-alkyl)-aminomethyl or a 5- to 7-membered cycloalkyleneiminomethyl group, $R^2$ denotes a fluorine, chlorine or bromine atom or a cyano group, $R^3$ denotes a phenyl or naphthyl group or a phenyl or naphthyl group mono- or disubstituted by a fluorine, chlorine, bromine or iodine atom, by a trifluoromethyl, $C_{1-3}$-alkyl or $C_{1-3}$-alkoxy group, while in the case of disubstitution the substituents may be identical or different and the above mentioned unsubstituted as well as the mono- and disubstituted phenyl and naphthyl groups may additionally be substituted by a fluorine, chlorine, bromine or iodine atom, by a $C_{1-3}$-alkyl, $C_{1-4}$-alkoxy, benzyloxy, carboxy, cyano, trifluoromethyl, nitro, amino, $C_{1-3}$-alkyl-carbonyl-amino, $C_{1-4}$-alkyloxy-carbonylamino, N—$C_{1-3}$-alkyl)-N—($C_{1-3}$-alkyl-carbonyl)-amino, phenyl-carbonylamino, N-($C_{1-3}$-alkyl)-N-(phenyl-carbonyl)-amino, benzyl-carbonylamino, N—($C_{1-3}$-alkyl)-N-(benzyl-carbonyl)-amino, hydroxy, $C_{1-3}$-alkylsulphonylamino, N—$C_{1-3}$-alkyl)-N—($C_{1-3}$-alkylsulphonyl)-amino, phenylsulphonylamino, N—($C_{1-3}$-alkyl)-N-(phenylsulphonyl)-amino, benzylsulphonylamino, N—($C_{1-3}$-alkyl)-N-(benzylsulphonyl)-amino, $C_{1-3}$-alkylamino or di-($C_{1-3}$-alkyl)-amino group, by a hydroxy-$C_{1-3}$-alkyl, cyano-$C_{1-3}$-alkyl, carboxy-$C_{1-3}$-alkyl, $C_{1-4}$-alkoxy-$C_{1-3}$-alkyl, amino-$C_{1-3}$-alkyl, $C_{1-3}$-alkylamino-$C_{1-3}$-alkyl, [di-($C_{1-3}$-alkyl)-amino]-$C_{1-3}$-alkyl, benzylamino-$C_{1-3}$-alkyl, dibenzylamino-$C_{1-3}$-alkyl, N-benzyl-N—($C_{1-3}$-alkyl)-amino-$C_{1-3}$-alkyl, benzylcarbonylamino-$C_{1-3}$-alkyl, N—($C_{1-3}$-alkyl)-N-(benzylcarbonyl)-amino-$C_{1-3}$-alkyl, phenylcarbonylamino-$C_{1-3}$-alkyl, N—($C_{1-3}$-alkyl)-N-(phenylcarbonyl)-amino-$C_{1-3}$-alkyl, phenylamino-$C_{1-3}$-alkyl, diphenylamino-$C_{1-3}$-alkyl, N-phenyl-N—($C_{1-3}$-alkyl)-amino-$C_{1-3}$-alkyl, heteroarylamino-$C_{1-3}$-alkyl, N-heteroaryl-N—($C_{1-3}$-alkyl)-amino-$C_{1-3}$-alkyl, $C_{1-4}$-alkyl-sulphonylamino-$C_{1-3}$-alkyl, N—($C_{1-3}$-alkyl)-N—($C_{1-4}$-alkyl-sulphonyl)-amino-$C_{1-3}$-alkyl, phenyl-sulphonylamino-$C_{1-3}$-alkyl, N—($C_{1-3}$-alkyl)-N-(phenyl-sulphonyl)-amino-$C_{1-3}$-alkyl, benzyl-sulphonylamino-$C_{1-3}$-alkyl, N—($C_{1-3}$-alkyl)-N-(benzyl-sulphonyl)-amino-$C_{1-3}$-alkyl, $C_{1-4}$-alkoxy-carbonyl-$C_{1-3}$-alkyl, N—$C_{1-4}$-alkoxy-carbonyl)-amino-$C_{1-3}$-alkyl, N—($C_{1-3}$-alkyl)-N—($C_{1-4}$-alkoxy-carbonyl)-amino-$C_{1-3}$-alkyl, aminocarbonyl-$C_{1-3}$-alkyl, ($C_{1-3}$-alkylamino)-carbonyl-$C_{1-3}$-alkyl, di-($C_{1-3}$-alkyl)-aminocarbonyl-$C_{1-3}$-alkyl, ($C_{1-6}$-alkyl-carbonyl)-amino-$C_{1-3}$-alkyl, N—($C_{1-3}$-alkyl)-N—($C_{1-6}$-alkyl-carbonyl)-amino-$C_{1-3}$-alkyl, ($C_{3-7}$-cycloalkyl-carbonyl)-amino-$C_{1-3}$-alkyl, N—($C_{1-3}$-alkyl)-N—$C_{3-7}$-cycloalkyl-carbonyl)-amino-$C_{1-3}$-alkyl, ($C_{3-7}$-cycloalkyl-$C_{1-3}$-alkyl-carbonyl)-amino-$C_{1-3}$-alkyl, N—($C_{1-3}$-alkyl)-N—($C_{3-7}$-cycloalkyl-$C_{1-3}$-alkyl-carbonyl)-amino-$C_{1-3}$-alkyl, ($C_{1-4}$-alkoxy-$C_{1-3}$-alkyl-carbonyl)-amino-$C_{1-3}$-alkyl, N—($C_{1-3}$-alkyl)-N—($C_{1-4}$-alkoxy-$C_{1-3}$-alkyl-carbonyl)-amino-$C_{1-3}$-alkyl, (heteroaryl-carbonyl)-amino-$C_{1-3}$-alkyl, N—($C_{1-3}$-alkyl)-N-(heteroaryl-carbonyl)-amino-$C_{1-3}$-alkyl, 4-($C_{1-3}$-alkyl)-piperazin-1-yl-carbonyl-($C_{1-3}$-alkyl), tetrazolyl-$C_{1-3}$-alkyl or heteroaryl-$C_{1-3}$-alkyl group, by a carboxy-$C_{2-3}$-alkenyl, aminocarbonyl-$C_{2-3}$-alkenyl, ($C_{1-3}$-alkyl-amino)-carbonyl-$C_{2-3}$-alkenyl, di-($C_{1-3}$-alkylamino)-carbonyl-$C_{2-3}$-alkenyl or $C_{1-4}$-alkoxy-carbonyl-$C_{2-3}$-alkenyl group or by a cycloalkyleneimino or cycloaklyleneimino-$C_{1-3}$-alkyl group each with 5 to 7 ring members, wherein in each case one or two methylene groups adjacent to the nitrogen atom may be replaced by a carbonyl or sulphonyl group or a —CH$_2$—CH$_2$— group linked to the imino group may be replaced by the group O—CO—, while the carbonyl group of the O—CO— group is linked to the imino group, while the substituents may be identical or different, $R^4$ denotes a benzopyrazolyl or 1-($C_{1-3}$-alkyl)-piperidin-4-yl group, a cyclohexyl group which is substituted by a N-[di-($C_{1-3}$-alkyl)-amino-$C_{1-3}$-alkyl-carbonyl]-amino or N-[di-($C_{1-3}$-alkyl)-amino-$C_{1-3}$-alkyl-carbonyl]-N—$C_{1-3}$-alkyl-amino group, or a phenyl, furyl, pyrrolyl, pyridinyl or naphthyl group, each of which is substituted in the carbon skeleton by a fluorine, chlorine, bromine or iodine atom, by a $C_{1-3}$-alkyl, $C_{1-4}$-alkoxy, cyano, nitro, carboxy or trifluoromethyl group, by a ω-amino-$C_{2-3}$-alkoxy, ω-[($C_{1-3}$-alkyl)-amino]-$C_{2-3}$-alkoxy, ω-[di-($C_{1-3}$-alkyl)-amino]-$C_{2-3}$-alkoxy, $C_{1-3}$-alkyl-sulphonyl, ($C_{1-3}$-alkyl)-amino-$C_{1-3}$-alkyl-sulphonyl, amino-$C_{1-3}$-alkyl-sulphonyl, di-($C_{1-3}$-alkyl)-amino-$C_{1-3}$-alkyl-sulphonyl, 4-($C_{1-3}$-alkyl)-piperazino or heteroaryl group, by a $C_{1-3}$-alkyl group which is terminally substituted by a carboxy, $C_{1-4}$-alkoxy-carbonyl, amino, $C_{1-3}$-alkylamino, di-($C_{1-3}$-alkyl)-amino, N—($C_{1-3}$-alkyl)-N-(ω-amino-$C_{2-3}$-alkyl)-amino, N-benzyl-N—($C_{1-3}$-alkyl)-amino, N-[ω-(di-($C_{1-3}$-alkyl)-amino)-$C_{2-3}$-alkyl]-N—($C_{1-3}$-alkyl)-amino, N-[di-($C_{1-3}$-alkyl)-amino-$C_{2-3}$-alkyl]-N—($C_{1-3}$-alkyl)-amino-carbonyl, N-(ω-hydroxy-$C_{2-3}$-alkyl)-N—($C_{1-3}$-alkyl)-amino, di-(ω-hydroxy-$C_{2-3}$-alkyl)-amino, N-(ω-$C_{1-3}$-alkoxy-$C_{2-3}$-alkoxy-$C_{1-3}$-alkyl)-N—($C_{1-3}$-alkyl)-amino, N—($C_{1-4}$-alkoxy-carbonyl)-amino, N—($C_{1-4}$-alkoxy-carbonyl)-N—($C_{1-3}$-alkyl)-amino, N-{ω-[N—($C_{1-4}$-alkoxy-carbonyl)-amino]-($C_{1-4}$-alkyl)}-N—($C_{1-3}$-alkyl)-amino, heteroaryl, triazolyl or by a 5- to 7-membered cycloalkyleneimino or cycloalkyleneiminocarbonyl group, while in the above mentioned cycloalkyleneimino groups one or two hydrogen atoms may each be replaced by a $C_{1-3}$-alkyl, $C_{1-4}$-alkoxy-carbonyl, amino, $C_{1-3}$-alkylamino or di-($C_{1-3}$-alkyl)-amino group and/or the methylene group in the 4 position of a 6- or 7-membered cycloalkyleneimino group may be replaced by one of the groups —NH, —N($C_{1-3}$-alkyl), —N($C_{1-4}$-alkoxy-carbonyl) or —O—, by a carbonyl group which is substituted by a $C_{1-3}$-alkoxy, N-[amino-$C_{1-3}$-alkyl]-amino, N-[($C_{1-3}$-alkyl)-amino-$C_{1-3}$-alkyl]-amino, N-[di-($C_{1-3}$-alkyl)-amino-$C_{1-3}$- alkyl]-amino, N-[amino-$C_{1-3}$-alkyl]-N—($C_{1-3}$-alkyl)-amino, N-[($C_{1-3}$-alkyl)-amino-$C_{1-3}$-alkyl]-N—($C_{1-3}$-alkyl)-amino, N-[di-($C_{1-3}$-alkyl)-amino-$C_{1-3}$-alkyl]-N—($C_{1-3}$-alkyl)-amino, N—($C_{3-7}$-cycloalkyl)-N—($C_{1-3}$-alkyl)-amino or 5- to 7-membered cycloalkyleneimino group, while the methylene group in the 4 position of a 6- or 7-membered cycloalkylene group may be replaced by a —NH, —N($C_{1-3}$-alkyl) or —N($C_{1-4}$-alkyloxy-carbonyl)- group, or by a group of formula

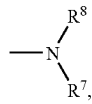

wherein
$R^7$ denotes a hydrogen atom or a $C_{1-4}$-alkyl, $C_{1-4}$-alkyl-carbonyl, benzylcarbonyl, heteroarylcarbonyl, cycloalkyleneimino-$C_{1-3}$-alkyl-carbonyl with 5 to 7 ring atoms in the cycloalkyleneimino moiety, $C_{1-3}$-alkoxy-$C_{1-3}$-alkyl-carbonyl, amino-$C_{1-3}$-alkyl-carbonyl, ($C_{1-3}$-alkyl)-amino-$C_{1-3}$-alkyl-carbonyl, di-($C_{1-3}$-alkyl)-amino-carbonyl-$C_{1-3}$-alkyl, $C_{1-4}$-alkylsulphonyl, phenylsulphonyl, heteroarylsulphonyl or benzylsulphonyl group or a phenylcarbonyl group optionally substituted in the phenyl moiety by one or two methoxy groups and
$R^8$ denotes a $C_{1-3}$-alkyl group, a $C_{2-4}$-alkyl group terminally substituted by an amino, ($C_{1-3}$-alkyl)-amino, di-($C_{1-3}$-alkyl)-amino or N-benzyl-N—($C_{1-3}$-alkyl)-amino group, an amino-carbonyl-$C_{1-3}$-alkyl, ($C_{1-3}$-alkyl)-amino-carbonyl-$C_{1-3}$-alkyl or di-($C_{1-3}$-alkyl)-amino-carbonyl-$C_{1-3}$-alkyl group,
a di-($C_{1-3}$-alkyl)-amino-$C_{1-3}$-alkyl-amino-carbonyl, 4-($C_{1-3}$-alkyl)-piperazin-1-yl-carbonyl, 4-($C_{1-3}$-alkyl)-piperazin-1-yl-aminocarbonyl, 1-($C_{1-3}$-alkyl)-piperidin-4-yl-aminocarbonyl, 1-($C_{1-3}$-alkyl)-piperidin-4-yl-oxy-carbonyl or (pyridinyl-$C_{1-3}$-alkyl)-aminocarbonyl group or
a $C_{1-4}$-alkyl-carbonyl group terminally substituted by a hydroxy, $C_{1-4}$-alkyloxy, amino, ($C_{1-3}$-alkyl)-amino, di-($C_{1-3}$-alkyl)-amino, (ω-hydroxy-$C_{2-3}$-alkyl)-amino, di-(ω-hydroxy-$C_{2-3}$-alkyl)-amino, (ω-alkoxy-$C_{2-3}$-alkyl)-amino, di-(ω-alkoxy-$C_{2-3}$-alkyl)-amino, $C_{1-3}$-alkyl-carbonyl-amino, N-benzyl-N—($C_{1-3}$-alkyl)-amino, N-[di-($C_{1-3}$-alkyl)-amino-$C_{1-3}$-alkyl]-N—($C_{1-3}$-alkyl)-amino, 1-($C_{1-3}$-alkyl)-piperidin-4-yl or heteroaryl group or by a 5- to 7-membered cycloalkyleneimino group,
while the cycloalkylene group may be substituted by a $C_{1-3}$-alkyl group and/or
one or two methylene groups linked to the imino group may be replaced by a carbonyl group and/or
the methylene group in the 4 position of a 6- or 7-membered cycloalkylimino group may be replaced by an —NH, —N($C_{1-3}$-alkyl), —N(benzyl), —N($C_{1-4}$-alkyoxy-carbonyl) or —O— and/or
a phenyl ring may be fused via two adjacent carbon atoms of the cycloalkyleneimino group,
while a 2- or 3-linked pyrrolyl group may additionally be substituted at the nitrogen atom by a $C_{1-3}$-alkyl group,
$R^5$ denotes a hydrogen atom or a $C_{1-3}$-alkyl group and
$R^6$ denotes a hydrogen atom or a nitro group, while the unsubstituted, mono- or disubstituted phenyl groups contained in the above definitions may additionally be substituted by a fluorine, chlorine, bromine or iodine atom or by a $C_{1-3}$-alkyl, $C_{1-3}$-alkoxy, benzyloxy, carboxy, cyano, trifluoromethyl, nitro, amino, hydroxy, $C_{1-3}$-alkylsulphonylamino, $C_{1-3}$-alkylamino or di-($C_{1-3}$-alkyl)-amino group or by two methyl groups,
the above mentioned alkyl groups including straight-chain and branched alkyl groups, wherein additionally one to 3 hydrogen atoms may be replaced by fluorine atoms,
while, unless otherwise stated, the expression a heteroaryl group refers to a monocyclic 5- or 6-membered heteroaryl group optionally substituted in the carbon skeleton by a $C_{1-3}$-alkyl group, wherein
the 6-membered heteroaryl group contains one, two or three nitrogen atoms and
the 5-membered heteroaryl group contains an imino group optionally substituted by a $C_{1-3}$-alkyl or phenyl-$C_{1-3}$-alkyl group, an oxygen or sulphur atom or
an imino group optionally substituted by a $C_{1-3}$-alkyl, amino-$C_{1-3}$-alkyl, [($C_{1-3}$-alkyl)-amino]-$C_{1-3}$-alkyl, [di-($C_{1-3}$-alkyl)-amino]-$C_{1-3}$-alkyl or phenyl-$C_{1-3}$-alkyl group or an oxygen or sulphur atom and additionally contains a nitrogen atom or
an imino group optionally substituted by a $C_{1-3}$-alkyl or phenyl-$C_{1-3}$-alkyl group and two nitrogen atoms,
and moreover a phenyl ring may be fused to the above mentioned monocyclic heterocyclic groups via two adjacent carbon atoms and the bonding takes place via a nitrogen atom or via a carbon atom of the heterocyclic moiety or a fused-on phenyl ring,
and additionally any carboxy, amino or imino group present may be substituted by a group which can be cleaved in vivo,
the tautomers, enantiomers, diastereomers, mixtures thereof and the salts thereof,
with the exception of the compounds
(Z)-3-[1-(4-piperidinomethyl-phenylamino)-1-phenyl-methylidene]-6-chloro-2-indolinone and
(Z)-3-[1-(4-piperidinomethyl-phenylamino)-1-phenyl-methylidene]-6-bromo-2-indolinone.
Preferred compounds of the above general formula I are those wherein
X denotes an oxygen or sulphur atom,
$R^1$ denotes a hydrogen atom, a $C_{1-4}$-alkoxy-carbonyl, $C_{1-3}$-alkyl-carbonyl, aminomethyl, $C_{1-3}$-alkylaminomethyl, di-($C_{1-3}$-alkyl)-aminomethyl or a 5- to 7-membered cycloalkyleneiminomethyl group,
$R^2$ denotes a fluorine, chlorine or bromine atom or a cyano group,
$R^3$ denotes a phenyl or naphthyl group or
a phenyl or naphthyl group mono- or disubstituted by a fluorine, chlorine, bromine or iodine atom, by a trifluoromethyl, $C_{1-3}$-alkyl or $C_{1-3}$-alkoxy group, while in the case of disubstitution the substituents may be identical or different and the above mentioned unsubstituted as well as the mono- and disubstituted phenyl and naphthyl groups may additionally be substituted
by a fluorine, chlorine, bromine or iodine atom,
by a $C_{1-3}$-alkyl, $C_{1-4}$-alkoxy, benzyloxy, carboxy, cyano, trifluoromethyl, nitro, amino, $C_{1-3}$-alkyl-carbonyl-amino, $C_{1-4}$-alkyloxy-carbonylamino, hydroxy, $C_{1-3}$-alkylsulphonylamino, $C_{1-3}$-alkylamino or di-($C_{1-3}$-alkyl)-amino group,
by a hydroxy-$C_{1-3}$-alkyl, cyano-$C_{1-3}$-alkyl, carboxy-$C_{1-3}$-alkyl, $C_{1-4}$-alkoxy-$C_{1-3}$-alkyl, amino-$C_{1-3}$-alkyl, $C_{1-3}$-alkylamino-$C_{1-3}$-alkyl, [di-($C_{1-3}$-alkyl)-amino]-$C_{1-3}$- alkyl, benzylamino-$C_{1-3}$-alkyl, dibenzylamino-$C_{1-3}$-alkyl, N-benzyl-N—($C_{1-3}$-alkyl)-amino-$C_{1-3}$-alkyl, benzylcarbonylamino-$C_{1-3}$-alkyl, phenylcarbonylamino-$C_{1-3}$-alkyl, phenylamino-$C_{1-3}$-alkyl, diphenylamino-$C_{1-3}$-alkyl, N-phenyl-N—($C_{1-3}$-alkyl)-amino-$C_{1-3}$-alkyl, heteroarylamino-$C_{1-3}$-alkyl, N-heteroaryl-N—($C_{1-3}$-alkyl)-amino-$C_{1-3}$-alkyl, $C_{1-4}$-alkyl-sulphonylamino-$C_{1-3}$-alkyl, phenyl-sulphonylamino-$C_{1-3}$-alkyl, benzyl-sulphonylamino-$C_{1-3}$-alkyl, $C_{1-4}$-alkoxy-carbonyl-$C_{1-3}$-alkyl, N—$C_{1-4}$-alkoxy-carbonyl)-amino-$C_{1-3}$-alkyl, aminocarbonyl-$C_{1-3}$-alkyl, ($C_{1-3}$-alkylamino)-carbonyl-$C_{1-3}$-alkyl, di-($C_{1-3}$-alkyl)-aminocarbonyl-$C_{1-3}$-alkyl ($C_{1-6}$-alkyl-carbonyl)-amino-$C_{1-3}$-alkyl, N—($C_{1-3}$-alkyl)-N—($C_{1-6}$alkyl-carbonyl)-amino-$C_{1-3}$-alkyl, ($C_{3-7}$-cycloalkyl-carbonyl)-amino-$C_{1-3}$-alkyl, N—($C_{1-3}$-alkyl)-N—($C_{3-7}$-cycloalkyl-carbonyl)-amino-$C_{1-3}$-alkyl, ($C_{3-7}$-cycloalkyl-$C_{1-3}$-alkyl-carbonyl)-amino-$C_{1-3}$-alkyl, N—($C_{1-3}$-alkyl)-N—($C_{3-7}$-cycloalkyl-$C_{1-3}$-alkyl-carbonyl)-amino-$C_{1-3}$-alkyl, ($C_{1-4}$-alkoxy-$C_{1-3}$-alkyl-carbonyl)-amino-$C_{1-3}$-alkyl, N—($C_{1-3}$-alkyl)-N—($C_{1-4}$-alkoxy-$C_{1-3}$-alkyl-carbonyl)-amino-$C_{1-3}$-alkyl, (heteroaryl-carbonyl)-amino-$C_{1-3}$-alkyl, N—$C_{1-3}$-alkyl)-N-(heteroaryl-carbonyl)-amino-$C_{1-3}$-alkyl, 4-($C_{1-3}$-alkyl)-piperazin-1-yl-carbonyl-($C_{1-3}$-alkyl), tetrazolyl-$C_{1-3}$-alkyl or imidazoyl-$C_{1-3}$-alkyl group, by a carboxy-$C_{2-3}$-alkenyl, aminocarbonyl-$C_{2-3}$-alkenyl or $C_{1-4}$-alkoxy-carbonyl-$C_{2-3}$-alkenyl group or by a 5- to 7-membered cycloalkyleneimino group wherein one or two methylene groups adjacent to the nitrogen atom may be replaced by a carbonyl group or a —$CH_2$—$CH_2$— group linked to the imino group may be replaced by the group —O—CO—, while the carbonyl group of the O—CO— group is linked to the imino group, while the substituents may be identical or different, $R^4$ denotes a benzopyrazolyl or 1-($C_{1-3}$-alkyl)-piperidin-4-yl group, a cyclohexyl group which is substituted by a N-[di-($C_{1-3}$-alkyl)-amino-$C_{1-3}$-alkyl-carbonyl]-amino or N-[di-($C_{1-3}$-alkyl)-amino-$C_{1-3}$-alkyl-carbonyl]-N—($C_{1-3}$-alkyl)-amino group, or a phenyl, furyl, pyrrolyl, pyridinyl or naphthyl group each of which may be substituted in the carbon skeleton by a fluorine, chlorine, bromine or iodine atom, by a $C_{1-3}$-alkyl, $C_{1-3}$-alkoxy, cyano, nitro, carboxy or trifluoromethyl group, by a ω-[di-($C_{1-3}$-alkyl)-amino]-$C_{2-3}$-alkoxy, $C_{1-3}$-alkylsulphonyl, di-($C_{1-3}$-alkyl)-amino-$C_{1-3}$-alkyl-sulphonyl, 4-($C_{1-3}$-alkyl)-piperazino, imidazolyl, $C_{1-3}$-alkyl-imidazolyl or [di-($C_{1-3}$-alkyl)-amino]-$C_{1-3}$-alkyl-imidazolyl group, by a $C_{1-3}$-alkyl group which is terminally substituted by a carboxy, $C_{1-4}$-alkoxy-carbonyl, amino, $C_{1-3}$-alkylamino, di-($C_{1-3}$-alkyl)-amino, N—($C_{1-3}$-alkyl)-N-(ω-amino-$C_{2-3}$-alkyl)-amino, N-benzyl-N—($C_{1-3}$-alkyl)-amino, N-[ω-(di-($C_{1-3}$-alkyl)-amino)-$C_{2-3}$-alkyl]-N—($C_{1-3}$-alkyl)-amino, N-[di-($C_{1-3}$-alkyl)-amino-$C_{1-3}$-alkyl]-N—($C_{1-3}$-alkyl)-amino-carbonyl, N-(ω-hydroxy-$C_{2-3}$-alkyl)-N—($C_{1-3}$-alkyl)-amino, di-(ω-hydroxy-$C_{2-3}$-alkyl)-amino, N-(ω-$C_{1-3}$-alkoxy-$C_{2-3}$-alkoxy-$C_{1-3}$-alkyl)-N—($C_{1-3}$-alkyl)-amino, N—($C_{1-4}$-alkoxy-carbonyl)-amino, N—($C_{1-4}$-alkoxy-carbonyl)-N—($C_{1-3}$-alkyl)-amino, N-{ω-[N—($C_{1-4}$-alkoxy-carbonyl)-amino]-($C_{1-4}$-alkyl)}-N—($C_{1-3}$-alkyl)-amino, pyridinyl, triazolyl, pyrrolidino, piperidino, di-($C_{1-3}$-alkyl)-piperidine, [di-($C_{1-3}$-alkyl)-amino]-piperidino, piperazino, morpholino, ($C_{1-3}$-alkyl)-piperazino, ($C_{1-3}$-alkyl)-piperazin-1-yl-carbonyl or 4-($C_{1-4}$-alkoxy-carbonyl)-piperazino group, by a carbonyl group which is substituted by a $C_{1-4}$-alkoxy, N-[di-($C_{1-3}$-alkyl)-amino-$C_{1-3}$-alkyl]-amino, N-[di-($C_{1-3}$-alkyl)-amino-$C_{1-3}$-alkyl]-N—($C_{1-3}$-alkyl)-amino, N—($C_{3-7}$-cycloalkyl)-N—($C_{1-3}$-alkyl)-amino, piperidino, piperazino, 4-($C_{1-4}$-alkyloxy-carbonyl)-piperazino or 4-($C_{1-3}$-alkyl)-piperazino group, or by a group of formula

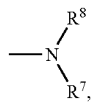

wherein $R^7$ denotes a hydrogen atom or a $C_{1-3}$-alkyl, $C_{1-3}$-alkyl-carbonyl, benzylcarbonyl, pyridinylcarbonyl, furanylcarbonyl, pyrrolidino-$C_{1-3}$-alkyl-carbonyl, $C_{1-3}$-alkoxy-$C_{1-3}$-alkyl-carbonyl, di-($C_{1-3}$-alkyl)-amino-carbonyl-$C_{1-3}$-alkyl, $C_{1-4}$-alkylsulphonyl or benzylsulphonyl group or a phenylcarbonyl group optionally substituted in the phenyl moiety by one or two methoxy groups and $R^8$ denotes a $C_{1-3}$-alkyl, di-($C_{1-3}$-alkyl)-amino-$C_{1-4}$-alkyl-amino-carbonyl or di-($C_{1-3}$-alkyl)-amino-carbonyl-$C_{1-3}$-alkyl group, a $C_{2-3}$-alkyl group terminally substituted by a di-($C_{1-3}$-alkyl)-amino or N-benzyl-N—($C_{1-3}$-alkyl)-amino group, a 4-($C_{1-3}$-alkyl)-piperazin-1-yl-carbonyl, 4-($C_{1-3}$-alkyl)-piperazin-1-yl-aminocarbonyl, 1-($C_{1-3}$-alkyl)-piperidin-4-yl-aminocarbonyl, 1-($C_{1-3}$-alkyl)-piperidin-4-yl-oxy-carbonyl or (pyridinyl-$C_{1-3}$-alkyl)-aminocarbonyl group or a $C_{1-4}$-alkyl-carbonyl group terminally substituted by a hydroxy, amino, di-($C_{1-3}$-alkyl)-amino, di-(ω-hydroxy-$C_{2-3}$-alkyl)-amino, $C_{1-3}$-alkyl-carbonyl-amino, N-benzyl-N—($C_{1-3}$-alkyl)-amino, N-[di-($C_{1-3}$-alkyl)-amino-$C_{1-3}$-alkyl]-N—($C_{1-3}$-alkyl)-amino, imidazolyl, piperazino, 4-($C_{1-3}$-alkyl)-piperazin-1-yl, 4-benzyl-piperazin-1-yl, 4-($C_{1-4}$-alkoxy-carbonyl)-piperazin-1-yl, 4-($C_{1-3}$-alkyl)-homopiperazin-1-yl, morpholino, pyrrolidino, piperidino, 1-($C_{1-3}$-alkyl)-piperidin-4-yl, 4-($C_{1-3}$-alkyl)-piperidin-1-yl or phthalimido group, while a 2- or 3-linked pyrrolyl group may additionally be substituted at the nitrogen atom by a $C_{1-3}$-alkyl group, $R^5$ denotes a hydrogen atom or a $C_{1-3}$-alkyl group and $R^6$ denotes a hydrogen atom or a nitro group, while the unsubstituted, mono- or disubstituted phenyl groups contained in the above definitions may additionally be substituted by a fluorine, chlorine, bromine or iodine atom or by a $C_{1-3}$-alkyl, $C_{1-3}$-alkoxy, benzyloxy, carboxy, cyano, trifluoromethyl, nitro, amino, hydroxy, $C_{1-3}$-alkylsulphonylamino, $C_{1-3}$-alkylamino or di-($C_{1-3}$-alkyl)-amino group or by two methyl groups, the above mentioned alkyl groups including straight-chain and branched alkyl groups, wherein additionally one to 3 hydrogen atoms may be replaced by fluorine atoms, while, unless otherwise stated, the expression a heteroaryl group refers to a monocyclic 5- or 6-membered heteroaryl group optionally substituted in the carbon skeleton by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two nitrogen atoms, and moreover a phenyl ring may be fused to the above mentioned monocyclic heterocyclic groups via two adjacent carbon atoms and the bonding takes place via a nitrogen atom or via a carbon atom of the heterocyclic moiety or a fused-on phenyl ring, and additionally any carboxy, amino or imino group present may be substituted by a group which can be cleaved in vivo, the tautomers, enantiomers, diastereomers, mixtures thereof and the salts thereof, with the exception of the compounds (Z)-3-[1-(4-piperidinomethyl-phenylamino)-1-phenyl-methylidene]-6-chloro-2-indolinone and (Z)-3-[1-(4-piperidinomethyl-phenylamino)-1-phenyl-methylidene]-6-bromo-2-indolinone.

A first sub-group of preferred compounds of general formula I deserving special mention comprises those wherein $R^1$, $R^2$, $R^3$, $R^5$, $R^6$ and X are as hereinbefore defined and $R^4$ denotes a benzopyrazolyl or 1-($C_{1-3}$-alkyl)-piperidin-4-yl group, a cyclohexyl group which is substituted by an N-[di-($C_{1-3}$-alkyl)-amino-$C_{1-3}$-alkyl-carbonyl]-amino or N-[di-($C_{1-3}$-alkyl)-amino-$C_{1-3}$-alkyl-carbonyl]-N—$C_{1-3}$-alkyl-amino group, or a phenyl, furyl, pyrrolyl, pyridinyl or naphthyl group, each of which may be substituted in the carbon skeleton by a fluorine, chlorine, bromine or iodine atom, by a $C_{1-3}$-alkyl, $C_{1-3}$-alkoxy, cyano, nitro, carboxy or trifluoromethyl group, by a ω-[di-($C_{1-3}$-alkyl)-amino]-$C_{2-3}$-alkoxy, $C_{1-3}$-alkyl-sulphonyl, di-($C_{1-3}$-alkyl)-amino-$C_{1-3}$-alkyl-sulphonyl, 4-($C_{1-3}$-alkyl)-piperazino, imidazolyl, $C_{1-3}$-alkyl-imidazolyl or [di-($C_{1-3}$-alkyl)-amino]-$C_{1-3}$-alkyl-imidazolyl group, by a carbonyl group which is substituted by a $C_{1-4}$-alkoxy, N-[di-($C_{1-3}$-alkyl)-amino-$C_{1-3}$-alkyl]-amino, N-[di-($C_{1-3}$-alkyl)-amino-$C_{1-3}$-alkyl]-N—$C_{1-3}$-alkyl-amino, N—($C_{3-7}$-cycloalkyl)-N—($C_{1-3}$-alkyl)-amino, piperidino, piperazino, 4-($C_{1-4}$-alkyloxy-carbonyl)-piperazino or 4-($C_{1-3}$-alkyl)-piperazino group, or by a group of formula

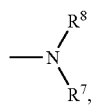

wherein $R^7$ denotes a hydrogen atom or a $C_{1-3}$-alkyl, $C_{1-3}$-alkyl-carbonyl, benzylcarbonyl, pyridinylcarbonyl, furanylcarbonyl, pyrrolidino-$C_{1-3}$-alkyl-carbonyl, $C_{1-3}$-alkoxy-$C_{1-3}$-alkyl-carbonyl, di-($C_{1-3}$-alkyl)-amino-carbonyl-$C_{1-3}$-alkyl, $C_{1-4}$-alkylsulphonyl or benzylsulphonyl group or a phenylcarbonyl group optionally substituted in the phenyl moiety by one or two methoxy groups and $R^8$ denotes a $C_{1-3}$-alkyl, di-($C_{1-3}$-alkyl)-amino-$C_{1-3}$-alkyl-amino-carbonyl or di-($C_{1-3}$-alkyl)-amino-carbonyl-$C_{1-3}$-alkyl group, a $C_{2-3}$-alkyl group terminally substituted by a di-($C_{1-3}$-alkyl)-amino or N-benzyl-N—($C_{1-3}$-alkyl)-amino group, a 4-($C_{1-3}$-alkyl)-piperazin-1-yl-carbonyl, 4-($C_{1-3}$-alkyl)-piperazin-1-yl-aminocarbonyl, 1-($C_{1-3}$-alkyl)-piperidin-4-yl-aminocarbonyl, 1-($C_{1-3}$-alkyl)-piperidin-4-yl-oxy-carbonyl or (pyridinyl-$C_{1-3}$-alkyl)-aminocarbonyl group or a $C_{1-4}$-alkyl-carbonyl group terminally substituted by a hydroxy, amino, di-($C_{1-3}$-alkyl)-amino, di-(ω-hydroxy-$C_{2-3}$-alkyl)-amino, $C_{1-3}$-alkyl-carbonyl-amino, N-benzyl-N—($C_{1-3}$-alkyl)-amino, N-[di-($C_{1-3}$-alkyl)-amino-$C_{1-3}$-alkyl]-N—($C_{1-3}$-alkyl)-amino, imidazolyl, piperazino, 4-($C_{1-3}$-alkyl)-piperazin-1-yl, 4-benzyl-piperazin-1-yl, 4-($C_{1-4}$-alkoxy-carbonyl)-piperazin-1-yl, 4-($C_{1-3}$-alkyl)-homopiperazin-1-yl, morpholino, pyrrolidino, piperidino, 1-($C_{1-3}$-alkyl)-piperidin-4-yl, 4-($C_{1-3}$-alkyl)-piperidin-1-yl or phthalimido group, while a 2- or 3-linked pyrrolyl group may additionally be substituted at the nitrogen atom by a $C_{1-3}$-alkyl group, while the unsubstituted, mono- or disubstituted phenyl groups contained in the above definitions may additionally be substituted by a fluorine, chlorine, bromine or iodine atom or by a $C_{1-3}$-alkyl, $C_{1-3}$-alkoxy, benzyloxy, carboxy, cyano, trifluoromethyl, nitro, amino, hydroxy, $C_{1-3}$-alkylsulphonylamino, $C_{1-3}$-alkylamino or di-($C_{1-3}$-alkyl)-amino group or by two methyl groups, the above mentioned alkyl groups including straight-chain and branched alkyl groups, wherein additionally one to 3 hydrogen atoms may be replaced by fluorine atoms, while, unless otherwise stated, the expression a heteroaryl group refers to a monocyclic 5- or 6-membered heteroaryl group optionally substituted in the carbon skeleton by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two nitrogen atoms, and moreover a phenyl ring may be fused to the above mentioned monocyclic heterocyclic groups via two adjacent carbon atoms and the bonding takes place via a nitrogen atom or via a carbon atom of the heterocyclic moiety or a fused-on phenyl ring, and additionally any carboxy, amino or imino group present may be substituted by a group which can be cleaved in vivo, the tautomers, enantiomers, diastereomers, mixtures thereof and the salts thereof.

A second sub-group of preferred compounds of general formula I deserving special mention are those wherein $R^1$, $R^2$, $R^4$, $R^5$, $R^6$ and X are as hereinbefore defined and $R^3$ denotes a phenyl or naphthyl group or a phenyl or naphthyl group mono- or disubstituted by a fluorine, chlorine, bromine or iodine atom, by a trifluoromethyl, $C_{1-3}$-alkyl or $C_{1-3}$-alkoxy group, while in the case of disubstitution the substituents may be identical or different and the above mentioned unsubstituted as well as the mono- and disubstituted phenyl and naphthyl groups may additionally be substituted by a fluorine, chlorine, bromine or iodine atom, by a $C_{1-3}$-alkyl, $C_{1-4}$-alkoxy, benzyloxy, carboxy, cyano, trifluoromethyl, nitro, amino, $C_{1-3}$-alkyl-carbonylamino, $C_{1-4}$-alkyloxy-carbonylamino, hydroxy, $C_{1-3}$-alkylsulphonylamino, $C_{1-3}$-alkylamino or di-($C_{1-3}$-alkyl)-amino group, by a hydroxy-$C_{1-3}$-alkyl, cyano-$C_{1-3}$-alkyl, carboxy-$C_{1-3}$-alkyl, $C_{1-4}$-alkoxy-$C_{1-3}$-alkyl, amino-$C_{1-3}$-alkyl, $C_{1-3}$-alkylamino-$C_{1-3}$-alkyl, [di-($C_{1-3}$-alkyl)-amino]-$C_{1-3}$-alkyl, benzylamino-$C_{1-3}$-alkyl, dibenzylamino-$C_{1-3}$-alkyl, N-benzyl-N—($C_{1-3}$-alkyl)-amino-$C_{1-3}$-alkyl, benzylcarbonylamino-$C_{1-3}$-alkyl, phenylcarbonylamino-$C_{1-3}$-alkyl, phenylamino-$C_{1-3}$-alkyl, diphenylamino-$C_{1-3}$-alkyl, N-phenyl-N—($C_{1-3}$-alkyl)-amino-$C_{1-3}$-alkyl, heteroarylamino-$C_{1-3}$-alkyl, N-heteroaryl-N—($C_{1-3}$-alkyl)-amino-$C_{1-3}$-alkyl, $C_{1-4}$-alkyl-sulphonylamino-$C_{1-3}$-alkyl, phenyl-sulphonylamino-$C_{1-3}$-alkyl, benzyl-sulphonylamino-$C_{1-3}$-alkyl, $C_{1-4}$-alkoxy-carbonyl-$C_{1-3}$-alkyl, N—$C_{1-4}$-alkoxy-carbonyl)-amino-$C_{1-3}$-alkyl, aminocarbonyl-$C_{1-3}$-alkyl, ($C_{1-3}$-alkylamino)-carbonyl-$C_{1-3}$-alkyl, di-($C_{1-3}$-alkyl)-aminocarbonyl-$C_{1-3}$-alkyl, ($C_{1-6}$-alkyl-carbonyl)-amino-$C_{1-3}$-alkyl, N—($C_{1-3}$-alkyl)-N—($C_{1-6}$-alkyl-carbonyl)-amino-$C_{1-3}$-alkyl, ($C_{3-7}$-cycloalkyl-carbonyl)-amino-$C_{1-3}$-alkyl, N—($C_{1-3}$-alkyl)-N—($C_{3-7}$-cycloalkyl-carbonyl)-amino-$C_{1-3}$-alkyl, ($C_{3-7}$-cycloalkyl-$C_{1-3}$-alkyl-carbonyl)-amino-$C_{1-3}$-alkyl, N—($C_{1-3}$-alkyl)-N—($C_{3-7}$-cycloalkyl-$C_{1-3}$-alkyl-carbonyl)-amino-$C_{1-3}$-alkyl, ($C_{1-4}$-alkoxy-$C_{1-3}$-alkyl-carbonyl)-amino-$C_{1-3}$-alkyl, N—($C_{1-3}$-alkyl)-N—($C_{1-4}$-alkoxy-$C_{1-3}$-alkyl-carbonyl)-amino-$C_{1-3}$-alkyl, (heteroaryl-carbonyl)-amino-$C_{1-3}$-alkyl, N—$C_{1-3}$-alkyl)-N-(heteroaryl-carbonyl)-amino-$C_{1-3}$-alkyl, 4-($C_{1-3}$-alkyl)-piperazin-1-yl-carbonyl-($C_{1-3}$-alkyl), tetrazolyl-$C_{1-3}$-alkyl or imidazoyl-$C_{1-3}$-alkyl group, by a carboxy-$C_{2-3}$-alkenyl, aminocarbonyl-$C_{2-3}$-alkenyl or $C_{1-4}$-alkoxy-carbonyl-$C_{2-3}$-alkenyl group or by a 5- to 7-membered cycloalkyleneimino group wherein one or two methylene groups adjacent to the nitrogen atom may be replaced by a carbonyl group or a —CH$_2$—CH$_2$— group linked to the imino group may be replaced by the group —O—CO—, while the carbonyl group of the —O—CO— group is linked to the imino group, while the substituents may be identical or different, and the unsubstituted, mono- or disubstituted phenyl groups contained in the above definitions may additionally be substituted by a fluorine, chlorine, bromine or iodine atom or by a $C_{1-3}$-alkyl, $C_{1-3}$-alkoxy, benzyloxy, carboxy, cyano, trifluoromethyl, nitro, amino, hydroxy, $C_{1-3}$-alkylsulphonylamino, $C_{1-3}$-alkylamino or di-($C_{1-3}$-alkyl)-amino group or by two methyl groups, the above mentioned alkyl groups including straight-chain and branched alkyl groups, wherein additionally one to 3 hydrogen atoms may be replaced by fluorine atoms, while, unless otherwise stated, the expression a heteroaryl group refers to a monocyclic 5- or 6-membered heteroaryl group optionally substituted in the carbon skeleton by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two nitrogen atoms, and moreover a phenyl ring may be fused to the above mentioned monocyclic heterocyclic groups via two adjacent carbon atoms and the bonding takes place via a nitrogen atom or via a carbon atom of the heterocyclic moiety or a fused-on phenyl ring, and additionally any carboxy, amino or imino group present may be substituted by a group which can be cleaved in vivo, the tautomers, enantiomers, diastereomers, mixtures thereof and the salts thereof.

Particularly preferred compounds of the above general formula I are those wherein X denotes an oxygen or sulphur atom, $R^1$ denotes a hydrogen atom, a $C_{1-4}$-alkoxy-carbonyl, $C_{1-3}$-alkyl-carbonyl, aminomethyl, $C_{1-3}$-alkylaminomethyl, di-($C_{1-3}$-alkyl)-aminomethyl or a 5- to 7-membered cycloalkyleneiminomethyl group, $R^2$ denotes a fluorine, chlorine or bromine atom or a cyano group, $R^3$ denotes a phenyl or naphthyl group or a phenyl or naphthyl group mono- or disubstituted by a fluorine, chlorine, bromine or iodine atom, by a trifluoromethyl, $C_{1-3}$-alkyl or $C_{1-3}$-alkoxy group, while in the case of disubstitution the substituents may be identical or different and the above mentioned unsubstituted as well as the mono- and disubstituted phenyl and naphthyl groups may additionally be substituted by a $C_{1-3}$-alkyl-carbonyl-amino, $C_{1-4}$-alkyloxy-carbonylamino, benzyloxy or hydroxy group, by a hydroxy-$C_{1-3}$-alkyl, carboxy-$C_{1-3}$-alkyl, $C_{1-4}$-alkoxy-$C_{1-3}$-alkyl, cyano-$C_{1-3}$-alkyl, benzylamino-$C_{1-3}$-alkyl, dibenzylamino-$C_{1-3}$-alkyl, N-benzyl-N—$C_{1-3}$-alkyl)-amino-$C_{1-3}$-alkyl, $C_{1-4}$-alkoxy-$C_{1-3}$-alkyl-carbonylamino-$C_{1-3}$-alkyl, $C_{3-7}$-cycloalkyl-carbonylamino-$C_{1-3}$-alkyl, $C_{3-7}$-cycloalkyl-$C_{1-3}$-alkyl-carbonylamino-$C_{1-3}$-alkyl, benzylcarbonylamino-$C_{1-3}$-alkyl, phenylcarbonylamino-$C_{1-3}$-alkyl, heteroaryl-carbonylamino-$C_{1-3}$-alkyl, phenylamino-$C_{1-3}$-alkyl, diphenylamino-$C_{1-3}$-alkyl, N-phenyl-N—$C_{1-3}$-alkyl)-amino-$C_{1-3}$-alkyl, heteroarylamino-$C_{1-3}$-alkyl, N-heteroaryl-N—$C_{1-3}$-alkyl)-amino-$C_{1-3}$-alkyl, $C_{1-4}$-alkyl-sulphonylamino-$C_{1-3}$-alkyl, phenyl-sulphonylamino-$C_{1-3}$-alkyl, benzyl-sulphonylamino-$C_{1-3}$-alkyl, $C_{1-4}$-alkoxy-carbonyl-$C_{1-3}$-alkyl, N—($C_{1-4}$-alkoxy-carbonyl)-amino-$C_{1-3}$-alkyl, aminocarbonyl-$C_{1-3}$-alkyl, ($C_{1-3}$-alkylamino)-carbonyl-$C_{1-3}$-alkyl, di-($C_{1-3}$-alkyl)-aminocarbonyl-$C_{1-3}$-alkyl, 4-($C_{1-3}$-alkyl)-piperazin-1-yl-carbonyl-($C_{1-3}$-alkyl) or tetrazolyl-$C_{1-3}$-alkyl group, by an aminocarbonyl-$C_{2-3}$-alkenyl or $C_{1-4}$-alkoxy-carbonyl-$C_{2-3}$-alkenyl group or by a 5- to 7-membered cycloalkyleneimino groups, wherein one or two methylene groups adjacent to the nitrogen atom may be replaced by a carbonyl group or a —CH$_2$—CH$_2$— group linked to the imino group may be replaced by the group —O—CO—, while the carbonyl group of the —O—CO— group is linked to the imino group, while the substituents may be identical or different, $R^4$ denotes a benzopyrazolyl or 1-($C_{1-3}$-alkyl)-piperidin-4-yl group, a cyclohexyl group which is substituted by a N-[di-($C_{1-3}$-alkyl)-amino-$C_{1-3}$-alkyl-carbonyl]-amino or N-[di-($C_{1-3}$-alkyl)-amino-$C_{1-3}$-alkyl-carbonyl]-N—($C_{1-3}$-alkyl)-amino group, or a phenyl, pyridinyl or naphthyl group or a pyrrolyl group optionally substituted at the nitrogen by a $C_{1-3}$-alkyl group, each of which may be substituted by a fluorine, chlorine, bromine or iodine atom, by a $C_{1-3}$-alkyl, $C_{1-3}$-alkoxy, cyano, nitro, carboxy or trifluoromethyl group, by a ω-[di-($C_{1-3}$-alkyl)-amino]-$C_{2-3}$-alkoxy, $C_{1-3}$-alkylsulphonyl, di-($C_{1-3}$-alkyl)-amino-$C_{1-3}$-alkyl-sulphonyl, 4-($C_{1-3}$-alkyl)-piperazino, imidazolyl, $C_{1-3}$-alkylimidazolyl or [di-($C_{1-3}$-alkyl)-amino]-$C_{1-3}$-alkyl-imidazolyl group, by a $C_{1-3}$-alkyl group which is terminally substituted by a carboxy, $C_{1-3}$-alkoxy-carbonyl, amino, $C_{1-3}$-alkylamino, di-($C_{1-3}$-alkyl)-amino, N—($C_{1-3}$-alkyl)-N-(a)-amino-$C_{2-3}$-alkyl)-amino, N-benzyl-N—($C_{1-3}$-alkyl)-amino, N-[ω-(di-($C_{1-3}$-alkyl)-amino)-$C_{2-3}$-alkyl]-N—($C_{1-3}$-alkyl)-amino, N-[di-($C_{1-3}$-alkyl)-amino-$C_{1-3}$-alkyl]-N—($C_{1-3}$-alkyl)-amino-carbonyl, N-(ω-hydroxy-$C_{2-3}$-alkyl)-N—($C_{1-3}$-alkyl)-amino, di-(ω-hydroxy-$C_{2-3}$-alkyl)-amino, N-(ω-$C_{1-3}$-alkoxy-$C_{2-3}$-alkoxy-$C_{1-3}$-alkyl)-N—($C_{1-3}$-alkyl)-amino, N—($C_{1-4}$-alkoxy-carbonyl)-amino, N—($C_{1-4}$-alkoxy-carbonyl)-N—($C_{1-3}$-alkyl)-amino, N-{ω-[N—($C_{1-4}$-alkoxy-carbonyl)-amino]-($C_{1-3}$-alkyl)}-N—($C_{1-3}$-alkyl)-amino, pyridinyl, triazolyl, pyrrolidino, piperidino, di-($C_{1-3}$-alkyl)-piperidine, [di-($C_{1-3}$-alkyl)-amino]-piperidino, piperazino, morpholino, ($C_{1-3}$-alkyl)-piperazino, 4-($C_{1-3}$-alkyl)-piperazino-carbonyl or 4-($C_{1-4}$-alkoxy-carbonyl)-piperazino group, by a carbonyl group which is substituted by a $C_{1-3}$-alkoxy, N-[di-($C_{1-3}$-alkyl)-amino-$C_{1-3}$-alkyl]-amino, N-[di-($C_{1-3}$-alkyl)-amino-$C_{1-3}$-alkyl]-N—($C_{1-3}$-alkyl)-amino, N—($C_{3-7}$-cycloalkyl)-N—($C_{1-3}$-alkyl)-amino, piperidino, piperazino, 4-($C_{1-4}$-alkyloxy-carbonyl)-piperazino or ($C_{1-3}$-alkyl)-piperazino group, or by a group of formula

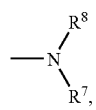

wherein $R^7$ denotes a hydrogen atom, a $C_{1-3}$-alkyl, $C_{1-3}$-alkyl-carbonyl, benzylcarbonyl, pyridinylcarbonyl, furanylcarbonyl, pyrrolidino-$C_{1-3}$-alkyl-carbonyl, $C_{1-3}$-alkoxy-$C_{1-3}$-alkyl-carbonyl, di-($C_{1-3}$-alkyl)-amino-carbonyl-$C_{1-3}$-alkyl, $C_{1-4}$-alkylsulphonyl or benzylsulphonyl group or a phenylcarbonyl group optionally substituted in the phenyl moiety by one or two methoxy groups and $R^8$ denotes a $C_{1-3}$-alkyl, ω-[di-($C_{1-3}$-alkyl)-amino]-$C_{2-3}$-alkyl, di-($C_{1-3}$-alkyl)-amino-carbonyl-$C_{1-3}$-alkyl, di-($C_{1-3}$-alkyl)-amino-$C_{1-3}$-alkyl-amino-carbonyl or ω-[N-benzyl-N—($C_{1-3}$-alkyl)-amino]-$C_{2-3}$-alkyl group or a 4-($C_{1-3}$-alkyl)-piperazin-1-yl-carbonyl, 4-($C_{1-3}$-alkyl)-piperazin-1-yl-aminocarbonyl, 1-($C_{1-3}$-alkyl)-piperidin-4-yl-aminocarbonyl, 1-($C_{1-3}$-alkyl)-piperidin-4-yl-oxy-carbonyl or (pyridinyl-$C_{1-3}$-alkyl)-aminocarbonyl group or a $C_{1-3}$-alkyl-carbonyl group terminally substituted by a hydroxy, amino, di-($C_{1-3}$-alkyl)-amino, di-(ω-hydroxy-$C_{2-3}$-alkyl)-amino, $C_{1-3}$-alkyl-carbonyl-amino, N-benzyl-N—($C_{1-3}$-alkyl)-amino, N-[di-($C_{1-3}$-alkyl)-amino-$C_{1-3}$-alkyl]-N—($C_{1-3}$-alkyl)-amino, imidazolyl, piperazino, 4-($C_{1-3}$-alkyl)-piperazin-1-yl, 4-benzyl-piperazin-1-yl, 4-($C_{1-4}$-alkoxy-carbonyl)-piperazin-1-yl, 4-($C_{1-3}$-alkyl)-homopiperazin-1-yl, morpholino, pyrrolidino, piperidino-, 1-($C_{1-3}$-alkyl)-piperidin-4-yl, 4-($C_{1-3}$-alkyl)-piperidin-1-yl or phthalimido group, $R^5$ denotes a hydrogen atom or a $C_{1-3}$-alkyl group and $R^6$ denotes a hydrogen atom or a nitro group, while the unsubstituted, mono- or disubstituted phenyl groups contained in the above definitions may additionally be substituted by a cyano or a methoxy group or by two methyl groups, and the above mentioned alkyl groups include straight-chain and branched alkyl groups, wherein additionally one to 3 hydrogen atoms may be replaced by fluorine atoms, while, unless otherwise stated, the expression a heteroaryl group refers to a monocyclic 5- or 6-membered heteroaryl group optionally substituted in the carbon skeleton by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two nitrogen atoms, and moreover a phenyl ring may be fused to the above mentioned monocyclic heterocyclic groups via two adjacent carbon atoms and the bonding takes place via a nitrogen atom or via a carbon atom of the heterocyclic moiety or a fused-on phenyl ring, and additionally any carboxy, amino or imino group present may be substituted by a group which can be cleaved in vivo, the tautomers, enantiomers, diastereomers, mixtures thereof and the salts thereof.

Most particularly preferred compounds of the above general formula I are those wherein X denotes an oxygen atom, $R^1$ denotes a hydrogen atom, $R^2$ denotes a fluorine, chlorine or bromine atom or a cyano group, $R^3$ denotes a phenyl group or a phenyl group monosubstituted by a fluorine, chlorine, bromine or iodine atom or by a $C_{1-3}$-alkoxy group, while the above mentioned unsubstituted and monosubstituted phenyl groups may additionally be substituted in the 3 or 4-position by a fluorine, chlorine or bromine atom, by a $C_{1-3}$-alkoxy or $C_{1-2}$-alkyl-carbonyl-amino group, by a carboxy-$C_{1-3}$-alkyl, $C_{1-4}$-alkoxy-carbonyl-$C_{1-3}$-alkyl, aminocarbonyl-$C_{1-3}$-alkyl, ($C_{1-2}$-alkylamino)-carbonyl-$C_{1-3}$-alkyl, di-($C_{1-2}$-alkyl)-amino-carbonyl-$C_{1-3}$- alkyl, ($C_{1-2}$-alkyl-carbonyl)-amino-$C_{1-3}$-alkyl or (phenyl-carbonyl)-amino-$C_{1-3}$-alkyl group, while the substituents may be identical or different, $R^4$ denotes a phenyl group which is substituted by a $C_{1-3}$-alkyl group terminally substituted by a di-($C_{1-2}$-alkyl)-amino group or by a group of formula

wherein $R^7$ denotes a $C_{1-2}$-alkyl, $C_{1-2}$-alkyl-carbonyl, di-($C_{1-2}$-alkyl)-amino-carbonyl-$C_{1-3}$-alkyl or $C_{1-3}$-alkylsulphonyl group and $R^8$ denotes a $C_{1-3}$-alkyl or ω-[di-($C_{1-2}$-alkyl)-amino]-$C_{2-3}$-alkyl group or a $C_{1-3}$-alkyl-carbonyl group terminally substituted by a di-($C_{1-2}$-alkyl)-amino, piperazino or 4-($C_{1-3}$-alkyl)-piperazin-1-yl group, $R^5$ denotes a hydrogen atom and $R^6$ denotes a hydrogen atom, while the above mentioned alkyl groups include straight-chain and branched alkyl groups, wherein additionally one to 3 hydrogen atoms may be replaced by fluorine atoms, while additionally any carboxy, amino or imino group present may be substituted by a group which can be cleaved in vivo, the tautomers, enantiomers, diastereomers, mixtures thereof and the salts thereof.

A first sub-group of most particularly preferred compounds of general formula I deserving special mention comprises those wherein $X, R^1, R^2, R^3, R^5$ and $R^6$ are as hereinbefore defined and $R^4$ denotes a phenyl group which is substituted by a group of formula

wherein $R^7$ denotes a $C_{1-2}$-alkyl, $C_{1-2}$-alkyl-carbonyl, di-($C_{1-2}$-alkyl)-amino-carbonyl-$C_{1-3}$-alkyl or $C_{1-3}$-alkylsulphonyl group and $R^8$ denotes a $C_{1-3}$-alkyl or ω-[di-($C_{1-2}$-alkyl)-amino]-$C_{2-3}$-alkyl group or a $C_{1-3}$-alkyl-carbonyl group terminally substituted by a di-($C_{1-2}$-alkyl)-amino, piperazino or 4-($C_{1-3}$-alkyl)-piperazin-1-yl group, the above mentioned alkyl groups including straight-chain and branched alkyl groups, wherein additionally one to 3 hydrogen atoms may be replaced by fluorine atoms, while additionally any carboxy, amino or imino group present may be substituted by a group which can be cleaved in vivo, the tautomers, enantiomers, diastereomers, mixtures thereof and the salts thereof.

A second sub-group of particularly preferred compounds of general formula I deserving special mention comprises those wherein $X, R^1, R^2, R^4, R^5$ and $R^6$ are as hereinbefore defined and $R^3$ denotes a phenyl group or a phenyl group monosubstituted by a fluorine, chlorine or bromine atom or by a $C_{1-3}$-alkoxy group, while the above mentioned unsubstituted and monosubstituted phenyl groups are additionally substituted in the 3- or 4-position by a fluorine, chlorine or bromine atom, by a $C_{1-3}$-alkoxy or $C_{1-2}$-alkyl-carbonyl-amino group or by a carboxy-$C_{1-3}$-alkyl, $C_{1-4}$-alkoxy-carbonyl-$C_{1-3}$-alkyl, aminocarbonyl-$C_{1-3}$-alkyl, ($C_{1-2}$-alkylamino)-carbonyl-$C_{1-3}$-alkyl, di-($C_{1-2}$-alkyl)-amino-carbonyl-$C_{1-3}$-alkyl, ($C_{1-2}$-alkyl-carbonyl)-amino-$C_{1-3}$-alkyl or (phenyl-carbonyl)-amino-$C_{1-3}$-alkyl group, while the substituents may be identical or different, the above mentioned alkyl groups including straight-chain and branched alkyl groups, wherein additionally one to 3 hydrogen atoms may be replaced by fluorine atoms, while additionally any carboxy, amino or imino group present may be substituted by a group which can be cleaved in vivo, the tautomers, enantiomers, diastereomers, mixtures thereof and the salts thereof.

A second sub-group of compounds of general formula I deserving particular mention comprises those wherein X denotes an oxygen atom, $R^1$ denotes a hydrogen atom, $R^2$ denotes a bromine atom, $R^3$ denotes a phenyl group, $R^4$ denotes a 1-($C_{1-3}$-alkyl)-piperidin-4-yl group or a phenyl group which is substituted in the 4-position by a $C_{1-3}$-alkyl group terminally substituted by a $C_{1-3}$-alkylamino, di-($C_{1-3}$-alkyl)-amino, N-[ω-(di-($C_{1-3}$-alkyl)-amino)-$C_{2-3}$-alkyl]-N—($C_{1-3}$-alkyl)-amino or N—($C_{1-4}$-alkyloxy-carbonyl)-N—($C_{1-3}$-alkyl)-amino group, by a 1-($C_{1-3}$-alkyl)-imidazol-2-yl or 4-($C_{1-3}$-alkyl)-piperazin-1-yl-carbonyl group or by a group of formula

wherein $R^7$ denotes a $C_{1-3}$-alkyl, $C_{1-3}$-alkyl-carbonyl, $C_{1-3}$-alkyl-sulphonyl or benzylsulphonyl group and $R^8$ denotes a ω-[di-($C_{1-3}$-alkyl)-amino]-$C_{2-3}$-alkyl, ω-[di-($C_{1-3}$-alkyl)-amino]-$C_{1-4}$-alkyl-carbonyl, ω-[4-($C_{1-3}$-alkyl)-piperazin-1-yl]-$C_{1-3}$-alkyl-carbonyl or ω-{N-[di-($C_{1-3}$-alkyl)-amino-$C_{2-3}$-alkyl]-N—$C_{1-3}$-alkyl)-amino}-$C_{1-3}$-alkyl-carbonyl group, $R^5$ denotes a hydrogen atom and $R^6$ denotes a hydrogen atom, the above mentioned alkyl groups including straight-chain and branched alkyl groups, wherein additionally one to 3 hydrogen atoms may be replaced by fluorine atoms, the tautomers, enantiomers, diastereomers, mixtures thereof and the salts thereof.

A third sub-group of compounds of general formula I deserving particular mention comprises those wherein X denotes an oxygen atom, $R^1$ denotes a hydrogen atom, $R^2$ denotes a fluorine atom, $R^3$ denotes a phenyl group which is optionally substituted in the 3- or 4-position by a fluorine or iodine atom or by a cyano-$C_{1-3}$-alkyl, amino-$C_{1-3}$-alkyl, $C_{1-3}$-alkylamino-$C_{1-3}$-alkyl, $C_{1-5}$-alkyl-carbonylamino-$C_{1-3}$-alkyl, $C_{1-4}$-alkyloxy-carbonyl-amino-$C_{1-3}$-alkyl, $C_{1-4}$-alkyloxy-$C_{1-3}$-alkyl-carbonyl-amino-$C_{1-3}$-alkyl, $C_{3-7}$-cycloalkyl-carbonyl-amino-$C_{1-3}$-alkyl, $C_{3-7}$-cycloalkyl-$C_{1-3}$-alkyl-carbonyl-amino-$C_{1-3}$-alkyl, N-(phenyl-carbonyl)-amino-$C_{1-3}$-alkyl, N-(benzyl-carbonyl)-amino-$C_{1-3}$-alkyl, heteroaryl-carbonyl-amino-$C_{1-3}$-alkyl, N—($C_{1-3}$-alkylsulphonyl)-amino-$C_{1-3}$-alkyl, N-(phenylsulphonyl)-amino-$C_{1-3}$-alkyl, N-(benzylsulphonyl)-amino-$C_{1-3}$-alkyl, carboxy-$C_{1-3}$-alkyl, $C_{1-4}$-alkoxy-carbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, 4-($C_{1-3}$-alkyl)-piperazin-1-yl-carbonyl-$C_{1-3}$-alkyl, 2-(aminocarbonyl)-$C_{2-3}$-alkenyl or 2-($C_{1-3}$-alkyloxy-carbonyl)-$C_{2-3}$-alkenyl group, or a phenyl group trisubstituted in the 3-, 4- and 5-position by fluorine atoms, $R^4$ denotes a phenyl group which may be substituted in the 4-position by a $C_{1-3}$-alkyl group terminally substituted by a pyrrolidin-1-yl, piperidin-1-yl, 4-($C_{1-3}$-alkyl)-piperazin-1-yl, $C_{1-3}$-alkylamino, di-($C_{1-3}$-alkyl)-amino, N-[di-($C_{1-3}$-alkyl)-amino-$C_{2-3}$-alkyl]-N—($C_{1-3}$-alkyl)-amino or N—($C_{1-4}$-alkyloxy-carbonyl)-N—($C_{1-3}$-alkyl)-amino group, by a $C_{1-3}$-alkyl-sulphonyl, 1-($C_{1-3}$-alkyl)-imidazol-2-yl or 4-($C_{1-3}$-alkyl)-piperazin-1-yl-carbonyl group or by a group of formula

wherein $R^7$ denotes a $C_{1-3}$-alkyl, $C_{1-3}$-alkyl-carbonyl, $C_{1-3}$-alkyl-sulphonyl or benzylsulphonyl group and $R^8$ denotes a $C_{1-3}$-alkyl, ω-[di-($C_{1-3}$-alkyl)-amino]-$C_{2-3}$-alkyl, ω-[di-($C_{1-3}$-alkyl)-amino]-$C_{1-3}$-alkyl-carbonyl, di-($C_{1-3}$-alkyl)-amino-carbonyl-$C_{1-3}$-alkyl, ω-[4-($C_{1-3}$-alkyl)-piperazin-1-yl]-$C_{1-3}$-alkyl-carbonyl or ω-{N-[di-($C_{1-3}$-alkyl)-amino-$C_{2-3}$-alkyl]-N—($C_{1-3}$-alkyl)-amino}-$C_{1-3}$-alkyl-carbonyl group, $R^5$ denotes a hydrogen atom and $R^6$ denotes a hydrogen atom, while the term heteroaryl group denotes a pyridinyl, furyl or thienyl group, while unsubstituted or monosubstituted phenyl groups contained in the above mentioned definitions may additionally be substituted by a methoxy group, the above mentioned alkyl groups include straight-chain and branched alkyl groups, wherein additionally one to 3 hydrogen atoms may be replaced by fluorine atoms, and any carboxy, amino or imino group present may be substituted by a group which can be cleaved in vivo, the tautomers, enantiomers, diastereomers, mixtures thereof and the salts thereof.

A fourth sub-group of compounds of general formula I deserving particular mention comprises those wherein X denotes an oxygen atom, $R^1$ denotes a hydrogen atom, $R^2$ denotes a cyano group, $R^3$ denotes a phenyl group optionally substituted by one or two methoxy groups, $R^4$ denotes a phenyl group which is substituted in the 3- or 4-position by a bromine atom, by a $C_{1-3}$-alkyl group terminally substituted by a pyrrolidin-1-yl, piperidin-1-yl, 4-($C_{1-3}$-alkyl)-piperazin-1-yl-carbonyl, $C_{1-3}$-alkylamino, di-($C_{1-3}$-alkyl)-amino, N-[di-($C_{1-3}$-alkyl)-amino-$C_{1-3}$-alkyl]-N—($C_{1-3}$-alkyl)-aminocarbonyl or N—($C_{1-4}$-alkyloxy-carbonyl)-N—($C_{1-3}$-alkyl)-amino group, by a ω-di-($C_{1-3}$-alkyl)-amino-$C_{2-3}$-alkoxy, N-(di-($C_{1-3}$-alkyl)-amino-$C_{2-3}$-alkyl)-amino-carbonyl, N-[di-($C_{1-3}$-alkyl)-amino-$C_{2-3}$-alkyl]-N—($C_{1-3}$-alkyl)-amino-carbonyl or 4-($C_{1-3}$-alkyl)-piperazin-1-yl-carbonyl group or by a group of formula

wherein $R^7$ denotes a hydrogen atom or a $C_{1-3}$-alkyl, $C_{1-3}$-alkyl-carbonyl or $C_{1-3}$-alkylsulphonyl group and $R^8$ denotes a ω-[di-($C_{1-3}$-alkyl)-amino]-($C_{2-3}$-alkyl), ω-[di-($C_{1-3}$-alkyl)-amino]-$C_{1-3}$-alkyl-carbonyl, ω-(piperazin-1-yl)-$C_{1-3}$-alkyl-carbonyl, ω-[4-($C_{1-3}$-alkyl)-piperazin-1-yl]-$C_{1-3}$-alkyl-carbonyl, ω-[4-($C_{1-4}$-alkyloxy-carbonyl)-piperazin-1-yl]-$C_{1-3}$-alkyl-carbonyl, ω-[4-($C_{1-3}$-alkyl)-homopiperazin-1-yl]-$C_{1-3}$-alkyl-carbonyl ω-morpholino-$C_{1-3}$-alkyl-carbonyl or ω-{N-[di-($C_{1-3}$-alkyl)-amino-$C_{1-3}$-alkyl]-N—($C_{1-3}$-alkyl)-amino}-$C_{1-3}$-alkyl-carbonyl group, $R^5$ denotes a hydrogen atom and $R^6$ denotes a hydrogen atom, while the above mentioned alkyl groups include straight-chain and branched alkyl groups, wherein additionally one to 3 hydrogen atoms may be replaced by fluorine atoms, and additionally any carboxy, amino or imino group present may be substituted by a group which can be cleaved in vivo, their stereoisomers and their salts.

A fifth sub-group of compounds of general formula I deserving particular mention comprises those wherein X denotes an oxygen or sulphur atom, $R^1$ denotes a hydrogen atom, $R^2$ denotes a chlorine atom, $R^3$ denotes a phenyl group which is optionally monosubstituted in the 3- or 4-position by a chlorine or iodine atom, by a cyano, hydroxy, benzyloxy, amino or nitro group or by an aminomethyl, acetylamino, phenylcarbonylamino-$C_{1-3}$-alkyl, $C_{1-3}$-alkylsulphonylamino-$C_{1-3}$-alkyl, phenylsulphonylamino-$C_{1-3}$-alkyl, acetylaminomethyl, imidazol-1-yl-methyl, 2-oxo-pyrrolidin-1-yl, 2-carboxy-ethyl, 2-methoxycarbonyl-ethyl, 2-aminocarbonyl-ethyl, 2-(methylaminocarbonyl)-ethyl or 2-methoxycarbonyl-ethenyl group, or a 3-hydroxy-4-nitro-phenyl, 4-amino-3-nitrophenyl or 3,4-dimethoxyphenyl group, $R^4$ denotes a 5-(4-methyl-piperazin-1-yl-carbonyl)-pyridin-2-yl, 2-[N-acetyl-N-(ω-dimethylamino-$C_{2-3}$-alkyl)- amino]-pyridin-5-yl, benzo-pyrazol-6-yl, 1-methyl-2-(4-methyl-piperazin-1-yl-carbonyl)-pyrrol-4-yl, 2-(N-dimethylamino-ethyl-N-methyl-aminocarbonyl)-pyrrol-4-yl, 1-methyl-2-(N-dimethylamino-ethyl-N-methyl-aminocarbonyl)-pyrrol-4-yl, 4-(N-dimethylamino-methylcarbonylamino)-cyclohexyl or 4-[(N-dimethylamino-methylcarbonyl)-N-methyl-amino]cyclohexyl group or a phenyl group which is substituted in the 3-position by a carboxy, carboxy-$C_{1-3}$-alkyl, $C_{1-4}$-alkoxy-carbonyl, $C_{1-4}$-alkoxy-carbonyl-$C_{1-3}$-alkyl, dimethylamino-$C_{1-3}$-alkyl or pyridin-4-yl-$C_{1-3}$-alkyl group or is substituted in the 4-position by a carboxy, ω-[di-($C_{1-3}$-alkyl)-amino]-$C_{2-3}$-alkoxy, ethoxycarbonyl, piperidin-1-yl-carbonyl, 4-($C_{1-4}$-alkyloxy-carbonyl)-piperazin-1-yl-carbonyl, N—($C_{3-7}$-cycloalkyl)-N—($C_{1-3}$-alkyl)-amino-carbonyl or N-[di-($C_{1-3}$-alkyl)-amino-$C_{1-3}$-alkyl]-N—($C_{1-3}$-alkyl)-aminocarbonyl group, by a [di-($C_{1-3}$-alkyl)-amino]-$C_{1-3}$-alkylsulphonyl group, by a $C_{1-3}$-alkyl group terminally substituted by a carboxy, $C_{1-4}$-alkyloxy-carbonyl, amino, $C_{1-3}$-alkylamino, di-($C_{1-3}$-alkyl)-amino, N-benzyl-N—$C_{1-3}$-alkyl)-amino, N-(2-hydroxyethyl)-N—($C_{1-3}$-alkyl)-amino, Di-(2-hydroxyethyl)-amino, triazolyl, N-(methoxyethoxyethyl)-N—($C_{1-3}$-alkyl)-amino, N-(amino-$C_{1-3}$-alkyl)-N—($C_{1-3}$-alkyl)-amino, N-[di-($C_{1-3}$-alkyl)-amino-$C_{1-3}$-alkyl]-N—($C_{1-3}$-alkyl)-amino, N-[di-($C_{1-3}$-alkyl)-amino-$C_{1-3}$-alkyl]-N—($C_{1-3}$-alkyl)-amino-carbonyl, N—($C_{1-4}$-alkyloxy-carbonyl-amino-$C_{1-3}$-alkyl)-N—($C_{1-3}$-alkyl)-amino, N—($C_{1-4}$-alkyloxy-carbonyl)-amino or N—$C_{1-4}$-alkyloxy-carbonyl)-N—($C_{1-3}$-alkyl)-amino group, by a 1-methyl-imidazol-2-yl, 5-methyl-1H-imidazol-4-yl, 1-[di-($C_{1-3}$-alkyl)-amino-$C_{1-3}$-alkyl]-imidazol-2-yl, 4-methyl-piperazin-1-yl, piperazinylcarbonyl or 4-methyl-piperazin-1-yl-carbonyl group or by a group of formula

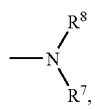

wherein $R^7$ denotes a hydrogen atom or a $C_{1-3}$-alkyl, $C_{1-3}$-alkylcarbonyl, di-($C_{1-3}$-alkyl)-amino-carbonyl-$C_{1-3}$-alkyl, benzylcarbonyl, pyridinylcarbonyl, furanylcarbonyl, methoxymethylcarbonyl, $C_{1-4}$-alkylsulphonyl or benzylsulphonyl group or a phenylcarbonyl group optionally substituted in the phenyl moiety by one or two methoxy groups and $R^8$ denotes a $C_{1-3}$-alkyl, ω-[di-($C_{1-3}$-alkyl)-amino]-$C_{2-3}$-alkyl, ω-[N-benzyl-N—$C_{1-3}$-alkyl)-amino]-$C_{2-3}$-alkyl, N-[di-($C_{1-3}$-alkyl)-amino-$C_{1-3}$-alkyl]-amino-carbonyl, (pyridinyl-$C_{1-3}$-alkyl)-amino-carbonyl, 1-($C_{1-3}$-alkyl)-piperidin-4-yl-amino-carbonyl-, 1-($C_{1-3}$-alkyl)-piperidin-4-yl-oxy-carbonyl, 4-($C_{1-3}$-alkyl)-piperazin-1-yl-amino-carbonyl, 4-($C_{1-3}$-alkyl)-piperazin-1-yl-carbonyl or di-($C_{1-3}$-alkyl)-aminocarbonyl-$C_{1-3}$-alkyl group or a $C_{1-4}$-alkyl-carbonyl group terminally substituted by a hydroxy, amino, di-($C_{1-3}$-alkyl)-amino, N-benzyl-N—($C_{1-3}$-alkyl)-amino, di-(2-hydroxyethyl)-amino, acetylamino, N-[di-($C_{1-3}$-alkyl)-amino-$C_{1-3}$-alkyl]-N—($C_{1-3}$-alkyl)-amino, imidazol-1-yl, piperazin-1-yl, 4-($C_{1-3}$-alkyl)-piperazin-1-yl, 4-benzyl-piperazin-1-yl, 4-($C_{1-4}$-alkyloxy-carbonyl)-piperazin-1-yl, 4-($C_{1-3}$-alkyl)-homopiperazin-1-yl, morpholin-4-yl, pyrrolidin-1-yl, piperidin-1-yl, 1-($C_{1-3}$-alkyl)-piperidin-4-yl or phthalimido group, $R^5$ denotes a hydrogen atom and $R^6$ denotes a hydrogen atom or a nitro group, while the unsubstituted or monosubstituted phenyl groups mentioned in the above definitions may additionally be substituted by a methoxy or a cyano group or by two methyl groups, the above mentioned alkyl groups including straight-chain and branched alkyl groups, wherein additionally one to 3 hydrogen atoms may be replaced by fluorine atoms, and additionally any carboxy, amino or imino group present may be substituted by a group which can be cleaved in vivo, the tautomers, enantiomers, diastereomers, mixtures thereof and the salts thereof.

Additional sub-groups of compounds of general formula I, of preferred, particularly preferred and most particularly preferred compounds of formula I and the sub-groups thereof which deserve special mention are those wherein X, $R^1$, $R^3$, $R^4$, $R^5$ and $R^6$ are each as hereinbefore defined and $R^2$ denotes fluorine.

Additional sub-groups of compounds of general formula I, of preferred, particularly preferred and most particularly preferred compounds of formula I and the sub-groups thereof which deserve special mention are those wherein X, $R^1$, $R^3$, $R^4$, $R^5$ and $R^6$ are each as hereinbefore defined and $R^2$ denotes chlorine.

Additional sub-groups of compounds of general formula I, of preferred, particularly preferred and most particularly preferred compounds of formula I and the sub-groups thereof which deserve special mention are those wherein X, $R^1$, $R^3$, $R^4$, $R^5$ and $R^6$ are each as hereinbefore defined and $R^2$ denotes bromine.

Additional sub-groups of compounds of general formula I, of preferred, particularly preferred and most particularly preferred compounds of formula I and the sub-groups thereof which deserve special mention are those wherein X, $R^1$, $R^3$, $R^4$, $R^5$ and $R^6$ are each as hereinbefore defined and $R^2$ denotes cyano.

The following compounds of general formula I are particularly preferred:

(a) 3-Z-[1-(4-(N-(2-dimethylamino-ethyl)-N-methylsulphonyl-amino)-anilino)-1-phenyl-methylene]-6-chloro-2-indolinone, (b) 3-Z-[1-(4-(N-(4-methyl-piperazin-1-yl-methylcarbonyl)-N-methyl-amino)-anilino)-1-phenyl-methylene]-6-chloro-2-indolinone, (c) 3-Z-[1-(4-(N-(3-dimethylamino-propyl)-N-acetyl-amino)-anilino)-1-phenyl-methylene]-6-chloro-2-indolinone, (d) 3-Z-[1-(4-(N-(4-ethyl-piperazin-1-yl-methylcarbonyl)-N-methyl-amino)-anilino)-1-phenyl-methylene]-6-chloro-2-indolinone, (e) 3-Z-[1-(4-(N-(2-dimethylamino-ethyl)-N-acetyl-amino)-anilino)-1-(3,4-dimethoxy-phenyl)-methylene]-6-chloro-2-indolinone, (f) 3-Z-[1-(4-(N-(4-methyl-piperazin-1-yl-methylcarbonyl)-N-methyl-amino)-anilino)-1-(3,4-dimethoxy-phenyl)-methylene]-6-chloro-2-indolinone, (g) 3-Z-[1-(4-(N-(3-dimethylamino-propyl)-N-acetyl-amino)-anilino)-1-phenyl-methylene]-6-bromo-2-indolinone, (h) 3-Z-[1-(4-(N-(4-methyl-piperazin-1-yl-methylcarbonyl)-N-methyl-amino)-anilino)-1-phenyl-methylene]-6-bromo-2-indolinone,
(i) 3-Z-[1-(4-(N-(3-dimethylamino-propyl)-N-acetyl-amino)-anilino)-1-phenyl-methylene]-6-cyano-2-indolinone,
(j) 3-Z-[1-(4-(N-(4-methyl-piperazin-1-yl-methylcarbonyl)-N-methyl-amino)-anilino)-1-phenyl-methylene]-6-cyano-2-indolinone,
(k) 3-Z-[1-(4-(N-(4-ethyl-piperazin-1-yl-methylcarbonyl)-N-methyl-amino)-anilino)-1-phenyl-methylene]-6-cyano-2-indolinone,
(l) 3-Z-[1-(4-(N-(dimethylamino-methylcarbonyl)-N-methyl-amino)-anilino)-1-phenyl-methylene]-6-fluoro-2-indolinone,
(m) 3-Z-[1-(4-(N-(2-dimethylamino-ethyl)-N-acetyl-amino)-anilino)-1-phenyl-methylene]-6-fluoro-2-indolinone,
(n) 3-Z-[1-(4-(N-(4-methyl-piperazin-1-yl-methylcarbonyl)-N-methyl-amino)-anilino)-1-phenyl-methylene]-6-fluoro-2-indolinone,
(o) 3-Z-[1-(4-(dimethylaminomethyl)-anilino)-1-(3-fluoro-phenyl)-methylene]-6-fluoro-2-indolinone,
(p) 3-Z-[1-(4-(N-(3-dimethylamino-propyl)-N-acetyl-amino)-anilino)-1-(3-fluoro-phenyl)-methylene]-6-fluoro-2-indolinone,
(q) 3-Z-[1-(4-(N-(4-methyl-piperazin-1-yl-methylcarbonyl)-N-methyl-amino)-anilino)-1-(3-fluoro-phenyl)-methylene]-6-fluoro-2-indolinone,
(r) 3-Z-[1-(4-dimethylaminomethyl-anilino)-1-(4-(2-carbamoyl-ethyl)-phenyl)-methylene]-6-fluoro-2-indolinone,
(s) 3-Z-[1-(4-(N-(piperazin-1-yl-methylcarbonyl)-N-methyl-amino)-anilino)-1-phenyl-methylene]-6-chloro-2-indolinone,
(t) 3-Z-[1-(4-dimethylaminomethyl-anilino)-1-(3-(2-carboxy-ethyl)-phenyl)-methylene]-6-chloro-2-indolinone,
(u) 3-Z-[1-(4-dimethylaminomethyl-anilino)-1-(4-(2-carboxy-ethyl)-phenyl)-methylene]-6-fluoro-2-indolinone,
(v) 3-Z-[1-(4-dimethylaminomethyl-anilino)-1-(3-(2-carboxy-ethyl)-phenyl)-methylene]-6-fluoro-2-indolinone,
(w) 3-Z-[1-(4-(N-(4-methyl-piperazin-1-yl-methylcarbonyl)-N-methyl-amino)-anilino)-1-(4-carboxymethyl-phenyl)-methylene]-6-fluoro-2-indolinone,
(x) 3-Z-[1-(4-dimethylaminomethyl-anilino)-1-(4-(2-methylcarbamoyl-ethyl)-phenyl)-methylene]-6-fluoro-2-indolinone,
(y) 3-Z-[1-(4-dimethylaminomethyl-anilino)-1-(3-(2-carbamoyl-ethyl)-phenyl)-methylene]-6-fluoro-2-indolinone,
(z) 3-Z-[1-(4-dimethylaminomethyl-anilino)-1-(3-(2-dimethylcarbamoyl-ethyl)-phenyl)-methylene]-6-fluoro-2-indolinone,
(aa) 3-Z-[1-(4-(N-(2-dimethylamino-ethyl)-N-methylsulphonyl-amino)-anilino)-1-(4-dimethylcarbamoylmethyl-phenyl)-methylene]-6-fluoro-2-indolinone,
(ab) 3-Z-[1-(4-(N-methyl-N-acetyl-amino)-anilino)-1-(4-(2-methylcarbamoyl-ethyl)-phenyl)-methylene]-6-fluoro-2-indolinone,
(ac) 3-Z-[1-(4-(N-(4-methyl-piperazin-1-yl-methylcarbonyl)-N-methyl-amino)-anilino)-1-(4-acetylamino-phenyl)-methylene]-6-chloro-2-indolinone,
(ad) 3-Z-[1-(4-dimethylaminomethyl-anilino)-1-(4-acetylaminomethyl-phenyl)-methylene]-6-chloro-2-indolinone,
(ae) 3-Z-[1-(4-dimethylaminomethyl-anilino)-1-(3-acetylaminomethyl-phenyl)-methylene]-6-fluoro-2-indolinone,
(af) 3-Z-[1-(4-dimethylaminomethyl-anilino)-1-(3-benzoylaminomethyl-phenyl)-methylene]-6-fluoro-2-indolinone
(ag) 3-Z-[1-(4-dimethylaminomethyl-anilino)-1-(3-(2-acetylamino-ethyl)-phenyl)-methylene]-6-fluoro-2-indolinone
(ah) 3-Z-[1-(4-(N-(2-dimethylamino-ethylcarbonyl)-N-methyl-amino)-anilino)-1-(4-(2-carboxy-ethyl)-phenyl)-methylene]-6-fluoro-2-indolinone,
(ai) 3-Z-[1-(4-(pyrrolidin-1-yl-methyl)-anilino)-1-(4-(2-carboxy-ethyl)-phenyl)-methylene]-6-fluoro-2-indolinone and
(aj) 3-Z-[1-(4-dimethylaminomethyl-anilino)-1-(4-(2-carboxy-ethyl)-phenyl)-methylene]-6-chloro-2-indolinone
(ak) 3-Z-[1-(4-diethylaminomethyl-anilino)-1-(4-(2-carboxy-ethyl)-phenyl)-methylene]-6-fluoro-2-indolinone
(al) 3-Z-[1-(4-(2-dimethylamino-ethyl)-anilino)-1-(4-(2-carboxy-ethyl)-phenyl)-methylene]-6-chloro-2-indolinone
(am) 3-Z-[1-(4-(pyrrolidin-1-yl-methyl)-anilino)-1-(4-(2-carboxy-ethyl)-phenyl)-methylene]-6-chloro-2-indolinone
(an) 3-Z-[1-(4-(pyrrolidin-1-yl-methyl)-anilino)-1-(4-(2-carboxy-ethyl)-phenyl)-methylene]-6-bromo-2-indolinone
(ap) 3-Z-[1-(4-(dimethylaminomethyl)-anilino)-1-(4-(2-carboxy-ethyl)-phenyl)-methylene]-6-bromo-2-indolinone
(ao) 3-Z-[1-(4-(diethylaminomethyl)-anilino)-1-(4-(2-carboxy-ethyl)-methylene]-6-bromo-2-indolinone while additionally any carboxy, amino or imino group present may be substituted by a group which can be cleaved in vivo, and the salts thereof.

According to the invention the new compounds may be obtained for example by the following methods known in principle from the literature:

a. reacting a compound of general formula

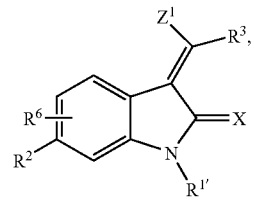

(V)

wherein the groups $Z^1$ and $R^3$ may optionally change positions, $X$, $R^2$, $R^3$ and $R^6$ are as hereinbefore defined, $R^{1'}$ has the meanings given for $R^1$ hereinbefore or denotes a protective group for the nitrogen atom of the lactam group, while $R^1$ may also denote a bond to a solid phase, optionally via a spacer, and $Z^1$ denotes a halogen atom, a hydroxy, alkoxy or arylalkoxy group, e.g. a chlorine or bromine atom, a methoxy, ethoxy or benzyloxy group, with an amine of general formula

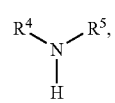

(VI)

wherein $R^4$ and $R^5$ are as hereinbefore defined, and if necessary subsequently cleaving any protective group used for the nitrogen atom of the lactam group or from a solid phase.

The protective group for the nitrogen atom of the lactam group may be for example an acetyl, benzoyl, ethoxycarbonyl, tert.butyloxycarbonyl or benzyloxycarbonyl group and the solid phase may be a resin such as a 4-(2',4'-dimethoxyphenylamino-methyl)-phenoxy resin, while the bond is conveniently made via the amino group, or a p-benzyloxybenzylalcohol resin, while the bond is conveniently made via an intermediate member such as a 2,5-dimethoxy-4-hydroxybenzyl derivative.

The reaction is expediently carried out in a solvent such as dimethylformamide, toluene, acetonitrile, tetrahydrofuran, dimethylsulphoxide, methylene chloride or mixtures thereof, optionally in the presence of an inert base such as triethylamine, N-ethyl-diisopropylamine or sodium hydrogen carbonate at temperatures between 20 and 175° C., while any protective group used may simultaneously be cleaved as a result of transamidation.

If $Z^1$ in a compound of general formula V denotes a halogen atom, then the reaction is preferably carried out in the presence of an inert base at temperatures between 20 and 120° C.

If $Z^1$ in a compound of general formula V denotes a hydroxy, alkoxy or arylalkoxy group, then the reaction is preferably carried out at temperatures between 20 and 200° C.

Any protective group used is optionally subsequently conveniently cleaved either by hydrolysis in an aqueous or alcoholic solvent, e.g. in methanol/water, ethanol/water, isopropanol/water, tetrahydrofuran/water, dioxane/water, dimethylformamide/water, methanol or ethanol in the presence of an alkali metal base such as lithium hydroxide, sodium hydroxide or potassium hydroxide at temperatures between 0 and 100° C., preferably at temperatures between 10 and 50° C., or advantageously by transamidation with an organic base such as ammonia, butylamine, dimethylamine or piperidine in a solvent such as methanol, ethanol, dimethylformamide and mixtures thereof or in an excess of the amine used at temperatures between 0 and 100° C., preferably at temperatures between 10 and 50° C.

The cleaving of any solid phase used is preferably carried out using trifluoroacetic acid and water at temperatures between 0 and 35° C., preferably at ambient temperature.

b. In order to prepare a compound of general formula I wherein $R^4$ contains the group $R^8$, where $R^8$ denotes a $C_{1-4}$-alkyl-carbonyl group terminally substituted by a hydroxy, $C_{1-3}$-alkyoxyl group, amino, ($C_{1-3}$-alkyl)-amino, di-($C_{1-3}$-alkyl)-amino, (ω-hydroxy-$C_{2-3}$-alkyl)-amino, di-(ω-hydroxy-$C_{2-3}$-alkyl)-amino, (ω-alkoxy-$C_{2-3}$-alkyl)-amino, di-(ω-alkoxy-$C_{2-3}$-alkyl)-amino, $C_{1-3}$-alkyl-carbonyl-amino, N-benzyl-N—$C_{1-3}$-alkyl-amino, N-[di-($C_{1-3}$-alkyl)-amino-$C_{1-3}$-alkyl]-N—$C_{1-3}$-alkyl-amino, 1-($C_{1-3}$-alkyl)-piperidin-4-yl- group or by a 5- to 7-membered cycloalkyleneimino group, while the cycloalkylene group may be substituted by a $C_{1-3}$-alkyl group and/or one or two methylene groups linked to the imino group may be replaced by a carbonyl group and/or the methylene group in the 4 position of a 6- or 7-membered cycloalkylimino group may be replaced by a —NH—, —N($C_{1-3}$-alkyl)-, —N(benzyl)-, —N($C_{1-4}$-alkoxy-carbonyl)- or —O— and/or a phenyl ring may be fused on via two adjacent carbon atoms of the cycloalkyleneimino group:

reacting a compound of general formula

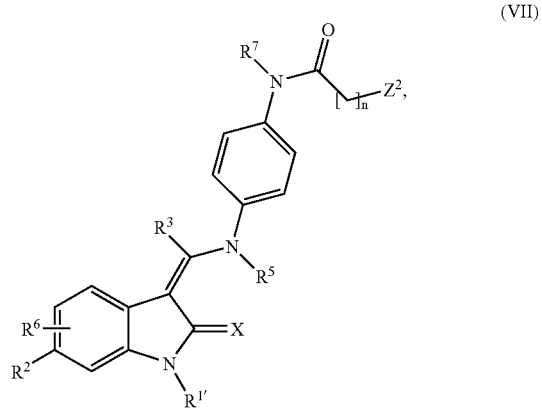

(VII)

wherein $R^2$, $R^3$, $R^5$, $R^6$, $R^7$ and X are as hereinbefore defined, $R^{1'}$ has the meanings given for $R^1$ hereinbefore or denotes a protective group for the nitrogen atom of the lactam group, while $R^{1'}$ may also denote a bond to a solid phase optionally formed via a spacer, n denotes the number 1, 2, 3 or 4 and $Z^2$ denotes a leaving group, for example a halogen atom or an alkyl or arylsulphonyloxy group such as the chlorine, bromine or iodine atom or the methylsulphonyloxy, ethylsulphonyloxy, p-toluenesulphonyloxy, or trifluoromethanesulphonyloxy group, with a hydroxide base such as sodium or potassium hydroxide or a compound of general formula

H—$R^{8'}$         (VIII), wherein $R^{8'}$ denotes a $C_{1-3}$-alkyloxy, amino, ($C_{1-3}$-alkyl)-amino, di-($C_{1-3}$-alkyl)-amino, (ω-hydroxy-$C_{2-3}$-alkyl)-amino, di-(ω-hydroxy-$C_{2-3}$-alkyl)-amino, (ω-alkoxy-$C_{2-3}$-alkyl)-amino, di-(ω-alkoxy-$C_{2-3}$-alkyl)-amino, $C_{1-3}$-alkyl-carbonyl-amino, N-benzyl-N—$C_{1-3}$-alkyl-amino, N-[di-($C_{1-3}$-alkyl)-amino-$C_{1-3}$-alkyl]-N—$C_{1-3}$-alkyl-amino or a 5- to 7-membered cycloalkyleneimino group, while the cycloalkylene group may be substituted by a $C_{1-3}$-alkyl group and/or one or two methylene groups linked to the imino group may be replaced by a carbonyl group and/or the methylene group in the 4 position of a 6- or 7-membered cycloalkylimino group may be replaced by a —NH—, —N($C_{1-3}$-alkyl), —N(benzyl), —N($C_{1-4}$-alkoxy-carbonyl) or —O— and/or a phenyl ring may be fused on via two adjacent carbon atoms of the cycloalkyleneimino group, and if necessary subsequently cleaving any protective group used for the nitrogen atom of the lactam group or from a solid phase.

The reaction is expediently carried out in a solvent such as methylene chloride, tetrahydrofuran, 1,4-dioxane, toluene, acetonitrile, dimethylsulphoxide, dimethylformamide, dimethylacetamide, N-methylpyrrolidone or mixtures thereof, optionally with the addition of water as cosolvent and/or with the addition of an inert auxiliary base, for example sodium hydrogen carbonate, pyridine, 2,4,6-trimethylpyridine, quinoline, triethylamine, N-ethyldiisopropylamine, N-ethyl-dicyclohexylamine, 1,4-diazabicyclo[2,2,2]octane or 1,8-diazabicyclo[5,4,0]undec-7-ene, at temperatures between −50°

C. and +100° C., preferably between −10° C. and +50° C., while any protective group used may simultaneously be cleaved as a result of transamidation.

If it is necessary to cleave a protective group used for the nitrogen atom of the lactam group or to cleave from a solid phase the same method is used as described under (a) above.

c. In order to prepare a compound of general formula I wherein $R^3$ denotes a phenyl or naphthyl group substituted by a carboxy-$C_{2-3}$-alkenyl, amino-carbonyl-$C_{2-3}$-alkenyl, ($C_{1-3}$-alkylamino)-carbonyl-$C_{2-3}$-alkenyl, di-($C_{1-3}$-alkyl-amino)-carbonyl-$C_{2-3}$-alkenyl or $C_{1-4}$-alkoxy-carbonyl-$C_{2-3}$-alkenyl group, reacting a compound of general formula

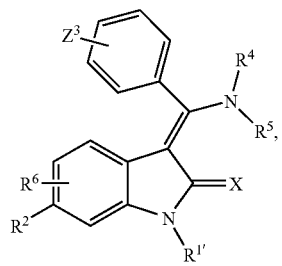

(IX)

wherein
$R^2$, $R^4$, $R^5$, $R^6$ and X are as hereinbefore defined, $R^{1'}$ has the meanings given for $R^1$ hereinbefore or denotes a protective group for the nitrogen atom of the lactam group, while $R^{1'}$ may also denote a bond to a solid phase optionally formed via a spacer, and $Z^3$ denotes a leaving group, for example a halogen atom or an alkyl or arylsulphonyloxy group such as the chlorine, bromine or iodine atom or the methylsulphonyloxy, ethylsulphonyloxy, p-toluenesulphonyloxy or trifluoromethane-sulphonyloxy group, with an alkene of general formula

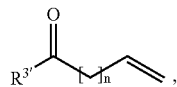

(X)

wherein
$R^{3'}$ denotes an amino, ($C_{1-3}$-alkylamino), di-($C_{1-3}$-alkylamino) or $C_{1-4}$-alkoxy- group and n is the number 0 or 1.

The reaction is conveniently carried out under palladium catalysis, for example with palladium(II)-acetate, palladium(II)-chloride, bis-(triphenylphosphine)-palladium(II)-acetate, bis-(triphenylphosphine)-palladium(II)-chloride, palladium/activated charcoal, bis-[1,2-bis-(diphenylphosphino)-ethane]-palladium(0), dichloro-(1,2-bis-(diphenylphosphino)-ethane)-palladium(II), tetrakistriphenylphosphine-palladium(0), tris-(dibenzylideneacetone)-dipalladium(0), 1,1'-bis-(diphenylphosphino)-ferrocene-dichloro-palladium(II) or tris-(dibenzylideneacetone)-dipalladium(0)-chloroform adduct in the presence of a base such as triethylamine, diisopropyl-ethylamine, lithium carbonate, potassium carbonate, sodium carbonate, caesium carbonate and a ligand such as triphenylphosphine, tri-ortho-tolyl-phosphine or tri-(tert.butyl)-phosphine in solvents such as acetonitrile, N-methyl-pyrrolidinone, dioxane or dimethylformamide and mixtures thereof.

If it is necessary to cleave a protective group used for the nitrogen atom of the lactam group or to cleave from a solid phase the same method is used as described under (a) above.

d. In order to prepare a compound of general formula I wherein $R^3$ denotes a phenyl or naphthyl group substituted by
carboxy-$C_{1-3}$-alkyl, $C_{1-4}$-alkoxy-carbonyl-$C_{1-3}$-alkyl, aminocarbonyl-$C_{1-3}$-alkyl, ($C_{1-3}$-alkylamino)-carbonyl-$C_{1-3}$-alkyl, di-($C_{1-3}$-alkyl)-amino-carbonyl-$C_{1-3}$-alkyl or 4-($C_{1-3}$-alkyl)-piperazin-1-yl-carbonyl-($C_{1-3}$-alkyl) groups, hydrogenating a compound of general formula

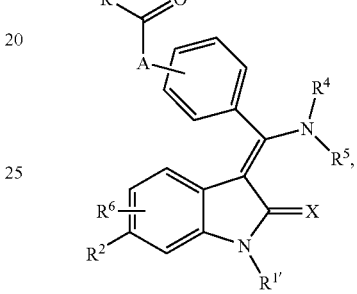

(XI)

wherein
$R^2$, $R^4$, $R^5$, $R^6$ and X are as hereinbefore defined, $R^{1'}$ has the meanings given for $R^1$ hereinbefore or denotes a protective group for the nitrogen atom of the lactam group, while $R^{1'}$ may also denote a bond to a solid phase optionally formed via a spacer, A denotes a $C_{2-3}$-alkenyl group and $R^{3'}$ denotes a hydroxy, $C_{1-4}$-alkoxy, amino, ($C_{1-3}$-alkylamino), di-($C_{1-3}$-alkyl)-amino or 4-($C_{1-3}$-alkyl)-piperazin-1-yl group.

The hydrogenation is preferably carried out by catalytic hydrogenation with hydrogen in the presence of a catalyst such as palladium/charcoal or platinum in a solvent such as methanol, ethanol, ethyl acetate, dimethylformamide, dimethylformamide/acetone or glacial acetic acid optionally with the addition of an acid such as hydrochloric acid at temperatures between 0 and 50° C., but preferably at ambient temperature, and under a hydrogen pressure of 1 to 7 bar, but preferably from 3 to 5 bar.

If it is necessary to cleave a protective group used for the nitrogen atom of the lactam group or to cleave from a solid phase the same method is used as described under (a) above.

If according to the invention a compound of general formula I is obtained which contains an alkoxycarbonyl group, this may be converted by hydrolysis into a corresponding carboxy compound, or if a compound of general formula I is obtained which contains an amino or alkylamino group, this may be converted by reductive alkylation into a corresponding alkylamino or dialkylamino compound, or if a compound of general formula I is obtained which contains a dialkylamino group, this may be converted by alkylation into a corresponding trialkylammonium compound, or if a compound of general formula I is obtained which contains an amino or alkylamino group, this may be converted by acylation or sulphonation into a corresponding acyl or sulphonyl compound, or if a compound of general formula I is obtained which contains a carboxy group, this may be converted by esterification or amidation into a corresponding ester or aminocarbonyl compound, or if a compound of general formula I is obtained which contains a cyclo-alkyleneimino group in which a methylene group is replaced by a sulphur atom, this may be converted by oxidation into a corresponding sulphinyl or sulphonyl compound, or if a compound of general formula I is obtained which contains a nitro group, this may be converted by reduction into a corresponding amino compound, or if a compound of general formula I is obtained which contains a cyano group, this may be converted by reduction into a corresponding aminomethyl compound, or if a compound of general formula I is obtained which contains an arylalkyloxy group, this may be converted with acid into a corresponding hydroxy compound, or if a compound of general formula I is obtained which contains an alkoxycarbonyl group, this may be converted by saponification into a corresponding carboxy compound, or if a compound of general formula I is obtained wherein $R_4$ denotes a phenyl group substituted by an amino, alkylamino, aminoalkyl or N-alkyl-amino group, this may be converted by reacting with a corresponding cyanate, isocyanate or carbamoyl halide into a corresponding urea compound of general formula I or if a compound of general formula I is obtained which contains a carbonyl group, this may be converted by reacting with phosphorus pentasulphide into a corresponding thiocarbonyl compound, or if a compound of general formula I is obtained wherein $R_4$ denotes a phenyl group substituted by an amino, alkylamino, aminoalkyl or N-alkyl-amino group, this may subsequently be converted by reacting with a corresponding compound which transfers the amidino group or by reacting with a corresponding nitrile into a corresponding guanidino compound of general formula I.

The subsequent hydrolysis is preferably carried out in an aqueous solvent, e.g. in water, methanol/water, ethanol/water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide at temperatures between 0 and 100° C., preferably at temperatures between 10 and 50° C.

The subsequent reductive alkylation is preferably carried out in a suitable solvent such as methanol, methanol/water, methanol/water/ammonia, ethanol, ether, tetrahydrofuran, dioxane or dimethylformamide, optionally with the addition of an acid such as hydrochloric acid in the presence of catalytically activated hydrogen, e.g. hydrogen in the presence of Raney nickel, platinum or palladium/charcoal, or in the presence of a metal hydride such as sodium borohydride, lithium borohydride, sodium cyanoborohydride or lithium aluminium hydride at temperatures between 0 and 100° C., preferably at temperatures between 20 and 80° C.

The subsequent alkylation is preferably carried out in a suitable solvent such as ether, tetrahydrofuran, dioxane, dichloromethane, acetone or acetonitrile in the presence of alkylating agents such as alkyl iodides, alkyl bromides, alkyl chlorides, alkyl-methanesulphonic acid esters, alkyl-para-toluenesulphonic acid esters or alkyl trifluoroacetates, at temperatures between 0 and 100° C., preferably at temperatures between 20 and 60° C.

The subsequent acylation or sulphonylation is conveniently carried out with the corresponding free acid or a corresponding reactive compound such as the anhydride, ester, imidazolide or halide thereof, preferably in a solvent such as methylene chloride, diethyl ether, tetrahydrofuran, toluene, dioxane, acetonitrile, dimethylsulphoxide or dimethylformamide, optionally in the presence of an inorganic or a tertiary organic base at temperatures between −20 and 200° C., preferably at temperatures between 20° C. and the boiling temperature of the solvent used. The reaction with the free acid may optionally take place in the presence of an acid-activating agent or a dehydrating agent, e.g. in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylamino-pyridine, N-methyl-morpholine or triethylamine, conveniently at temperatures between 0 and 150° C., preferably at temperatures between 0 and 100° C. The reaction with a corresponding reactive compound may optionally take place in the presence of a tertiary organic base such as triethylamine, N-ethyl-diisopropylamine, N-methyl-morpholine or pyridine or using an anhydride in the presence of the corresponding acid at temperatures between 0 and 150° C., preferably at temperatures between 50 and 100° C.

The subsequent esterification or amidation is conveniently carried out by reacting a corresponding reactive carboxylic acid derivative with a corresponding alcohol or amine as hereinbefore described.

The esterification or amidation is preferably carried out in a solvent such as methylene chloride, diethyl ether, tetrahydrofuran, toluene, dioxane, acetonitrile, dimethylsulphoxide or dimethylformamide, optionally in the presence of an inorganic or a tertiary organic base, preferably at temperatures between 20° C. and the boiling temperature of the solvent used. The reaction is carried out with a corresponding acid, preferably in the presence of a dehydrating agent, e.g. in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine, conveniently at temperatures between 0 and 150° C., preferably at temperatures between 0and 100° C., and the acylation with a corresponding reactive compound such as the anhydride, ester, imidazolide or halide thereof may optionally be carried out in the presence of a tertiary organic base such as triethylamine, N-ethyl-diisopropylamine or N-methyl-morpholine at temperatures between 0 and 150° C., preferably at temperatures between 50 and 100° C.

The subsequent oxidation of the sulphur atom is preferably carried out in a solvent or mixture of solvents, e.g. in water, water/pyridine, acetone, methylene chloride, acetic acid, acetic acid/acetic anhydride, dilute sulphuric acid or trifluoroacetic acid, conveniently at temperatures between −80 and 100° C., depending on the oxidising agent used.

In order to prepare a corresponding sulphinyl compound of general formula I the oxidation is conveniently carried out with one equivalent of the oxidising agent used, e.g. with hydrogen peroxide in glacial acetic acid, trifluoroacetic acid or formic acid at 0 to 20° C. or in acetone at 0 to 60° C., with a peracid such as performic acid in glacial acetic acid or trifluoroacetic acid at 0 to 50° C. or with m-chloroperbenzoic acid in methylene chloride, chloroform or dioxane at −20 to 80° C., with sodium metaperiodate in aqueous methanol or ethanol at −15 to 25° C., with bromine in glacial acetic acid or aqueous acetic acid optionally in the presence of a weak base such as sodium acetate, with N-bromosuccinimide in ethanol, with tert.butylhypochlorite in methanol at −80 to −30° C., with iodobenzodichloride in aqueous pyridine at 0 to 50° C., with nitric acid in glacial acetic acid at 0 to 20° C., with chromic acid in glacial acetic acid or in acetone at 0 to 20° C. and with sulphurylchloride in methylene chloride at −70° C., and the thioether-chlorine complex thus obtained is conveniently hydrolysed with aqueous ethanol.

In order to prepare a sulphonyl compound of general formula I oxidation is carried out starting from a corresponding sulphinyl compound, conveniently with one or more equivalents of the oxidising agent used, or starting from a corresponding mercapto compound, conveniently with two or more equivalents of the oxidising agent used, e.g. with hydrogen peroxide in glacial acetic acid/acetic anhydride, trifluoroacetic acid or in formic acid at 20 to 100° C. or in acetone at 0 to 60° C., with a peracid such as performic acid or m-chloroperbenzoic acid in glacial acetic acid, trifluoroacetic acid, methylene chloride or chloroform at temperatures between 0 and 60° C., with nitric acid in glacial acetic acid at 0 to 20° C., with chromic acid, sodium periodate or potassium permanganate in acetic acid, water/sulphuric acid or in acetone at 0 to 20° C.

The subsequent reduction of a nitro group is preferably carried out by hydrogenolysis, e.g. with hydrogen in the presence of a catalyst such as palladium/charcoal or Raney nickel in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and under a hydrogen pressure of 1 to 7 bar, but preferably 3 to 5 bar.

The subsequent hydrogenation of a cyano group is preferably carried out by hydrogenolysis, e.g. with hydrogen in the presence of a catalyst such as palladium/charcoal or Raney nickel in a solvent such as methanol, ethanol, ethyl acetate, methylene chloride, dimethylformamide, dimethylformamide/acetone or glacial acetic acid, optionally with the addition of an acid such as hydrochloric acid or glacial acetic acid at temperatures between 0 and 50° C., but preferably at ambient temperature, and under a hydrogen pressure of 1 to 7 bar, but preferably from 3 to 5 bar.

Expediently, a corresponding urea compound of general formula I is subsequently prepared with an inorganic cyanate or a corresponding isocyanate or carbamoylchloride, preferably in a solvent such as dimethylformamide and optionally in the presence of a tertiary organic base such as triethylamine at temperatures between 0 and 50° C., preferably at ambient temperature.

Expediently, a corresponding thiocarbonyl compound of general formula I is subsequently prepared with phosphorus pentasulphide or (p-methoxy-phenyl)-thionophosphine-sulphide dimer (Lawesson's reagent) preferably in a solvent such as pyridine or toluene at temperatures between 80 and 120° C., preferably at 120° C.

Expediently, a corresponding guanidino compound of general formula I is subsequently prepared by reacting with a compound which transfers the amidino group, such as 3,5-dimethylpyrazole-1-carboxylic acid amidine, preferably in a solvent such as dimethylformamide and optionally in the presence of a tertiary organic base such as triethylamine at temperatures between 0 and 50° C., preferably at ambient temperature.

In the reactions described hereinbefore, any reactive groups present such as carboxy, hydroxy, amino, alkylamino or imino groups may be protected during the reaction by conventional protecting groups which are cleaved again after the reaction.

For example, a protecting group for a carboxy group may be a trimethylsilyl, methyl, ethyl, tert.butyl, benzyl or tetrahydropyranyl group and protecting groups for a hydroxy, amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxan/water, in the presence of an acid such as trifluoroacetic acid, hydrochloric acid or sulphuric acid or in the presence of an alkali metal base such as lithium hydroxide, sodium hydroxide or potassium hydroxide at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of 1 to 7 bar, but preferably 3 to 5bar.

A methoxybenzyl group may also be cleaved in the presence of an oxidising agent such as cerium(IV)ammonium nitrate in a solvent such as methylene chloride, acetonitrile or acetonitrile/water at temperatures of between 0 and 50° C., but preferably at ambient temperature.

A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxan, ethyl acetate or ether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

Moreover, chiral compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, N-acetylglutamic acid, aspartic acid, N-acetylaspartic acid or quinic acid. An optically active alcohol may be for example (+) or (−)-menthol and an optically active acyl group in amides, for example, may be a (+)- or (−)-menthyloxycarbonyl group.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid, maleic acid, methanesulphonic acid, ethanesulphonic acid, para-toluenesulphonic acid, phenylsulphonic acid or L-(+)-mandelic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

For compounds of general formula I which contain 2 or more acidic or basic groups, salts with 2 or more inorganic or organic bases or acids may also be used (so-called disalts etc.).

The compounds of general formulae V to XI used as starting products are known from the literature in some cases or may be obtained by methods known from the literature or may be obtained by methods described hereinbefore and in the Examples. For example, the compounds of general formula IX are described in German Patent Application 198 44 003.

As already mentioned hereinbefore, the new compounds of general formula I have valuable pharmacological properties, particularly an inhibiting effect on various kinases, especially receptor tyrosine kinases such as VEGFR1, VEGFR2, VEGFR3, PDGFRα, PDGFRβ, FGFR1, FGFR3, EGFR, HER2, c-Kit, IGF1R and HGFR, Flt-3, as well as on the proliferation of cultivated human cells, particularly endothelial cells, e.g. in angiogenesis, but also on the proliferation of other cells, particularly tumour cells.

The biological properties of the new compounds were tested by the following standard method as described:

Human umbilical endothelial cells (HUVEC) were cultivated in IMDM (Gibco BRL), supplemented with 10% foetal calf serum (FBS) (Sigma), 50 µM of β-mercaptoethanol (Fluka), standard antibiotics, 15 µg/ml of endothelial cell growth factor (ECGS, Collaborative Biomedical Products) and 100 µg/ml of heparin (Sigma) on gelatine-coated culture dishes (0.2% gelatine, Sigma) at 37° C., under 5% $CO_2$ in a water-saturated atmosphere.

In order to investigate the inhibitory activity of the compounds according to the invention the cells were "starved" for 16 hours, i.e. kept in culture medium without growth factors (ECGS+heparin). The cells were detached from the culture dishes using trypsin/EDTA and washed once in serum-containing medium. Then they were seeded out in amounts of $2.5 \times 10^3$ cells per well.

The proliferation of the cells was stimulated with 5 ng/ml of $VEGF_{165}$ (vascular endothelial growth factor; H. Weich, GBF Braunschweig) and 10 µg/ml of heparin. As a control, 6 wells in each dish were not stimulated.

The compounds according to the invention were dissolved in 100% dimethylsulphoxide and added to the cultures in various dilutions as triple measurements, the maximum dimethylsulphoxide concentration being 0.3%.

The cells were incubated for 76 hours at 37° C., then for a further 16 hours $^3$H-thymidine (0.1 µCi/well, Amersham) was added in order to determine the DNA synthesis. Then the radioactively labelled cells were immobilised on filter mats and the radioactivity incorporated was measured in a β-counter. In order to determine the inhibitory activity of the compounds according to the invention the mean value of the non-stimulated cells was subtracted from the mean value of the factor-stimulated cells (in the presence or absence of the compounds according to the invention).

The relative cell proliferation was calculated as a percentage of the control (HUVEC without inhibitor) and the concentration of active substance which inhibits the proliferation of the cells by 50% ($IC_{50}$) was determined.

The compounds of general formula I according to the invention have an $IC_{50}$ of between 50 µM and 1 nM.

In view of their inhibitory effect on the proliferation of cells, particularly endothelial and tumour cells, the compounds of general formula I are suitable for treating diseases in which the proliferation of cells, particularly endothelial cells, plays a part.

Thus, for example, the proliferation of endothelial cells and the concomitant neovascularisation constitute a crucial stage in tumour progression (Folkman J. et al., Nature 339, 58-61, (1989); Hanahan D. and Folkman J., Cell 86, 353-365, (1996)). Furthermore, the proliferation of endothelial cells is also important in haemangiomas, in metastasisation, rheumatoid arthritis, psoriasis and ocular neovascularisation (Folkman J., Nature Med. 1, 27-31, (1995)). The therapeutic usefulness of inhibitors of endothelial cell proliferation was demonstrated in the animal model for example by O'Reilly et al. and Parangi et al. (O'Reilly M. S. et al., Cell 88, 277-285, (1997); Parangi S. et al., Proc Natl Acad Sci USA 93, 2002-2007, (1996)).

The compounds of general formula I, their tautomers, their stereoisomers or the physiologically acceptable salts thereof are thus suitable, for example, for treating tumours (e.g. plate epithelial carcinoma, astrocytoma, Kaposi's sarcoma, glioblastoma, lung cancer, bladder cancer, head and neck carcinoma, oesophageal cancer, melanoma, ovarian cancer, prostate cancer, breast cancer, small-cell lung cancer, glioma, colorectal cancer, pancreatic cancer, urogenital cancer and gastrointestinal cancer as well as haematological cancers such as e.g. multiple myeloma and acute myeloid leukaemia), psoriasis, arthritis (e.g. rheumatoid arthritis), haemangioma, angiofibroma, eye diseases (e.g. diabetic retinopathy), neovascular glaucoma, kidney diseases (e.g. glomerulonephritis), diabetic nephropathy, malignant nephrosclerosis, thrombic microangiopathic syndrome, transplant rejections and glomerulopathy, fibrotic diseases (e.g. cirrhosis of the liver), mesangial cell proliferative diseases, arteriosclerosis, damage to the nerve tissue and for inhibiting the reocclusion of blood vessels after treatment with a balloon catheter, in vascular prosthetics or after the fitting of mechanical devices for holding the blood vessels open (e.g. stents), or other diseases in which cell proliferation or angiogenesis are involved.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastin, taxol), compounds which interact with nucleic acids (e.g. cisplatin, cyclophosphamide, adriamycin), hormone antagonists (e.g. tamoxifen), steroids and their analogues (e.g. dexamethasone), inhibitors of metabolic processes (e.g. 5-FU etc.), cytokines (e.g. interferons), kinase inhibitors (e.g. EGFR kinase inhibitors such as e.g. Iressa; Gleevec), receptor tyrosine kinase inhibitors with an allosteric effect, antibodies (e.g. herceptin), COX-2 inhibitors, or in conjunction with radiotherapy, etc. These combinations may be administered either simultaneously or sequentially.

The Examples that follow are intended to illustrate the invention more fully:

| Example | Name |
|---|---|
| 1.0 | 3-Z-[1-(4-(N-(2-dimethylamino-ethyl)-N-methylsulphonyl-amino)-anilino)-1-phenyl-methylene]-6-chloro-2-indolinone |
| 1.1 | 3-Z-[1-(4-(N-(dimethylamino-methylcarbonyl)-N-methyl-amino)-anilino)-1-phenyl-methylene]-6-chloro-2-indolinone |
| 1.2 | 3-Z-[1-(4-ethoxycarbonyl-anilino)-1-phenyl-methylene]-6-chloro-2-indolinone |
| 1.3 | 3-Z-[1-(4-(N-(dimethylamino-carbonylmethyl)-N-methylsulphonyl-amino)-anilino)-1-phenyl-methylene]-6-chloro-2-indolinone |
| 1.4 | 3-Z-[1-(4-(N-Methyl-N-methylsulphonyl-amino)-anilino)-1-phenyl-methylene]-6-chloro-2-indolinone |
| 1.5 | 3-Z-[1-(4-(N-Methyl-N-acetyl-amino)-anilino)-1-phenyl-methylene]-6-chloro-2-indolinone |
| 1.6 | 3-Z-[1-(4-(N-(2-dimethylamino-ethyl)-N-ethylsulphonyl-amino)-anilino)-1-phenyl-methylene]-6-chloro-2-indolinone |
| 1.7 | 3-Z-[1-(4-(N-(2-dimethylamino-ethyl)-N-propionyl-amino)-anilino)-1-phenyl-methylene]-6-chloro-2-indolinone |
| 1.8 | 3-Z-[1-(4-(N-(3-dimethylaminopropyl)-N-methylsulphonyl-amino)-anilino)-1-phenyl-methylene]-6-chloro-2-indolinone |
| 1.9 | 3-Z-[1-(4-(N-(2-dimethylamino-ethyl)-N-butyryl-amino)-anilino)-1-phenyl-methylene]-6-chloro-2-indolinone |
| 1.10 | 3-Z-[1-(4-(N-(2-dimethylamino-ethyl)-N-isobutyryl-amino)-anilino)-1-phenyl-methylene]-6-chloro-2-indolinone |
| 1.11 | 3-Z-[1-(4-(N-(2-dimethylamino-ethyl)-N-acetyl-amino)-anilino)-1-phenyl-methylene]-6-chloro-2-indolinone |
| 1.12 | 3-Z-[1-(4-(N-(2-dimethylamino-ethyl)-N-benzoyl-amino)-anilino)-1-phenyl-methylene]-6-chloro-2-indolinone |
| 1.13 | 3-Z-[1-(4-(N-(2-dimethylamino-ethyl)-N-phenylacetyl-amino)-anilino)-1-phenyl-methylene]-6-chloro-2-indolinone |
| 1.14 | 3-Z-[1-(4-(N-(2-dimethylamino-ethyl)-N-(pyrid-3-yl-carbonyl)-amino)-anilino)-1-phenyl-methylene]-6-chloro-2-indolinone |
| 1.15 | 3-Z-[1-(4-(N-(2-dimethylamino-ethyl)-N-(furan-2-yl-carbonyl)-amino)-anilino)-1-phenyl-methylene]-6-chloro-2-indolinone |
| 1.16 | 3-Z-[1-(4-(N-2-dimethylamino-ethyl)-N-(2-methoxy-benzoyl)-amino)-anilino)-1-phenyl-methylene]-6-chloro-2-indolinone |
| 1.17 | 3-Z-[1-(4-(N-(2-dimethylamino-ethyl)-N-propylsulphonyl-amino)-anilino)-1-phenyl-methylene]-6-chloro-2-indolinone |
| 1.18 | 3-Z-[1-(4-(N-(2-dimethylamino-ethyl)-N-isopropylsulphonyl-amino)-anilino)-1-phenyl-methylene]-6-chloro-2-indolinone |
| 1.19 | 3-Z-[1-(4-(N-(2-dimethylamino-ethyl)-N-benzylsulphonyl-amino)-anilino)-1-phenyl-methylene]-6-chloro-2-indolinone |
| 1.20 | 3-Z-[1-(4-(N-(4-benzyl-piperazin-1-yl-methylcarbonyl)-N-methyl-amino)-anilino)-1-phenyl-methylene]-6-chloro-2-indolinone |
| 1.21 | 3-Z-[1-(4-(N-(morpholin-4-yl-methylcarbonyl)-N-methyl-amino)-anilino)-1-phenyl-methylene]-6-chloro-2-indolinone |
| 1.22 | 3-Z-[1-(4-(N-(piperidin-1-yl-methylcarbonyl)-N-methyl-amino)-anilino)-1-phenyl-methylene]-6-chloro-2-indolinone |
| 1.23 | 3-Z-[1-(4-(N-(benzylmethylamino-methylcarbonyl)-N-methyl-amino)-anilino)-1-phenyl-methylene]-6-chloro-2-indolinone |
| 1.24 | 3-Z-[1-(4-(dimethylamino-methyl)-anilino)-1-phenyl-methylene]-6-chloro-2-indolinone |
| 1.25 | 3-Z-[1-(4-((2,6-dimethyl-piperidin-1-yl)-methyl)-anilino)-1-phenyl-methylene]-6-chloro-2-indolinone |
| 1.26 | 3-Z-[1-(4-((N-(2-(2-methoxy-ethoxy)-ethyl)-N-methyl-amino)-methyl)-anilino)-1-phenyl-methylene]-6-chloro-2-indolinone |

-continued

| Example | Name |
|---|---|
| 1.27 | 3-Z-[1-(4-(triazol-1-yl-methyl)-anilino)-1-phenyl-methylene]-6-chloro-2-indolinone |
| 1.28 | 3-Z-[1-(4-(di-(2-hydroxy-ethyl)-amino-methyl)-anilino)-1-phenyl-methylene]-6-chloro-2-indolinone |
| 1.29 | 3-Z-[1-(4-(5-methyl-imidazol-4-yl)-anilino)-1-phenyl-methylene]-6-chloro-2-indolinone |
| 1.30 | 3-Z-[1-(4-(N-tert.butoxycarbonyl-ethylamino-methyl)-anilino)-1-phenyl-methylene]-6-chloro-2-indolinone |
| 1.31 | 3-Z-[1-(4-(1-methyl-imidazol-2-yl)-anilino)-1-phenyl-methylene]-6-chloro-2-indolinone |
| 1.32 | 3-Z-[1-(4-(morpholin-4-yl-methyl)-anilino)-1-phenyl-methylene]-6-chloro-2-indolinone |
| 1.33 | 3-Z-[1-(4-(N-benzyl-N-methyl-amino-methyl)-anilino)-1-phenyl-methylene]-6-chloro-2-indolinone |
| 1.34 | 3-Z-[1-(4-(pyrrolidin-1-yl-methyl)-anilino)-1-phenyl-methylene]-6-chloro-2-indolinone |
| 1.35 | 3-Z-[1-(4-((4-methyl-piperazin-1-yl)-methyl)-anilino)-1-phenyl-methylene]-6-chloro-2-indolinone |
| 1.36 | 3-Z-[1-(4-(N-(2-dimethylamino-ethyl)-N-butylsulphonyl-amino)-anilino)-1-phenyl-methylene]-6-chloro-2-indolinone |
| 1.37 | 3-Z-[1-(4-(N-(2-dimethylamino-ethyl)-N-methoxyacetyl-amino)-anilino)-1-phenyl-methylene]-6-chloro-2-indolinone |
| 1.38 | 3-Z-[1-(4-(N-(2-dimethylamino-ethyl)-N-(3,4-dimethoxy-benzoyl)-amino)-anilino)-1-phenyl-methylene]-6-chloro-2-indolinone |
| 1.39 | 3-Z-[1-(4-(N-(2-hydroxy-ethyl)-N-methyl-amino-methyl)-anilino)-1-phenyl-methylene]-6-chloro-2-indolinone |
| 1.40 | 3-Z-[1-(4-(N-(2-benzylmethylamino-ethyl)-N-propionyl-amino)-anilino)-1-phenyl-methylene]-6-chloro-2-indolinone |
| 1.41 | 3-Z-[1-(4-(N-(2-dimethylamino-ethyl)-N-(pyrid-4-yl-carbonyl)-amino)-anilino)-1-phenyl-methylene]-6-chloro-2-indolinone |
| 1.42 | 3-Z-[1-(4-(N-(phthalimido-2-yl-methylcarbonyl)-N-methyl-amino)-anilino)-1-phenyl-methylene]-6-chloro-2-indolinone |
| 1.43 | 3-Z-[1-(4-(N-tert.butoxycarbonyl-methylamino-methyl)-anilino)-1-phenyl-methylene]-6-chloro-2-indolinone |
| 1.44 | 3-Z-[1-(4-(N-(4-methyl-piperazin-1-yl-methylcarbonyl)-N-methyl-amino)-anilino)-1-phenyl-methylene]-6-chloro-2-indolinone |
| 1.45 | 3-Z-[1-(4-(N-(di-(2-hydroxy-ethyl)-amino-methylcarbonyl)-N-methyl-amino)-anilino)-1-phenyl-methylene]-6-chloro-2-indolinone |
| 1.46 | 3-Z-[1-(4-(N-(pyrrolidin-1-yl-methylcarbonyl)-N-methyl-amino)-anilino)-1-phenyl-methylene]-6-chloro-2-indolinone |
| 1.47 | 3-Z-[1-(4-(N-(N-(2-dimethylamino-ethyl)-N-methyl-amino-methylcarbonyl)-N-methyl-amino)-anilino)-1-phenyl-methylene]-6-chloro-2-indolinone |
| 1.48 | 3-Z-[1-(4-(N-(imidazol-1-yl-methylcarbonyl)-N-methyl-amino)-anilino)-1-phenyl-methylene]-6-chloro-2-indolinone |
| 1.49 | 3-Z-[1-(4-(4-methyl-piperazin-1-yl-carbonyl)-anilino)-1-phenyl-methylene]-6-chloro-2-indolinone |
| 1.50 | 3-Z-[1-(4-(N-(2-(4-tert.butoxycarbonyl-piperazin-1-yl)-ethylcarbonyl)-N-methyl-amino)-anilino)-1-phenyl-methylene]-6-chloro-2-indolinone |
| 1.51 | 3-Z-[1-(4-(N-(2-benzylmethylamino-ethyl)-N-acetyl-amino)-anilino)-1-phenyl-methylene]-6-chloro-2-indolinone |
| 1.52 | 3-Z-[1-(4-((4-tert.butoxycarbonyl-piperazin-1-yl)-methyl)-anilino)-1-phenyl-methylenel]-6-chloro-2-indolinone |
| 1.53 | 3-Z-[1-(4-(N-(dimethylamino-methylcarbonyl)-N-methyl-amino)-3-methoxy-anilino)-1-phenyl-methylene]-6-chloro-2-indolinone |
| 1.54 | 3-Z-[1-(3-(dimethylamino-methyl)-anilino)-1-phenyl-methylene]-6-chloro-2-indolinone |
| 1.55 | 3-Z-[1-(3-(pyridin-4-yl-methyl)-anilino)-1-phenyl-methylene]-6-chloro-2-indolinone |
| 1.56 | 3-Z-[1-(4-(4-methyl-piperazin-1-yl-carbonyl)-pyridin-2-yl-amino)-1-phenyl-methylene]-6-chloro-2-indolinone |
| 1.57 | 3-Z-[1-(Indazol-6-yl-amino)-1-phenyl-methylene]-6-chloro-2-indolinone |
| 1.58 | 3-Z-[1-(4-(N-(2-dimethylamino-ethyl)-N-acetyl-amino)-(pyridin-3-yl-amino))-1-phenyl-methylene]-6-chloro-2-indolinone |
| 1.59 | trans-3-Z-[1-(4-(N-(dimethylamino-methylcarbonyl)-amino)-cyclohexylamino)-1-phenyl-methylene]-6-chloro-2-indolinone |
| 1.60 | cis-3-Z-[1-(4-(N-(dimethylamino-methylcarbonyl)-N-methyl-amino)-cyclohexylamino)-1-phenyl-methylene]-6-chloro-2-indolinone |
| 1.61 | 3-Z-[1-(4-(4-methyl-piperazin-1-yl-carbonyl)-3-methyl-pyrrol-3-yl-amino)-1-phenyl-methylene]-6-chloro-2-indolinone |
| 1.62 | 3-Z-[1-(4-(N-(2-dimethylamino-ethyl)-N-methyl-carbamoyl)-3-methyl-pyrrol-3-yl-amino)-1-phenyl-methylene]-6-chloro-2-indolinone |
| 1.63 | 3-Z-[1-(4-(N-(3-dimethylamino-propyl)-N-acetyl-amino)-anilino)-1-phenyl-methylene]-6-chloro-2-indolinone |
| 1.64 | 3-Z-[1-(4-(2-diethylamino-ethyl-sulphonyl)-anilino)-1-phenyl-methylene]-6-chloro-2-indolinone |

-continued

| Example | Name |
|---|---|
| 1.65 | 3-Z-[1-(4-(1-(2-dimethylamino-ethyl)-imidazol-2-yl)-anilino)-1-phenyl-methylene]-6-chloro-2-indolinone |
| 1.66 | 3-Z-[1-(4-(piperidin-1-yl-carbonyl)-anilino)-1-phenyl-methylene]-6-chloro-2-indolinone |
| 1.67 | 3-Z-[1-(4-(4-tert.butoxycarbonyl-piperazin-1-yl-carbonyl)-anilino)-1-phenyl-methylene]-6-chloro-2-indolinone |
| 1.68 | 3-Z-[1-(4-(N-cyclohexyl-N-methyl-carbamoyl)-anilino)-1-phenyl-methylene]-6-chloro-2-indolinone |
| 1.69 | 3-Z-[1-(4-(N-(2-dimethylamino-ethyl-carbonyl)-N-methyl-amino)-anilino)-1-phenyl-methylene]-6-chloro-2-indolinone |
| 1.70 | 3-Z-[1-(4-(N-(2-dimethylamino-ethyl)-N-methyl-amino-methyl)-anilino)-1-phenyl-methylene]-6-chloro-2-indolinone |
| 1.71 | 3-Z-[1-(4-(N-(2-(4-methyl-piperazin-1-yl)-ethyl-carbonyl)-N-methyl-amino)-anilino)-1-phenyl-methylene]-6-chloro-2-indolinone |
| 1.72 | 3-Z-[1-(4-(2-dimethylamino-ethoxy)-anilino)-1-phenyl-methylene]-6-chloro-2-indolinone |
| 1.73 | 3-Z-[1-(4-((4-dimethylamino-piperidin-1-yl)-methyl)-anilino)-1-phenyl-methylene]-6-chloro-2-indolinone |
| 1.74 | 3-Z-[1-(3-methoxycarbonylmethyl-anilino)-1-phenyl-methylene]-6-chloro-2-indolinone |
| 1.75 | 3-Z-[1-(3-methoxycarbonyl-anilino)-1-phenyl-methylene]-6-chloro-2-indolinone |
| 1.76 | 3-Z-[1-(4-(2-dimethylamino-ethyl)-anilino)-1-phenyl-methylene]-6-chloro-2-indolinone |
| 1.77 | 3-Z-[1-(4-(N-tert.butoxycarbonyl-amino-methyl)-anilino)-1-phenyl-methylene]-6-chloro-2-indolinone |
| 1.78 | 3-Z-[1-(4-(N-(dimethylamino-methylcarbonyl)-N-isopropyl-amino)-anilino)-1-phenyl-methylene]-6-chloro-2-indolinone |
| 1.79 | 3-Z-[1-(4-(N-(4-tert.butoxycarbonyl-piperazin-1-yl-methylcarbonyl)-N-isopropyl-amino)-anilino)-1-phenyl-methylene]-6-chloro-2-indolinone |
| 1.80 | 3-Z-[1-(4-(diethylamino-methyl)-anilino)-1-phenyl-methylene]-6-chloro-2-indolinone |
| 1.81 | 3-Z-[1-(4-(N-propyl-N-methyl-amino-methyl)-anilino)-1-phenyl-methylene]-6-chloro-2-indolinone |
| 1.82 | 3-Z-[1-(4-(4-methyl-piperazin-1-yl)-anilino)-1-phenyl-methylene]-6-chloro-2-indolinone |
| 1.83 | 3-Z-[1-(4-(N-(2-dimethylamino-ethyl)-N-methyl-carbamoyl)-anilino)-1-phenyl-methylene]-6-chloro-2-indolinone |
| 1.84 | 3-Z-[1-(4-(N-(4-tert.butoxycarbonyl-piperazin-1-yl-methylcarbonyl)-N-methyl-amino)-anilino)-1-phenyl-methylene]-6-chloro-2-indolinone |
| 1.85 | 3-Z-[1-(4-(N-(hydroxy-methylcarbonyl)-N-methyl-amino)-anilino)-1-phenyl-methylene]-6-chloro-2-indolinone |
| 1.86 | 3-Z-[1-(4-(N-(2-dimethylamino-ethyl)-N-methyl-amino)-anilino)-1-phenyl-methylene]-6-chloro-2-indolinone |
| 1.87 | 3-Z-[1-(4-(N-(N-(tert.butoxycarbonyl-3-amino-propyl)-N-methyl)-amino-methyl)-anilino)-1-phenyl-methylene]-6-chloro-2-indolinone |
| 1.88 | 3-Z-[1-(4-(N-(4-methyl-homopiperazin-1-yl-methylcarbonyl)-N-methyl-amino)-anilino)-1-phenyl-methylene]-6-chloro-2-indolinone |
| 1.89 | 3-Z-[1-(4-(N-(dimethylamino-methylcarbonyl)-N-methyl-amino)-3-cyano-anilino)-1-phenyl-methylene]-6-chloro-2-indolinone |
| 1.90 | 3-Z-[1-(4-(N-(4-ethyl-piperazin-1-yl-methylcarbonyl)-N-methyl-amino)-anilino)-1-phenyl-methylene]-6-chloro-2-indolinone |
| 1.91 | 3-Z-[1-(4-(N-(1-methyl-piperidin-4-yl-methylcarbonyl)-N-methyl-amino)-anilino)-1-phenyl-methylene]-6-chloro-2-indolinone |
| 1.92 | 3-Z-[1-(4-(N-(4-methyl-piperazin-1-yl-methylcarbonyl)-amino)-anilino)-1-phenyl-methylene]-6-chloro-2-indolinone |
| 1.93 | 3-Z-[1-(4-(N-(3-dimethylamino-propyl)-N-methyl-carbamoylmethyl)-anilino)-1-phenyl-methylene]-6-chloro-2-indolinone |
| 1.94 | 3-Z-[1-(4-(N-(2-dimethylamino-ethyl)-N-methyl-carbamoylmethyl)-anilino)-1-phenyl-methylene]-6-chloro-2-indolinone |
| 1.95 | 3-Z-[1-(4-(4-methyl-piperazin-1-yl-carbonylmethyl)-anilino)-1-phenyl-methylene]-6-chloro-2-indolinone |
| 1.96 | 3-Z-[1-(4-(N-(4-dimethylamino-butyl-carbonyl)-N-methyl-amino)-anilino)-1-phenyl-methylene]-6-chloro-2-indolinone |
| 1.97 | 3-Z-[1-(4-(N-(dimethylamino-methylcarbonyl)-N-methyl-amino)-2,3-dimethyl-anilino)-1-phenyl-methylene]-6-chloro-2-indolinone |
| 1.98 | 3-Z-[1-(4-(N-(4-methyl-piperazin-1-yl-methylcarbonyl)-amino)-2,3-dimethyl-anilino)-1-phenyl-methylene]-6-chloro-2-indolinone |
| 1.99 | 3-Z-[1-(4-(N-(4-methyl-piperazin-1-yl-aminocarbonyl)-N-methyl-amino)-anilino)-1-phenyl-methylene]-6-chloro-2-indolinone |
| 1.100 | 3-Z-[1-(4-ethoxycarbonylmethyl-anilino)-1-phenyl-methylene]-6-chloro-2-indolinone |
| 1.101 | 3-Z-[1-(4-(N-(1-methyl-piperidin-4-yl-aminocarbonyl)-N-methyl-amino)-anilino)-1-phenyl-methylene]-6-chloro-2-indolinone |
| 1.102 | 3-Z-[1-(4-(N-(3-dimethylamino-propyl-carbonyl)-N-methyl-amino)-anilino)-1-phenyl-methylene]-6-chloro-2-indolinone |

-continued

| Example | Name |
|---|---|
| 1.103 | 3-Z-[1-(4-(N-(4-methyl-piperazin-1-yl-carbonyl)-N-methyl-amino)-anilino)-1-phenyl-methylene]-6-chloro-2-indolinone |
| 1.104 | 3-Z-[1-(4-(N-(N-(3-dimethylamino-propyl)-aminocarbonyl)-N-methyl-amino)-anilino)-1-phenyl-methylene]-6-chloro-2-indolinone |
| 1.105 | 3-Z-[1-(4-(N-(pyridin-4-yl-methylaminocarbonyl)-N-methyl-amino)-anilino)-1-phenyl-methylene]-6-chloro-2-indolinone |
| 1.106 | 3-Z-[1-(4-(N-(1-methyl-piperidin-4-oxy-carbonyl)-N-methyl-amino)-anilino)-1-phenyl-methylene]-6-chloro-2-indolinone |
| 2.0 | 3-Z-[1-(4-(N-(2-dimethylamino-ethyl)-N-methylsulphonyl-amino)-anilino)-1-phenyl-methylene]-6-chloro-5-nitro-2-indolinone |
| 2.1 | 3-Z-[1-(4-(N-(dimethylamino-methylcarbonyl)-N-methyl-amino)-anilino)-1-phenyl-methylene]-6-chloro-5-nitro-2-indolinone |
| 2.2 | 3-Z-[1-(4-(dimethylamino-methyl)-anilino)-1-phenyl-methylene]-6-chloro-5-nitro-2-indolinone |
| 2.3 | 3-Z-[1-(4-(N-(2-dimethylamino-ethyl)-N-acetyl-amino)-anilino)-1-phenyl-methylene]-6-chloro-5-nitro-2-indolinone |
| 3.0 | 3-Z-[1-(4-(N-(dimethyl-carbamoyl-methyl)-N-(2-pyrrolidin-1-yl-ethyl-carbonyl)-amino)-anilino)-1-phenyl-methylene]-6-chloro-2-indolinone |
| 3.1 | 3-Z-[1-(4-(N-(dimethyl-carbamoyl-methyl)-N-(pyrrolidin-1-yl-methyl-carbonyl)-amino)-anilino)-1-phenyl-methylene]-6-chloro-2-indolinone |
| 3.2 | 3-Z-[1-(4-(N-(dimethyl-carbamoyl-methyl)-N-(2-dimethylamino-ethyl-carbonyl)-amino)-anilino)-1-phenyl-methylene]-6-chloro-2-indolinone |
| 3.3 | 3-Z-[1-(4-(N-(dimethyl-carbamoyl-methyl)-N-(dimethylamino-methylcarbonyl)-amino)-anilino)-1-phenyl-methylene]-6-chloro-2-indolinone |
| 4.0 | 3-Z-[1-(4-(N-methyl-N-methylsulphonyl-amino)-anilino)-1-(3-iod-phenyl)-methylene]-6-chloro-2-indolinone |
| 4.1 | 3-Z-[1-(4-(dimethylamino-methyl)-anilino)-1-(3-iod-phenyl)-methylene]-6-chloro-2-indolinone |
| 4.2 | 3-Z-[1-(4-(N-(dimethylamino-methylcarbonyl)-N-methyl-amino)-anilino)-1-(4-chloro-phenyl)-methylene]-6-chloro-2-indolinone |
| 4.3 | 3-Z-[1-(4-(N-(2-dimethylamino-ethyl)-N-acetyl-amino)-anilino)-1-(4-chloro-phenyl)-methylene]-6-chloro-2-indolinone |
| 4.4 | 3-Z-[1-(4-(N-(4-methyl-piperazin-1-yl-methylcarbonyl)-N-methyl-amino)-anilino)-1-(4-chloro-phenyl)-methylene]-6-chloro-2-indolinone |
| 4.5 | 3-Z-[1-(4-(N-(3-dimethylamino-propyl)-N-acetyl-amino)-anilino)-1-(4-chloro-phenyl)-methylene]-6-chloro-2-indolinone |
| 4.6 | 3-Z-[1-(4-(dimethylamino-methyl)-anilino)-1-(4-chloro-phenyl)-methylene]-6-chloro-2-indolinone |
| 4.7 | 3-Z-[1-(4-(dimethylamino-methyl)-anilino)-1-(4-benzyloxy-phenyl)-methylene]-6-chloro-2-indolinone |
| 4.8 | 3-Z-[1-(4-(N-(dimethylamino-methylcarbonyl)-N-methyl-amino)-anilino)-1-(4-benzyloxy-phenyl)-methylene]-6-chloro-2-indolinone |
| 4.9 | 3-Z-[1-(4-(N-(4-methyl-piperazin-1-yl-methylcarbonyl)-N-methyl-amino)-anilino)-1-(4-benzyloxy-phenyl)-methylene]-6-chloro-2-indolinone |
| 4.10 | 3-Z-[1-(4-(N-(2-dimethylamino-ethyl)-N-acetyl-amino)-anilino)-1-(4-benzyloxy-phenyl)-methylene]-6-chloro-2-indolinone |
| 4.11 | 3-Z-[1-(4-(N-(2-dimethylamino-propyl)-N-acetyl-amino)-anilino)-1-(4-benzyloxy-phenyl)-methylene]-6-chloro-2-indolinone |
| 4.12 | 3-Z-[1-(4-(N-(2-dimethylamino-ethyl)-N-acetyl-amino)-anilino)-1-(3,4-dimethoxy-phenyl)-methylene]-6-chloro-2-indolinone |
| 4.13 | 3-Z-[1-(4-(N-(4-methyl-piperazin-1-yl-methylcarbonyl)-N-methyl-amino)-anilino)-1-(3,4-dimethoxy-phenyl)-methylene]-6-chloro-2-indolinone |
| 4.14 | 3-Z-[1-(4-(N-(2-dimethylamino-ethyl)-N-methylsulphonyl-amino)-anilino)-1-(3,4-dimethoxy-phenyl)-methylene]-6-chloro-2-indolinone |
| 4.15 | 3-Z-[1-(4-(dimethylamino-methyl)-anilino)-1-(3,4-dimethoxy-phenyl)-methylene]-6-chloro-2-indolinone |
| 4.16 | 3-Z-[1-(4-(N-(2-dimethylamino-ethyl)-N-methyl-carbamoyl)-anilino)-1-(3,4-dimethoxy-phenyl)-methylene]-6-chloro-2-indolinone |
| 4.17 | 3-Z-[1-(4-(dimethylamino-methyl)-anilino)-1-(3-hydroxy-4-nitro-phenyl)-methylene]-6-chloro-2-indolinone |
| 5.0 | 3-Z-[1-(4-(N-(dimethylamino-methylcarbonyl)-N-methyl-amino)-anilino)-1-(4-(imidazol-1-yl-methyl)-phenyl)-methylene]-6-chloro-2-indolinone |
| 5.1 | 3-Z-[1-(4-(N-(2-dimethylamino-ethyl)-N-acetyl-amino)-anilino)-1-(4-(imidazol-1-yl-methyl)-phenyl)-methylene]-6-chloro-2-indolinone |
| 5.2 | 3-Z-[1-(4-(N-(4-methyl-piperazin-1-yl-methylcarbonyl)-N-methyl-amino)-anilino)-1-(4-(imidazol-1-yl-methyl)-phenyl)-methylene]-6-chloro-2-indolinone |
| 5.3 | 3-Z-[1-(4-(N-3-dimethylamino-propyl)-N-acetyl-amino)-anilino)-1-(4-(imidazol-1-yl-methyl)-phenyl)-methylene]-6-chloro-2-indolinone |
| 5.4 | 3-Z-[1-(4-(pyrrolidin-1-yl-methyl)-anilino)-1-(4-(2-oxo-pyrrolidin-1-yl)-phenyl)-methylene]-6-chloro-2-indolinone |
| 5.5 | 3-Z-[1-(4-(N-(dimethylamino-methylcarbonyl)-N-methyl-amino)-anilino)-1-(4-(2-oxo-pyrrolidin-1-yl)-phenyl)-methylene]-6-chloro-2-indolinone |
| 5.6 | 3-Z-[1-(4-(dimethylamino-methyl)-anilino)-1-(4-(2-oxo-pyrrolidin-1-yl)-phenyl)-methylene]-6-chloro-2-indolinone |

-continued

| Example | Name |
|---|---|
| 5.7 | 3-Z-[1-(4-(4-methyl-piperazin-1-yl-carbonyl)-anilino)-1-(4-(2-oxo-pyrrolidin-1-yl)-phenyl)-methylene]-6-chloro-2-indolinone |
| 5.8 | 3-Z-[1-(4-(N-(3-dimethylamino-propyl)-N-acetyl-amino)-anilino)-1-(4-(2-oxo-pyrrolidin-1-yl)-phenyl)-methylene]-6-chloro-2-indolinone |
| 5.9 | 3-Z-[1-(4-(2-diethylamino-ethyl-sulphonyl)-anilino)-1-(4-(2-oxo-pyrrolidin-1-yl)-phenyl)-methylene]-6-chloro-2-indolinone |
| 5.10 | 3-Z-[1-(4-(ethylmethylamino-methyl)-anilino)-1-(4-(2-oxo-pyrrolidin-1-yl)-phenyl)-methylene]-6-chloro-2-indolinone |
| 5.11 | 3-Z-[1-(4-(N-tert.butoxycarbonyl-methylamino-methyl)-anilino)-1-(4-(2-oxo-pyrrolidin-1-yl)-phenyl)-methylene]-6-chloro-2-indolinone |
| 5.12 | 3-Z-[1-(4-(N-(dimethylamino-methylcarbonyl)-N-methyl-amino)-anilino)-1-(4-amino-3-nitro-phenyl)-methylene]-6-chloro-2-indolinone |
| 5.13 | 3-Z-[1-(4-(N-(2-dimethylamino-ethyl)-N-methylsulphonyl-amino)-anilino)-1-(4-amino-3-nitro-phenyl)-methylene]-6-chloro-2-indolinone |
| 5.14 | 3-Z-[1-(4-(pyrrolidin-1-yl-methyl)-anilino)-1-(4-amino-3-nitro-phenyl)-methylene]-6-chloro-2-indolinone |
| 5.15 | 3-Z-[1-(4-(4-methyl-piperazin-1-yl-carbonyl)-anilino)-1-(4-amino-3-nitro-phenyl)-methylene]-6-chloro-2-indolinone |
| 5.16 | 3-Z-[1-(4-(N-(2-dimethylamino-ethyl)-N-acetyl-amino)-anilino)-1-(4-amino-3-nitro-phenyl)-methylene]-6-chloro-2-indolinone |
| 5.17 | 3-Z-[1-(4-(N-(3-dimethylamino-propyl)-N-acetyl-amino)-anilino)-1-(4-amino-3-nitro-phenyl)-methylene]-6-chloro-2-indolinone |
| 5.18 | 3-Z-[1-(4-(dimethylamino-methyl)-anilino)-1-(4-nitro-phenyl)-methylene]-6-chloro-2-indolinone |
| 5.19 | 3-Z-[1-(4-(N-(2-dimethylamino-ethyl)-N-acetyl-amino)-anilino)-1-(4-nitro-phenyl)-methylene]-6-chloro-2-indolinone |
| 5.20 | 3-Z-[1-(4-(N-(4-methyl-piperazin-1-yl-methylcarbonyl)-N-methyl-amino)-anilino)-1-(4-nitro-phenyl)-methylene]-6-chloro-2-indolinone |
| 5.21 | 3-Z-[1-(4-(N-(dimethylamino-methylcarbonyl)-N-methyl-amino)-anilino)-1-(4-nitro-phenyl)-methylene]-6-chloro-2-indolinone |
| 5.22 | 3-Z-[1-(4-(4-methyl-piperazin-1-yl-carbonyl)-anilino)-1-(4-nitro-phenyl)-methylene]-6-chloro-2-indolinone |
| 5.23 | 3-Z-[1-(4-(dimethylamino-methyl)-anilino)-1-(4-cyano-phenyl)-methylene]-6-chloro-2-indolinone |
| 6.0 | 3-Z-[1-(4-(N-(2-dimethylamino-ethyl)-N-methylsulphonyl-amino)-anilino)-1-phenyl-methylene]-6-bromo-2-indolinone |
| 6.1 | 3-Z-[1-(4-(N-(dimethylamino-methylcarbonyl)-N-methyl-amino)-anilino)-1-phenyl-methylene]-6-bromo-2-indolinone |
| 6.2 | 3-Z-[1-(4-(dimethylamino-methyl)-anilino)-1-phenyl-methylene]-6-bromo-2-indolinone |
| 6.3 | 3-Z-[1-(4-(N-(2-dimethylamino-ethyl)-N-acetyl-amino)-anilino)-1-phenyl-methylene]-6-bromo-2-indolinone |
| 6.4 | 3-Z-[1-(4-methyl-piperidin-1-yl-amino)-1-phenyl-methylene]-6-bromo-2-indolinone |
| 6.5 | 3-Z-[1-(4-(N-tert.butoxycarbonyl-ethylamino-methyl)-anilino)-1-phenyl-methylene]-6-bromo-2-indolinone |
| 6.6 | 3-Z-[1-(4-(1-methyl-imidazol-2-yl)-anilino)-1-phenyl-methylene]-6-bromo-2-indolinone |
| 6.7 | 3-Z-[1-(4-(N-(2-dimethylamino-ethyl)-N-benzylsulphonyl-amino)-anilino)-1-phenyl-methylene]-6-bromo-2-indolinone |
| 6.8 | 3-Z-[1-(4-(N-(2-dimethylamino-ethyl)-N-(n-propylsulphonyl)-amino)-anilino)-1-phenyl-methylene]-6-bromo-2-indolinone |
| 6.9 | 3-Z-[1-(4-(4-methyl-piperazin-1-yl-carbonyl)-anilino)-1-phenyl-methylene]-6-bromo-2-indolinone |
| 6.10 | 3-Z-[1-(4-(N-(3-dimethylamino-propyl)-N-acetyl-amino)-anilino)-1-phenyl-methylene]-6-bromo-2-indolinone |
| 6.11 | 3-Z-[1-(4-(N-(4-methyl-piperazin-1-yl-methylcarbonyl)-N-methyl-amino)-anilino)-1-phenyl-methylene]-6-bromo-2-indolinone |
| 6.12 | 3-Z-[1-(4-(pyrrolidin-1-yl-methyl)-anilino)-1-phenyl-methylene]-6-bromo-2-indolinone |
| 6.13 | 3-Z-[1-(4-(N-(N-(2-dimethylamino-ethyl)-N-methyl-amino-methylcarbonyl)-N-methyl-amino)-anilino)-1-phenyl-methylene]-6-bromo-2-indolinone |
| 6.14 | 3-Z-[1-(4-((4-methyl-piperazin-1-yl)-methyl)-anilino)-1-phenyl-methylene]-6-bromo-2-indolinone |
| 6.15 | 3-Z-[1-(4-(N-((2-dimethylamino-ethyl)-carbonyl)-N-methyl-amino)-anilino)-1-phenyl-methylene]-6-bromo-2-indolinone |
| 6.16 | 3-Z-[1-(4-(N-(2-dimethylamino-ethyl)-N-methyl-amino-methyl)-anilino)-1-phenyl-methylene]-6-bromo-2-indolinone |
| 6.17 | 3-Z-[1-(4-(N-tert.butoxycarbonyl-methylamino-methyl)-anilino)-1-phenyl-methylene]-6-bromo-2-indolinone |
| 7.0 | 3-Z-[1-(4-(N-(2-dimethylamino-ethyl)-N-methylsulphonyl-amino)-anilino)-1-phenyl-methylene]-6-cyano-2-indolinone |
| 7.1 | 3-Z-[1-(4-(N-(dimethylamino-methylcarbonyl)-N-methyl-amino)-anilino)-1-phenyl-methylene]-6-cyano-2-indolinone |
| 7.2 | 3-Z-[1-(4-(dimethylamino-methyl)-anilino)-1-phenyl-methylene]-6-cyano-2-indolinone |

-continued

| Example | Name |
|---|---|
| 7.3 | 3-Z-[1-(4-(N-(2-dimethylamino-ethyl)-N-acetyl-amino)-anilino)-1-phenyl-methylene]-6-cyano-2-indolinone |
| 7.4 | 3-Z-[1-(4-bromo-anilino)-1-phenyl-methylene]-6-cyano-2-indolinone |
| 7.5 | 3-Z-[1-(4-(N-tert.butoxycarbonyl-ethylamino-methyl)-anilino)-1-phenyl-methylene]-6-cyano-2-indolinone |
| 7.6 | 3-Z-[1-(4-(piperidin-1-yl-methyl)-anilino)-1-phenyl-methylene]-6-cyano-2-indolinone |
| 7.7 | 3-Z-[1-(4-(2-dimethylamino-ethoxy)-anilino)-1-phenyl-methylene]-6-cyano-2-indolinone |
| 7.8 | 3-Z-[1-(4-(N-(2-dimethylamino-ethyl)-carbamoyl)-anilino)-1-phenyl-methylene]-6-cyano-2-indolinone |
| 7.9 | 3-Z-[1-(4-(4-methyl-piperazin-1-yl-carbonyl)-anilino)-1-phenyl-methylene]-6-cyano-2-indolinone |
| 7.10 | 3-Z-[1-(4-(N-(3-dimethylamino-propyl)-N-acetyl-amino)-anilino)-1-phenyl-methylene]-6-cyano-2-indolinone |
| 7.11 | 3-Z-[1-(4-(N-(4-methyl-piperazin-1-yl-methylcarbonyl)-N-methyl-amino)-anilino)-1-phenyl-methylene]-6-cyano-2-indolinone |
| 7.12 | 3-Z-[1-(4-(pyrrolidin-1-yl-methyl)-anilino)-1-phenyl-methylene]-6-cyano-2-indolinone |
| 7.13 | 3-Z-[1-(4-(N-(N-(2-dimethylamino-ethyl)-N-methyl-amino-methylcarbonyl)-N-methyl-amino)-anilino)-1-phenyl-methylene]-6-cyano-2-indolinone |
| 7.14 | 3-Z-[1-(4-(N-(3-dimethylamino-propyl)-carbamoyl)-anilino)-1-phenyl-methylene]-6-cyano-2-indolinone |
| 7.15 | 3-Z-[1-(4-(N-(2-dimethylamino-ethyl)-N-methyl-carbamoyl)-anilino)-1-phenyl-methylene]-6-cyano-2-indolinone |
| 7.16 | 3-Z-[1-(4-(N-(3-dimethylamino-propyl)-N-methyl-carbamoyl)-anilino)-1-phenyl-methylene]-6-cyano-2-indolinone |
| 7.17 | 3-Z-[1-(4-(N-((2-dimethylamino-ethyl)-carbonyl)-N-methyl-amino)-anilino)-1-phenyl-methylene]-6-cyano-2-indolinone |
| 7.18 | 3-Z-[1-(4-(N-(4-tert.butoxycarbonyl-piperazin-1-yl-methylcarbonyl)-N-methyl-amino)-anilino)-1-phenyl-methylene]-6-cyano-2-indolinone |
| 7.19 | 3-Z-[1-(3-(dimethylamino-methyl)-anilino)-1-phenyl-methylene]-6-cyano-2-indolinone |
| 7.20 | 3-Z-[1-(3-(N-(2-dimethylamino-ethyl)-N-methyl-carbamoyl)-anilino)-1-phenyl-methylene]-6-cyano-2-indolinone |
| 7.21 | 3-Z-[1-(4-(N-(morpholin-4-yl-methylcarbonyl)-N-methyl-amino)-anilino)-1-phenyl-methylene]-6-cyano-2-indolinone |
| 7.22 | 3-Z-[1-(4-(N-(4-methyl-homopiperazin-1-yl-methylcarbonyl)-N-methyl-amino)-anilino)-1-phenyl-methylene]-6-cyano-2-indolinone |
| 7.23 | 3-Z-[1-(4-(N-(4-ethyl-piperazin-1-yl-methylcarbonyl)-N-methyl-amino)-anilino)-1-phenyl-methylene]-6-cyano-2-indolinone |
| 7.24 | 3-Z-[1-(3-(N-(4-methyl-piperazin-1-yl-methylcarbonyl)-N-methyl-amino)-anilino)-1-phenyl-methylene]-6-cyano-2-indolinone |
| 7.25 | 3-Z-[1-(3-(N-(dimethylamino-methylcarbonyl)-N-methyl-amino)-anilino)-1-phenyl-methylene]-6-bromo-2-indolinone |
| 7.26 | 3-Z-[1-(3-(N-(4-methyl-piperazin-1-yl-methylcarbonyl)-amino)-anilino)-1-phenyl-methylene]-6-cyano-2-indolinone |
| 7.27 | 3-Z-[1-(4-(N-(3-dimethylamino-propyl)-N-methyl-carbamoylmethyl)-anilino)-1-phenyl-methylene]-6-cyano-2-indolinone |
| 7.28 | 3-Z-[1-(4-(N-(2-dimethylamino-ethyl)-N-methyl-carbamoylmethyl)-anilino)-1-phenyl-methylene]-6-cyano-2-indolinone |
| 7.29 | 3-Z-[1-(4-(4-methyl-piperazin-1-yl-carbonylmethyl)-anilino)-1-phenyl-methylene]-6-cyano-2-indolinone |
| 8.0 | 3-Z-[1-(4-(N-(2-dimethylamino-ethyl)-N-methylsulphonyl-amino)-anilino)-1-phenyl-methylene]-6-fluoro-2-indolinone |
| 8.1 | 3-Z-[1-(4-(N-(dimethylamino-methylcarbonyl)-N-methyl-amino)-anilino)-1-phenyl-methylene]-6-fluoro-2-indolinone |
| 8.2 | 3-Z-[1-(4-(dimethylamino-methyl)-anilino)-1-phenyl-methylene]-6-fluoro-2-indolinone |
| 8.3 | 3-Z-[1-(4-(N-(2-dimethylamino-ethyl)-N-acetyl-amino)-anilino)-1-phenyl-methylene]-6-fluoro-2-indolinone |
| 8.4 | 3-Z-[1-(4-(N-tert.butoxycarbonyl-ethylamino-methyl)-anilino)-1-phenyl-methylene]-6-fluoro-2-indolinone |
| 8.5 | 3-Z-[1-(4-(1-methyl-imidazol-2-yl)-anilino)-1-phenyl-methylene]-6-fluoro-2-indolinone |
| 8.6 | 3-Z-[1-(4-(N-(2-dimethylamino-ethyl)-N-propylsulphonyl-amino)-anilino)-1-phenyl-methylene]-6-fluoro-2-indolinone |
| 8.7 | 3-Z-[1-(4-(4-methyl-piperazin-1-yl-carbonyl)-anilino)-1-phenyl-methylene]-6-fluoro-2-indolinone |
| 8.8 | 3-Z-[1-(4-(N-(3-dimethylamino-propyl)-N-acetyl-amino)-anilino)-1-phenyl-methylene]-6-fluoro-2-indolinone |
| 8.9 | 3-Z-[1-(4-(N-(4-methyl-piperazin-1-yl-methylcarbonyl)-N-methyl-amino)-anilino)-1-phenyl-methylene]-6-fluoro-2-indolinone |
| 8.10 | 3-Z-[1-(4-(pyrrolidin-1-yl-methyl)-anilino)-1-phenyl-methylene]-6-fluoro-2-indolinone |

-continued

| Example | Name |
|---|---|
| 8.11 | 3-Z-[1-(4-(N-(N-(2-dimethylamino-ethyl)-N-methyl-amino-methylcarbonyl)-N-methyl-amino)-anilino)-1-phenyl-methylene]-6-fluoro-2-indolinone |
| 8.12 | 3-Z-[1-(4-((4-methyl-piperazin-1-yl)-methyl)-anilino)-1-phenyl-methylene]-6-fluoro-2-indolinone |
| 8.13 | 3-Z-[1-(4-(N-((2-dimethylamino-ethyl)-carbonyl)-N-methyl-amino)-anilino)-1-phenyl-methylene]-6-fluoro-2-indolinone |
| 8.14 | 3-Z-[1-(4-(N-(2-dimethylamino-ethyl)-N-methyl-amino-methyl)-anilino)-1-phenyl-methylene]-6-fluoro-2-indolinone |
| 8.15 | 3-Z-[1-(4-(piperidin-1-yl-methyl)-anilino)-1-phenyl-methylene]-6-fluoro-2-indolinone |
| 8.16 | 3-Z-[1-(4-(N-tert.butoxycarbonyl-methylamino-methyl)-anilino)-1-phenyl-methylene]-6-fluoro-2-indolinone |
| 8.17 | 3-Z-[1-(4-(N-methyl-N-methylsulphonyl-amino)-anilino)-1-phenyl-methylene]-6-fluoro-2-indolinone |
| 8.18 | 3-Z-[1-(4-methylsulphonyl-anilino)-1-phenyl-methylene]-6-fluoro-2-indolinone |
| 8.19 | 3-Z-[1-(4-(N-methyl-N-acetyl-amino)-anilino)-1-phenyl-methylene]-6-fluoro-2-indolinone |
| 8.20 | 3-Z-(1-anilino-1-phenyl-methylen)-6-fluoro-2-indolinone |
| 8.21 | 3-Z-[1-(4-(N-(dimethylamino-carbonylmethyl)-N-methylsulphonyl-amino)-anilino)-1-phenyl-methylene]-6-fluoro-2-indolinone |
| 9.0 | 3-Z-[1-(4-(dimethylaminomethyl)-anilino)-1-(4-iod-phenyl)-methylene]-6-fluoro-2-indolinone |
| 9.1 | 3-Z-[1-(4-(dimethylaminomethyl)-anilino)-1-(3-fluoro-phenyl)-methylene]-6-fluoro-2-indolinone |
| 9.2 | 3-Z-[1-(4-(N-(3-dimethylamino-propyl)-N-acetyl-amino)-anilino)-1-(3-fluoro-phenyl)-methylene]-6-fluoro-2-indolinone |
| 9.3 | 3-Z-[1-(4-(N-(4-methyl-piperazin-1-yl-methylcarbonyl)-N-methyl-amino)-anilino)-1-(3-fluoro-phenyl)-methylene]-6-fluoro-2-indolinone |
| 9.4 | 3-Z-[1-(4-(dimethylaminomethyl)-anilino)-1-(4-(2-acetylamino-ethyl)-phenyl)-methylene]-6-fluoro-2-indolinone |
| 9.5 | 3-Z-[1-(4-N-(3-dimethylamino-propyl-)-N-acetyl-amino)-anilino)-1-(4-(2-acetylamino-ethyl)-phenyl)-methylene]-6-fluoro-2-indolinone |
| 9.6 | 3-Z-[1-(4-(N-(4-methyl-piperazin-1-yl-methylcarbonyl)-N-methyl-amino)-anilino)-1-(4-(2-acetylamino-ethyl)-phenyl)-methylene]-6-fluoro-2-indolinone |
| 9.7 | 3-Z-[1-(4-(dimethylaminomethyl)-anilino)-1-(3,4,5-trifluoro-phenyl)-methylene]-6-fluoro-2-indolinone |
| 9.8 | 3-Z-[1-(4-(N-(3-dimethylamino-propyl)-N-acetyl-amino)-anilino)-1-(3,4,5-trifluoro-phenyl)-methylene]-6-fluoro-2-indolinone |
| 9.9 | 3-Z-[1-(4-(N-(4-methyl-piperazin-1-yl-methylcarbonyl)-N-methyl-amino)-anilino)-1-(3,4,5-trifluoro-phenyl)-methylene]-6-fluoro-2-indolinone |
| 9.10 | 3-Z-[1-(4-(dimethylaminomethyl)-anilino)-1-(4-methoxycarbonylmethyl-phenyl)-methylene]-6-fluoro-2-indolinone |
| 9.11 | 3-Z-[1-(4-(dimethylaminomethyl)-anilino)-1-(3-iod-phenyl)-methylene]-6-fluoro-2-indolinone |
| 9.12 | 3-Z-[1-(4-(dimethylaminomethyl)-anilino)-1-(3-methoxycarbonylmethyl-phenyl)-methylene]-6-fluoro-2-indolinone |
| 9.13 | 3-Z-[1-(4-(dimethylaminomethyl)-anilino)-1-(3-(N-tert.butoxycarbonyl-aminomethyl)-phenyl)-methylene]-6-fluoro-2-indolinone |
| 9.14 | 3-Z-[1-(4-(N-(2-dimethylamino-ethyl)-N-methylsulphonyl-amino)-anilino)-1-(4-methoxycarbonylmethyl-phenyl)-methylene]-6-fluoro-2-indolinone |
| 9.15 | 3-Z-[1-(4-(N-(4-methyl-piperazin-1-yl-methylcarbonyl)-N-methyl-amino)-anilino)-1-(4-methoxycarbonylmethyl-phenyl)-methylene]-6-fluoro-2-indolinone |
| 9.16 | 3-Z-[1-(4-(dimethylaminomethyl)-anilino)-1-(3-cyanomethyl-phenyl)-methylene]-6-fluoro-2-indolinone |
| 9.17 | 3-Z-[1-(4-(N-(4-methyl-piperazin-1-yl-methylcarbonyl)-N-methyl-amino)-anilino)-1-(4-(N-tert.butoxycarbonyl-aminomethyl)-phenyl)-methylene]-6-fluoro-2-indolinone |
| 9.18 | 3-Z-[1-(4-(dimethylaminomethyl)-anilino)-1-(4-(N-tert.butoxycarbonyl-aminomethyl)-phenyl)-methylene]-6-fluoro-2-indolinone |
| 9.19 | 3-Z-[1-(4-(dimethylaminomethyl)-anilino)-1-(3-(N-tert.butoxycarbonyl-2-amino-ethyl)-phenyl)-methylene]-6-fluoro-2-indolinone |
| 9.20 | 3-Z-[1-(4-(N-acetyl-N-methyl-amino)-anilino)-1-(4-(2-methoxycarbonyl-ethyl)-phenyl)-methylene]-6-fluoro-2-indolinone |
| 9.21 | 3-Z-[1-(4-(N-(4-methyl-piperazin-1-yl-methylcarbonyl)-N-methyl-amino)-anilino)-1-(4-(2-methoxycarbonyl-ethyl)-phenyl)-methylene]-6-fluoro-2-indolinone |
| 9.22 | 3-Z-[1-(4-(N-(2-dimethylamino-ethyl)-N-methylsulphonyl-amino)-anilino)-1-(4-methoxycarbonylmethyl-phenyl)-methylene]-6-fluoro-2-indolinone |
| 9.23 | 3-Z-[1-(4-(N-(3-dimethylamino-propyl)-N-acetyl-amino)-anilino)-1-4-(2-methoxycarbonyl-ethyl)-phenyl)-methylene]-6-fluoro-2-indolinone |

-continued

| Example | Name |
|---|---|
| 9.24 | 3-Z-[1-(4-(N-tert.butoxycarbonyl-methylamino-methyl)-anilino)-1-(4-(2-methoxycarbonyl-ethyl)-phenyl)-methylene]-6-fluoro-2-indolinone |
| 9.25 | 3-Z-[1-(4-(4-methyl-piperazin-1-yl-carbonyl)-anilino)-1-(4-(2-methoxycarbonyl-ethyl)-phenyl)-methylene]-6-fluoro-2-indolinone |
| 9.26 | 3-Z-[1-(4-(1-methyl-imidazol-2-yl)-anilino)-1-(4-(2-methoxycarbonyl-ethyl)-phenyl)-methylene]-6-fluoro-2-indolinone |
| 9.27 | 3-Z-[1-(4-methylsulphonyl-anilino)-1-(4-(2-methoxycarbonyl-ethyl)-phenyl)-methylene]-6-fluoro-2-indolinone |
| 9.28 | 3-Z-[1-(4-(N-(4-methyl-piperazin-1-yl-methylcarbonyl)-N-methyl-amino)-anilino)-1-(3-methoxycarbonylmethyl-phenyl)-methylene]-6-fluoro-2-indolinone |
| 9.29 | 3-Z-[1-(4-(N-(2-dimethylamino-ethyl)-N-methylsulphonyl-amino)-anilino)-1-(3-methoxycarbonylmethyl-phenyl)-methylene]-6-fluoro-2-indolinone |
| 9.30 | 3-Z-[1-(4-(4-methyl-piperazin-1-yl-carbonyl)-anilino)-1-(3-methoxycarbonylmethyl-phenyl)-methylene]-6-fluoro-2-indolinone |
| 9.31 | 3-Z-[1-(4-(N-(dimethylamino-methylcarbonyl)-N-methyl-amino)-anilino)-1-(3-methoxycarbonylmethyl-phenyl)-methylene]-6-fluoro-2-indolinone |
| 9.32 | 3-Z-[1-(4-(N-(3-dimethylamino-propyl)-N-acetyl-amino)-anilino)-1-(3-methoxycarbonylmethyl-phenyl)-methylene]-6-fluoro-2-indolinone |
| 9.33 | 3-Z-[1-(4-(N-(2-dimethylamino-ethyl)-N-acetyl-amino)-anilino)-1-(3-methoxycarbonylmethyl-phenyl)-methylene]-6-fluoro-2-indolinone |
| 9.34 | 3-Z-[1-(4-(N-(4-dimethylamino-butylcarbonyl)-N-methyl-amino)-anilino)-1-(3-methoxycarbonylmethyl-phenyl)-methylene]-6-fluoro-2-indolinone |
| 9.35 | 3-Z-[1-anilino-1-(4-methoxycarbonylmethyl-phenyl)-methylene]-6-fluoro-2-indolinone |
| 9.36 | 3-Z-[1-(4-(1-methyl-imidazol-2-yl)-anilino)-1-(4-methoxycarbonylmethyl-phenyl)-methylene]-6-fluoro-2-indolinone |
| 9.37 | 3-Z-[1-(4-(4-methyl-piperazin-1-yl-carbonyl)-anilino)-1-(4-methoxycarbonylmethyl-phenyl)-methylene]-6-fluoro-2-indolinone |
| 9.38 | 3-Z-[1-(4-(N-(dimethylamino-carbonylmethyl)-N-methylsulphonyl-amino)-anilino)-1-(4-methoxycarbonylmethyl-phenyl)-methylene]-6-fluoro-2-indolinone |
| 9.39 | 3-Z-[1-(4-(N-(dimethylamino-methylcarbonyl)-N-methyl-amino)-anilino)-1-(4-methoxycarbonylmethyl-phenyl)-methylene]-6-fluoro-2-indolinone |
| 9.40 | 3-Z-[1-(4-(N-methyl-N-acetyl-amino)-anilino)-1-(4-methoxycarbonylmethyl-phenyl)-methylene]-6-fluoro-2-indolinone |
| 9.41 | 3-Z-[1-(4-(N-(2-dimethylamino-ethylcarbonyl)-N-methyl-amino)-anilino)-1-(4-methoxycarbonylmethyl-phenyl)-methylene]-6-fluoro-2-indolinone |
| 9.42 | 3-Z-[1-(4-methylsulphonyl-anilino)-1-(4-methoxycarbonylmethyl-phenyl)-methylene]-6-fluoro-2-indolinone |
| 9.43 | 3-Z-[1-(4-(N-(3-dimethylamino-propylcarbonyl)-N-methyl-amino)-anilino)-1-(4-methoxycarbonylmethyl-phenyl)-methylene]-6-fluoro-2-indolinone |
| 9.44 | 3-Z-[1-(4-(N-(3-dimethylamino-propyl)-N-acetyl-amino)-anilino)-1-(4-methoxycarbonylmethyl-phenyl)-methylene]-6-fluoro-2-indolinone |
| 9.45 | 3-Z-[1-anilino-1-(3-methoxycarbonylmethyl-phenyl)-methylene]-6-fluoro-2-indolinone |
| 9.46 | 3-Z-[1-(4-methylsulphonyl-anilino)-1-(3-methoxycarbonylmethyl-phenyl)-methylene]-6-fluoro-2-indolinone |
| 9.47 | 3-Z-[1-(4-(1-methyl-imidazol-2-yl)-anilino)-1-(3-methoxycarbonylmethyl-phenyl)-methylene]-6-fluoro-2-indolinone |
| 9.48 | 3-Z-[1-(4-(N-(dimethylamino-carbonylmethyl)-N-methylsulphonyl-amino)-anilino)-1-(3-methoxycarbonylmethyl-phenyl)-methylene]-6-fluoro-2-indolinone |
| 9.49 | 3-Z-[1-(4-(N-(3-dimethylamino-propylcarbonyl))-N-methyl-amino)-anilino)-1-(3-methoxycarbonylmethyl-phenyl)-methylene]-6-fluoro-2-indolinone |
| 9.50 | 3-Z-[1-(4-(N-(2-dimethylamino-ethylcarbonyl)-N-methyl-amino)-anilino)-1-(3-methoxycarbonylmethyl-phenyl)-methylene]-6-fluoro-2-indolinone |
| 9.51 | 3-Z-[1-(4-(N-(4-methyl-piperazin-1-yl-methylcarbonyl)-N-methyl-amino)-anilino)-1-(3-(2-methoxycarbonyl-ethyl)-phenyl)-methylene]-6-fluoro-2-indolinone |
| 9.52 | 3-Z-[1-(4-(N-(2-dimethylamino-ethyl)-N-methylsulphonyl-amino)-anilino)-1-(3-(2-methoxycarbonyl-ethyl)-phenyl)-methylene]-6-fluoro-2-indolinone |
| 9.53 | 3-Z-[1-(4-(N-(dimethylamino-methylcarbonyl)-N-methyl-amino)-anilino)-1-(3-(2-methoxycarbonyl-ethyl)-phenyl)-methylene]-6-fluoro-2-indolinone |
| 9.54 | 3-Z-[1-(4-(N-(3-dimethylamino-propyl)-N-acetyl-amino)-anilino)-1-(3-(2-methoxycarbonyl-ethyl)-phenyl)-methylene]-6-fluoro-2-indolinone |
| 9.55 | 3-Z-[1-(4-(N-(4-methyl-piperazin-1-yl-methylcarbonyl)-N-methyl-amino)-anilino)-1-(3-(N-tert.butoxycarbonyl-aminomethyl)-phenyl)-methylene]-6-fluoro-2-indolinone |
| 9.56 | 3-Z-[1-(4-(N-methyl-N-acetyl-amino)-anilino)-1-(3-acetylaminomethyl-phenyl)-methylene]-6-chloro-2-indolinone |

-continued

| Example | Name |
|---|---|
| 9.57 | 3-Z-[1-(4-(N-(3-dimethylamino-propyl)-N-acetyl-amino)-anilino)-1-(3-acetylaminomethyl-phenyl)-methylene]-6-chloro-2-indolinone |
| 9.58 | 3-Z-[1-(4-(N-(2-dimethylamino-ethyl)-N-methylsulphonyl-amino)-anilino)-1-(3-acetylaminomethyl-phenyl)-methylene]-6-chloro-2-indolinone |
| 9.59 | 3-Z-[1-(4-(N-(dimethylamino-methylcarbonyl)-N-methyl-amino)-anilino)-1-(3-acetylaminomethyl-phenyl)-methylene]-6-chloro-2-indolinone |
| 9.60 | 3-Z-[1-(4-(2-dimethylamino-ethyl)-anilino)-1-(4-(2-methoxycarbonyl-ethyl)-phenyl)-methylene]-6-fluoro-2-indolinone |
| 9.61 | 3-Z-[1-(4-(N-(2-dimethylamino-ethylcarbonyl)-N-methyl-amino)-anilino)-1-(4-(2-methoxycarbonyl-ethyl)-phenyl)-methylene]-6-fluoro-2-indolinone |
| 9.62 | 3-Z-[1-(4-(N-(dimethylamino-methylcarbonyl)-N-methyl-amino)-anilino)-1-(4-(2-methoxycarbonyl-ethyl)-phenyl)-methylene]-6-fluoro-2-indolinone |
| 9.63 | 3-Z-[1-(4-(2-dimethylamino-ethyl)-anilino)-1-(3-(2-ethoxycarbonyl-ethyl)-phenyl)-methylene]-6-fluoro-2-indolinone |
| 9.64 | 3-Z-[1-(4-(N-(2-dimethylamino-ethyl)-N-acetyl-amino)-anilino)-1-(4-(2-methoxycarbonyl-ethyl)-phenyl)-methylene]-6-fluoro-2-indolinone |
| 9.65 | 3-Z-[1-(4-(N-(3-dimethylamino-propylcarbonyl)-N-methyl-amino)-anilino)-1-(3-(2-ethoxycarbonyl-ethyl)-phenyl)-methylene]-6-fluoro-2-indolinone |
| 9.66 | 3-Z-[1-(4-(N-(4-dimethylamino-butylcarbonyl)-N-methyl-amino)-anilino)-1-(3-(2-ethoxycarbonyl-ethyl)-phenyl)-methylene]-6-fluoro-2-indolinone |
| 9.67 | 3-Z-[1-(4-(1-methyl-imidazol-2-yl)-anilino)-1-(3-(2-ethoxycarbonyl-ethyl)-phenyl)-methylene]-6-fluoro-2-indolinone |
| 9.68 | 3-Z-[1-(4-(N-(4-dimethylamino-butylcarbonyl)-N-methyl-amino)-anilino)-1-(4-(2-methoxycarbonyl-ethyl)-phenyl)-methylene]-6-fluoro-2-indolinone |
| 9.69 | 3-Z-[1-anilino-1-(4-(2-methoxycarbonyl-ethyl)-phenyl)-methylene]-6-fluoro-2-indolinone |
| 9.70 | 3-Z-[1-(4-(pyrrolidin-1-yl-methyl)-anilino)-1-(4-(2-methoxycarbonyl-ethyl)-phenyl)-methylene]-6-fluoro-2-indolinone |
| 9.71 | 3-Z-[1-(4-(diethylaminomethyl)-anilino)-1-(4-(2-methoxycarbonyl-ethyl)-phenyl)-methylene]-6-fluoro-2-indolinone |
| 9.72 | 3-Z-[1-(4-(N-tert.butoxycarbonyl-amino-methyl)-anilino)-1-(4-(2-methoxycarbonyl-ethyl)-phenyl)-methylene]-6-fluoro-2-indolinone |
| 9.73 | 3-Z-[1-(4-(2-dimethylamino-ethyl)-anilino)-1-(3-methoxycarbonylmethyl-phenyl)-methylene]-6-fluoro-2-indolinone |
| 9.74 | 3-Z-[1-(4-(2-dimethylamino-ethyl)-anilino)-1-(4-methoxycarbonylmethyl-phenyl)-methylene]-6-fluoro-2-indolinone |
| 9.75 | 3-Z-[1-(4-(dimethylaminomethyl)-anilino)-1-(3-(2-ethoxycarbonyl-ethyl)-phenyl)-methylene]-6-fluoro-2-indolinone |
| 9.76 | 3-Z-[1-(4-(2-dimethylamino-ethyl)-anilino)-1-(4-(2-methoxycarbonyl-ethyl)-phenyl)-methylene]-6-chloro-2-indolinone |
| 9.77 | 3-Z-[1-(4-(1-methyl-imidazol-2-yl)-anilino)-1-(4-(2-ethoxycarbonyl-ethyl)-phenyl)-methylene]-6-chloro-2-indolinone |
| 9.78 | 3-Z-[1-(4-dimethylaminomethyl-anilino)-1-(4-(2-methoxycarbonyl-ethyl)-phenyl)-methylene]-6-chloro-2-indolinone |
| 9.79 | 3-Z-[1-(4-dimethylaminomethyl-anilino)-1-(4-(2-ethoxycarbonyl-ethyl)-phenyl)-methylene]-6-fluoro-2-indolinone |
| 9.80 | 3-Z-[1-(4-((4-methyl-piperazin-1-yl)-methyl)-anilino)-1-(3-(2-methoxycarbonyl-ethyl)-phenyl)-methylene]-6-fluoro-2-indolinone |
| 9.81 | 3-Z-[1-(4-(imidazol-1-yl-methyl)-anilino)-1-(3-(2-methoxycarbonyl-ethyl)-phenyl)-methylene]-6-fluoro-2-indolinone |
| 9.82 | 3-Z-[1-(4-((4-methyl-piperazin-1-yl)-methyl)-anilino)-1-(4-(2-methoxycarbonyl-ethyl)-phenyl)-methylene]-6-fluoro-2-indolinone |
| 9.83 | 3-Z-[1-(4-(imidazol-1-yl-methyl)-anilino)-1-(4-(2-methoxycarbonyl-ethyl)-phenyl)-methylene]-6-fluoro-2-indolinone |
| 9.84 | 3-Z-[1-(4-(N-(2-dimethylamino-ethyl)-N-methyl-aminomethyl)-anilino)-1-(4-(2-methoxycarbonyl-ethyl)-phenyl)-methylene]-6-fluoro-2-indolinone |
| 9.85 | 3-Z-[1-(4-(N-(2-dimethylamino-ethyl)-N-methyl-aminomethyl)-anilino)-1-(3-(2-ethoxycarbonyl-ethyl)-phenyl)-methylene]-6-fluoro-2-indolinone |
| 9.86 | 3-Z-[1-(4-(pyrrolidin-1-yl-methyl)-anilino)-1-(4-(2-methoxycarbonyl-ethyl)-phenyl)-methylene]-6-chloro-2-indolinone |
| 9.87 | 3-Z-[1-anilino-1-(3-(2-ethoxycarbonyl-ethyl)-phenyl)-methylene]-6-fluoro-2-indolinone |
| 9.88 | 3-Z-[1-(4-(N-tert.butoxycarbonyl-amino-methyl)-anilino)-1-(3-(2-ethoxycarbonyl-ethyl)-phenyl)-methylene]-6-fluoro-2-indolinone |
| 9.89 | 3-Z-[1-(4-(N-tert.butoxycarbonyl-methylamino-methyl)-anilino)-1-(3-(2-ethoxycarbonyl-ethyl)-phenyl)-methylene]-6-fluoro-2-indolinone |
| 9.90 | 3-Z-[1-(4-dimethylaminomethyl-anilino)-1-(3-methoxycarbonylmethoxy-phenyl)-methylene]-6-fluoro-2-indolinone |
| 9.91 | 3-Z-[1-(4-dimethylaminomethyl-anilino)-1-(4-methoxycarbonylmethoxy-phenyl)-methylene]-6-fluoro-2-indolinone |
| 9.92 | 3-Z-[1-(4-dimethylaminomethyl-anilino)-1-(3-(2-ethoxycarbonyl-ethoxy)-phenyl)-methylene]-6-fluoro-2-indolinone |

-continued

| Example | Name |
|---|---|
| 9.93 | 3-Z-[1-(4-(pyrrolidin-1-yl-methyl)-anilino)-1-(4-(2-methoxycarbonyl-ethyl)-phenyl)-methylene]-6-bromo-2-indolinone |
| 9.94 | 3-Z-[1-(4-(dimethylaminomethyl)-anilino)-1-(4-(2-methoxycarbonyl-ethyl)-phenyl)-methylene]-6-bromo-2-indolinone |
| 9.95 | 3-Z-[1-(4-(diethylaminomethyl)-anilino)-1-(4-(2-methoxycarbonyl-ethyl)-phenyl)-methylene]-6-bromo-2-indolinone |
| 9.96 | 3-Z-[1-(3-(dimethylaminomethyl-anilino)-1-(4-(2-methoxycarbonyl-ethyl)-phenyl)-methylene]-6-fluoro-2-indolinone |
| 9.97 | 3-Z-[1-(3-dimethylaminomethyl-anilino)-1-(3-(2-ethoxycarbonyl-ethyl)-phenyl)-methylene]-6-fluoro-2-indolinone |
| 9.98 | 3-Z-[1-(3-dimethylaminomethyl-anilino)-1-(4-(2-methoxycarbonyl-ethyl)-phenyl)-methylene]-6-chloro-2-indolinone |
| 10.0 | 3-Z-[1-(4-(dimethylaminomethyl)-anilino)-1-(3,4-dimethoxy-phenyl)-methylene]-6-cyano-2-indolinone |
| 11.0 | 3-Z-[1-(4-(N-methyl-N-methylsulphonyl-amino)-anilino)-1-(3-(2-methoxycarbonyl-vinyl)-phenyl)-methylene]-6-chloro-2-indolinone |
| 11.1 | 3-Z-[1-(4-(dimethylaminomethyl)-anilino)-1-(4-(2-methoxycarbonyl-vinyl)-phenyl)-methylene]-6-chloro-2-indolinone |
| 11.2 | 3-Z-[1-(4-(dimethylaminomethyl)-anilino)-1-(4-(2-carbamoyl-vinyl)-phenyl)-methylene]-6-fluoro-2-indolinone |
| 11.3 | 3-Z-[1-(4-(dimethylaminomethyl)-anilino)-1-(4-(2-methoxycarbonyl-vinyl)-phenyl)-methylene]-6-fluoro-2-indolinone |
| 11.4 | 3-Z-[1-(4-(dimethylaminomethyl)-anilino)-1-(3-(2-methoxycarbonyl-vinyl)-phenyl)-methylene]-6-fluoro-2-indolinone |
| 12.0 | 3-Z-[1-(4-dimethylaminomethyl-anilino)-1-(3-(2-methoxycarbonyl-ethyl)-phenyl)-methylene]-6-chloro-2-indolinone |
| 12.1 | 3-Z-[1-(4-(N-methyl-N-methylsulphonyl-amino)-anilino)-1-(3-(2-methoxycarbonyl-ethyl)-phenyl)-methylene]-6-chloro-2-indolinone |
| 12.2 | 3-Z-[1-(4-dimethylaminomethyl-anilino)-1-(4-(2-carbamoyl-ethyl)-phenyl)-methylene]-6-fluoro-2-indolinone |
| 12.3 | 3-Z-[1-(4-dimethylaminomethyl-anilino)-1-(4-(2-methoxycarbonyl-ethyl)-phenyl)-methylene]-6-fluoro-2-indolinone |
| 12.4 | 3-Z-[1-(4-dimethylaminomethyl-anilino)-1-(3-(2-methoxycarbonyl-ethyl)-phenyl)-methylene]-6-fluoro-2-indolinone |
| 13.0 | 3-Z-[1-(4-dimethylaminomethyl-anilino)-1-(4-amino-phenyl)-methylene]-6-chloro-2-indolinone |
| 13.1 | 3-Z-[1-(4-(N-((2-dimethylamino-ethyl)-Carbonyl)-N-methyl-amino)-anilino)-1-(4-amino-phenyl)-methylene]-6-chloro-2-indolinone |
| 13.2 | 3-Z-[1-(4-(N-(4-methyl-piperazin-1-yl-methylcarbonyl)-N-methyl-amino)-anilino)-1-(4-amino-phenyl)-methylene]-6-chloro-2-indolinone |
| 13.3 | 3-Z-[1-(4-(N-(2-dimethylamino-ethyl)-N-acetyl-amino)-anilino)-1-(4-amino-phenyl)-methylene]-6-chloro-2-indolinone |
| 13.4 | 3-Z-[1-(4-(4-methyl-piperazin-1-yl-carbonyl)-anilino)-1-(4-amino-phenyl)-methylene]-6-chloro-2-indolinone |
| 14.0 | 3-Z-[1-(4-dimethylaminomethyl-anilino)-1-(4-aminomethyl-phenyl)-methylene]-6-chloro-2-indolinone |
| 15.0 | 3-Z-[1-(4-(N-((4-methyl-piperazin-1-yl)-methylcarbonyl)-N-methyl-amino)-anilino)-1-(4-aminomethyl-phenyl)-methylene]-6-chloro-2-indolinone |
| 16.0 | 3-Z-[1-(4-(N-((4-methyl-piperazin-1-yl)-methylcarbonyl)-N-methyl-amino)-anilino)-1-(4-hydroxy-phenyl)-methylene]-6-chloro-2-indolinone |
| 16.1 | 3-Z-[1-(4-(N-((2-dimethylamino-ethyl)-carbonyl)-N-methyl-amino)-anilino)-1-(4-hydroxy-phenyl)-methylene]-6-chloro-2-indolinone |
| 16.2 | 3-Z-[1-(4-(N-(2-dimethylamino-ethyl)-N-acetyl-amino)-anilino)-1-(4-hydroxy-phenyl)-methylene]-6-chloro-2-indolinone |
| 16.3 | 3-Z-[1-(4-(N-(3-dimethylamino-propyl)-N-acetyl-amino)-anilino)-1-(4-hydroxy-phenyl)-methylene]-6-chloro-2-indolinone |
| 16.4 | 3-Z-[1-(4-dimethylaminomethyl-anilino)-1-(4-hydroxy-phenyl)-methylene]-6-chloro-2-indolinone |
| 17.0 | 3-Z-[1-(4-ethylaminomethyl-anilino)-1-phenyl-methylene]-6-chloro-2-indolinone-trifluoroacetate |
| 17.1 | 3-Z-[1-(4-methylamino-methyl-anilino)-1-phenyl-methylene]-6-chloro-2-indolinone |
| 17.2 | 3-Z-[1-(4-(N-(2-piperazin-1-yl-ethylcarbonyl)-N-methyl-amino)-anilino)-1-phenyl-methylene]-6-chloro-2-indolinone |
| 17.3 | 3-Z-[1-(4-(piperazin-1-yl-methyl)-anilino)-1-phenyl-methylene]-6-chloro-2-indolinone |
| 17.4 | 3-Z-[1-(4-(piperazin-1-yl-carbonyl)-anilino)-1-phenyl-methylene]-6-chloro-2-indolinone |
| 17.5 | 3-Z-[1-(4-(amino-methyl)-anilino)-1-phenyl-methylene]-6-chloro-2-indolinone |
| 17.6 | 3-Z-[1-(4-(N-(piperazin-1-yl-methylcarbonyl)-N-isopropyl-amino)-anilino)-1-phenyl-methylene]-6-chloro-2-indolinone |
| 17.7 | 3-Z-[1-(4-(N-(piperazin-1-yl-methylcarbonyl)-N-methyl-amino)-anilino)-1-phenyl-methylene]-6-chloro-2-indolinone |
| 17.8 | 3-Z-[1-(4-(N-(N-(3-amino-propyl)-N-methyl)-amino-methyl)-anilino)-1-phenyl-methylene]-6-chloro-2-indolinone |

-continued

| Example | Name |
|---|---|
| 17.9 | 3-Z-[1-(4-(methylamino-methyl)-anilino)-1-(4-(2-oxo-pyrrolidin-1-yl)-phenyl)-methylene]-6-chloro-2-indolinone |
| 17.10 | 3-Z-[1-(4-(ethylamino-methyl)-anilino)-1-phenyl-methylene]-6-bromo-2-indolinone |
| 17.11 | 3-Z-[1-(4-(methylamino-methyl)-anilino)-1-phenyl-methylene]-6-bromo-2-indolinone |
| 17.12 | 3-Z-[1-(4-(ethylamino-methyl)-anilino)-1-phenyl-methylene]-6-cyano-2-indolinone |
| 17.13 | 3-Z-[1-(4-(piperazin-1-yl-methylcarbonyl)-N-methyl-amino)-anilino)-1-phenyl-methylene]-6-cyano-2-indolinone |
| 17.14 | 3-Z-[1-(4-(ethylamino-methyl)-anilino)-1-phenyl-methylene]-6-fluoro-2-indolinone |
| 17.15 | 3-Z-[1-(4-(methylamino-methyl)-anilino)-1-phenyl-methylene]-6-fluoro-2-indolinone |
| 17.16 | 3-Z-[1-(4-(dimethylaminomethyl)-anilino)-1-(3-aminomethyl-phenyl)-methylene]-6-fluoro-2-indolinone |
| 17.17 | 3-Z-[1-(4-(dimethylaminomethyl)-anilino)-1-(3-(2-amino-ethyl)-phenyl)-methylene]-6-fluoro-2-indolinone |
| 17.18 | 3-Z-[1-(4-(dimethylaminomethyl)-anilino)-1-(4-aminomethyl-phenyl)-methylene]-6-fluoro-2-indolinone |
| 17.19 | 3-Z-[1-(4-(N-(4-methyl-piperazin-1-yl-methylcarbonyl)-N-methyl-amino)-anilino)-1-(4-aminomethyl-phenyl)-methylene]-6-fluoro-2-indolinone |
| 17.20 | 3-Z-[1-(4-(methylamino-methyl)-anilino)-1-(4-(2-carboxy-ethyl)-phenyl)-methylene]-6-fluoro-2-indolinone |
| 17.21 | 3-Z-[1-(4-(methylamino-methyl)-anilino)-1-(4-(2-methylcarbamoyl-ethyl)-phenyl)-methylene]-6-fluoro-2-indolinone |
| 17.22 | 3-Z-[1-(4-(N-(4-methyl-piperazin-1-yl-methylcarbonyl)-N-methyl-amino)-anilino)-1-(3-aminomethyl-phenyl)-methylene]-6-fluoro-2-indolinone |
| 17.23 | 3-Z-[1-(4-(amino-methyl)-anilino)-1-(4-(2-methoxycarbonyl-ethyl)-phenyl)-methylene]-6-fluoro-2-indolinone |
| 17.24 | 3-Z-[1-(4-(amino-methyl)-anilino)-1-(3-(2-ethoxycarbonyl-ethyl)-phenyl)-methylene]-6-fluoro-2-indolinone |
| 17.25 | 3-Z-[1-(4-(methylamino-methyl)-anilino)-1-(3-(2-ethoxycarbonyl-ethyl)-phenyl)-methylene]-6-fluoro-2-indolinone |
| 18.0 | 3-Z-[1-(4-(N-aminomethylcarbonyl-N-methyl-amino)-anilino)-1-phenyl-methylene]-6-chloro-2-indolinone |
| 19.0 | 3-Z-[1-(4-carboxy-anilino)-1-phenyl-methylene]-6-chloro-2-indolinone |
| 19.1 | 3-Z-[1-(4-carboxymethyl-anilino)-1-phenyl-methylene]-6-chloro-2-indolinone |
| 19.2 | 3-Z-[1-(3-carboxymethyl-anilino)-1-phenyl-methylene]-6-chloro-2-indolinone |
| 19.3 | 3-Z-[1-(3-carboxy-anilino)-1-phenyl-methylene]-6-chloro-2-indolinone |
| 20.0 | 3-Z-[1-(4-dimethylaminomethyl-anilino)-1-(3-(2-carboxy-ethyl)-phenyl)-methylene]-6-chloro-2-indolinone |
| 20.1 | 3-Z-[1-(4-dimethylaminomethyl-anilino)-1-(4-(2-carboxy-ethyl)-phenyl)-methylene]-6-fluoro-2-indolinone |
| 20.2 | 3-Z-[1-(4-dimethylaminomethyl-anilino)-1-(3-carboxymethyl-phenyl)-methylene]-6-fluoro-2-indolinone |
| 20.3 | 3-Z-[1-(4-dimethylaminomethyl-anilino)-1-(3-(2-carboxy-ethyl)-phenyl)-methylene]-6-fluoro-2-indolinone |
| 20.4 | 3-Z-[1-(4-dimethylaminomethyl-anilino)-1-(4-carboxymethyl-phenyl)-methylene]-6-fluoro-2-indolinone |
| 20.5 | 3-Z-[1-(4-(N-(4-methyl-piperazin-1-yl-methylcarbonyl)-N-methyl-amino)-anilino)-1-(4-carboxymethyl-phenyl)-methylene]-6-fluoro-2-indolinone |
| 20.6 | 3-Z-[1-(4-(N-(2-dimethylamino-ethyl)-N-methylsulphonyl-amino)-anilino)-1-(4-carboxymethyl-phenyl)-methylene]-6-fluoro-2-indolinone |
| 20.7 | 3-Z-[1-(4-(N-methyl-N-acetyl-amino)-anilino)-1-(4-(2-carboxy-ethyl)-phenyl)-methylene]-6-fluoro-2-indolinone |
| 20.8 | 3-Z-[1-(4-(N-(4-methyl-piperazin-1-yl-methylcarbonyl)-N-methyl-amino)-anilino)-1-(4-(2-carboxy-ethyl)-phenyl)-methylene]-6-fluoro-2-indolinone |
| 20.9 | 3-Z-[1-(4-(N-(2-dimethylamino-ethyl)-N-methylsulphonyl-amino)-anilino)-1-(4-(2-carboxy-ethyl)-phenyl)-methylene]-6-fluoro-2-indolinone |
| 20.10 | 3-Z-[1-(4-(N-(3-dimethylamino-propyl)-N-acetyl-amino)-anilino)-1-(4-(2-carboxy-ethyl)-phenyl)-methylene]-6-fluoro-2-indolinone |
| 20.11 | 3-Z-[1-(4-(N-tert.butoxycarbonyl-methylamino-methyl)-anilino)-1-(4-(2-carboxy-ethyl)-phenyl)-methylene]-6-fluoro-2-indolinone |
| 20.12 | 3-Z-[1-(4-(4-methyl-piperazin-1-yl-carbonyl)-anilino)-1-(4-(2-carboxy-ethyl)-phenyl)-methylene]-6-fluoro-2-indolinone |
| 20.13 | 3-Z-[1-(4-(1-methyl-imidazol-2-yl)-anilino)-1-(4-(2-carboxy-ethyl)-phenyl)-methylene]-6-fluoro-2-indolinone |
| 20.14 | 3-Z-[1-(4-methylsulphonyl-anilino)-1-(4-(2-carboxy-ethyl)-phenyl)-methylene]-6-fluoro-2-indolinone |
| 20.15 | 3-Z-[1-(4-(4-methyl-piperazin-1-yl-carbonyl)-anilino)-1-(3-carboxymethyl-phenyl)-methylene]-6-fluoro-2-indolinone |
| 20.16 | 3-Z-[1-(4-(N-(4-methyl-piperazin-1-yl-methylcarbonyl)-N-methyl-amino)-anilino)-1-(3-carboxymethyl-phenyl)-methylene]-6-fluoro-2-indolinone |

-continued

| Example | Name |
|---|---|
| 20.17 | 3-Z-[1-(4-(N-(dimethylamino-methylcarbonyl)-N-methyl-amino)-anilino)-1-(3-carboxymethyl-phenyl)-methylene]-6-fluoro-2-indolinone |
| 20.18 | 3-Z-[1-(4-(N-(4-dimethylamino-butylcarbonyl)-N-methyl-amino)-anilino)-1-(3-carboxymethyl-phenyl)-methylene]-6-fluoro-2-indolinone |
| 20.19 | 3-Z-[1-anilino-1-(3-carboxymethyl-phenyl)-methylene]-6-fluoro-2-indolinone |
| 20.20 | 3-Z-[1-(4-methylsulphonyl-anilino)-1-(3-carboxymethyl-phenyl)-methylene]-6-fluoro-2-indolinone |
| 20.21 | 3-Z-[1-4-(1-methyl-imidazol-2-yl)-anilino)-1-(3-carboxymethyl-phenyl)-methylene]-6-fluoro-2-indolinone |
| 20.22 | 3-Z-[1-(4-(N-(dimethylamino-carbonylmethyl)-N-methylsulphonyl-amino)-anilino)-1-(3-carboxymethyl-phenyl)-methylene]-6-fluoro-2-indolinone |
| 20.23 | 3-Z-[1-anilino-1-(4-carboxymethyl-phenyl)-methylene]-6-fluoro-2-indolinone |
| 20.24 | 3-Z-[1-(4-(1-methyl-imidazol-2-yl)-anilino)-1-(4-carboxymethyl-phenyl)-methylene]-6-fluoro-2-indolinone |
| 20.25 | 3-Z-[1-(4-(N-(3-dimethylamino-propylcarbonyl)-N-methyl-amino)-anilino)-1-(4-carboxymethyl-phenyl)-methylene]-6-fluoro-2-indolinone |
| 20.26 | 3-Z-[1-(4-(N-(dimethylamino-methylcarbonyl)-N-methyl-amino)-anilino)-1-(4-carboxymethyl-phenyl)-methylene]-6-fluoro-2-indolinone |
| 20.27 | 3-Z-[1-(4-(4-methyl-piperazin-1-yl-carbonyl)-anilino)-1-(4-carboxymethyl-phenyl)-methylene]-6-fluoro-2-indolinone |
| 20.28 | 3-Z-[1-(4-methylsulphonyl-anilino)-1-(4-carboxymethyl-phenyl)-methylene]-6-fluoro-2-indolinone |
| 20.29 | 3-Z-[1-(4-(N-methyl-N-acetyl-amino)-anilino)-1-(4-carboxymethyl-phenyl)-methylene]-6-fluoro-2-indolinone |
| 20.30 | 3-Z-[1-(4-(N-(dimethylamino-carbonylmethyl)-N-methylsulphonyl-amino)-anilino)-1-(4-carboxymethyl-phenyl)-methylene]-6-fluoro-2-indolinone |
| 20.31 | 3-Z-[1-(4-(N-(2-dimethylamino-ethylcarbonyl)-N-methyl-amino)-anilino)-1-(4-carboxymethyl-phenyl)-methylene]-6-fluoro-2-indolinone |
| 20.32 | 3-Z-[1-(4-(N-(3-dimethylamino-propylcarbonyl)-N-methyl-amino)-anilino)-1-(4-carboxymethyl-phenyl)-methylene]-6-fluoro-2-indolinone |
| 20.33 | 3-Z-[1-(4-(N-(4-methyl-piperazin-1-yl-methylcarbonyl)-N-methyl-amino)-anilino)-1-(3-(2-carboxy-ethyl)-phenyl)-methyl-ene]-6-fluoro-2-indolinone |
| 20.34 | 3-Z-[1-(4-(N-(2-dimethylamino-ethyl)-N-methylsulphonyl-amino)-anilino)-1-(3-carboxymethyl-phenyl)-phenyl)-methylene]-6-fluoro-2-indolinone |
| 20.35 | 3-Z-[1-(4-(N-(2-dimethylamino-ethyl)-N-methylsulphonyl-amino)-anilino)-1-(3-(2-carboxy-ethyl-phenyl)-phenyl)-methylene]-6-fluoro-2-indolinone |
| 20.36 | 3-Z-[1-(4-(N-(dimethylamino-methylcarbonyl)-N-methyl-amino)-anilino)-1-(3-(2-carboxy-ethyl)-phenyl)-methylene]-6-fluoro-2-indolinone |
| 20.37 | 3-Z-[1-(4-(N-(dimethylamino-propyl)-N-acetyl-amino)-anilino)-1-(3-2-carboxy-ethyl)-phenyl)-methylene]-6-fluoro-2-indolinone |
| 20.38 | 3-Z-[1-(4-(N-(dimethylamino-methylcarbonyl)-N-methyl-amino)-anilino)-1-(4-(2-carboxy-ethyl)-phenyl)-methylene]-6-fluoro-2-indolinone |
| 20.39 | 3-Z-[1-(4-(2-dimethylamino-ethyl)-anilino)-1-(4-(2-carboxy-ethyl)-phenyl)-methylene]-6-fluoro-2-indolinone |
| 20.40 | 3-Z-[1-(4-(N-(2-dimethylamino-ethylcarbonyl)-N-methyl-amino)-anilino)-1-(4-(2-carboxy-ethyl)-phenyl)-methylene]-6-fluoro-2-indolinone |
| 20.41 | 3-Z-[1-(4-(2-dimethylamino-ethyl)-anilino)-1-(3-(2-carboxy-ethyl)-phenyl)-methylene]-6-fluoro-2-indolinone |
| 20.42 | 3-Z-[1-(4-(2-dimethylamino-ethyl)-N-acetyl-amino)-anilino)-1-(4-(2-carboxy-ethyl)-phenyl)-methylene]-6-fluoro-2-indolinone |
| 20.43 | 3-Z-[1-(4-(N-(3-dimethylamino-propylcarbonyl)-N-methyl-amino)-anilino)-1-(3-(2-carboxy-ethyl)-phenyl)-methylene]-6-fluoro-2-indolinone |
| 20.44 | 3-Z-[1-(4-(N-(4-dimethylamino-butylcarbonyl)-N-methyl-amino)-anilino)-1-(3-(2-carboxy-ethyl)-phenyl)-methylene]-6-fluoro-2-indolinone |
| 20.45 | 3-Z-[1-(4-(1-methyl-imidazol-2-yl)-anilino)-1-(3-(2-carboxy-ethyl)-phenyl)-methylene]-6-fluoro-2-indolinone |
| 20.46 | 3-Z-[1-(4-(N-(4-dimethylamino-butylcarbonyl)-N-methyl-amino)-anilino)-1-(4-(2-carboxy-ethyl)-phenyl)-methylene]-6-fluoro-2-indolinone |
| 20.47 | 3-Z-[1-anilino-1-(4-(2-carboxy-ethyl)-phenyl)-methylene]-6-fluoro-2-indolinone |
| 20.48 | 3-Z-[1-(4-(pyrrolidin-1-yl-methyl)-anilino)-1-(4-(2-carboxy-ethyl)-phenyl)-methylene]-6-fluoro-2-indolinone |
| 20.49 | 3-Z-[1-(4-(diethylaminomethyl)-anilino)-1-(4-(2-carboxy-ethyl)-phenyl)-methylene]-6-fluoro-2-indolinone |
| 20.50 | 3-Z-[1-(4-aminomethyl-anilino)-1-(4-(2-carboxy-ethyl)-phenyl)-methylene]-6-fluoro-2-indolinone |
| 20.51 | 3-Z-[1-(4-(2-dimethylamino-ethyl)-anilino)-1-(3-carboxymethyl-phenyl)-methylene]-6-fluoro-2-indolinone |
| 20.52 | 3-Z-[1-(4-(2-dimethylamino-ethyl)-anilino)-1-(4-carboxymethyl-phenyl)-methylene]-6-fluoro-2-indolinone |
| 20.53 | 3-Z-[1-(4-(2-dimethylamino-ethyl)-anilino)-1-(4-(2-carboxyl-ethyl)-phenyl)-methylene]-6-chloro-2-indolinone |

| Example | Name |
|---|---|
| 20.54 | 3-Z-[1-(4-(1-methyl-imidazol-2-yl)-anilino)-1-(4-(2-carboxy-ethyl)-phenyl)-methylene]-6-chloro-2-indolinone |
| 20.55 | 3-Z-[1-(4-dimethylaminomethyl-anilino)-1-(4-(2-carboxy-ethyl)-phenyl)-methylene]-6-chloro-2-indolinone |
| 20.56 | 3-Z-[1-(4-((4-methyl-piperazin-1-yl)-methyl)-anilino)-1-(3-(2-carboxy-ethyl)-phenyl)-methylene]-6-fluoro-2-indolinone |
| 20.57 | 3-Z-[1-(4-(imidazol-1-yl-methyl)-anilino)-1-(3-(2-carboxy-ethyl)-phenyl)-methylene]-6-fluoro-2-indolinone |
| 20.58 | 3-Z-[1-(4-(N-(2-dimethylamino-ethyl)-N-methyl-aminomethyl)-anilino)-1-(3-(2-carboxy-ethyl)-phenyl)-methylene]-6-fluoro-2-indolinone |
| 20.59 | 3-Z-[1-(4-((4-methyl-piperazin-1-yl)-methyl)-anilino)-1-(4-(2-carboxy-ethyl)-phenyl)-methylene]-6-fluoro-2-indolinone |
| 20.60 | 3-Z-[1-(4-(imidazol-1-yl-methyl)-anilino)-1-(4-(2-carboxy-ethyl)-phenyl)-methylene]-6-fluoro-2-indolinone |
| 20.61 | 3-Z-[1-(4-(pyrrolidin-1-yl-methyl)-anilino)-1-(4-(2-carboxy-ethyl)-phenyl)-methylene]-6-chloro-2-indolinone |
| 20.62 | 3-Z-[1-(4-(N-(2-dimethylamino-ethyl)-N-methyl-aminomethyl)-anilino)-1-(4-(2-carboxy-ethyl)-phenyl)-methylene]-6-fluoro-2-indolinone |
| 20.63 | 3-Z-[1-anilino-1-(3-(2-carboxy-ethyl)-phenyl)-methylene]-6-fluoro-2-indolinone |
| 20.64 | 3-Z-[1-(4-aminomethyl-anilino)-1-(3-(2-carboxy-ethyl)-phenyl)-methylene]-6-fluoro-2-indolinone |
| 20.65 | 3-Z-[1-(4-methylaminomethyl-anilino)-1-(3-(2-carboxy-ethyl)-phenyl)-methylene]-6-fluoro-2-indolinone |
| 20.66 | 3-Z-[1-(4-dimethylaminomethyl-anilino)-1-(3-carboxymethoxy-phenyl)-methylene]-6-fluoro-2-indolinone |
| 20.67 | 3-Z-[1-(4-dimethylaminomethyl-anilino)-1-(4-carboxymethoxy-phenyl)-methylene]-6-fluoro-2-indolinone |
| 10.68 | 3-Z-[1-(4-(pyrrolidin-1-yl-methyl)-anilino)-1-(4-(2-carboxy-ethyl)-phenyl)-methylene]-6-bromo-2-indolinone |
| 10.69 | 3-Z-[1-(4-(dimethylaminomethyl)-anilino)-1-(4-(2-carboxy-ethyl)-phenyl)-methylene]-6-bromo-2-indolinone |
| 10.70 | 3-Z-[1-(4-(diethylaminomethyl)-anilino)-1-(4-(2-carboxy-ethyl)-methylene]-6-bromo-2-indolinone |
| 20.71 | 3-Z-[1-(3-dimethylaminomethyl-anilino)-1-(4-(2-carboxy-ethyl)-phenyl)-methylene]-6-fluoro-2-indolinone |
| 20.72 | 3-Z-[1-(3-dimethylaminomethyl-anilino)-1-(3-(2-carboxy-ethyl)-phenyl)-methylene]-6-fluoro-2-indolinone |
| 20.73 | 3-Z-[1-(3-dimethylaminomethyl-anilino)-1-(4-(2-carboxy-ethyl)-phenyl)-methylene]-6-chloro-2-indolinone |
| 21.0 | 3-Z-[1-(4-dimethylaminomethyl-anilino)-1-(3-(2-carbamoyl-ethyl)-phenyl)-methylene]-6-chloro-2-indolinone |
| 21.1 | 3-Z-[1-(4-dimethylaminomethyl-anilino)-1-(3-(2-methylcarbamoyl-ethyl)-phenyl)-methylene]-6-chloro-2-indolinone |
| 21.2 | 3-Z-[1-(4-dimethylaminomethyl-anilino)-1-(4-(2-methylcarbamoyl-ethyl)-phenyl)-methylene]-6-fluoro-2-indolinone |
| 21.3 | 3-Z-[1-(4-dimethylaminomethyl-anilino)-1-(3-dimethylcarbamoylmethyl-phenyl)-methylene]-6-fluoro-2-indolinone |
| 21.4 | 3-Z-[1-(4-dimethylaminomethyl-anilino)-1-(3-(2-carbamoyl-ethyl)-phenyl)-methylene]-6-fluoro-2-indolinone |
| 21.5 | 3-Z-[1-(4-dimethylaminomethyl-anilino)-1-(3-(2-methylcarbamoyl-ethyl)-phenyl)-methylene]-6-fluoro-2-indolinone |
| 21.6 | 3-Z-[1-(4-dimethylaminomethyl-anilino)-1-(3-(2-dimethylcarbamoyl-ethyl)-phenyl)-methylene]-6-fluoro-2-indolinone |
| 21.7 | 3-Z-[1-(4-dimethylaminomethyl-anilino)-1-(3-carbamoylmethyl-phenyl)-methylene]-6-fluoro-2-indolinone |
| 21.8 | 3-Z-[1-(4-dimethylaminomethyl-anilino)-1-(3-methylcarbamoylmethyl-phenyl)-methylene]-6-fluoro-2-indolinone |
| 21.9 | 3-Z-[1-(4-dimethylaminomethyl-anilino)-1-(4-carbamoylmethyl-phenyl)-methylene]-6-fluoro-2-indolinone |
| 21.10 | 3-Z-[1-(4-dimethylaminomethyl-anilino)-1-(4-(2-dimethylcarbamoyl-ethyl)-phenyl)-methylene]-6-fluoro-2-indolinone |
| 21.11 | 3-Z-[1-(4-dimethylaminomethyl-anilino)-1-(4-(2-(4-methyl-piperazin-1-yl-carbonyl)-ethyl)-phenyl)-methylene]-6-fluoro-2-indolinone |
| 21.12 | 3-Z-[1-(4-(N-(4-methyl-piperazin-1-yl-methylcarbonyl)-N-methyl-amino)-anilino)-1-(4-carbamoylmethyl-phenyl)-methylene]-6-fluoro-2-indolinone |
| 21.13 | 3-Z-[1-(4-(N-(2-dimethylamino-ethyl)-N-methylsulphonyl-amino)-anilino)-1-(4-carbamoylmethyl-phenyl)-methylene]-6-fluoro-2-indolinone |
| 21.14 | 3-Z-[1-(4-dimethylaminomethyl-anilino)-1-(4-dimethylcarbamoylmethyl-phenyl)-methylene]-6-fluoro-2-indolinone |
| 21.15 | 3-Z-[1-(4-dimethylaminomethyl-anilino)-1-(4-methylcarbamoylmethyl-phenyl)-methylene]-6-fluoro-2-indolinone |
| 21.16 | 3-Z-[1-(4-(N-(2-dimethylamino-ethyl)-N-methylsulphonyl-amino)-anilino)-1-(4-methylcarbamoylmethyl-phenyl)-methylene]-6-fluoro-2-indolinone |

-continued

| Example | Name |
|---|---|
| 21.17 | 3-Z-[1-(4-(N-(2-dimethylamino-ethyl)-N-methylsulphonyl-amino)-anilino)-1-(4-dimethylcarbamoylmethyl-phenyl)-methylene]-6-fluoro-2-indolinone |
| 21.18 | 3-Z-[1-(4-(N-(4-methyl-piperazin-1-yl-methylcarbonyl)-N-methyl-amino)-anilino)-1-(4-methylcarbamoylmethyl-phenyl)-methylene]-6-fluoro-2-indolinone |
| 21.19 | 3-Z-[1-(4-(N-methyl-N-acetyl-amino)-anilino)-1-(4-(2-methylcarbamoyl-ethyl)-phenyl)-methylene]-6-fluoro-2-indolinone |
| 21.20 | 3-Z-[1-(4-(N-(4-methyl-piperazin-1-yl-methylcarbonyl)-N-methyl-amino)-anilino)-1-(4-(2-methylcarbamoyl-ethyl)-phenyl)-methylene]-6-fluoro-2-indolinone |
| 21.21 | 3-Z-[1-(4-(N-(2-dimethylamino-ethyl)-N-methylsulphonyl-amino)-anilino)-1-(4-(2-methylcarbamoyl-ethyl)-phenyl)-methylene]-6-fluoro-2-indolinone |
| 21.22 | 3-Z-[1-(4-(N-tert.butoxycarbonyl-methylamino-methyl)-anilino)-1-(4-(2-methylcarbamoyl-ethyl)-phenyl)-methylene]-6-fluoro-2-indolinone |
| 21.23 | 3-Z-[1-(4-(1-methyl-imidazol-2-yl)-anilino)-1-(4-(2-methylcarbamoyl-ethyl)-phenyl)-methylene]-6-fluoro-2-indolinone |
| 21.24 | 3-Z-[1-(4-methylsulphonyl-anilino)-1-(4-(2-methylcarbamoyl-ethyl)-phenyl)-methylene]-6-fluoro-2-indolinone |
| 21.25 | 3-Z-[1-(4-(4-methyl-piperazin-1-yl-carbonyl)-anilino)-1-(4-(2-methylcarbamoyl-ethyl)-phenyl)-methylene]-6-fluoro-2-indolinone |
| 21.26 | 3-Z-[1-(4-(4-methyl-piperazin-1-yl-carbonyl)-anilino)-1-(3-methylcarbamoylmethyl-phenyl)-methylene]-6-fluoro-2-indolinone |
| 21.27 | 3-Z-[1-(4-(N-(4-methyl-piperazin-1-yl-methylcarbonyl)-N-methyl-amino)-anilino)-1-(3-methylcarbamoylmethyl-phenyl)-methylene]-6-fluoro-2-indolinone |
| 22.0 | 3-Z-[1-(4-(4-methyl-piperazin-1-yl-methyl)-anilino)-1-phenyl-methylene]-6-chloro-1,3-dihydro-indol-2-thion |
| 23.0 | 3-Z-[1-(4-(N-acetylaminomethylcarbonyl-N-methyl-amino)-anilino)-1-phenyl-methylene]-6-chloro-2-indolinone |
| 23.1 | 3-Z-[1-(4-(N-(2-dimethylamino-ethyl)-N-acetyl-amino)-anilino)-1-(4-acetylamino-phenyl)-methylene]-6-chloro-2-indolinone |
| 23.2 | 3-Z-[1-(4-(N-(dimethylamino-methylcarbonyl)-N-methyl-amino)-anilino)-1-(4-acetylamino-phenyl)-methylene]-6-chloro-2-indolinone |
| 23.3 | 3-Z-[1-(4-(N-(4-methyl-piperazin-1-yl-methylcarbonyl)-N-methyl-amino)-anilino)-1-(4-acetylamino-phenyl)-methylene]-6-chloro-2-indolinone |
| 23.4 | 3-Z-[1-(4-(piperazin-1-yl-carbonyl)-anilino)-1-(4-acetylamino-phenyl)-methylene]-6-chloro-2-indolinone |
| 23.5 | 3-Z-[1-(4-dimethylaminomethyl-anilino)-1-(4-acetylamino-phenyl)-methylene]-6-chloro-2-indolinone |
| 23.6 | 3-Z-[1-(4-dimethylaminomethyl-anilino)-1-(4-acetylaminomethyl-phenyl)-methylene]-6-chloro-2-indolinone |
| 23.7 | 3-Z-[1-(4-(N-(4-methyl-piperazin-1-yl-methylcarbonyl)-N-methyl-amino)-anilino)-1-(4-acetylaminomethyl-phenyl)-methylene]-6-chloro-2-indolinone |
| 23.8 | 3-Z-[1-(4-dimethylaminomethyl-anilino)-1-(4-benzoylamino-phenyl)-methylene]-6-chloro-2-indolinone |
| 23.9 | 3-Z-[1-(4-(N-(4-methyl-piperazin-1-yl-methylcarbonyl)-N-methyl-amino)-anilino)-1-(4-benzoylaminomethyl-phenyl)-methylene]-6-chloro-2-indolinone |
| 23.10 | 3-Z-[1-(4-dimethylaminomethyl-anilino)-1-(3-acetylaminomethyl-phenyl)-methylene]-6-fluoro-2-indolinone |
| 23.11 | 3-Z-[1-(4-dimethylaminomethyl-anilino)-1-(3-propionylaminomethyl-phenyl)-methylene]-6-fluoro-2-indolinone |
| 23.12 | 3-Z-[1-(4-dimethylaminomethyl-anilino)-1-(3-benzoylaminomethyl-phenyl)-methylene]-6-fluoro-2-indolinone |
| 23.13 | 3-Z-[1-(4-dimethylaminomethyl-anilino)-1-(3-phenylacetylaminomethyl-phenyl)-methylene]-6-fluoro-2-indolinone |
| 23.14 | 3-Z-[1-(4-dimethylaminomethyl-anilino)-1-(3-(2-acetylamino-ethyl)-phenyl)-methylene]-6-fluoro-2-indolinone |
| 23.15 | 3-Z-[1-(4-dimethylaminomethyl-anilino)-1-(3-(2-benzoylamino-ethyl)-phenyl)-methylene]-6-fluoro-2-indolinone |
| 23.16 | 3-Z-[1-(4-dimethylaminomethyl-anilino)-1-(3-(2-propionylamino-ethyl)-phenyl)-methylene]-6-fluoro-2-indolinone |
| 23.17 | 3-Z-[1-(4-dimethylaminomethyl-anilino)-1-(3-(2-phenylacetylamino-ethyl)-phenyl)-methylene]-6-fluoro-2-indolinone |
| 23.18 | 3-Z-[1-(4-dimethylaminomethyl-anilino)-1-(4-acetylaminomethyl-phenyl)-methylene]-6-fluoro-2-indolinone |
| 23.19 | 3-Z-[1-(4-dimethylaminomethyl-anilino)-1-(4-propionylaminomethyl-phenyl)-methylene]-6-fluoro-2-indolinone |
| 23.20 | 3-Z-[1-(4-dimethylaminomethyl-anilino)-1-(4-phenylacetylaminomethyl-phenyl)-methylene]-6-fluoro-2-indolinone |
| 23.21 | 3-Z-[1-(4-(N-(4-methyl-piperazin-1-yl-methylcarbonyl)-N-methyl-amino)-anilino)-1-(4-acetylaminomethyl-phenyl)-methylene]-6-fluoro-2-indolinone |

-continued

| Example | Name |
|---|---|
| 23.22 | 3-Z-[1-(4-(N-(4-methyl-piperazin-1-yl-methylcarbonyl)-N-methyl-amino)-anilino)-1-(4-propionylaminomethyl-phenyl)-methylene]-6-fluoro-2-indolinone |
| 23.23 | 3-Z-[1-(4-(N-(4-methyl-piperazin-1-yl-methylcarbonyl)-N-methyl-amino)-anilino)-1-(4-phenylacetylaminomethyl-phenyl)-methylene]-6-fluoro-2-indolinone |
| 23.24 | 3-Z-[1-(4-(N-(4-methyl-piperazin-1-yl-methylcarbonyl)-N-methyl-amino)-anilino)-1-(3-cyclopropylcarbonylaminomethyl-phenyl)-methylene]-6-fluoro-2-indolinone |
| 23.25 | 3-Z-[1-(4-(N-(4-methyl-piperazin-1-yl-methylcarbonyl)-N-methyl-amino)-anilino)-1-(3-cyclobutylcarbonylaminomethyl-phenyl)-methylene]-6-fluoro-2-indolinone |
| 23.26 | 3-Z-[1-(4-(N-(4-methyl-piperazin-1-yl-methylcarbonyl)-N-methyl-amino)-anilino)-1-(3-(pyridin-2-yl-carbonylaminomethyl)-phenyl)-methylene]-6-fluoro-2-indolinone |
| 23.27 | 3-Z-[1-(4-(N-(4-methyl-piperazin-1-yl-methylcarbonyl)-N-methyl-amino)-anilino)-1-(3-cyclohexylcarbonylaminomethyl-phenyl)-methylene]-6-fluoro-2-indolinone |
| 23.28 | 3-Z-[1-(4-(N-(4-methyl-piperazin-1-yl-methylcarbonyl)-N-methyl-amino)-anilino)-1-(3-(pyridin-3-yl-carbonylaminomethyl)-phenyl)-methylene]-6-fluoro-2-indolinone |
| 23.29 | 3-Z-[1-(4-(N-(4-methyl-piperazin-1-yl-methylcarbonyl)-N-methyl-amino)-anilino)-1-(3-isobutyrylaminomethyl-phenyl)-methylene]-6-fluoro-2-indolinone |
| 23.30 | 3-Z-[1-(4-(N-(4-methyl-piperazin-1-yl-methylcarbonyl)-N-methyl-amino)-anilino)-1-(3-(3-methylbutyryl-aminomethyl-phenyl)-methylene]-6-fluoro-2-indolinone |
| 23.31 | 3-Z-[1-(4-(N-(4-methyl-piperazin-1-yl-methylcarbonyl)-N-methyl-amino)-anilino)-1-(3-cyclohexylmethylcarbonylaminomethyl-phenyl)-methylene]-6-fluoro-2-indolinone |
| 23.32 | 3-Z-[1-(4-(N-(4-methyl-piperazin-1-yl-methylcarbonyl)-N-methyl-amino)-anilino)-1-(3-methoxyacetylaminomethyl-phenyl)-methylene]-6-fluoro-2-indolinone |
| 23.33 | 3-Z-[1-(4-(N-(4-methyl-piperazin-1-yl-methylcarbonyl)-N-methyl-amino)-anilino)-1-(3-(2-methoxybenzoyl-aminomethyl)-phenyl)-methylene]-6-fluoro-2-indolinone |
| 23.34 | 3-Z-[1-(4-(N-(4-methyl-piperazin-1-yl-methylcarbonyl)-N-methyl-amino)-anilino)-1-(3-tert.butylacetylaminomethyl-phenyl)-methylene]-6-fluoro-2-indolinone |
| 23.35 | 3-Z-[1-(4-(N-(4-methyl-piperazin-1-yl-methylcarbonyl)-N-methyl-amino)-anilino)-1-(3-(2-thiophen-carbonylaminomethyl)-phenyl)-methylene]-6-fluoro-2-indolinone |
| 23.36 | 3-Z-[1-(4-(N-(4-methyl-piperazin-1-yl-methylcarbonyl)-N-methyl-amino)-anilino)-1-(3-pivaloylaminomethyl-phenyl)-methylene]-6-fluoro-2-indolinone |
| 23.37 | 3-Z-[1-(4-(N-(4-methyl-piperazin-1-yl-methylcarbonyl)-N-methyl-amino)-anilino)-1-(3-(2-furoylaminomethyl)-phenyl)-methylene]-6-fluoro-2-indolinone |
| 23.38 | 3-Z-[1-(4-(N-(4-methyl-piperazin-1-yl-methylcarbonyl)-N-methyl-amino)-anilino)-1-(3-acetylaminomethyl-phenyl)-methylene]-6-fluoro-2-indolinone |
| 23.39 | 3-Z-[1-(4-(N-(4-methyl-piperazin-1-yl-methylcarbonyl)-N-methyl-amino)-anilino)-1-(3-propionylaminomethyl-phenyl)-methylene]-6-fluoro-2-indolinone |
| 23.40 | 3-Z-[1-(4-(N-(4-methyl-piperazin-1-yl-methylcarbonyl)-N-methyl-amino)-anilino)-1-(3-benzoylaminomethyl-phenyl)-methylene]-6-fluoro-2-indolinone |
| 23.41 | 3-Z-[1-(4-(N-(4-methyl-piperazin-1-yl-methylcarbonyl)-N-methyl-amino)-anilino)-1-(3-phenylacetylaminomethyl-phenyl)-methylene]-6-fluoro-2-indolinone |
| 23.42 | 3-Z-[1-(4-dimethylaminomethyl-anilino)-1-(3-cyclopropylcarbonylaminomethyl-phenyl)-methylene]-6-fluoro-2-indolinone |
| 23.43 | 3-Z-[1-(4-dimethylaminomethyl-anilino)-1-(3-cyclobutylcarbonylaminomethyl-phenyl)-methylene]-6-fluoro-2-indolinone |
| 23.44 | 3-Z-[1-(4-dimethylaminomethyl-anilino)-1-(3-(pyridin-2-yl-carbonylaminomethyl)-phenyl)-methylene]-6-fluoro-2-indolinone |
| 23.45 | 3-Z-[1-(4-dimethylaminomethyl-anilino)-1-(3-cyclohexylcarbonylaminomethyl-phenyl)-methylene]-6-fluoro-2-indolinone |
| 23.46 | 3-Z-[1-(4-dimethylaminomethyl-anilino)-1-(3-(pyridin-3-yl-carbonylaminomethyl)-phenyl)-methylene]-6-fluoro-2-indolinone |
| 23.47 | 3-Z-[1-(4-dimethylaminomethyl-anilino)-1-(3-isobutyrylaminomethyl-phenyl)-methylene]-6-fluoro-2-indolinone |
| 23.48 | 3-Z-[1-(4-dimethylaminomethyl-anilino)-1-(3-(3-methylbutyrylaminomethyl-phenyl)-methylene]-6-fluoro-2-indolinone |

-continued

| Example | Name |
|---|---|
| 23.49 | 3-Z-[1-(4-dimethylaminomethyl-anilino)-1-(3-cyclohexylmethylcarbonylaminomethyl-phenyl)-methylene]-6-fluoro-2-indolinone |
| 23.50 | 3-Z-[1-(4-dimethylaminomethyl-anilino)-1-(3-methoxyacetylaminomethyl-phenyl)-methylene]-6-fluoro-2-indolinone |
| 23.51 | 3-Z-[1-(4-dimethylaminomethyl-anilino)-1-(3-(2-methoxybenzoyl-aminomethyl)-phenyl)-methylene]-6-fluoro-2-indolinone |
| 23.52 | 3-Z-[1-(4-dimethylaminomethyl-anilino)-1-(3-tert.butylacetylaminomethyl-phenyl)-methylene]-6-fluoro-2-indolinone |
| 23.53 | 3-Z-[1-(4-dimethylaminomethyl-anilino)-1-(3-(2-thiophen-carbonylaminomethyl)-phenyl)-methylene]-6-fluoro-2-indolinone |
| 23.54 | 3-Z-[1-(4-dimethylaminomethyl-anilino)-1-(3-pivaloylaminomethyl-phenyl)-methylene]-6-fluoro-2-indolinone |
| 23.55 | 3-Z-[1-(4-dimethylaminomethyl-anilino)-1-(3-(2-furoylaminomethyl)-phenyl)-methylene]-6-fluoro-2-indolinone |
| 23.56 | 3-Z-[1-(4-dimethylaminomethyl-anilino)-1-(3-(pyridin-4-yl-carbonylaminomethyl)-phenyl)-methylene]-6-fluoro-2-indolinone |
| 24.0 | 3-Z-[1-(4-dimethylaminomethyl-anilino)-1-(4-phenylsulphonylaminomethyl-phenyl)-methylene]-6-chloro-2-indolinone |
| 24.1 | 3-Z-[1-(4-(N-(4-methyl-piperazin-1-yl-methylcarbonyl)-N-methyl-amino)-anilino)-1-(4-methylsulphonylaminomethyl-phenyl)-methylene]-6-chloro-2-indolinone |
| 24.2 | 3-Z-[1-(4-dimethylaminomethyl-anilino)-1-(4-methylsulphonylaminomethyl-phenyl)-methylene]-6-chloro-2-indolinone |
| 24.3 | 3-Z-[1-(4-(N-(4-methyl-piperazin-1-yl-methylcarbonyl)-N-methyl-amino)-anilino)-1-(4-phenylsulphonylaminomethyl-phenyl)-methylene]-6-chloro-2-indolinone |
| 24.4 | 3-Z-[1-(4-dimethylaminomethyl-anilino)-1-(3-methylsulphonylaminomethyl-phenyl)-methylene]-6-fluoro-2-indolinone |
| 24.5 | 3-Z-[1-(4-dimethylaminomethyl-anilino)-1-(3-ethylsulphonylaminomethyl-phenyl)-methylene]-6-fluoro-2-indolinone |
| 24.6 | 3-Z-[1-(4-dimethylaminomethyl-anilino)-1-(3-phenylsulphonylaminomethyl-phenyl)-methylene]-6-fluoro-2-indolinone |
| 24.7 | 3-Z-[1-(4-dimethylaminomethyl-anilino)-1-(3-(2-ethylsulphonylamino-ethyl)-phenyl)-methylene]-6-fluoro-2-indolinone |
| 24.8 | 3-Z-[1-(4-dimethylaminomethyl-anilino)-1-(4-methylsulphonylaminomethyl-phenyl)-methylene]-6-fluoro-2-indolinone |
| 24.9 | 3-Z-[1-(4-dimethylaminomethyl-anilino)-1-(4-ethylsulphonylaminomethyl-phenyl)-methylene]-6-fluoro-2-indolinone |
| 24.10 | 3-Z-[1-(4-dimethylaminomethyl-anilino)-1-(4-benzylsulphonylaminomethyl-phenyl)-methylene]-6-fluoro-2-indolinone |
| 24.11 | 3-Z-[1-(4-(N-(4-methyl-piperazin-1-yl-methylcarbonyl)-N-methyl-amino)-anilino)-1-(4-methylsulphonylaminomethyl-phenyl)-methylene]-6-fluoro-2-indolinone |
| 24.12 | 3-Z-[1-(4-(N-(4-methyl-piperazin-1-yl-methylcarbonyl)-N-methyl-amino)-anilino)-1-(4-ethylsulphonylaminomethyl-phenyl)-methylene]-6-fluoro-2-indolinone |
| 24.13 | 3-Z-[1-(4-(N-(4-methyl-piperazin-1-yl-methylcarbonyl)-N-methyl-amino)-anilino)-1-(4-benzylsulphonylaminomethyl-phenyl)-methylene]-6-fluoro-2-indolinone |
| 25.0 | 3-Z-[1-(4-trimethylammoniummethyl-anilino)-1-(4-(2-carboxy-ethyl)-phenyl)-methylene]-6-fluoro-2-indolinone-iodide |
| 25.1 | 3-Z-[1-(4-trimethylammoniummethyl-anilino)-1-(3-(2-carboxy-ethyl)-phenyl)-methylene]-6-fluoro-2-indolinone-iodide |
| 26.0 | 3-Z-[1-(4-guanidinomethyl-anilino)-1-(4-(2-carboxy-ethyl)-phenyl)-methylene]-6-fluoro-2-indolinone |
| 26.1 | 3-Z-[1-(4-guanidinomethyl-anilino)-1-(3-(2-carboxy-ethyl)-phenyl)-methylene]-6-fluoro-2-indolinone |

Abbreviations used:
HOBt = 1-hydroxy-1H-benzotriazole
TBTU = O-benzotrialzol-1-yl-N,N,N',N'-tetramethyluronium-tetrafluoroborate Preparation of the Starting Compounds:

EXAMPLE I dimethyl 2-(4-fluoro-2-nitrophenyl)-malonate 185 g of potassium-tert-butoxide are added to a solution of 188 ml of dimethyl malonate in 970 ml of N-methylpyrrolidone, while cooling with ice, and the mixture is stirred for 2 hours. 150 ml of 2,5-difluoronitrobenzene are added dropwise to the resulting suspension over a period of 30 minutes and then stirred for 6 hours at 85° C. The mixture is poured onto 4 litres of ice water and 250 ml of concentrated hydrochloric acid and extracted with 2 litres of ethyl acetate. The organic phase is dried with sodium sulphate and evaporated down. The oily residue is stirred twice with water and then taken up in 600 ml ethyl acetate. The solution is dried with sodium sulphate and evaporated to dryness. The crystallised crude product is recrystallised from 600 ml ethyl acetate/hexane=2:8 and dried.

Yield: 222 g (59% of theory) $R_f$ value: 0.40 (silica gel, cyclohexane/ethyl acetate=5:1) $C_{11}H_{10}FNO_6$ Mass spectrum: m/z=270 [M–H]$^-$ The following compounds are prepared analogously to Example I:

(I.1) diethyl 2-(4-bromo-2-nitrophenyl)-malonate from 2,5-dibromonitrobenzene and diethyl malonate $R_f$ value: 0.40 (silica gel, petroleum ether/ethyl acetate=5:1) $C_{13}H_{14}BrNO_6$ Mass spectrum: m/z=359/361 [M]$^+$ (I.2) dimethyl 2-(4-cyano-2-nitrophenyl)-malonate from 4-chloro-3-nitro-benzonitrile and dimethyl malonate $R_f$ value: 0.50 (silica gel, methylene chloride/methanol=50:1) $C_{12}H_{10}N_2O_6$ Mass spectrum: m/z=277 [M–H]$^-$

EXAMPLE II methyl 4-cyano-2-nitrophenylacetate 14.2 g dimethyl 2-(4-cyano-2-nitrophenyl)-malonate (educt I.2) are dissolved in 200 ml dimethylsulphoxide and 4.5 g lithium chloride and 1.0 ml of water is added. The solution is stirred for 3.5 hours at 100° C., then combined with 300 ml ice water and left to stand for 12 hours. The precipitate formed is suction filtered, taken up in methylene chloride and washed with water. The organic phase is dried over sodium sulphate, concentrated in the rotary evaporator and dried.

Yield: 7.7 g (68% of theory) $R_f$ value: 0.40 (silica gel, methylene chloride/methanol=50:1 $C_{10}H_8N_2O_4$ Mass spectrum: m/z=219 [M–H]$^-$

EXAMPLE III 4-fluoro-2-nitrophenylacetic acid 50.0 g of dimethyl 2-(4-fluoro-2-nitrophenyl)-malonate (educt I) are stirred in 400 ml of 6 molar hydrochloric acid for 20 hours at 100° C., then combined with 400 ml of water and cooled to 0° C. The precipitate formed is suction filtered, washed with water and 100 ml petroleum ether and dried.

Yield: 34.5 g (94% of theory) $R_f$ value: 0.30 (silica gel, cyclohexane/ethyl acetate)=5:2 $C_8H_6FNO_4$ Mass spectrum: m/z=154 [M-COO—H]$^-$

EXAMPLE IV 6-fluoro-2-indolinone 119 g 4-fluoro-2-nitrophenylacetic acid (educt III) are hydrogenated in 600 ml acetic acid with the addition of 20 g palladium on activated charcoal (10%) under 50 psi of hydrogen pressure. The catalyst is suction filtered and the solvent is distilled off. The crude product is extracted with 500 ml petroleum ether, suction filtered, washed with water and dried.

Yield: 82.5 g (91% of theory) $R_f$ value: 0.30 (silica gel, petroleum ether/ethyl acetate=1:1) $C_8H_6FNO$ Mass spectrum: m/z=150 [M–H]$^-$ The following compounds are prepared analogously to Example IV:

(IV.1) 6-bromo-2-indolinone from diethyl 2-(4-bromo-2-nitrophenyl)-malonate (educt I.1) with Raney nickel as hydrogenation catalyst $R_f$ value: 0.45 (silica gel, petroleum ether/ethyl acetate=1:1) $C_8H_6BrNO$ Mass spectrum: m/z=210/212 [M–H]$^-$ (IV.2) 6-cyano-2-indolinone from methyl 4-cyano-2-nitrophenylacetate (educt II) with palladium/calcium carbonate as hydrogenation catalyst $R_f$ value: 0.45 (silica gel, methylene chloride/methanol=9:1) $C_9H_6N_2O$ Mass spectrum: m/z=157 [M–H]$^-$

EXAMPLE V 1-acetyl-6-fluoro-2-indolinone 82.5 g 6-fluoro-2-indolinone (educt IV) are stirred in 180 ml acetic anhydride for 3 hours at 130° C. After cooling to ambient temperature the precipitate is suction filtered, washed with 100 ml of petroleum ether and dried.

Yield: 64.8 g (61% of theory) $R_f$ value: 0.75 (silica gel, petroleum ether/ethyl acetate=1:1) $C_{10}H_8FNO_2$ Mass spectrum: m/z=192 [M–H]$^-$ The following compounds are prepared analogously to Example V:

(V.1) 1-acetyl-6-chloro-2-indolinone from 6-chloro-2-indolinone and acetic anhydride $R_f$ value: 0.55 (silica gel, petroleum ether/ethyl acetate=2:3) $C_{11}H_{10}ClNO_6$ Mass spectrum: m/z=208/210 [M–H]$^-$ (V.2) 1-acetyl-6-bromo-2-indolinone from 6-bromo-2-indolinone (educt IV.1) and acetic anhydride $R_f$ value: 0.60 (silica gel, petroleum ether/ethyl acetate=2:1) $C_{10}H_8BrNO_2$ Mass spectrum: m/z=253/255 [M]$^+$ (V.3) 1-acetyl-6-cyano-2-indolinone from 6-cyano-2-indolinone (educt IV.2) and acetic anhydride $R_f$ value: 0.60 (silica gel, methylene chloride/methanol=50:1) $C_{11}H_8N_2O_2$ Mass spectrum: m/z=199 [M–H]$^-$

EXAMPLE VI 1-acetyl-5-nitro-6-chloro-2-indolinone 2.75 g 1-acetyl-6-chloro-2-indolinone (educt V.1) are placed in 40 ml concentrated sulphuric acid and at −10° C. 1.05 g of ammonium nitrate are added. The mixture is stirred for 1.5 hours at ambient temperature. After this time the mixture is poured onto ice water and stirred for a further 20 minutes. The solution is neutralised with concentrated ammonia, the precipitate formed is suction filtered and washed with a little ethanol and ether.

Yield: 2.80 g (84% of theory) $C_{10}H_7ClN_2O_4$ Mass spectrum: m/z=254 [M]$^+$

EXAMPLE VII 1-acetyl-3-[1-hydroxy-1-(3-iodo-phenyl)-methylene]-6-chloro-2-indolinone 10.5 g 1-acetyl-6-chloro-2-indolinone (educt V.1), 13.6 g 3-iodobenzoic acid and 17.7 g TBTU are placed in 100 ml of dimethylformamide, 35 ml triethylamine are added and the mixture is stirred for 12 hours at ambient temperature. After this time the solvent is eliminated, the residue is combined with water, suction filtered and washed with a little water, methanol and ether and dried in vacuo at 100° C.

Yield: 12.9 g (59% of theory) $R_f$ value: 0.80 (silica gel, methylene chloride/methanol=9:1) $C_{17}H_{11}ClINO_3$ Mass spectrum: m/z=438/440 [M–H]$^-$ The following compounds are prepared analogously to Example VII:

(VII.1) 1-acetyl-3-[1-hydroxy-1-(4-methoxycarbonylmethyl-phenyl)-methylene]-6-fluoro-2-indolinone
from 1-acetyl-6-fluoro-2-indolinone (educt V) and methyl (4-carboxyphenyl)-acetate (prepared according to Tetrahedron 1997, 53, 7335-7340)

(VII.2) 1-acetyl-3-[1-hydroxy-1-(4-chloro-phenyl)-methylene]-6-chloro-2-indolinone
from 1-acetyl-6-chloro-2-indolinone (educt V.1) and 4-chloro-benzoic acid (VII.3) 1-acetyl-3-[1-hydroxy-1-(4-benzyloxy-phenyl)-methylene]-6-chloro-2-indolinone
from 1-acetyl-6-chloro-2-indolinone (educt V.1) and 4-benzyloxy-benzoic acid (VII.4) 1-acetyl-3-[1-hydroxy-1-(3,4-dimethoxy-phenyl)-methylene]-6-chloro-2-indolinone
from 1-acetyl-6-chloro-2-indolinone (educt V.1) and 3,4-dimethoxy-benzoic acid (VII.5) 1-acetyl-3-[1-hydroxy-1-(3,4-dimethoxy-phenyl)-methylene]-6-cyano-2-indolinone
from 1-acetyl-6-cyano-2-indolinone (educt V.3) and 3,4-dimethoxy-benzoic acid (VII.6) 1-acetyl-3-[1-hydroxy-1-(3-nitro-4-hydroxy-phenyl)-methylene]-6-chloro-2-indolinone
from 1-acetyl-6-chloro-2-indolinone (educt V.1) and 3-nitro-4-hydroxy-benzoic acid (VII.7) 1-acetyl-3-[1-hydroxy-1-(3-fluoro-phenyl)-methylene]-6-fluoro-2-indolinone
from 1-acetyl-6-fluoro-2-indolinone (educt V) and 3-fluoro-benzoic acid (VII.8) 1-acetyl-3-[1-hydroxy-1-(4-(2-acetylamino-ethyl)-phenyl)-methylene]-6-fluoro-2-indolinone
from 1-acetyl-6-fluoro-2-indolinone (educt V) and 4-(2-acetylamino-ethyl)-benzoic acid (prepared according to J. Am. Chem. Soc. 1943, 65, 2377)

(VII.9) 1-acetyl-3-[1-hydroxy-1-(3,4,5-trifluoro-phenyl)-methylene]-6-fluoro-2-indolinone
from 1-acetyl-6-fluoro-2-indolinone (educt V) and 3,4,5-trifluoro-benzoic acid (VII.10) 1-acetyl-3-[1-hydroxy-1-(3-methoxycarbonylmethyl-phenyl)-methylene]-6-fluoro-2-indolinone
from 1-acetyl-6-fluoro-2-indolinone (educt V) and (3-carboxyphenyl)-acetate methyl (prepared analogously to Tetrahedron 1997, 53, 7335-7340)

(VII.11) 1-acetyl-3-[1-hydroxy-1-(3-(N-tert.butoxycarbonyl-aminomethyl)-phenyl)-methylene]-6-fluoro-2-indolinone
from 1-acetyl-6-fluoro-2-indolinone (educt V) and 3-(N-tert.butoxycarbonyl-aminomethyl)-benzoic acid (prepared according to Tetrahedron 1997, 53, 7335-7340)

(VII.12) 1-acetyl-3-[1-hydroxy-1-(3-cyanomethyl-phenyl)-methylene]-6-fluoro-2-indolinone
from 1-acetyl-6-fluoro-2-indolinone (educt V) and (3-carboxy-phenyl)-acetonitrile (prepared according to J. Prakt. Chem. 1998, 340, 367-374)

(VII.13) 1-acetyl-3-[1-hydroxy-1-(4-(N-tert.butoxycarbonyl-aminomethyl)-phenyl)-methylene]-6-fluoro-2-indolinone
from 1-acetyl-6-fluoro-2-indolinone (educt V) and 4-(N-tert.butoxycarbonyl-aminomethyl)-benzoic acid (prepared according to Bioorg. Med. Chem. Lett 2000, 10, 553-557)

(VII.14) 1-acetyl-3-[1-hydroxy-1-(4-iodo-phenyl)-methylene]-6-fluoro-2-indolinone
from 1-acetyl-6-fluoro-2-indolinone (educt V) and 4-iodo-benzoic acid (VII.15) 1-acetyl-3-[1-hydroxy-1-(4-iodo-phenyl)-methylene]-6-chloro-2-indolinone
from 1-acetyl-6-chloro-2-indolinone (educt V.1) and 4-iodo-benzoic acid (VII.16) 1-acetyl-3-[1-hydroxy-1-(3-iodo-phenyl)-methylene]-6-fluoro-2-indolinone
from 1-acetyl-6-fluoro-2-indolinone (educt V) and 3-iodo-benzoic acid (VII.17) 1-acetyl-3-[1-hydroxy-1-(4-(2-methoxycarbonyl-ethyl)-phenyl)-methylene]-6-fluoro-2-indolinone
from 1-acetyl-6-fluoro-2-indolinone (educt V) and 4-(2-methoxycarbonylethyl)-benzoic acid (prepared analogously to Tetrahedron 1997, 53, 7335-7340)

(VII.18) 1-acetyl-3-[1-hydroxy-1-(3-(2-methoxycarbonyl-ethyl)-phenyl)-methylene]-6-fluoro-2-indolinone
from 1-acetyl-6-fluoro-2-indolinone (educt V) and 3-(2-methoxycarbonylethyl)-benzoic acid (prepared analogously to Tetrahedron 1997, 53, 7335-7340)

(VII.19) 1-acetyl-3-[1-hydroxy-1-(3-(N-tert.butoxycarbonyl-2-aminoethyl)-phenyl)-methylene]-6-fluoro-2-indolinone
from 1-acetyl-6-fluoro-2-indolinone (educt V) and 3-(N-tert.butoxycarbonyl-2-aminoethyl)-benzoic acid (prepared analogously to Bioorg. Med. Chem. Lett 2000, 10, 553-557)

(VII.20) 1-acetyl-3-[1-hydroxy-1-(4-(N-tert.butoxycarbonyl-2-aminoethyl)-phenyl)-methylene]-6-fluoro-2-indolinone
from 1-acetyl-6-fluoro-2-indolinone (educt V) and 4-(N-tert.butoxycarbonyl-2-aminoethyl)-benzoic acid (prepared analogously to Bioorg. Med. Chem. Lett 2000, 10, 553-557)

(VII.21) 1-acetyl-3-[1-hydroxy-1-(4-acetylamino-3-nitro-phenyl)-methylene]-6-chloro-2-indolinone
from 1-acetyl-6-chloro-2-indolinone (educt V.1) and 3-acetylamino-4-nitro-benzoic acid (VII.22) 1-acetyl-3-[1-hydroxy-1-(4-(imidazol-1-yl-methyl)-phenyl)-methylene]-6-chloro-2-indolinone
from 1-acetyl-6-chloro-2-indolinone (educt V.1) and 4-(imidazol-1-yl-methyl)-benzoic acid (prepared according to J. Med. Chem. 1987, 30, 1342-1347)

(VII.23) 1-acetyl-3-[1-hydroxy-1-(4-(2-oxo-pyrrolidin-1-yl)-phenyl)-methylene]-6-chloro-2-indolinone
from 1-acetyl-6-chloro-2-indolinone (educt V.1) and 4-(2-oxo-pyrrolidin-1-yl)-benzoic acid (prepared according to J. Med. Chem. 1999, 42, 2332-2343)

(VII.24) 1-acetyl-3-[1-hydroxy-1-(4-nitro-phenyl)-methylene]-6-chloro-2-indolinone
from 1-acetyl-6-chloro-2-indolinone (educt V.1) and 4-nitro-benzoic acid (VII.25) 1-acetyl-3-[1-hydroxy-1-(4-cyano-phenyl)-methylene]-6-chloro-2-indolinone
from 1-acetyl-6-chloro-2-indolinone (educt V.1) and 4-cyano-benzoic acid (VII.26) 1-acetyl-3-[1-hydroxy-1-(3-acetylaminomethyl-phenyl)-methylene]-6-fluoro-2-indolinone
from 1-acetyl-6-fluoro-2-indolinone (educt V) and 3-acetylaminomethyl-benzoic acid (prepared according to J. Med. Chem. 1997, 40, 4030-4052)

(VII.27) 1-acetyl-3-[1-hydroxy-1-(3-(2-ethoxycarbonyl-ethyl)-phenyl)-methylene]-6-fluoro-2-indolinone
from 1-acetyl-6-fluoro-2-indolinone (educt V) and 3-(2-ethoxycarbonylethyl)-benzoic acid (prepared analogously to Tetrahedron 1997, 53, 7335-7340)

(VII.28) 1-acetyl-3-[1-hydroxy-1-(4-(2-methoxycarbonyl-ethyl)-phenyl)-methylene]-6-chloro-2-indolinone
from 1-acetyl-6-chloro-2-indolinone (educt V.1) and 4-(2-methoxycarbonylethyl)-benzoic acid (prepared analogously to Tetrahedron 1997, 53, 7335-7340)

(VII.29) 1-acetyl-3-[1-hydroxy-1-(4-(2-ethoxycarbonyl-ethyl)-phenyl)-methylene]-6-fluoro-2-indolinone from 1-acetyl-6-fluoro-2-indolinone (educt V) and 4-(2-ethoxycarbonylethyl)-benzoic acid (prepared analogously to Tetrahedron 1997, 53, 7335-7340)

(VII.30) 1-acetyl-3-[1-hydroxy-1-(3-methoxycarbonylmethyloxy-phenyl)-methylene]-6-fluoro-2-indolinone from 1-acetyl-6-fluoro-2-indolinone (educt V) and 3-methoxycarbonyl-methyloxy-benzoic acid (for preparation see Tetrahedron Letters 1998, 39, 8563-8566)

(VII.31) 1-acetyl-3-[1-hydroxy-1-(4-methoxycarbonylmethyloxy-phenyl)-methylene]-6-fluoro-2-indolinone from 1-acetyl-6-fluoro-2-indolinone (educt V) and 4-methoxycarbonyl-methyloxy-benzoic acid (prepared analogously to Tetrahedron Letters 1998, 39, 8563-8566)

(VII.32) 1-acetyl-3-[1-hydroxy-1-(3-(2-ethoxycarbonyl-ethyloxy)-phenyl)-methylene]-6-fluoro-2-indolinone from 1-acetyl-6-fluoro-2-indolinone (educt V) and 3-(2-ethoxycarbonyl-ethyloxy)-benzoic acid (for preparation see PCT Int. Appl. WO9620173, 60)

(VII.33) 1-acetyl-3-[1-hydroxy-1-(4-(2-ethoxycarbonyl-ethyloxy)-phenyl)-methylene]-6-fluoro-2-indolinone from 1-acetyl-6-fluoro-2-indolinone (educt V) and 4-(2-ethoxycarbonyl-ethyloxy)-benzoic acid (for preparation see PCT Int. Appl. WO9620173, 58)

EXAMPLE VIII 1-acetyl-3-[1-methoxy-1-(3-iodo-phenyl)-methylene]-6-chloro-2-indolinone 2.36 g of trimethyloxonium tetrafluoroborate are added batchwise to a solution of 3.52 g of 1-acetyl-3-[1-hydroxy-1-(3-iodo-phenyl)-methylene]-6-chloro-2-indolinone (educt VII) and 2.72 ml of ethyldiisopropylamine in 80 ml dichloromethane and the mixture is stirred for one hour at ambient temperature. Then another 1.4 ml ethyldiisopropylamine and 1.2 g trimethyloxonium tetrafluoroborate are added and the mixture is stirred for a further two hours at ambient temperature. Then it is extracted with water, the organic phase is dried over magnesium sulphate and evaporated to dryness. The residue is recrystallised from ether and dried in vacuo at 80° C.

Yield: 2.40 g (66% of theory) $R_f$ value: 0.60 (silica gel, petroleum ether/dichloromethane/ethyl acetate=5:4:1) $C_{18}H_{13}ClINO_3$ Mass spectrum: m/z=438/440 [M–H]$^-$ M.p. 185-187° C.

The following compounds are prepared analogously to Example VIII:

(VIII.1) 1-acetyl-3-[1-methoxy-1-(4-methoxycarbonylmethyl-phenyl)-methylene]-6-fluoro-2-indolinone from 1-acetyl-3-[1-hydroxy-1-(4-methoxycarbonylmethyl-phenyl)-methylene]-6-fluoro-2indolinone (educt VII.1)

(VIII.2) 1-acetyl-3-[1-methoxy-1-(4-chloro-phenyl)-methylene]-6-chloro-2-indolinone from 1-acetyl-3-[1-hydroxy-1-(4-chloro-phenyl)-methylene]-6-chloro-2-indolinone (educt VII.2)

(VIII.3) 1-acetyl-3-[1-methoxy-1-(4-benzyloxy-phenyl)-methylene]-6-chloro-2-indolinone from 1-acetyl-3-[1-hydroxy-1-(4-benzyloxy-phenyl)-methylene]-6-chloro-2-indolinone (educt VII.3)

(VIII.4) 1-acetyl-3-[1-methoxy-1-(3,4-dimethoxy-phenyl)-methylene]-6-chloro-2-indolinone from 1-acetyl-3-[1-hydroxy-1-(3,4-dimethoxy-phenyl)-methylene]-6-chloro-2-indolinone (educt VII.4)

(VIII.5) 1-acetyl-3-[1-methoxy-1-(3,4-dimethoxy-phenyl)-methylene]-6-cyano-2-indolinone from 1-acetyl-3-[1-hydroxy-1-(3,4-dimethoxy-phenyl)-methylene]-6-cyano-2-indolinone (educt VII.5)

(VIII.6) 1-acetyl-3-[1-methoxy-1-(3-nitro-4-hydroxy-phenyl)-methylene]-6-chloro-2-indolinone from 1-acetyl-3-[1-hydroxy-1-(3-nitro-4-hydroxy-phenyl)-methylene]-6-chloro-2-indolinone (educt VII.6)

(VIII.7) 1-acetyl-3-[1-methoxy-1-(3-fluoro-phenyl)-methylene]-6-fluoro-2-indolinone from 1-acetyl-3-[1-hydroxy-1-(3-fluoro-phenyl)-methylene]-6-fluoro-2-indolinone (educt VII.7)

(VIII.8) 1-acetyl-3-[1-methoxy-1-(4-(2-acetylamino-ethyl)-phenyl)-methylene]-6-fluoro-2-indolinone from 1-acetyl-3-[1-hydroxy-1-(4-(2-acetylamino-ethyl)-phenyl)-methylene]-6-fluoro-2-indolinone (educt VII.8)

(VIII.9) 1-acetyl-3-[1-methoxy-1-(3,4,5-trifluoro-phenyl)-methylene]-6-fluoro-2-indolinone from 1-acetyl-3-[1-hydroxy-1-(3,4,5-trifluoro-phenyl)-methylene]-6-fluoro-2-indolinone (educt VII.9)

(VIII.10) 1-acetyl-3-[1-methoxy-1-(3-methoxycarbonylmethyl-phenyl)-methylene]-6-fluoro-2-indolinone from 1-acetyl-3-[1-hydroxy-1-(3-methoxycarbonylmethyl-phenyl)-methylene]-6-fluoro-2-indolinone (educt VII.10)

(VIII.11) 1-acetyl-3-[1-methoxy-1-(3-(N-tert.butoxycarbonyl-aminomethyl)-phenyl)-methylene]-6-fluoro-2-indolinone from 1-acetyl-3-[1-hydroxy-1-(3-(N-tert.butoxycarbonyl-aminomethyl)-phenyl)-methylene]-6-fluoro-2-indolinone (educt VII.11)

(VIII.12) 1-acetyl-3-[1-methoxy-1-(3-cyanomethyl-phenyl)-methylene]-6-fluoro-2-indolinone from 1-acetyl-3-[1-hydroxy-1-(3-cyanomethyl-phenyl)-methylene]-6-fluoro-2-indolinone (educt VII.12)

(VIII.13) 1-acetyl-3-[1-methoxy-1-(4-(N-tert.butoxycarbonyl-aminomethyl)-phenyl)-methylene]-6-fluoro-2-indolinone from 1-acetyl-3-[1-hydroxy-1-(4-(N-tert.butoxycarbonyl-aminomethyl)-phenyl)-methylene]-6-fluoro-2-indolinone (educt VII.13)

(VIII.14) 1-acetyl-3-[1-methoxy-1-(4-iodo-phenyl)-methylene]-6-fluoro-2-indolinone from 1-acetyl-3-[1-hydroxy-1-(4-iodo-phenyl)-methylene]-6-fluoro-2-indolinone (educt VII.14)

(VIII.15) 1-acetyl-3-[1-methoxy-1-(4-iodo-phenyl)-methylene]-6-chloro-2-indolinone from 1-acetyl-3-[1-hydroxy-1-(4-iodo-phenyl)-methylene]-6-chloro-2-indolinone (educt VII.15)

(VIII.16) 1-acetyl-3-[1-methoxy-1-(3-iodo-phenyl)-methylene]-6-fluoro-2-indolinone from 1-acetyl-3-[1-hydroxy-1-(3-iodo-phenyl)-methylene]-6-fluoro-2-indolinone (educt VII.16)

(VIII.17) 1-acetyl-3-[1-methoxy-1-(3-(2-methoxycarbonyl-ethyl)-phenyl)-methylene]-6-fluoro-2-indolinone from 1-acetyl-3-[1-hydroxy-1-(3-(2-methoxycarbonyl-ethyl)-phenyl)-methylene]-6-fluoro-2-indolinone (educt VII.17)

(VIII.18) 1-acetyl-3-[1-methoxy-1-(4-(2-methoxycarbonyl-ethyl)-phenyl)-methylene]-6-fluoro-2-indolinone from 1-acetyl-3-[1-hydroxy-1-(4-(2-methoxycarbonyl-ethyl)-phenyl)-methylene]-6-fluoro-2-indolinone (educt VII.18)

(VIII.19) 1-acetyl-3-[1-methoxy-1-(4-(N-tert.butoxycarbonyl-2-aminoethyl)-phenyl)-methylene]-6-fluoro-2-indolinone from 1-acetyl-3-[1-hydroxy-1-(4-(N-tert.butoxycarbonyl-2-aminoethyl)-phenyl)-methylene]-6-fluoro-2-indolinone (educt VII.20)

(VIII.20) 1-acetyl-3-[1-methoxy-1-(3-(N-tert.butoxycarbonyl-2-aminoethyl)-phenyl)-methylene]-6-fluoro-2-indolinone from 1-acetyl-3-[1-hydroxy-1-(3-(N-tert.butoxycarbonyl-2-aminoethyl)-phenyl)-methylene]-6-fluoro-2-indolinone (educt VII.19)

(VIII.21) 1-acetyl-3-[1-methoxy-1-(3-acetylaminomethyl-phenyl)-methylene]-6-fluoro-2-indolinone from 1-acetyl-3-[1-hydroxy-1-(3-acetylaminomethyl-phenyl)-methylene]-6-fluoro-2-indolinone (educt VII.26)

(VIII.22) 1-acetyl-3-[1-methoxy-1-(3-(2-ethoxycarbonyl-ethyl)-phenyl)-methylene]-6-fluoro-2-indolinone from 1-acetyl-3-[1-hydroxy-1-(3-(2-ethoxycarbonyl-ethyl)-phenyl)-methylene]-6-fluoro-2-indolinone (educt VII.27)

(VIII.23) 1-acetyl-3-[1-methoxy-1-(4-(2-methoxycarbonyl-ethyl)-phenyl)-methylene]-6-chloro-2-indolinone from 1-acetyl-3-[1-hydroxy-1-(4-(2-methoxycarbonyl-ethyl)-phenyl)-methylene]-6-chloro-2-indolinone (educt VII.28)

(VIII.24) 1-acetyl-3-[1-methoxy-1-(4-(2-ethoxycarbonyl-ethyl)-phenyl)-methylene]-6-fluoro-2-indolinone from 1-acetyl-3-[1-hydroxy-1-(4-(2-ethoxycarbonyl-ethyl)-phenyl)-methylene]-6-fluoro-2-indolinone (educt VII.29)

(VIII.25) 1-acetyl-3-[1-methoxy-1-(4-methoxycarbonylmethyloxy-phenyl)-methylene]-6-fluoro-2-indolinone from 1-acetyl-3-[1-hydroxy-1-(4-methoxycarbonylmethyloxy-phenyl)-methylene]-6-fluoro-2-indolinone (educt VII.30)

(VIII.26) 1-acetyl-3-[1-methoxy-1-(3-methoxycarbonylmethyloxy-phenyl)-methylene]-6-fluoro-2-indolinone from 1-acetyl-3-[1-hydroxy-1-(3-methoxycarbonylmethyloxy-phenyl)-methylene]-6-fluoro-2-indolinone (educt VII.31)

(VIII.27) 1-acetyl-3-[1-methoxy-1-(3-(2-ethoxycarbonyl-ethyloxy)-phenyl)-methylene]-6-fluoro-2-indolinone from 1-acetyl-3-[1-hydroxy-1-(3-(2-ethoxycarbonyl-ethyloxy)-phenyl)-methylene]-6-fluoro-2-indolinone (educt VII.32)

(VIII.28) 1-acetyl-3-[1-methoxy-1-(4-(2-ethoxycarbonyl-ethyloxy)-phenyl)-methylene]-6-fluoro-2-indolinone from 1-acetyl-3-[1-hydroxy-1-(4-(2-ethoxycarbonyl-ethyloxy)-phenyl)-methylene]-6-fluoro-2-indolinone (educt VII.33)

EXAMPLE IX 1-acetyl-3-[1-ethoxy-1-phenyl-methylene]-6-chloro-2-indolinone

A solution of 41.9 g 1-acetyl-6-chloro-2-indolinone (educt V.1) and 136 ml triethyl orthobenzoate in 150 ml acetic anhydride is stirred for six hours at 120° C. After cooling the mixture is evaporated down by half, the crystals precipitated are suction filtered and dried at 100° C. in vacuo.

Yield: 38.0 g (56% of theory) $R_f$ value: 0.60 (silica gel, petroleum ether/dichloromethane/ethyl acetate 5:4:1) $C_{19}H_{16}ClNO_3$ Mass spectrum: m/z=342/344 [M+H]$^+$ M.p. 185-187° C.

The following compounds are prepared analogously to Example IX:

(IX.1) 1-acetyl-3-[1-ethoxy-1-phenyl-methylene]-6-bromo-2-indolinone from 1-acetyl-6-bromo-2-indolinone (educt V.2)

(IX.2) 1-acetyl-3-[1-ethoxy-1-phenyl-methylene]-6-cyano-2-indolinone from 1-acetyl-6-cyano-2-indolinone (educt V.3)

(IX.3) 1-acetyl-3-[1-ethoxy-1-phenyl-methylene]-6-fluoro-2-indolinone from 1-acetyl-6-fluoro-2-indolinone (educt V)

(IX.4) 1-acetyl-3-[1-ethoxy-1-phenyl-methylene]-5-nitro-6-chloro-2-indolinone from 1-acetyl-5-nitro-6-chloro-2-indolinone (educt VI)

EXAMPLE X 1-acetyl-3-[1-chloro-1-(4-acetylamino-3-nitro-phenyl)methylene]-2-indolinone A suspension of 11.4 g of 1-acetyl-3-(1-hydroxy-1-(4-acetylamino-3-nitro-phenyl)methylene)-2-indolinone (educt VII.21) and 9.37 g of phosphorus pentachloride in 200 ml dioxane is stirred for 4 hours at 100° C. After the addition of a further 2.0 g of phosphorus pentachloride the mixture is stirred for a further 3 hours at 100° C. Then the solvent is distilled off, the residue is stirred with 100 ml of ethyl acetate, suction filtered, washed with ethyl acetate and dried at 60° C.

Yield: 6.40 g (53% of theory) $R_f$ value: 0.70 (silica gel, dichloromethane/ethyl acetate=9:1) $C_{19}H_{14}ClN_3O_5$ Mass spectrum: m/z=398/400 [M−H]$^-$ The following compounds are prepared analogously to Example X:

(X.1) 1-acetyl-3-[1-chloro-1-(4-(imidazol-1-yl-methyl)-phenyl)-methylene]-6-chloro-2-indolinone from 1-acetyl-3-[1-hydroxy-1-(4-(imidazol-1-yl-methyl)-phenyl)-methylene]-6-chloro-2-indolinone (educt VII.22)

(X.2) 1-acetyl-3-[1-chloro-1-(4-(2-oxo-pyrrolidin-1-yl)-phenyl)-methylene]-6-chloro-2-indolinone from 1-acetyl-3-[1-chloro-1-(4-(2-oxo-pyrrolidin-1-yl)-methyl)-phenyl)-methylene]-6-chloro-2-indolinone (educt VII.23)

(X.3) 1-acetyl-3-[1-chloro-1-(4-nitro-phenyl)-methylene]-6-chloro-2-indolinone from 1-acetyl-3-[1-chloro-1-(4-nitro-methyl)-phenyl)-methylene]-6-chloro-2-indolinone (educt VII.24)

(X.4) 1-acetyl-3-[1-chloro-1-(4-cyano-phenyl)-methylene]-6-chloro-2-indolinone from 1-acetyl-3-[1-chloro-1-(4-cyano-methyl)-phenyl)-methylene]-6-chloro-2-indolinone (educt VII.25)

EXAMPLE XI

N-2-dimethylamino-ethyl)-4-nitro-benzamide 1.25 ml N,N-dimethylaminoethylamine are dissolved with 3 ml triethylamine in 20 ml methylene chloride and cooled to 0° C. Then 2 g of 4nitrobenzoic acid chloride are added batchwise and the mixture is stirred for 5 minutes in the cold and for 20 minutes at ambient temperature. Finally, the precipitate is removed by suction filtering and the organic phase is washed with water, dried over sodium sulphate and concentrated in the rotary evaporator.

Yield: 1.8 g (70% of theory) $R_f$ value: 0.78 (silica gel, methylene chloride/methanol=9:1) $C_{11}H_{15}N_3O_3$ Mass spectrum: m/z=238 [M+H]$^+$ The following compounds are prepared analogously to Example XI:

(XI.1) N-(2-dimethylamino-ethyl)-N-methyl-4-nitro-benzamide
(XI.2) N-(3-dimethylamino-propyl)-4-nitro-benzamide
(XI.3) N-(3-dimethylamino-propyl)-N-methyl-4-nitro-benzamide
(XI.4) N-(2-dimethylamino-ethyl)-N-ethyl-4-nitro-benzamide.
(XI.5) N-(2-(tert-butyloxycarbonyl-methylamino-ethyl)-N-methyl-4-nitro-benzamide
(XI.6) N,N-bis-(2-diethylamino-ethyl)-4-nitro-benzamide
(XI.7) N-(2-tert-butyloxycarbonyl-amino-ethyl)-4-nitro-benzamide
(XI.8) N-(2-dimethylamino-ethyl)-3-nitro-benzamide
(XI.9) N-(2-dimethylamino-ethyl)-N-methyl-3-nitro-benzamide
(XI.10) N-(3-dimethylamino-propyl)-3-nitro-benzamide
(XI.11) N-(3-dimethylamino-propyl)-N-methyl-3-nitro-benzamide
(XI.12) 2-N-(dimethylamino-methyl)-carbamoyl-5-nitro-furan
(XI.13) 4-(4-methyl-piperazin-1-yl-carbonyl)-nitrobenzene
(XI.14) 4-(piperidin-1-yl-carbonyl)-nitrobenzene
(XI.15) N-cyclohexyl-N-methyl-4-nitro-benzamide
(XI.16) N-isopropyl-4-nitro-benzamide
(XI.17) 4-(2,3,4,5-tetrahydro-1(H)-benzo[d]azepin-3-yl-carbonyl)-nitrobenzene
(XI.18) 4-(4-hydroxy-piperidin-1-yl-carbonyl)-nitrobenzene
(XI.19) 4-(4-tert-butyloxycarbonyl-piperazin-1-yl-carbonyl)-nitrobenzene
(XI.20) 4-(4-tert-butyloxycarbonyl-[1,4]diazepan-1-yl-carbonyl)-nitrobenzene
(XI.21) 4-(N-(3-dimethylamino-propyl)-N-methyl-carbamoylmethyl)-nitrobenzene
(XI.22) 4-(N-(2-dimethylamino-ethyl)-N-methyl-carbamoylmethyl)-nitrobenzene
(XI.23) 4-[(4-methyl-piperazin-1-yl)-carbonylmethyl]-nitrobenzene

EXAMPLE XII 2-amino-5-(4-methyl-piperazin-1-yl-carbonyl)-pyridine 3.00 g 6-amino-nicotinic acid are dissolved in 30 ml of dimethylformamide and 4.05 g of N,N-carbonyldiimidazole are added. The mixture is briefly heated to 70° C. and then stirred for a further hour at ambient temperature. After this time 4.85 ml of N-methylpiperazine are added and the mixture is stirred for 12 hours at ambient temperature. The solvent is eliminated and the residue is purified through a silica gel column with methylene chloride/ethanol/ammonia 7:1: 0.1 as eluant.

Yield: 4.1 g (86% of theory) $R_f$ value: 0.60 (silica gel, methylene chloride/ethanol/ammonia=5:1:0.1) $C_{11}H_{16}N_4O$ Mass spectrum: m/z=221 $[M+H]^+$ The following compounds are prepared analogously to Example XII:
(XII.1) 4-nitro-1-methyl-2-[(2-dimethylamino-ethyl)-N-methyl-carbamoyl]-pyrrole
(XII.2) 4-nitro-1-methyl-2-[(4-methyl-piperazin-1-yl)-carbonyl]-pyrrole

EXAMPLE XIII 4-(dimethylamino-ethoxy)-nitrobenzene 5.2 g p-nitrophenol are dissolved in 200 ml acetone and 7.2 g 2-chloro-N,N-dimethylethylamin-hydrochloride and 11 g potassium carbonate are added. The mixture is stirred for 12 hours at reflux temperature. After cooling the salts are filtered off, the filtrate is evaporated down and the residue is taken up in methylene chloride. The organic phase is washed with water, dried over sodium sulphate and finally the solvent is eliminated.

Yield: 4.1 g (53% of theory) $R_f$ value: 0.45 (silica gel, methylene chloride/methanol=9:1) $C_{10}H_{14}N_2O_3$ Mass spectrum: m/z=211 $[M+H]^+$

EXAMPLE XIV

4-{N-[(4-methyl-piperazin-1-yl)-aminocarbonyl]-N-methyl-amino}-nitrobenzene 11.6 ml of phosgene solution in toluene (20%) are dissolved in 20 ml of tetrahydrofuran and 3.0 g of N-methyl-4-nitroaniline and 2.8 ml triethylamine in 30 ml of tetrahydrofuran are added dropwise at 0° C. The mixture is stirred for 0.5 hours at 0° C. and for a further hour at ambient temperature. Then it is cooled again to 0° C., 5.4 ml of 1-amino-4-methyl-piperazine in 10 ml of tetrahydrofuran are added and the mixture is stirred for 2 hours at ambient temperature. After this time the solvent is eliminated, the residue is taken up in ethyl acetate and extracted with water. The organic phase is dried over sodium sulphate and finally the solvent is removed. The residue is purified through an aluminium oxide column (activity 2-3) with methylene chloride/ethanol 40:1 as eluant.

Yield: 3.3 g (56% of theory) $R_f$ value: 0.30 (aluminium oxide, methylene chloride/ethanol=40:1) M.p. 170-172° C. $C_{13}H_{19}N_5O_3$ Mass spectrum: m/z=294 $[M+H]^+$ The following compounds are prepared analogously to Example XIV:
(XIV.1) 4-{N-[(1-methyl-piperidin-4-yl)-aminocarbonyl]-N-methyl-amino}-nitrobenzene
(XIV.2) 4-{N-[(4-methyl-piperazin-1-yl)-carbonyl]-N-methyl-amino}-nitrobenzene
(XIV.3) 4-{N-[N-(3-dimethylamino-propyl)-aminocarbonyl]-N-methyl-amino}-nitrobenzene
(XIV.4) 4-[N-(pyridin-4-yl-methylaminocarbonyl)-N-methyl-amino]-nitrobenzene
(XIV.5) 4-{N-[(1-methyl-piperidin-4-oxy)-carbonyl]-N-methyl-amino}-nitrobenzene

EXAMPLE XV

The syntheses of the following compounds are already described in International Application WO 01/27081:
(XV.1) 4-[(2,6-dimethyl-piperidin-1-yl)-methyl]-aniline
(XV.2) N-(2-dimethylamino-ethyl)-N-methylsulphonyl-p-phenylenediamine
(XV.3) 3-(dimethylaminomethyl)-aniline
(XV.4) 4-(dimethylaminomethyl)-aniline
(XV.5) 4-(2-dimethylamino-ethyl)-aniline
(XV.6) 4-[N-(2-dimethylamino-ethyl)-N-acetyl-amino]-aniline
(XV.7) 4-[N-(3-dimethylamino-propyl)-N-acetyl-amino]-aniline
(XV.8) 4-[N-(2-dimethylamino-ethyl)-N-benzoyl-amino]-aniline (XV.9) 4-[N-(2-dimethylamino-ethyl)-N-propionyl-amino]-aniline
(XV.10) 4-[N-(2-dimethylamino-ethyl)-N-butyryl-amino]-aniline
(XV.11) 4-[N-(2-dimethylamino-ethyl)-N-isobutyryl-amino]-aniline
(XV.12) 4-(N-tert.butoxycarbonyl-aminomethyl)-aniline
(XV.13) 4-(N-ethyl-N-tert.butoxycarbonyl-aminomethyl)-aniline
(XV.14) 4-[N-(4-chlorophenyl-methyl)-N-tert.butoxycarbonyl-aminomethyl]-aniline
(XV.15) 4-(N-cyclohexyl-N-tert.butoxycarbonyl-aminomethyl)-aniline
(XV.16) 4-(N-isopropyl-N-tert.butoxycarbonyl-aminomethyl)-aniline
(XV.17) 4-(N-propyl-N-tert.butoxycarbonyl-aminomethyl)-aniline
(XV.18) 4-(N-methyl-N-tert.butoxycarbonyl-aminomethyl)-aniline
(XV.19) 4-(N-butyl-N-tert.butoxycarbonyl-aminomethyl)-aniline
(XV.20) 4-(N-methoxycarbonyl-methyl-N-tert.butoxycarbonyl-aminomethyl)-aniline
(XV.21) 4-(N-benzyl-N-tert.butoxycarbonyl-aminomethyl)-aniline
(XV.22) 4-(pyrrolidin-1-yl-methyl)-aniline
(XV.23) 4-(morpholin-4-yl-methyl)-aniline
(XV.24) 4-(hexamethyleneiminomethyl)-aniline
(XV.25) 4-(4-hydroxy-piperidin-1-yl-methyl)-aniline
(XV.26) 4-(4-methoxy-piperidin-1-yl-methyl)-aniline
(XV.27) 4-(4-methyl-piperidin-1-yl-methyl)-aniline
(XV.28) 4-(4-ethyl-piperidin-1-yl-methyl)-aniline
(XV.29) 4-(4-isopropyl-piperidin-1-yl-methyl)-aniline
(XV.30) 4-(4-phenyl-piperidin-1-yl-methyl)-aniline
(XV.31) 4-(4-benzyl-piperidin-1-yl-methyl)-aniline
(XV.32) 4-(4-ethoxycarbonyl-piperidin-1-yl-methyl)-aniline
(XV.33) 4-(N,N-dipropyl-aminomethyl)-aniline
(XV.34) 4-(4-tert.butoxycarbonyl-piperazin-1-yl-methyl)-aniline
(XV.35) 4-(2-morpholin-4-yl-ethyl)-aniline
(XV.36) 4-(2-pyrrolidin-1-yl-ethyl)-aniline
(XV.37) 4-(2-piperidin-1-yl-ethyl)-aniline
(XV.38) 4-(N-propyl-N-benzyl-aminomethyl)-aniline
(XV.39) 4-[N-(n-hexyl)-N-methyl-aminomethyl]-aniline
(XV.40) 4-[N-methyl-N-(4-chlorbenzyl)-aminomethyl]-aniline
(XV.41) 4-[N-methyl-N-(4-brombenzyl)-aminomethyl]-aniline
(XV.42) 4-[N-methyl-N-(4-methylbenzyl)-aminomethyl]-aniline
(XV.43) 4-[N-methyl-N-(4-fluorbenzyl)-aminomethyl]-aniline
(XV.44) 4-[N-methyl-N-(3-chlorbenzyl)-aminomethyl]-aniline
(XV.45) 4-[N-methyl-N-(3,4-dimethoxybenzyl)-aminomethyl]-aniline
(XV.46) 4-[N-methyl-N-(4-methoxybenzyl)-aminomethyl]-aniline
(XV.47) 4-(N-2,2,2-trifluorethyl-N-benzyl-aminomethyl)-aniline
(XV.48) 4-[N-2,2,2-trifluorethyl-N-(4-chlorbenzyl)-aminomethyl]-aniline
(XV.49) 4-(thiomorpholin-4-yl-methyl)-aniline
(XV.50) 4-(1-oxo-thiomorpholin-4-yl-methyl)-aniline
(XV.51) 4-(1,1-dioxo-thiomorpholin-4-yl-methyl)-aniline
(XV.52) 4-(azetidin-1-yl-methyl)-aniline
(XV.53) 4-(3,4-dihydropyrrolidin-1-yl-methyl)-aniline
(XV.54) 4-(3,4-dihydropiperidin-1-yl-methyl)-aniline
(XV.55) 4-(2-methoxycarbonyl-pyrrolidin-1-yl-methyl)-aniline
(XV.56) 4-(3,5-dimethyl-piperidin-1-yl-methyl)-aniline
(XV.57) 4-(4-phenyl-piperazin-1-yl-methyl)-aniline
(XV.58) 4-(4-phenyl-4-hydroxy-piperidin-1-yl-methyl)-aniline
(XV.59) 4-[N-(3,4,5-trimethoxy-benzyl)-N-methyl-aminomethyl]-aniline
(XV.60) 4-[N-(3,4-dimethoxy-benzyl)-N-ethyl-aminomethyl]-aniline
(XV.61) 4-(N-benzyl-N-ethyl-aminomethyl)-aniline
(XV.62) 4-[N-(2,6-dichlorobenzyl)-N-methyl-aminomethyl]-aniline
(XV.63) 4-[N-(4-trifluoromethylbenzyl)-N-methyl-aminomethyl]-aniline
(XV.64) 4-(N-benzyl-N-isopropyl-aminomethyl)-aniline
(XV.65) 4-(N-benzyl-N-tert.butyl-aminomethyl)-aniline
(XV.66) 4-(diethylamino-methyl)-aniline
(XV.67) 4-(2-diethylamino-ethyl)-aniline
(XV.68) 4-(N,N-diisopropyl-aminomethyl)-aniline
(XV.69) 4-(N,N-diisobutyl-aminomethyl)-aniline
(XV.70) 4-(2,3,4,5-tetrahydro-benzo(d)azepin-3-yl-methyl)-aniline
(XV.71) 4-(2,3-dihydro-isoindol-2-yl-methyl)-aniline
(XV.72) 4-(6,7-dimethoxy-1,2,3,4-tetrahydro-isoquinolin-2-yl-methyl)-aniline
(XV.73) 4-(1,2,3,4-tetrahydro-isoquinolin-2-yl-methyl)-aniline
(XV.74) 4-[N-(2-hydroxy-ethyl)-N-benzyl-aminomethyl]-aniline
(XV.75) 4-[N-(1-ethyl-pentyl)-N-(pyridin-2-yl-methyl)-aminomethyl]-aniline
(XV.76) 4-(piperidin-1-yl-methyl)-3-nitro-aniline
(XV.77) 4-(piperidin-1-yl-methyl)-3-amino-aniline
(XV.78) 4-(N-benzyl-N-methyl-aminomethyl)-aniline
(XV.79) 4-(N-ethyl-N-methyl-aminomethyl)-aniline
(XV.80) 4-(N-phenethyl-N-methyl-aminomethyl)-aniline
(XV.81) 4-[N-(3,4-dihydroxy-phenethyl)-N-methyl-aminomethyl]-aniline
(XV.82) 4-[N-(3,4,5-trimethoxy-phenethyl)-N-methyl-aminomethyl]-aniline
(XV.83) 4-[N-(3,4-dimethoxy-phenethyl)-N-methyl-aminomethyl]-aniline
(XV.84) 4-[N-(3,4-dimethoxy-benzyl)-N-methyl-aminomethyl]-aniline
(XV.85) 4-[N-(4-chloro-benzyl)-N-methyl-aminomethyl]-aniline
(XV.86) 4-[N-(4-bromo-benzyl)-N-methyl-aminomethyl]-aniline
(XV.87) 4-[N-(4-fluoro-benzyl)-N-methyl-aminomethyl]-aniline
(XV.88) 4-[N-(4-methyl-benzyl)-N-methyl-aminomethyl]-aniline
(XV.89) 4-[N-(4-nitro-phenethyl)-N-methyl-aminomethyl]-aniline
(XV.90) 4-(N-phenethyl-N-benzyl-aminomethyl)-aniline
(XV.91) 4-(N-phenethyl-N-cyclohexyl-aminomethyl)-aniline
(XV.92) 4-[N-(2-(pyridin-2-yl)-ethyl)-N-methyl-aminomethyl]-aniline
(XV.93) 4-[N-(2-(pyridin-4-yl)-ethyl)-N-methyl-aminomethyl]-aniline
(XV.94) 4-[N-(pyridin-4-yl-methyl)-N-methyl-aminomethyl]-aniline
(XV.95) 4-(N,N-dibenzylaminomethyl)-aniline (XV.96) 4-[N-(4-nitro-benzyl)-N-propyl-aminomethyl]-aniline
(XV.97) 4-[N-benzyl-N-(3-cyano-propyl)-aminomethyl]-aniline
(XV.98) 4-(N-benzyl-N-allyl-aminomethyl)-aniline
(XV.99) 4-[N-benzyl-N-(2,2,2-trifluorethyl)-aminomethyl]-aniline
(XV.100) 4-[(benzo(1,3)dioxol-5-yl-methyl)-methyl-aminomethyl]-aniline
(XV.101) 4-(7-chloro-2,3,4,5-tetrahydro-benzo(d)azepin-3-yl-methyl)-aniline
(XV.102) 4-(7,8-dichloro-2,3,4,5-tetrahydro-benzo(d)azepin-3-yl-methyl)-aniline
(XV.103) 4-(7-methoxy-2,3,4,5-tetrahydro-benzo(d)azepin-3-yl-methyl)-aniline
(XV.104) 4-(7-methyl-2,3,4,5-tetrahydro-benzo(d)azepin-3-yl-methyl)-aniline
(XV.105) 4-(7,8-dimethoxy-2,3,4,5-tetrahydro-benzo(d)azepin-3-yl-methyl)-aniline
(XV.106) 4-(6,7-dichloro-1,2,3,4-tetrahydro-isoquinolin-2-yl-methyl)-aniline
(XV.107) 4-(6,7-dimethyl-1,2,3,4-tetrahydro-isoquinolin-2-yl-methyl)-aniline
(XV.108) 4-(6-chloro-1,2,3,4-tetrahydro-isoquinolin-2-yl-methyl)-aniline
(XV.109) 4-(7-chloro-1,2,3,4-tetrahydro-isoquinolin-2-yl-methyl)-aniline
(XV.110) 4-(6-methoxy-1,2,3,4-tetrahydro-isoquinolin-2-yl-methyl)-aniline
(XV.111) 4-(7-methoxy-1,2,3,4-tetrahydro-isoquinolin-2-yl-methyl)-aniline
(XV.112) 4-(2,3,4,5-tetrahydro-azepino(4,5-b)pyrazin-3-yl-methyl)-aniline
(XV.113) 4-(7-amino-2,3,4,5-tetrahydro-azepino(4,5-b)pyrazin-3-yl-methyl)-aniline
(XV.114) 4-(2-amino-5,6,7,8-tetrahydro-azepino(4,5-d)thiazol-6-yl-methyl)-aniline
(XV.115) 4-(5,6,7,8-tetrahydro-azepino(4,5-d)thiazol-6-yl-methyl)-aniline
(XV.116) 4-(4-methyl-piperazin-1-yl)-aniline
(XV.117) 4-[N-(2-dimethylamino-ethyl)-N-methyl-amino]-aniline
(XV.118) 4-[N-(3-dimethylamino-propyl)-N-methyl-amino]-aniline
(XV.119) N-(3-dimethylamino-propyl)-N-methylsulphonyl-p-phenylenediamine
(XV.120) 4-[(N-dimethylaminocarbonylmethyl-N-methylsulphonyl)-amino]-aniline
(XV.121) N-(4-aminophenyl)-N-methyl-methanesulphonamide
(XV.122) 4-(imidazol-4-yl)-aniline
(XV.123) 4-(tetrazol-5-yl)-aniline
(XV.124) 3-[N-(2-dimethylamino-ethyl)-N-propionyl-amino]-aniline
(XV.125) N-(dimethylamino-methylcarbonyl)-N-methyl-p-phenylenediamine
(XV.126) N-[(2-dimethylamino-ethyl)-carbonyl]-N-methyl-p-phenylenediamine
(XV.127) N-dimethylaminocarbonylmethyl-N-acetyl-p-phenylenediamine
(XV.128) N-methylaminocarbonylmethyl-N-methylsulphonyl-p-phenylenediamine
(XV.129) N-aminocarbonylmethyl-N-methylsulphonyl-p-phenylenediamine
(XV.130) 4-(imidazolidin-2,4-dion-5-yliden-methyl)-aniline
(XV.131) 4-(imidazolidin-2,4-dion-5-yl-methyl)-aniline
(XV.132) 4-(2-oxo-pyrrolidin-1-yl-methyl)-aniline
(XV.133) N-cyanomethyl-N-methylsulphonyl-p-phenylenediamine
(XV.134) 4-[2-(imidazol-4-yl)-ethyl]-aniline
(XV.135) 4-[(4-methyl-piperazin-1-yl)-methyl]-aniline
(XV.136) 4-[N-(2-(N-benzyl-N-methyl-amino)-ethyl)-N-methylsulphonyl-amino]-aniline
(XV.137) 4-[N-(3-(N-benzyl-N-methyl-amino)-propyl)-N-methylsulphonyl-amino]-aniline
(XV.138) N-cyclohexyl-p-phenylenediamine
(XV.139) 4-(pyridin-4-yl-methyl)-aniline
(XV.140) 4-(imidazol-1-yl-methyl)-aniline
(XV.141) 4-benzyl-aniline
(XV.142) N-(3-trifluoracetylamino-propyl)-N-methylsulphonyl-p-phenylenediamine
(XV.143) tert.butyl 4-amino-phenylacetate
(XV.144) 4-(imidazol-2-yl)-aniline
(XV.145) 4-(1-methyl-imidazol-2-yl)-aniline
(XV.146) 4-(1-ethyl-imidazol-2-yl)-aniline
(XV.147) 4-(1-benzyl-imidazol-2-yl)-aniline
(XV.148) 4-[N-(2-dimethylamino-ethyl)-N-methylsulphonyl-amino]-3-amino-aniline
(XV.149) 4-[N-(2-dimethylamino-ethyl)-N-methylsulphonyl-amino]-3-chloro-aniline
(XV.150) 4-[N-(2-dimethylamino-ethyl)-N-acetyl-amino]-3-amino-aniline
(XV.151) 4-[N-(2-dimethylamino-ethyl)-N-acetyl-amino]-3-bromo-aniline
(XV.152) 4-[2-(4-hydroxy-piperidin-1-yl)-ethyl-amino]-aniline
(XV.153) N-(2-dimethylamino-ethyl)-N-ethylsulphonyl-p-phenylenediamine
(XV.154) N-(2-dimethylamino-ethyl)-N-propylsulphonyl-p-phenylenediamine
(XV.155) N-(2-dimethylamino-ethyl)-N-isopropylsulphonyl-p-phenylenediamine
(XV.156) N-(2-dimethylamino-ethyl)-N-butylsulphonyl-p-phenylenediamine
(XV.157) N-(2-dimethylamino-ethyl)-N-benzylsulphonyl-p-phenylenediamine
(XV.158) N-(2-dimethylamino-ethyl)-N-phenylsulphonyl-p-phenylenediamine
(XV.159) 4-((3-hydroxy-pyrrolidin-1-yl)-methyl)-aniline
(XV.160) 4-[N-(2-dimethylamino-ethyl)-N-(furan-2-carbonyl)-amino]-aniline
(XV.161) 4-[N-(2-dimethylamino-ethyl)-N-(2-methoxy-benzoyl)-amino]-aniline
(XV.162) 4-[N-(2-dimethylamino-ethyl)-N-(pyridine-3-carbonyl)-amino]-aniline
(XV.163) 4-[N-(2-dimethylamino-ethyl)-N-(phenyl-acetyl)-amino]-aniline
(XV.164) N-(piperidin-1-yl-methylcarbonyl)-N-methyl-p-phenylenediamine
(XV.165) N-(morpholin-4-yl-methylcarbonyl)-N-methyl-p-phenylenediamine
(XV.166) N-[(4-benzyl-piperazin-1-yl)-methylcarbonyl]-N-methyl-p-phenylenediamine
(XV.167) N-(pyrrolidin-1-yl-methylcarbonyl)-N-methyl-p-phenylenediamine
(XV.168) 4-(5-methyl-imidazol-4-yl)-aniline
(XV.169) N-[(2-dimethylamino-ethyl)-carbonyl]-N-isopropyl-p-phenylenediamine
(XV.170) N-[(2-dimethylamino-ethyl)-carbonyl]-N-benzyl-p-phenylenediamine
(XV.171) N-(N-aminocarbonylmethyl-N-methyl-amino)-methylcarbonyl)-N-methyl-p-phenylenediamine
(XV.172) N-[(N-benzyl-N-methyl-amino)-methylcarbonyl]-N-methyl-p-phenylenediamine (XV.173) N-[di-(2-methoxyethyl)-amino-methylcarbonyl]-N-methyl-p-phenylenediamine
(XV.174) N-[(2-(4-tert.butoxycarbonyl-piperazin-1-yl)-ethyl)-carbonyl]-N-methyl-p-phenylenediamine
(XV.175) N-[(2-(piperidin-1-yl)-ethyl)-carbonyl]-N-methyl-p-phenylenediamine
(XV.176) N-[(2-(N-benzyl-N-methyl-amino)-ethyl)-carbonyl]-N-methyl-p-phenylenediamine
(XV.177) N-(dimethylaminomethylcarbonyl)-N-isopropyl-p-phenylenediamine
(XV.178) N-(piperidin-1-yl-methylcarbonyl)-N-isopropyl-p-phenylenediamine
(XV.179) N-[(4-tert.butoxycarbonyl-piperazin-1-yl)-methylcarbonyl]-N-isopropyl-p-phenylenediamine
(XV.180) N-[(N-benzyl-N-methyl-amino)-methylcarbonyl]-N-benzyl-p-phenylenediamine
(XV.181) N-(dimethylaminomethylcarbonyl)-N-benzyl-p-phenylenediamine
(XV.182) N-(piperidin-1-yl-methylcarbonyl)-N-benzyl-p-phenylenediamine
(XV.183) 4-(1,2,4-triazol-1-yl-methyl)-aniline
(XV.184) 4-(1,2,3-triazol-2-yl-methyl)-aniline
(XV.185) 4-(1,2,3-triazol-1-yl-methyl)-aniline
(XV.186) 4-[(N-ethoxycarbonylmethyl-N-methyl-amino)-methyl]-aniline
(XV.187) 4-[(N-aminocarbonylmethyl-N-methyl-amino)-methyl]-aniline
(XV.188) 4-(azetidin-1-yl-methyl)-aniline
(XV.189) 4-[(di-(2-methoxy-ethyl)-amino)-methyl]-aniline
(XV.190) 4-[(N-(2-(2-methoxy-ethoxy)-ethyl)-N-methyl-amino)-methyl]-aniline
(XV.191) 4-[N-(N-tert.butoxycarbonyl-3-amino-propyl)-N-methyl-aminomethyl]-aniline
(XV.192) 4-[(N-(methylcarbamoyl-methyl)-N-methyl-amino)-methyl]-aniline
(XV.193) 4-[(N-(dimethylcarbamoyl-methyl)-N-methyl-amino)-methyl]-aniline
(XV.194) 4-[(N-propyl-N-methyl-amino)-methyl]-aniline
(XV.195) 4-[(N-(2-dimethylamino-ethyl)-N-methyl-amino)-methyl]-aniline
(XV.196) 4-[(N-(3-dimethylamino-propyl)-N-methyl-amino)-methyl]-aniline
(XV.197) 4-[(N-(2-methoxy-ethyl)-N-methyl-amino)-methyl]-aniline
(XV.198) 4-[(N-(2-hydroxy-ethyl)-N-methyl-amino)-methyl]-aniline
(XV.199) 4-[(N-(dioxolan-2-yl-methyl)-N-methyl-amino)-methyl]-aniline
(XV.200) 4-(3-oxo-piperazin-1-yl-methyl)-aniline
(XV.201) N-[di-(2-hydroxyethyl)-amino-methylcarbonyl]-N-methyl-p-phenylenediamine
(XV.202) N-[(N-(2-methoxyethyl)-N-methyl-amino)-methylcarbonyl]-N-methyl-p-phenylenediamine
(XV.203) N-[(N-(2-dimethylamino-ethyl)-N-methyl-amino)-methylcarbonyl]-N-methyl-p-phenylenediamine
(XV.204) N-[(4-methyl-piperazin-1-yl)-methylcarbonyl]-N-methyl-p-phenylenediamine
(XV.205) N-[(imidazol-1-yl)-methylcarbonyl]-N-methyl-p-phenylenediamine
(XV.206) N-[(phthalimido-2-yl)-methylcarbonyl]-N-methyl-p-phenylenediamine
(XV.207) 4-(piperidin-1-yl-methyl)-aniline The following compounds are prepared analogously to Example XV:

(XV.208) N-(dimethylcarbamoylmethyl)-p-phenylenediamine
(XV.209) di-(2-hydroxyethyl)-aminomethyl-aniline
(XV.210) 4-[N-(2-dimethylamino-ethyl)-N-(methoxy-acetyl)-amino]-aniline
(XV.211) 4-[N-(2-dimethylamino-ethyl)-N-(3,4-dimethoxy-benzoyl)-amino]-aniline
(XV.212) 4-[N-(2-(N-benzyl-N-methyl-amino)-ethyl)-N-propionyl-amino]-aniline
(XV.213) 4-[N-(2-dimethylamino-ethyl)-N-(pyridine-4-carbonyl)-amino]-aniline
(XV.214) 4-[N-(2-(N-benzyl-N-methyl-amino)-ethyl)-N-acetyl-amino]-aniline
(XV.215) N-(dimethylaminomethylcarbonyl)-N-methyl-3-methoxy-p-phenylenediamine
(XV.216) N-(dimethylaminomethylcarbonyl)-N-methyl-3-cyano-p-phenylenediamine
(XV.217) 3-(pyridin-4-yl-methyl)-aniline
(XV.218) 4-amino-N-(2-dimethylamino-ethyl)-benzamide
(XV.219) 4-amino-N-(2-dimethylamino-ethyl)-N-methyl-benzamide
(XV.220) 4-amino-N-(3-dimethylamino-propyl)-benzamide
(XV.221) 4-amino-N-(3-dimethylamino-propyl)-N-methyl-benzamide
(XV.222) 4-amino-N-(2-dimethylamino-ethyl)-N-ethyl-benzamide
(XV.223) 4-amino-N-(2-(tert-butyloxycarbonyl-methylamino-ethyl)-N-ethyl-benzamide
(XV.224) 4-amino-N,N-bis-(2-diethylamino-ethyl)-benzamide
(XV.225) 4-amino-N-(2-tert-butyloxycarbonyl-amino-ethyl)-benzamide.
(XV.226) 3-amino-N-(2-dimethylamino-ethyl)-benzamide
(XV.227) 3-amino-N-(2-dimethylamino-ethyl)-N-methyl-benzamide
(XV.228) 3-amino-N-(3-dimethylamino-propyl)-benzamide
(XV.229) 3-amino-N-(3-dimethylamino-propyl)-N-methyl-benzamide
(XV.230) 5-amino-2-N-(dimethylamino-methyl)-carbamoyl-furan
(XV.231) 4-(4-methyl-piperazin-1-yl-carbonyl)-aniline
(XV.232) 4-(piperidin-1-yl-carbonyl)-aniline
(XV.233) 4-amino-N-cyclohexyl-N-methyl-benzamide
(XV.234) 4-amino-N-isopropyl-benzamide
(XV.235) 4-(2,3,4,5-tetrahydro-1(H)-benzo[d]azepin-3-yl-carbonyl)-aniline
(XV.236) 4-(4-hydroxy-piperidin-1-yl-carbonyl)-aniline
(XV.237) 4-(4-tert-butyloxycarbonyl-piperazin-1-yl-carbonyl)-aniline
(XV.238) 4-(4-tert-butyloxycarbonyl-[1,4]diazepan-1-yl-carbonyl)-aniline
(XV.239) 4-amino-1-methyl-2-[N-(2-dimethylamino-ethyl)-N-methyl-carbamoyl]-pyrrole
(XV.240) 4-amino-1-methyl-2-[(4-methyl-piperazin-1-yl)-carbonyl]-pyrrole
(XV.241) N-(2-dimethylamino-ethyl)-N-acetyl-2,5-diamino-pyridine
(XV.242) 4-(1-(2-dimethylamino-ethyl)-imidazol-2-yl)-aniline
(XV.243) N-[(2-(4-methyl-piperazin-1-yl)-ethyl)-carbonyl]-N-methyl-p-phenylenediamine
(XV.244) N-[(2-dimethylamino-ethyl)-carbonyl]-N-methyl-p-phenylenediamine
(XV.245) trans-N-dimethylaminomethylcarbonyl-N'-(tert.-butoxycarbonyl)-cyclohexyl-1,4-diamine
(XV.246) 4-(2-dimethylamino-ethoxy)-aniline (XV.247) 4-[(4-dimethylamino-piperidin-1-yl)-methyl]-aniline
(XV.248) N-[(4-tert.butoxycarbonyl-piperazin-1-yl)-methylcarbonyl]-N-methyl-p-phenylenediamine
(XV.249) N-hydroxymethylcarbonyl-N-methyl-p-phenylenediamine
(XV.250) 4-[N-(N-tert.butoxycarbonyl-3-aminopropyl)-N-methyl-aminomethyl]-aniline
(XV.251) N-[(4-methyl-homopiperazin-1-yl)-methylcarbonyl]-N-methyl-p-phenylenediamine
(XV.252) N-[(4-ethyl-piperazin-1-yl)-methylcarbonyl]-N-methyl-p-phenylenediamine
(XV.253) N-[(4-methyl-piperazin-1-yl)-methylcarbonyl]-p-phenylenediamine
(XV.254) N-[(1-methyl-piperidin-4-yl)-methylcarbonyl]-N-methyl-p-phenylenediamine
(XV.255) 4-(N-(3-dimethylamino-propyl)-N-methyl-carbamoylmethyl)-aniline
(XV.256) 4-(N-(2-dimethylamino-ethyl)-N-methyl-carbamoylmethyl)-aniline
(XV.257) 4-[(4-methyl-piperazin-1-yl)-carbonylmethyl]-aniline
(XV.258) N-(4-dimethylaminobutylcarbonyl)-N-methyl-p-phenylenediamine
(XV.259) N-dimethylaminomethylcarbonyl-N'-(tert.-butoxycarbonyl)-2,3-dimethyl-p-phenylenediamine
(XV.260) N-[(4-methyl-piperazin-1-yl)-methylcarbonyl]-N'-(tert.-butoxycarbonyl)-2,3-dimethyl-p-phenylenediamine
(XV.261) N-[(4-methyl-piperazin-1-yl)-aminocarbonyl]-N-methyl-p-phenylenediamine
(XV.262) N-[(4-methyl-piperazin-1-yl)-methylcarbonyl]-N-methyl-m-phenylenediamine
(XV.263) N-[(4-methyl-piperazin-1-yl)-methylcarbonyl]-m-phenylenediamine
(XV.264) N-dimethylaminomethylcarbonyl-N-methyl-m-phenylenediamine
(XV.265) N-[(1-methyl-piperidin-4-yl)-aminocarbonyl]-N-methyl-p-phenylenediamine
(XV.266) N-[(3-dimethylamino-propyl)-carbonyl]-N-methyl-p-phenylenediamine
(XV.267) N-[(4-methyl-piperazin-1-yl)-carbonyl]-N-methyl-p-phenylenediamine
(XV.268) N-[N-(3-dimethylamino-propyl)-aminocarbonyl]-N-methyl-p-phenylenediamine
(XV.269) N-(pyridin-4-yl-methylaminocarbonyl)-N-methyl-p-phenylenediamine
(XV.270) N-(1-methyl-piperidin-4-oxy-carbonyl)-N-methyl-p-phenylenediamine

EXAMPLE XVI trans-N-dimethylaminomethylcarbonyl-cyclohexyl-1,4-diamine-trifluor0acetate 400 mg of trans-N-dimethylaminomethylcarbonyl-N'-(tert.-butoxycarbonyl)-cyclohexyl-1,4-diamine (educt XV.245) are dissolved in 12 ml methylene chloride and 5.0 ml of trifluoroacetic acid are added. The mixture is stirred for 0.5 hours at ambient temperature, evaporated down, combined with toluene and concentrated again in the rotary evaporator.

Yield: 420 mg (100% of theory), $C_{10}H_{21}N_3O$ Mass spectrum: m/z=200 $[M+H]^+$ The following compounds are prepared analogously to Example XVI:

(XVI.1) N-dimethylaminomethylcarbonyl-2,3-dimethyl-p-phenylenediamine
(XVI.2) N-[(4-methyl-piperazin-1-yl)-methylcarbonyl]-2,3-dimethyl-p-phenylenediamine

EXAMPLE XVII cis-N-dimethylaminomethylcarbonyl-N-methyl-cyclohexyl-1,4-diamin-trifluoroacetate 5.0 g of N-dimethylaminomethylcarbonyl-N-methyl-p-phenylenediamine (educt XV.125) are dissolved in 250 ml glacial acetic acid and 500 mg of Nishimura catalyst (Rh (III)-/Pt(IV)-oxide) are added. The mixture is hydrogenated for 9 hours at ambient temperature under 50 psi, evaporated down, combined with water and then neutralised with sodium hydrogen carbonate solution. After evaporation the residue is taken up in methylene chloride, filtered, dried over sodium sulphate and finally the solvent is eliminated.

Yield: 1.5 g (29% of theory), $C_{11}H_{23}N_3O$ Mass spectrum: m/z=213 $[M]^+$

EXAMPLE XVIII

N-acetyl-4-(2-diethylamino-ethyl-sulphonyl)-aniline 9.0 g of 4-acetamido-phenylsulphinic acid are dissolved in 10 ml of water and 45 ml of 1N sodium hydroxide solution and 9.47 g of 2-chlorotriethylamine hydrochloride are added. The mixture is stirred for 5 hours at reflux temperature. After cooling, sodium hydroxide solution is added until an alkaline reaction is obtained, the mixture is extracted with ethyl acetate, dried over magnesium sulphate and finally the solvent is eliminated.

Yield: 9.85 g (73% of theory), $C_{14}H_{22}N_2O_3S$ Mass spectrum: m/z=298 $[M]^+$

EXAMPLE XIX 4-(2-diethylamino-ethyl-sulphonyl)-aniline 9.85 g of N-acetyl-4-(2-diethylamino-ethyl-sulphonyl)-aniline (educt XVII) are dissolved in 25 ml of ethanol and 100 ml of 3N hydrochloric acid are added. The mixture is stirred for 1 hour at reflux temperature. After cooling it is neutralised, extracted three times with methylene chloride, dried over magnesium sulphate and finally the solvent is eliminated.

Yield: 5.75 g (68% of theory), $C_{12}H_{20}N_2O_2S$ Mass spectrum: m/z=257 $[M+H]^+$

EXAMPLE XX

3-Z-[1-(4-(dimethylcarbamoylmethylamino)-anilino)-1-phenyl-methylene]-6-chloro-2-indolinone 6.0 g of 1-acetyl-3-(1-ethoxy-1-phenylmethylen)-6-chloro-2-indolinone (educt IX) and 3.9 g of N-(dimethylcarbamoylmethyl)-p-phenylenediamine (educt XV.208) are dissolved in 50 ml of dimethylformamide and stirred for 4.5 hours at 120° C. After cooling water is added, the precipitate formed is suction filtered and washed with methanol. The product is purified through a silica gel column with methylene chloride/methanol (100:1) as eluant and finally recrystallised from ether.

Yield: 4.4 g (49% of theory), M.p. 208-211° C. $C_{27}H_{25}ClN_4O_3$ Mass spectrum: m/z=487/489 $[M-H]^-$

EXAMPLE XXI

3-Z-[1-(4-(N-(dimethyl-carbamoyl-methyl)-N-(2-bromo-ethyl-carbonyl)-amino)-anilino)-1-phenyl-methylene]-6-chloro-2-indolinone 500 mg of 3-Z-[1-(4-(dimethylcarbamoylmethylamino)-anilino)-1-phenyl-methylene]-6-chloro-2-indolinone (educt XX) and 430 mg sodium hydrogen carbonate are placed in 10 ml of methylene chloride and 190 mg of 3-bromopropionic acid chloride are slowly added. The mixture is stirred for 1 hour at ambient temperature. Then it is filtered and the filtrate is evaporated down. The precipitate formed is recrystallised from methanol.

Yield: 270 mg (42% of theory) $R_f$ value: 0.50 (silica gel, methylene chloride/methanol=9:1) $C_{30}H_{28Br}ClN_4O_4$ Mass spectrum: m/z=621/623/625 [M-H]$^-$ The following compound is prepared analogously to Example XXI:
(XXI.1)  3-Z-[1-(4-(N-(dimethyl-carbamoyl-methyl)-N-(bromo-acetyl)-amino)-anilino)-1-phenyl-methylene]-6-chloro-indolinone
from 3-Z-[1-(4-(dimethylcarbamoylmethylamino)-anilino)-1-phenyl-methylene]-6-chloro-2-indolinone (educt XX) and bromoacetylchloride Preparation of the End Compounds:

EXAMPLE 1.0

3-Z-[1-(4-(N-(2-dimethylamino-ethyl)-N-methylsulphonyl-amino)-anilino)-1-phenyl-methylene]-6-chloro-2-indolinone 0.3 g of 1-acetyl-3-(1-ethoxy-1-phenylmethylen)-6-chloro-2-indolinone (educt IX) and 0.5 g of N-(2-dimethylamino-ethyl)-N-methylsulphonyl-p-phenylenediamine (educt XV.2) are dissolved in 20 ml of dimethylformamide and stirred for 3 hours at 120° C. After cooling 0.8 ml of piperidine are added and the mixture is stirred for a further hour at ambient temperature. The solvent is eliminated and the residue is purified through a silica gel column with methylene chloride/methanol (15:1) as eluant.

Yield: 0.2 g (40% of theory), $R_f$ value: 0.5 (silica gel, methylene chloride/methanol=9:1)  M.p. 237-239° C. $C_{26}H_{27}ClN_4O_3S$ Mass spectrum: m/z=511/513 [M+H]$^+$ The following compounds of general formula I-1 are prepared analogously to Example 1.0:

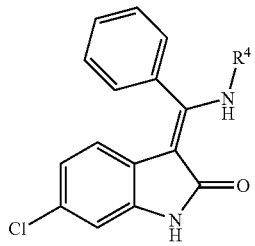

(I-1)

| Example | R$^4$ | R$^{4'}$ | educt | empirical formula | mass spectrum | m.p. [° C.] | R$_f$ value* |
|---|---|---|---|---|---|---|---|
| 1.1 | 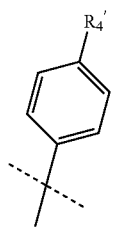 | —N(Me)—(CO)—CH$_2$—NMe$_2$ | XV.125 | C$_{26}$H$_{25}$ClN$_4$O$_2$ | 461/463 [M + H]$^+$ | 237-239 | 0.55 (A) |
| 1.2 | 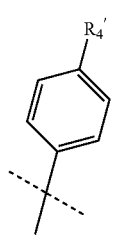 | —COOEt | — | C$_{24}$H$_{19}$ClN$_2$O$_3$ | 417/419 [M − H]$^-$ | 266-268 | 0.50 (B) |

-continued
(I-1)
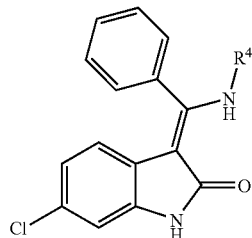
| Example | R⁴ | R⁴' | educt | empirical formula | mass spectrum | m.p. [° C.] | $R_f$ value* |
|---|---|---|---|---|---|---|---|
| 1.3 | 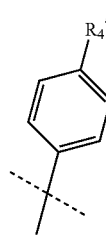 | —N(SO₂Me)—(CH₂)—(CO)—NMe₂ | XV.120 | $C_{26}H_{25}ClN_4O_4S$ | 523/525 [M − H]⁻ | 254 | 0.50 (C) |
| 1.4 | 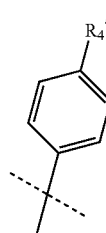 | —N(SO₂Me)—CH₃ | XV.121 | $C_{23}H_{20}ClN_3O_3S$ | 452/454 [M − H]⁻ | 276-278 | 0.50 (C) |
| 1.5 | 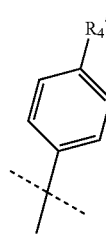 | —N(COMe)—CH₃ | — | $C_{24}H_{20}ClN_3O_2$ | 416/418 [M − H]⁻ | 308 (decomp.) | 0.50 (C) |

-continued
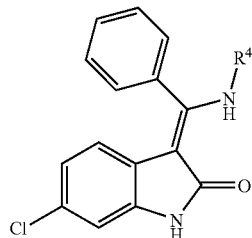
(I-1)
| Example | R⁴ | R⁴' | educt | empirical formula | mass spectrum | m.p. [°C.] | $R_f$ value* |
|---|---|---|---|---|---|---|---|
| 1.6 | 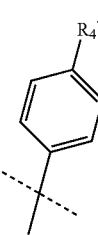 | —N(SO₂Et)—(CH₂)₂—NMe₂ | XV.153 | $C_{27}H_{29}ClN_4O_3S$ | 523/525 [M − H]⁻ | 220 | 0.50 (C) |
| 1.7 | 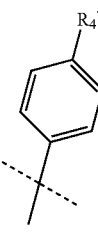 | —N(COEt)—(CH₂)₂—NMe₂ | XV.9 | $C_{28}H_{29}ClN_4O_2$ | 487/489 [M − H]⁻ | 144 | 0.50 (C) |
| 1.8 | 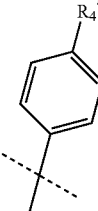 | —N(SO₂Me)—(CH₂)₃—NMe₂ | XV.119 | $C_{27}H_{29}ClN_4O_3S$ | 524/526 [M]⁺ | 214 | 0.50 (A) |

-continued
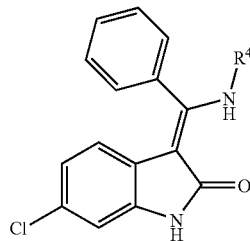
(I-1)
| Example | R⁴ | R⁴' | educt | empirical formula | mass spectrum | m.p. [°C.] | $R_f$ value* |
|---|---|---|---|---|---|---|---|
| 1.9 | 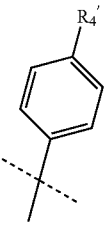 | —N(CO-nPr)—(CH$_2$)$_2$—NMe$_2$ | XV.10 | $C_{29}H_{31}ClN_4O_2$ | 501/503 [M − H]⁻ | 218 | 0.50 (A) |
| 1.10 | 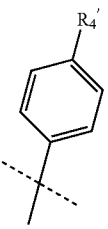 | —N(CO-iPr)—(CH$_2$)$_2$—NMe$_2$ | XV.11 | $C_{29}H_{31}ClN_4O_2$ | 501/503 [M − H]⁻ | 239 | 0.50 (A) |
| 1.11 | 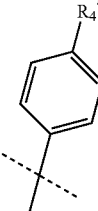 | —N(COMe)—(CH$_2$)$_2$—NMe$_2$ | XV.6 | $C_{27}H_{27}ClN_4O_2$ | 475/477 [M + H]⁺ | 170 | 0.50 (A) |

-continued
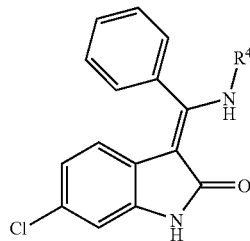
(I-1)
| Example | R⁴ | R⁴' | educt | empirical formula | mass spectrum | m.p. [° C.] | $R_f$ value* |
|---|---|---|---|---|---|---|---|
| 1.12 | 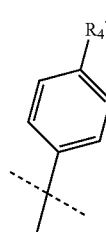 | —N(COPh)—(CH₂)₂—NMe₂ | XV.8 | $C_{32}H_{29}ClN_4O_2$ | 537/539 [M + H]⁺ | 215 | 0.50 (A) |
| 1.13 | 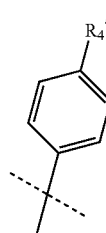 | —N(CO-Bn)—(CH₂)₂—NMe₂ | XV.163 | $C_{33}H_{31}ClN_4O_2$ | 551/553 [M + H]⁺ | 233 | 0.50 (A) |
| 1.14 | 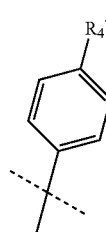 | —N[CO-(3-pyridyl)]-(CH₂)₂—NMe₂ | XV.162 | $C_{31}H_{28}ClN_5O_2$ | 538/540 [M + H]⁺ | 134 | 0.50 (A) |

-continued
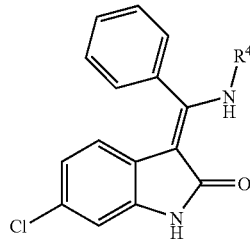
(I-1)
| Example | R⁴ | R⁴' | educt | empirical formula | mass spectrum | m.p. [°C.] | $R_f$ value* |
|---|---|---|---|---|---|---|---|
| 1.15 | 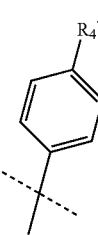 | —N[CO-(2-furanyl)]-(CH$_2$)$_2$—NMe$_2$ | XV.160 | C$_{30}$H$_{27}$ClN$_4$O$_3$ | 527/529 [M + H]$^+$ | 236 | 0.50 (A) |
| 1.16 | 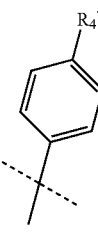 | —N[CO-(2-MeO-phenyl)]-(CH$_2$)$_2$—NMe$_2$ | XV.161 | C$_{33}$H$_{31}$ClN$_4$O$_3$ | 567/569 [M + H]$^+$ | 148 | 0.50 (A) |
| 1.17 | 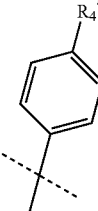 | —N(SO$_2$-nPr)-(CH$_2$)$_2$—NMe$_2$ | XV.154 | C$_{28}$H$_{31}$ClN$_4$O$_3$S | 537/539 [M − H]$^-$ | 222 | 0.50 (C) |

-continued
(I-1)
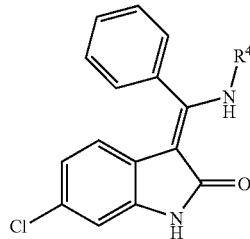
| Example | R⁴ | R⁴' | educt | empirical formula | mass spectrum | m.p. [° C.] | $R_f$ value* |
|---|---|---|---|---|---|---|---|
| 1.18 | 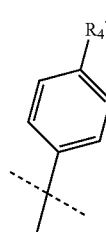 | —N(SO₂-iPr)-(CH₂)₂—NMe₂ | XV.155 | $C_{28}H_{31}ClN_4O_3S$ | 537/539 [M − H]⁻ | 167 | 0.50 (C) |
| 1.19 | 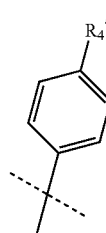 | —N(SO₂Bn)—(CH₂)₂—NMe₂ | XV.157 | $C_{32}H_{31}ClN_4O_3S$ | 585/587 [M − H]⁻ | 132 | 0.50 (C) |
| 1.20 | 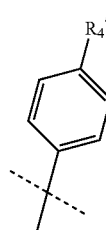 | 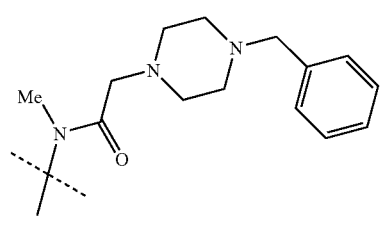 | XV.166 | $C_{35}H_{34}ClN_5O_2$ | 590/592 [M − H]⁻ | 235 | 0.50 (A) |

-continued
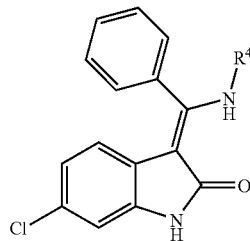
(I-1)
| Example | $R^4$ | $R^{4'}$ | educt | empirical formula | mass spectrum | m.p. [° C.] | $R_f$ value* |
|---|---|---|---|---|---|---|---|
| 1.21 | 4-($R_4'$)-phenyl | Me-N(tBu)-C(=O)-CH$_2$-morpholine | XV.165 | $C_{28}H_{27}ClN_4O_3$ | 501/503 [M − H]$^-$ | 259 | 0.50 (A) |
| 1.22 | 4-($R_4'$)-phenyl | Me-N(tBu)-C(=O)-CH$_2$-piperidine | XV.164 | $C_{29}H_{29}ClN_4O_2$ | 501/503 [M + H]$^+$ | 235 | 0.50 (A) |
| 1.23 | 4-($R_4'$)-phenyl | Me-N(tBu)-C(=O)-CH$_2$-N(Me)-CH$_2$-Ph | XV.172 | $C_{26}H_{26}ClN_5O_5S$ | 535/537 [M − H]$^-$ | 181 | 0.50 (A) |

-continued
(I-1)
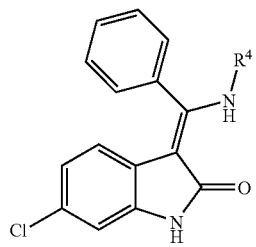
| Example | R⁴ | R⁴' | educt | empirical formula | mass spectrum | m.p. [° C.] | Rf value* |
|---|---|---|---|---|---|---|---|
| 1.24 | (R4' on para-position of phenyl) | —CH₂—NMe₂ | XV.4 | C₂₄H₂₂ClN₃O | 403/405 [M]⁺ | 207 | 0.50 (A) |
| 1.25 | (R4' on para-position of phenyl) | 2,6-dimethylpiperidinylmethyl | XV.1 | C₂₉H₃₀ClN₃O | 470/472 [M − H]⁻ | 226 | 0.50 (A) |
| 1.26 | (R4' on para-position of phenyl) | —CH₂—C(Me)₂—N(Me)—CH₂CH₂—O—CH₂CH₂—OMe | XV.190 | C₂₈H₃₀ClN₃O₃ | 492/494 [M + H]⁺ | 140 | 0.50 (A) |

-continued
(I-1)
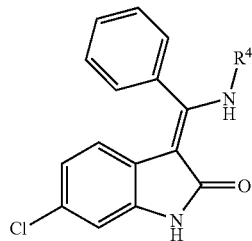
| Example | R⁴ | R⁴' | educt | empirical formula | mass spectrum | m.p. [° C.] | R_f value* |
|---|---|---|---|---|---|---|---|
| 1.27 | ![R4'-phenyl-CH2-] | ![neopentyl-triazole] | XV.185 | C₂₄H₁₈ClN₅O | 450/452 [M + Na]⁺ | 230 | 0.50 (A) |
| 1.28 | ![R4'-phenyl-CH2-] | ![neopentyl-N(CH2CH2OH)2] | XV.209 | C₂₆H₂₆ClN₃O₃ | 462/464 [M − H]⁻ | 228 | 0.50 (A) |
| 1.29 | ![R4'-phenyl-CH2-] | ![methyl-imidazole] | XV.168 | C₂₅H₁₉ClN₄O | 427/429 [M + H]⁺ | 290 (decomp.) | 0.50 (A) |

-continued
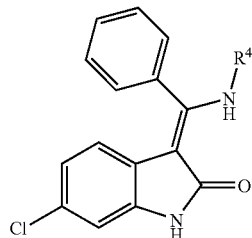
(I-1)
| Example | R⁴ | R⁴' | educt | empirical formula | mass spectrum | m.p. [° C.] | R_f value* |
|---|---|---|---|---|---|---|---|
| 1.30 | 4-tBu-phenyl (R₄') | N(Et)C(O)OtBu-neopentyl | XV.13 | C₂₉H₃₀ClN₃O₃ | 502/504 [M − H]⁻ | 201 | 0.50 (A) |
| 1.31 | 4-tBu-phenyl (R₄') | (1-Me-imidazol-2-yl)methyl | XV.145 | C₂₅H₁₉ClN₄O | 427/429 [M + H]⁺ | 279 | 0.50 (A) |
| 1.32 | 4-tBu-phenyl (R₄') | morpholinomethyl | XV.23 | C₂₆H₂₄ClN₃O₂ | 446/448 [M + H]⁺ | 245 | 0.50 (A) |

-continued
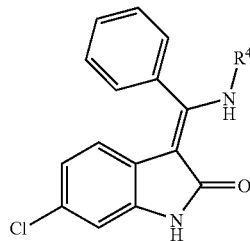
(I-1)
| Example | R⁴ | R⁴' | educt | empirical formula | mass spectrum | m.p. [°C.] | R_f value* |
|---|---|---|---|---|---|---|---|
| 1.33 | 4-R₄'-phenyl | —CH₂—(NBnMe) | XV.78 | $C_{30}H_{26}ClN_3O$ | 502/504 [M + Na]⁺ | 168 | 0.50 (A) |
| 1.34 | 4-R₄'-phenyl | neopentyl-pyrrolidine | XV.22 | $C_{26}H_{24}ClN_3O$ | 430/432 [M + H]⁺ | 226 | 0.50 (A) |
| 1.35 | 4-R₄'-phenyl | neopentyl-N-methylpiperazine | XV.135 | $C_{27}H_{27}ClN_4O$ | 459/461 [M + H]⁺ | 228-230 | 0.40 (D) |

-continued
(I-1)
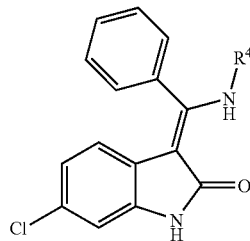
| Example | R⁴ | R⁴' | educt | empirical formula | mass spectrum | m.p. [° C.] | $R_f$ value* |
|---|---|---|---|---|---|---|---|
| 1.36 | 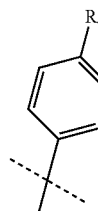 | —N(SO₂-nBu)-(CH₂)₂—NMe₂ | XV.156 | $C_{29}H_{33}ClN_4O_3S$ | 553/555 [M + H]⁺ | 185 | 0.70 (A) |
| 1.37 | 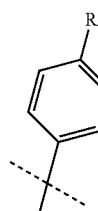 | —N(CO—CH₂—OMe)—(CH₂)₂—NMe₂ | XV.210 | $C_{28}H_{29}ClN_4O_3$ | 505/507 [M + H]⁺ | 174 | 0.40 (A) |
| 1.38 | 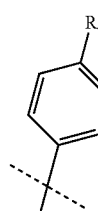 | —N[CO-(3,4-dimethoxy-phenyl)]-(CH₂)₂—NMe₂ | XV.211 | $C_{34}H_{33}ClN_4O_4$ | 597/599 [M + H]⁺ | 174 | 0.50 (A) |

-continued
(I-1)
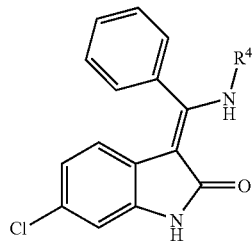
| Example | R⁴ | R⁴' | educt | empirical formula | mass spectrum | m.p. [° C.] | $R_f$ value* |
|---|---|---|---|---|---|---|---|
| 1.39 | 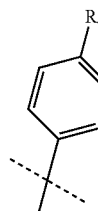 | 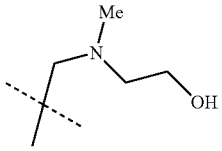 | XV.198 | $C_{25}H_{24}ClN_3O_2$ | 434/436 [M + H]⁺ | 208 | 0.30 (A) |
| 1.40 | 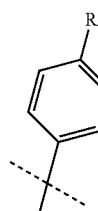 | —N(COEt)—(CH₂)₂— (NBnMe) | XV.212 | $C_{34}H_{33}ClN_4O_2$ | 565/567 [M + H]⁺ | 158 | 0.80 (A) |
| 1.41 | 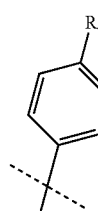 | —N[CO-(4-pyridyl)]-(CH₂)₂—NMe₂ | XV.213 | $C_{31}H_{28}ClN_5O_2$ | 538/540 [M + H]⁺ | 199 | 0.25 (A) |

-continued
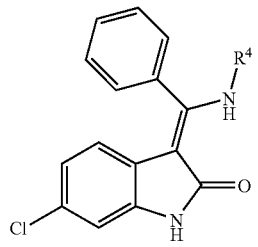
(I-1)
| Example | R⁴ | R⁴' | educt | empirical formula | mass spectrum | m.p. [°C.] | R_f value* |
|---|---|---|---|---|---|---|---|
| 1.42 | 4-R₄'-phenyl (tBu) | CH₂-C(=O)-phthalimide with N-Me | XV.206 | $C_{32}H_{23}ClN_4O_4$ | 561/563 [M − H]⁻ | 274 | 0.50 (A) |
| 1.43 | 4-R₄'-phenyl (tBu) | CH₂-N(Me)-C(=O)-OtBu | XV.18 | $C_{28}H_{28}ClN_3O_3$ | 488/490 [M − H]⁻ | 171-173 | 0.50 (A) |
| 1.44 | 4-R₄'-phenyl (tBu) | CH₂-piperazine(N-Me) with N(Me)-C(=O) | XV.204 | $C_{29}H_{30}ClN_5O_2$ | 515/517 [M]⁺ | 265-269 | 0.50 (E) |

-continued
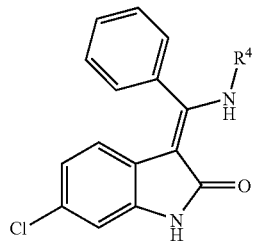
(I-1)
| Example | R[4] | R[4'] | educt | empirical formula | mass spectrum | m.p. [° C.] | R$_f$ value* |
|---|---|---|---|---|---|---|---|
| 1.45 | 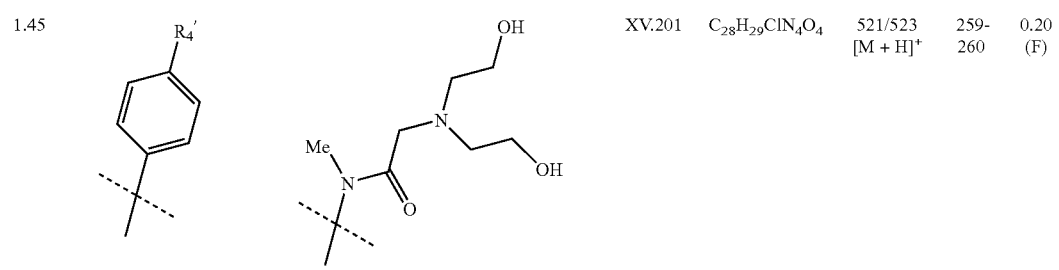 | | XV.201 | C$_{28}$H$_{29}$ClN$_4$O$_4$ | 521/523 [M + H]$^+$ | 259-260 | 0.20 (F) |
| 1.46 | 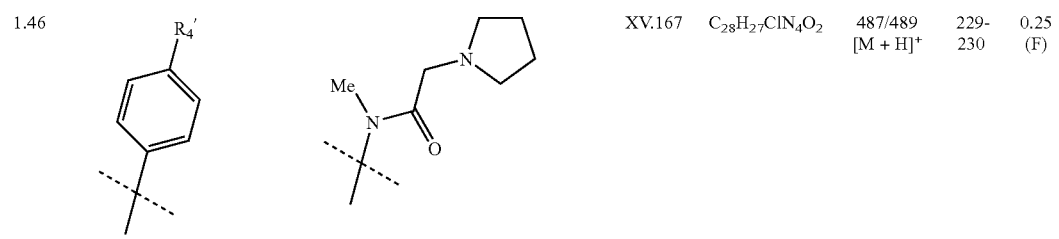 | | XV.167 | C$_{28}$H$_{27}$ClN$_4$O$_2$ | 487/489 [M + H]$^+$ | 229-230 | 0.25 (F) |
| 1.47 | 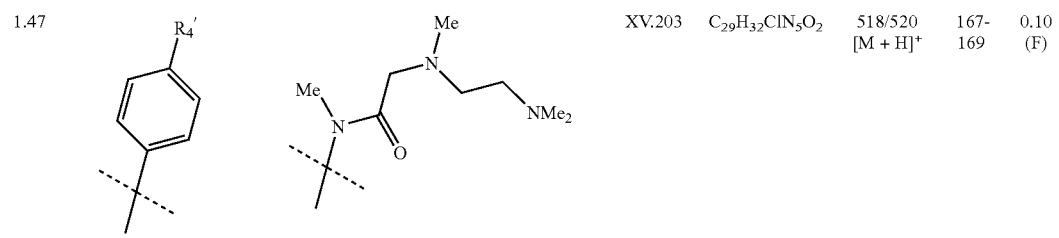 | | XV.203 | C$_{29}$H$_{32}$ClN$_5$O$_2$ | 518/520 [M + H]$^+$ | 167-169 | 0.10 (F) |

-continued
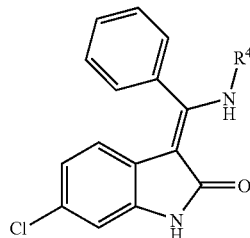
(I-1)
| Example | R⁴ | R⁴' | educt | empirical formula | mass spectrum | m.p. [°C.] | R_f value* |
|---|---|---|---|---|---|---|---|
| 1.48 | 4-R₄'-phenyl | N-methyl-N-tBu-(imidazol-1-yl)acetamide | XV.205 | C₂₇H₂₂ClN₅O₂ | 484/486 [M + H]⁺ | 288-289 | 0.25 (F) |
| 1.49 | 4-R₄'-phenyl | 2-methyl-2-(4-methylpiperazin-1-ylcarbonyl)-tBu | XV.231 | C₂₇H₂₅ClN₄O₂ | 473/475 [M + H]⁺ | 274 | 0.25 (F) |
| 1.50 | 4-R₄'-phenyl | N-methyl-N-tBu-3-(4-tBuoxycarbonylpiperazin-1-yl)propanamide | XV.174 | C₃₄H₃₈ClN₅O₄ | 614/616 [M − H]⁻ | 134 | 0.25 (A) |

-continued
(I-1)
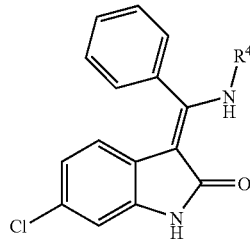
| Example | R⁴ | R⁴' | educt | empirical formula | mass spectrum | m.p. [° C.] | R_f value* |
|---|---|---|---|---|---|---|---|
| 1.51 | 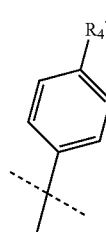 | —N(COMe)—(CH₂)₂— (NBnMe) | XV.214 | $C_{33}H_{31}ClN_4O_2$ | 551/553 [M + H]⁺ | 195 | 0.25 (A) |
| 1.52 | 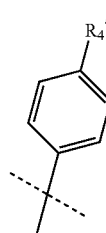 | 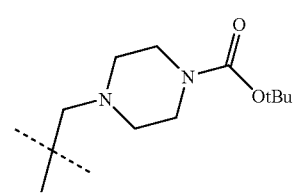 | XV.34 | $C_{31}H_{33}ClN_4O_3$ | 545/547 [M + H]⁺ | 225 | 0.25 (A) |
| 1.53 | 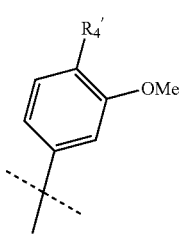 | —N(Me)—(CO)—CH₂— NMe₂ | XV.215 | $C_{27}H_{27}ClN_4O_3$ | 491/493 [M + H]⁺ | 238- 241 | 0.30 (A) |

-continued
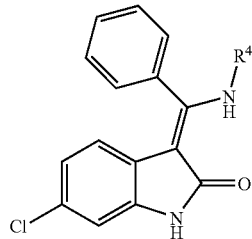
(I-1)
| Example | R⁴ | R⁴' | educt | empirical formula | mass spectrum | m.p. [°C.] | R_f value* |
|---|---|---|---|---|---|---|---|
| 1.54 | 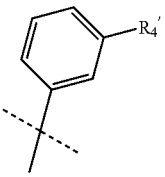 | —CH₂—NMe₂ | XV.3 | $C_{24}H_{22}ClN_3O$ | 402/404 [M − H]⁻ | 193 | 0.25 (A) |
| 1.55 | 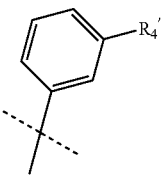 | —CH₂-(4-pyridyl) | XV.217 | $C_{27}H_{20}ClN_3O$ | 438/440 [M + H]⁺ | 243 | 0.45 (A) |
| 1.56 | 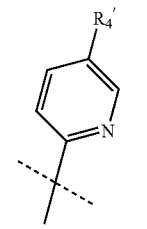 | 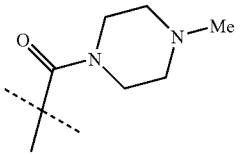 | XII | $C_{26}H_{24}ClN_5O_2$ | 473/475 [M + H]⁺ | 265 | 0.45 (G) |

-continued
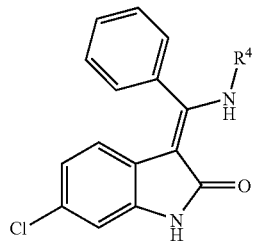
(I-1)
| Example | R⁴ | R⁴' | educt | empirical formula | mass spectrum | m.p. [° C.] | R_f value* |
|---|---|---|---|---|---|---|---|
| 1.57 | 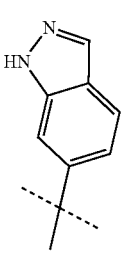 | — | — | $C_{22}H_{15}ClN_4O$ | 385/387 $[M-H]^-$ | 328-330 | 0.40 (F) |
| 1.58 | 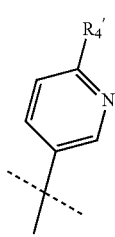 | —N(COMe)—(CH$_2$)$_2$—NMe$_2$ | XV.241 | $C_{26}H_{26}ClN_5O_2$ | 476/478 $[M+H]^+$ | 176-177 | 0.60 (H) |
| 1.59 | 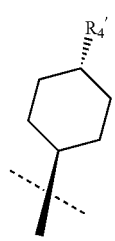 | —NH—(CO)—CH$_2$—NMe$_2$ | XVI | $C_{25}H_{29}ClN_4O_2$ | 453/455 $[M+H]^+$ | n.d. | 0.40 (A) |

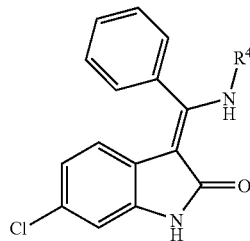
(I-1)
| Example | R⁴ | R⁴' | educt | empirical formula | mass spectrum | m.p. [°C.] | R_f value* |
|---|---|---|---|---|---|---|---|
| 1.60 | 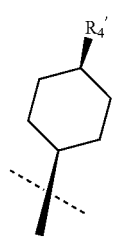 | —N(Me)—(CO)—CH₂—NMe₂ | XVII | $C_{26}H_{31}ClN_4O_2$ | 467/469 [M + H]⁺ | 257-260 | 0.20 (F) |
| 1.61 | 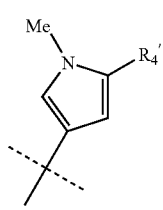 | 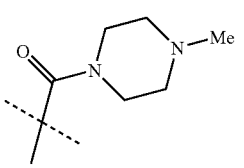 | XV.240 | $C_{26}H_{26}ClN_5O_2$ | 476/478 [M + H]⁺ | 296-299 | 0.55 (I) |
| 1.62 | 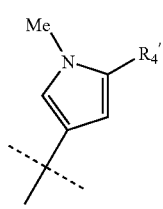 | —CO—NMe—(CH₂)₂—NMe₂ | XV.239 | $C_{26}H_{28}ClN_5O_2$ | 478/480 [M + H]⁺ | 230-232 | 0.30 (K) |

-continued
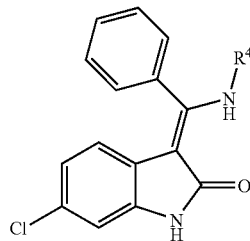
(I-1)
| Example | R[4] | R[4'] | educt | empirical formula | mass spectrum | m.p. [° C.] | R$_f$ value* |
|---|---|---|---|---|---|---|---|
| 1.63 | 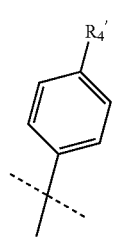 | —N(COMe)—(CH$_2$)$_3$—NMe$_2$ | XV.7 | C$_{28}$H$_{29}$ClN$_4$O$_2$ | 489/491 [M + H]$^+$ | 187 | 0.20 (A) |
| 1.64 | 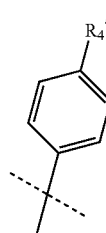 | —SO$_2$—(CH$_2$)$_2$—NEt$_2$ | XIX | C$_{27}$H$_{28}$ClN$_3$O$_3$S | 510/512 [M + H]$^+$ | 154- 159 | 0.40 (F) |
| 1.65 | 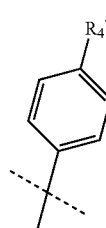 | 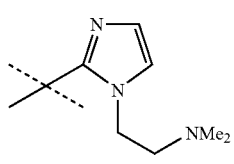 | XV.242 | C$_{28}$H$_{26}$ClN$_5$O | 484/486 [M + H]$^+$ | 211- 216 | 0.20 (L) |

-continued
(I-1)
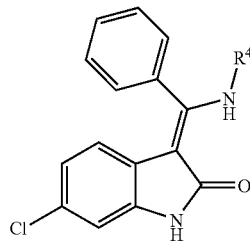
| Example | R⁴ | R⁴' | educt | empirical formula | mass spectrum | m.p. [° C.] | R_f value* |
|---|---|---|---|---|---|---|---|
| 1.66 | | | XV.232 | $C_{27}H_{24}ClN_3O_2$ | 458/460 [M + H]⁺ | 270 | 0.20 (A) |
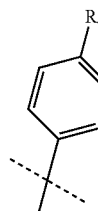
| 1.67 | | | XV.237 | $C_{31}H_{31}ClN_4O_4$ | 559/561 [M + H]⁺ | 255-256 | 0.20 (A) |
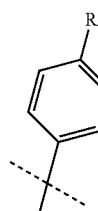
| 1.68 | | | XV.233 | $C_{29}H_{28}ClN_3O_2$ | 486/488 [M + H]⁺ | 164 | 0.20 (A) |
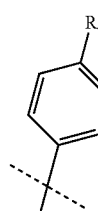

-continued
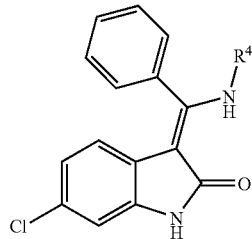
(I-1)
| Example | R⁴ | R⁴' | educt | empirical formula | mass spectrum | m.p. [°C.] | R_f value* |
|---|---|---|---|---|---|---|---|
| 1.69 | 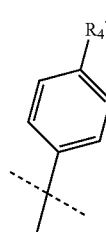 | —N(Me)—(CO)—(CH₂)₂—NMe₂ | XV.126 | $C_{27}H_{27}ClN_4O_2$ | 475/477 [M + H]⁺ | 219-221 | 0.20 (A) |
| 1.70 | 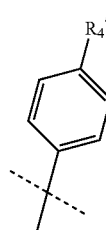 | —CH₂—NMe—(CH₂)₂—NMe₂ | XV.195 | $C_{27}H_{29}ClN_4O$ | 461/463 [M + H]⁺ | 151 | 0.25 (A) |
| 1.71 | 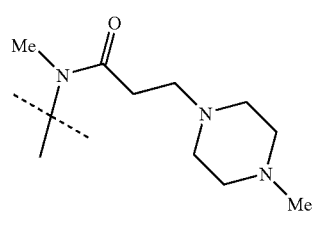 | 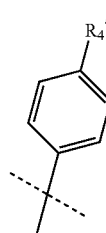 | XV.243 | $C_{30}H_{32}ClN_5O_2$ | 528/520 [M − H]⁻ | 204-208 | 0.25 (A) |

-continued
(I-1)
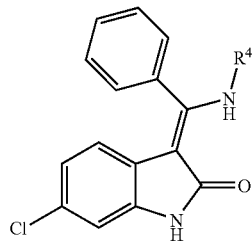
| Example | R⁴ | R⁴' | educt | empirical formula | mass spectrum | m.p. [° C.] | R_f value* |
|---|---|---|---|---|---|---|---|
| 1.72 | 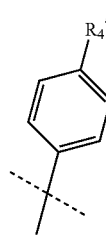 | —O—(CH₂)₂—NMe₂ | XV.246 | $C_{25}H_{24}ClN_3O_2$ | 532/534 [M − H]⁻ | 212-214 | 0.25 (A) |
| 1.73 | 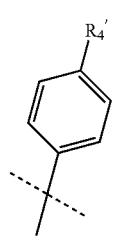 | 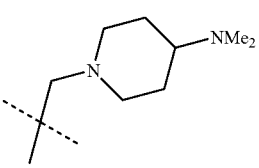 | XV.247 | $C_{29}H_{31}ClN_4O$ | 485/487 [M − H]⁻ | 198 | 0.25 (A) |
| 1.74 | 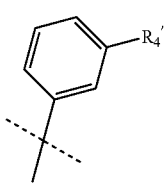 | —CH₂—COOMe | — | $C_{24}H_{19}ClN_2O_3$ | 417/419 [M − H]⁻ | 192 | 0.25 (A) |

-continued
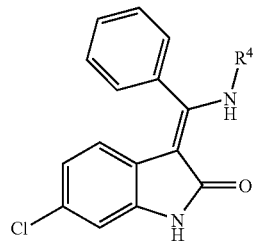
(I-1)
| Example | R⁴ | R⁴' | educt | empirical formula | mass spectrum | m.p. [°C.] | $R_f$ value* |
|---|---|---|---|---|---|---|---|
| 1.75 | 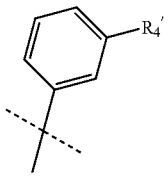 | —COOMe | — | $C_{23}H_{17}ClN_2O_3$ | 403/405 [M − H]⁻ | 209 | n. d. |
| 1.76 | 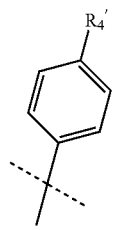 | —(CH₂)₂—NMe₂ | XV.5 | $C_{25}H_{24}ClN_3O$ | 416/418 [M − H]⁻ | 217 | 0.25 (A) |
| 1.77 | 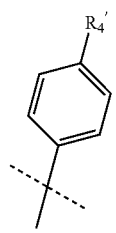 | | XV.12 | $C_{27}H_{26}ClN_3O_3$ | 474/476 [M − H]⁻ | 203 | 0.25 (A) |

-continued
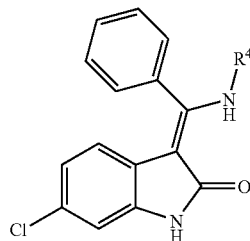
(I-1)
| Example | R⁴ | R⁴' | educt | empirical formula | mass spectrum | m.p. [° C.] | R_f value* |
|---|---|---|---|---|---|---|---|
| 1.78 | 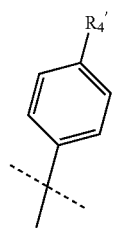 | —N(iPr)-(CO)—CH₂—NMe₂ | XV.177 | $C_{28}H_{29}ClN_4O_2$ | 487/489 [M − H]⁻ | 216 | 0.25 (A) |
| 1.79 | 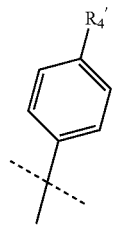 | | XV.179 | $C_{35}H_{40}ClN_5O_4$ | 628/630 [M − H]⁻ | 164 | 0.25 (A) |
| 1.80 | 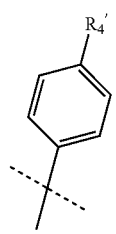 | —CH₂—NEt₂ | XV.66 | $C_{26}H_{26}ClN_3O$ | 430/432 [M − H]⁻ | 244 | 0.25 (A) |

-continued
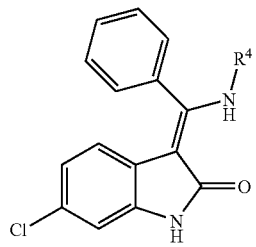
(I-1)
| Example | R⁴ | R⁴' | educt | empirical formula | mass spectrum | m.p. [° C.] | R_f value* |
|---|---|---|---|---|---|---|---|
| 1.81 | 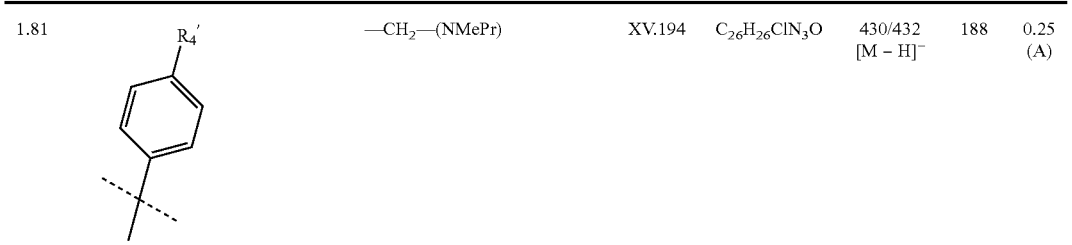 | —CH₂—(NMePr) | XV.194 | C₂₆H₂₆ClN₃O | 430/432 [M − H]⁻ | 188 | 0.25 (A) |
| 1.82 | 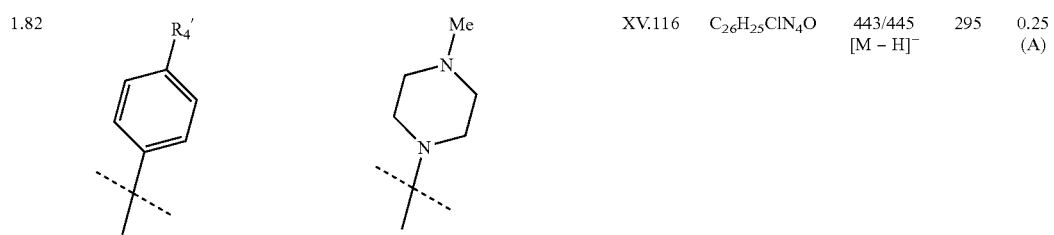 | | XV.116 | C₂₆H₂₅ClN₄O | 443/445 [M − H]⁻ | 295 | 0.25 (A) |
| 1.83 | 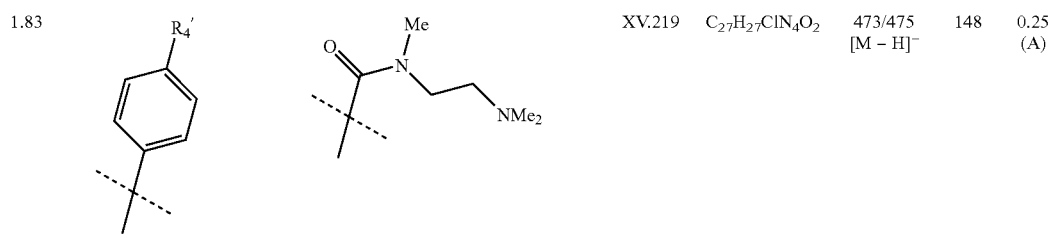 | | XV.219 | C₂₇H₂₇ClN₄O₂ | 473/475 [M − H]⁻ | 148 | 0.25 (A) |

-continued
(I-1)
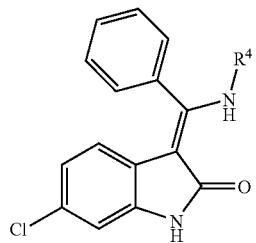
| Example | R⁴ | R⁴' | educt | empirical formula | mass spectrum | m.p. [° C.] | $R_f$ value* |
|---|---|---|---|---|---|---|---|
| 1.84 | 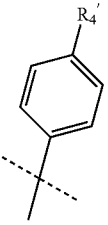 | 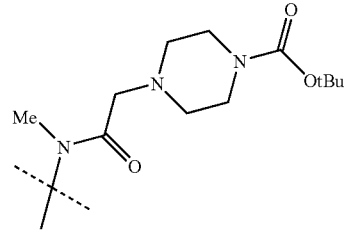 | XV.248 | $C_{33}H_{36}ClN_5O_4$ | 602/604 [M + H]⁺ | 199 | 0.25 (A) |
| 1.85 | 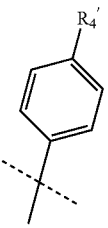 | —N(Me)—(CO)—CH₂— OH | XV.249 | $C_{24}H_{20}ClN_3O_3$ | 432/434 [M − H]⁻ | 250 | 0.25 (A) |
| 1.86 | 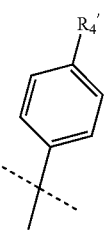 | —N(Me)—(CH₂)₂— NMe₂ | XV.117 | $C_{26}H_{27}ClN_4O$ | 445/447 [M − H]⁻ | 238 | n. d. |

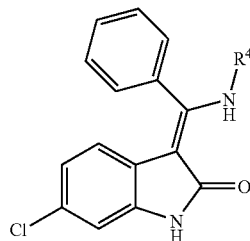
(I-1)
| Example | R⁴ | R⁴' | educt | empirical formula | mass spectrum | m.p. [° C.] | R$_f$ value* |
|---|---|---|---|---|---|---|---|
| 1.87 | 4-tBu-C₆H₄- | -N(Me)-CH₂CH(Me)CH₂-N(Me)-CH₂CH₂CH₂-NH-C(O)-OtBu | XV.250 | C$_{31}$H$_{35}$ClN$_4$O$_3$ | 545/547 [M − H]⁻ | 148 | 0.25 (A) |
| 1.88 | 4-tBu-C₆H₄- | -N(Me)-CH(tBu)-C(O)-CH₂-(4-methyl-1,4-diazepan-1-yl) | XV.251 | C$_{30}$H$_{32}$ClN$_5$O$_2$ | 528/530 [M − H]⁻ | 223 | 0.25 (A) |
| 1.89 | 2-CN-4-tBu-C₆H₃- | —N(Me)—(CO)—CH₂—NMe₂ | XV.216 | C$_{27}$H$_{24}$ClN$_5$O$_2$ | 486/488 [M + H]⁺ | 226-228 | 0.40 (A) |

-continued
(I-1)
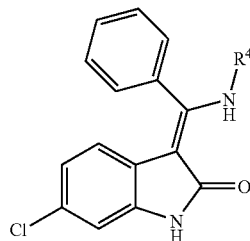
| Example | R⁴ | R⁴' | educt | empirical formula | mass spectrum | m.p. [° C.] | R_f value* |
|---|---|---|---|---|---|---|---|
| 1.90 | 4-sub phenyl (R₄') | Me-N(-)-C(O)-CH₂-N(piperazine)-Et | XV.252 | C₃₀H₃₂ClN₅O₂ | 528/530 [M − H]⁻ | 255-257 | 0.35 (F) |
| 1.91 | 4-sub phenyl (R₄') | Me-N(-)-C(O)-CH₂-(piperidine)-N-Me | XV.254 | C₃₀H₃₁ClN₄O₂ | 515/517 [M + H]⁺ | 280-283 | 0.30 (M) |
| 1.92 | 4-sub phenyl (R₄') | H-N(-)-C(O)-CH₂-N(piperazine)-N-Me | XV.253 | C₂₈H₂₈ClN₅O₂ | 502/504 [M + H]⁺ | 251-255 | 0.45 (A) |

-continued
(I-1)
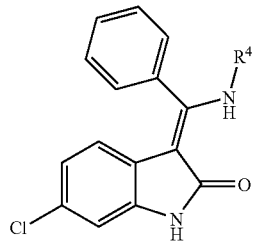
| Example | R⁴ | R⁴' | educt | empirical formula | mass spectrum | m.p. [° C.] | R_f value* |
|---|---|---|---|---|---|---|---|
| 1.93 | 4-R₄'-phenyl | C(CH₃)₂-C(=O)-N(CH₃)-(CH₂)₃-N(CH₃)₂ | XV.255 | C₂₉H₃₁ClN₄O₂ | 503/505 [M + H]⁺ | 215-224 | 0.30 (F) |
| 1.94 | 4-R₄'-phenyl | C(CH₃)₂-C(=O)-N(CH₃)-(CH₂)₂-N(CH₃)₂ | XV.256 | C₂₈H₂₉ClN₄O₂ | 489/491 [M + H]⁺ | 150-158 | 0.40 (A) |
| 1.95 | 4-R₄'-phenyl | C(CH₃)₂-C(=O)-(4-methylpiperazin-1-yl) | XV.257 | C₂₈H₂₇ClN₄O₂ | 487/489 [M + H]⁺ | 244-248 | 0.40 (A) |

-continued
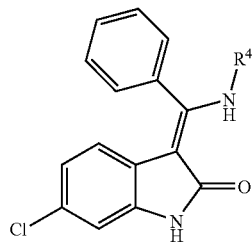
(I-1)
| Example | R⁴ | R⁴' | educt | empirical formula | mass spectrum | m.p. [° C.] | $R_f$ value* |
|---|---|---|---|---|---|---|---|
| 1.96 | (4-tBu-phenyl) | -(CH₂)₄-N(CH₃)₂ with Me-N-C(O)- | XV.258 | $C_{29}H_{31}ClN_4O_2$ | 503/505 [M + H]⁺ | 216-218 | 0.80 (N) |
| 1.97 | (2,3-diMe-4-tBu-phenyl) | —NH—(CO)—CH₂—NMe₂ | XVI.1 | $C_{27}H_{27}ClN_4O_2$ | 475/477 [M + H]⁺ | 246-250 | 0.50 (F) |
| 1.98 | (2,3-diMe-4-tBu-phenyl) | —NH—C(O)—CH₂—(N-methylpiperazinyl) | XVI.2 | $C_{30}H_{32}ClN_5O_2$ | 530/532 [M + H]⁺ | 271-275 | 0.50 (F) |

-continued
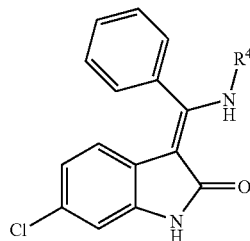
(I-1)
| Example | R⁴ | R⁴' | educt | empirical formula | mass spectrum | m.p. [° C.] | R_f value* |
|---|---|---|---|---|---|---|---|
| 1.99 | ![R4'-phenyl] | ![Me-N(Me)-C(O)-NH-N-piperazine-Me, tBu] | XV.261 | $C_{28}H_{29}ClN_6O_2$ | 517/519 [M + H]⁺ | 250-253 | 0.50 (D) |
| 1.100 | ![R4'-phenyl] | —CH₂—COOEt | — | $C_{25}H_{21}ClN_2O_3$ | 433/435 [M + H]⁺ | 166 | 0.70 (A) |
| 1.101 | ![R4'-phenyl] | ![Me-N(Me)-C(O)-NH-piperidine-N-Me, tBu] | XV.265 | $C_{29}H_{30}ClN_5O_2$ | 516/518 [M + H]⁺ | 265-270 | 0.35 (O) |

-continued
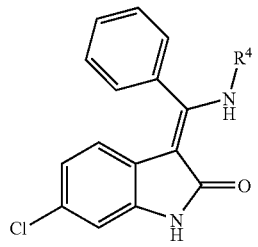
(I-1)
| Example | R⁴ | R⁴' | educt | empirical formula | mass spectrum | m.p. [°C.] | R_f value* |
|---|---|---|---|---|---|---|---|
| 1.102 | 4-tBu-phenyl | -CH(Me)-CH₂CH₂CH₂-N(CH₃)₂ via N(Me)C(O) | XV.266 | C₂₈H₂₉ClN₄O₂ | 489/491 [M + H]⁺ | 238-242 | 0.35 (F) |
| 1.103 | 4-tBu-phenyl | N-methyl-piperazine-carbonyl-N(Me)- | XV.267 | C₂₈H₂₈ClN₅O₂ | 502/504 [M + H]⁺ | 290-293 | 0.50 (A) |
| 1.104 | 4-tBu-phenyl | -N(Me)-C(O)-NH-CH₂CH₂CH₂-N(CH₃)₂ | XV.268 | C₂₈H₃₀ClN₅O₂ | 504/506 [M + H]⁺ | 192-195 | 0.60 (O) |

-continued

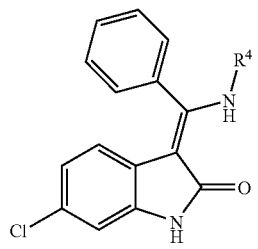
(I-1)

| Example | R⁴ | R⁴' | educt | empirical formula | mass spectrum | m.p. [° C.] | $R_f$ value* |
|---|---|---|---|---|---|---|---|
| 1.105 | 4-tBu-phenyl (R₄') | pyridin-4-yl-methyl-NH-C(O)-N(Me)- | XV.269 | $C_{29}H_{24}ClN_5O_2$ | 510/512 [M + H]⁺ | 222-223 | 0.60 (A) |
| 1.106 | 4-tBu-phenyl (R₄') | (1-methylpiperidin-4-yl)-O-C(O)-N(Me)- | XV.270 | $C_{29}H_{29}ClN_4O_3$ | 517/519 [M + H]⁺ | 237-240 | 0.30 (A) |

*Eluant mixtures:
(A): silica gel, methylene chloride/methanol 9:1
(B): silica gel, toluene/ethyl acetate 9:1
(C): silica gel, methylene chloride/methanol 10:1
(D): silica gel, methylene chloride/methanol 5:1
(E): silica gel, methylene chloride/methanol/ammonia 5:1:0.01
(F): silica gel, methylene chloride/methanol/ammonia 9:1:0.1
(G): silica gel, methylene chloride/ethanol 5:1
(H): silica gel, methylene chloride/methanol/ammonia 10:1:0.1
(I): silica gel, methylene chloride/ethanol 15:1
(K): silica gel, methylene chloride/ethanol/ammonia 20:1:0.1
(L): silica gel, methylene chloride/ethanol 10:1
(M): silica gel, methylene chloride/methanol/ammonia 9:1:0.01
(N): aluminium oxide, methylene chloride/ethanol 30:1
(O): aluminium oxide, methylene chloride/ethanol 20:1

EXAMPLE 2.0

3-Z-[1-(4-(N-(2-dimethylamino-ethyl)-N-methylsulphonyl-amino)-anilino)-1-phenyl-methylene]-6-chloro-5-nitro-2-indolinone 0.4 g of 1-acetyl-3-(1-ethoxy-1-phenylmethylen)-6-chloro-5-nitro-2-indolinone (educt IX.4) and 0.3 g of N-(2-dimethylamino-ethyl)-N-methylsulphonyl-p-phenylenediamine (educt XV.2) are dissolved in 5 ml of dimethylformamide and stirred at 80° C. for 4 hours. After cooling, 1.0 ml piperidine is added and the mixture is stirred for a further 3 hours at ambient temperature. The solvent is eliminated and the residue is purified through a silica gel column with methylene chloride/methanol (9:1) as eluant.

Yield: 0.4 g (79% of theory), $R_f$ value: 0.5 (silica gel, methylene chloride/methanol=9:1) M.p. 224° C. $C_{26}H_{26}ClN_5O_5S$ Mass spectrum: m/z=556/558 [M+H]⁺

The following compounds of general formula I-2 are prepared analogously to Example 2.0:

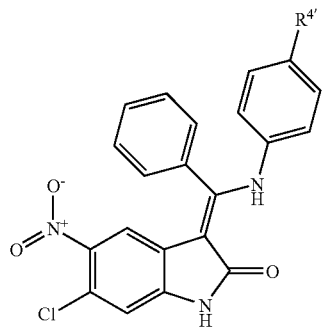

(I-2)

| Example | R4' | educt | empirical formula | mass spectrum | m.p. [° C.] | Rf value* |
|---|---|---|---|---|---|---|
| 2.1 | —N(Me)—(CO)—CH$_2$—NMe$_2$ | XV.125 | C$_{26}$H$_{24}$ClN$_5$O$_4$ | 506/508 [M + H]$^+$ | 266 | 0.50 (A) |
| 2.2 | —CH$_2$—NMe$_2$ | XV.4 | C$_{24}$H$_{21}$ClN$_4$O$_3$ | 447/449 [M − H]$^-$ | 260 | 0.50 (A) |
| 2.3 | —N(COMe)—(CH$_2$)$_2$—NMe$_2$ | XV.6 | C$_{27}$H$_{26}$ClN$_5$O$_4$ | 520/522 [M + H]$^+$ | 226 | 0.50 (A) |

*Eluant mixture:
(A): silica gel, methylene chloride/methanol 9:1

EXAMPLE 3.0

3-Z-[1-(4-(N-(dimethyl-carbamoyl-methyl)-N-(2-pyrrolidin-1-yl-ethyl-carbonyl)-amino)-anilino)-1-phenyl-methylene]-6-chloro-2-indolinone 0.3 g of 3-Z-[1-(4-(N-(dimethyl-carbamoyl-methyl)-N-(2-bromo-ethyl-carbonyl)-amino)-anilino)-1-phenyl-methylene]-6-chloro-2-indolinone (educt XXI) and 0.1 ml of pyrrolidine are dissolved in 6 ml of dimethylformamide and stirred for 1.5 hours at ambient temperature. After cooling, 1.1 ml of 1N sodium hydroxide solution are added and the mixture is stirred for another hour at ambient temperature. Water is added, the precipitate formed is suction filtered and purified through a silica gel column with a gradient of methylene chloride and methanol/ammonia as eluant.

Yield: 0.1 g (57% of theory), R$_f$ value: 0.20 (silica gel, methylene chloride/methanol/ammonia=9:1:0.1) M.p. 224-226° C. C$_{32}$H$_{34}$ClN$_5$O$_3$ Mass spectrum: m/z=570/572 [M−H]$^-$ The following compounds of general formula I-3 are prepared analogously to Example 3.0:

(I-3)

| Example | R4' | educt | empirical formula | mass spectrum | m.p. [° C.] | Rf value* |
|---|---|---|---|---|---|---|
| 3.1 | 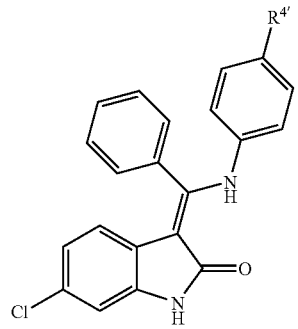 | XXI.1 | C$_{31}$H$_{32}$ClN$_5$O$_3$ | 556/558 [M − H]$^-$ | 115-117 | 0.30 (A) |

-continued (I-3)

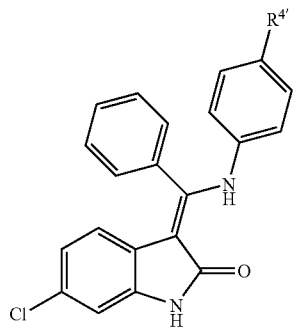

| Example | R4' | educt | empirical formula | mass spectrum | m.p. [° C.] | R$_f$value* |
|---|---|---|---|---|---|---|
| 3.2 | 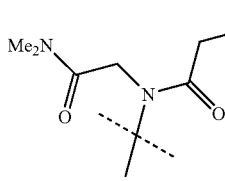 NMe$_2$ | XXI | C$_{30}$H$_{32}$ClN$_5$O$_3$ | 546/548 [M + H]$^+$ | 226 | 0.25 (A) |
| 3.3 | 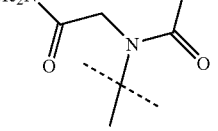 NMe$_2$ | XXI.1 | C$_{29}$H$_{30}$ClN$_5$O$_3$ | 532/534 [M + H]$^+$ | 276-279 | 0.25 (A) |

*Eluant mixture:
(A): silica gel, methylene chloride/methanol/ammonia 9:1:0.1

EXAMPLE 4.0

3-Z-[1-(4-(N-methyl-N-methylsulphonyl-amino)-anilino)-1-(3-iodo-phenyl)-methylene]-6-chloro-2-indolinone 0.9 g of 1-acetyl-3-(1-methoxy-1-(3-iodo-phenyl)-methylene)-6-chloro-2-indolinone (educt VIII) and 0.5 g of N-methyl-N-methylsulphonyl-p-phenylenediamine (educt XV.121) are dissolved in 10 ml of dimethylformamide and stirred at 120° C. for 3 hours. After cooling, 1.5 ml of piperidine are added and the mixture is stirred for another hour at ambient temperature. Water is added, the precipitate obtained is suction filtered, washed with a little water, methanol and ether and finally dried in vacuo at 100° C.

Yield: 0.9 g (74% of theory), R$_f$ value: 0.6 (silica gel, methylene chloride/methanol=9:1) M.p. 292-294° C. C$_{23}$H$_{19}$ClIN$_3$O$_3$S Mass spectrum: m/z=578/580 [M–H]$^-$ The following compounds of general formula I-4 are prepared analogously to Example 4.0:

(I-4)

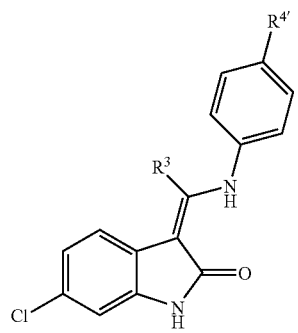

| Example | R³ | R⁴' | educts | empirical formula | mass spectrum | m.p. [° C.] | $R_f$ value* |
|---|---|---|---|---|---|---|---|
| 4.1 | 3-iodophenyl | —CH₂—NMe₂ | VIII XV.4 | $C_{24}H_{21}ClIN_3O$ | 529/531 $[M + H]^+$ | 238-240 | 0.30 (A) |
| 4.2 | 4-chlorophenyl | —N(Me)—(CO)—CH₂—NMe₂ | VIII.2 XV.125 | $C_{26}H_{24}Cl_2N_4O_2$ | 495/497 $[M + H]^+$ | 277-279 | 0.20 (B) |
| 4.3 | 4-chlorophenyl | —N(COMe)—(CH₂)₂—NMe₂ | VIII.2 XV.6 | $C_{27}H_{26}Cl_2N_4O_2$ | 507/509 $[M - H]^-$ | 241-243 | 0.10 (B) |
| 4.4 | 4-chlorophenyl | —N(Me)—C(O)—CH₂—N(piperazinyl-N-Me) | VIII.2 XV.204 | $C_{29}H_{29}Cl_2N_5O_2$ | 548/550 $[M - H]^-$ | 266-268 | 0.10 (B) |
| 4.5 | 4-chlorophenyl | —N(COMe)—(CH₂)₃—NMe₂ | VIII.2 XV.7 | $C_{28}H_{28}Cl_2N_4O_2$ | 521/523 $[M - H]^-$ | 241-242 | 0.10 (B) |
| 4.6 | 4-chlorophenyl | —CH₂—NMe₂ | VIII.2 XV.4 | $C_{24}H_{21}Cl_2N_3O$ | 438/440 $[M + H]^+$ | 243-244 | 0.10 (B) |

-continued (I-4)

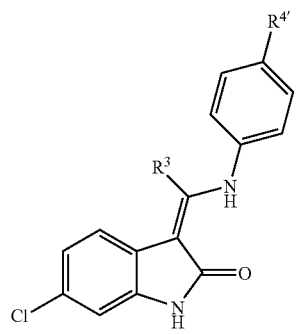

| Example | R³ | R⁴' | educts | empirical formula | mass spectrum | m.p. [°C.] | $R_f$ value* |
|---|---|---|---|---|---|---|---|
| 4.7 | BnO-C₆H₄- | —CH₂—NMe₂ | VIII.3 XV.4 | $C_{31}H_{28}ClN_3O_2$ | 510/512 [M + H]⁺ | 224-226 | 0.30 (B) |
| 4.8 | BnO-C₆H₄- | —N(Me)—(CO)—CH₂—NMe₂ | VIII.3 XV.125 | $C_{33}H_{31}ClN_4O_3$ | 567/569 [M + H]⁺ | 269-271 | 0.10 (B) |
| 4.9 | BnO-C₆H₄- | -N(Me)-C(=O)-CH₂-piperazine-N-Me | VIII.3 XV.204 | $C_{36}H_{36}ClN_5O_3$ | 622/624 [M + H]⁺ | 247-248 | 0.20 (B) |
| 4.10 | BnO-C₆H₄- | —N(COMe)—(CH₂)₂—NMe₂ | VIII.3 XV.6 | $C_{34}H_{33}ClN_4O_3$ | 581/583 [M + H]⁺ | 207-209 | 0.10 (B) |
| 4.11 | BnO-C₆H₄- | —N(COMe)—(CH₂)₃—NMe₂ | VIII.3 XV.7 | $C_{35}H_{35}ClN_4O_3$ | 595/597 [M + H]⁺ | 223-224 | 0.10 (B) |
| 4.12 | 3,4-(MeO)₂-C₆H₃- | —N(COMe)—(CH₂)₂—NMe₂ | VIII.4 XV.6 | $C_{29}H_{31}ClN_4O_4$ | 533/535 [M − H]⁻ | 128-130 | 0.75 (C) |

-continued

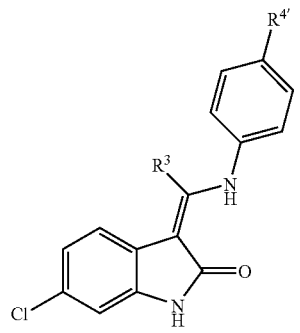

(I-4)

*Eluant mixtures:
(A): silica gel, methylene chloride/methanol 9:1
(B): silica gel, methylene chloride/ethanol 10:1
(C): silica gel, methylene chloride/methanol 4:1
(D): silica gel, methylene chloride/methanol/acetic acid 9:1:0.1

| Example | $R^3$ | $R^{4'}$ | educts | empirical formula | mass spectrum | m.p. [°C.] | $R_f$ value* |
|---|---|---|---|---|---|---|---|
| 4.13 | 3,4-dimethoxyphenyl-C(Me)₂- | -N(Me)-C(=O)-CH₂-N(piperazinyl)-N-Me | VIII.4 XV.204 | $C_{31}H_{34}ClN_5O_4$ | 574/576 [M − H]⁻ | 208-210 | 0.65 (C) |
| 4.14 | 3,4-dimethoxyphenyl-C(Me)₂- | —N(SO₂Me)—(CH₂)₂—NMe₂ | VIII.4 XV.2 | $C_{28}H_{31}ClN_4O_5S$ | 569/571 [M − H]⁻ | 198-200 | 0.75 (C) |
| 4.15 | 3,4-dimethoxyphenyl-C(Me)₂- | —CH₂—NMe₂ | VIII.4 XV.4 | $C_{26}H_{26}ClN_3O_3$ | 462/464 [M − H]⁻ | 239-240 | 0.70 (C) |
| 4.16 | 3,4-dimethoxyphenyl-C(Me)₂- | -C(=O)-N(Me)-(CH₂)₂-NMe₂ | VIII.4 XV.219 | $C_{29}H_{31}ClN_4O_4$ | 533/535 [M − H]⁻ | 147-149 | 0.70 (C) |
| 4.17 | 3-nitro-4-hydroxyphenyl-C(Me)₂- | —CH₂—NMe₂ | VIII.6 XV.4 | $C_{24}H_{21}ClN_4O_4$ | 465/467 [M + H]⁺ | 230 (decomp.) | 0.15 (D) |

EXAMPLE 5.0

3-Z-[1-(4-(N-(dimethylamino-methylcarbonyl)-N-methyl-amino)-anilino)-1-(4-(imidazol-1-yl-methyl)-phenyl)-methylene]-6-chloro-2-indolinone 0.7 g of 1-acetyl-3-(1-chloro-1-(4-(imidazol-1-yl-methyl)-phenyl)-methylene)-6-chloro-2-indolinone (educt X.1), 0.4 g of N-(dimethylamino-methylcarbonyl)-N-methyl-p-phenylenediamine (educt XV.125) and 1.2 ml of triethylamine are dissolved in 10 ml of dimethylformamide and stirred for 15 hours at 60° C. After cooling, 10 ml of methanol and 2 ml concentrated ammonia are added and the mixture is stirred for a further three hours at ambient temperature. Water is added and the mixture is extracted with ethyl acetate. The organic phase is washed three times with water, dried over sodium sulphate and concentrated in the rotary evaporator. The residue is purified through a silica gel column with methylene chloride/methanol/ammonia 10:1:0.1 as eluant.

Yield: 0.1 g (5% of theory), $R_f$ value: not determined M.p. 268-269° C. $C_{30}H_{29}ClN_6O_2$ Mass spectrum: m/z=541/543 [M+H]$^+$ The following compounds of general formula I-5 are prepared analogously to Example 5.0:

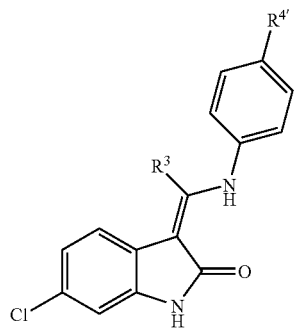

(I-5)

| Example | R$^3$ | R$^{4'}$ | educts | empirical formula | mass spectrum | m.p. [° C.] | R$_f$ value* |
|---|---|---|---|---|---|---|---|
| 5.1 | imidazol-1-yl-methyl-phenyl | —N(COMe)—(CH$_2$)$_2$—NMe$_2$ | X.1 XV.6 | $C_{31}H_{31}ClN_6O_2$ | 555/557 [M + H]$^+$ | 258-259 | n. d. |
| 5.2 | imidazol-1-yl-methyl-phenyl | Me-N(Me)-C(O)-CH$_2$-N(piperazinyl)-Me | X.1 XV.204 | $C_{33}H_{34}ClN_7O_2$ | 594/596 [M − H]$^-$ | 227 | n. d. |
| 5.3 | imidazol-1-yl-methyl-phenyl | —N(COMe)—(CH$_2$)$_3$—NMe$_2$ | X.1 XV.7 | $C_{32}H_{33}ClN_6O_2$ | 567/569 [M − H]$^-$ | 239-240 | 0.20 (A) |

-continued

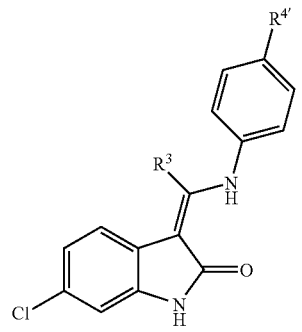

(I-5)

| Example | R³ | R⁴' | educts | empirical formula | mass spectrum | m.p. [° C.] | R_f value* |
|---|---|---|---|---|---|---|---|
| 5.4 | 1-(4-substituted-phenyl)-pyrrolidin-2-one | neopentyl-pyrrolidine | X.2 XV.22 | $C_{30}H_{29}ClN_4O_2$ | 511/513 [M − H]⁻ | 228-238 | 0.30 (B) |
| 5.5 | 1-(4-substituted-phenyl)-pyrrolidin-2-one | —N(Me)—(CO)—CH₂—NMe₂ | X.2 XV.125 | $C_{30}H_{30}ClN_5O_3$ | 542/544 [M − H]⁻ | 304-311 | 0.30 (B) |
| 5.6 | 1-(4-substituted-phenyl)-pyrrolidin-2-one | —CH₂—NMe₂ | X.2 XV.4 | $C_{28}H_{27}ClN_4O_2$ | 485/487 [M − H]⁻ | 266-267 | 0.30 (B) |
| 5.7 | 1-(4-substituted-phenyl)-pyrrolidin-2-one | 4-methylpiperazine acyl | X.2 XV.231 | $C_{31}H_{30}ClN_5O_3$ | 556/558 [M + H]⁺ | 277-280 | 0.40 (B) |

-continued
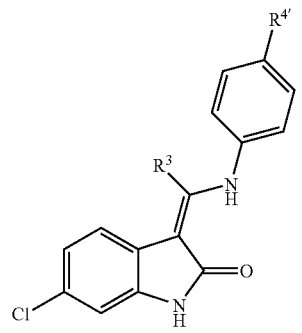
(I-5)
| Example | R³ | R⁴' | educts | empirical formula | mass spectrum | m.p. [° C.] | $R_f$ value* |
|---|---|---|---|---|---|---|---|
| 5.8 | (1-(4-tBu-phenyl)-pyrrolidin-2-one) | —N(COMe)—(CH₂)₃—NMe₂ | X.2 XV.7 | $C_{32}H_{34}ClN_5O_3$ | 570/572 [M − H]⁻ | n. d. | 0.10 (B) |
| 5.9 | (1-(4-tBu-phenyl)-pyrrolidin-2-one) | —SO₂—(CH₂)₂—NEt₂ | X.2 XIX | $C_{31}H_{33}ClN_4O_4S$ | 591/593 [M − H]⁻ | n. d. | 0.40 (B) |
| 5.10 | (1-(4-tBu-phenyl)-pyrrolidin-2-one) | —CH₂—NEtMe | X.2 XV.79 | $C_{29}H_{29}ClN_4O_2$ | 501/503 [M + H]⁺ | 246-249 | 0.35 (C) |
| 5.11 | (1-(4-tBu-phenyl)-pyrrolidin-2-one) | —CH₂—C(Me)(N(Me)C(O)OtBu)— | X.2 XV.18 | $C_{32}H_{33}ClN_4O_4$ | 573/575 [M + H]⁺ | 227-231 | 0.80 (D) |

-continued
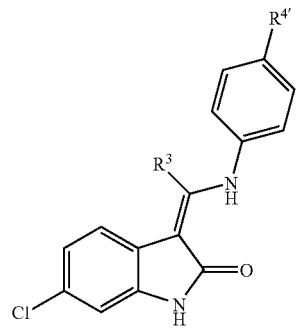
(I-5)
| Example | R³ | R⁴' | educts | empirical formula | mass spectrum | m.p. [° C.] | $R_f$ value* |
|---|---|---|---|---|---|---|---|
| 5.12 | H₂N—C₆H₃(NO₂)—  (4-tBu) | —N(Me)—(CO)—CH₂—NMe₂ | X XV.125 | $C_{26}H_{25}ClN_6O_4$ | 521/523 [M + H]⁺ | 254-256 | 0.40 (B) |
| 5.13 | H₂N—C₆H₃(NO₂)—  (4-tBu) | —N(SO₂Me)—(CH₂)₂—NMe₂ | X XV.2 | $C_{26}H_{27}ClN_6O_5S$ | 571/573 [M + H]⁺ | 218-220 | 0.50 (B) |
| 5.14 | H₂N—C₆H₃(NO₂)—  (4-tBu) | CH₂-pyrrolidine (neopentyl) | X XV.22 | $C_{26}H_{24}ClN_5O_3$ | 488/490 [M − H]⁻ | 170 (decomp.) | 0.30 (B) |
| 5.15 | H₂N—C₆H₃(NO₂)—  (4-tBu) | C(Me)₂—C(O)—N(piperazine)-Me | X XV.231 | $C_{27}H_{25}ClN_6O_4$ | 531/533 [M − H]⁻ | 190-195 | 0.30 (E) |

-continued (I-5)

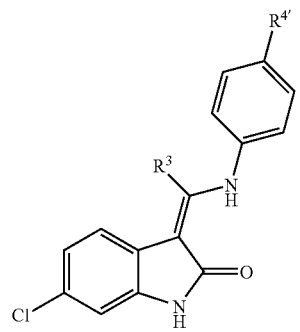

| Example | R³ | R⁴' | educts | empirical formula | mass spectrum | m.p. [° C.] | R_f value* |
|---|---|---|---|---|---|---|---|
| 5.16 | ![H₂N-phenyl with NO₂ and tBu] | —N(COMe)—(CH₂)₂—NMe₂ | X XV.6 | $C_{27}H_{27}ClN_6O_4$ | 533/535 [M − H]⁻ | 248-250 | 0.30 (F) |
| 5.17 | ![H₂N-phenyl with NO₂ and tBu] | —N(COMe)—(CH₂)₃—NMe₂ | X XV.7 | $C_{28}H_{29}ClN_6O_4$ | 547/549 [M − H]⁻ | 168-170 | 0.30 (G) |
| 5.18 | ![NO₂-phenyl with tBu] | —CH₂—NMe₂ | X.3 XV.4 | $C_{24}H_{21}ClN_4O_3$ | 447/449 [M − H]⁻ | 290-292 | 0.30 (H) |
| 5.19 | ![NO₂-phenyl with tBu] | —N(COMe)—(CH₂)₂—NMe₂ | X.3 XV.6 | $C_{27}H_{25}ClN_5O_4$ | 518/520 [M − H]⁻ | 243-244 | 0.35 (I) |
| 5.20 | ![NO₂-phenyl with tBu] | ![N(Me)C(O)CH₂-piperazine-Me] | X.3 XV.201 | $C_{29}H_{29}ClN_6O_4$ | 559/561 [M − H]⁻ | 265-266 | 0.25 (I) |

-continued

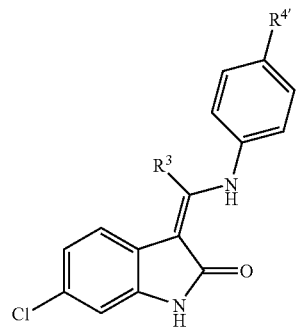

(I-5)

| Example | R³ | R⁴' | educts | empirical formula | mass spectrum | m.p. [° C.] | R_f value* |
|---|---|---|---|---|---|---|---|
| 5.21 | O⁻–N⁺(=O)–C₆H₄– | —N(Me)—(CO)—CH₂—NMe₂ | X.3 XV.125 | $C_{26}H_{24}ClN_5O_4$ | 506/508 [M + H]⁺ | 290 | 0.35 (I) |
| 5.22 | O⁻–N⁺(=O)–C₆H₄– | piperazine-C(O)-C(Me)₂- N-Me | X.3 XV.231 | $C_{27}H_{24}ClN_5O_4$ | 518/520 [M + H]⁺ | 297-298 | 0.40 (I) |
| 5.23 | NC–C₆H₄– | —CH₂—NMe₂ | X.4 XV.4 | $C_{25}H_{21}ClN_4O$ | 427/429 [M − H]⁻ | n. d. | 0.10 (K) |

*Eluant mixtures:
(A): silica gel, methylene chloride/methanol/ammonia 10:1:0.1
(B): silica gel, methylene chloride/methanol/ammonia 9:1:0.1
(C): silica gel, ethyl acetate/methanol/ammonia 7:3:0.1
(D): silica gel, ethyl acetate/ammonia 10:1
(E): silica gel, ethyl acetate/methanol/ammonia 8:2:0.2
(F): silica gel, ethyl acetate/methanol/ammonia 8.5:1.5:0.15
(G): silica gel, methylene chloride/methanol/ammonia 8.5:1.5:0.15
(H): silica gel, methylene chloride/ethanol 5:1
(I): silica gel, methylene chloride/ethanol/ammonia 20:1:0.1
(K): silica gel, methylene chloride/methanol 9:1

EXAMPLE 6.0

3-Z-[1-(4-(N-(2-dimethylamino-ethyl)-N-methylsulphonyl-amino)-anilino)-1-phenyl-methylene]-6-bromo-2-indolinone 1.0 g of 1-acetyl-3-(1-ethoxy-1-phenylmethylen)-6-bromo-2-indolinone (educt IX.1) and 0.7 g of N-(2-dimethylamino-ethyl)-N-methylsulphonyl-p-phenylenediamine (educt XV.2) are dissolved in 4 ml of dimethylformamide and stirred for 2 hours at 120° C. After cooling a little methanol is added and the precipitate formed is suction filtered. Then the residue is suspended in a little ethanol, 3.3 ml of 1 N sodium hydroxide solution are added and the mixture is stirred for another hour at ambient temperature. After this time water is added, the precipitate is suction filtered and washed with water, methanol and ether.

Yield: 0.7 g (50% of theory), $R_f$ value: 0.35 (silica gel, methylene chloride/methanol=9:1) M.p. 204-205° C. $C_{26}H_{27}BrN_4O_3S$ Mass spectrum: m/z=555/557 [M]⁺

The following compounds of general formula I-6 are prepared analogously to Example 6.0:

(I-6)
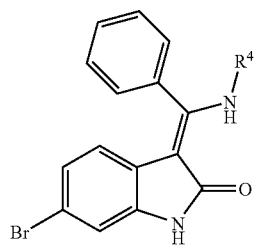
| Example | R⁴ | R⁴' | educt | empirical formula | mass spectrum | m.p. [°C.] | R_f value* |
|---|---|---|---|---|---|---|---|
| 6.1 | R₄'—⟨phenyl⟩— | —N(Me)—(CO)—CH₂—NMe₂ | XV.125 | $C_{26}H_{25}BrN_4O_2$ | 505/507 $[M+H]^+$ | 253-256 | 0.35 (A) |
| 6.2 | R₄'—⟨phenyl⟩— | —CH₂—NMe₂ | XV.4 | $C_{24}H_{22}BrN_3O$ | 448/450 $[M+H]^+$ | 236-238 | 0.20 (A) |
| 6.3 | R₄'—⟨phenyl⟩— | —N(COMe)—(CH₂)₂—NMe₂ | XV.6 | $C_{27}H_{27}BrN_4O_2$ | 517/519 $[M-H]^-$ | 147 | 0.25 (A) |
| 6.4 | N-CH₃ piperidin-4-yl | — | — | $C_{21}H_{22}BrN_3O$ | 411/413 $[M]^+$ | 358 | 0.20 (A) |

-continued
(I-6)
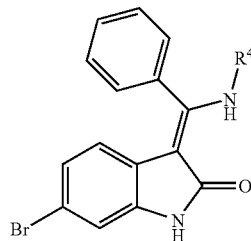
| Example | R⁴ | R⁴' | educt | empirical formula | mass spectrum | m.p. [° C.] | R$_f$ value* |
|---|---|---|---|---|---|---|---|
| 6.5 | R₄'—⟨phenyl⟩ | —CH₂C(CH₃)₂—N(Et)—C(O)—OtBu | XV.13 | $C_{29}H_{30}BrN_3O_3$ | 546/548 [M − H]⁻ | 186-188 | 0.60 (A) |
| 6.6 | R₄'—⟨phenyl⟩ | 2-(1-methylimidazolyl)methyl | XV.145 | $C_{25}H_{19}BrN_4O$ | 469/471 [M − H]⁻ | 302-304 | 0.50 (A) |
| 6.7 | R₄'—⟨phenyl⟩ | —N(SO₂Bn)—(CH₂)₂—NMe₂ | XV.157 | $C_{32}H_{31}BrN_4O_3S$ | 629/631 [M − H]⁻ | 131-134 | 0.25 (A) |
| 6.8 | R₄'—⟨phenyl⟩ | —N(SO₂nPr)—(CH₂)₂—NMe₂ | XV.153 | $C_{28}H_{31}BrN_4O_3S$ | 581/583 [M − H]⁻ | 228-230 | 0.25 (A) |
| 6.9 | R₄'—⟨phenyl⟩ | —C(CH₃)₂—C(O)—N(4-methylpiperazinyl) | XV.231 | $C_{27}H_{25}BrN_4O_2$ | 515/517 [M − H]⁻ | 268-270 | 0.25 (A) |

-continued (I-6)

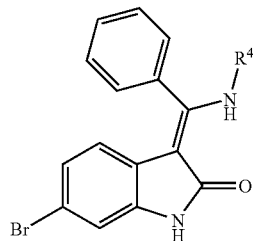

| Example | R⁴ | R⁴' | educt | empirical formula | mass spectrum | m.p. [° C.] | R_f value* |
|---|---|---|---|---|---|---|---|
| 6.10 | R₄' on phenyl | —N(COMe)—(CH₂)₃—NMe₂ | XV.7 | $C_{28}H_{29}BrN_4O_2$ | 531/533 [M − H]⁻ | 138 | 0.25 (A) |
| 6.11 | R₄' on phenyl | Me-N-CH₂-C(O)-N(Me)- linked to 4-methylpiperazine | XV.204 | $C_{29}H_{30}BrN_5O_2$ | 560/562 [M + H]⁺ | 276-278 | 0.40 (A) |
| 6.12 | R₄' on phenyl | CH₂-pyrrolidine | XV.22 | $C_{26}H_{24}BrN_3O$ | 474/476 [M + H]⁺ | 243-247 | 0.50 (B) |
| 6.13 | R₄' on phenyl | Me-N(Me)-C(O)-CH₂-N(Me)-CH₂CH₂-NMe₂ | XV.203 | $C_{29}H_{32}BrN_5O_2$ | 562/564 [M + H]⁺ | 178 | 0.60 (C) |
| 6.14 | R₄' on phenyl | CH₂-(4-methylpiperazine) | XV.135 | $C_{27}H_{27}BrN_4O$ | 503/505 [M + H]⁺ | 247 | 0.70 (D) |

-continued (I-6)

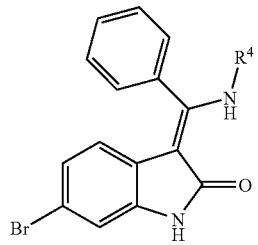

| Example | R⁴ | R⁴' | educt | empirical formula | mass spectrum | m.p. [° C.] | R_f value* |
|---|---|---|---|---|---|---|---|
| 6.15 | R₄'— (phenyl ring, para) | —N(Me)—(CO)—(CH₂)₂—NMe₂ | XV.126 | $C_{27}H_{27}BrN_4O_2$ | 519/521 [M + H]⁺ | 229 | 0.30 (D) |
| 6.16 | R₄'— (phenyl ring, para) | —CH₂—NMe—(CH₂)₂—NMe₂ | XV.195 | $C_{27}H_{29}BrN_4O$ | 505/507 [M + H]⁺ | 160 | 0.20 (D) |
| 6.17 | R₄'— (phenyl ring, para) | —CH₂—N(Me)—C(O)—OtBu | XV.18 | $C_{28}H_{28}BrN_3O_3$ | 532/534 [M − H]⁻ | 212-215 | 0.55 (E) |

(A): silica gel, methylene chloride/methanol 9:1
(B): silica gel, methylene chloride/methanol/ammonia 9:1:0.01
(C): aluminium oxide, methylene chloride/methanol 9:1
(D): silica gel, methylene chloride/methanol/ammonia 5:1:0.1
(E): silica gel, methylene chloride/methanol/ammonia 9:1:0.1

EXAMPLE 7.0

3-Z-[1-(4-(N-(2-dimethylamino-ethyl)-N-methylsulphonyl-amino)-anilino)-1-phenyl-methylene]-6-cyano-2-indolinone 67 mg of 1-acetyl-3-(1-ethoxy-1-phenylmethylen)-6-cyano-2-indolinone (educt IX.2) and 60 mg of N-(2-dimethylamino-ethyl)-N-methylsulphonyl-p-phenylenediamine (educt XV.2) are dissolved in 5 ml of dimethylformamide and stirred for 1.5 hours at 80° C. After cooling, 2 ml concentrated ammonia solution are added and the mixture is stirred for a further 10 minutes at ambient temperature. After this time water is added, the precipitate is suction filtered, dissolved again in methylene chloride/methanol and dried over sodium sulphate. After removal of the solvent the residue is washed with ether and dried at 80° C.

Yield: 28 mg (26% of theory), $R_f$ value: 0.15 (silica gel, methylene chloride/methanol=9:1) M.p. 270° C. $C_{27}H_{27}N_5O_3S$ Mass spectrum: m/z=501 [M]⁺

The following compounds of general formula I-7 are prepared analogously to Example 7.0:

(I-7)
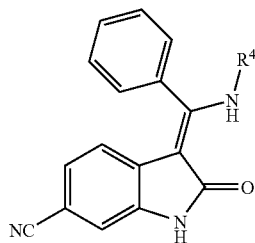
| Example | R⁴ | R⁴' | educt | empirical formula | mass spectrum | m.p. [° C.] | $R_f$ value* |
|---|---|---|---|---|---|---|---|
| 7.1 | R₄'–C₆H₄– | —N(Me)—(CO)—CH₂—NMe₂ | XV.125 | $C_{27}H_{25}N_5O_2$ | 452 [M + H]⁺ | 263-266 | 0.10 (A) |
| 7.2 | R₄'–C₆H₄– | —CH₂—NMe₂ | XV.4 | $C_{25}H_{22}N_4O$ | 393 [M − H]⁻ | 267-269 | 0.60 (B) |
| 7.3 | R₄'–C₆H₄– | —N(COMe)—(CH₂)₂—NMe₂ | XV.6 | $C_{28}H_{27}N_5O_2$ | 464 [M − H]⁻ | 277-280 | 0.40 (A) |
| 7.4 | R₄'–C₆H₄– | —Br | — | $C_{22}H_{14}BrN_3O$ | 414/416 [M − H]⁻ | 338-340 | 0.30 (A) |
| 7.5 | R₄'–C₆H₄– | —CH₂C(Me)₂CH₂—N(Et)—C(O)—OtBu | XV.13 | $C_{30}H_{30}N_4O_3$ | 493 [M − H]⁻ | 201-204 | 0.55 (A) |

-continued
(I-7)
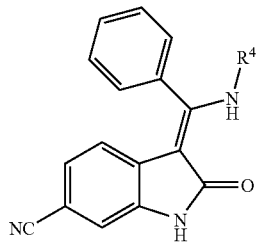
| Example | R⁴ | R⁴' | educt | empirical formula | mass spectrum | m.p. [° C.] | R_f value* |
|---|---|---|---|---|---|---|---|
| 7.6 | 4-R₄'-phenyl | -CH₂-C(CH₃)₂-piperidinyl | XV.207 | C₂₈H₂₆N₄O | 433 [M − H]⁻ | 259 | 0.25 (A) |
| 7.7 | 4-R₄'-phenyl | —O—(CH₂)₂—NMe₂ | XV.246 | C₂₆H₂₄N₄O₂ | 423 [M − H]⁻ | 256-258 | 0.50 (B) |
| 7.8 | 4-R₄'-phenyl | -C(CH₃)₂-C(O)NH-CH₂CH₂-NMe₂ | XV.218 | C₂₇H₂₅N₄O₂ | 450 [M − H]⁻ | 258-260 | 0.20 (B) |
| 7.9 | 4-R₄'-phenyl | -C(CH₃)₂-C(O)-N-methylpiperazinyl | XV.231 | C₂₈H₂₅N₅O₂ | 462 [M − H]⁻ | 328-329 | 0.75 (B) |
| 7.10 | 4-R₄'-phenyl | —N(COMe)—(CH₂)₃—NMe₂ | XV.7 | C₂₉H₂₉N₅O₂ | 478 [M − H]⁻ | 262 | n. d. |

-continued
(I-7)
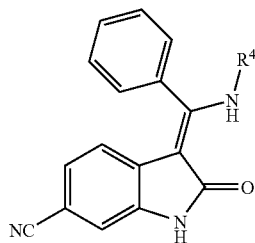
| Example | R⁴ | R⁴' | educt | empirical formula | mass spectrum | m.p. [° C.] | R_f value* |
|---|---|---|---|---|---|---|---|
| 7.11 | 4-R₄'-phenyl | -N(Me)-C(=O)-CH₂-N(4-Me-piperazine) | XV.204 | $C_{30}H_{30}N_6O_2$ | 507 [M + H]⁺ | 305-307 | 0.15 (A) |
| 7.12 | 4-R₄'-phenyl | -CH₂-C(Me)₂-pyrrolidine | XV.22 | $C_{27}H_{24}N_4O$ | 421 [M + H]⁺ | 248 | 0.10 (A) |
| 7.13 | 4-R₄'-phenyl | -N(Me)-C(=O)-CH₂-N(Me)-CH₂CH₂-NMe₂ | XV.203 | $C_{30}H_{32}N_6O_2$ | 509 [M + H]⁺ | 218-220 | 0.40 (C) |
| 7.14 | 4-R₄'-phenyl | -C(=O)-NH-CH₂CH₂CH₂-NMe₂ | XV.220 | $C_{28}H_{27}N_5O_2$ | 466 [M + H]⁺ | 247-249 | 0.10 (B) |
| 7.15 | 4-R₄'-phenyl | -C(=O)-N(Me)-CH₂CH₂-NMe₂ | XV.219 | $C_{28}H_{27}N_5O_2$ | 466 [M + H]⁺ | 208-210 | 0.45 (B) |

-continued
(I-7)
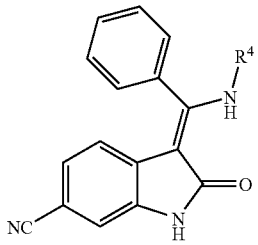
| Example | R⁴ | R⁴' | educt | empirical formula | mass spectrum | m.p. [° C.] | R_f value* |
|---|---|---|---|---|---|---|---|
| 7.16 | ![R4'-para-phenyl] | Me-N(CO-)-CH₂CH₂CH₂-NMe₂ | XV.221 | C₂₉H₂₉N₅O₂ | 480 [M + H]⁺ | 264-267 | 0.10 (B) |
| 7.17 | ![R4'-para-phenyl] | —N(Me)—(CO)—(CH₂)₂—NMe₂ | XV.126 | C₂₈H₂₇N₅O₂ | 466 [M + H]⁺ | 274 | 0.15 (A) |
| 7.18 | ![R4'-para-phenyl] | Me-N(CO-)-CH₂-N(piperazine)-CO-OtBu | XV.248 | C₃₄H₃₆N₆O₄ | 593 [M + H]⁺ | 251-254 | 0.30 (A) |
| 7.19 | ![R4'-meta-phenyl] | —CH₂—NMe₂ | XV.3 | C₂₅H₂₂N₄O | 393 [M − H]⁻ | 232 | 0.35 (A) |
| 7.20 | ![R4'-meta-phenyl] | Me-N(CO-)-CH₂CH₂-NMe₂ | XV.227 | C₂₈H₂₇N₅O₂ | 466 [M + H]⁺ | 188-191 | 0.40 (C) |

-continued
(I-7)
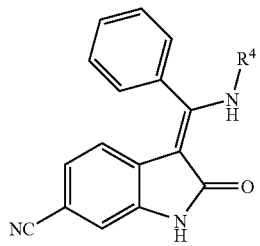
| Example | R⁴ | R⁴' | educt | empirical formula | mass spectrum | m.p. [° C.] | R_f value* |
|---|---|---|---|---|---|---|---|
| 7.21 | 4-R₄'-phenyl | Me-N(-)-C(O)-CH₂-morpholine | XV.165 | $C_{29}H_{27}N_5O_3$ | 494 [M + H]⁺ | 301 | 0.30 (A) |
| 7.22 | 4-R₄'-phenyl | Me-N(-)-C(O)-CH₂-(4-Me-[1,4]diazepan-1-yl) | XV.251 | $C_{31}H_{32}N_6O_2$ | 519 [M − H]⁻ | 250 | n. d. |
| 7.23 | 4-R₄'-phenyl | Me-N(-)-C(O)-CH₂-(4-Et-piperazin-1-yl) | XV.252 | $C_{31}H_{32}N_6O_2$ | 519 [M − H]⁻ | 276 | 0.45 (B) |
| 7.24 | 3-R₄'-phenyl | Me-N(-)-C(O)-CH₂-(4-Me-piperazin-1-yl) | XV.262 | $C_{30}H_{30}N_6O_2$ | 507 [M + H]⁺ | 199 | 0.50 (B) |
| 7.25 | 3-R₄'-phenyl | —N(Me)—(CO)—CH₂—NMe₂ | XV.264 | $C_{27}H_{25}N_5O_2$ | 452 [M + H]⁺ | 199 | 0.50 (B) |

-continued (I-7)

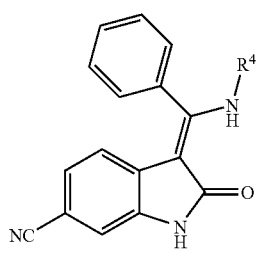

| Example | R⁴ | R⁴' | educt | empirical formula | mass spectrum | m.p. [° C.] | R_f value* |
|---|---|---|---|---|---|---|---|
| 7.26 | 3-R₄'-phenyl | -NH-CH₂-C(=O)-piperazine-N-Me | XV.263 | C₂₉H₂₈N₆O₂ | 493 [M + H]⁺ | 196 | 0.30 (A) |
| 7.27 | 4-R₄'-phenyl | -N(CH₃)-C(=O)-CH(CH₃)-N(CH₃)-CH₂CH₂CH₂-N(CH₃)₂ | XV.255 | C₃₀H₃₁N₅O₂ | 494 [M + H]⁺ | 201 | 0.45 (C) |
| 7.28 | 4-R₄'-phenyl | -N(CH₃)-C(=O)-CH(CH₃)-N(CH₃)-CH₂CH₂-N(CH₃)₂ | XV.256 | C₂₉H₂₉N₅O₂ | 480 [M + H]⁺ | 206 | 0.25 (C) |
| 7.29 | 4-R₄'-phenyl | -C(=O)-piperazine-N-CH₃ | XV.257 | C₂₉H₂₇N₅O₂ | 478 [M + H]⁺ | 256 | 0.30 (C) |

(A): silica gel, methylene chloride/methanol 9:1
(B): silica gel, methylene chloride/methanol 4:1
(C): silica gel, methylene chloride/methanol/ammonia 9:1:0.1

EXAMPLE 8.0

3-Z-[1-(4-(N-(2-dimethylamino-ethyl)-N-methylsulphonyl-amino)-anilino)-1-phenyl-methylene]-6-fluoro-2-indolinone 325 mg of 1-acetyl-3-(1-ethoxy-1-phenylmethylen)-6-fluoro-2-indolinone (educt IX.3) and 310 mg N-(2-dimethylamino-ethyl)-N-methylsulphonyl-p-phenylenediamine (educt XV.2) are dissolved in 2 ml of dimethylformamide and stirred for 4 hours at 120° C. After cooling methanol and water are added, the mixture is extracted with ethyl acetate and the organic phase is concentrated in the rotary evaporator. The residue obtained is purified through a silica gel column with methylene chloride/methanol 9:1 as eluant. The product is suspended in a little ethanol to eliminate the acetyl group, 1.3 ml of 1 N sodium hydroxide solution are added and the mixture is stirred for another hour at ambient temperature. After this time water is added, the precipitate is suction filtered and washed with water, methanol and ether. The residue is dried in vacuo at 100° C.

Yield: 0.3 g (61% of theory), $R_f$ value: 0.25 (silica gel, methylene chloride/methanol/ammonia=9:1:0.1) M.p. 259-261° C. $C_{26}H_{27}FN_4O_3S$ Mass spectrum: m/z=493 [M−H]⁻

The following compounds of general formula I-8 are prepared analogously to Example 8.0:

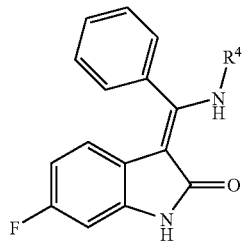

(I-8)

| Example | R⁴ | R⁴' | educt | empirical formula | mass spectrum | m.p. [° C.] | $R_f$ value* |
|---|---|---|---|---|---|---|---|
| 8.1 | R₄'-C₆H₄- | —N(Me)-(CO)—CH₂—NMe₂ | XV.125 | $C_{26}H_{25}FN_4O_2$ | 445 [M + H]⁺ | 226 | 0.25 (A) |
| 8.2 | R₄'-C₆H₄- | —CH₂—NMe₂ | XV.4 | $C_{24}H_{22}FN_3O$ | 386 [M − H]⁻ | 229-232 | 0.35 (A) |
| 8.3 | R₄'-C₆H₄- | —N(COMe)-(CH₂)₂—NMe₂ | XV.6 | $C_{27}H_{27}FN_4O_2$ | 459 [M + H]⁺ | 225-227 | 0.25 (A) |
| 8.4 | R₄'-C₆H₄- | —CH₂-C(Me)₂-N(Et)-C(O)-OtBu | XV.13 | $C_{29}H_{30}FN_3O_3$ | 486 [M − H]⁻ | 182 | 0.50 (B) |

-continued
(I-8)
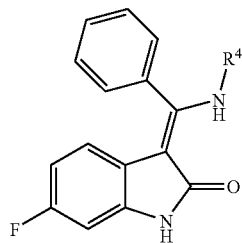
| Example | R⁴ | R⁴' | educt | empirical formula | mass spectrum | m.p. [° C.] | R_f value* |
|---|---|---|---|---|---|---|---|
| 8.5 | 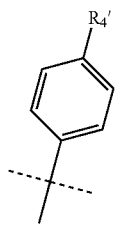 | 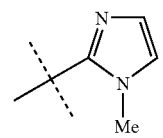 | XV.145 | $C_{25}H_{19}FN_4O$ | 411 [M + H]⁺ | 290 | 0.50 (C) |
| 8.6 | 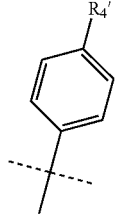 | —N(SO₂nPr)—(CH₂)₂—NMe₂ | XV.154 | $C_{28}H_{31}FN_4O_3S$ | 521 [M − H]⁻ | 227 | 0.35 (A) |
| 8.7 | 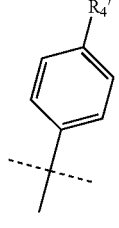 | 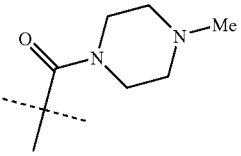 | XV.231 | $C_{27}H_{25}FN_4O_2$ | 457 [M + H]⁺ | 118 | 0.35 (A) |
| 8.8 | 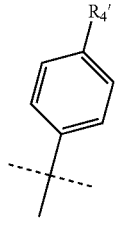 | —N(COMe)-(CH₂)₃—NMe₂ | XV.7 | $C_{28}H_{29}FN_4O_2$ | 473 [M + H]⁺ | 214 | 0.25 (A) |

-continued
(I-8)
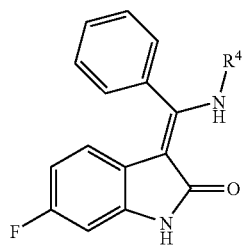
| Example | R[4] | R[4'] | educt | empirical formula | mass spectrum | m.p. [°C.] | $R_f$ value* |
|---|---|---|---|---|---|---|---|
| 8.9 | 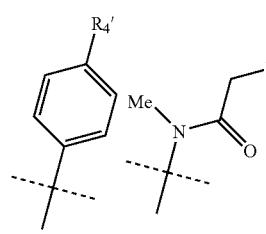 | | XV.204 | $C_{29}H_{30}FN_5O_2$ | 500 [M + H]$^+$ | 230 | 0.30 (A) |
| 8.10 | | | XV.22 | $C_{26}H_{24}FN_3O$ | 414 [M + H]$^+$ | 220 | 0.25 (A) |
| 8.11 | 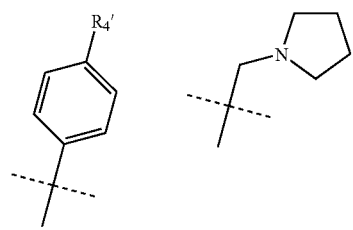 | | XV.203 | $C_{29}H_{32}FN_5O_2$ | 500 [M − H]$^-$ | 150 | 0.25 (D) |
| 8.12 | 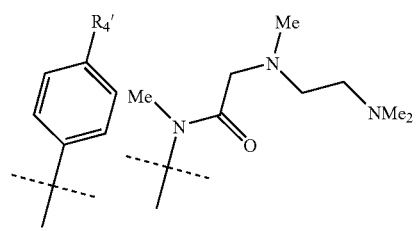 | | XV.135 | $C_{27}H_{27}FN_4O$ | 443 [M + H]$^+$ | 198 | 0.15 (A) |
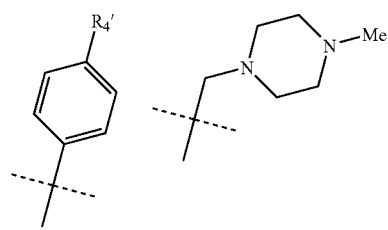

-continued
(I-8)
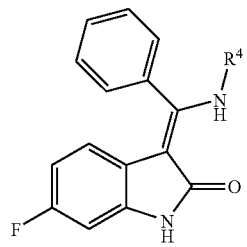
| Example | R⁴ | R⁴' | educt | empirical formula | mass spectrum | m.p. [° C.] | R_f value* |
|---|---|---|---|---|---|---|---|
| 8.13 | R₄' (4-tBu-phenyl) | —N(Me)-(CO)—(CH₂)₂—NMe₂ | XV.126 | $C_{27}H_{27}FN_4O_2$ | 459 [M + H]⁺ | 201 | 0.40 (A) |
| 8.14 | R₄' (4-tBu-phenyl) | —CH₂—NMe-(CH₂)₂—NMe₂ | XV.195 | $C_{27}H_{29}FN_4O$ | 445 [M + H]⁺ | 141 | 0.30 (A) |
| 8.15 | R₄' (4-tBu-phenyl) | CH₂-piperidine | XV.207 | $C_{27}H_{26}FN_3O$ | 426 [M − H]⁻ | 223 | 0.60 (A) |
| 8.16 | R₄' (4-tBu-phenyl) | —CH₂—N(Me)—C(O)—OtBu | XV.18 | $C_{28}H_{28}FN_3O_3$ | 474 [M + H]⁺ | 168 | 0.55 (B) |
| 8.17 | R₄' (4-tBu-phenyl) | —NMe-SO₂Me | XV.121 | $C_{23}H_{20}FN_3O_3S$ | 438 [M + H]⁺ | 295-300 | 0.60 (A) |

(I-8)

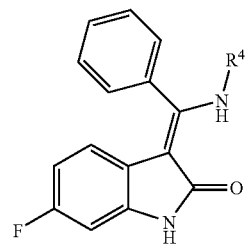

| Example | R⁴ | R⁴' | educt | empirical formula | mass spectrum | m.p. [°C.] | R$_f$ value* |
|---|---|---|---|---|---|---|---|
| 8.18 | R₄'–⌬ (4-phenyl) | —SO₂Me | — | $C_{22}H_{17}FN_2O_3S$ | 409 [M + H]⁺ | 255-260 | 0.50 (A) |
| 8.19 | R₄'–⌬ (4-phenyl) | —N(COMe)-CH₃ | — | $C_{24}H_{20}FN_3O_2$ | 402 [M + H]⁺ | 310-315 | 0.45 (A) |
| 8.20 | ⌬ (phenyl) | — | — | $C_{21}H_{15}FN_2O$ | 331 [M + H]⁺ | 299-305 | 0.60 (A) |
| 8.21 | R₄'–⌬ (4-phenyl) | —N(SO₂Me)-(CH₂)—(CO)—NMe₂ | XV.120 | $C_{26}H_{25}FN_4O_4S$ | 509 [M + H]⁺ | 270-274 | 0.50 (E) |

(A): silica gel, methylene chloride/methanol/ammonia 9:1:0.1
(B): silica gel, methylene chloride/methanol/ammonia 10:1:0.1
(C): silica gel, methylene chloride/methanol 9:1
(D): silica gel, methylene chloride/methanol/ammonia 7:1:0.1
(E): aluminium oxide, methylene chloride/methanol 19:1

EXAMPLE 9.0

3-Z-[1-(4-(dimethylaminomethyl)-anilino)-1-(4-iodo-phenyl)-methylene]-6-fluoro-2-indolinone 3.5 g of 1-acetyl-3-(1-methoxy-1-(4-iodo-phenyl)-methylene)-6-fluoro-2-indolinone (educt VIII.14) and 1.6 g of 4-(dimethylaminomethyl)-aniline (educt XV.4) are dissolved in 30 ml of dimethylformamide and stirred for 2 hours at 120° C. After cooling the solvent is eliminated, the residue is taken up in 30 ml of methanol and 2 spatula tips of sodium methoxide are added. After a yellow precipitate has formed the solvent is removed by suction filtering, the residue is washed with a little methanol and ether and finally dried in vacuo at 100° C.

Yield: 1.9 g (46% of theory), R$_f$ value: 0.3 (silica gel, methylene chloride/methanol=9:1) M.p. 243-246° C. $C_{24}H_{21}FIN_3O$ Mass spectrum: m/z=514 [M+H]⁺

The following compounds of general formula I-9a are prepared analogously to Example 9.0:

(I-9a)
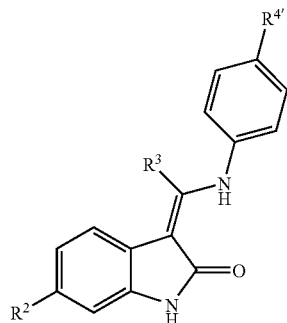
| Example | R³ | R⁴' | educts | empirical formula | mass spectrum | m.p. [° C.] | R_f value* | Example |
|---|---|---|---|---|---|---|---|---|
| 9.1 | —F | 3-F-phenyl | —CH₂—NMe₂ | VIII.7 XV.4 | C₂₄H₂₁F₂N₃O | 404 [M − H]⁻ | 225-227 | 0.20 (A) |
| 9.2 | —F | 3-F-phenyl | —N(COMe)-(CH₂)₃—NMe₂ | VIII.7 XV.7 | C₂₈H₂₈F₂N₄O₂ | 491 [M + H]⁺ | 160-163 | 0.20 (A) |
| 9.3 | —F | 3-F-phenyl | Me-N(Me)-C(O)-CH₂-N(piperazine)-N-Me | VIII.7 XV.204 | C₂₉H₂₉F₂N₅O₂ | 518 [M + H]⁺ | 218-220 | 0.40 (A) |
| 9.4 | —F | H₃C-C(O)-N(H)-CH₂CH₂-(4-phenyl) | —CH₂—NMe₂ | VIII.8 XV.4 | C₂₈H₂₉FN₄O₂ | 471 [M − H]⁻ | 106-110 | 0.25 (A) |

-continued
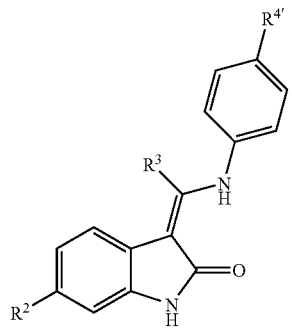
(I-9a)
| Example | R³ | R⁴' | educts | empirical formula | mass spectrum | m.p. [° C.] | R_f value* | Example |
|---|---|---|---|---|---|---|---|---|
| 9.5 | —F | H₃C—C(=O)—N(H)—CH₂—(4-tBu-C₆H₄)— | —N(COMe)-(CH₂)₃—NMe₂ | VIII.8 XV.7 | $C_{32}H_{36}FN_5O_3$ 558 $[M + H]^+$ | 194-196 | 0.25 (A) |  |
| 9.6 | —F | H₃C—C(=O)—N(H)—CH₂—(4-tBu-C₆H₄)— | Me-N(tBu)-C(=O)-CH₂-N(piperazine)-N-Me | VIII.8 XV.204 | $C_{33}H_{37}FN_6O_3$ 583 $[M - H]^-$ | 238-240 | 0.25 (A) |  |
| 9.7 | —F | (3,4,5-triF-4-tBu-C₆H₂)— | —CH₂—NMe₂ | VIII.9 XV.4 | $C_{24}H_{19}F_4N_3O$ 440 $[M - H]^-$ | 267-269 | 0.35 (A) |  |
| 9.8 | —F | (3,4,5-triF-4-tBu-C₆H₂)— | —N(COMe)-(CH₂)₃—NMe₂ | VIII.9 XV.7 | $C_{28}H_{26}F_4N_4O_2$ 527 $[M + H]^+$ | 210-212 | 0.15 (A) |  |

-continued

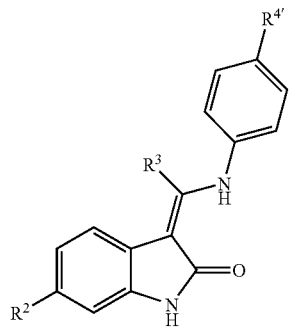

(I-9a)

| Example | R³ | R⁴' | educts | empirical formula | mass spectrum | m.p. [° C.] | R$_f$ value* | Example |
|---|---|---|---|---|---|---|---|---|
| 9.9 | —F | 3,4,5-trifluoro, 4-tBu-phenyl (see structure) | Me-N(Me)-C(O)-CH₂-N(piperazine)-Me | VIII.9 XV.204 | $C_{29}H_{27}F_4N_5O_2$ 554 $[M + H]^+$ | 216- 218 | 0.20 (A) |
| 9.10 | —F | 4-(CH₂C(O)OMe)-phenyl (see structure) | —CH₂—NMe₂ | VIII.1 XV.4 | $C_{27}H_{26}FN_3O_3$ 460 $[M + H]^+$ | 173- 176 | 0.30 (A) |
| 9.11 | —F | 3-I-phenyl (see structure) | —CH₂—NMe₂ | VIII.16 XV.4 | $C_{24}H_{21}FIN_3O$ 514 $[M + H]^+$ | 198- 200 | 0.30 (B) |
| 9.12 | —F | 3-(CH₂C(O)OMe)-phenyl (see structure) | —CH₂—NMe₂ | VIII.10 XV.4 | $C_{27}H_{26}FN_3O_3$ 458 $[M - H]^-$ | 195- 198 | 0.25 (A) |
| 9.13 | —F | 3-(NHC(O)OtBu-CH₂)-phenyl (see structure) | —CH₂—NMe₂ | VIII.11 XV.4 | $C_{30}H_{33}FN_4O_3$ 517 $[M + H]^+$ | 230- 240 | 0.30 (A) |

-continued
(I-9a)
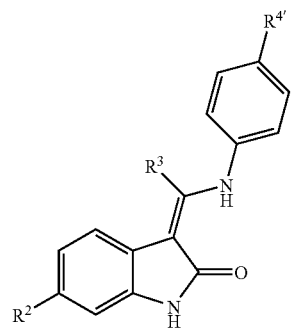
| Example | R³ | R⁴' | educts | empirical formula | mass spectrum | m.p. [°C.] | R_f value* | Example |
|---|---|---|---|---|---|---|---|---|
| 9.14 | —F | (4-tBu-C₆H₄)-CH₂-C(O)-OMe | —N(SO₂Me)-(CH₂)₂—NMe₂ | VIII.1 XV.2 | $C_{29}H_{31}FN_4O_5S$ | 567 [M + H]⁺ | 188-189 | 0.40 (A) |
| 9.15 | —F | (4-tBu-C₆H₄)-CH₂-C(O)-OMe | Me-N(tBu)-C(O)-CH₂-N(piperazine)-Me | VIII.1 XV.204 | $C_{32}H_{34}FN_5O_4$ | 572 [M + H]⁺ | 200-203 | 0.35 (C) |
| 9.16 | —F | (3-tBu-C₆H₄)-CH₂-CN | —CH₂—NMe₂ | VIII.12 XV.4 | $C_{26}H_{23}FN_4O$ | 427 [M + H]⁺ | 130-135 | 0.25 (A) |
| 9.17 | —F | (4-tBu-C₆H₄)-CH₂-NH-C(O)-OtBu | Me-N(tBu)-C(O)-CH₂-N(piperazine)-Me | VIII.13 XV.204 | $C_{35}H_{41}FN_6O_4$ | 629 [M + H]⁺ | 215-220 | 0.35 (A) |

-continued (I-9a)

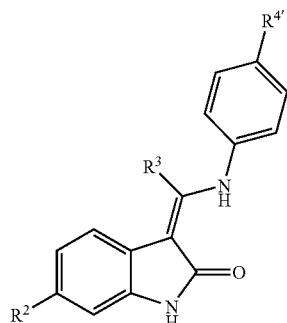

| Example | R³ | R⁴' | educts | empirical formula | mass spectrum | m.p. [°C.] | R_f value* | Example |
|---|---|---|---|---|---|---|---|---|
| 9.18 | —F | OtBu, HN-C(O)- on benzyl with p-tBu | —CH₂—NMe₂ | VIII.13 XV.4 | $C_{30}H_{33}FN_4O_3$ | 517 $[M+H]^+$ | 186-190 | 0.35 (A) |
| 9.19 | —F | OtBu, O=C-NH-CH₂CH₂- on phenyl with m-tBu | —CH₂—NMe₂ | VIII.20 XV.4 | $C_{31}H_{35}FN_4O_3$ | 531 $[M+H]^+$ | n.b. | 0.40 (A) |
| 9.20 | —F | OMe, methyl ester-CH₂CH₂- on phenyl with p-tBu | —NMe-(COMe) | VIII.18 — | $C_{28}H_{26}FN_3O_4$ | 488 $[M+H]^+$ | 166-170 | 0.40 (A) |
| 9.21 | —F | OMe, methyl ester-CH₂CH₂- on phenyl with p-tBu; Me-N(tBu)-C(O)-CH₂-N(piperazine)-N-Me | VIII.18 XV.204 | $C_{33}H_{36}FN_5O_4$ | 586 $[M+H]^+$ | 176-180 | 0.30 (A) |

-continued (I-9a)

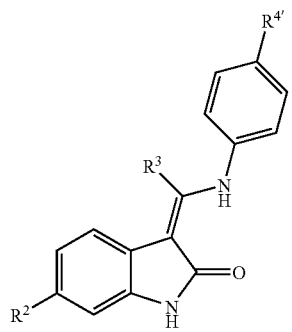

| Example | R³ | R⁴' | educts | empirical formula | mass spectrum | m.p. [° C.] | $R_f$ value* | Example |
|---|---|---|---|---|---|---|---|---|
| 9.22 | —F | OMe, –(CH₂)₂–C(O)O– attached to 4-position of phenyl (with tBu-like dashed bond) | —N(SO₂Me)-(CH₂)₂—NMe₂ | VIII.18 XV.2 | $C_{30}H_{33}FN_4O_5S$ | 581 $[M+H]^+$ | 195-198 | 0.45 (A) |
| 9.23 | —F | OMe, –(CH₂)₂–C(O)O– attached to 4-position of phenyl | —N(COMe)-(CH₂)₃—NMe₂ | VIII.18 XV.7 | $C_{32}H_{35}FN_4O_4$ | 559 $[M+H]^+$ | 100-104 | 0.50 (A) |
| 9.24 | —F | OMe, –(CH₂)₂–C(O)O– attached to 4-position of phenyl | Me-N(CH₂-)-C(O)-OtBu | VIII.18 XV.18 | $C_{32}H_{34}FN_3O_5$ | 558 $[M-H]^-$ | 132-137 | 0.80 (D) |
| 9.25 | —F | OMe, –(CH₂)₂–C(O)O– attached to 4-position of phenyl | 4-methylpiperazin-1-yl C(O)C(Me)₂– | VIII.18 XV.231 | $C_{31}H_{31}FN_4O_4$ | 543 $[M+H]^+$ | 234-236 | 0.60 (A) |

-continued (I-9a)

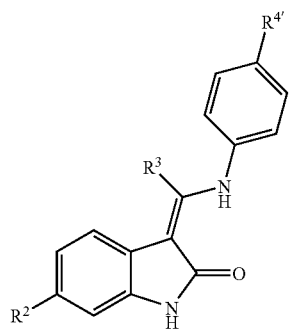

| Example | R³ | R⁴' | educts | empirical formula | mass spectrum | m.p. [° C.] | $R_f$ value* | Example |
|---|---|---|---|---|---|---|---|---|
| 9.26 | —F | OMe, phenyl-CH₂CH₂C(O)OMe (para, dashed) | N-methyl-2-tert-butylimidazole | VIII.18 XV.145 | $C_{29}H_{25}FN_4O_3$ | 497 $[M + H]^+$ | 110-115 | 0.40 (A) |
| 9.27 | —F | OMe, phenyl-CH₂CH₂C(O)OMe (para, dashed) | —SO₂Me | VIII.18 — | $C_{26}H_{23}FN_2O_5S$ | 495 $[M + H]^+$ | 130-137 | 0.60 (A) |
| 9.28 | —F | phenyl-CH₂C(O)OMe (meta, dashed) | Me-N(Me)-C(O)-CH₂-N(piperazine)-N-Me | VIII.10 XV.204 | $C_{32}H_{34}FN_5O_4$ | 572 $[M + H]^+$ | 189 | 0.60 (B) |
| 9.29 | —F | phenyl-CH₂C(O)OMe (meta, dashed) | —N(SO₂Me)-(CH₂)₂—NMe₂ | VIII.10 XV.2 | $C_{29}H_{31}FN_4O_5S$ | 567 $[M + H]^+$ | n.b. | 0.60 (B) |

-continued

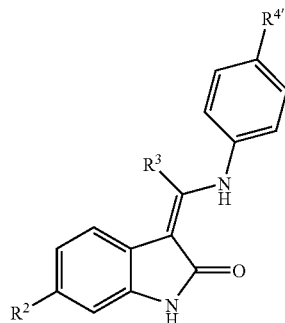

(I-9a)

| Example | R³ | R⁴' | educts | empirical formula | mass spectrum | m.p. [° C.] | R_f value* | Example |
|---|---|---|---|---|---|---|---|---|
| 9.30 | —F | methyl 3-(tert-butyl)phenylacetate | | VIII.10 XV.231 | $C_{30}H_{29}FN_4O_4$ | 529 $[M + H]^+$ | 201- 203 | 0.60 (B) |
| 9.31 | —F | methyl 3-(tert-butyl)phenylacetate | —N(Me)-(CO)—CH₂—NMe₂ | VIII.10 XV.125 | $C_{29}H_{29}FN_4O_4$ | 517 $[M + H]^+$ | 126 | 0.60 (B) |
| 9.32 | —F | methyl 3-(tert-butyl)phenylacetate | —N(COMe)-(CH₂)₂—NMe₂ | VIII.10 XV.6 | $C_{30}H_{31}FN_4O_4$ | 531 $[M + H]^+$ | 179 | 0.50 (B) |
| 9.33 | —F | methyl 3-(tert-butyl)phenylacetate | —N(COMe)-(CH₂)₃—NMe₂ | VIII.10 XV.7 | $C_{31}H_{33}FN_4O_4$ | 545 $[M + H]^+$ | 123 | 0.20 (B) |

-continued (I-9a)

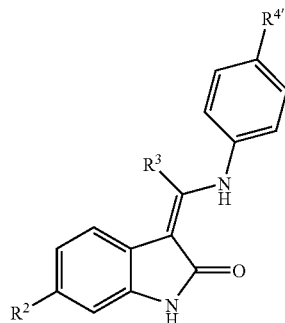

| Example | R³ | R⁴' | educts | empirical formula | mass spectrum | m.p. [°C.] | R$_f$ value* | Example |
|---|---|---|---|---|---|---|---|---|
| 9.34 | —F | (3-position methyl phenylacetate, t-Bu) | —N(Me)-(CO)—(CH₂)₄—NMe₂ | VIII.10 XV.258 | $C_{32}H_{35}FN_4O_4$ | 559 [M + H]⁺ | 201 | 0.20 (B) |
| 9.35 | —F | (4-position methyl phenylacetate, t-Bu) | —H | VIII.1 | $C_{24}H_{19}FN_2O_3$ | 403 [M + H]⁺ | 198-206 | 0.80 (A) |
| 9.36 | —F | (4-position methyl phenylacetate, t-Bu) | (2-t-Bu-1-Me-imidazole) | VIII.1 XV.145 | $C_{28}H_{23}FN_4O_3$ | 483 [M + H]⁺ | 223-226 | 0.75 (A) |
| 9.37 | —F | (4-position methyl phenylacetate, t-Bu) | (4-methylpiperazine pivaloyl) | VIII.1 XV.231 | $C_{30}H_{29}FN_4O_4$ | 529 [M + H]⁺ | 215-220 | 0.30 (A) |

-continued
(I-9a)
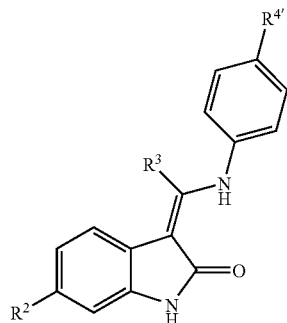
| Example | R³ | R⁴' | educts | empirical formula | mass spectrum | m.p. [° C.] | $R_f$ value* | Example |
|---|---|---|---|---|---|---|---|---|
| 9.38 | —F | CH2-C6H4-) | —N(SO₂Me)-(CH₂)—(CO)—NMe₂ | VIII.1 XV.120 | $C_{29}H_{29}FN_4O_6S$ 581 $[M+H]^+$ | 227- 230 | 0.65 | (A) |
| 9.39 | —F | CH2-C6H4-) | —N(Me)-(CO)—CH₂—NMe₂ | VIII.1 XV.125 | $C_{29}H_{29}FN_4O_4$ 517 $[M+H]^+$ | 128- 130 | 0.45 | (A) |
| 9.40 | —F | CH2-C6H4-) | —N(COMe)-CH₃ | VIII.1 — | $C_{27}H_{24}FN_3O_4$ 474 $[M+H]^+$ | 218- 223 | 0.40 | (A) |
| 9.41 | —F | CH2-C6H4-) | —N(Me)-(CO)—(CH₂)₂—NMe₂ | VIII.1 XV.126 | $C_{30}H_{31}FN_4O_4$ 531 $[M+H]^+$ | 192- 194 | 0.40 | (A) |

-continued
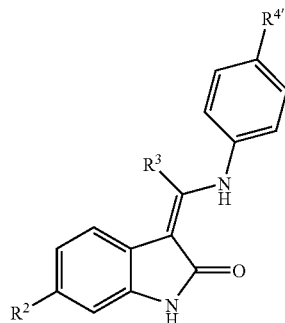
(I-9a)
| Example | R³ | R⁴' | educts | empirical formula | mass spectrum | m.p. [° C.] | R_f value* | Example |
|---|---|---|---|---|---|---|---|---|
| 9.42 | —F | (4-CH₂C(O)OMe-phenyl) | —SO₂Me | VIII.1 — | $C_{25}H_{21}FN_2O_5S$ 481 $[M+H]^+$ | 205-214 | 0.65 | (A) |
| 9.43 | —F | (4-CH₂C(O)OMe-phenyl) | —N(Me)-(CO)—(CH₂)₃—NMe₂ | VIII.1 XV.266 | $C_{31}H_{33}FN_4O_4$ 545 $[M+H]^+$ | 190-193 | 0.15 | (A) |
| 9.44 | —F | (4-CH₂C(O)OMe-phenyl) | —N(COMe)-(CH₂)₃—NMe₂ | VIII.1 XV.7 | $C_{31}H_{33}FN_4O_4$ 545 $[M+H]^+$ | 184-188 | 0.50 | (A) |
| 9.45 | —F | (3-CH₂C(O)OMe-phenyl) | —H | VIII.10 — | $C_{24}H_{19}FN_2O_3$ 403 $[M+H]^+$ | 114 | 0.70 | (B) |

-continued

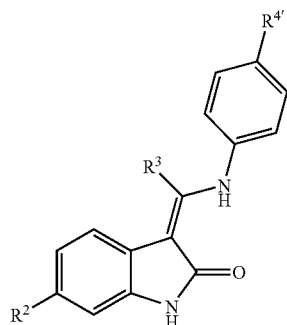

(I-9a)

| Example | R³ | R⁴' | educts | empirical formula | mass spectrum | m.p. [° C.] | $R_f$ value* | Example |
|---|---|---|---|---|---|---|---|---|
| 9.46 | —F | (methyl 3-substituted phenylacetate) | —SO₂Me | VIII.10 | $C_{25}H_{21}FN_2O_5S$ 481 $[M + H]^+$ | — | 129 | 0.60 (B) |
| 9.47 | —F | (methyl 3-substituted phenylacetate) | (1-methyl-2-substituted imidazole) | VIII.10 XV.145 | $C_{28}H_{23}FN_4O_3$ 483 $[M + H]^+$ | — | 125 | 0.60 (B) |
| 9.48 | —F | (methyl 3-substituted phenylacetate) | —N(SO₂Me)-(CH₂)—(CO)—NMe₂ | VIII.10 XV.120 | $C_{29}H_{29}FN_4O_6S$ 581 $[M + H]^+$ | — | 163 | 0.60 (B) |
| 9.49 | —F | (methyl 3-substituted phenylacetate) | —N(Me)-(CO)—(CH₂)₃—NMe₂ | VIII.10 XV.266 | $C_{31}H_{33}FN_4O_4$ 545 $[M + H]^+$ | — | 101 | 0.10 (B) |

-continued

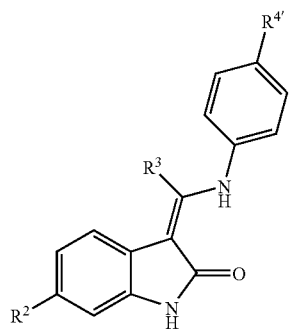

(I-9a)

| Example | R³ | R⁴' | educts | empirical formula | mass spectrum | m.p. [° C.] | R_f value* | Example |
|---|---|---|---|---|---|---|---|---|
| 9.50 | —F | methyl 3-substituted phenylacetate | —N(Me)-(CO)—(CH$_2$)$_2$—NMe$_2$ | VIII.10 XV.126 | $C_{30}H_{31}FN_4O_4$ | 531 [M + H]⁺ | 161 | 0.20 (B) |
| 9.51 | —F | methyl 3-substituted phenylpropanoate | Me-N(—)—C(O)—CH$_2$—N(piperazinyl)-Me | VIII.17 XV.204 | $C_{30}H_{31}FN_4O_4$ | 586 [M + H]⁺ | 181-183 | 0.20 (B) |
| 9.52 | —F | methyl 3-substituted phenylpropanoate | —N(SO$_2$Me)-(CH$_2$)$_2$—NMe$_2$ | VIII.17 XV.2 | $C_{30}H_{33}FN_4O_5S$ | 581 [M + H]⁺ | 158-160 | 0.35 (B) |
| 9.53 | —F | methyl 3-substituted phenylpropanoate | —N(Me)-(CO)—CH$_2$—NMe$_2$ | VIII.17 XV.125 | $C_{30}H_{31}FN_4O_4$ | 531 [M + H]⁺ | n.b. | 0.40 (B) |

-continued

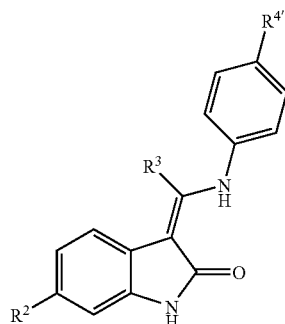
(I-9a)

| Example | R³ | R⁴' | educts | empirical formula | mass spectrum | m.p. [° C.] | $R_f$ value* | Example |
|---|---|---|---|---|---|---|---|---|
| 9.54 | —F | MeO—C(O)—CH₂CH₂—(3-C₆H₄)— | —N(COMe)-(CH₂)₃—NMe₂ | VIII.17 XV.7 | $C_{32}H_{35}FN_4O_4$ 559 $[M+H]^+$ | n.b. | 0.50 (E) | |
| 9.55 | —F | tBuO-C(O)-NH-CH₂-(3-C₆H₄)-C(CH₃)₂— | Me-N(C(O)CH₂-piperazine-N-Me)-C(CH₃)₂— | VIII.11 XV.204 | $C_{35}H_{41}FN_6O_4$ 629 $[M+H]^+$ | n.b. | 0.35 (A) | |
| 9.56 | —F | CH₃-C(O)-NH-CH₂-(3-C₆H₄)-C(CH₃)₂— | —NMe-(CO)—CH₃ | VIII.21 | $C_{27}H_{25}FN_4O_3$ 473 $[M+H]^+$ | 122-126 | 0.50 (F) | |
| 9.57 | —F | CH₃-C(O)-NH-CH₂-(3-C₆H₄)-C(CH₃)₂— | —N(COMe)-(CH₂)₃—NMe₂ | VIII.21 XV.7 | $C_{31}H_{34}FN_5O_3$ 544 $[M+H]^+$ | 80-83 | 0.25 (A) | |

-continued
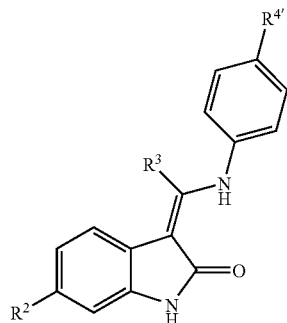
(I-9a)
| Example | R³ | R⁴' | educts | empirical formula | mass spectrum | m.p. [°C.] | $R_f$ value* | Example |
|---|---|---|---|---|---|---|---|---|
| 9.58 | —F | (3-tBu-phenyl-CH₂-NH-CO-CH₃) | —N(SO₂Me)-(CH₂)₂—NMe₂ | VIII.21 XV.2 | $C_{29}H_{32}FN_5O_4S$ 566 $[M + H]^+$ | 190-195 | 0.30 (A) |
| 9.59 | —F | (3-tBu-phenyl-CH₂-NH-CO-CH₃) | —N(Me)-(CO)—CH₂—NMe₂ | VIII.21 XV.125 | $C_{29}H_{30}FN_5O_3$ 516 $[M + H]^+$ | 238-241 | 0.30 (G) |
| 9.60 | —F | OMe (4-tBu-phenyl-CH₂-CH₂-CO-O—) | —(CH₂)₂—NMe₂ | VIII.18 XV.5 | $C_{29}H_{30}FN_3O_3$ 488 $[M + H]^+$ | 205-208 | 0.55 (G) |
| 9.61 | —F | OMe (4-tBu-phenyl-CH₂-CH₂-CO-O—) | —N(Me)-(CO)—(CH₂)₂—NMe₂ | VIII.18 XV.126 | $C_{31}H_{31}FN_4O_4$ 543 $[M − H]^−$ | 196-202 | 0.20 (A) |

-continued
(I-9a)
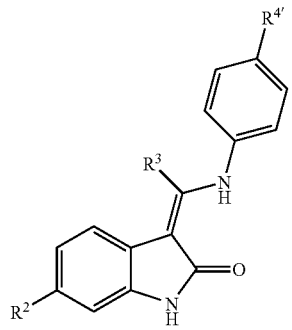
| Example | R³ | R⁴' | educts | empirical formula | mass spectrum | m.p. [° C.] | $R_f$ value* | Example |
|---|---|---|---|---|---|---|---|---|
| 9.62 | —F | OMe, phenyl-CH₂CH₂C(O)O- (para) | —N(Me)-(CO)—CH₂—NMe₂ | VIII.18 XV.125 | $C_{30}H_{31}FN_4O_4$ 531 $[M + H]^+$ | 177-182 | 0.30 (A) | |
| 9.63 | —F | EtO, phenyl-CH₂CH₂C(O)O- (meta) | —(CH₂)₂—NMe₂ | VIII.22 XV.5 | $C_{30}H_{32}FN_3O_3$ 500 $[M − H]^-$ | 100-105 | 0.35 (B) | |
| 9.64 | —F | OMe, phenyl-CH₂CH₂C(O)O- (para) | —N(COMe)-(CH₂)₂—NMe₂ | VIII.18 XV.6 | $C_{31}H_{33}FN_4O_4$ 545 $[M + H]^+$ | 167-169 | 0.40 (A) | |
| 9.65 | —F | EtO, phenyl-CH₂CH₂C(O)O- (meta) | —N(Me)-(CO)—(CH₂)₃—NMe₂ | VIII.22 XV.266 | $C_{33}H_{37}FN_4O_4$ 571 $[M − H]^-$ | n.d. | 0.35 (A) | |

-continued
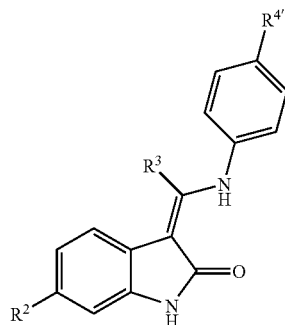
(I-9a)
| Example | R³ | R⁴' | educts | empirical formula | mass spectrum | m.p. [° C.] | $R_f$ value* | Example |
|---|---|---|---|---|---|---|---|---|
| 9.66 | —F | EtO-C(=O)-CH₂-CH₂-C₆H₄- (3-tBu) | —N(Me)-(CO)—(CH₂)₄—NMe₂ | VIII.22 XV.258 | $C_{34}H_{39}FN_4O_4$ 585 [M − H]⁻ | n.d. | 0.40 (A) |
| 9.67 | —F | EtO-C(=O)-CH₂-CH₂-C₆H₄- (3-tBu) | 2-tBu-1-Me-imidazole | VIII.22 XV.145 | $C_{30}H_{27}FN_4O_3$ 511 [M + H]⁺ | 95-105 | 0.25 (B) |
| 9.68 | —F | OMe-C(=O)-CH₂-CH₂-C₆H₄- (4-tBu) | —N(Me)-(CO)—(CH₂)₄—NMe₂ | VIII.18 XV.258 | $C_{33}H_{37}FN_4O_4$ 573 [M + H]⁺ | 173-175 | 0.20 (A) |
| 9.69 | —F | OMe-C(=O)-CH₂-CH₂-C₆H₄- (4-tBu) | —H | VIII.18 — | $C_{25}H_{21}FN_2O_3$ 417 [M + H]⁺ | 168-174 | 0.65 (A) |

-continued (I-9a)

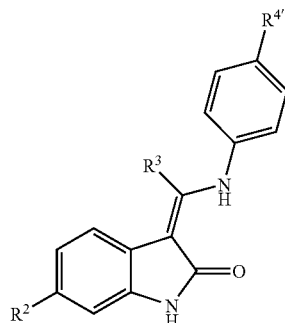

| Example | R³ | R⁴' | educts | empirical formula | mass spectrum | m.p. [° C.] | R_f value* | Example |
|---|---|---|---|---|---|---|---|---|
| 9.70 | —F | OMe, (methyl 3-(4-substituted phenyl)propanoate) | pyrrolidine-CH₂- (neopentyl) | VIII.18 XV.22 | $C_{30}H_{30}FN_3O_3$ 500 [M + H]⁺ | 168–173 | 0.40 | (B) |
| 9.71 | —F | OMe, (methyl 3-(4-substituted phenyl)propanoate) | —CH₂—NEt₂ | VIII.18 XV.66 | $C_{30}H_{32}FN_3O_3$ 502 [M + H]⁺ | n.d. | 0.45 | (B) |
| 9.72 | —F | OMe, (methyl 3-(4-substituted phenyl)propanoate) | NH-Boc neopentyl (CH₂NHC(O)OtBu) | VIII.18 XV.12 | $C_{31}H_{32}FN_3O_5$ 544 [M − H]⁻ | n.d. | 0.30 | (G) |
| 9.73 | —F | OMe, (methyl 2-(3-substituted phenyl)acetate) | —(CH₂)₂—NMe₂ | VIII.10 XV.5 | $C_{28}H_{28}FN_3O_3$ 472 [M − H]⁻ | 165–170 | 0.25 | (B) |

(I-9a)

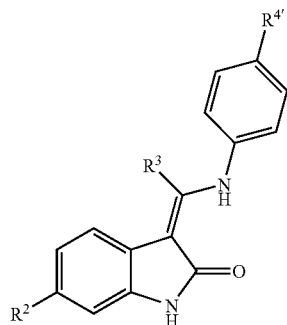

| Example | R³ | R⁴' | educts | empirical formula | mass spectrum | m.p. [° C.] | R_f value* | Example |
|---|---|---|---|---|---|---|---|---|
| 9.74 | —F | OMe group (methyl 4-substituted phenylacetate) | —(CH₂)₂—NMe₂ | VIII.1 XV.5 | $C_{28}H_{28}FN_3O_3$ | 472 [M − H]⁻ | 193-197 | 0.25 (B) |
| 9.75 | —F | EtO group (ethyl 3-substituted phenylpropanoate) | —CH₂—NMe₂ | VIII.22 XV.4 | $C_{29}H_{30}FN_3O_3$ | 488 [M + H]⁺ | 48-52 | 0.45 (B) |
| 9.76 | —Cl | OMe group (methyl 4-substituted phenylpropanoate) | —(CH₂)₂—NMe₂ | VIII.23 XV.5 | $C_{29}H_{30}ClN_3O_3$ | 504/506 [M + H]⁺ | 156-160 | 0.30 (H) |
| 9.77 | —Cl | OMe group (methyl 4-substituted phenylpropanoate) | 1-methyl-imidazole substituent | VIII.23 XV.145 | $C_{29}H_{25}ClN_4O_3$ | 513/515 [M + H]⁺ | 110 | 0.40 (H) |

-continued

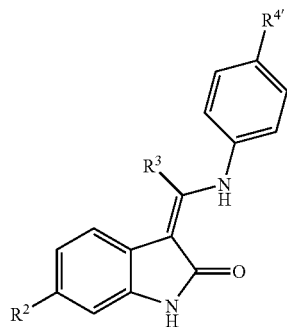
(I-9a)

| Example | $R^3$ | $R^{4'}$ | educts | empirical formula | mass spectrum | m.p. [°C.] | $R_f$ value* | Example |
|---|---|---|---|---|---|---|---|---|
| 9.78 | —Cl | OMe, (4-tBu-phenyl)-CH₂CH₂-C(=O)-O- | —CH₂—NMe₂ | VIII.23 XV.4 | $C_{28}H_{28}ClN_3O_3$ 490/492 $[M+H]^+$ | 173-175 | 0.70 | (I) |
| 9.79 | —F | OEt, (4-tBu-phenyl)-CH₂CH₂-C(=O)-O- | —CH₂—NMe₂ | VIII.24 XV.4 | $C_{29}H_{30}FN_3O_3$ 488 $[M+H]^+$ | 158-161 | 0.35 | (B) |
| 9.80 | —F | MeO, (3-(N-Me-piperazinyl-CH₂-C(Me)₂)-phenyl)-CH₂CH₂-C(=O)-O- | | VIII.17 XV.135 | $C_{31}H_{33}FN_4O_3$ 529 $[M+H]^+$ | 147-150 | 0.50 | (I) |
| 9.81 | —F | MeO, (3-(imidazolyl-CH₂-C(Me)₂)-phenyl)-CH₂CH₂-C(=O)-O- | | VIII.17 XV.140 | $C_{29}H_{25}FN_4O_3$ 497 $[M+H]^+$ | 182-185 | 0.60 | (K) |

-continued (I-9a)

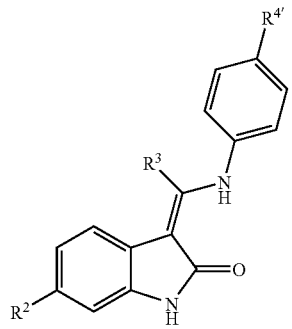

| Example | $R^3$ | $R^{4'}$ | educts | empirical formula | mass spectrum | m.p. [° C.] | $R_f$ value* | Example |
|---|---|---|---|---|---|---|---|---|
| 9.82 | —F | OMe, (structure: methyl 3-(4-tert-butylphenyl)propanoate) | (structure: 1-methyl-4-neopentylpiperazine), —Me | VIII.18 XV.135 | $C_{31}H_{33}FN_4O_3$ 529 $[M + H]^+$ | 184 | 0.35 (B) | |
| 9.83 | —F | OMe, (structure: methyl 3-(4-tert-butylphenyl)propanoate) | (structure: 1-neopentylimidazole) | VIII.18 XV.140 | $C_{29}H_{25}FN_4O_3$ 497 $[M + H]^+$ | 233 | 0.45 (B) | |
| 9.84 | —F | OMe, (structure: methyl 3-(4-tert-butylphenyl)propanoate) | —CH$_2$—NMe-(CH$_2$)$_2$—NMe$_2$ | VIII.18 XV.195 | $C_{31}H_{35}FN_4O_3$ 531 $[M + H]^+$ | 120 | 0.40 (B) | |
| 9.85 | —F | EtO, (structure: ethyl 3-(3-tert-butylphenyl)propanoate) | —CH$_2$—NMe-(CH$_2$)$_2$—NMe$_2$ | VIII.22 XV.195 | $C_{32}H_{37}FN_4O_3$ 545 $[M + H]^+$ | n.d. | 0.40 (K) | |

-continued

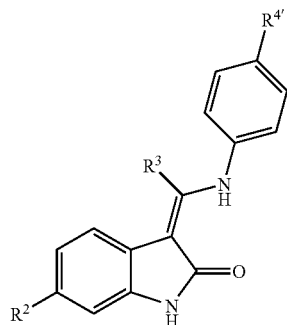

(I-9a)

| Example | R³ | R⁴' | educts | empirical formula | mass spectrum | m.p. [° C.] | R_f value* | Example |
|---|---|---|---|---|---|---|---|---|
| 9.86 | —Cl | OMe, phenyl-CH₂CH₂C(O)OMe with t-Bu | pyrrolidine-CH₂-C(CH₃)₂- | VIII.23 XV.22 | $C_{30}H_{30}ClN_3O_3$ 516/518 $[M+H]^+$ | 195-197 | 0.30 (H) | |
| 9.87 | —F | EtO-C(O)CH₂CH₂-phenyl-t-Bu | —H | VIII.22 | $C_{26}H_{23}FN_2O_3$ 431 $[M+H]^+$ | 156-160 | 0.80 (M) | |
| 9.88 | —F | EtO-C(O)CH₂CH₂-phenyl-t-Bu | BocNH-CH₂-C(CH₃)₂- | VIII.22 XV.12 | $C_{32}H_{34}FN_3O_5$ 560 $[M+H]^+$ | n.d. | 0.50 (L) | |
| 9.89 | —F | EtO-C(O)CH₂CH₂-phenyl-t-Bu | Boc(Me)N-CH₂-C(CH₃)₂- | VIII.22 XV.18 | $C_{33}H_{36}FN_3O_5$ 574 $[M+H]^+$ | n.d. | 0.60 (L) | |

-continued
(I-9a)
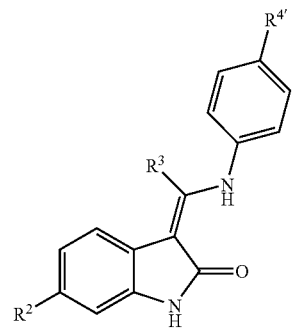
| Example | R³ | R⁴' | educts | empirical formula | mass spectrum | m.p. [° C.] | $R_f$ value* | Example |
|---|---|---|---|---|---|---|---|---|
| 9.90 | —F | 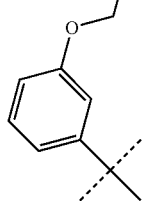 | —CH₂—NMe₂ | VIII.25 XV.4 | $C_{27}H_{26}FN_3O_4$ 476 $[M + H]^+$ | 129 | 0.25 | (B) |
| 9.91 | —F | 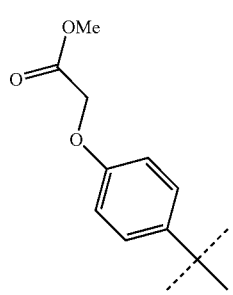 | —CH₂—NMe₂ | VIII.26 XV.4 | $C_{27}H_{26}FN_3O_4$ 476 $[M + H]^+$ | 155 | 0.25 | (B) |
| 9.92 | —F | 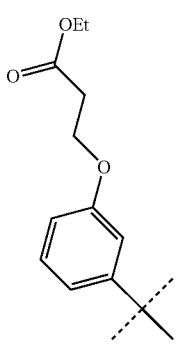 | —CH₂—NMe₂ | VIII.27 XV.4 | $C_{28}H_{28}FN_3O_4$ 504 $[M + H]^+$ | n.d. | 0.20 | (B) |

-continued

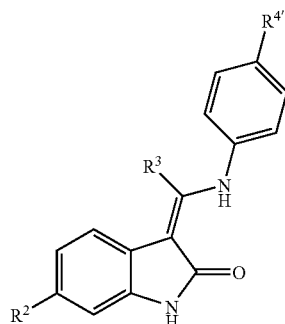
(I-9a)

| Example | R³ | R⁴' | educts | empirical formula | mass spectrum | m.p. [°C.] | $R_f$ value* | Example |
|---|---|---|---|---|---|---|---|---|
| 9.93 | —Br | OMe, structure with ester-phenyl group | structure with pyrrolidine-CH₂-C(CH₃)₂- | VIII.18 XV.22 | $C_{30}H_{30}BrN_3O_3$ 560/562 $[M+H]^+$ | 230–235 | 0.45 (B) | |
| 9.94 | —Br | OMe, structure with ester-phenyl group | —CH₂—NMe₂ | VIII.18 XV.4 | $C_{28}H_{28}BrN_3O_3$ 534/536 $[M+H]^+$ | 178–180 | 0.35 (B) | |
| 9.95 | —Br | OMe, structure with ester-phenyl group | —CH₂—NEt₂ | VIII.18 XV.66 | $C_{30}H_{32}BrN_3O_3$ 562/264 $[M+H]^+$ | 173–176 | 0.40 (B) | |

*Eluant mixtures:
(A): silica gel, methylene chloride/methanol/ammonia 9:1:0.1
(B): silica gel, methylene chloride/methanol 9:1
(C): silica gel, methylene chloride/methanol/ammonia 8:1:0.1
(D): silica gel, methylene chloride/methanol/ammonia 10:1:0.1
(E): silica gel, methylene chloride/methanol/ammonia 5:1:0.01
(F): silica gel, ethyl acetate/methanol/ammonia = 9:1:0.1
(G): aluminium oxide, methylene chloride/methanol = 19:1
(H): silica gel, methylene chloride/methanol/ammonia 9:1:0.01
(I): silica gel, methylene chloride/methanol 5:1
(K): aluminium oxide, methylene chloride/ethanol = 20:1
(L): silica gel, petroleum ether/ethyl acetate 1:1

The following compounds of general formula I-9b are prepared analogously to Example 9.0:

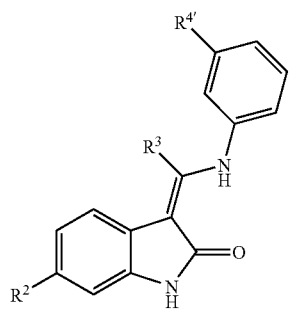

(I-9b)

| Example | $R^2$ | $R^3$ | $R^{4'}$ | educts | empirical formula | mass spectrum | mp. [° C.] | $R_f$ value* |
|---|---|---|---|---|---|---|---|---|
| 9.96 | —F | OMe (with propanoate-phenyl-t-Bu para group) | —CH$_2$—NMe$_2$ | VIII.18 XV.3 | C$_{28}$H$_{28}$FN$_3$O$_3$ | 474 [M + H]$^+$ | 176-179 | 0.40 (A) |
| 9.97 | —F | EtO (with propanoate-phenyl-t-Bu meta group) | —CH$_2$—NMe$_2$ | VIII.22 XV.3 | C$_{29}$H$_{30}$FN$_3$O$_3$ | 486 [M − H]$^-$ | n.d. | 0.45 (B) |
| 9.98 | —Cl | OMe (with propanoate-phenyl-t-Bu para group) | —CH$_2$—NMe$_2$ | VIII.23 XV.3 | C$_{28}$H$_{28}$ClN$_3$O$_3$ | 490/492 [M + H]$^+$ | 163-165 | 0.40 (A) |

*eluant mixtures:
(A): silica gel, methylene chloride/methanol 9:1
(B): silica gel, methylene chloride/methanol/ammonia 9:1:0.1

EXAMPLE 10.0

3-Z-[1-(4-(dimethylaminomethyl)-anilino)-1-(3,4-dimethoxy-phenyl)-methylene]-6-cyano-2-indolinone 130 mg of 1-acetyl-3-(1-methoxy-1-(3,4-dimethoxy-phenyl)-methylene)-6-cyano-2-indolinone (educt VIII.5) and 58 mg of 4-(dimethylaminomethyl)-aniline (educt XV.4) are dissolved in 5 ml of dimethylformamide and stirred for 2 hours at 80° C. After cooling the solvent is eliminated and the residue is purified through a silica gel column with methylene chloride/methanol 9:1 as eluant.

Yield: 21 mg (12% of theory), $R_f$ value: 0.35 (silica gel, methylene chloride/methanol=9:1) M.p. 265° C. $C_{27}H_{26}N_4O_3$

EXAMPLE 11.0

3-Z-[1-(4-(N-methyl-N-methylsulphonyl-amino)-anilino)-1-(3-(2-methoxycarbonyl-vinyl)-phenyl)-methylene]-6-chloro-2-indolinone 580 mg of 3-Z-[1-(4-(N-methyl-N-methylsulphonyl-amino)-anilino)-1-(3-iodo-phenyl)-methylene]-6-chloro-2-indolinone (educt 4.0) and 140 ml methyl acrylate are dissolved in 20 ml acetonitrile and 11 ml of dimethylformamide and 11 mg of palladium(II)-acetate, 2 ml of triethylamine and 30 mg of tri-ortho-tolyl-phosphine are added. The solution is stirred for 10 hours at 90° C. under nitrogen as protective gas. After cooling it is filtered through Celite, the solvent is eliminated and the residue is purified through a silica gel column with methylene chloride/methanol 20:1 as eluant.

Yield: 450 mg (84% of theory), $R_f$ value: 0.30 (silica gel, toluene/ethyl acetate=1:1) M.p. 228-232° C. $C_{27}H_{24}ClN_3O_5S$ Mass spectrum: m/z=537/539 $[M]^+$ The following compounds of general formula I-11 are prepared analogously to Example 11.0:

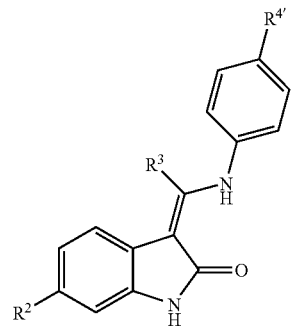

(I-11)

| Example | $R^2$ | $R^3$ | $R^{4'}$ | educt | empirical formula | mass spectrum | m.p. [° C.] | $R_f$ value* |
|---|---|---|---|---|---|---|---|---|
| 11.1 | —Cl | 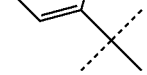 | —CH$_2$—NMe$_2$ | 4.1 | $C_{28}H_{26}ClN_3O_3$ | 486/488 $[M-H]^-$ | 150-155 | 0.50 (A) |
| 11.2 | —F | NH$_2$ 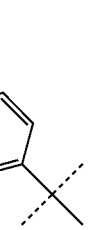 | —CH$_2$—NMe$_2$ | 9.0 | $C_{27}H_{25}FN_4O_2$ | 455 $[M-H]^-$ | 269-270 | 0.20 (B) |

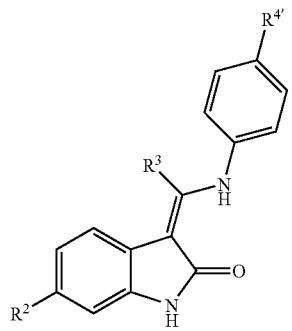

(I-11)

| Example | R² | R³ | R⁴' | educt | empirical formula | mass spectrum | m.p. [° C.] | $R_f$ value* |
|---|---|---|---|---|---|---|---|---|
| 11.3 | —F | OMe 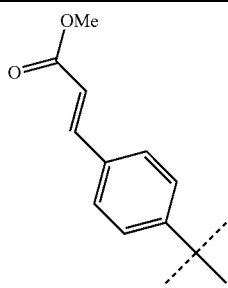 | —CH₂—NMe₂ | 9.0 | $C_{28}H_{26}FN_3O_3$ | 470 [M − H]⁻ | 205-208 | 0.65 (A) |
| 11.4 | —F | 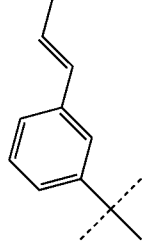 | —CH₂—NMe₂ | 4.1 | $C_{28}H_{26}FN_3O_3$ | 472 [M + H]⁺ | 138-140 | 0.45 (A) |

*Eluant mixtures:
(A): silica gel, methylene chloride/methanol 5:1
(B): silica gel, methylene chloride/methanol/ammonia 9:1:0.01

EXAMPLE 12.0

3-Z-[1-(4-dimethylaminomethyl-anilino)-1-(3-(2-methoxycarbonyl-ethyl)-phenyl)-methylene]-6-chloro-2-indolinone 1.0 g of 3-Z-[1-(4-(dimethylaminomethyl)-anilino)-1-(3-(2-methoxycarbonyl-vinyl)-phenyl)-methylene]-6-chloro-2-indolinone (educt 11.1) are dissolved in 100 ml of methanol and 200 mg of 10% palladium/charcoal is added as catalyst. Then the mixture is hydrogenated for 6 hours at ambient temperature under 50 psi of hydrogen pressure. After the reaction has ended the catalyst is filtered off, the solvent is eliminated and the residue is dried in vacuo at 100° C.

Yield: 900 mg (90% of theory), $R_f$ value: 0.40 (silica gel, methylene chloride/methanol=9:1) M.p. 160° C. $C_{28}H_{28}ClN_3O_3$ Mass spectrum: m/z=490/492 [M+H]⁺

The following compounds of general formula I-12 are prepared analogously to Example 12.0:

(I-12)
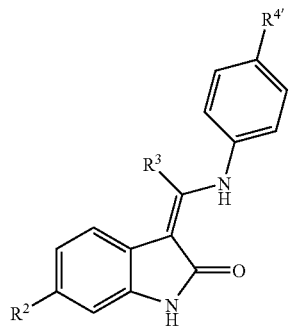
| Example | $R^2$ | $R^3$ | $R^{4'}$ | educt | empirical formula | mass spectrum | m.p. [°C.] | $R_f$ value* |
|---|---|---|---|---|---|---|---|---|
| 12.1 | —Cl | 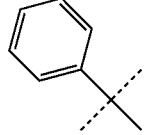 | —N(Me)-SO$_2$Me | 11.0 | C$_{27}$H$_{26}$ClN$_3$O$_5$S | 538/540 [M − H]$^-$ | 148-150 | 0.50 (A) |
| 12.2 | —F | 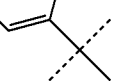 | —CH$_2$—NMe$_2$ | 11.2 | C$_{27}$H$_{27}$FN$_4$O$_2$ | 459 [M + H]$^+$ | 150 | 0.70 (B) |

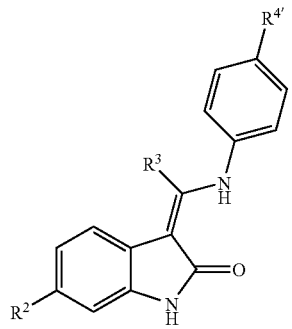

(I-12)

| Example | R² | R³ | R⁴' | educt | empirical formula | mass spectrum | m.p. [°C.] | $R_f$ value* |
|---|---|---|---|---|---|---|---|---|
| 12.3 | —F | 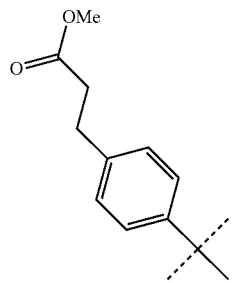 OMe | —CH₂—NMe₂ | 11.3 | $C_{28}H_{28}FN_3O_3$ | 474 [M + H]⁺ | 140 | 0.35 (A) |
| 12.4 | —F | 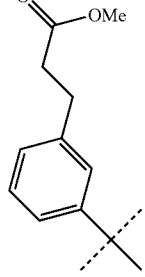 OMe | —CH₂—NMe₂ | 11.4 | $C_{28}H_{28}FN_3O_3$ | 474 [M + H]⁺ | 140-142 | 0.30 (A) |

*Eluant mixtures:
(A): silica gel, methylene chloride/methanol 9:1
(B): silica gel, methylene chloride/methanol/ammonia 5:1:0.01

EXAMPLE 13.0

3-Z-[1-(4-dimethylaminomethyl-anilino)-1-(4-amino-phenyl)-methylene]-6-chloro-2-indolinone 130 mg of 3-Z-[1-(4-dimethylaminomethyl-anilino)-1-(4-nitro-phenyl)-methylene]-6-chloro-2-indolinone (educt 5.18) are dissolved in 20 ml of ethanol and 20 ml of ethyl acetate and 100 mg of Raney nickel are added as catalyst. Then the mixture is hydrogenated for 20 hours at ambient temperature. After the end of the reaction the catalyst is filtered off, the solvent is eliminated, the residue is washed with a little diisopropylether and purified through a silica gel column with methylene chloride/ethanol/ammonia 30:1:0.1 as eluant. The product is washed with a little diisopropylether and dried in vacuo.

Yield: 80 mg (66% of theory), $R_f$ value: 0.60 (silica gel, methylene chloride/ethanol/ammonia=20:1:0.1) M.p. 263-264° C. $C_{24}H_{23}ClN_4O$ Mass spectrum: m/z=419/421 [M+H]⁺

The following compounds of general formula I-13 are prepared analogously to Example 13.0:

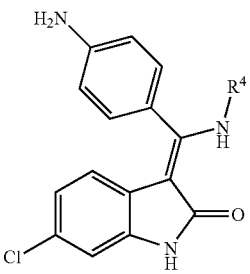
(I-13)
| Example | R⁴ | R⁴' | educt | empirical formula | mass spectrum | m.p. [° C.] | R_f value* |
|---|---|---|---|---|---|---|---|
| 13.1 | R₄' (phenyl) | —N(Me)-(CO)—CH₂—NMe₂ | 5.21 | $C_{26}H_{26}ClN_5O_2$ | 476/478 [M + H]⁺ | 275-276 | 0.10 (A) |
| 13.2 | R₄' (phenyl) | Me-N-C(O)-CH₂-N(piperazinyl)-N-Me | 5.20 | $C_{29}H_{31}ClN_6O_2$ | 529/531 [M + H]⁺ | 268-269 | 0.15 (A) |
| 13.3 | R₄' (phenyl) | —N(COMe)-(CH₂)₂—NMe₂ | 5.19 | $C_{27}H_{28}ClN_5O_2$ | 490/492 [M + H]⁺ | 270 | 0.25 (A) |
| 13.4 | R₄' (phenyl) | C(O)-N(piperazinyl)-N-Me | 5.22 | $C_{27}H_{26}ClN_5O_2$ | 488/490 [M + H]⁺ | 279-280 | 0.30 (A) |
*Eluant mixtures:
(A): silica gel, methylene chloride/ethanol/ammonia 20:1:0.1

EXAMPLE 14.0

3-Z-[1-(4-dimethylaminomethyl-anilino)-1-(4-aminomethyl-phenyl)-methylene]-6-chloro-2-indolinone 900 mg of 3-Z-[1-(4-dimethylaminomethyl-anilino)-1-(4-cyano-phenyl)-methylene]-6-chloro-2-indolinone (educt 5.23) are dissolved in 20 ml of methylene chloride, 30 ml of methanolic ammonia are added and 200 mg of Raney nickel are added as catalyst. Then the mixture is hydrogenated for 2 hours 15 minutes at ambient temperature and under 50 psi hydrogen pressure. After the end of the reaction the catalyst is filtered off, the solvent is eliminated and the residue is washed with a little methanol and diethyl ether. To liberate the base the residue is taken up in 1N sodium hydroxide solution and extracted four times with methylene chloride/methanol 9:1. The combined organic phases are washed with water and dried over sodium sulphate. The product is washed with a little diethyl ether and dried in vacuo.

Yield: 680 mg (75% of theory), $R_f$ value: 0.60 (silica gel, methylene chloride/methanol/ammonia=9:1:0.1) M.p. 211-214° C. $C_{25}H_{25}ClN_4O$ Mass spectrum: m/z=433/435 [M+H]$^+$

EXAMPLE 15.0

3-Z-[1-(4-(N-((4-methyl-piperazin-1-yl)-methylcarbonyl)-N-methyl-amino)-anilino)-1-(4-aminomethyl-phenyl)-methylene]-6-chloro-2-indolinone 1.39 g of 1-acetyl-3-Z-[1-(4-(N-((4-methyl-piperazin-1-yl)-methylcarbonyl)-N-methyl-amino)-anilino)-1-(4-cyano-phenyl)-methylene]-6-chloro-2-indolinone are dissolved in 20 ml methylene chloride, 30 ml of methanolic ammonia are added and 200 mg Raney nickel are added as catalyst. Then the mixture is hydrogenated for 2 hours at ambient temperature under 50 psi hydrogen pressure. After the end of the reaction the catalyst is filtered off, the solvent is eliminated and the residue is washed with a little methanol and diethyl ether. To liberate the base the residue is taken up in 1N sodium hydroxide solution and extracted four times with methylene chloride/methanol 9:1. The combined organic phases are washed with water and dried over sodium sulphate. The product is purified through a silica gel column with a gradient of methylene chloride and methylene chloride/methanol/ammonia 8:1:0.1 as eluant. The product is washed with a little diethyl ether and dried in vacuo.

Yield: 700 mg (54% of theory), $R_f$ value: 0.15 (silica gel, methylene chloride/methanol/ammonia=9:1:0.1) M.p. 232-235° C. $C_{30}H_{33}ClN_6O_2$ Mass spectrum: m/z=544/546 [M]$^+$

EXAMPLE 16.0

3-Z-[1-(4-(N-((4-methyl-piperazin-1-yl)-methylcarbonyl)-N-methyl-amino)-anilino)-1-(4-hydroxy-phenyl)-methylene]-6-chloro-2-indolinone 100 mg of 3-Z-[1-(4-(N-((4-methyl-piperazin-1-yl)-methylcarbonyl)-N-methyl-amino)-anilino)-1-(4-benzyloxy-phenyl)-methylene]-6-chloro-2-indolinone (educt 4.9) are dissolved in 2 ml trifluoroacetic acid and stirred for 5 hours at 50° C. After the end of the reaction the solvent is eliminated. To liberate the base the residue is taken up in water and concentrated ammonia is added until an alkaline reaction is obtained. The precipitate formed is suction filtered, washed with water and at 100° C. dried.

Yield: 10 mg (12% of theory), $R_f$ value: 0.30 (silica gel, methylene chloride/methanol=4:1) M.p. 174-176° C. $C_{29}H_{30}ClN_5O_3$ Mass spectrum: m/z=532/534 [M+H]$^+$ The following compounds of general formula I-16 are prepared analogously to Example 16.0:

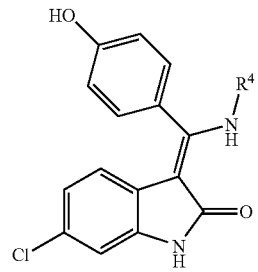

(I-16)

| Example | R$^4$ | R$^{4'}$ | educt | empirical formula | mass spectrum | m.p. [° C.] | R$_f$ value* |
|---|---|---|---|---|---|---|---|
| 16.1 | R$_4'$ | —N(Me)-(CO)—CH$_2$—NMe$_2$ | 4.8 | $C_{26}H_{25}ClN_4O_3$ | 477/479 [M + H]$^+$ | 239-241 | 0.50 (A) |

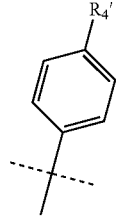

-continued (I-16)

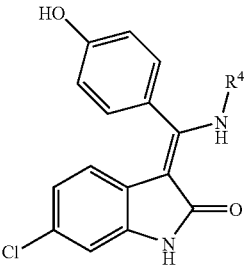

| Example | R⁴ | R⁴' | educt | empirical formula | mass spectrum | m.p. [° C.] | R_f value* |
|---|---|---|---|---|---|---|---|
| 16.2 | 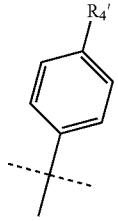 | —N(COMe)-(CH₂)₂—NMe₂ | 4.10 | $C_{27}H_{27}ClN_4O_3$ | 491/493 [M + H]⁺ | 249-251 | 0.40 (A) |
| 16.3 | 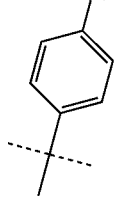 | —N(COMe)-(CH₂)₃—NMe₂ | 4.11 | $C_{28}H_{29}ClN_4O_3$ | 503/505 [M − H]⁻ | 169-170 | 0.30 (A) |
| 16.4 | 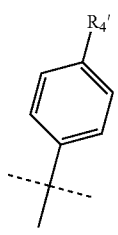 | —CH₂—NMe₂ | 4.7 | $C_{24}H_{22}ClN_3O_2$ | 418/420 [M − H]⁻ | 215-217 | 0.05 (B) |

*Eluant mixtures:
(A): silica gel, methylene chloride/methanol 4:1
(A): silica gel, methylene chloride/ethanol 10.1

EXAMPLE 17.0

3-Z-[1-(4-ethylaminomethyl-anilino)-1-phenyl-methylene]-6-chloro-2-indolinone-trifluoroacetate 180 mg of 3-Z-[1-(4-(N-tert.butoxycarbonyl-ethylaminomethyl)-anilino)-1-phenyl-methylene]-6-chloro-2-indolinone (educt 1.30) are dissolved in 5 ml methylene chloride and 0.5 ml of trifluoroacetic acid are added. The mixture is stirred for 10 hours at ambient temperature. After this time the solvent is largely eliminated and the precipitate formed is suction filtered.

Yield: 110 mg (60% of theory), R_f value: 0.20 (silica gel, methylene chloride/methanol=9:1) M.p. 260° C. $C_{24}H_{22}ClN_3O$ Mass spectrum: m/z=402/404 [M−H]⁻

The following compounds of general formula I-17 are prepared analogously to Example 17.0:

(I-17)

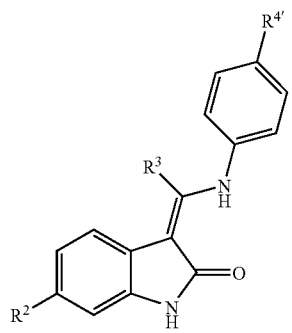

| Example | R² | R³ | R⁴' | educt | empirical formula | mass spectrum | m.p. [° C.] | $R_f$ value* |
|---|---|---|---|---|---|---|---|---|
| 17.1 | —Cl | phenyl (C(CH₃)₂) | —CH₂—NHMe | 1.43 | $C_{23}H_{20}ClN_3O$ | 388/390 [M − H]⁻ | 250 | 0.15 (A) |
| 17.2 | —Cl | phenyl (C(CH₃)₂) | Me-N(C(CH₃)₂-)-C(O)-CH₂CH₂-piperazine-NH | 1.50 | $C_{29}H_{30}ClN_5O_2$ | 514/516 [M − H]⁻ | 224 | 0.25 (A) |
| 17.3 | —Cl | phenyl (C(CH₃)₂) | -CH₂-piperazine-NH (C(CH₃)₂) | 1.52 | $C_{26}H_{25}ClN_4O$ | 443/445 [M − H]⁻ | 240 | 0.25 (A) |
| 17.4 | —Cl | phenyl (C(CH₃)₂) | -C(O)-piperazine-NH (C(CH₃)₂) | 1.67 | $C_{26}H_{23}ClN_4O_2$ | 457/459 [M − H]⁻ | 289 | 0.25 (A) |
| 17.5 | —Cl | phenyl (C(CH₃)₂) | —CH₂—NH₂ | 1.77 | $C_{22}H_{18}ClN_3O$ | 374/376 [M − H]⁻ | 265 | 0.70 (B) |
| 17.6 | —Cl | phenyl (C(CH₃)₂) | Me₂CH-N(C(CH₃)₂-)-C(O)-CH₂-piperazine-NH | 1.79 | $C_{30}H_{32}ClN_5O_2$ | 528/530 [M − H]⁻ | 164 | 0.70 (B) |

(I-17)

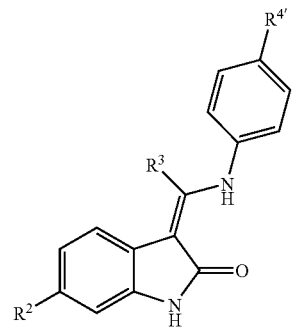

| Example | R² | R³ | R⁴' | educt | empirical formula | mass spectrum | m.p. [° C.] | R$_f$ value* |
|---|---|---|---|---|---|---|---|---|
| 17.7 | —Cl | phenyl (tert-butyl attached) | piperazine-N-CH₂-C(O)-N(CH₃)-C(CH₃)₃ | 1.84 | $C_{28}H_{28}ClN_5O_2$ | 500/502 [M − H]⁻ | 172 | 0.70 (B) |
| 17.8 | —Cl | phenyl (tert-butyl attached) | H₂N-CH₂CH₂CH₂-N(Me)-CH₂-C(CH₃)₃ | 1.87 | $C_{26}H_{27}ClN_4O$ | 447/449 [M + H]⁺ | 221 | 0.70 (B) |
| 17.9 | —Cl | 1-(4-substituted phenyl)pyrrolidin-2-one | —CH₂—NHMe | 5.11 | $C_{27}H_{25}ClN_4O_2$ | 473/475 [M + H]⁺ | 240-244 | 0.25 (C) |
| 17.10 | —Br | phenyl (tert-butyl attached) | —CH₂—NHEt | 6.5 | $C_{24}H_{22}BrN_3O$ | 446/448 [M − H]⁻ | 274-276 | 0.10 (A) |
| 17.11 | —Br | phenyl (tert-butyl attached) | —CH₂—NHMe | 6.17 | $C_{23}H_{20}BrN_3O$ | 456/458 [M + H]⁺ | 252-255 | 0.40 (C) |
| 17.12 | —CN | phenyl (tert-butyl attached) | —CH₂—NHEt | 7.5 | $C_{25}H_{22}N_4O$ | 393 [M − H]⁻ | 249 | 0.25 (A) |

-continued
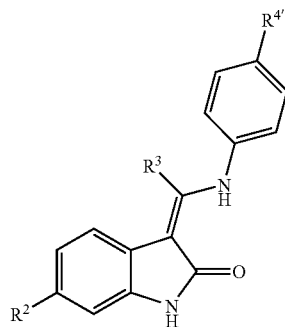
(I-17)
| Example | R² | R³ | R⁴' | educt | empirical formula | mass spectrum | m.p. [° C.] | $R_f$ value* |
|---|---|---|---|---|---|---|---|---|
| 17.13 | —CN | phenyl | piperazine-CH₂-C(O)-N(CH₃)- | 7.18 | $C_{29}H_{28}N_6O_2$ | 491 [M − H]⁻ | 146 | 0.15 (A) |
| 17.14 | —F | phenyl | —CH₂—NHEt | 8.4 | $C_{24}H_{22}FN_3O$ | 386 [M − H]⁻ | 285-288 | 0.40 (D) |
| 17.15 | —F | phenyl | —CH₂—NHMe | 8.16 | $C_{23}H_{20}FN_3O$ | 372 [M − H]⁻ | 251 | 0.15 (C) |
| 17.16 | —F | 3-(aminomethyl)phenyl (NH₂) | —CH₂—NMe₂ | 9.13 | $C_{25}H_{25}FN_4O$ | 415 [M − H]⁻ | 168-175 | 0.25 (C) |
| 17.17 | —F | 3-(2-aminoethyl)phenyl (NH₂) | —CH₂—NMe₂ | 9.19 | $C_{26}H_{27}FN_4O$ | 431 [M + H]⁺ | 155-160 | 0.45 (E) |
| 17.18 | —F | 4-(aminomethyl)phenyl (NH₂) | —CH₂—NMe₂ | 9.18 | $C_{25}H_{25}FN_4O$ | 417 [M + H]⁺ | 203-207 | 0.25 (C) |

-continued
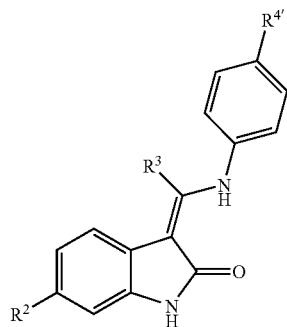
(I-17)
| Example | R² | R³ | R⁴' | educt | empirical formula | mass spectrum | m.p. [° C.] | R_f value* |
|---|---|---|---|---|---|---|---|---|
| 17.19 | —F | –CH₂–C₆H₄–C(CH₃)₃ with NH₂ | –CH₂–C(O)–N(CH₃)– piperazine-NMe | 9.17 | $C_{30}H_{33}FN_6O_2$ | 529 [M + H]⁺ | 170-175 | 0.15 (C) |
| 17.20 | —F | –CH₂–CH₂–C₆H₄–C(CH₃)₃ with COOH | —CH₂—NHMe | 20.11 | $C_{26}H_{24}FN_3O_3$ | 446 [M + H]⁺ | 245-251 | 0.20 (F) |
| 17.21 | —F | –CH₂–CH₂–C₆H₄–C(CH₃)₃ with C(O)NHCH₃ | —CH₂—NHMe | 21.22 | $C_{26}H_{24}FN_3O_3$ | 459 [M + H]⁺ | 239-243 | 0.30 (C) |
| 17.22 | —F | meta-tBu benzyl NH₂ | –CH₂–C(O)–N(CH₃)– piperazine-NMe | 9.55 | $C_{30}H_{33}FN_6O_2$ | 529 [M + H]⁺ | n.d. | n.d. |

(I-17)

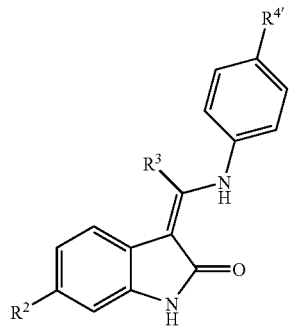

| Example | R² | R³ | R⁴' | educt | empirical formula | mass spectrum | m.p. [°C.] | $R_f$ value* |
|---|---|---|---|---|---|---|---|---|
| 17.23 | —F | OMe, (CH₂)₂-phenyl-C(CH₃)₃ (para) with C(=O)O- | —CH₂—NH₂ | 9.72 | $C_{26}H_{24}FN_3O_3$ | 444 [M − H]⁻ | 158-163 | 0.25 (C) |
| 17.24 | —F | EtO, (CH₂)₂-phenyl-C(CH₃)₃ (meta) with C(=O)O- | —CH₂—NH₂ | 9.88 | $C_{27}H_{26}FN_3O_3$ | 460 [M + H]⁺ | 205-210 | 0.30 (D) |
| 17.25 | —F | EtO, (CH₂)₂-phenyl-C(CH₃)₃ (meta) with C(=O)O- | —CH₂—NHMe | 9.89 | $C_{28}H_{28}FN_3O_3$ | 474 [M + H]⁺ | 148-150 | 0.30 (D) |

*Eluant mixtures:
(A): silica gel, methylene chloride/methanol 9:1
(B): silica gel, methylene chloride/methanol 10:1
(C): silica gel, methylene chloride/methanol/ammonia 9:1:0.1
(D): silica gel, methylene chloride/methanol/ammonia 9:1:0.01
(E): silica gel, methylene chloride/methanol/ammonia 8:2:0.2
(F): Reversed phase RP8, methanol/saline solution (5%) = 3:2

EXAMPLE 18.0

3-Z-[1-(4-(N-aminomethylcarbonyl-N-methyl-amino)-amino)-anilino)-1-phenyl-methylene]-6-chloro-2-indolinone 600 mg of 3-Z-[1-(4-(N-phthalimido-2-yl-methylcarbonyl)-N-methyl-amino)-anilino)-1-phenyl-methylene]-6-chloro-2-indolinone (educt 1.42) are dissolved in 30 ml of ethanol and 500 mg of hydrazine hydrate (80%) are added. The mixture is stirred for 4 hours at 50° C. After cooling 20 ml methylene chloride are added and the precipitate formed is suction filtered. The filtrate is concentrated by evaporation and purified through a silica gel column with methylene chloride/methanol/ammonia 10:1:0.1 as eluant.

Yield: 100 mg (22% of theory), $R_f$ value: 0.40 (silica gel, methylene chloride/methanol/ammonia=9:1:0.1) M.p. 204-206° C. $C_{24}H_{21}ClN_4O_2$ Mass spectrum: m/z=432/434 $[M]^+$

EXAMPLE 19.0

3-Z-[1-(4-carboxy-anilino)-1-phenyl-methylene]-6-chloro-2-indolinone 450 mg of 3-Z-[1-(4-ethoxycarbonyl-anilino)-1-phenyl-methylene]-6-chloro-2-indolinone (educt 1.2) are dissolved in 10 ml of ethanol and 2 ml of 1N sodium hydroxide solution are added. The mixture is stirred for 3 hours at 80° C. After cooling, 2 ml of 1N hydrochloric acid are added and the mixture is stirred for half an hour at ambient temperature. The precipitate formed is suction filtered and washed with ethanol and diethyl ether.

Yield: 320 mg (76% of theory), $R_f$ value: 0.40 (silica gel, methylene chloride/ethanol=9:1) M.p. 333-334° C. (decomposition) $C_{22}H_{15}ClN_2O_3$ Mass spectrum: m/z=389/391 $[M-H]^-$ The following compounds of general formula I-19 are prepared analogously to Example 19.0:

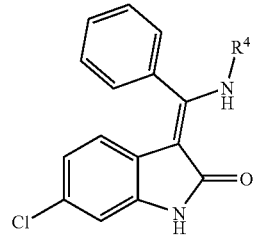

(I-19)

| Example | $R^4$ | $R^{4'}$ | educt | empirical formula | mass spectrum | m.p. [° C.] | $R_f$ value* |
|---|---|---|---|---|---|---|---|
| 19.1 | ![R4' para] | —CH$_2$—COOH | 1.100 | $C_{23}H_{17}ClN_2O_3$ | 403/405 $[M-H]^-$ | 277 | 0.25 (A) |
| 19.2 | ![R4' meta] | —CH$_2$—COOH | 1.74 | $C_{23}H_{17}ClN_2O_3$ | 403/405 $[M-H]^-$ | 209 | 0.15 (A) |
| 19.3 | ![R4' meta] | —COOH | 1.75 | $C_{22}H_{15}ClN_2O_3$ | 389/391 $[M-H]^-$ | 321 | 0.25 (A) |

*Eluant mixtures:

(A): silica gel, methylene chloride/methanol 9:1

EXAMPLE 20.0

3-Z-[1-(4-dimethylaminomethyl-anilino)-1-(3-(2-carboxy-ethyl)-phenyl)-methylene]-6-chloro-2-indolinone 900 mg of 3-Z-[1-(4-dimethylaminomethyl-anilino)-1-(3-(2-methoxycarbonyl-ethyl)-phenyl)-methylene]-6-chloro-2-indolinone (educt 12.0) are dissolved in 10 ml of ethanol and 5 ml of 1N sodium hydroxide solution are added. The mixture is stirred for 5 hours at ambient temperature. After cooling, 5 ml of 1N hydrochloric acid are added. The precipitate formed is suction filtered and washed with water.

Yield: 830 mg (95% of theory), $R_f$ value: 0.50 (Reversed phase RP8, methanol/saline solution (5%)=4:1) M.p. 210-215° C. $C_{27}H_{26}ClN_3O_3$ Mass spectrum: m/z=476/478 [M+H]$^+$ The following compounds of general formula I-20a are prepared analogously to Example 20.0:

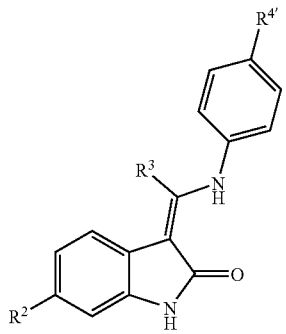

(I-20a)

| Example | R$^2$ | R$^3$ | R$^{4'}$ | educt | empirical formula | mass spectrum | m.p. [° C.] | R$_f$ value* |
|---|---|---|---|---|---|---|---|---|
| 20.1 | —F | (3-(2-carboxyethyl)phenyl, para-substituted) | —CH$_2$—NMe$_2$ | 12.3 | C$_{27}$H$_{26}$FN$_3$O$_3$ | 460 [M + H]$^+$ | 250 | 0.65 (A) |
| 20.2 | —F | (3-(carboxymethyl)phenyl, meta-substituted) | —CH$_2$—NMe$_2$ | 9.12 | C$_{26}$H$_{24}$FN$_3$O$_3$ | 444 [M − H]$^−$ | 278-282 | 0.10 (B) |
| 20.3 | —F | (3-(2-carboxyethyl)phenyl, meta-substituted) | —CH$_2$—NMe$_2$ | 12.4 | C$_{27}$H$_{26}$FN$_3$O$_3$ | 458 [M − H]$^−$ | 198-200 | 0.20 (C) |

-continued

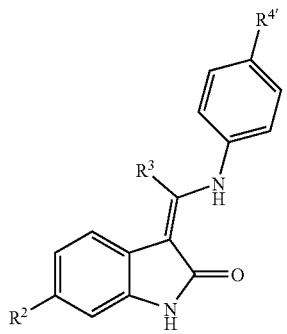

(I-20a)

| Example | $R^2$ | $R^3$ | $R^{4'}$ | educt | empirical formula | mass spectrum | m.p. [°C.] | $R_f$ value* |
|---|---|---|---|---|---|---|---|---|
| 20.4 | —F | 4-(tert-butyl)phenylacetic acid | —CH$_2$—NMe$_2$ | 9.10 | C$_{26}$H$_{24}$FN$_3$O$_3$ | 444 [M − H]$^-$ | 212-216 | 0.30 (D) |
| 20.5 | —F | 4-(tert-butyl)phenylacetic acid | H$_3$C—N(tBu)—C(O)—CH$_2$—N(piperazine)NMe | 9.15 | C$_{31}$H$_{32}$FN$_5$O$_4$ | 558 [M + H]$^+$ | 260-263 | 0.20 (D) |
| 20.6 | —F | 4-(tert-butyl)phenylacetic acid | —N(SO$_2$Me)-(CH$_2$)$_2$—NMe$_2$ | 9.14 | C$_{28}$H$_{29}$FN$_4$O$_5$S | 553 [M + H]$^+$ | 246-249 | 0.30 (D) |
| 20.7 | —F | 3-(4-tert-butylphenyl)propanoic acid | —NMe-(CO)—CH$_3$ | 9.20 | C$_{27}$H$_{24}$FN$_3$O$_4$ | 474 [M + H]$^+$ | 286-290 | 0.60 (E) |

-continued

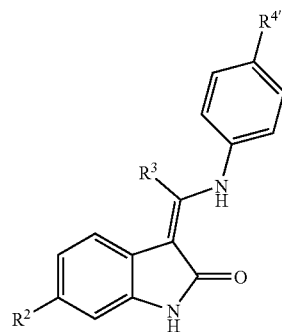

(I-20a)

| Example | R² | R³ | R⁴' | educt | empirical formula | mass spectrum | m.p. [° C.] | R_f value* |
|---|---|---|---|---|---|---|---|---|
| 20.8 | —F | OH, propanoic acid on p-tBu-phenyl | H₃C-N(tBu)-C(O)-CH₂-N(piperazine)NMe | 9.21 | C₃₂H₃₄FN₅O₄ | 570 [M − H]⁻ | 215-222 | 0.20 (D) |
| 20.9 | —F | OH, propanoic acid on p-tBu-phenyl | —N(SO₂Me)-(CH₂)₂—NMe₂ | 9.22 | C₂₉H₃₁FN₄O₅S | 567 [M + H]⁺ | 160-165 | 0.20 (D) |
| 20.10 | —F | OH, propanoic acid on p-tBu-phenyl | —N(COMe)-(CH₂)₃—NMe₂ | 9.23 | C₃₁H₃₃FN₄O₄ | 545 [M + H]⁺ | 153-158 | 0.15 (D) |
| 20.11 | —F | OH, propanoic acid on p-tBu-phenyl | Me-N(CH₂C(Me)₂-)-C(O)-OtBu | 9.24 | C₃₁H₃₂FN₃O₅ | 546 [M + H]⁺ | 215-219 | 0.60 (E) |

-continued

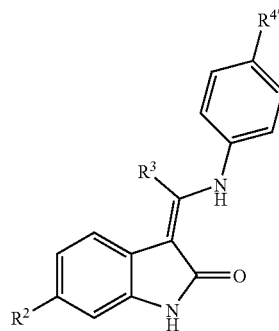
(I-20a)

| Example | R² | R³ | R⁴' | educt | empirical formula | mass spectrum | m.p. [° C.] | R_f value* |
|---|---|---|---|---|---|---|---|---|
| 20.12 | —F | (3-(4-tert-butylphenyl)propanoic acid, OH) | (4-methylpiperazin-1-yl carbonyl isopropyl) | 9.25 | $C_{30}H_{29}FN_4O_4$ | 529 $[M+H]^+$ | 179-186 | 0.25 (E) |
| 20.13 | —F | (3-(4-tert-butylphenyl)propanoic acid, OH) | (2-tert-butyl-1-methylimidazol-1-yl) | 9.26 | $C_{28}H_{23}FN_4O_3$ | 483 $[M+H]^+$ | 264-267 | 0.65 (E) |
| 20.14 | —F | (3-(4-tert-butylphenyl)propanoic acid, OH) | —SO₂Me | 9.27 | $C_{25}H_{21}FN_2O_5S$ | 481 $[M+H]^+$ | 146-155 | 0.70 (E) |
| 20.15 | —F | (2-(3-tert-butylphenyl)acetic acid, OH) | (4-methylpiperazin-1-yl carbonyl isopropyl) | 9.30 | $C_{29}H_{27}FN_4O_4$ | 515 $[M+H]^+$ | 251 | 0.70 (E) |

-continued
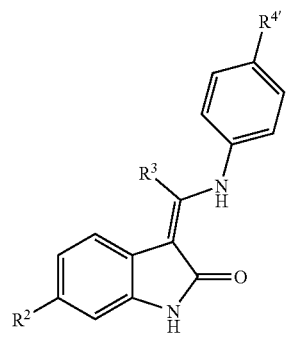
(I-20a)
| Example | R² | R³ | R⁴' | educt | empirical formula | mass spectrum | m.p. [° C.] | $R_f$ value* |
|---|---|---|---|---|---|---|---|---|
| 20.16 | —F | 3-tBu-phenyl-CH(OH)-C(O)- | H₃C-N(tBu)-C(O)-CH₂-N(piperazinyl-NMe) | 9.28 | $C_{31}H_{32}FN_5O_4$ | 558 [M + H]⁺ | 234 | 0.10 (E) |
| 20.17 | —F | 3-tBu-phenyl-CH(OH)-C(O)- | —N(Me)-(CO)—CH₂—NMe₂ | 9.31 | $C_{28}H_{27}FN_4O_4$ | 503 [M + H]⁺ | 203 | 0.60 (E) |
| 20.18 | —F | 3-tBu-phenyl-CH(OH)-C(O)- | —N(Me)-(CO)—(CH₂)₄—NMe₂ | 9.34 | $C_{31}H_{33}FN_4O_4$ | 545 [M + H]⁺ | 251 | n.b. |
| 20.19 | —F | 3-tBu-phenyl-CH(OH)-C(O)- | —H | 9.45 | $C_{23}H_{17}FN_2O_3$ | 387 [M − H]⁺ | 130 | 0.60 (E) |

-continued (I-20a)

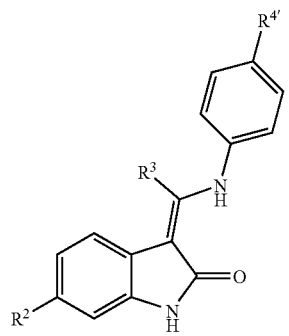

| Example | $R^2$ | $R^3$ | $R^{4'}$ | educt | empirical formula | mass spectrum | m.p. [°C.] | $R_f$ value* |
|---|---|---|---|---|---|---|---|---|
| 20.20 | —F | 3-(HOOC-CH$_2$)-C$_6$H$_4$-C(CH$_3$)$_2$- (OH on acid) | —SO$_2$Me | 9.46 | C$_{24}$H$_{19}$FN$_2$O$_5$S | 467 [M + H]$^+$ | 139 | 0.55 (E) |
| 20.21 | —F | 3-(HOOC-CH$_2$)-C$_6$H$_4$-C(CH$_3$)$_2$- | 2-(1-methylimidazolyl) | 9.47 | C$_{27}$H$_{21}$FN$_4$O$_3$ | 469 [M + H]$^+$ | 157 | 0.35 (E) |
| 20.22 | —F | 3-(HOOC-CH$_2$)-C$_6$H$_4$-C(CH$_3$)$_2$- | —N(SO$_2$Me)- (CH$_2$)—(CO)— NMe$_2$ | 9.48 | C$_{28}$H$_{27}$FN$_4$O$_6$S | 567 [M + H]$^+$ | 183 | 0.55 (E) |
| 20.23 | —F | 4-(HOOC-CH$_2$)-C$_6$H$_4$-C(CH$_3$)$_2$- | —H | 9.35 | C$_{23}$H$_{17}$FN$_2$O$_3$ | 389 [M + H]$^+$ | 237-240 | 0.10 (D) |

-continued

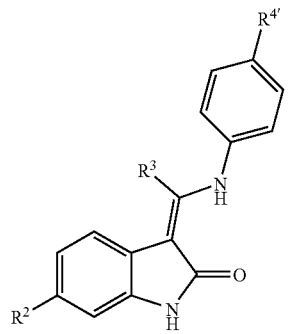

(I-20a)

| Example | R² | R³ | R⁴' | educt | empirical formula | mass spectrum | m.p. [° C.] | R_f value* |
|---|---|---|---|---|---|---|---|---|
| 20.24 | —F | 4-tert-butylphenyl-CH₂-C(=O)-OH | 2-tert-butyl-1-methyl-imidazol-5-yl | 9.36 | C₂₇H₂₁FN₄O₃ | 469 [M + H]⁺ | 259-265 | 0.15 (D) |
| 20.25 | —F | 4-tert-butylphenyl-CH₂-C(=O)-OH | —N(COMe)-(CH₂)₃—NMe₂ | 9.44 | C₃₀H₃₁FN₄O₄ | 531 [M + H]⁺ | 274-278 | 0.15 (D) |
| 20.26 | —F | 4-tert-butylphenyl-CH₂-C(=O)-OH | —N(Me)-(CO)—CH₂—NMe₂ | 9.39 | C₂₈H₂₇FN₄O₄ | 503 [M + H]⁺ | 258-264 | 0.20 (D) |
| 20.27 | —F | 4-tert-butylphenyl-CH₂-C(=O)-OH | 4-methylpiperazinyl-C(=O)-C(Me)₂- | 9.37 | C₂₉H₂₇FN₄O₄ | 515 [M + H]⁺ | 279-282 | 0.15 (D) |

-continued

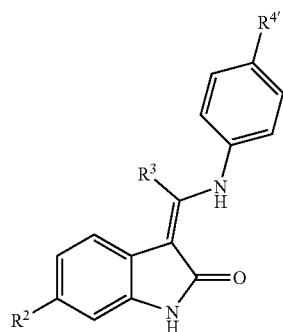

(I-20a)

| Example | $R^2$ | $R^3$ | $R^{4'}$ | educt | empirical formula | mass spectrum | m.p. [° C.] | $R_f$ value* |
|---|---|---|---|---|---|---|---|---|
| 20.28 | —F | 4-(carboxymethyl)phenyl with C(=O)OH | —SO$_2$Me | 9.42 | $C_{24}H_{19}FN_2O_5S$ | 467 [M + H]$^+$ | 260-266 | 0.35 (F) |
| 20.29 | —F | 4-(carboxymethyl)phenyl with C(=O)OH | —N(COMe)-CH$_3$ | 9.40 | $C_{26}H_{22}FN_3O_4$ | 460 [M + H]$^+$ | 290-294 | 0.30 (F) |
| 20.30 | —F | 4-(carboxymethyl)phenyl with C(=O)OH | —N(SO$_2$Me)-CH$_2$—(CO)—NMe$_2$ | 9.38 | $C_{28}H_{27}FN_4O_6S$ | 567 [M + H]$^+$ | 238-242 | 0.30 (F) |
| 20.31 | —F | 4-(carboxymethyl)phenyl with C(=O)OH | —N(Me)-(CO)—(CH$_2$)$_2$—NMe$_2$ | 9.41 | $C_{29}H_{29}FN_4O_4$ | 517 [M + H]$^+$ | 250-255 | 0.35 (F) |

-continued
(I-20a)
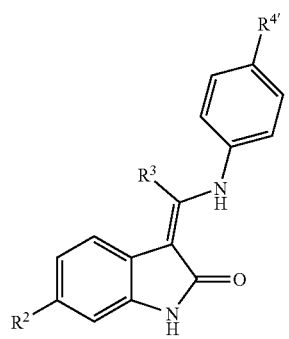
| Example | R² | R³ | R⁴' | educt | empirical formula | mass spectrum | m.p. [° C.] | R_f value* |
|---|---|---|---|---|---|---|---|---|
| 20.32 | —F | 4-(HOOC-CH₂-)phenyl | —N(Me)-(CO)—(CH₂)₃—NMe₂ | 9.43 | $C_{30}H_{31}FN_4O_4$ | 531 [M + H]⁺ | 184-190 | 0.25 (F) |
| 20.33 | —F | 3-(HOOC-CH₂CH₂-)phenyl | H₃C-N(tBu)-CO-CH₂-N(piperazine)NMe | 9.51 | $C_{32}H_{34}FN_5O_4$ | 572 [M − H]⁻ | 170-175 | 0.40 (C) |
| 20.34 | —F | 3-(HOOC-CH₂-)phenyl | —N(SO₂Me)-(CH₂)₂—NMe₂ | 9.29 | $C_{28}H_{29}FN_4O_5S$ | 553 [M + H]⁺ | 180 | 0.60 (C) |
| 20.35 | —F | 3-(HOOC-CH₂CH₂-)phenyl | —N(SO₂Me)-(CH₂)₂—NMe₂ | 9.52 | $C_{29}H_{31}FN_4O_5S$ | 567 [M + H]⁺ | 196-199 | 0.30 (C) |

-continued
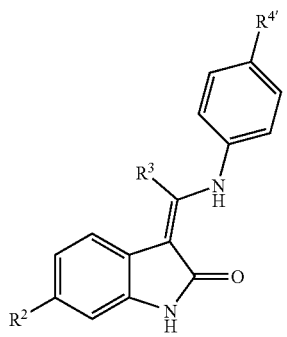
(I-20a)
| Example | $R^2$ | $R^3$ | $R^{4'}$ | educt | empirical formula | mass spectrum | m.p. [° C.] | $R_f$ value* |
|---|---|---|---|---|---|---|---|---|
| 20.36 | —F | 3-(2-carboxyethyl)phenyl | —N(Me)-(CO)—CH$_2$—NMe$_2$ | 9.53 | $C_{29}H_{29}FN_4O_4$ | 517 [M + H]$^+$ | 150 | 0.20 (C) |
| 20.37 | —F | 3-(2-carboxyethyl)phenyl | —N(COMe)-(CH$_2$)$_3$—NMe$_2$ | 9.54 | $C_{31}H_{33}FN_4O_4$ | 545 [M + H]$^+$ | 206-210 | 0.30 (A) |
| 20.38 | —F | 4-(2-carboxyethyl)phenyl | —N(Me)-(CO)—CH$_2$—NMe$_2$ | 9.62 | $C_{29}H_{29}FN_4O_4$ | 517 [M + H]$^+$ | 231-236 | 0.60 (A) |
| 20.39 | —F | 4-(2-carboxyethyl)phenyl | —(CH$_2$)$_2$—NMe$_2$ | 9.60 | $C_{28}H_{28}FN_3O_3$ | 474 [M + H]$^+$ | 218-222 | 0.50 (A) |

-continued
(I-20a)
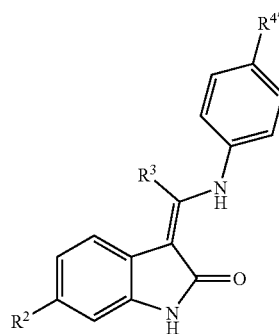
| Example | $R^2$ | $R^3$ | $R^{4'}$ | educt | empirical formula | mass spectrum | m.p. [° C.] | $R_f$ value* |
|---|---|---|---|---|---|---|---|---|
| 20.40 | —F | OH, 4-(CH₂CH₂COOH)phenyl | —N(Me)-(CO)—(CH₂)₂—NMe₂ | 9.61 | $C_{30}H_{31}FN_4O_4$ | 531 [M + H]⁺ | 215-218 | 0.50 (A) |
| 20.41 | —F | 3-(CH₂CH₂COOH)phenyl | —(CH₂)₂—NMe₂ | 9.63 | $C_{28}H_{28}FN_3O_3$ | 474 [M + H]⁺ | 172-177 | 0.15 (G) |
| 20.42 | —F | OH, 4-(CH₂CH₂COOH)phenyl | —N(COMe)-(CH₂)₂—NMe₂ | 9.64 | $C_{30}H_{31}FN_4O_4$ | 531 [M + H]⁺ | 230-234 | 0.50 (A) |
| 20.43 | —F | 3-(CH₂CH₂COOH)phenyl | —N(Me)-(CO)—(CH₂)₃—NMe₂ | 9.65 | $C_{31}H_{33}FN_4O_4$ | 545 [M + H]⁺ | 170-175 | 0.30 (E) |

-continued
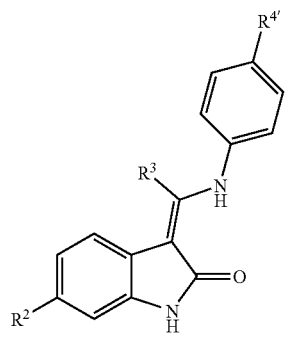
(I-20a)
| Example | R² | R³ | R⁴' | educt | empirical formula | mass spectrum | m.p. [° C.] | R_f value* |
|---|---|---|---|---|---|---|---|---|
| 20.44 | —F | 3-(tert-butyl)phenyl-CH₂CH₂-C(O)OH | —N(Me)-(CO)—(CH₂)₄—NMe₂ | 9.66 | C₃₂H₃₅FN₄O₄ | 559 [M + H]⁺ | 142-146 | 0.10 (G) |
| 20.45 | —F | 3-(tert-butyl)phenyl-CH₂CH₂-C(O)OH | 1-methyl-2-imidazolyl | 9.67 | C₂₈H₂₃FN₄O₃ | 483 [M + H]⁺ | 262-269 | 0.20 (E) |
| 20.46 | —F | 4-(tert-butyl)phenyl-CH₂CH₂-C(O)OH | —N(Me)-(CO)—(CH₂)₄—NMe₂ | 9.68 | C₃₂H₃₅FN₄O₄ | 559 [M + H]⁺ | 234-236 | 0.30 (A) |
| 20.47 | —F | 4-(tert-butyl)phenyl-CH₂CH₂-C(O)OH | —H | 9.69 | C₂₄H₁₉FN₂O₃ | 403 [M + H]⁺ | 231-233 | 0.20 (A) |

-continued
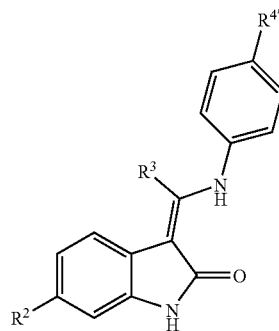
(I-20a)
| Example | $R^2$ | $R^3$ | $R^{4'}$ | educt | empirical formula | mass spectrum | m.p. [° C.] | $R_f$ value* |
|---|---|---|---|---|---|---|---|---|
| 20.48 | —F | 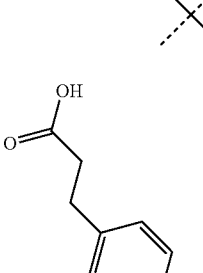 | 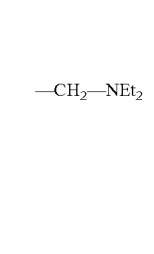 | 9.70 | $C_{29}H_{28}FN_3O_3$ | 486 $[M + H]^+$ | 205-210 | 0.10 (E) |
| 20.49 | —F | 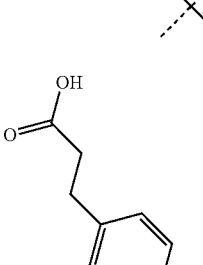 | —CH$_2$—NEt$_2$ | 9.71 | $C_{29}H_{30}FN_3O_3$ | 488 $[M + H]^+$ | 145-150 | 0.15 (E) |
| 20.50 | —F | 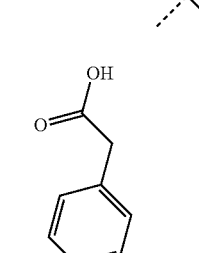 | —CH$_2$—NH$_2$ | 17.23 | $C_{25}H_{22}FN_3O_3$ | 430 $[M + H]^-$ | 280-285 | 0.05 (H) |
| 20.51 | —F | 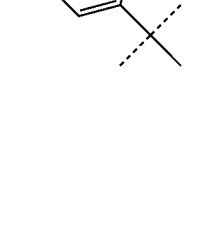 | —(CH$_2$)$_2$—NMe$_2$ | 9.73 | $C_{27}H_{26}FN_3O_3$ | 460 $[M + H]^+$ | 273-276 | 0.15 (E) |

-continued
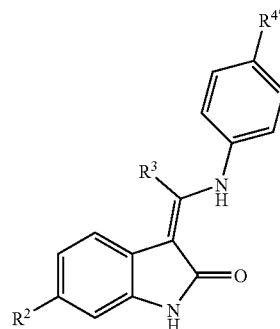
(I-20a)
| Example | $R^2$ | $R^3$ | $R^{4'}$ | educt | empirical formula | mass spectrum | m.p. [°C.] | $R_f$ value* |
|---|---|---|---|---|---|---|---|---|
| 20.52 | —F | 4-(HOOC-CH$_2$-)-C$_6$H$_4$- | —(CH$_2$)$_2$—NMe$_2$ | 9.74 | C$_{27}$H$_{26}$FN$_3$O$_3$ | 460 [M + H]$^+$ | 230-235 | 0.05 (E) |
| 20.53 | —Cl | 4-(HOOC-CH$_2$CH$_2$-)-C$_6$H$_4$- | —(CH$_2$)$_2$—NMe$_2$ | 9.76 | C$_{28}$H$_{28}$ClN$_3$O$_3$ | 490/492 [M + H]$^+$ | 255-258 | 0.50 (A) |
| 20.54 | —Cl | 4-(HOOC-CH$_2$CH$_2$-)-C$_6$H$_4$- | 1-methyl-imidazol-2-yl | 9.77 | C$_{28}$H$_{23}$ClN$_4$O$_3$ | 499/501 [M + H]$^+$ | 296-300 | 0.50 (A) |
| 20.55 | —Cl | 4-(HOOC-CH$_2$CH$_2$-)-C$_6$H$_4$- | —CH$_2$—NMe$_2$ | 9.78 | C$_{27}$H$_{26}$ClN$_3$O$_3$ | 476/478 [M + H]$^+$ | 228-230 | 0.50 (A) |

-continued
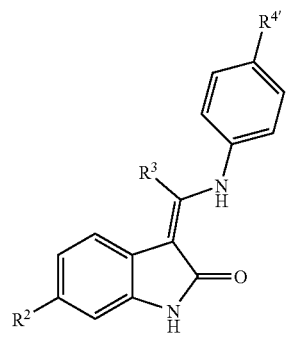
(I-20a)
| Example | R² | R³ | R⁴' | educt | empirical formula | mass spectrum | m.p. [° C.] | R_f value* |
|---|---|---|---|---|---|---|---|---|
| 20.56 | —F | 3-(HOOC-CH₂-CH₂-)phenyl | 4-methylpiperazinyl-CH₂-C(CH₃)₂- | 9.80 | C₃₀H₃₁FN₄O₃ | 515 [M + H]⁺ | 210-215 | 0.40 (A) |
| 20.57 | —F | 3-(HOOC-CH₂-CH₂-)phenyl | imidazolyl-CH₂-C(CH₃)₂- | 9.81 | C₂₈H₂₃FN₄O₃ | 483 [M + H]⁺ | 240-245 | 0.50 (A) |
| 20.58 | —F | 3-(HOOC-CH₂-CH₂-)phenyl | —CH₂—NMe—(CH₂)₂—NMe₂ | 9.85 | C₃₀H₃₃FN₄O₃ | 517 [M + H]⁺ | n.d. | 0.30 (I) |
| 20.59 | —F | 4-(HOOC-CH₂-CH₂-)phenyl | 4-methylpiperazinyl-CH₂-C(CH₃)₂- | 9.82 | C₃₀H₃₁FN₄O₃ | 515 [M + H]⁺ | 275 | 0.35 (A) |

-continued
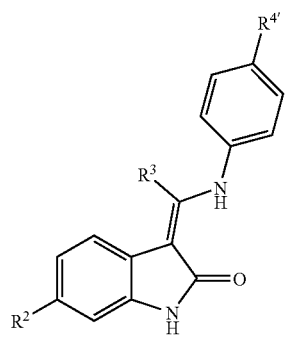
(I-20a)
| Example | $R^2$ | $R^3$ | $R^{4'}$ | educt | empirical formula | mass spectrum | m.p. [° C.] | $R_f$ value* |
|---|---|---|---|---|---|---|---|---|
| 20.60 | —F | 4-(HOOC-CH2CH2)-C6H4- | imidazol-1-yl-CH2-C(CH3)2- | 9.83 | $C_{28}H_{23}FN_4O_3$ | 483 [M + H]$^+$ | 280 | 0.55 (A) |
| 20.61 | —Cl | 4-(HOOC-CH2CH2)-C6H4- | pyrrolidin-1-yl-CH2-C(CH3)2- | 9.86 | $C_{29}H_{28}ClN_3O_3$ | 502/504 [M + H]$^+$ | 260-266 | 0.50 (A) |
| 20.62 | —F | 4-(HOOC-CH2CH2)-C6H4- | —CH2—NMe-(CH2)2—NMe2 | 9.84 | $C_{30}H_{33}FN_4O_3$ | 517 [M + H]$^+$ | n.d. | 0.05 (E) |
| 20.63 | —F | 3-(HOOC-CH2CH2)-C6H4- | —H | 9.87 | $C_{24}H_{19}FN_2O_3$ | 403 [M + H]$^+$ | 110-112 | 0.60 (K) |

-continued
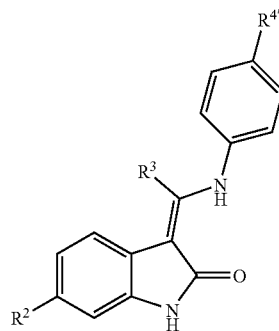
(I-20a)
| Example | R² | R³ | R⁴' | educt | empirical formula | mass spectrum | m.p. [° C.] | R_f value* |
|---|---|---|---|---|---|---|---|---|
| 20.64 | —F | HO-C(=O)-CH₂CH₂-(3-tBu-phenyl) | —CH₂—NH₂ | 17.24 | $C_{25}H_{22}FN_3O_3$ | 432 [M + H]⁺ | 260-263 | 0.60 (A) |
| 20.65 | —F | HO-C(=O)-CH₂CH₂-(3-tBu-phenyl) | —CH₂—NHMe | 17.25 | $C_{26}H_{24}FN_3O_3$ | 446 [M + H]⁺ | 265-270 | 0.60 (A) |
| 20.66 | —F | HO-C(=O)-CH₂-O-(3-tBu-phenyl) | —CH₂—NMe₂ | 9.90 | $C_{26}H_{24}FN_3O_4$ | 462 [M + H]⁺ | 250 | 0.10 (M) |
| 20.67 | —F | HO-C(=O)-CH₂-O-(4-tBu-phenyl) | —CH₂—NMe₂ | 9.91 | $C_{26}H_{24}FN_3O_4$ | 462 [M + H]⁺ | 247 | 0.15 (M) |

-continued

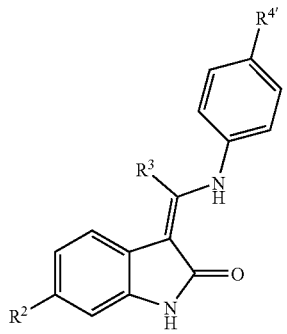

(I-20a)

| Example | R² | R³ | R⁴' | educt | empirical formula | mass spectrum | m.p. [° C.] | R_f value* |
|---|---|---|---|---|---|---|---|---|
| 20.68 | —Br | 3-(4-substituted-phenyl)propanoic acid with OH | pyrrolidinylmethyl-neopentyl | 9.93 | $C_{29}H_{28}BrN_3O_3$ | 546/548 $[M + H]^+$ | 290-293 | 0.30 (E) |
| 20.69 | —Br | 3-(4-substituted-phenyl)propanoic acid with OH | —CH₂—NMe₂ | 9.94 | $C_{27}H_{26}BrN_3O_3$ | 520/522 $[M + H]^+$ | 243-246 | 0.25 (E) |
| 20.70 | —Br | 3-(4-substituted-phenyl)propanoic acid with OH | —CH₂—NEt₂ | 9.95 | $C_{29}H_{30}BrN_3O_3$ | 548/550 $[M + H]^+$ | 252-255 | 0.35 (E) |

*Eluant mixtures:
(A): Reversed phase RP8, methanol/saline solution (5%) = 4:1
(B): silica gel, methylene chloride/methanol = 8:2
(C): silica gel, methylene chloride/methanol = 5:1
(D): Reversed phase RP8, methanol/saline solution (5%) = 3:2
(E): silica gel, methylene chloride/methanol = 9:1
(F): Reversed phase RP8, methanol/saline solution (5%) = 7:3
(G): silica gel, methylene chloride/methanol/ammonia = 9:1:0,1
(H): aluminium oxide, methylene chloride/methanol = 19:1
(I): Reversed Phase RP8, methanol/saline solution (5%) = 4:2
(K): silica gel, petroleum ether/ethyl acetate = 1:1
(M): silica gel, methylene chloride/methanol = 4:1

The following compounds of general formula I-20b are prepared analogously to Example 20.0:

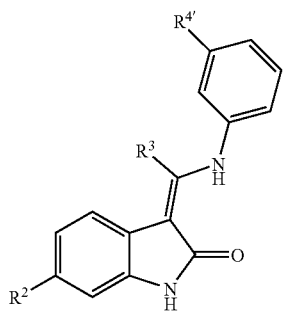

(I-20b)

| Example | $R^2$ | $R^3$ | $R^{4'}$ | educt | empirical formula | mass spectrum | m.p. [°C.] | $R_f$ value* |
|---|---|---|---|---|---|---|---|---|
| 20.71 | —F | OH (3-(4-tert-butylphenyl)propanoic acid) | —CH$_2$—NMe$_2$ | 9.96 | C$_{27}$H$_{26}$FN$_3$O$_3$ | 460 [M + H]$^+$ | 150 | 0.20 (A) |
| 20.72 | —F | OH (3-(3-tert-butylphenyl)propanoic acid) | —CH$_2$—NMe$_2$ | 9.97 | C$_{27}$H$_{26}$FN$_3$O$_3$ | 460 [M + H]$^+$ | 105-109 | 0.30 (B) |
| 20.73 | —Cl | OH (3-(4-tert-butylphenyl)propanoic acid) | —CH$_2$—NMe$_2$ | 9.98 | C$_{27}$H$_{26}$ClN$_3$O$_3$ | 476/478 [M + H]$^+$ | 230-235 | 0.50 (C) |

*Eluant mixtures:
(A): silica gel, methylene chloride/methanol = 5:1
(B): silica gel, methylene chloride/methanol = 9:1
(C): Reversed Phase RP8, methanol/saline solution (5%) = 4:1

EXAMPLE 21.0

3-Z-[1-(4-dimethylaminomethyl-anilino)-1-(3-(2-carbamoyl-ethyl)-phenyl)-methylene]-6-chloro-2-indolinone 480 mg of 3-Z-[1-(4-dimethylaminomethyl-anilino)-1-(3-(2-carboxyethyl)-phenyl)-methylene]-6-chloro-2-indolinone (educt 20.0), 350 mg TBTU, 150 mg HOBt and 420 ml triethylamine are dissolved in 10 ml of dimethylformamide and 620 mg of N-hydroxysuccinimide-ammonium salt are added. The mixture is stirred for 20 hours at ambient temperature. After the solvent has been eliminated the residue is suspended in a little ethyl acetate and water, filtered off and washed with water. The residue is purified through an aluminium oxide column (activity 2-3) with methylene chloride/ethanol 20:1 as eluant. The product is recrystallised from diethyl ether and dried in vacuo at 100° C.

Yield: 370 mg (78% of theory), $R_f$ value: 0.40 (aluminium oxide, methylene chloride/ethanol=20:1) M.p. 222-225° C. $C_{27}H_{27}ClN_4O_2$ Mass spectrum: m/z=475/477 [M+H]$^+$ The following compounds of general formula I-21 are prepared analogously to Example 21.0:

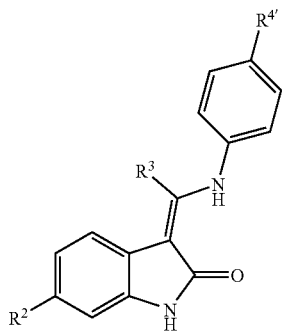
(I-21)

| Example | $R^2$ | $R^3$ | $R^{4'}$ | educt | empirical formula | mass spectrum | m.p. [° C.] | $R_f$ value* |
|---|---|---|---|---|---|---|---|---|
| 21.1 | —Cl | (3-phenyl)-CH₂CH₂-C(O)-NHCH₃ | —CH₂—NMe₂ | 20.0** | $C_{28}H_{29}ClN_4O_2$ | 489/491 [M + H]$^+$ | 223-225 | 0.50 (A) |
| 21.2 | —F | (4-phenyl)-CH₂CH₂-C(O)-NHCH₃ | —CH₂—NMe₂ | 20.1** | $C_{28}H_{29}FN_4O_2$ | 473 [M + H]$^+$ | 148-150 | 0.40 (B) |
| 21.3 | —F | (3-phenyl)-CH₂-C(O)-NMe₂ | —CH₂—NMe₂ | 20.2*** | $C_{28}H_{29}FN_4O_2$ | 473 [M + H]$^+$ | 98-103 | 0.30 (C) |

-continued
(I-21)
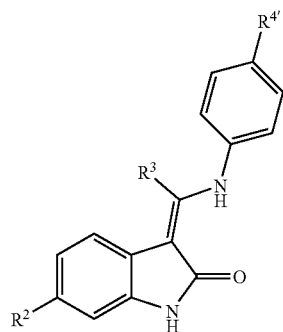
| Example | R² | R³ | R⁴' | educt | empirical formula | mass spectrum | m.p. [° C.] | R_f value* |
|---|---|---|---|---|---|---|---|---|
| 21.4 | —F | O=C(NH₂)–CH₂CH₂–C₆H₄–(m) | —CH₂—NMe₂ | 20.3 | C₂₇H₂₇FN₄O₂ | 459 [M + H]⁺ | 223-225 | 0.50 (A) |
| 21.5 | —F | O=C(NHMe)–CH₂CH₂–C₆H₄–(m) | —CH₂—NMe₂ | 20.3** | C₂₈H₂₉FN₄O₂ | 473 [M + H]⁺ | 210-213 | 0.70 (A) |
| 21.6 | —F | O=C(NMe₂)–CH₂CH₂–C₆H₄–(m) | —CH₂—NMe₂ | 20.3*** | C₂₉H₃₁FN₄O₂ | 487 [M + H]⁺ | 213-215 | 0.80 (A) |
| 21.7 | —F | O=C(NMe₂)–CH₂–C₆H₄–(m) | —CH₂—NMe₂ | 20.2 | C₂₆H₂₅FN₄O₂ | 443 [M − H]⁻ | 115-120 | 0.25 (C) |

-continued
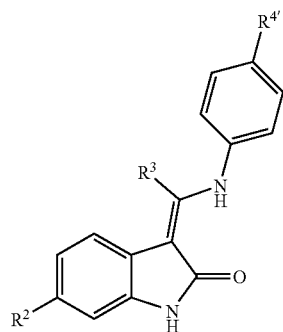
(I-21)
| Example | $R^2$ | $R^3$ | $R^{4'}$ | educt | empirical formula | mass spectrum | m.p. [° C.] | $R_f$ value* |
|---|---|---|---|---|---|---|---|---|
| 21.8 | —F | NHMe, O, phenyl with t-Bu (meta) | —CH$_2$—NMe$_2$ | 20.2** | $C_{27}H_{27}FN_4O_2$ | 457 [M − H]$^-$ | 222-225 | 0.25 (C) |
| 21.9 | —F | O, NH$_2$, phenyl with t-Bu (para) | —CH$_2$—NMe$_2$ | 20.4 | $C_{26}H_{25}FN_4O_2$ | 443 [M − H]$^-$ | 143-146 | 0.40 (D) |
| 21.10 | —F | NMe$_2$, O, phenyl-CH$_2$ with t-Bu (para) | —CH$_2$—NMe$_2$ | 20.1*** | $C_{29}H_{31}FN_4O_2$ | 487 [M + H]$^+$ | 198-200 | 0.60 (B) |
| 21.11 | —F | Me-piperazine-C(O)-CH$_2$-phenyl-t-Bu | —CH$_2$—NMe$_2$ | 20.1**** | $C_{32}H_{36}FN_5O_2$ | 542 [M + H]$^+$ | 175 | 0.60 (B) |

-continued
(I-21)
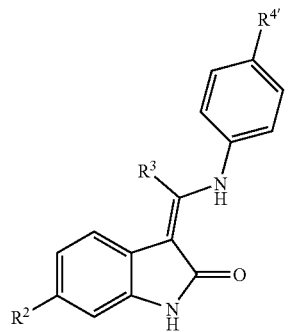
| Example | R² | R³ | R⁴' | educt | empirical formula | mass spectrum | m.p. [° C.] | R_f value* |
|---|---|---|---|---|---|---|---|---|
| 21.12 | —F | NH2-phenyl, tBu-like attachment) O=C(NH2)CH2-C6H4- | H3C\N(tBu)C(O)CH2-N(piperazine)-NMe | 20.5 | C₃₁H₃₃FN₆O₃ | 557 [M + H]⁺ | 150-156 | 0.40 (E) |
| 21.13 | —F | O=C(NH2)CH2-C6H4- | —N(SO₂Me)-(CH₂)₂—NMe₂ | 20.6 | C₂₈H₃₀FN₅O₄S | 552 [M + H]⁺ | 197-199 | 0.50 (D) |
| 21.14 | —F | O=C(NMe2)CH2-C6H4- | —CH₂—NMe₂ | 20.4*** | C₂₈H₂₉FN₄O₂ | 473 [M + H]⁺ | 147-152 | 0.35 (D) |
| 21.15 | —F | O=C(NHMe)CH2-C6H4- | —CH₂—NMe₂ | 20.4** | C₂₇H₂₇FN₄O₂ | 459 [M + H]⁺ | 208-214 | 0.35 (D) |

-continued
(I-21)
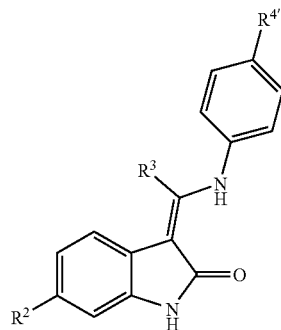
| Example | R² | R³ | R⁴' | educt | empirical formula | mass spectrum | m.p. [° C.] | R_f value* |
|---|---|---|---|---|---|---|---|---|
| 21.16 | —F | O=C(NHMe)-CH₂-C₆H₄-C(CH₃)₃ (4-tBu-benzyl C(O)NHMe) | —N(SO₂Me)-(CH₂)₂—NMe₂ | 20.6** | C₂₉H₃₂FN₅O₄S | 566 [M + H]⁺ | 218-222 | 0.70 (F) |
| 21.17 | —F | O=C(NMe₂)-CH₂-C₆H₄-C(CH₃)₃ | —N(SO₂Me)-(CH₂)₂—NMe₂ | 20.6*** | C₃₀H₃₄FN₅O₄S | 580 [M + H]⁺ | 199-205 | 0.40 (C) |
| 21.18 | —F | O=C(NHMe)-CH₂-C₆H₄-C(CH₃)₃ | —N(Me)-C(O)-CH₂-N(piperazinyl-NMe) | 20.5** | C₃₂H₃₅FN₆O₃ | 571 [M + H]⁺ | 155-160 | 0.20 (C) |
| 21.19 | —F | O=C(NHCH₃)-CH₂CH₂-C₆H₄-C(CH₃)₃ | —N(Me)-(CO)—CH₃ | 20.7** | C₂₈H₂₇FN₄O₃ | 487 [M + H]⁺ | 137-145 | 0.50 (C) |

-continued
(I-21)
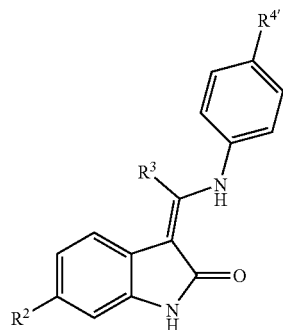
| Example | R² | R³ | R⁴' | educt | empirical formula | mass spectrum | m.p. [° C.] | R_f value* |
|---|---|---|---|---|---|---|---|---|
| 21.20 | —F | NHCH₃ | | 20.8** | C₃₃H₃₇FN₆O₃ | 585 [M + H]⁺ | 211-219 | 0.40 (C) |
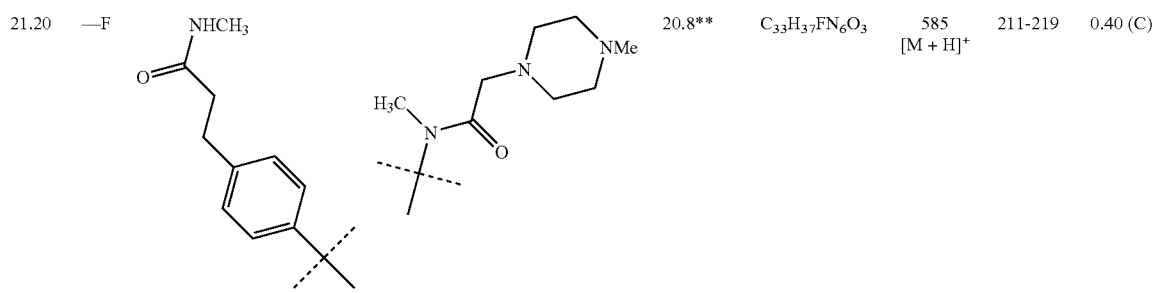
| 21.21 | —F | NHCH₃ | —N(SO₂Me)-(CH₂)₂—NMe₂ | 20.9** | C₃₀H₃₄FN₅O₄S | 578 [M − H]⁻ | 192-200 | 0.50 (C) |
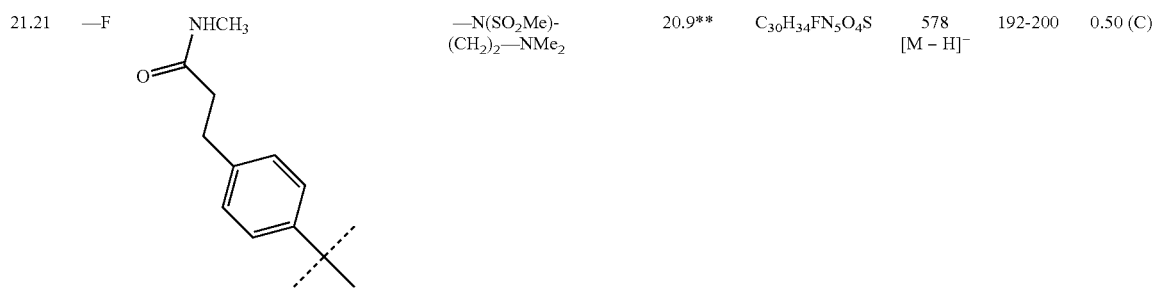
| 21.22 | —F | NHCH₃ | | 20.11** | C₃₂H₃₅FN₄O₄ | 559 [M + H]⁺ | 180-187 | 0.50 (C) |
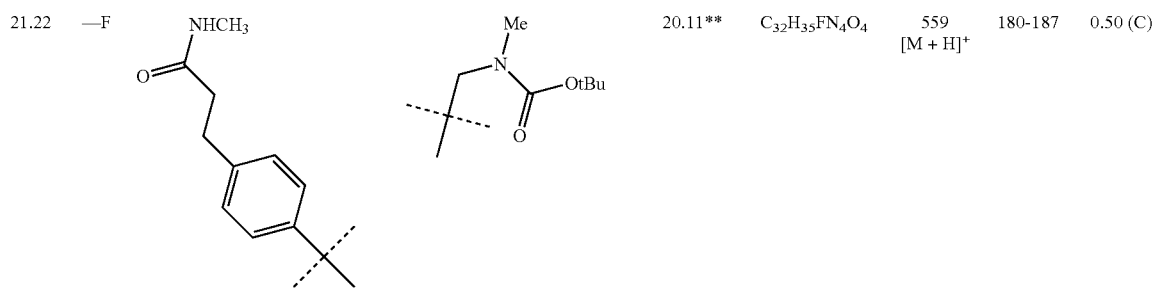

-continued
(I-21)
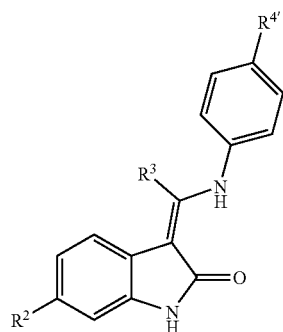
| Example | R² | R³ | R⁴' | educt | empirical formula | mass spectrum | m.p. [° C.] | R_f value* |
|---|---|---|---|---|---|---|---|---|
| 21.23 | —F | 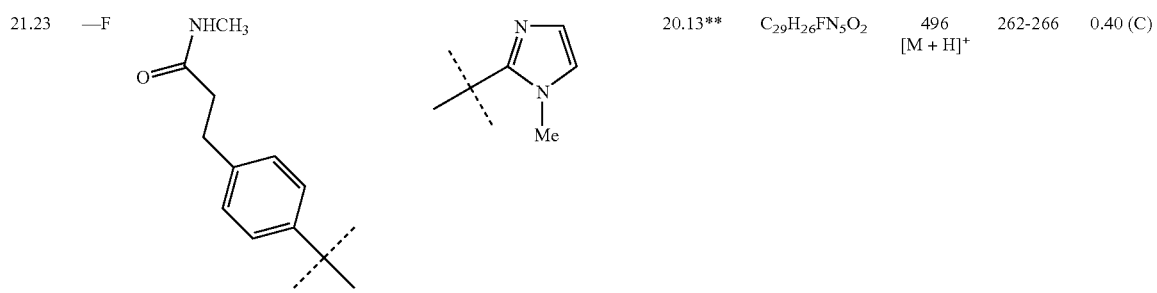 | | 20.13** | $C_{29}H_{26}FN_5O_2$ | 496 [M + H]⁺ | 262-266 | 0.40 (C) |
| 21.24 | —F | 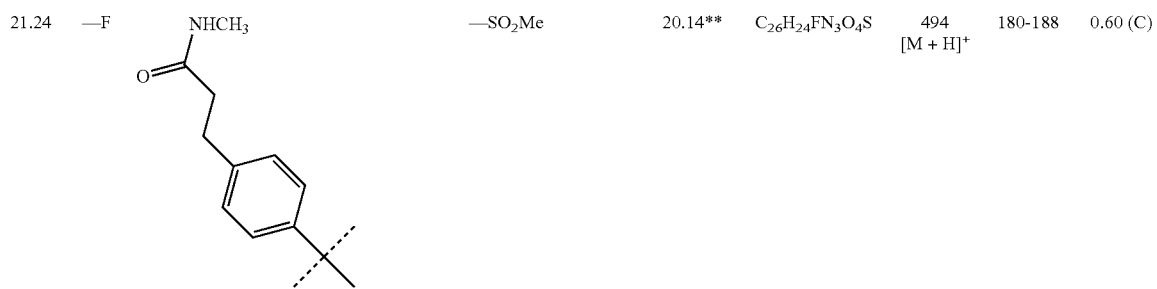 | —SO₂Me | 20.14** | $C_{26}H_{24}FN_3O_4S$ | 494 [M + H]⁺ | 180-188 | 0.60 (C) |
| 21.25 | —F | 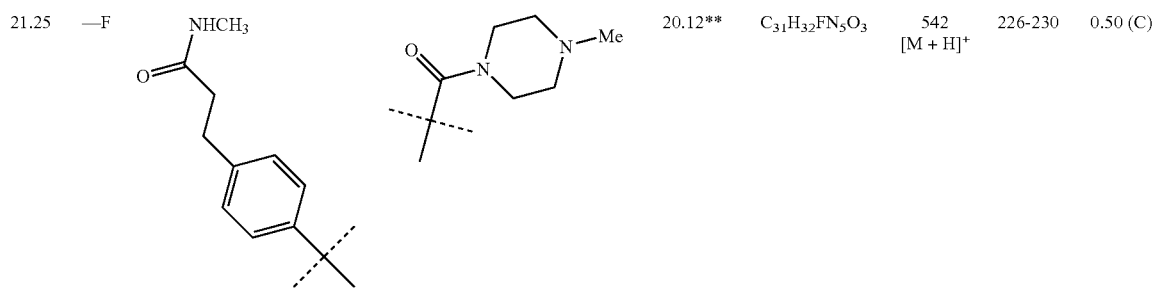 | | 20.12** | $C_{31}H_{32}FN_5O_3$ | 542 [M + H]⁺ | 226-230 | 0.50 (C) |

-continued

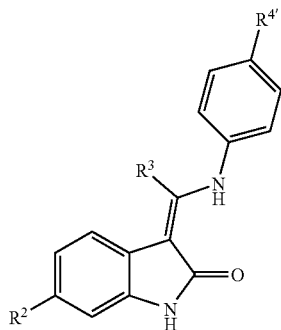

(I-21)

| Example | R² | R³ | R⁴' | educt | empirical formula | mass spectrum | m.p. [° C.] | R_f value* |
|---|---|---|---|---|---|---|---|---|
| 21.26 | —F | (see structure) | (see structure) | 20.16** | $C_{32}H_{35}FN_6O_3$ | 571 [M + H]⁺ | 213 | 0.10 (G) |
| 21.27 | —F | (see structure) | (see structure) | 20.15** | $C_{30}H_{30}FN_5O_3$ | 528 [M + H]⁺ | 245 | 0.40 (G) |

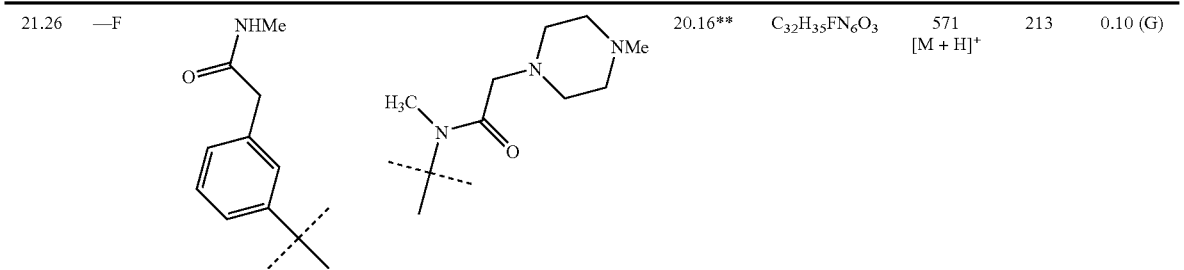

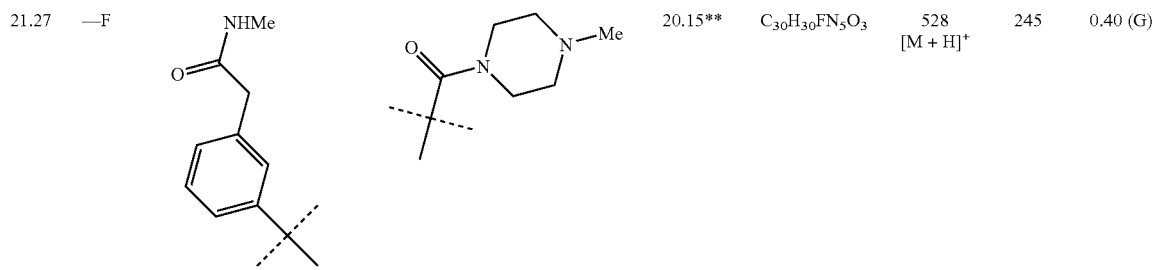

*Eluant mixtures:
(A): silica gel, methylene chloride/methanol/ammonia = 5:1:0.01
(B): aluminium oxide, methylene chloride/ethanol = 20:1
(C): silica gel, methylene chloride/methanol/ammonia = 9:1:0.1
(D): silica gel, methylene chloride/methanol/ammonia = 6:1:0.1
(E): silica gel, methylene chloride/methanol/ammonia = 5:1:0.1
(F): silica gel, methylene chloride/methanol/ammonia = 7:1:0.1
(G): silica gel, methylene chloride/methanol = 9:1
**with methylammonium chloride as base equivalent
***with dimethylammonium chloride as base equivalent
****with piperidine hydrochloride as base equivalent

EXAMPLE 22.0

3-Z-[1-(4-(4-methyl-piperazin-1-yl-methyl)-anilino)-1-phenyl-methylene]-6-chloro-1,3-dihydro-indol-2-thione 460 mg of 3-Z-[1-(4-(4-methyl-piperazin-1-yl-methyl)-anilino)-1-phenyl-methylene]-6-chloro-2-indolinone (educt 1.35) are dissolved in 5 ml of pyridine and 220 mg of phosphorus pentasulphide are added. The mixture is stirred for 2 hours at 120° C. After cooling it is diluted with water and 0.5 ml of concentrated ammonia is added. The precipitate formed is suction filtered and purified through a silica gel column with methylene chloride/methanol 9:1 as eluant. The product is recrystallised from petroleum ether and dried in vacuo at 100° C.

Yield: 300 mg (63% of theory), $R_f$ value: 0.50 (silica gel, methylene chloride/methanol=9:1) M.p. 250-252° C. $C_{27}H_{27}ClN_4S$ Mass spectrum: m/z=475/477 $[M+H]^+$

EXAMPLE 23.0

3-Z-[1-(4-(N-acetylaminomethylcarbonyl-N-methyl-amino)-anilino)-1-phenyl-methylene]-6-chloro-2-indolinone 61 mg of 3-Z-[1-(4-(N-aminomethylcarbonyl-N-methyl-amino)-anilino)-1-phenyl-methylene]-6-chloro-2-indolinone (educt 18.0) are dissolved in 3 ml acetic acid and 0.1 ml acetic anhydride are added. The mixture is stirred for 1.5 hours at ambient temperature. After this time the solvent is eliminated, the residue is suspended in a little water and suction filtered. The product is dried in vacuo at 100° C.

Yield: 60 mg (90% of theory), $R_f$ value: 0.50 (silica gel, methylene chloride/methanol=9:1) M.p. 291-292° C. $C_{26}H_{23}ClN_4O_3$ Mass spectrum: m/z=497/499 $[M+Na]^+$ The following compounds of general formula I-23 are prepared analogously to Example 23.0:

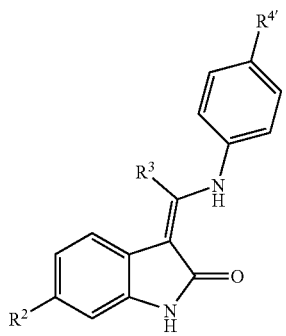

(I-23)

| Example | $R^2$ | $R^3$ | $R^{4'}$ | educt | empirical formula | mass spectrum | m.p. [° C.] | $R_f$ value* |
|---------|-------|-------|----------|-------|-------------------|---------------|-------------|--------------|
| 23.1 | —Cl | | —N(COMe)-(CH$_2$)$_2$—NMe$_2$ | 13.3 | $C_{29}H_{30}ClN_5O_3$ | 530/532 $[M - H]^-$ | 187-188 | 0.15 (A) |
| 23.2 | —Cl | | —N(Me)-(CO)—CH$_2$—NMe$_2$ | 13.1 | $C_{28}H_{28}ClN_5O_3$ | 518/520 $[M + H]^+$ | 249-250 | 0.15 (A) |
| 23.3 | —Cl | | | 13.2 | $C_{31}H_{33}ClN_6O_3$ | 571/573 $[M - H]^-$ | 168-170 | 0.10 (A) |

-continued
(I-23)
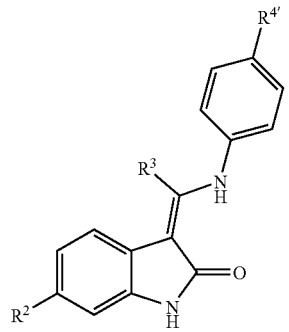
| Example | R² | R³ | R⁴' | educt | empirical formula | mass spectrum | m.p. [° C.] | $R_f$ value* |
|---|---|---|---|---|---|---|---|---|
| 23.4 | —Cl | (acetamido-4-tert-butylphenyl) | (1-methylpiperazinyl carbonyl isopropyl) | 13.4 | $C_{29}H_{28}ClN_5O_3$ | 528/530 [M − H]⁻ | 160 | 0.15 (A) |
| 23.5 | —Cl | (acetamido-4-tert-butylphenyl) | —CH₂—NMe₂ | 13.0 | $C_{26}H_{25}ClN_4O_2$ | 459/461 [M − H]⁻ | 158-159 | 0.25 (A) |
| 23.6 | —Cl | (4-tert-butylbenzyl acetamido) | —CH₂—NMe₂ | 14.0 | $C_{27}H_{27}ClN_4O_2$ | 473/475 [M − H]⁻ | 219-220 | 0.30 (B) |

-continued
(I-23)
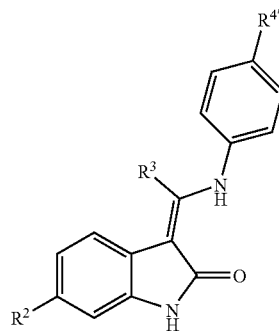
| Example | R² | R³ | R⁴' | educt | empirical formula | mass spectrum | m.p. [° C.] | R_f value* |
|---|---|---|---|---|---|---|---|---|
| 23.7 | —Cl | 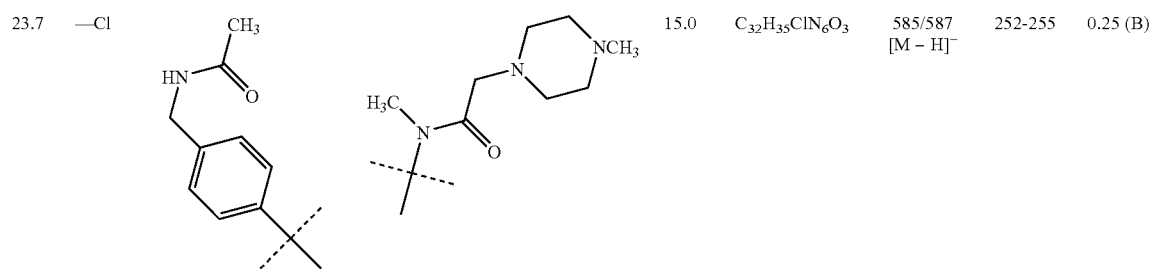 | | 15.0 | C₃₂H₃₅ClN₆O₃ | 585/587 [M − H]⁻ | 252-255 | 0.25 (B) |
| 23.8 | —Cl | 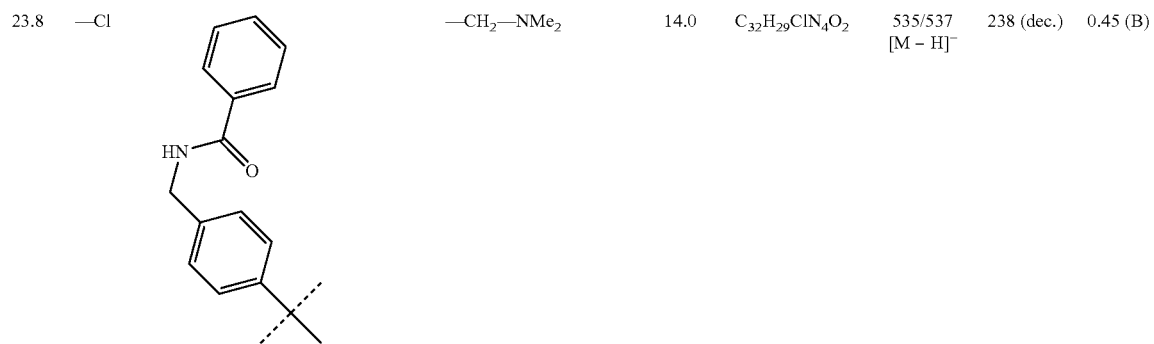 | —CH₂—NMe₂ | 14.0 | C₃₂H₂₉ClN₄O₂ | 535/537 [M − H]⁻ | 238 (dec.) | 0.45 (B) |
| 23.9 | —Cl | 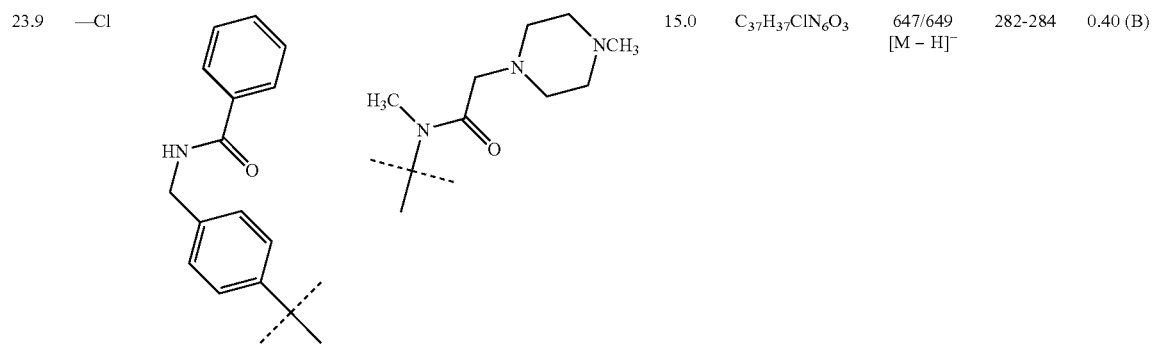 | | 15.0 | C₃₇H₃₇ClN₆O₃ | 647/649 [M − H]⁻ | 282-284 | 0.40 (B) |

-continued
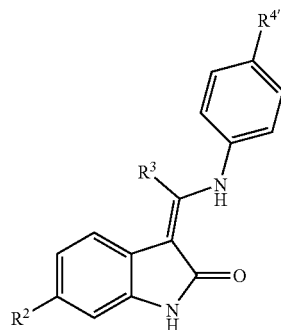
(I-23)
| Example | R² | R³ | R⁴' | educt | empirical formula | mass spectrum | m.p. [° C.] | R_f value* |
|---|---|---|---|---|---|---|---|---|
| 23.10 | —F | 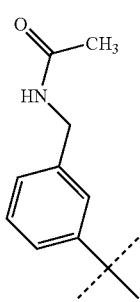 | —CH₂—NMe₂ | 17.16 | $C_{27}H_{27}FN_4O_2$ | 457 [M − H]⁻ | 245-250 | 0.40 (C) |
| 23.11 | —F | 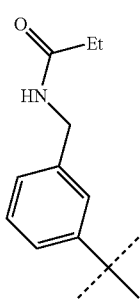 | —CH₂—NMe₂ | 17.16 | $C_{28}H_{29}FN_4O_2$ | 471 [M − H]⁻ | 212-214 | 0.35 (D) |
| 23.12 | —F | 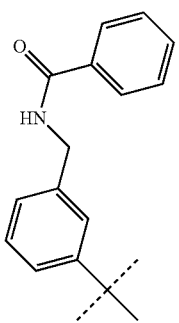 | —CH₂—NMe₂ | 17.16 | $C_{32}H_{29}FN_4O_2$ | 519 [M − H]⁻ | 237-240 | 0.40 (D) |

-continued
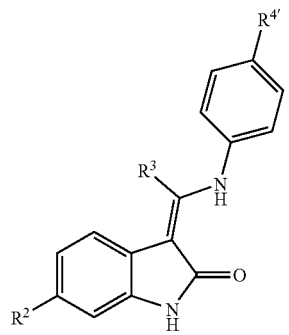
(I-23)
| Example | R² | R³ | R⁴' | educt | empirical formula | mass spectrum | m.p. [° C.] | R_f value* |
|---|---|---|---|---|---|---|---|---|
| 23.13 | —F | (phenylacetamide-3-tBu-benzyl) | —CH₂—NMe₂ | 17.16 | C₃₃H₃₁FN₄O₂ | 533 [M − H]⁻ | 187-190 | 0.30 (D) |
| 23.14 | —F | (acetamide-3-tBu-phenethyl) | —CH₂—NMe₂ | 17.17 | C₂₈H₂₉FN₄O₂ | 471 [M − H]⁻ | 234-237 | 0.30 (D) |
| 23.15 | —F | (benzamide-3-tBu-phenethyl) | —CH₂—NMe₂ | 17.17 | C₃₃H₃₁FN₄O₂ | 533 [M − H]⁻ | 144-150 | 0.45 (C) |

-continued
(I-23)
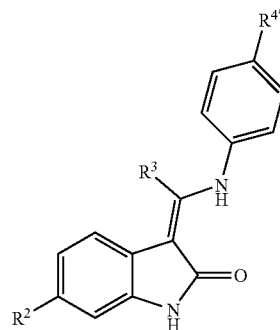
| Example | $R^2$ | $R^3$ | $R^{4'}$ | educt | empirical formula | mass spectrum | m.p. [° C.] | $R_f$ value* |
|---|---|---|---|---|---|---|---|---|
| 23.16 | —F | Et, C(=O)NH-CH2CH2-(3-tBu-C6H4)- | —CH2—NMe2 | 17.17 | $C_{29}H_{31}FN_4O_2$ | 485 [M − H]− | 235-237 | 0.25 (D) |
| 23.17 | —F | PhCH2C(=O)NH-CH2CH2-(3-tBu-C6H4)- | —CH2—NMe2 | 17.17 | $C_{34}H_{33}FN_4O_2$ | 547 [M − H]− | 217-220 | 0.30 (D) |
| 23.18 | —F | CH3C(=O)NH-CH2-(4-tBu-C6H4)- | —CH2—NMe2 | 17.18 | $C_{27}H_{27}FN_4O_2$ | 457 [M − H]− | 112-120 | 0.25 (D) |

-continued
(I-23)
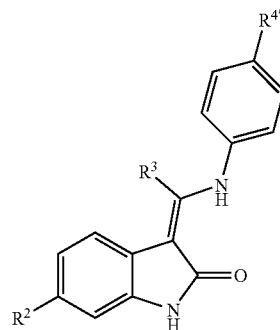
| Example | R² | R³ | R⁴' | educt | empirical formula | mass spectrum | m.p. [° C.] | R_f value* |
|---|---|---|---|---|---|---|---|---|
| 23.19 | —F | 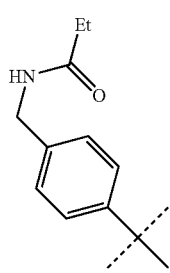 Et | —CH₂—NMe₂ | 17.18 | $C_{28}H_{29}FN_4O_2$ | 586 [M + H]⁺ | 176-180 | 0.30 (D) |
| 23.20 | —F | 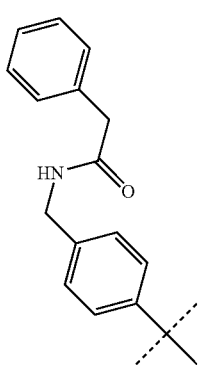 | —CH₂—NMe₂ | 17.18 | $C_{33}H_{31}FN_4O_2$ | 535 [M + H]⁺ | 80-85 | 0.35 (D) |
| 23.21 | —F | 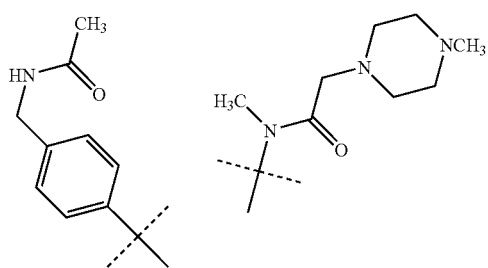 | | 17.19 | $C_{32}H_{35}FN_6O_3$ | 569 [M − H]⁻ | 230-235 | 0.35 (D) |

-continued
(I-23)
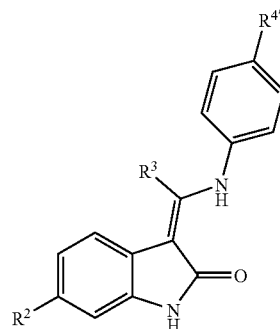
| Example | $R^2$ | $R^3$ | $R^{4'}$ | educt | empirical formula | mass spectrum | m.p. [° C.] | $R_f$ value* |
|---|---|---|---|---|---|---|---|---|
| 23.22 | —F | Et-C(O)NH-CH2-C6H4-C(CH3)3 | (CH3)3C-N(CH3)-C(O)-CH2-N(piperazine)-NCH3 | 17.19 | $C_{33}H_{37}FN_6O_3$ | 583 [M − H]⁻ | 205-210 | 0.30 (D) |
| 23.23 | —F | Ph-CH2-C(O)NH-CH2-C6H4-C(CH3)3 | (CH3)3C-N(CH3)-C(O)-CH2-N(piperazine)-NCH3 | 17.19 | $C_{38}H_{39}FN_6O_3$ | 546 [M − H]⁻ | 217-220 | 0.35 (D) |
| 23.24 | —F | cyclopropyl-C(O)NH-CH2-C6H4-C(CH3)3 | (CH3)3C-N(CH3)-C(O)-CH2-N(piperazine)-NCH3 | 17.22 | $C_{34}H_{37}FN_6O_3$ | 597 [M + H]⁺ | 209-212 | 0.30 (D) |

-continued (I-23)

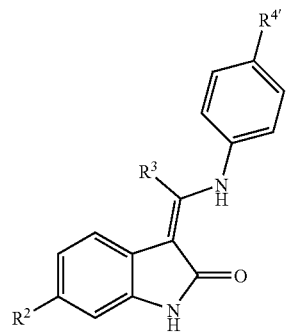

| Example | R² | R³ | R⁴' | educt | empirical formula | mass spectrum | m.p. [° C.] | R_f value* |
|---|---|---|---|---|---|---|---|---|
| 23.25 | —F | (cyclobutanecarboxamide-CH₂-3-tert-butylphenyl) | (N-methyl-N-tert-butyl-2-(4-methylpiperazin-1-yl)acetamide) | 17.22 | C₃₅H₃₉FN₆O₃ | 611 [M + H]⁺ | 190-193 | 0.30 (D) |
| 23.26 | —F | (pyridine-2-carboxamide-CH₂-3-tert-butylphenyl) | (N-methyl-N-tert-butyl-2-(4-methylpiperazin-1-yl)acetamide) | 17.22 | C₃₆H₃₆FN₇O₃ | 634 [M + H]⁺ | 160-163 | 0.30 (D) |
| 23.27 | —F | (cyclohexanecarboxamide-CH₂-3-tert-butylphenyl) | (N-methyl-N-tert-butyl-2-(4-methylpiperazin-1-yl)acetamide) | 17.22 | C₃₇H₄₃FN₆O₃ | 639 [M + H]⁺ | 223-227 | 0.30 (D) |

-continued
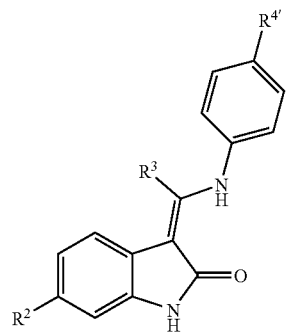
(I-23)
| Example | R² | R³ | R⁴' | educt | empirical formula | mass spectrum | m.p. [° C.] | R_f value* |
|---|---|---|---|---|---|---|---|---|
| 23.28 | —F | | | 17.22 | $C_{36}H_{36}FN_7O_3$ | 634 [M + H]⁺ | 170-175 | 0.25 (D) |
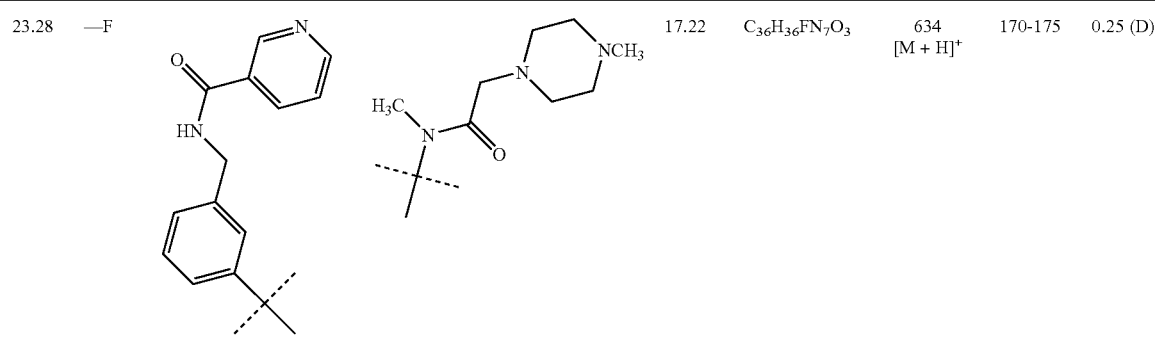
| 23.29 | —F | | | 17.22 | $C_{34}H_{39}FN_6O_3$ | 599 [M + H]⁺ | 194-196 | 0.20 (D) |
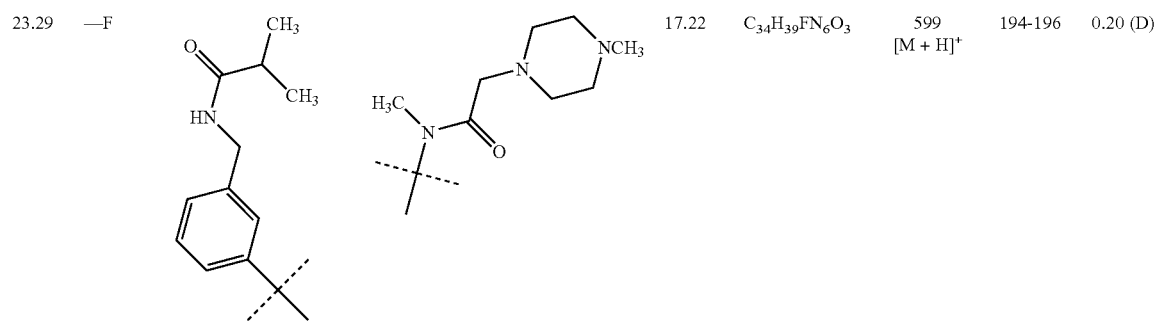
| 23.30 | —F | | | 17.22 | $C_{35}H_{41}FN_6O_3$ | 613 [M + H]⁺ | 197-200 | 0.70 (E) |
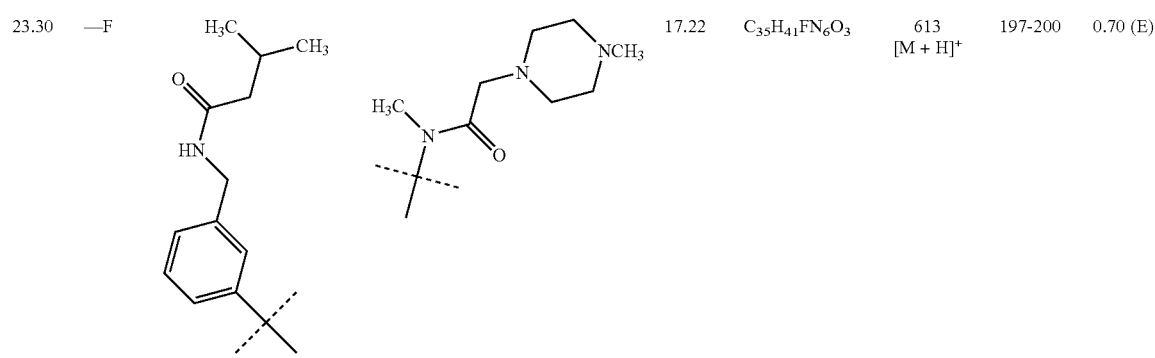

-continued
(I-23)
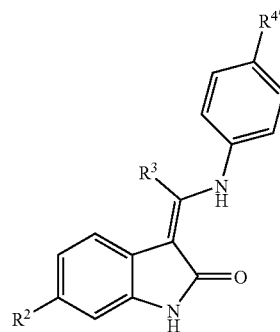
| Example | R² | R³ | R⁴' | educt | empirical formula | mass spectrum | m.p. [° C.] | R_f value* |
|---|---|---|---|---|---|---|---|---|
| 23.31 | —F | cyclohexyl-CH₂-C(O)-NH-CH₂-(3-tBu-C₆H₄)- | -C(CH₃)(N(CH₃)C(O)CH₂-N(piperazine)NCH₃) | 17.22 | C₃₈H₄₅FN₆O₃ | 653 [M + H]⁺ | 130-135 | 0.75 (E) |
| 23.32 | —F | MeO-CH₂-C(O)-NH-CH₂-(3-tBu-C₆H₄)- | -C(CH₃)(N(CH₃)C(O)CH₂-N(piperazine)NCH₃) | 17.22 | C₃₃H₃₇FN₆O₄ | 601 [M + H]⁺ | 155-159 | 0.60 (E) |
| 23.33 | —F | (2-MeO-C₆H₄)-C(O)-NH-CH₂-(3-tBu-C₆H₄)- | -C(CH₃)(N(CH₃)C(O)CH₂-N(piperazine)NCH₃) | 17.22 | C₃₈H₃₉FN₆O₄ | 663 [M + H]⁺ | 168-172 | 0.35 (C) |

-continued

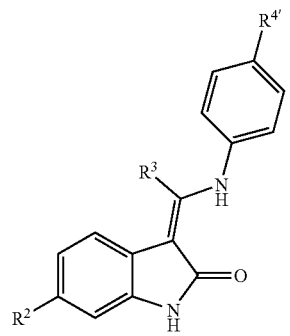

(I-23)

| Example | R² | R³ | R⁴' | educt | empirical formula | mass spectrum | m.p. [° C.] | R_f value* |
|---|---|---|---|---|---|---|---|---|
| 23.34 | —F | (structure: C(CH₃)₃-CH₂-C(=O)-NH-CH₂-(3-tBu-phenyl)) | (structure: 4-(N-methylpiperazinyl)-CH₂-C(=O)-N(CH₃)-C(CH₃)₂-) | 17.22 | $C_{36}H_{43}FN_6O_3$ | 627 [M + H]⁺ | 85-90 | 0.35 (C) |
| 23.35 | —F | (structure: thiophene-2-C(=O)-NH-CH₂-(3-tBu-phenyl)) | (structure: 4-(N-methylpiperazinyl)-CH₂-C(=O)-N(CH₃)-C(CH₃)₂-) | 17.22 | $C_{35}H_{35}FN_6O_3S$ | 639 [M + H]⁺ | 170-175 | 0.25 (C) |
| 23.36 | —F | (structure: (CH₃)₃C-C(=O)-NH-CH₂-(3-tBu-phenyl)) | (structure: 4-(N-methylpiperazinyl)-CH₂-C(=O)-N(CH₃)-C(CH₃)₂-) | 17.22 | $C_{35}H_{41}FN_6O_3$ | 613 [M + H]⁺ | 242-245 | 0.30 (C) |

-continued
(I-23)
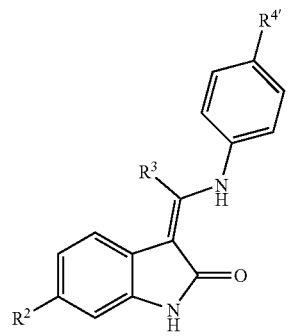
| Example | $R^2$ | $R^3$ | $R^{4'}$ | educt | empirical formula | mass spectrum | m.p. [°C.] | $R_f$ value* |
|---|---|---|---|---|---|---|---|---|
| 23.37 | —F | | | 17.22 | $C_{35}H_{35}FN_6O_4$ | 623 [M + H]$^+$ | 155-160 | 0.65 (F) |
| 23.38 | —F | | | 17.22 | $C_{32}H_{35}FN_6O_3$ | 571 [M + H]$^+$ | 190-195 | 0.60 (F) |
| 23.39 | —F | | | 17.22 | $C_{33}H_{37}FN_6O_3$ | 585 [M + H]$^+$ | 203-209 | 0.65 (E) |

-continued (I-23)

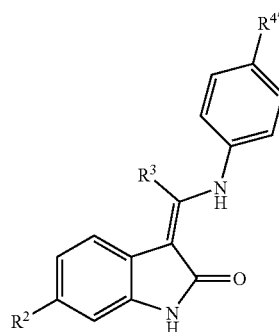

| Example | R² | R³ | R⁴' | educt | empirical formula | mass spectrum | m.p. [° C.] | R_f value* |
|---|---|---|---|---|---|---|---|---|
| 23.40 | —F | ![3-tert-butylbenzyl benzamide group] | ![N-methyl-N-tert-butyl-2-(4-methylpiperazin-1-yl)acetamide group] | 17.22 | $C_{37}H_{37}FN_6O_3$ | 633 [M + H]⁺ | 145-150 | 0.60 (F) |
| 23.41 | —F | ![3-tert-butylbenzyl phenylacetamide group] | ![N-methyl-N-tert-butyl-2-(4-methylpiperazin-1-yl)acetamide group] | 17.22 | $C_{38}H_{39}FN_6O_3$ | 647 [M + H]⁺ | 148-151 | 0.65 (F) |
| 23.42 | —F | ![3-tert-butylbenzyl cyclopropanecarboxamide group] | —CH₂—NMe₂ | 17.16 | $C_{29}H_{29}FN_4O_2$ | 485 [M + H]⁺ | 216-220 | 0.35 (D) |

-continued
(I-23)
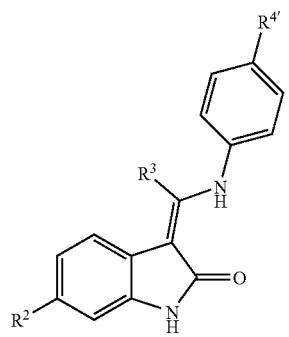
| Example | R² | R³ | R⁴' | educt | empirical formula | mass spectrum | m.p. [° C.] | R_f value* |
|---|---|---|---|---|---|---|---|---|
| 23.43 | —F | (cyclobutyl-C(O)-NH-CH₂-(3-tBu-phenyl)-) | —CH₂—NMe₂ | 17.16 | C₃₀H₃₁FN₄O₂ | 499 [M + H]⁺ | 214-217 | 0.35 (D) |
| 23.44 | —F | (pyridin-2-yl-C(O)-NH-CH₂-(3-tBu-phenyl)-) | —CH₂—NMe₂ | 17.16 | C₃₁H₂₈FN₅O₂ | 522 [M + H]⁺ | 205-210 | 0.35 (D) |
| 23.45 | —F | (cyclohexyl-C(O)-NH-CH₂-(3-tBu-phenyl)-) | —CH₂—NMe₂ | 17.16 | C₃₂H₃₅FN₄O₂ | 527 [M + H]⁺ | 235-237 | 0.35 (D) |

-continued
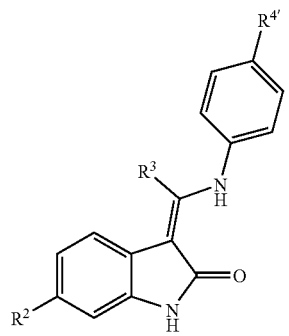
(I-23)
| Example | $R^2$ | $R^3$ | $R^{4'}$ | educt | empirical formula | mass spectrum | m.p. [° C.] | $R_f$ value* |
|---|---|---|---|---|---|---|---|---|
| 23.46 | —F | (nicotinamide-N-CH₂-(3-tBu-phenyl)) | —CH₂—NMe₂ | 17.16 | $C_{31}H_{28}FN_5O_2$ | 520 [M − H]⁻ | 135-140 | 0.20 (D) |
| 23.47 | —F | (isobutyramide-N-CH₂-(3-tBu-phenyl)) | —CH₂—NMe₂ | 17.16 | $C_{29}H_{31}FN_4O_2$ | 487 [M + H]⁺ | 210-215 | 0.20 (D) |
| 23.48 | —F | (3-methylbutyramide-N-CH₂-(3-tBu-phenyl)) | —CH₂—NMe₂ | 17.16 | $C_{30}H_{33}FN_4O_2$ | 501 [M + H]⁺ | 202-206 | 0.25 (D) |

-continued
(I-23)
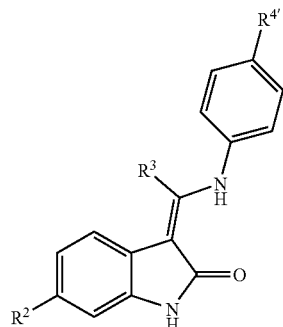
| Example | R² | R³ | R⁴' | educt | empirical formula | mass spectrum | m.p. [° C.] | R_f value* |
|---|---|---|---|---|---|---|---|---|
| 23.49 | —F | 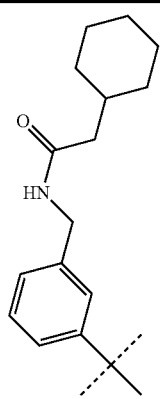 | —CH₂—NMe₂ | 17.16 | $C_{33}H_{37}FN_4O_2$ | 541 $[M + H]^+$ | 198-203 | 0.35 (D) |
| 23.50 | —F | 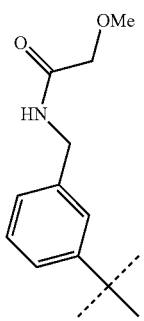 | —CH₂—NMe₂ | 17.16 | $C_{28}H_{29}FN_4O_3$ | 489 $[M + H]^+$ | 173-177 | 0.35 (D) |
| 23.51 | —F | 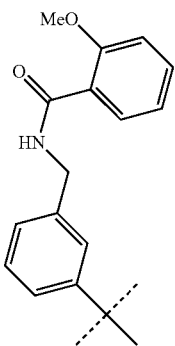 | —CH₂—NMe₂ | 17.16 | $C_{33}H_{31}FN_4O_3$ | 549 $[M - H]^-$ | 202-207 | 0.50 (C) |

(I-23)
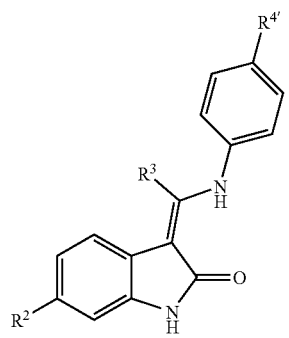
| Example | R² | R³ | R⁴' | educt | empirical formula | mass spectrum | m.p. [° C.] | $R_f$ value* |
|---|---|---|---|---|---|---|---|---|
| 23.52 | —F | 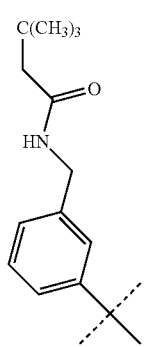 | —CH₂—NMe₂ | 17.16 | $C_{31}H_{35}FN_4O_2$ | 513 [M − H]⁻ | 203-209 | 0.45 (C) |
| 23.53 | —F | 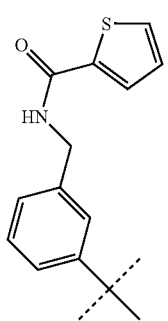 | —CH₂—NMe₂ | 17.16 | $C_{30}H_{27}FN_4O_2S$ | 527 [M + H]⁺ | 245-250 | 0.35 (C) |
| 23.54 | —F | 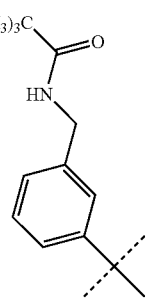 | —CH₂—NMe₂ | 17.16 | $C_{30}H_{33}FN_4O_2$ | 501 [M + H]⁺ | 248-252 | 0.45 (C) |

-continued

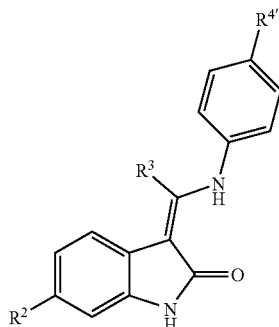

(I-23)

| Example | R² | R³ | R⁴' | educt | empirical formula | mass spectrum | m.p. [° C.] | $R_f$ value* |
|---|---|---|---|---|---|---|---|---|
| 23.55 | —F | (furan-2-carbonyl-NH-CH₂-(3-tert-butylphenyl)) | —CH₂—NMe₂ | 17.16 | $C_{30}H_{27}FN_4O_3$ | 511 [M + H]⁺ | 216-219 | 0.30 (C) |
| 23.56 | —F | (pyridin-4-carbonyl-NH-CH₂-(3-tert-butylphenyl)) | —CH₂—NMe₂ | 17.16 | $C_{31}H_{28}FN_5O_2$ | 522 [M + H]⁺ | 167-170 | 0.20 (D) |

*Eluant mixtures:
(A): silica gel, methylene chloride/ethanol/ammonia = 20:1:0.01
(B): silica gel, methylene chloride/methanol/ammonia = 9:1:0.01
(C): aluminium oxide, methylene chloride/methanol = 19:1
(D): silica gel, methylene chloride/methanol/ammonia = 9:1:0.1
(E): silica gel, methylene chloride/methanol/ammonia = 8:2:0.2
(F): aluminium oxide, methylene chloride/methanol = 9:1

The following were alternatively used as acylating agents:

benzoylchloride, propionylchloride, phenylacetylchloride, cyclopropanecarbonylchloride, cyclobutanecarbonylchloride, pyridin-2-yl-carbonylchloride, pyridin-3-yl-carbonylchloride, pyridin-4-yl-carbonylchloride, cyclohexylcarbonylchloride, isobutyrylchloride, 3-methyl-butyrylchloride, cyclohexylmethylcarbonylchloride, methoxyacetylchloride, 2-methoxy-benzoylchloride, tert.-butylacetylchloride, thiophen-2-carbonylchloride, pivaloylchloride, 2-furoyl-chloride.

EXAMPLE 24.0

3-Z-[1-(4-dimethylaminomethyl-anilino)-1-(4-phenylsulphonylaminomethyl-phenyl)-methylene]-6-chloro-2-indolinone 100 mg of 3-Z-[1-(4-dimethylaminomethyl-anilino)-1-(4-aminomethyl-phenyl)-methylene]-6-chloro-2-indolinone (educt 14.0) are dissolved in 5 ml methylene chloride and at 0° C. 5 ml of pyridine and 45 µl of benzenesulphonylchloride are added. The mixture is stirred for 10 minutes at 0° C. and then for 2 hours at ambient temperature. After this time the solvent is eliminated, the residue is suspended in 1N sodium hydroxide solution, suction filtered and washed with a little water. The product is dried at 100° C.

Yield: 87 mg (66% of theory), $R_f$ value: 0.30 (silica gel, methylene chloride/methanol/ammonia=9:1:0.1) M.p. 170° C. (decomp.) $C_{31}H_{29}ClN_4O_3S$ Mass spectrum: m/z=573/575 $[M+H]^+$ The following compounds of general formula I-24 are prepared analogously to Example 24.0:

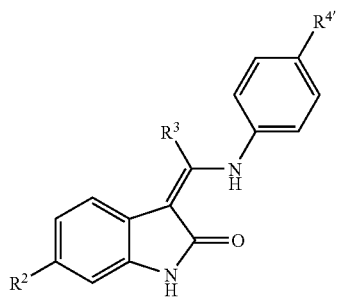

(I-24)

| Example | $R^2$ | $R^3$ | $R^{4'}$ | educt | empirical formula | mass spectrum | m.p. [° C.] | $R_f$ value* |
|---|---|---|---|---|---|---|---|---|
| 24.1 | —Cl | HN—S(=O)(=O)—CH₃ benzyl with 4-tert-butyl | CH₂—C(=O)—N(CH₃)—CH₂—piperazine-NCH₃ | 15.0** | $C_{31}H_{35}ClN_6O_4S$ | 621/623 $[M-H]^-$ | 260-263 | 0.20 (A) |
| 24.2 | —Cl | HN—S(=O)(=O)—CH₃ benzyl with 4-tert-butyl | —CH₂—NMe₂ | 14.0** | $C_{26}H_{27}ClN_4O_3S$ | 511/513 $[M+H]^+$ | n.d. | 0.35 (A) |

-continued

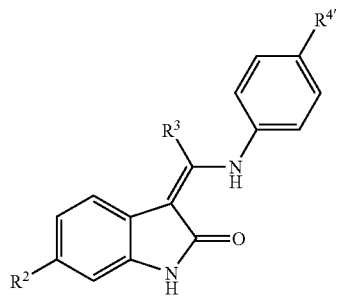

(I-24)

| Example | R² | R³ | R⁴' | educt | empirical formula | mass spectrum | m.p. [° C.] | R_f value* |
|---|---|---|---|---|---|---|---|---|
| 24.3 | —Cl | HN-S(O)₂-C₆H₄-C(CH₃)₃ (4-tert-butylphenyl sulfonamidomethyl) | H₃C-N(tBu)-C(O)-CH₂-N(piperazine)-NCH₃ | 15.0 | C₃₆H₃₇ClN₆O₄S | 683/685 [M − H]⁻ | 248-251 | 0.35 (A) |
| 24.4 | —F | O=S(O)(CH₃)-NH-CH₂-C₆H₄-C(CH₃)₃ (3-tert-butylphenyl methanesulfonamidomethyl) | —CH₂—NMe₂ | 17.16** | C₂₆H₂₇FN₄O₃S | 495 [M + H]⁺ | 170-180 | 0.30 (B) |
| 24.5 | —F | O=S(O)(Et)-NH-CH₂-C₆H₄-C(CH₃)₃ (3-tert-butylphenyl ethanesulfonamidomethyl) | —CH₂—NMe₂ | 17.16*** | C₂₆H₂₇FN₄O₃S | 509 [M + H]⁺ | 200-204 | 0.40 (C) |

-continued
(I-24)
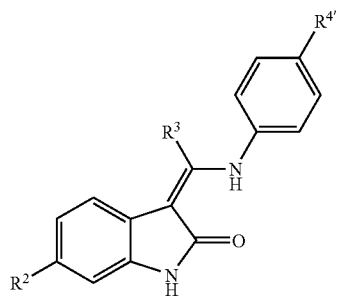
| Example | R² | R³ | R⁴' | educt | empirical formula | mass spectrum | m.p. [° C.] | R_f value* |
|---|---|---|---|---|---|---|---|---|
| 24.6 | —F | (benzenesulfonamide with 3-tert-butylbenzyl) | —CH₂—NMe₂ | 17.16 | C₃₁H₂₉FN₄O₃S | 557 [M + H]⁺ | 125-130 | 0.30 (B) |
| 24.7 | —F | (ethanesulfonamide with 3-tert-butylphenethyl) | —CH₂—NMe₂ | 17.17*** | C₂₈H₃₁FN₄O₃S | 521 [M − H]⁻ | 100-110 | 0.35 (B) |
| 24.8 | —F | (methanesulfonamide with 4-tert-butylbenzyl) | —CH₂—NMe₂ | 17.18** | C₂₆H₂₇FN₄O₃S | 493 [M − H]⁻ | 80-85 | 0.35 (B) |

-continued
(I-24)
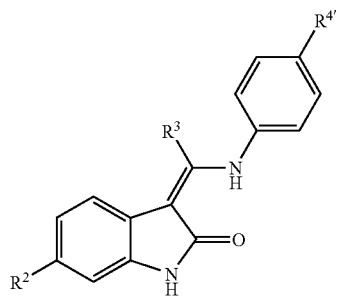
| Example | R² | R³ | R⁴' | educt | empirical formula | mass spectrum | m.p. [° C.] | R_f value* |
|---------|-----|-----|------|-------|-------------------|---------------|-------------|-----------|
| 24.9 | —F | (4-tBu-benzyl)-NH-SO₂-Et | —CH₂—NMe₂ | 17.18*** | C₂₇H₂₉FN₄O₃S | 507 [M − H]⁻ | 90-100 | 0.40 (B) |
| 24.10 | —F | (4-tBu-benzyl)-NH-SO₂-CH₂-Ph | —CH₂—NMe₂ | 17.18**** | C₃₂H₃₁FN₄O₃S | 571 [M + H]⁺ | 115-120 | 0.35 (B) |
| 24.11 | —F | (4-tBu-benzyl)-NH-SO₂-CH₃ | —C(CH₃)₂—N(CH₃)—C(O)—CH₂—(4-methylpiperazin-1-yl) | 17.19** | C₃₁H₃₅FN₆O₄S | 605 [M − H]⁻ | 205-210 | 0.25 (B) |

-continued

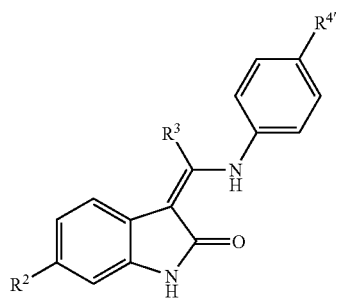
(I-24)

| Example | $R^2$ | $R^3$ | $R^{4'}$ | educt | empirical formula | mass spectrum | m.p. [°C.] | $R_f$ value* |
|---|---|---|---|---|---|---|---|---|
| 24.12 | —F | 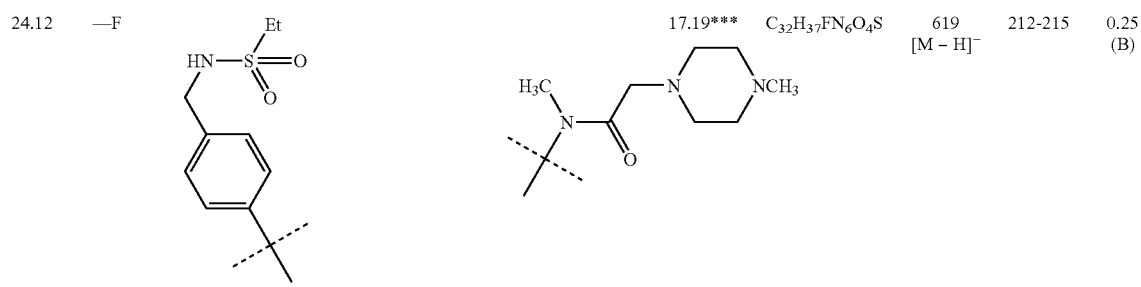 | | 17.19*** | $C_{32}H_{37}FN_6O_4S$ | 619 [M − H]⁻ | 212-215 | 0.25 (B) |
| 24.13 | —F | 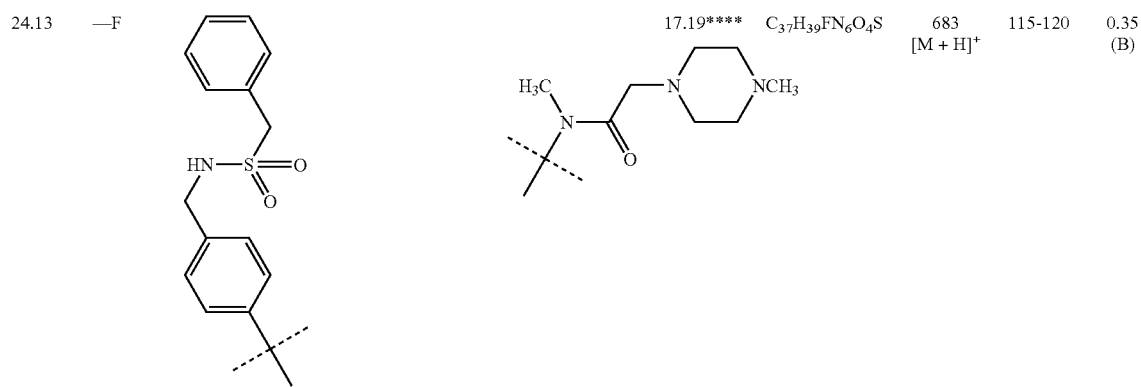 | | 17.19**** | $C_{37}H_{39}FN_6O_4S$ | 683 [M + H]⁺ | 115-120 | 0.35 (B) |

*Eluant mixtures:
(A): silica gel, methylene chloride/methanol/ammonia = 9:1:0.01
(B): silica gel, methylene chloride/methanol/ammonia = 9:1:0.1
(C): aluminium oxide, methylene chloride/methanol = 19:1
**with methanesulphonylchloride as sulphonating agent
***with ethanesulphonylchloride as sulphonating agent
****with α-toluenesulphonylchloride as sulphonating agent

EXAMPLE 25.0

3-Z-[1-(4-Trimethylammoniummethyl-anilino)-1-(4-(2-carboxy-ethyl)-phenyl)-methylene]-6-fluoro-2-indolinone-iodide 200 mg of 3-Z-[1-(4-dimethylaminomethyl-anilino)-1-(4-(2-carboxy-ethyl)-phenyl)-methylene]6-fluoro-2-indolinone (educt 20.1) are dissolved in 40 ml of acetone and 250 ml of methyl iodide are added. The mixture is stirred for 20 hours at ambient temperature. After this time the precipitated residue is suction filtered. The product is dried at 80° C. in vacuo.

Yield: 200 mg (83% of theory), $R_f$-value: 0.50 (Reversed Phase RP8, methanol/saline solution (5%)=4:1) Mp. 210° C. $C_{28}H_{29}FN_3O_3I$ Mass spectrum: m/z=474 $[M+H]^+$ The following compound of general formula I-25 is prepared analogously to Example 25.0:

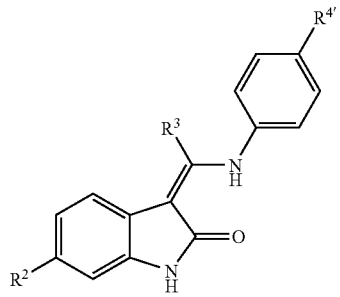

(I-25)

| Example | R² | R³ | R⁴' | educt | empirical formula | mass spectrum | m.p. [° C.] | $R_f$ value* |
|---|---|---|---|---|---|---|---|---|
| 25.1 | —F | (3-phenylpropanoic acid, —OH) | —CH₂N⁺(Me)₃ I⁻ | 20.3 | $C_{28}H_{29}FN_3O_3I$ | 474 $[M+H]^+$ | 150 | 0.50 (A) |

*eluant mixtures:
(A): Reversed Phase RP8, methanol/saline solution (5%) = 4:1

EXAMPLE 26.0

3-Z-[1-(4-Guanidinomethyl-anilino)-1-(4-(2-carboxy-ethyl)-phenyl)-methylene]-6-fluoro-2-indolinone-iodide 170 mg of 3-Z-[1-(4-aminomethyl-anilino)-1-(4-(2-carboxy-ethyl)-phenyl)-methylene]-6-fluoro-2-indolinone (educt 20.50) are dissolved in 20 ml tetrahydrofuran and 390 mg of 3,5-dimethylpyrazole-1-carboxylic acid amidine nitrate and 330 ml of diethylisopropylamine are added. The mixture is refluxed for 10 hours with stirring. After this time the solvent is evaporated down, water is added and the residue precipitated is suction filtered. The product is dried at 80° C.

Yield: 150 mg (81% of theory), $R_f$-value: 0.40 (silica gel, methylene chloride/methanol/acetic acid=5:1:0.1) Mp. 290° C. $C_{26}H_{24}FN_5O_3$ Mass spectrum: m/z=474 $[M+H]^+$ The following compound of general formula I-26 is prepared analogously to Example 26.0:

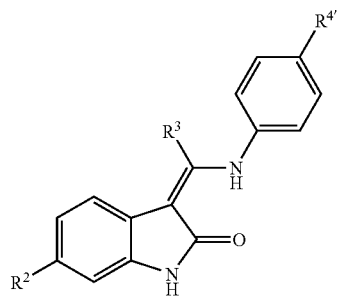

(I-26)

| Example | R² | R³ | R⁴' | educt | empirical formula | mass spectrum | m.p. [°C.] | $R_f$ value* |
|---|---|---|---|---|---|---|---|---|
| 26.1 | —F | | | 20.64 | $C_{26}H_{24}FN_5O_3$ | 474 [M + H]⁺ | 305 | 0.70 (A) |

*eluant mixtures:
(A): Reversed Phase RP8, methanol/saline solution (5%) = 4:1

EXAMPLE 27.0

3-Z-[1-(4-(N-(4-methyl-piperazin-1-yl-methylcarbonyl)-N-methyl-amino)-anilino)-1-phenyl-methylene]-6-chloro-2-indolinonexethanesulphonic acid a) 3-Z-[1-(4-(N-(4-methyl-piperazin-1-yl-methylcarbonyl)-N-methyl-amino)-anilino)-1-phenyl-methylene]-6-chloro-2-indolinone 10.25 g of 1-acetyl-3-(1-ethoxy-1-phenylmethylen)-6-chloro-2-indolinone (educt IX) and 8.6 g of N-[(4-methyl-piperazin-1-yl)-methylcarbonyl]-N-methyl-p-phenylenediamine (educt XV.204) are dissolved in 100 ml of dimethylformamide and stirred for 4 hours at 120° C. After cooling, 20 ml of 6 N sodium hydroxide solution are added and the mixture is stirred for another hour at ambient temperature. Water is added, the precipitate formed is suction filtered and washed with a little water and 200 ml of ethanol. The residue is dissolved in methylene chloride, extracted with water and dried over sodium sulphate. After the solvent has been eliminated the substance is again washed with a little methanol and dried in vacuo at 100° C.

Yield: 15.48 g (74% of theory), $R_f$ value: 0.50 (silica gel, methylene chloride/methanol/ammonia 5:1:0.01) IR spectrum: 1645 cm⁻¹ M.p. 265-269° C. $C_{29}H_{30}ClN_5O_2$ Mass spectrum: m/z 515/517 [M]⁺

| Elemental analysis: | calculated: | C 67.49 | H 5.86 | Cl 6.87 | N 13.57 |
|---|---|---|---|---|---|
| | found: | C 67.42 | H 5.83 | Cl 6.97 | N 13.59 | b) 3-Z-[1-(4-(N-(4-methyl-piperazin-1-yl-methylcarbonyl)-N-methyl-amino)-anilino)-1-phenyl-methylene]-6-chloro-2-indolinonexethanesulphonic acid 1.5 g of 3-Z-[1-(4-(N-(4-methyl-piperazin-1-yl-methylcarbonyl)-N-methyl-amino)-anilino)-1-phenyl-methylene]-6-chloro-2-indolinone are placed in 22.5 ml of methanol, the mixture is heated to 50° C. and 0.25 ml of ethanesulphonic acid in 0.14 g water are added dropwise. The mixture is slowly cooled to ambient temperature, lastly by means of an ice bath to 0° C. The precipitate formed is suction filtered and washed with a little tert.butylmethylether. The residue is dried in vacuo at 40° C.

Yield: 1.7 g (93% of theory), IR spectrum: 1655 cm⁻¹ M.p. 307° C. $C_{29}H_{30}ClN_5O_2 \times C_2H_6O_3S$ Mass spectrum: m/z=516/518 [M+H]⁺

EXAMPLE 28

| Dry ampoule containing 75 mg of active substance per 10 ml Composition: | |
|---|---|
| Active substance | 75.0 mg |
| Mannitol | 50.0 mg |
| water for injections | ad 10.0 ml |

Preparation:

Active substance and mannitol are dissolved in water. After packaging, the solution is freeze-dried. To produce the solution ready for use, the product is dissolved in water for injections.

EXAMPLE 29

Dry ampoule containing 35 mg of active substance per 2 ml
Composition:

| | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

EXAMPLE 30

Tablet containing 50 mg of active substance
Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the Tablets: 9 mm.

EXAMPLE 31

Tablet containing 350 mg of active substance
Composition:

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation (1), (2) and (3) are mixed together and granulated with an aqueous solution of (4). (5) is added to the dried granulated material. From this mixture tablets are pressed, biplanar, faceted on both sides and with a dividing notch on one side.

Diameter of the Tablets: 12 mm.

EXAMPLE 32

Capsules containing 50 mg of active substance
Composition:

| | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

EXAMPLE 33

Capsules containing 350 mg of active substance
Composition:

| | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

EXAMPLE 34

Suppositories containing 100 mg of active substance
1 suppository contains:

| | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2000.0 mg |

Preparation:

The polyethyleneglycol is melted together with polyethylene sorbitan monostearate. At 40° C. the ground active substance is homogeneously dispersed in the melt. It is cooled to 38° C. and poured into slightly chilled suppository moulds.

The following compounds may be prepared analogously to the foregoing Examples:
(1) 3-Z-[1-(4-(N-(2-dimethylamino-ethyl)-carbamoyl)-anilino)-1-phenyl-methylene]-6-chloro-2-indolinone
(2) 3-Z-[1-(4-(N-(2-dimethylamino-ethyl)-N-ethyl-carbamoyl)-anilino)-1-phenyl-methylene]-6-chloro-2-indolinone (3) 3-Z-[1-(4-(N-(3-dimethylamino-propyl)-N-methyl-carbamoyl)-anilino)-1-phenyl-methylene]-6-chloro-2-indolinone
(4) 3-Z-[1-(4-(N-(3-dimethylamino-propyl)-carbamoyl)-anilino)-1-phenyl-methylene]-6-chloro-2-indolinone
(5) 3-Z-[1-(4-(N-(3-dimethylamino-propyl)-N-ethyl-carbamoyl)-anilino)-1-phenyl-methylene]-6-chloro-2-indolinone
(6) 3-Z-[1-(3-(N-(2-dimethylamino-ethyl)-N-methyl-carbamoyl)-anilino)-1-phenyl-methylene]-6-chloro-2-indolinone
(7) 3-Z-[1-(3-(N-(2-dimethylamino-ethyl)-carbamoyl)-anilino)-1-phenyl-methylene]-6-chloro-2-indolino
(8) 3-Z-[1-(3-(N-(2-dimethylamino-ethyl)-N-ethyl-carbamoyl)-anilino)-1-phenyl-methylene]-6-chloro-2-indolino
(9) 3-Z-[1-(3-(N-(3-dimethylamino-propyl)-N-methyl-carbamoyl)-anilino)-1-phenyl-methylene]-6-chloro-2-indolinone
(10) 3-Z-[1-(3-(N-(3-dimethylamino-propyl)-carbamoyl)-anilino)-1-phenyl-methylene]-6-chloro-2-indolinone
(11) 3-Z-[1-(3-(N-(3-dimethylamino-propyl)-N-ethyl-carbamoyl)-anilino)-1-phenyl-methylene]-6-chloro-2-indolinone
(12) 3-Z-[1-(3-(N-(4-methyl-piperazin-1-yl-methylcarbonyl)-N-methyl-amino)-anilino)-1-phenyl-methylene]-6-chloro-2-indolinone
(13) 3-Z-[1-(3-(N-(dimethylamino-methylcarbonyl)-N-methyl-amino)-anilino)-1-phenyl-methylene]-6-chloro-2-indolinone
(14) 3-Z-[1-(4-methylsulphonyl-anilino)-1-phenyl-methylene]-6-chloro-2-indolinone
(15) 3-Z-[1-anilino-1-phenyl-methylene]-6-chloro-2-indolinone
(16) 3-Z-[1-(4-nitro-anilino)-1-phenyl-methylene]-6-chloro-2-indolinone
(17) 3-Z-[1-(4-fluoro-anilino)-1-phenyl-methylene]-6-chloro-2-indolinone
(18) 3-Z-[1-(4-chloro-anilino)-1-phenyl-methylene]-6-chloro-2-indolinone
(19) 3-Z-[1-(4-bromo-anilino)-1-phenyl-methylene]-6-chloro-2-indolinone
(20) 3-Z-[1-(4-iodo-anilino)-1-phenyl-methylene]-6-chloro-2-indolinone
(21) 3-Z-[1-(4-cyano-anilino)-1-phenyl-methylene]-6-chloro-2-indolinone
(22) 3-Z-[1-(4-methoxy-anilino)-1-phenyl-methylene]-6-chloro-2-indolinone
(23) 3-Z-[1-(4-ethoxy-anilino)-1-phenyl-methylene]-6-chloro-2-indolinone
(24) 3-Z-[1-(4-trifluoromethyl-anilino)-1-phenyl-methylene]-6-chloro-2-indolinone
(25) 3-Z-[1-(4-methylmercapto-anilino)-1-phenyl-methylene]-6-chloro-2-indolinone
(26) 3-Z-[1-(4-(isopropylaminomethyl)-anilino)-1-phenyl-methylene]-6-chloro-2-indolinone
(27) 3-Z-[1-(4-(anilinomethyl)-anilino)-1-phenyl-methylene]-6-chloro-2-indolinone
(28) 3-Z-[1-(4-(isobutylaminomethyl)-anilino)-1-phenyl-methylene]-6-chloro-2-indolinone
(29) 3-Z-[1-(4-(cyclohexylaminomethyl)-anilino)-1-phenyl-methylene]-6-chloro-2-indolinone
(30) 3-Z-[1-(4-(benzylaminomethyl)-anilino)-1-phenyl-methylene]-6-chloro-2-indolinone
(31) 3-Z-[1-(4-((N-isopropyl-N-methyl-amino)-methyl)-anilino)-1-phenyl-methylene]-6-chloro-2-indolinone
(32) 3-Z-[1-(4-((N-ethyl-N-propyl-amino)-methyl)-anilino)-1-phenyl-methylene]-6-chloro-2-indolinone
(33) 3-Z-[1-(4-((N-ethyl-N-isopropyl-amino)-methyl)-anilino)-1-phenyl-methylene]-6-chloro-2-indolinone
(34) 3-Z-[1-(4-(dipropylaminomethyl)-anilino)-1-phenyl-methylene]-6-chloro-2-indolinone
(35) 3-Z-[1-(4-(diisopropylaminomethyl)-anilino)-1-phenyl-methylene]-6-chloro-2-indolinone
(36) 3-Z-[1-(4-((N-benzyl-N-ethyl-amino)-methyl)-anilino)-1-phenyl-methylene]-6-chloro-2-indolinone
(37) 3-Z-[1-(4-(dibenzylaminomethyl)-anilino)-1-phenyl-methylene]-6-chloro-2-indolinone
(38) 3-Z-[1-(4-(3,6-dihydro-2H-pyridine-1-yl-methyl)-anilino)-1-phenyl-methylene]-6-chloro-2-indolinone
(39) 3-Z-[1-(4-(3,5-dimethyl-piperidin-1-yl-methyl)-anilino)-1-phenyl-methylene]-6-chloro-2-indolinone
(40) 3-Z-[1-(4-(azepan-1-yl-methyl)-anilino)-1-phenyl-methylene]-6-chloro-2-indolinone
(41) 3-Z-[1-(4-(2-amino-ethyl)-anilino)-1-phenyl-methylene]-6-chloro-2-indolinone
(42) 3-Z-[1-(4-(2-methylamino-ethyl)-anilino)-1-phenyl-methylene]-6-chloro-2-indolinone
(43) 3-Z-[1-(4-(2-ethylamino-ethyl)-anilino)-1-phenyl-methylene]-6-chloro-2-indolinone
(44) 3-Z-[1-(4-(2-diethylamino-ethyl)-anilino)-1-phenyl-methylene]-6-chloro-2-indolinone
(45)-Z-[1-(4-(2-piperidin-1-yl-ethyl)-anilino)-1-phenyl-methylene]-6-chloro-2-indolinone
(46) 3-Z-[1-(4-(2-acetylamino-ethyl)-anilino)-1-phenyl-methylene]-6-chloro-2-indolinone
(47) 3-Z-[1-(4-(3-amino-propyl)-anilino)-1-phenyl-methylene]-6-chloro-2-indolinone
(48) 3-Z-[1-(4-(3-dimethylamino-propyl)-anilino)-1-phenyl-methylene]-6-chloro-2-indolinone
(49) 3-Z-[1-(4-(N-ethylaminomethylcarbonyl-N-methyl-amino)-anilino)-1-phenyl-methylene]-6-chloro-2-indolinone
(50) 3-Z-[1-(4-(N-diethylaminomethylcarbonyl-N-methyl-amino)-anilino)-1-phenyl-methylene]-6-chloro-2-indolinone
(51) 3-Z-[1-(4-(N-dipropylaminomethylcarbonyl-N-methyl-amino)-anilino)-1-phenyl-methylene]-6-chloro-2-indolinone
(52) 3-Z-[1-(4-(N—((N-ethyl-N-methyl-amino)-methylcarbonyl)-N-methyl-amino)-anilino)-1-phenyl-methylene]-6-chloro-2-indolinone
(53) 3-Z-[1-(4-(N—((N-ethyl-N-propyl-amino)-methylcarbonyl)-N-methyl-amino)-anilino)-1-phenyl-methylene]-6-chloro-2-indolinone
(54) 3-Z-[1-(4-(N—((N-methyl-N-propyl-amino)-methylcarbonyl)-N-methyl-amino)-anilino)-1-phenyl-methylene]-6-chloro-2-indolinone
(55) 3-Z-[1-(4-(N-dimethylaminomethylcarbonyl-N-ethyl-amino)-anilino)-1-phenyl-methylene]-6-chloro-2-indolinone
(56) 3-Z-[1-(4-(N-dimethylaminomethylcarbonyl-N-propyl-amino)-anilino)-1-phenyl-methylene]-6-chloro-2-indolinone
(57) 3-Z-[1-(4-(N-dimethylaminomethylcarbonyl-N-butyl-amino)-anilino)-1-phenyl-methylene]-6-chloro-2-indolinone
(58) 3-Z-[1-(4-(N-(2-amino-ethylcarbonyl)-N-methyl-amino)-anilino)-1-phenyl-methylene]-6-chloro-2-indolinone
(59) 3-Z-[1-(4-(N-(2-diethylamino-ethylcarbonyl)-N-methyl-amino)-anilino)-1-phenyl-methylene]-6-chloro-2-indolinone
(60) 3-Z-[1-(4-(N-acetyl-N-(2-aminoethyl)-amino)-anilino)-1-phenyl-methylene]-6-chloro-2-indolinone

(61) -Z-[1-(4-(N-acetyl-N-(2-methylamino-ethyl)-amino)-anilino)-1-phenyl-methylene]-6-chloro-2-indolinone
(62) 3-Z-[1-(4-(N-acetyl-N-(3-amino-propyl)-amino)-anilino)-1-phenyl-methylene]-6-chloro-2-indolinone
(63) 3-Z-[1-(4-(N-acetyl-N-(3-methylamino-propyl)-amino)-anilino)-1-phenyl-methylene]-6-chloro-2-indolinone
(64) 3-Z-[1-(4-(N-acetyl-N-(2-piperidin-1-yl-ethyl)-amino)-anilino)-1-phenyl-methylene]-6-chloro-2-indolinone
(65) 3-Z-[1-(4-(N-acetyl-N-(aminocarbonylmethyl)-amino)-anilino)-1-phenyl-methylene]-6-chloro-2-indolinone
(66) 3-Z-[1-(4-(N-acetyl-N-(piperidin-1-yl-carbonylmethyl)-amino)-anilino)-1-phenyl-methylene]6-chloro-2-indolinone
(67) 3-Z-[1-(4-(N-(2-ethylamino-ethyl)-N-methylsulphonyl-amino)-anilino)-1-phenyl-methylene]-6-chloro-2-indolinone
(68) 3-Z-[1-(4-(N-(2-diethylamino-ethyl)-N-methylsulphonyl-amino)-anilino)-1-phenyl-methylene]-6-chloro-2-indolinone
(69) 3-Z-[1-(4-(N-(2-pyrrolidin-1-yl-ethyl)-N-methylsulphonyl-amino)-anilino)-1-phenyl-methylene]-6-chloro-2-indolinone
(70) 3-Z-[1-(4-(N-(2-piperidin-1-yl-ethyl)-N-methylsulphonyl-amino)-anilino)-1-phenyl-methylene]-6-chloro-2-indolinone
(71) 3-Z-[1-(4-(N-(2-piperazin-1-yl-ethyl)-N-methylsulphonyl-amino)-anilino)-1-phenyl-methylene]-6-chloro-2-indolinone
(72) 3-Z-[1-(4-(N-(2-(4-morpholin-1-yl)-ethyl)-N-methylsulphonyl-amino)-anilino)-1-phenyl-methylene]-6-chloro-2-indolinone
(73) 3-Z-[1-(4-(2-diethylamino-ethoxy)-anilino)-1-phenyl-methylene]-6-chloro-2-indolinone
(74) 3-Z-[1-(4-(3-dimethylamino-propoxy)-anilino)-1-phenyl-methylene]-6-chloro-2-indolinone
(75) 3-Z-[1-(4((N-phenethyl-N-methyl-amino)-methyl)-anilino)-1-phenyl-methylene]-6-chloro-2-indolinone
(76) 3-Z-[1-(4-carbamoylmethyl-anilino)-1-phenyl-methylene]-6-chloro-2-indolinone
(77) 3-Z-[1-(4-methylcarbamoylmethyl-anilino)-1-phenyl-methylene]-6-chloro-2-indolinone
(78) 3-Z-[1-(4-dimethylcarbamoylmethyl-anilino)-1-phenyl-methylene]-6-chloro-2-indolinone
(79) 3-Z-[1-(4-tetrazol-5-yl-anilino)-1-phenyl-methylene]-6-chloro-2-indolinone
(80) 3-Z-[1-(4-((2-methoxy-ethyl)-amino-methyl)-anilino)-1-phenyl-methylene]-6-chloro-2-indolinone
(81) 3-Z-[1-(4-(di-(2-methoxy-ethyl)-amino-methyl)-anilino)-1-phenyl-methylene]-6-chloro-2-indolinone
(82) 3-Z-[1-(4-((N-tert.butoxycarbonyl-2-amino-ethyl)-amino-methyl)-anilino)-1-phenyl-methylene]-6-chloro-2-indolinone
(83) 3-Z-[1-(4-((N-tert.butoxycarbonyl-3-amino-propyl)-amino-methyl)-anilino)-1-phenyl-methylene]-6-chloro-2-indolinone
(84) 3-Z-[1-(4-((2-amino-ethyl)-amino-methyl)-anilino)-1-phenyl-methylene]-6-chloro-2-indolinone
(85) 3-Z-[1-(4-((3-amino-propyl)-amino-methyl)-anilino)-1-phenyl-methylene]-6-chloro-2-indolinone
(86) 3-Z-[1-(4-((2-acetylamino-ethyl)-amino-methyl)-anilino)-1-phenyl-methylene]-6-chloro-2-indolinone
(87) 3-Z-[1-(4-((3-acetylamino-propyl)-amino-methyl)-anilino)-1-phenyl-methylene]-6-chloro-2-indolinone
(88) 3-Z-[1-(4-((2-methylsulphonylamino-ethyl)-amino-methyl)-anilino)-1-phenyl-methylene]-6-chloro-2-indolinone
(89) 3-Z-[1-(4-((3-methylsulphonylamino-propyl)-amino-methyl)-anilino)-1-phenyl-methylene]-6-chloro-2-indolinone
(90) 3-Z-[1-(4-(N-(2-amino-ethyl)-N-methyl-amino-methyl)-anilino)-1-phenyl-methylene]-6-chloro-2-indolinone
(91) 3-Z-[1-(4-(N-(2-methylamino-ethyl)-N-methyl-amino-methyl)-anilino)-1-phenyl-methylene]-6-chloro-2-indolinone
(92) 3-Z-[1-(4-(N-(2-acetylamino-ethyl)-N-methyl-amino-methyl)-anilino)-1-phenyl-methylene]-6-chloro-2-indolinone
(93) 3-Z-[1-(4-(N-(2-methylsulphonylamino-ethyl)-N-methyl-amino-methyl)-anilino)-1-phenyl-methylene]-6-chloro-2-indolinone
(94) 3-Z-[1-(4-(carbamoylmethyl-amino-methyl)-anilino)-1-phenyl-methylene]-6-chloro-2-indolinone
(95) 3-Z-[1-(4-(dimethylcarbamoyl-methyl-amino-methyl)-anilino)-1-phenyl-methylene]-6-chloro-2-indolinone
(96) 3-Z-[1-(4-(methylcarbamoyl-methyl-amino-methyl)-anilino)-1-phenyl-methylene]-6-chloro-2-indolinone
(97) 3-Z-[1-(4-(N-(pyridin-4-yl-methylcarbonyl)-amino)-anilino)-1-phenyl-methylene]-6-chloro-2-indolinone
(98) 3-Z-[1-(4-(N-(4-propyl-piperazin-1-yl-methylcarbonyl)-N-methyl-amino)-anilino)-1-phenyl-methylene]-6-chloro-2-indolinone
(99) 3-Z-[1-(4-(N-(4-butyl-piperazin-1-yl-methylcarbonyl)-N-methyl-amino)-anilino)-1-phenyl-methylene]-6-chloro-2-indolinone
(100) 3-Z-[1-(4-(N-(4-isopropyl-piperazin-1-yl-methylcarbonyl)-N-methyl-amino)-anilino)-1-phenyl-methylene]-6-chloro-2-indolinone
(101) 3-Z-[1-(4-(N-(4-(2-hydroxy-ethyl)-piperazin-1-yl-methylcarbonyl)-N-methyl-amino)-anilino)-1-phenyl-methylene]-6-chloro-2-indolinone
(102) 3-Z-[1-(4-(N-(4-(2-methoxy-ethyl)-piperazin-1-yl-methylcarbonyl)-N-methyl-amino)-anilino)-1-phenyl-methylene]-6-chloro-2-indolinone
(103) 3-Z-[1-(4-(N-(4-(2-ethoxy-ethyl)-piperazin-1-yl-methylcarbonyl)-N-methyl-amino)-anilino)-1-phenyl-methylene]-6-chloro-2-indolinone
(104) 3-Z-[1-(4-(N-(4-(2-amino-ethyl)-piperazin-1-yl-methylcarbonyl)-N-methyl-amino)-anilino)-1-phenyl-methylene]-6-chloro-2-indolinone
(105) 3-Z-[1-(4-(N-(4-(2-dimethylamino-ethyl)-piperazin-1-yl-methylcarbonyl)-N-methyl-amino)-anilino)-1-phenyl-methylene]-6-chloro-2-indolinone
(106) 3-Z-[1-(4-(N-(4-(2-phenyl-piperazin-1-yl-methylcarbonyl)-N-methyl-amino)-anilino)-1-phenyl-methylene]-6-chloro-2-indolinone
(107) 3-Z-[1-(4-(N-(4-(5-methyl-2,5-diaza-bicyclo[2.2.1]-hept-2-yl)-methylcarbonyl)-N-methyl-amino)-anilino)-1-phenyl-methylene]-6-chloro-2-indolinone
(108) 3-Z-[1-(4-(N-(homopiperazin-1-yl-methylcarbonyl)-N-methyl-amino)-anilino)-1-phenyl-methylene]-6-chloro-2-indolinone
(109) 3-Z-[1-(4-(N-(3,4,5-trimethyl-piperazin-1-yl-methylcarbonyl)-N-methyl-amino)-anilino)-1-phenyl-methylene]-6-chloro-2-indolinone
(110) 3-Z-[1-(4-(N-(2,4,6-trimethyl-piperazin-1-yl-methylcarbonyl)-N-methyl-amino)-anilino)-1-phenyl-methylene]-6-chloro-2-indolinone (111) 3-Z-[1-(4-(N-(trans-2,4,5-trimethyl-piperazin-1-yl-methylcarbonyl)-N-methyl-amino)-anilino)-1-phenyl-methylene]-6-chloro-2-indolinone
(112) 3-Z-[1-(4-(N-(cis-2,4,5-trimethyl-piperazin-1-yl-methylcarbonyl)-N-methyl-amino)-anilino)-1-phenyl-methylene]-6-chloro-2-indolinone
(113) 3-Z-[1-(4-(N-(2,4-dimethyl-piperazin-1-yl-methylcarbonyl)-N-methyl-amino)-anilino)-1-phenyl-methylene]-6-chloro-2-indolinone
(114) 3-Z-[1-(4-(N-(3,4-dimethyl-piperazin-1-yl-methylcarbonyl)-N-methyl-amino)-anilino)-1-phenyl-methylene]-6-chloro-2-indolinone
(115) 3-Z-[1-(4-(N-(4-methyl-piperazin-1-yl-methylcarbonyl)-N-ethyl-amino)-anilino)-1-phenyl-methylene]-6-chloro-2-indolinone
(116) 3-Z-[1-(4-(N-(4-methyl-piperazin-1-yl-methylcarbonyl)-N-propyl-amino)-anilino)-1-phenyl-methylene]-6-chloro-2-indolinone
(117) 3-Z-[1-(4-(N-(4-methyl-piperazin-1-yl-methylcarbonyl)-N-isopropyl-amino)-anilino)-1-phenyl-methylene]-6-chloro-2-indolinone
(118) 3-Z-[1-(4-(N-(4-methyl-piperazin-1-yl-methylcarbonyl)-N-butyl-amino)-anilino)-1-phenyl-methylene]-6-chloro-2-indolinone
(119) 3-Z-[1-(4-(N-(4-methyl-piperazin-1-yl-methylcarbonyl)-N-phenyl-amino)-anilino)-1-phenyl-methylene]-6-chloro-2-indolinone
(120) 3-Z-[1-(4-(N-(4-methyl-piperazin-1-yl-methylcarbonyl)-N-benzyl-amino)-anilino)-1-phenyl-methylene]-6-chloro-2-indolinone
(121) 3-Z-[1-(4-(N-(4-methyl-piperazin-1-yl-methylcarbonyl)-N-aminocarbonylmethyl-amino)-anilino)-1-phenyl-methylene]-6-chloro-2-indolinone
(122) 3-Z-[1-(4-(N-(4-methyl-piperazin-1-yl-methylcarbonyl)-N-dimethylaminocarbonylmethyl-amino)-anilino)-1-phenyl-methylene]-6-chloro-2-indolinone
(123) 3-Z-[1-(4-(N-(4-methyl-piperazin-1-yl-methylcarbonyl)-N-methyl-amino)-3-bromo-anilino)-1-phenyl-methylene]-6-chloro-2-indolinone
(124) 3-Z-[1-(4-(N-(4-methyl-piperazin-1-yl-methylcarbonyl)-N-methyl-amino)-3-chloro-anilino)-1-phenyl-methylene]-6-chloro-2-indolinone
(125) 3-Z-[1-(4-(N-(4-methyl-piperazin-1-yl-methylcarbonyl)-N-methyl-amino)-3-fluoro-anilino)-1-phenyl-methylene]-6-chloro-2-indolinone
(126) 3-Z-[1-(4-(N-(4-methyl-piperazin-1-yl-methylcarbonyl)-N-methyl-amino)-3-methyl-anilino)-1-phenyl-methylene]-6-chloro-2-indolinone
(127) 3-Z-[1-(4-(N-(4-methyl-piperazin-1-yl-methylcarbonyl)-N-methyl-amino)-3-methoxy-anilino)-1-phenyl-methylene]-6-chloro-2-indolinone
(128) 3-Z-[1-(4-(N-(4-methyl-piperazin-1-yl-methylcarbonyl)-N-methyl-amino)-3-hydroxy-anilino)-1-phenyl-methylene]-6-chloro-2-indolinone
(129) 3-Z-[1-(4-(N-(4-methyl-piperazin-1-yl-methylcarbonyl)-N-methyl-amino)-3-cyano-anilino)-1-phenyl-methylene]-6-chloro-2-indolinone
(130) 3-Z-[1-(4-(N-(4-methyl-piperazin-1-yl-methylcarbonyl)-N-methyl-amino)-3-trifluormethyl-anilino)-1-phenyl-methylene]-6-chloro-2-indolinone
(131) 3-Z-[1-(4-(N-(4-methyl-piperazin-1-yl-methylcarbonyl)-N-methyl-amino)-3-aminocarbonyl-anilino)-1-phenyl-methylene]-6-chloro-2-indolinone
(132) 3-Z-[1-(4-(N-(4-methyl-piperazin-1-yl-methylcarbonyl)-N-methyl-amino)-3-amino-anilino)-1-phenyl-methylene]-6-chloro-2-indolinone
(133) 3-Z-[1-(4-(N-(4-methyl-piperazin-1-yl-methylcarbonyl)-N-methyl-amino)-3-nitro-anilino)-1-phenyl-methylene]-6-chloro-2-indolinone
(134) 3-Z-[1-(4-(N-(4-methyl-piperazin-1-yl-methylcarbonyl)-N-methyl-amino)-3-acetylamino-anilino)-1-phenyl-methylene]-6-chloro-2-indolinone
(135) 3-Z-[1-(4-(N-(4-methyl-piperazin-1-yl-methylcarbonyl)-N-methyl-amino)-3-methylsulphonylamino-anilino)-1-phenyl-methylene]-6-chloro-2-indolinone
(136) 3-Z-[1-(4-(N-(4-methyl-piperazin-1-yl-methylcarbonyl)-N-methyl-amino)-3,5-dibromo-anilino)-1-phenyl-methylene]-6-chloro-2-indolinone
(137) 3-Z-[1-(4-(N-(4-methyl-piperazin-1-yl-methylcarbonyl)-N-methyl-amino)-3,5-dichloro-anilino)-1-phenyl-methylene]-6-chloro-2-indolinone
(138) 3-Z-[1-(4-(N-(4-methyl-piperazin-1-yl-methylcarbonyl)-N-methyl-amino)-anilino)-1-phenyl-methylene]-5-nitro-6-chloro-2-indolinone
(139) 3-Z-[1-(4-(N-(4-methyl-piperazin-1-yl-methylcarbonyl)-N-methyl-amino)-(pyridin-3-yl-amino))-1-phenyl-methylene]-6-chloro-2-indolinone
(140) 3-Z-[1-(4-(N-(4-methyl-piperazin-1-yl-methylcarbonyl)-N-methyl-amino)-(pyridin-2-yl-amino))-1-phenyl-methylene]-6-chloro-2-indolinone
(141) 3-Z-[1-(4-(N-(4-methyl-piperazin-1-yl-methylcarbonyl)-amino)-3-bromo-anilino)-1-phenyl-methylene]-6-chloro-2-indolinone
(142) 3-Z-[1-(4-(N-(4-methyl-piperazin-1-yl-methylcarbonyl)-amino)-3-chloro-anilino)-1-phenyl-methylene]-6-chloro-2-indolinone
(143) 3-Z-[1-(4-(N-(4-methyl-piperazin-1-yl-methylcarbonyl)-amino)-3-fluoro-anilino)-1-phenyl-methylene]-6-chloro-2-indolinone
(144) 3-Z-[1-(4-(N-(4-methyl-piperazin-1-yl-methylcarbonyl)-amino)-3-methyl-anilino)-1-phenyl-methylene]-6-chloro-2-indolinone
(145) 3-Z-[1-(4-(N-(4-methyl-piperazin-1-yl-methylcarbonyl)-amino)-3-methoxy-anilino)-1-phenyl-methylene]-6-chloro-2-indolinone
(146) 3-Z-[1-(4-(N-(4-methyl-piperazin-1-yl-methylcarbonyl)-amino)-3-hydroxy-anilino)-1-phenyl-methylene]-6-chloro-2-indolinone
(147) 3-Z-[1-(4-(N-(4-methyl-piperazin-1-yl-methylcarbonyl)-amino)-3-cyano-anilino)-1-phenyl-methylene]-6-chloro-2-indolinone
(148) 3-Z-[1-(4-(N-(4-methyl-piperazin-1-yl-methylcarbonyl)-amino)-3-trifluormethyl-anilino)-1-phenyl-methylene]-6-chloro-2-indolinone
(149) 3-Z-[1-(4-(N-(4-methyl-piperazin-1-yl-methylcarbonyl)-amino)-3-aminocarbonyl-anilino)-1-phenyl-methylene]-6-chloro-2-indolinone
(150) 3-Z-[1-(4-(N-(4-methyl-piperazin-1-yl-methylcarbonyl)-amino)-3-amino-anilino)-1-phenyl-methylene]-6-chloro-2-indolinone
(151) 3-Z-[1-(4-(N-(4-methyl-piperazin-1-yl-methylcarbonyl)-amino)-3-nitro-anilino)-1-phenyl-methylene]-6-chloro-2-indolinone
(152) 3-Z-[1-(4-(N-(4-methyl-piperazin-1-yl-methylcarbonyl)-amino)-3-acetylamino-anilino)-1-phenyl-methylene]-6-chloro-2-indolinone
(153) 3-Z-[1-(4-(N-(4-methyl-piperazin-1-yl-methylcarbonyl)-amino)-3-methylsulphonylamino-anilino)-1-phenyl-methylene]-6-chloro-2-indolinone
(154) 3-Z-[1-(4-(N-(4-methyl-piperazin-1-yl-methylcarbonyl)-amino)-3,5-dibromo-anilino)-1-phenyl-methylene]-6-chloro-2-indolinone (155) 3-Z-[1-(4-(N-(4-methyl-piperazin-1-yl-methylcarbonyl)-amino)-3,5-dichloro-anilino)-1-phenyl-methylene]-6-chloro-2-indolinone
(156) 3-Z-[1-(4-(N-(2-dimethylamino-ethyl)-N-methylsulphonyl-amino)-anilino)-1-(4-(2-oxo-oxazolidin-3-yl)-phenyl)-methylene]-6-chloro-2-indolinone
(157) 3-Z-[1-(4-(N-(dimethylamino-methylcarbonyl)-N-methyl-amino)-anilino)-1-(4-(2-oxo-oxazolidin-3-yl)-phenyl)-methylene]-6-chloro-2-indolinone
(158) 3-Z-[1-(4-(N-(2-dimethylamino-ethyl)-N-acetyl-amino)-anilino)-1-(4-(2-oxo-oxazolidin-3-yl)-phenyl)-methylene]-6-chloro-2-indolinone
(159) 3-Z-[1-(4-(N-(3-dimethylamino-propyl)-N-acetyl-amino)-anilino)-1-(4-(2-oxo-oxazolidin-3-yl)-phenyl)-methylene]-6-chloro-2-indolinone
(160) 3-Z-[1-(4-(dimethylamino-methyl)-anilino)-1-(4-(2-oxo-oxazolidin-3-yl)-phenyl)-methylene]-6-chloro-2-indolinone
(161) 3-Z-[1-(4-ethylaminomethyl-anilino)-1-(4-(2-oxo-oxazolidin-3-yl)-phenyl)-methylene]-6-chloro-2-indolinone
(162) 3-Z-[1-(4-(N-(4-methyl-piperazin-1-yl-methylcarbonyl)-N-methyl-amino)-anilino)-1-(4-(2-oxo-oxazolidin-3-yl)-phenyl)-methylene]-6-chloro-2-indolinone
(163) 3-Z-[1-(4-(4-methyl-piperazin-1-yl-carbonyl)-anilino)-1-(4-methoxycarbonylamino-phenyl)-methylene]-6-chloro-2-indolinone
(164) 3-Z-[1-(4-(N-(2-dimethylamino-ethyl)-N-methylsulphonyl-amino)-anilino)-1-(4-methoxycarbonylamino-phenyl)-methylene]-6-chloro-2-indolinone
(165) 3-Z-[1-(4-(N-(dimethylamino-methylcarbonyl)-N-methyl-amino)-anilino)-1-(4-methoxycarbonylamino-phenyl)-methylene]-6-chloro-2-indolinone
(166) 3-Z-[1-(4-(N-(2-dimethylamino-ethyl)-N-acetyl-amino)-anilino)-1-(4-methoxycarbonylamino-phenyl)-methylene]-6-chloro-2-indolinone
(167) 3-Z-[1-(4-(N-(3-dimethylamino-propyl)-N-acetyl-amino)-anilino)-1-(4-methoxycarbonylamino-phenyl)-methylene]-6-chloro-2-indolinone
(168) 3-Z-[1-(4-(dimethylamino-methyl)-anilino)-1-(4-methoxycarbonylamino-phenyl)-methylene]-6-chloro-2-indolinone
(169) 3-Z-[1-(4-ethylaminomethyl-anilino)-1-(4-methoxycarbonylamino-phenyl)-methylene]-6-chloro-2-indolinone
(170) 3-Z-[1-(4-(N-(4-methyl-piperazin-1-yl-methylcarbonyl)-N-methyl-amino)-anilino)-1-(4-methoxycarbonylamino-phenyl)-methylene]-6-chloro-2-indolinone
(171) 3-Z-[1-(4-(4-methyl-piperazin-1-yl-carbonyl)-anilino)-1-(4-methoxycarbonylamino-phenyl)-methylene]-6-chloro-2-indolinone
(172) 3-Z-[1-(4-(N-(pyridin-4-yl-methylcarbonyl)-amino)-anilino)-1-phenyl-methylene]-6-cyano-2-indolinone
(173) 3-Z-[1-(4-(N-(2-dimethylamino-ethyl)-N-methylsulphonyl-amino)-anilino)-1-(4-(2-oxo-pyrrolidine-2-yl)-phenyl)-methylene]-6-cyano-2-indolinone
(174) 3-Z-[1-(4-(N-(dimethylamino-methylcarbonyl)-N-methyl-amino)-anilino)-1-(4-(2-oxo-pyrrolidine-2-yl)-phenyl)-methylene]-6-cyano-2-indolinone
(175) 3-Z-[1-(4-(N-(2-dimethylamino-ethyl)-N-acetyl-amino)-anilino)-1-(4-(2-oxo-pyrrolidine-2-yl)-phenyl)-methylene]-6-cyano-2-indolinone
(176) 3-Z-[1-(4-(N-(3-dimethylamino-propyl)-N-acetyl-amino)-anilino)-1-(4-(2-oxo-pyrrolidine-2-yl)-phenyl)-methylene]-6-cyano-2-indolinone
(177) 3-Z-[1-(4-(dimethylamino-methyl)-anilino)-1-(4-(2-oxo-pyrrolidine-2-yl)-phenyl)-methylene]-6-cyano-2-indolinone
(178) 3-Z-[1-(4-ethylaminomethyl-anilino)-1-(4-(2-oxo-pyrrolidine-2-yl)-phenyl)-methylene]-6-cyano-2-indolinone
(179) 3-Z-[1-(4-(N-(4-methyl-piperazin-1-yl-methylcarbonyl)-N-methyl-amino)-anilino)-1-(4-(2-oxo-pyrrolidine-2-yl)-phenyl)-methylene]-6-cyano-2-indolinone
(180) 3-Z-[1-(4-(4-methyl-piperazin-1-yl-carbonyl)-anilino)-1-(4-(2-oxo-pyrrolidine-2-yl)-phenyl)-methylene]-6-cyano-2-indolinone
(181) 3-Z-[1-(4-(N-(4-methyl-piperazin-1-yl-methylcarbonyl)-N-methyl-amino)-anilino)-1-(3,4-dimethoxy-phenyl)-methylene]-6-cyano-2-indolinone
(182) 3-Z-[1-(4-(N-(2-dimethylamino-ethyl)-N-ethylsulphonyl-amino)-anilino)-1-phenyl-methylene]-6-fluoro-2-indolinone
(183) 3-Z-[1-(4-(N-(2-dimethylamino-ethyl)-N-propionyl-amino)-anilino)-1-phenyl-methylene]-6-fluoro-2-indolinone
(184) 3-Z-[1-(4-(N-(3-dimethylaminopropyl)-N-methylsulphonyl-amino)-anilino)-1-phenyl-methylene]-6-fluoro-2-indolinone
(185) 3-Z-[1-(4-(N-(2-dimethylamino-ethyl)-N-butyryl-amino)-anilino)-1-phenyl-methylene]-6-fluoro-2-indolinone
(186) 3-Z-[1-(4-(N-(2-dimethylamino-ethyl)-N-isobutyryl-amino)-anilino)-1-phenyl-methylene]-6-fluoro-2-indolinone
(187) 3-Z-[1-(4-(N-(2-dimethylamino-ethyl)-N-acetyl-amino)-anilino)-1-phenyl-methylene]-6-fluoro-2-indolinone
(188) 3-Z-[1-(4-(N-(2-dimethylamino-ethyl)-N-benzoyl-amino)-anilino)-1-phenyl-methylene]-6-fluoro-2-indolinone
(189) 3-Z-[1-(4-(N-(2-dimethylamino-ethyl)-N-phenylacetyl-amino)-anilino)-1-phenyl-methylene]-6-fluoro-2-indolinone
(190) 3-Z-[1-(4-(N-(2-dimethylamino-ethyl)-N-(pyrid-3-yl-carbonyl)-amino)-anilino)-1-phenyl-methylene]-6-fluoro-2-indolinone
(191) 3-Z-[1-(4-(N-(2-dimethylamino-ethyl)-N-(furan-2-yl-carbonyl)-amino)-anilino)-1-phenyl-methylene]-6-fluoro-2-indolinone
(192) 3-Z-[1-(4-(N-(2-dimethylamino-ethyl)-N-(2-methoxy-benzoyl)-amino)-anilino)-1-phenyl-methylene]-6-fluoro-2-indolinone
(193) 3-Z-[1-(4-(N-(2-dimethylamino-ethyl)-N-isopropylsulphonyl-amino)-anilino)-1-phenyl-methylene]-6-fluoro-2-indolinone
(194) 3-Z-[1-(4-(N-(2-dimethylamino-ethyl)-N-benzylsulphonyl-amino)-anilino)-1-phenyl-methylene]-6-fluoro-2-indolinone
(195) 3-Z-[1-(4-(N-(4-benzyl-piperazin-1-yl-methylcarbonyl)-N-methyl-amino)-anilino)-1-phenyl-methylene]-6-fluoro-2-indolinone
(196) 3-Z-[1-(4-(N-(piperazin-1-yl-methylcarbonyl)-N-methyl-amino)-anilino)-1-phenyl-methylene]-6-fluoro-2-indolinone
(197) 3-Z-[1-(4-(N-(morpholin-4-yl-methylcarbonyl)-N-methyl-amino)-anilino)-1-phenyl-methylene]-6-fluoro-2-indolinone
(198) 3-Z-[1-(4-(N-(piperidin-1-yl-methylcarbonyl)-N-methyl-amino)-anilino)-1-phenyl-methylene]-6-fluoro-2-indolinone
(199) 3-Z-[1-(4-(N-(benzylmethylamino-methylcarbonyl)-N-methyl-amino)-anilino)-1-phenyl-methylene]-6-fluoro-2-indolinone (200) 3-Z-[1-(4-(N-(methylamino-methylcarbonyl)-N-methyl-amino)-anilino)-1-phenyl-methylene]-6-fluoro-2-indolinone
(201) 3-Z-[1-(4-((2,6-dimethyl-piperidin-1-yl)-methyl)-anilino)-1-phenyl-methylene]-6-fluoro-2-indolinone
(202) 3-Z-[1-(4-((N-(2-(2-methoxy-ethoxy)-ethyl)-N-methyl-amino)-methyl)-anilino)-1-phenyl-methylene]-6-fluoro-2-indolinone
(203) 3-Z-[1-(4-(triazol-1-yl-methyl)-anilino)-1-phenyl-methylene]-6-fluoro-2-indolinone
(204) 3-Z-[1-(4-(di-(2-hydroxy-ethyl)-amino-methyl)-anilino)-1-phenyl-methylene]-6-fluoro-2-indolinone
(205) 3-Z-[1-(4-(5-methyl-imidazol-4-yl)-anilino)-1-phenyl-methylene]-6-fluoro-2-indolinone
(206) 3-Z-[1-(4-(morpholin-4-yl-methyl)-anilino)-1-phenyl-methylene]-6-fluoro-2-indolinone
(207) 3-Z-[1-(4-(N-benzyl-N-methyl-amino-methyl)-anilino)-1-phenyl-methylene]-6-fluoro-2-indolinone
(208) 3-Z-[1-(4-(N-(2-dimethylamino-ethyl)-N-butylsulphonyl-amino)-anilino)-1-phenyl-methylene]-6-fluoro-2-indolinone
(209) 3-Z-[1-(4-(N-(2-dimethylamino-ethyl)-N-methoxyacetyl-amino)-anilino)-1-phenyl-methylene]-6-fluoro-2-indolinone
(210) 3-Z-[1-(4-(N-(2-dimethylamino-ethyl)-N-(3,4-dimethoxy-benzoyl)-amino)-anilino)-1-phenyl-methylene]-6-fluoro-2-indolinone
(211) 3-Z-[1-(4-(N-(2-hydroxy-ethyl)-N-methyl-amino-methyl)-anilino)-1-phenyl-methylene]-6-fluoro-2-indolinone
(212) 3-Z-[1-(4-(N-(2-benzylmethylamino-ethyl)-N-propionyl-amino)-anilino)-1-phenyl-methylene]-6-fluoro-2-indolinone
(213) 3-Z-[1-(4-(N-(2-methylamino-ethyl)-N-propionyl-amino)-anilino)-1-phenyl-methylene]-6-fluoro-2-indolinone
(214) 3-Z-[1-(4-(N-(2-dimethylamino-ethyl)-N-(pyrid-4-yl-carbonyl)-amino)-anilino)-1-phenyl-methylene]-6-fluoro-2-indolinone
(215) 3-Z-[1-(4-(N-(phthalimido-2-yl-methylcarbonyl)-N-methyl-amino)-anilino)-1-phenyl-methylene]-6-fluoro-2-indolinone
(216) 3-Z-[1-(4-(N-aminomethylcarbonyl-N-methyl-amino)-anilino)-1-phenyl-methylene]-6-fluoro-2-indolinone
(217) 3-Z-[1-(4-(N-tert.butoxycarbonyl-methylamino-methyl)-anilino)-1-phenyl-methylene]-6-fluoro-2-indolinone
(218) 3-Z-[1-(4-(N-(di-(2-hydroxy-ethyl)-amino-methylcarbonyl)-N-methyl-amino)-anilino)-1-phenyl-methylene]-6-fluoro-2-indolinone
(219) 3-Z-[1-(4-(N-(pyrrolidin-1-yl-methylcarbonyl)-N-methyl-amino)-anilino)-1-phenyl-methylene]-6-fluoro-2-indolinone
(220) 3-Z-[1-(4-(N-(imidazol-1-yl-methylcarbonyl)-N-methyl-amino)-anilino)-1-phenyl-methylene]-6-fluoro-2-indolinone
(221) 3-Z-[1-(4-(N-(2-(4-tert.butoxycarbonyl-piperazin-1-yl)-ethylcarbonyl)-N-methyl-amino)-anilino)-1-phenyl-methylene]-6-fluoro-2-indolinone
(222) 3-Z-[1-(4-(N-(2-(piperazin-1-yl)-ethylcarbonyl)-N-methyl-amino)-anilino)-1-phenyl-methylene]-6-fluoro-2-indolinone
(223) 3-Z-[1-(4-(N-(2-benzylmethylamino-ethyl)-N-acetyl-amino)-anilino)-1-phenyl-methylene]-6-fluoro-2-indolinone
(224) 3-Z-[1-(4-(N-(2-methylamino-ethyl)-N-acetyl-amino)-anilino)-1-phenyl-methylene]-6-fluoro-2-indolinone
(225) 3-Z-[1-(4-((4-tert.butoxycarbonyl-piperazin-1-yl)-methyl)-anilino)-1-phenyl-methylene]-6-fluoro-2-indolinone
(226) 3-Z-[1-(4-(piperazin-1-yl-methyl)-anilino)-1-phenyl-methylene]-6-fluoro-2-indolinone
(227) 3-Z-[1-(4-(N-(dimethylamino-methylcarbonyl)-N-methyl-amino)-3-methoxy-anilino)-1-phenyl-methylene]-6-fluoro-2-indolinone
(228) 3-Z-[1-(3-(dimethylamino-methyl)-anilino)-1-phenyl-methylene]-6-fluoro-2-indolinone
(229) 3-Z-[1-(4-(4-methyl-piperazin-1-yl-carbonyl)-pyridin-2-yl-amino)-1-phenyl-methylene]-6-fluoro-2-indolinone
(230) 3-Z-[1-(4-(N-(2-dimethylamino-ethyl)-N-acetyl-amino)-(pyridin-3-yl-amino))-1-phenyl-methylene]-6-fluoro-2-indolinone
(231) 3-Z-[1-(4-(4-methyl-piperazin-1-yl-carbonyl)-3-methyl-pyrrol-3-yl-amino)-1-phenyl-methylene]-6-fluoro-2-indolinone
(232) 3-Z-[1-(4-(N-(2-dimethylamino-ethyl)-N-methyl-carbamoyl)-3-methyl-pyrrol-3-yl-amino)-1-phenyl-methylene]-6-fluoro-2-indolinone
(233) 3-Z-[1-(4-(2-diethylamino-ethyl-sulphonyl)-anilino)-1-phenyl-methylene]-6-fluoro-2-indolinone
(234) 3-Z-[1-(4-(1-(2-dimethylamino-ethyl)-imidazol-2-yl)-anilino)-1-phenyl-methylene]-6-fluoro-2-indolinone
(235) 3-Z-[1-(4-(piperidin-1-yl-carbonyl)-anilino)-1-phenyl-methylene]-6-fluoro-2-indolinone
(236) 3-Z-[1-(4-(4-tert.butoxycarbonyl-piperazin-1-yl-carbonyl)-anilino)-1-phenyl-methylene]-6-fluoro-2-indolinone
(237) 3-Z-[1-(4-(piperazin-1-yl-carbonyl)-anilino)-1-phenyl-methylene]-6-fluoro-2-indolinone
(238) 3-Z-[1-(4-(N-cyclohexyl-N-methyl-carbamoyl)-anilino)-1-phenyl-methylene]-6-fluoro-2-indolinone
(239) 3-Z-[1-(4-(N-(2-(4-methyl-piperazin-1-yl)-ethyl-carbonyl)-N-methyl-amino)-anilino)-1-phenyl-methylene]-6-fluoro-2-indolinone
(240) 3-Z-[1-(4-(2-dimethylamino-ethoxy)-anilino)-1-phenyl-methylene]-6-fluoro-2-indolinone
(241) 3-Z-[1-(4-((4-dimethylamino-piperidin-1-yl)-methyl)-anilino)-1-phenyl-methylene]-6-fluoro-2-indolinone
(242) 3-Z-[1-(4-(2-dimethylamino-ethyl)-anilino)-1-phenyl-methylene]-6-fluoro-2-indolinone
(243) 3-Z-[1-(4-(N-tert.butoxycarbonyl-amino-methyl)-anilino)-1-phenyl-methylene]-6-fluoro-2-indolinone
(244) 3-Z-[1-(4-aminomethyl-anilino)-1-phenyl-methylene]-6-fluoro-2-indolinone
(245) 3-Z-[1-(4-(N-(dimethylamino-methylcarbonyl)-N-isopropyl-amino)-anilino)-1-phenyl-methylene]-6-fluoro-2-indolinone
(246) 3-Z-[1-(4-(N-(4-tert.butoxycarbonyl-piperazin-1-yl-methylcarbonyl)-N-isopropyl-amino)-anilino)-1-phenyl-methylene]-6-fluoro-2-indolinone
(247) 3-Z-[1-(4-(N-(piperazin-1-yl-methylcarbonyl)-N-isopropyl-amino)-anilino)-1-phenyl-methylene]-6-fluoro-2-indolinone
(248) 3-Z-[1-(4-(diethylamino-methyl)-anilino)-1-phenyl-methylene]-6-fluoro-2-indolinone
(249) 3-Z-[1-(4-(N-propyl-N-methyl-amino-methyl)-anilino)-1-phenyl-methylene]-6-fluoro-2-indolinone
(250) 3-Z-[1-(4-(4-methyl-piperazin-1-yl)-anilino)-1-phenyl-methylene]-6-fluoro-2-indolinone (251) 3-Z-[1-(4-(N-(2-dimethylamino-ethyl)-N-methyl-carbamoyl)-anilino)-1-phenyl-methylene]-6-fluoro-2-indolinone (252) 3-Z-[1-(4-(N-(4-tert.butoxycarbonyl-piperazin-1-yl-methylcarbonyl)-N-methyl-amino)-anilino)-1-phenyl-methylene]-6-fluoro-2-indolinone (253) 3-Z-[1-(4-(N-(piperazin-1-yl-methylcarbonyl)-N-methyl-amino)-anilino)-1-phenyl-methylene]-6-fluoro-2-indolinone (254) 3-Z-[1-(4-(N-(hydroxy-methylcarbonyl)-N-methyl-amino)-anilino)-1-phenyl-methylene]-6-fluoro-2-indolinone (255) 3-Z-[1-(4-(N-(2-dimethylamino-ethyl)-N-methyl-amino)-anilino)-1-phenyl-methylene]-6-fluoro-2-indolinone (256) 3-Z-[1-(4-(N—(N-(tert.butoxycarbonyl-3-amino-propyl)-N-methyl)-amino-methyl)-anilino)-1-phenyl-methylene]-6-fluoro-2-indolinone (257) 3-Z-[1-(4-(N—(N-(3-amino-propyl)-N-methyl)-amino-methyl)-anilino)-1-phenyl-methylene]-6-fluoro-2-indolinone (258) 3-Z-[1-(4-(N-(4-methyl-homopiperazin-1-yl-methylcarbonyl)-N-methyl-amino)-anilino)-1-phenyl-methylene]-6-fluoro-2-indolinone (259) 3-Z-[1-(4-(N-(dimethylamino-methylcarbonyl)-N-methyl-amino)-3-cyano-anilino)-1-phenyl-methylene]-6-fluoro-2-indolinone (260) 3-Z-[1-(4-(N-(4-ethyl-piperazin-1-yl-methylcarbonyl)-N-methyl-amino)-anilino)-1-phenyl-methylene]-6-fluoro-2-indolinone (261) 3-Z-[1-(4-(N-(1-methyl-piperidin-4-yl-methylcarbonyl)-N-methyl-amino)-anilino)-1-phenyl-methylene]-6-fluoro-2-indolinone (262) 3-Z-[1-(4-(N-(4-methyl-piperazin-1-yl-methylcarbonyl)-amino)-anilino)-1-phenyl-methylene]-6-fluoro-2-indolinone (263) 3-Z-[1-(4-(N-(3-dimethylamino-propyl)-N-methyl-carbamoylmethyl)-anilino)-1-phenyl-methylene]-6-fluoro-2-indolinone (264) 3-Z-[1-(4-(N-(2-dimethylamino-ethyl)-N-methyl-carbamoylmethyl)-anilino)-1-phenyl-methylene]-6-fluoro-2-indolinone (265) 3-Z-[1-(4-(4-methyl-piperazin-1-yl-carbonylmethyl)-anilino)-1-phenyl-methylene]-6-fluoro-2-indolinone (266) 3-Z-[1-(4-(N-(4-dimethylamino-butyl-carbonyl)-N-methyl-amino)-anilino)-1-phenyl-methylene]-6-fluoro-2-indolinone (267) 3-Z-[1-(4-(N-(4-methyl-piperazin-1-yl-aminocarbonyl)-N-methyl-amino)-anilino)-1-phenyl-methylene]-6-fluoro-2-indolinone (268) 3-Z-[1-(4-(N-(1-methyl-piperidin-4-yl-aminocarbonyl)-N-methyl-amino)-anilino)-1-phenyl-methylene]-6-fluoro-2-indolinone (269) 3-Z-[1-(4-(N-(3-dimethylamino-propyl-carbonyl)-N-methyl-amino)-anilino)-1-phenyl-methylene]-6-fluoro-2-indolinone (270) 3-Z-[1-(4-(N-(4-methyl-piperazin-1-yl-carbonyl)-N-methyl-amino)-anilino)-1-phenyl-methylene]-6-fluoro-2-indolinone (271) 3-Z-[1-(4-(N—(N-(3-dimethylamino-propyl)-aminocarbonyl)-N-methyl-amino)-anilino)-1-phenyl-methylene]-6-fluoro-2-indolinone (272) 3-Z-[1-(4-(N-(pyridin-4-yl-methylaminocarbonyl)-N-methyl-amino)-anilino)-1-phenyl-methylene]-6-fluoro-2-indolinone (273) 3-Z-[1-(4-(N-(1-methyl-piperidin-4-oxy-carbonyl)-N-methyl-amino)-anilino)-1-phenyl-methylene]-6-fluoro-2-indolinone (274) 3-Z-[1-(4-(N-(2-dimethylamino-ethyl)-N-methylsulphonyl-amino)-anilino)-1-(4-(2-oxo-oxazolidin-3-yl)-phenyl)-methylene]-6-fluoro-2-indolinone (275) 3-Z-[1-(4-(N-(dimethylamino-methylcarbonyl)-N-methyl-amino)-anilino)-1-(4-(2-oxo-oxazolidin-3-yl)-phenyl)-methylene]-6-fluoro-2-indolinone (276) 3-Z-[1-(4-(N-(2-dimethylamino-ethyl)-N-acetyl-amino)-anilino)-1-(4-(2-oxo-oxazolidin-3-yl)-phenyl)-methylene]-6-fluoro-2-indolinone (277) 3-Z-[1-(4-(N-(3-dimethylamino-propyl)-N-acetyl-amino)-anilino)-1-(4-(2-oxo-oxazolidin-3-yl)-phenyl)-methylene]-6-fluoro-2-indolinone (278) 3-Z-[1-(4-(dimethylamino-methyl)-anilino)-1-(4-(2-oxo-oxazolidin-3-yl)-phenyl)-methylene]-6-fluoro-2-indolinone (279) 3-Z-[1-(4-ethylaminomethyl-anilino)-1-(4-(2-oxo-oxazolidin-3-yl)-phenyl)-methylene]-6-fluoro-2-indolinone (280) 3-Z-[1-(4-(N-(4-methyl-piperazin-1-yl-methylcarbonyl)-N-methyl-amino)-anilino)-1-(4-(2-oxo-oxazolidin-3-yl)-phenyl)-methylene]-6-fluoro-2-indolinone (281) 3-Z-[1-(4-(4-methyl-piperazin-1-yl-carbonyl)-anilino)-1-(4-methoxycarbonylamino-phenyl)-methylene]-6-fluoro-2-indolinone (282) 3-Z-[1-(4-(N-(2-dimethylamino-ethyl)-N-methylsulphonyl-amino)-anilino)-1-(4-methoxycarbonylamino-phenyl)-methylene]-6-fluoro-2-indolinone (283) 3-Z-[1-(4-(N-(dimethylamino-methylcarbonyl)-N-methyl-amino)-anilino)-1-(4-methoxycarbonylamino-phenyl)-methylene]-6-fluoro-2-indolinone (284) 3-Z-[1-(4-(N-(2-dimethylamino-ethyl)-N-acetyl-amino)-anilino)-1-(4-methoxycarbonylamino-phenyl)-methylene]-6-fluoro-2-indolinone (285) 3-Z-[1-(4-(N-(3-dimethylamino-propyl)-N-acetyl-amino)-anilino)-1-(4-methoxycarbonylamino-phenyl)-methylene]-6-fluoro-2-indolinone (286) 3-Z-[1-(4-(dimethylamino-methyl)-anilino)-1-(4-methoxycarbonylamino-phenyl)-methylene]-6-fluoro-2-indolinone (287) 3-Z-[1-(4-ethylaminomethyl-anilino)-1-(4-methoxycarbonylamino-phenyl)-methylene]-6-fluoro-2-indolinone (288) 3-Z-[1-(4-(N-(4-methyl-piperazin-1-yl-methylcarbonyl)-amino)-N-methyl-anilino)-1-(4-methoxycarbonylamino-phenyl)-methylene]-6-fluoro-2-indolinone (289) 3-Z-[1-(4-(4-methyl-piperazin-1-yl-carbonyl)-anilino)-1-(4-methoxycarbonylamino-phenyl)-methylene]-6-fluoro-2-indolinone (290) 3-Z-[1-(4-(N-(2-dimethylamino-ethyl)-N-methylsulphonyl-amino)-anilino)-1-(4-(2-oxo-pyrrolidine-2-yl)-phenyl)-methylene]-6-fluoro-2-indolinone (291) 3-Z-[1-(4-(N-(dimethylamino-methylcarbonyl)-N-methyl-amino)-anilino)-1-(4-(2-oxo-pyrrolidine-2-yl)-phenyl)-methylene]-6-fluoro-2-indolinone (292) 3-Z-[1-(4-(N-(2-dimethylamino-ethyl)-N-acetyl-amino)-anilino)-1-(4-(2-oxo-pyrrolidine-2-yl)-phenyl)-methylene]-6-fluoro-2-indolinone (293) 3-Z-[1-(4-(N-(3-dimethylamino-propyl)-N-acetyl-amino)-anilino)-1-(4-(2-oxo-pyrrolidine-2-yl)-phenyl)-methylene]-6-fluoro-2-indolinone (294) 3-Z-[1-(4-(dimethylamino-methyl)-anilino)-1-(4-(2-oxo-pyrrolidine-2-yl)-phenyl)-methylene]-6-fluoro-2-indolinone (295) 3-Z-[1-(4-ethylaminomethyl-anilino)-1-(4-(2-oxo-pyrrolidine-2-yl)-phenyl)-methylene]-6-fluoro-2-indolinone
(296) 3-Z-[1-(4-(N-(4-methyl-piperazin-1-yl-methylcarbonyl)-N-methyl-amino)-anilino)-1-(4-(2-oxo-pyrrolidine-2-yl)-phenyl)-methylene]-6-fluoro-2-indolinone
(297) 3-Z-[1-(4-(4-methyl-piperazin-1-yl-carbonyl)-anilino)-1-(4-(2-oxo-pyrrolidine-2-yl)-phenyl)-methylene]-6-fluoro-2-indolinone
(298) 3-Z-[1-(4-(N-(2-dimethylamino-ethyl)-N-methylsulphonyl-amino)-anilino)-1-(4-(2-carboxy-ethyl)-phenyl)-methylene]-6-chloro-2-indolinone
(299) 3-Z-[1-(4-(N-(dimethylamino-methylcarbonyl)-N-methyl-amino)-anilino)-1-(4-(2-carboxy-ethyl)-phenyl)-methylene]-6-chloro-2-indolinone
(300) 3-Z-[1-(4-(N-(2-dimethylamino-ethyl)-N-acetyl-amino)-anilino)-1-(4-(2-carboxy-ethyl)-phenyl)-methylene]-6-chloro-2-indolinone
(301) 3-Z-[1-(4-(N-(2-methylamino-ethyl)-N-acetyl-amino)-anilino)-1-(4-(2-carboxy-ethyl)-phenyl)-methylene]-6-chloro-2-indolinone
(302) 3-Z-[1-(4-(N-(3-dimethylamino-propyl)-N-acetyl-amino)-anilino)-1-(4-(2-carboxy-ethyl)-phenyl)-methylene]-6-chloro-2-indolinone
(303) 3-Z-[1-(4-(N-(3-methylamino-propyl)-N-acetyl-amino)-amino)-1-(4-(2-carboxy-ethyl)-phenyl)-methylene]-6-chloro-2-indolinone
(304)
(305) 3-Z-[1-(4-(3-dimethylamino-propyl)-anilino)-1-(4-(2-carboxy-ethyl)-phenyl)-methylene]-6-chloro-2-indolinone
(306) 3-Z-[1-(4-ethylaminomethyl-anilino)-1-(4-(2-carboxy-ethyl)-phenyl)-methylene]-6-chloro-2-indolinone
(307) 3-Z-[1-(4-methylaminomethyl-anilino)-1-(4-(2-carboxy-ethyl)-phenyl)-methylene]-6-chloro-2-indolinone
(308) 3-Z-[1-(4-(N-(4-methyl-piperazin-1-yl-methylcarbonyl)-N-methyl-amino)-anilino)-1-(4-(2-carboxy-ethyl)-phenyl)-methylene]-6-chloro-2-indolinone
(309) 3-Z-[1-(4-(4-methyl-piperazin-1-yl-carbonyl)-anilino)-1-(4-(2-carboxy-ethyl)-phenyl)-methylene]-6-chloro-2-indolinone
(310) 3-Z-[1-(4-(N-(3-dimethylamino-propyl)-N-methylsulphonyl-amino)-anilino)-1-(4-(2-carboxy-ethyl)-phenyl)-methylene]-6-chloro-2-indolinone
(311) 3-Z-[1-(4-(N-(2-dimethylamino-ethyl)-N-propylsulphonyl-amino)-anilino)-1-(4-(2-carboxy-ethyl)-phenyl)-methylene]-6-chloro-2-indolinone
(312) 3-Z-[1-(4-aminomethyl-anilino)-1-(4-(2-carboxy-ethyl)-phenyl)-methylene]-6-chloro-2-indolinone
(313)
(314) 3-Z-[1-(3-(methylamino-methyl)-anilino)-1-(4-(2-carboxy-ethyl)-phenyl)-methylene]-6-chloro-2-indolinone
(315) 3-Z-[1-(3-(2-dimethylamino-ethyl)-anilino)-1-(4-(2-carboxy-ethyl)-phenyl)-methylene]-6-chloro-2-indolinone
(316) 3-Z-[1-(3-(3-dimethylamino-propyl)-anilino)-1-(4-(2-carboxy-ethyl)-phenyl)-methylene]-6-chloro-2-indolinone
(317)
(318) 3-Z-[1-(4-(N-(dimethylamino-carbonylmethyl)-N-methylsulphonyl-amino)-anilino)-1-(4-(2-carboxy-ethyl)-phenyl)-methylene]-6-chloro-2-indolinone
(319) 3-Z-[1-(4-(N-methyl-N-methylsulphonyl-amino)-anilino)-1-(4-(2-carboxy-ethyl)-phenyl)-methylene]-6-chloro-2-indolinone
(320) 3-Z-[1-(4-(N-methyl-N-acetyl-amino)-anilino)-1-(4-(2-carboxy-ethyl)-phenyl)-methylene]-6-chloro-2-indolinone
(321)
(322) 3-Z-[1-(4-(N—(N-(2-dimethylamino-ethyl)-N-methyl-amino-methylcarbonyl)-N-methyl-amino)-anilino)-1-(4-(2-carboxy-ethyl)-phenyl)-methylene]-6-chloro-2-indolinone
(323) 3-Z-[1-(4-(2-diethylamino-ethyl-sulphonyl)-anilino)-1-(4-(2-carboxy-ethyl)-phenyl)-methylene]-6-chloro-2-indolinone
(324) 3-Z-[1-(4-(N-(2-dimethylamino-ethyl-carbonyl)-N-methyl-amino)-anilino)-1-(4-(2-carboxy-ethyl)-phenyl)-methylene]-6-chloro-2-indolinone
(325) 3-Z-[1-(4-(N-(2-dimethylamino-ethyl)-N-methyl-amino-methyl)-anilino)-1-(4-(2-carboxy-ethyl)-phenyl)-methylene]-6-chloro-2-indolinone
(326) 3-Z-[1-(4-(2-dimethylamino-ethoxy)-anilino)-1-(4-(2-carboxy-ethyl)-phenyl)-methylene]-6-chloro-2-indolinone
(327) 3-Z-[1-(4-(N-(4-dimethylamino-butyl-carbonyl)-N-methyl-amino)-anilino)-1-(4-(2-carboxy-ethyl)-phenyl)-methylene]-6-chloro-2-indolinone
(328) 3-Z-[1-(4-(N-(3-dimethylamino-propyl-carbonyl)-N-methyl-amino)-anilino)-1-(4-(2-carboxy-ethyl)-phenyl)-methylene]-6-chloro-2-indolinone
(329) 3-Z-[1-(4-(methylethylamino-methyl)-anilino)-1-(4-(2-carboxy-ethyl)-phenyl)-methylene]-6-chloro-2-indolinone
(330) 3-Z-[1-(4-(methylpropylamino-methyl)-anilino)-1-(4-(2-carboxy-ethyl)-phenyl)-methylene]-6-chloro-2-indolinone
(331) 3-Z-[1-(4-(methylbenzylamino-methyl)-anilino)-1-(4-(2-carboxy-ethyl)-phenyl)-methylene]-6-chloro-2-indolinone
(332) 3-Z-[1-(4-(N-(2-dimethylamino-ethyl)-N-methyl-amino-methyl)-anilino)-1-(4-(2-carboxy-ethyl)-phenyl)-methylene]-6-chloro-2-indolinone
(333) 3-Z-[1-(4-(piperidin-1-yl-methyl)-anilino)-1-(4-(2-carboxy-ethyl)-phenyl)-methylene]-6-chloro-2-indolinone
(334) 3-Z-[1-(4-(azetidin-1-yl-methyl)-anilino)-1-(4-(2-carboxy-ethyl)-phenyl)-methylene]-6-chloro-2-indolinone
(335) 3-Z-[1-(4-((4-methyl-piperazin-1-yl)-methyl)-anilino)-1-(4-(2-carboxy-ethyl)-phenyl)-methylene]-6-chloro-2-indolinone
(336) 3-Z-[1-(4-(piperazin-1-yl-methyl)-anilino)-1-(4-(2-carboxy-ethyl)-phenyl)-methylene]-6-chloro-2-indolinone
(337) 3-Z-[1-(4-(morpholin-4-yl-methyl)-anilino)-1-(4-(2-carboxy-ethyl)-phenyl)-methylene]-6-chloro-2-indolinone
(338) 3-Z-[1-(4-(thiomorpholin-4-yl-methyl)-anilino)-1-(4-(2-carboxy-ethyl)-phenyl)-methylene]-6-chloro-2-indolinone
(339) 3-Z-[1-(4-(imidazol-1-yl-methyl)-anilino)-1-(4-(2-carboxy-ethyl)-phenyl)-methylene]-6-chloro-2-indolinone
(340) 3-Z-[1-(4-(N-(2-dimethylamino-ethyl)-N-methylsulphonyl-amino)-anilino)-1-(3-(2-carboxy-ethyl)-phenyl)-methylene]-6-chloro-2-indolinone
(341) 3-Z-[1-(4-(N-(dimethylamino-methylcarbonyl)-N-methyl-amino)-anilino)-1-(3-(2-carboxy-ethyl)-phenyl)-methylene]-6-chloro-2-indolinone
(342) 3-Z-[1-(4-(N-(2-dimethylamino-ethyl)-N-acetyl-amino)-anilino)-1-(3-(2-carboxy-ethyl)-phenyl)-methylene]-6-chloro-2-indolinone (343) 3-Z-[1-(4-(N-(2-methylamino-ethyl)-N-acetyl-amino)-anilino)-1-(3-(2-carboxy-ethyl)-phenyl)-methylene]-6-chloro-2-indolinone
(344) 3-Z-[1-(4-(N-(3-dimethylamino-propyl)-N-acetyl-amino)-anilino)-1-(3-(2-carboxy-ethyl)-phenyl)-methylene]-6-chloro-2-indolinone
(345) 3-Z-[1-(4-(N-(3-methylamino-propyl)-N-acetyl-amino)-anilino)-1-(3-(2-carboxy-ethyl)-phenyl)-methylene]-6-chloro-2-indolinone
(346) 3-Z-[1-(4-(3-dimethylamino-propyl)-anilino)-1-(3-(2-carboxy-ethyl)-phenyl)-methylene]-6-chloro-2-indolinone
(347) 3-Z-[1-(4-ethylaminomethyl-anilino)-1-(3-(2-carboxy-ethyl)-phenyl)-methylene]-6-chloro-2-indolinone
(348) 3-Z-[1-(4-methylaminomethyl-anilino)-1-(3-(2-carboxy-ethyl)-phenyl)-methylene]-6-chloro-2-indolinone
(349) 3-Z-[1-(4-(N-(4-methyl-piperazin-1-yl-methylcarbonyl)-N-methyl-amino)-anilino)-1-(3-(2-carboxy-ethyl)-phenyl)-methylene]-6-chloro-2-indolinone
(350) 3-Z-[1-(4-(4-methyl-piperazin-1-yl-carbonyl)-anilino)-1-(3-(2-carboxy-ethyl)-phenyl)-methylene]-6-chloro-2-indolinone
(351) 3-Z-[1-(4-(N-(3-dimethylamino-propyl)-N-methylsulphonyl-amino)-anilino)-1-(3-(2-carboxy-ethyl)-phenyl)-methylene]-6-chloro-2-indolinone
(352) 3-Z-[1-(4-(N-(2-dimethylamino-ethyl)-N-propylsulphonyl-amino)-anilino)-1-(3-(2-carboxy-ethyl)-phenyl)-methylene]-6-chloro-2-indolinone
(353) 3-Z-[1-(4-aminomethyl-anilino)-1-(3-(2-carboxy-ethyl)-phenyl)-methylene]-6-chloro-2-indolinone
(354) 3-Z-[1-(3-(dimethylamino-methyl)-anilino)-1-(3-(2-carboxy-ethyl)-phenyl)-methylene]-6-chloro-2-indolinone
(355) 3-Z-[1-(3-(methylamino-methyl)-anilino)-1-(3-(2-carboxy-ethyl)-phenyl)-methylene]-6-chloro-2-indolinone
(356) 3-Z-[1-(3-(2-dimethylamino-ethyl)-anilino)-1-(3-(2-carboxy-ethyl)-phenyl)-methylene]-6-chloro-2-indolinone
(357) 3-Z-[1-(3-(3-dimethylamino-propyl)-anilino)-1-(3-(2-carboxy-ethyl)-phenyl)-methylene]-6-chloro-2-indolinone
(358) 3-Z-[1-(4-(2-dimethylamino-ethyl)-anilino)-1-(3-(2-carboxy-ethyl)-phenyl)-methylene]-6-chloro-2-indolinone
(359) 3-Z-[1-(4-(N-(dimethylamino-carbonylmethyl)-N-methylsulphonyl-amino)-anilino)-1-(3-(2-carboxy-ethyl)-phenyl)-methylene]-6-chloro-2-indolinone
(360) 3-Z-[1-(4-(N-methyl-N-methylsulphonyl-amino)-anilino)-1-(3-(2-carboxy-ethyl)-phenyl)-methylene]-6-chloro-2-indolinone
(361) 3-Z-[1-(4-(N-methyl-N-acetyl-amino)-anilino)-1-(3-(2-carboxy-ethyl)-phenyl)-methylene]-6-chloro-2-indolinone
(362) 3-Z-[1-(4-(1-methyl-imidazol-2-yl)-anilino)-1-(3-(2-carboxy-ethyl)-phenyl)-methylene]-6-chloro-2-indolinone
(363) 3-Z-[1-(4-(N—(N-(2-dimethylamino-ethyl)-N-methyl-amino-methylcarbonyl)-N-methyl-amino)-anilino)-1-(3-(2-carboxy-ethyl)-phenyl)-methylene]-6-chloro-2-indolinone
(364) 3-Z-[1-(4-(2-diethylamino-ethyl-sulphonyl)-anilino)-1-(3-(2-carboxy-ethyl)-phenyl)-methylene]-6-chloro-2-indolinone
(365) 3-Z-[1-(4-(N-(2-dimethylamino-ethyl-carbonyl)-N-methyl-amino)-anilino)-1-(3-(2-carboxy-ethyl)-phenyl)-methylene]-6-chloro-2-indolinone
(366) 3-Z-[1-(4-(N-(2-dimethylamino-ethyl)-N-methyl-amino-methyl)-anilino)-1-(3-(2-carboxy-ethyl)-phenyl)-methylene]-6-chloro-2-indolinone
(367) 3-Z-[1-(4-(2-dimethylamino-ethoxy)-anilino)-1-(3-(2-carboxy-ethyl)-phenyl)-methylene]-6-chloro-2-indolinone
(368) 3-Z-[1-(4-(N-(4-dimethylamino-butyl-carbonyl)-N-methyl-amino)-anilino)-1-(3-(2-carboxy-ethyl)-phenyl)-methylene]-6-chloro-2-indolinone
(369) 3-Z-[1-(4-(N-(3-dimethylamino-propyl-carbonyl)-N-methyl-amino)-anilino)-1-(3-(2-carboxy-ethyl)-phenyl)-methylene]-6-chloro-2-indolinone
(370) 3-Z-[1-(4-(methylethylamino-methyl)-anilino)-1-(3-(2-carboxy-ethyl)-phenyl)-methylene]-6-chloro-2-indolinone
(371) 3-Z-[1-(4-(methylpropylamino-methyl)-anilino)-1-(3-(2-carboxy-ethyl)-phenyl)-methylene]-6-chloro-2-indolinone
(372) 3-Z-[1-(4-(methylbenzylamino-methyl)-anilino)-1-(3-(2-carboxy-ethyl)-phenyl)-methylene]-6-chloro-2-indolinone
(373) 3-Z-[1-(4-(diethylamino-methyl)-anilino)-1-(3-(2-carboxy-ethyl)-phenyl)-methylene]-6-chloro-2-indolinone
(374) 3-Z-[1-(4-(N-(2-dimethylamino-ethyl)-N-methyl-amino-methyl)-anilino)-1-(3-(2-carboxy-ethyl)-phenyl-methylene]-6-chloro-2-indolinone
(375) 3-Z-[1-(4-(piperidin-1-yl-methyl)-anilino)-1-(3-(2-carboxy-ethyl)-phenyl)-methylene]-6-chloro-2-indolinone
(376) 3-Z-[1-(4-(pyrrolidin-1-yl-methyl)-anilino)-1-(3-(2-carboxy-ethyl)-phenyl)-methylene]-6-chloro-2-indolinone
(377) 3-Z-[1-(4-(azetidin-1-yl-methyl)-anilino)-1-(3-(2-carboxy-ethyl)-phenyl)-methylene]-6-chloro-2-indolinone
(378) 3-Z-[1-(4-((4-methyl-piperazin-1-yl)-methyl)-anilino)-1-(3-(2-carboxy-ethyl)-phenyl)-methylene]-6-chloro-2-indolinone
(379) 3-Z-[1-(4-(piperazin-1-yl-methyl)-anilino)-1-(3-(2-carboxy-ethyl)-phenyl)-methylene]-6-chloro-2-indolinone
(380) 3-Z-[1-(4-(morpholin-4-yl-methyl)-anilino)-1-(3-(2-carboxy-ethyl)-phenyl)-methylene]-6-chloro-2-indolinone
(381) 3-Z-[1-(4-(thiomorpholin-4-yl-methyl)-anilino)-1-(3-(2-carboxy-ethyl)-phenyl)-methylene]-6-chloro-2-indolinone
(382) 3-Z-[1-(4-(imidazol-1-yl-methyl)-anilino)-1-(3-(2-carboxy-ethyl)-phenyl)-methylene]-6-chloro-2-indolinone
(383) 3-Z-[1-(4-(N-(2-dimethylamino-ethyl)-N-methylsulphonyl-amino)-anilino)-1-(4-carboxymethyl-phenyl)-methylene]-6-chloro-2-indolinone
(384) 3-Z-[1-(4-(N-(dimethylamino-methylcarbonyl)-N-methyl-amino)-anilino)-1-(4-carboxymethyl-phenyl)-methylene]-6-chloro-2-indolinone
(385) 3-Z-[1-(4-(N-(2-dimethylamino-ethyl)-N-acetyl-amino)-anilino)-1-(4-carboxymethyl-phenyl)-methylene]-6-chloro-2-indolinone
(386) 3-Z-[1-(4-(N-(2-methylamino-ethyl)-N-acetyl-amino)-anilino)-1-(4-carboxymethyl-phenyl)-methylene]-6-chloro-2-indolinone
(387) 3-Z-[1-(4-(N-(3-dimethylamino-propyl)-N-acetyl-amino)-anilino)-1-(4-carboxymethyl-phenyl)-methylene]-6-chloro-2-indolinone
(388) 3-Z-[1-(4-(N-(3-methylamino-propyl)-N-acetyl-amino)-anilino)-1-(4-carboxymethyl-phenyl)-methylene]-6-chloro-2-indolinone (389) 3-Z-[1-(4-(dimethylamino-methyl)-anilino)-1-(4-carboxymethyl-phenyl)-methylene]-6-chloro-2-indolinone
(390) 3-Z-[1-(4-(3-dimethylamino-propyl)-anilino)-1-(4-carboxymethyl-phenyl)-methylene]-6-chloro-2-indolinone
(391) 3-Z-[1-(4-ethylaminomethyl-anilino)-1-(4-carboxymethyl-phenyl)-methylene]-6-chloro-2-indolinone
(392) 3-Z-[1-(4-methylaminomethyl-anilino)-1-(4-carboxymethyl-phenyl)-methylene]-6-chloro-2-indolinone
(393) 3-Z-[1-(4-(N-(4-methyl-piperazin-1-yl-methylcarbonyl)-N-methyl-amino)-anilino)-1-(4-carboxymethyl-phenyl)-methylene]-6-chloro-2-indolinone
(394) 3-Z-[1-(4-(4-methyl-piperazin-1-yl-carbonyl)-anilino)-1-(4-carboxymethyl-phenyl)-methylene]-6-chloro-2-indolinone
(395) 3-Z-[1-(4-(N-(3-dimethylamino-propyl)-N-methylsulphonyl-amino)-anilino)-1-(4-carboxymethyl-phenyl)-methylene]-6-chloro-2-indolinone
(396) 3-Z-[1-(4-(N-(2-dimethylamino-ethyl)-N-propylsulphonyl-amino)-anilino)-1-(4-carboxymethyl-phenyl)-methylene]-6-chloro-2-indolinone
(397) 3-Z-[1-(4-aminomethyl-anilino)-1-(4-carboxymethyl-phenyl)-methylene]-6-chloro-2-indolinone
(398) 3-Z-[1-(3-(dimethylamino-methyl)-anilino)-1-(4-carboxymethyl-phenyl)-methylene]-6-chloro-2-indolinone
(399) 3-Z-[1-(3-(methylamino-methyl)-anilino)-1-(4-carboxymethyl-phenyl)-methylene]-6-chloro-2-indolinone
(400) 3-Z-[1-(3-(2-dimethylamino-ethyl)-anilino)-1-(4-carboxymethyl-phenyl)-methylene]-6-chloro-2-indolinone
(401) 3-Z-[1-(3-(3-dimethylamino-propyl)-anilino)-1-(4-carboxymethyl-phenyl)-methylene]-6-chloro-2-indolinone
(402) 3-Z-[1-(4-(2-dimethylamino-ethyl)-anilino)-1-(4-carboxymethyl-phenyl)-methylene]-6-chloro-2-indolinone
(403) 3-Z-[1-(4-(N-(dimethylamino-carbonylmethyl)-N-methylsulphonyl-amino)-anilino)-1-(4-carboxymethyl-phenyl)-methylene]-6-chloro-2-indolinone
(404) 3-Z-[1-(4-(N-methyl-N-methylsulphonyl-amino)-anilino)-1-(4-carboxymethyl-phenyl)-methylene]-6-chloro-2-indolinone
(405) 3-Z-[1-(4-(N-methyl-N-acetyl-amino)-anilino)-1-(4-carboxymethyl-phenyl)-methylene]-6-chloro-2-indolinone
(406) 3-Z-[1-(4-(1-methyl-imidazol-2-yl)-anilino)-1-(4-carboxymethyl-phenyl)-methylene]-6-chloro-2-indolinone
(407) 3-Z-[1-(4-(N—(N-(2-dimethylamino-ethyl)-N-methyl-amino-methylcarbonyl)-N-methyl-amino)-anilino)-1-(4-carboxymethyl-phenyl)-methylene]-6-chloro-2-indolinone
(408) 3-Z-[1-(4-(2-diethylamino-ethyl-sulphonyl)-anilino)-1-(4-carboxymethyl-phenyl)-methylene]-6-chloro-2-indolinone
(409) 3-Z-[1-(4-(N-(2-dimethylamino-ethyl-carbonyl)-N-methyl-amino)-anilino)-1-(4-carboxymethyl-phenyl)-methylene]-6-chloro-2-indolinone
(410) 3-Z-[1-(4-(N-(2-dimethylamino-ethyl)-N-methyl-amino-methyl)-anilino)-1-(4-carboxymethyl-phenyl)-methylene]-6-chloro-2-indolinone
(411) 3-Z-[1-(4-(2-dimethylamino-ethoxy)-anilino)-1-(4-carboxymethyl-phenyl)-methylene]-6-chloro-2-indolinone
(412) 3-Z-[1-(4-(N-(4-dimethylamino-butyl-carbonyl)-N-methyl-amino)-anilino)-1-(4-carboxymethyl-phenyl)-methylene]-6-chloro-2-indolinone
(413) 3-Z-[1-(4-(N-(3-dimethylamino-propyl-carbonyl)-N-methyl-amino)-anilino)-1-(4-carboxymethyl-phenyl)-methylene]-6-chloro-2-indolinone
(414) 3-Z-[1-(4-(N-(2-dimethylamino-ethyl)-N-methylsulphonyl-amino)-anilino)-1-(3-carboxymethyl-phenyl)-methylene]-6-chloro-2-indolinone
(415) 3-Z-[1-(4-(N-(dimethylamino-methylcarbonyl)-N-methyl-amino)-anilino)-1-(3-carboxymethyl-phenyl)-methylene]-6-chloro-2-indolinone
(416) 3-Z-[1-(4-(N-(2-dimethylamino-ethyl)-N-acetyl-amino)-anilino)-1-(3-carboxymethyl-phenyl)-methylene]-6-chloro-2-indolinone
(417) 3-Z-[1-(4-(N-(2-methylamino-ethyl)-N-acetyl-amino)-anilino)-1-(3-carboxymethyl-phenyl)-methylene]-6-chloro-2-indolinone
(418) 3-Z-[1-(4-(N-(3-dimethylamino-propyl)-N-acetyl-amino)-anilino)-1-(3-carboxymethyl-phenyl)-methylene]-6-chloro-2-indolinone
(419) 3-Z-[1-(4-(N-(3-methylamino-propyl)-N-acetyl-amino)-anilino)-1-(3-carboxymethyl-phenyl)-methylene]-6-chloro-2-indolinone
(420) 3-Z-[1-(4-(dimethylamino-methyl)-anilino)-1-(3-carboxymethyl-phenyl)-methylene]-6-chloro-2-indolinone
(421) 3-Z-[1-(4-(3-dimethylamino-propyl)-anilino)-1-(3-carboxymethyl-phenyl)-methylene]-6-chloro-2-indolinone
(422) 3-Z-[1-(4-ethylaminomethyl-anilino)-1-(3-carboxymethyl-phenyl)-methylene]-6-chloro-2-indolinone
(423) 3-Z-[1-(4-methylaminomethyl-anilino)-1-(3-carboxymethyl-phenyl)-methylene]-6-chloro-2-indolinone
(424) 3-Z-[1-(4-(N-(4-methyl-piperazin-1-yl-methylcarbonyl)-N-methyl-amino)-anilino)-1-(3-carboxymethyl-phenyl)-methylene]-6-chloro-2-indolinone
(425) 3-Z-[1-(4-(4-methyl-piperazin-1-yl-carbonyl)-anilino)-1-(3-carboxymethyl-phenyl)-methylene]-6-chloro-2-indolinone
(426) 3-Z-[1-(4-(N-(3-dimethylamino-propyl)-N-methylsulphonyl-amino)-anilino)-1-(3-carboxymethyl-phenyl)-methylene]-6-chloro-2-indolinone
(427) 3-Z-[1-(4-(N-(2-dimethylamino-ethyl)-N-propylsulphonyl-amino)-anilino)-1-(3-carboxymethyl-phenyl)-methylene]-6-chloro-2-indolinone
(428) 3-Z-[1-(4-aminomethyl-anilino)-1-(3-carboxymethyl-phenyl)-methylene]-6-chloro-2-indolinone
(429) 3-Z-[1-(3-(dimethylamino-methyl)-anilino)-1-(3-carboxymethyl-phenyl)-methylene]-6-chloro-2-indolinone
(430) 3-Z-[1-(3-(methylamino-methyl)-anilino)-1-(3-carboxymethyl-phenyl)-methylene]-6-chloro-2-indolinone
(431) 3-Z-[1-(3-(2-dimethylamino-ethyl)-anilino)-1-(3-carboxymethyl-phenyl)-methylene]-6-chloro-2-indolinone
(432) 3-Z-[1-(3-(3-dimethylamino-propyl)-anilino)-1-(3-carboxymethyl-phenyl)-methylene]-6-chloro-2-indolinone
(433) 3-Z-[1-(4-(2-dimethylamino-ethyl)-anilino)-1-(3-carboxymethyl-phenyl)-methylene]-6-chloro-2-indolinone
(434) 3-Z-[1-(4-(N-(dimethylamino-carbonylmethyl)-N-methylsulphonyl-amino)-anilino)-1-(3-carboxymethyl-phenyl)-methylene]-6-chloro-2-indolinone
(435) 3-Z-[1-(4-(N-methyl-N-methylsulphonyl-amino)-anilino)-1-(3-carboxymethyl-phenyl)-methylene]-6-chloro-2-indolinone
(436) 3-Z-[1-(4-(N-methyl-N-acetyl-amino)-anilino)-1-(3-carboxymethyl-phenyl)-methylene]-6-chloro-2-indolinone
(437) 3-Z-[1-(4-(1-methyl-imidazol-2-yl)-anilino)-1-(3-carboxymethyl-phenyl)-methylene]-6-chloro-2-indolinone
(438) 3-Z-[1-(4-(N—(N-(2-dimethylamino-ethyl)-N-methyl-amino-methylcarbonyl)-N-methyl-amino)-anilino)-1-(3-carboxymethyl-phenyl)-methylene]-6-chloro-2-indolinone (439) 3-Z-[1-(4-(2-diethylamino-ethyl-sulphonyl)-anilino)-1-(3-carboxymethyl-phenyl)-methylene]-6-chloro-2-indolinone
(440) 3-Z-[1-(4-(N-(2-dimethylamino-ethyl-carbonyl)-N-methyl-amino)-anilino)-1-(3-carboxymethyl-phenyl)-methylene]-6-chloro-2-indolinone
(441) 3-Z-[1-(4-(N-(2-dimethylamino-ethyl)-N-methyl-amino-methyl)-anilino)-1-(3-carboxymethyl-phenyl)-methylene]-6-chloro-2-indolinone
(442) 3-Z-[1-(4-(2-dimethylamino-ethoxy)-anilino)-1-(3-carboxymethyl-phenyl)-methylene]-6-chloro-2-indolinone
(443) 3-Z-[1-(4-(N-(4-dimethylamino-butyl-carbonyl)-N-methyl-amino)-anilino)-1-(3-carboxymethyl-phenyl)-methylene]-6-chloro-2-indolinone
(444) 3-Z-[1-(4-(N-(3-dimethylamino-propyl-carbonyl)-N-methyl-amino)-anilino)-1-(3-carboxymethyl-phenyl)-methylene]-6-chloro-2-indolinone
(445)
(446)
(447) 3-Z-[1-(4-(N-(2-methylamino-ethyl)-N-acetyl-amino)-anilino)-1-(4-(2-carboxy-ethyl)-phenyl)-methylene]-6-fluoro-2-indolinone
(448) 3-Z-[1-(4-(N-(3-methylamino-propyl)-N-acetyl-amino)-anilino)-1-(4-(2-carboxy-ethyl)-phenyl)-methylene]-6-fluoro-2-indolinone
(449) 3-Z-[1-(4-(3-dimethylamino-propyl)-anilino)-1-(4-(2-carboxy-ethyl)-phenyl)-methylene]-6-fluoro-2-indolinone
(450) 3-Z-[1-(4-ethylaminomethyl-anilino)-1-(4-(2-carboxy-ethyl)-phenyl)-methylene]-6-fluoro-2-indolinone
(451) 3-Z-[1-(4-(N-(3-dimethylamino-propyl)-N-methylsulphonyl-amino)-anilino)-1-(4-(2-carboxy-ethyl)-phenyl)-methylene]-6-fluoro-2-indolinone
(452) 3-Z-[1-(4-(N-(2-dimethylamino-ethyl)-N-propylsulphonyl-amino)-anilino)-1-(4-(2-carboxy-ethyl)-phenyl)-methylene]-6-fluoro-2-indolinone
(453)
(454)
(455) 3-Z-[1-(3-(methylamino-methyl)-anilino)-1-(4-(2-carboxy-ethyl)-phenyl)-methylene]-6-fluoro-2-indolinone
(456) 3-Z-[1-(3-(2-dimethylamino-ethyl)-anilino)-1-(4-(2-carboxy-ethyl)-phenyl)-methylene]-6-fluoro-2-indolinone
(457) 3-Z-[1-(3-(3-dimethylamino-propyl)-anilino)-1-(4-(2-carboxy-ethyl)-phenyl)-methylene]-6-fluoro-2-indolinone
(458)
(459) 3-Z-[1-(4-(N-(dimethylamino-carbonylmethyl)-N-methylsulphonyl-amino)-anilino)-1-(4-(2-carboxy-ethyl)-phenyl)-methylene]-6-fluoro-2-indolinone
(460) 3-Z-[1-(4-(N-methyl-N-methylsulphonyl-amino)-anilino)-1-(4-(2-carboxy-ethyl)-phenyl)-methylene]-6-fluoro-2-indolinone
(461) 3-Z-[1-(4-(N—(N-(2-dimethylamino-ethyl)-N-methyl-amino-methylcarbonyl)-N-methyl-amino)-anilino)-1-(4-(2-carboxy-ethyl)-phenyl)-methylene]-6-fluoro-2-indolinone
(462) 3-Z-[1-(4-(2-diethylamino-ethyl-sulphonyl)-anilino)-1-(4-(2-carboxy-ethyl)-phenyl)-methylene]-6-fluoro-2-indolinone
(463)
(464)
(465) 3-Z-[1-(4-(2-dimethylamino-ethoxy)-anilino)-1-(4-(2-carboxy-ethyl)-phenyl)-methylene]-6-fluoro-2-indolinone
(466)
(467) 3-Z-[1-(4-(N-(3-dimethylamino-propyl-carbonyl)-N-methyl-amino)-anilino)-1-(4-(2-carboxy-ethyl)-phenyl)-methylene]-6-fluoro-2-indolinone
(468) 3-Z-[1-(4-(methylethylamino-methyl)-anilino)-1-(4-(2-carboxy-ethyl)-phenyl)-methylene]-6-fluoro-2-indolinone
(469) 3-Z-[1-(4-(methylpropylamino-methyl)-anilino)-1-(4-(2-carboxy-ethyl)-phenyl)-methylene]-6-fluoro-2-indolinone
(470) 3-Z-[1-(4-(methylbenzylamino-methyl)-anilino)-1-(4-(2-carboxy-ethyl)-phenyl)-methylene]-6-fluoro-2-indolinone
(471) 3-Z-[1-(4-(piperidin-1-yl-methyl)-anilino)-1-(4-(2-carboxy-ethyl)-phenyl)-methylene]-6-fluoro-2-indolinone
(472) 3-Z-[1-(4-(azetidin-1-yl-methyl)-anilino)-1-(4-(2-carboxy-ethyl)-phenyl)-methylene]-6-fluoro-2-indolinone
(473) 3-Z-[1-(4-(piperazin-1-yl-methyl)-anilino)-1-(4-(2-carboxy-ethyl)-phenyl)-methylene]-6-fluoro-2-indolinone
(474) 3-Z-[1-(4-(morpholin-4-yl-methyl)-anilino)-1-(4-(2-carboxy-ethyl)-phenyl)-methylene]-6-fluoro-2-indolinone
(475) 3-Z-[1-(4-(thiomorpholin-4-yl-methyl)-anilino)-1-(4-(2-carboxy-ethyl)-phenyl)-methylene]-6-fluoro-2-indolinone
(476) 3-Z-[1-(4-(N-(2-dimethylamino-ethyl)-N-acetyl-amino)-anilino)-1-(3-(2-carboxy-ethyl)-phenyl)-methylene]-6-fluoro-2-indolinone
(477) 3-Z-[1-(4-(N-(2-methylamino-ethyl)-N-acetyl-amino)-anilino)-1-(3-(2-carboxy-ethyl)-phenyl)-methylene]-6-fluoro-2-indolinone
(478) 3-Z-[1-(4-(N-(3-methylamino-propyl)-N-acetyl-amino)-anilino)-1-(3-(2-carboxy-ethyl)-phenyl)-methylene]-6-fluoro-2-indolinone
(479) 3-Z-[1-(4-(3-dimethylamino-propyl)-anilino)-1-(3-(2-carboxy-ethyl)-phenyl)-methylene]-6-fluoro-2-indolinone
(480) 3-Z-[1-(4-ethylaminomethyl-anilino)-1-(3-(2-carboxy-ethyl)-phenyl)-methylene]-6-fluoro-2-indolinone
(481)
(482) 3-Z-[1-(4-(4-methyl-piperazin-1-yl-carbonyl)-anilino)-1-(3-(2-carboxy-ethyl)-phenyl)-methylene]-6-fluoro-2-indolinone
(483) 3-Z-[1-(4-(N-(3-dimethylamino-propyl)-N-methylsulphonyl-amino)-anilino)-1-(3-(2-carboxy-ethyl)-phenyl)-methylene]-6-fluoro-2-indolinone
(484) 3-Z-[1-(4-(N-(2-dimethylamino-ethyl)-N-propylsulphonyl-amino)-anilino)-1-(3-(2-carboxy-ethyl)-phenyl)-methylene]-6-fluoro-2-indolinone
(485)
(486)
(487) 3-Z-[1-(3-(methylamino-methyl)-anilino)-1-(3-(2-carboxy-ethyl)-phenyl)-methylene]-6-fluoro-2-indolinone
(488) 3-Z-[1-(3-(2-dimethylamino-ethyl)-anilino)-1-(3-(2-carboxy-ethyl)-phenyl)-methylene]-6-fluoro-2-indolinone
(489) 3-Z-[1-(3-(3-dimethylamino-propyl)-anilino)-1-(3-(2-carboxy-ethyl)-phenyl)-methylene]-6-fluoro-2-indolinone
(490)
(491) 3-Z-[1-(4-(N-(dimethylamino-carbonylmethyl)-N-methylsulphonyl-amino)-anilino)-1-(3-(2-carboxy-ethyl)-phenyl)-methylene]-6-fluoro-2-indolinone
(492) 3-Z-[1-(4-(N-methyl-N-methylsulphonyl-amino)-anilino)-1-(3-(2-carboxy-ethyl)-phenyl)-methylene]-6-fluoro-2-indolinone
(493) 3-Z-[1-(4-(N-methyl-N-acetyl-amino)-anilino)-1-(3-(2-carboxy-ethyl)-phenyl)-methylene]-6-fluoro-2-indolinone
(494)

(495) 3-Z-[1-(4-(N—(N-(2-dimethylamino-ethyl)-N-methyl-amino-methylcarbonyl)-N-methyl-amino)-anilino)-1-(3-(2-carboxy-ethyl)-phenyl)-methylene]-6-fluoro-2-indolinone
(496) 3-Z-[1-(4-(2-diethylamino-ethyl-sulphonyl)-anilino)-1-(3-(2-carboxy-ethyl)-phenyl)-methylene]-6-fluoro-2-indolinone
(497) 3-Z-[1-(4-(N-(2-dimethylamino-ethyl-carbonyl)-N-methyl-amino)-anilino)-1-(3-(2-carboxy-ethyl)-phenyl)-methylene]-6-fluoro-2-indolinone
(498) 3-Z-[1-(4-(N-(2-dimethylamino-ethyl)-N-methyl-amino-methyl)-anilino)-1-(3-(2-carboxy-ethyl)-phenyl)-methylene]-6-fluoro-2-indolinone
(499) 3-Z-[1-(4-(2-dimethylamino-ethoxy)-anilino)-1-(3-(2-carboxy-ethyl)-phenyl)-methylene]-6-fluoro-2-indolinone
(500)
(501)
(502) 3-Z-[1-(4-(methylethylamino-methyl)-anilino)-1-(3-(2-carboxy-ethyl)-phenyl)-methylene]-6-fluoro-2-indolinone
(503) 3-Z-[1-(4-(methylpropylamino-methyl)-anilino)-1-(3-(2-carboxy-ethyl)-phenyl)-methylene]-6-fluoro-2-indolinone
(504) 3-Z-[1-(4-(methylbenzylamino-methyl)-anilino)-1-(3-(2-carboxy-ethyl)-phenyl)-methylene]-6-fluoro-2-indolinone
(505) 3-Z-[1-(4-(diethylamino-methyl)-anilino)-1-(3-(2-carboxy-ethyl)-phenyl)-methylene]-6-fluoro-2-indolinone
(506) 3-Z-[1-(4-(piperidin-1-yl-methyl)-anilino)-1-(3-(2-carboxy-ethyl)-phenyl)-methylene]-6-fluoro-2-indolinone
(507) 3-Z-[1-(4-(pyrrolidin-1-yl-methyl)-anilino)-1-(3-(2-carboxy-ethyl)-phenyl)-methylene]-6-fluoro-2-indolinone
(508) 3-Z-[1-(4-(azetidin-1-yl-methyl)-anilino)-1-(3-(2-carboxy-ethyl)-phenyl)-methylene]-6-fluoro-2-indolinone
(509) 3-Z-[1-(4-(piperazin-1-yl-methyl)-anilino)-1-(3-(2-carboxy-ethyl)-phenyl)-methylene]-6-fluoro-2-indolinone
(510) 3-Z-[1-(4-(morpholin-4-yl-methyl)-anilino)-1-(3-(2-carboxy-ethyl)-phenyl)-methylene]-6-fluoro-2-indolinone
(511) 3-Z-[1-(4-(thiomorpholin-4-yl-methyl)-anilino)-1-(3-(2-carboxy-ethyl)-phenyl)-methylene]-6-fluoro-2-indolinone
(512) 3-Z-[1-(4-(N-(2-dimethylamino-ethyl)-N-acetyl-amino)-anilino)-1-(4-carboxymethyl-phenyl)-methylene]-6-fluoro-2-indolinone
(513) 3-Z-[1-(4-(N-(2-methylamino-ethyl)-N-acetyl-amino)-anilino)-1-(4-carboxymethyl-phenyl)-methylene]-6-fluoro-2-indolinone
(514) 3-Z-[1-(4-(N-(3-methylamino-propyl)-N-acetyl-amino)-anilino)-1-(4-carboxymethyl-phenyl)-methylene]-6-fluoro-2-indolinone
(515) 3-Z-[1-(4-(3-dimethylamino-propyl)-anilino)-1-(4-carboxymethyl-phenyl)-methylene]-6-fluoro-2-indolinone
(516) 3-Z-[1-(4-ethylaminomethyl-anilino)-1-(4-carboxymethyl-phenyl)-methylene]-6-fluoro-2-indolinone
(517) 3-Z-[1-(4-methylaminomethyl-anilino)-1-(4-carboxymethyl-phenyl)-methylene]-6-fluoro-2-indolinone
(518) 3-Z-[1-(4-(N-(3-dimethylamino-propyl)-N-methylsulphonyl-amino)-anilino)-1-(4-carboxymethyl-phenyl)-methylene]-6-fluoro-2-indolinone
(519) 3-Z-[1-(4-(N-(2-dimethylamino-ethyl)-N-propylsulphonyl-amino)-anilino)-1-(4-carboxymethyl-phenyl)-methylene]-6-fluoro-2-indolinone
(520) 3-Z-[1-(4-aminomethyl-anilino)-1-(4-carboxymethyl-phenyl)-methylene]-6-fluoro-2-indolinone
(521) 3-Z-[1-(3-(dimethylamino-methyl)-anilino)-1-(4-carboxymethyl-phenyl)-methylene]-6-fluoro-2-indolinone
(522) 3-Z-[1-(3-(methylamino-methyl)-anilino)-1-(4-carboxymethyl-phenyl)-methylene]-6-fluoro-2-indolinone
(523) 3-Z-[1-(3-(2-dimethylamino-ethyl)-anilino)-1-(4-carboxymethyl-phenyl)-methylene]-6-fluoro-2-indolinone
(524) 3-Z-[1-(3-(3-dimethylamino-propyl)-anilino)-1-(4-carboxymethyl-phenyl)-methylene]-6-fluoro-2-indolinone
(525)
(526) 3-Z-[1-(4-(N-methyl-N-methylsulphonyl-amino)-anilino)-1-(4-carboxymethyl-phenyl)-methylene]-6-fluoro-2-indolinone
(527) 3-Z-[1-(4-(N—(N-(2-dimethylamino-ethyl)-N-methyl-amino-methylcarbonyl)-N-methyl-amino)-anilino)-1-(4-carboxymethyl-phenyl)-methylene]-6-fluoro-2-indolinone
(528) 3-Z-[1-(4-(2-diethylamino-ethyl-sulphonyl)-anilino)-1-(4-carboxymethyl-phenyl)-methylene]-6-fluoro-2-indolinone
(529) 3-Z-[1-(4-(N-(2-dimethylamino-ethyl)-N-methyl-amino-methyl)-anilino)-1-(4-carboxymethyl-phenyl)-methylene]-6-fluoro-2-indolinone
(530) 3-Z-[1-(4-(2-dimethylamino-ethoxy)-anilino)-1-(4-carboxymethyl-phenyl)-methylene]-6-fluoro-2-indolinone
(531) 3-Z-[1-(4-(N-(4-dimethylamino-butyl-carbonyl)-N-methyl-amino)-anilino)-1-(4-carboxymethyl-phenyl)-methylene]-6-fluoro-2-indolinone
(532) 3-Z-[1-(4-(N-(2-dimethylamino-ethyl)-N-acetyl-amino)-anilino)-1-(3-carboxymethyl-phenyl)-methylene]-6-fluoro-2-indolinone
(533) 3-Z-[1-(4-(N-(2-methylamino-ethyl)-N-acetyl-amino)-anilino)-1-(3-carboxymethyl-phenyl)-methylene]-6-fluoro-2-indolinone
(534) 3-Z-[1-(4-(N-(3-dimethylamino-propyl)-N-acetyl-amino)-anilino)-1-(3-carboxymethyl-phenyl)-methylene]-6-fluoro-2-indolinone
(535) 3-Z-[1-(4-(N-(3-methylamino-propyl)-N-acetyl-amino)-anilino)-1-(3-carboxymethyl-phenyl)-methylene]-6-fluoro-2-indolinone
(536) 3-Z-[1-(4-(3-dimethylamino-propyl)-anilino)-1-(3-carboxymethyl-phenyl)-methylene]-6-fluoro-2-indolinone
(537) 3-Z-[1-(4-ethylaminomethyl-anilino)-1-(3-carboxymethyl-phenyl)-methylene]-6-fluoro-2-indolinone
(538) 3-Z-[1-(4-methylaminomethyl-anilino)-1-(3-carboxymethyl-phenyl)-methylene]-6-fluoro-2-indolinone
(539) 3-Z-[1-(4-(N-(3-dimethylamino-propyl)-N-methylsulphonyl-amino)-anilino)-1-(3-carboxymethyl-phenyl)-methylene]-6-fluoro-2-indolinone
(540) 3-Z-[1-(4-(N-(2-dimethylamino-ethyl)-N-propylsulphonyl-amino)-anilino)-1-(3-carboxymethyl-phenyl)-methylene]-6-fluoro-2-indolinone
(541) 3-Z-[1-(4-aminomethyl-anilino)-1-(3-carboxymethyl-phenyl)-methylene]-6-fluoro-2-indolinone
(542) 3-Z-[1-(3-(dimethylamino-methyl)-anilino)-1-(3-carboxymethyl-phenyl)-methylene]-6-fluoro-2-indolinone
(543) 3-Z-[1-(3-(methylamino-methyl)-anilino)-1-(3-carboxymethyl-phenyl)-methylene]-6-fluoro-2-indolinone
(544) 3-Z-[1-(3-(2-dimethylamino-ethyl)-anilino)-1-(3-carboxymethyl-phenyl)-methylene]-6-fluoro-2-indolinone (545) 3-Z-[1-(3-(3-dimethylamino-propyl)-anilino)-1-(3-carboxymethyl-phenyl)-methylene]-6-fluoro-2-indolinone
(546)
(547) 3-Z-[1-(4-(N-methyl-N-methylsulphonyl-amino)-anilino)-1-(3-carboxymethyl-phenyl)-methylene]-6-fluoro-2-indolinone
(548) 3-Z-[1-(4-(N-methyl-N-acetyl-amino)-anilino)-1-(3-carboxymethyl-phenyl)-methylene]-6-fluoro-2-indolinone
(549) 3-Z-[1-(4-(N—(N-(2-dimethylamino-ethyl)-N-methyl-amino-methylcarbonyl)-N-methyl-amino)-anilino)-1-(3-carboxymethyl-phenyl)-methylene]-6-fluoro-2-indolinone
(550) 3-Z-[1-(4-(2-diethylamino-ethyl-sulphonyl)-anilino)-1-(3-carboxymethyl-phenyl)-methylene]-6-fluoro-2-indolinone
(551) 3-Z-[1-(4-(N-(2-dimethylamino-ethyl-carbonyl)-N-methyl-amino)-anilino)-1-(3-carboxymethyl-phenyl)-methylene]-6-fluoro-2-indolinone
(552) 3-Z-[1-(4-(N-(2-dimethylamino-ethyl)-N-methyl-amino-methyl)-anilino)-1-(3-carboxymethyl-phenyl)-methylene]-6-fluoro-2-indolinone
(553) 3-Z-[1-(4-(2-dimethylamino-ethoxy)-anilino)-1-(3-carboxymethyl-phenyl)-methylene]-6-fluoro-2-indolinone
(554) 3-Z-[1-(4-(N-(3-dimethylamino-propyl-carbonyl)-N-methyl-amino)-anilino)-1-(3-carboxymethyl-phenyl)-methylene]-6-fluoro-2-indolinone
(555) 3-Z-[1-(4-(N-(2-dimethylamino-ethyl)-N-methylsulphonyl-amino)-anilino)-1-(4-(2-carboxy-ethyl)-phenyl)-methylene]-6-bromo-2-indolinone
(556) 3-Z-[1-(4-(N-(dimethylamino-methylcarbonyl)-N-methyl-amino)-anilino)-1-(4-(2-carboxy-ethyl)-phenyl)-methylene]-6-bromo-2-indolinone
(557) 3-Z-[1-(4-(N-(2-dimethylamino-ethyl)-N-acetyl-amino)-anilino)-1-(4-(2-carboxy-ethyl)-phenyl)-methylene]-6-bromo-2-indolinone
(558) 3-Z-[1-(4-(N-(2-methylamino-ethyl)-N-acetyl-amino)-anilino)-1-(4-(2-carboxy-ethyl)-phenyl)-methylene]-6-bromo-2-indolinone
(559) 3-Z-[1-(4-(N-(3-dimethylamino-propyl)-N-acetyl-amino)-anilino)-1-(4-(2-carboxy-ethyl)-phenyl)-methylene]-6-bromo-2-indolinone
(560) 3-Z-[1-(4-(N-(3-methylamino-propyl)-N-acetyl-amino)-anilino)-1-(4-(2-carboxy-ethyl)-phenyl)-methylene]-6-bromo-2-indolinone
(561) 3-Z-[1-(4-(3-dimethylamino-propyl)-anilino)-1-(4-(2-carboxy-ethyl)-phenyl)-methylene]-6-bromo-2-indolinone
(562) 3-Z-[1-(4-ethylaminomethyl-anilino)-1-(4-(2-carboxy-ethyl)-phenyl)-methylene]-6-bromo-2-indolinone
(563) 3-Z-[1-(4-methylaminomethyl-anilino)-1-(4-(2-carboxy-ethyl)-phenyl)-methylene]-6-bromo-2-indolinone
(564) 3-Z-[1-(4-(N-(4-methyl-piperazin-1-yl-methylcarbonyl)-N-methyl-amino)-anilino)-1-(4-(2-carboxy-ethyl)-phenyl)-methylene]-6-bromo-2-indolinone
(565) 3-Z-[1-(4-(4-methyl-piperazin-1-yl-carbonyl)-anilino)-1-(4-(2-carboxy-ethyl)-phenyl)-methylene]-6-bromo-2-indolinone
(566) 3-Z-[1-(4-(N-(3-dimethylamino-propyl)-N-methylsulphonyl-amino)-anilino)-1-(4-(2-carboxy-ethyl)-phenyl)-methylene]-6-bromo-2-indolinone
(567) 3-Z-[1-(4-(N-(2-dimethylamino-ethyl)-N-propylsulphonyl-amino)-anilino)-1-(4-(2-carboxy-ethyl)-phenyl)-methylene]-6-bromo-2-indolinone
(568) 3-Z-[1-(4-aminomethyl-anilino)-1-(4-(2-carboxy-ethyl)-phenyl)-methylene]-6-bromo-2-indolinone
(569) 3-Z-[1-(3-(dimethylamino-methyl)-anilino)-1-(4-(2-carboxy-ethyl)-phenyl)-methylene]-6-bromo-2-indolinone
(570) 3-Z-[1-(3-(methylamino-methyl)-anilino)-1-(4-(2-carboxy-ethyl)-phenyl)-methylene]-6-bromo-2-indolinone
(571) 3-Z-[1-(3-(2-dimethylamino-ethyl)-anilino)-1-(4-(2-carboxy-ethyl)-phenyl)-methylene]-6-bromo-2-indolinone
(572) 3-Z-[1-(3-(3-dimethylamino-propyl)-anilino)-1-(4-(2-carboxy-ethyl)-phenyl)-methylene]-6-bromo-2-indolinone
(573) 3-Z-[1-(4-(2-dimethylamino-ethyl)-anilino)-1-(4-(2-carboxy-ethyl)-phenyl)-methylene]-6-bromo-2-indolinone
(574) 3-Z-[1-(4-(N-(dimethylamino-carbonylmethyl)-N-methylsulphonyl-amino)-anilino)-1-(4-(2-carboxy-ethyl)-phenyl)-methylene]-6-bromo-2-indolinone
(575) 3-Z-[1-(4-(N-methyl-N-methylsulphonyl-amino)-anilino)-1-(4-(2-carboxy-ethyl)-phenyl)-methylene]-6-bromo-2-indolinone
(576) 3-Z-[1-(4-(N-methyl-N-acetyl-amino)-anilino)-1-(4-(2-carboxy-ethyl)-phenyl)-methylene]-6-bromo-2-indolinone
(577) 3-Z-[1-(4-(1-methyl-imidazol-2-yl)-anilino)-1-(4-(2-carboxy-ethyl)-phenyl)-methylene]-6-bromo-2-indolinone
(578) 3-Z-[1-(4-(N—(N-(2-dimethylamino-ethyl)-N-methyl-amino-methylcarbonyl)-N-methyl-amino)-anilino)-1-(4-(2-carboxy-ethyl)-phenyl)-methylene]-6-bromo-2-indolinone
(579) 3-Z-[1-(4-(2-diethylamino-ethyl-sulphonyl)-anilino)-1-(4-(2-carboxy-ethyl)-phenyl)-methylene]-6-bromo-2-indolinone
(580) 3-Z-[1-(4-(N-(2-dimethylamino-ethyl-carbonyl)-N-methyl-amino)-anilino)-1-(4-(2-carboxy-ethyl)-phenyl)-methylene]-6-bromo-2-indolinone
(581) 3-Z-[1-(4-(N-(2-dimethylamino-ethyl)-N-methyl-amino-methyl)-anilino)-1-(4-(2-carboxy-ethyl)-phenyl)-methylene]-6-bromo-2-indolinone
(582) 3-Z-[1-(4-(2-dimethylamino-ethoxy)-anilino)-1-(4-(2-carboxy-ethyl)-phenyl)-methylene]-6-bromo-2-indolinone
(583) 3-Z-[1-(4-(N-(4-dimethylamino-butyl-carbonyl)-N-methyl-amino)-anilino)-1-(4-(2-carboxy-ethyl)-phenyl)-methylene]-6-bromo-2-indolinone
(584) 3-Z-[1-(4-(N-(3-dimethylamino-propyl-carbonyl)-N-methyl-amino)-anilino)-1-(4-(2-carboxy-ethyl)-phenyl)-methylene]-6-bromo-2-indolinone
(585) 3-Z-[1-(4-(methylethylamino-methyl)-anilino)-1-(4-(2-carboxy-ethyl)-phenyl)-methylene]-6-bromo-2-indolinone
(586) 3-Z-[1-(4-(methylpropylamino-methyl)-anilino)-1-(4-(2-carboxy-ethyl)-phenyl)-methylene]-6-bromo-2-indolinone
(587) 3-Z-[1-(4-(methylbenzylamino-methyl)-anilino)-1-(4-(2-carboxy-ethyl)-phenyl)-methylene]-6-bromo-2-indolinone
(588) 3-Z-[1-(4-(N-(2-dimethylamino-ethyl)-N-methyl-amino-methyl)-anilino)-1-(4-(2-carboxy-ethyl)-phenyl-methylene]-6-bromo-2-indolinone
(589) 3-Z-[1-(4-(piperidin-1-yl-methyl)-anilino)-1-(4-(2-carboxy-ethyl)-phenyl)-methylene]-6-bromo-2-indolinone
(590) 3-Z-[1-(4-(azetidin-1-yl-methyl)-anilino)-1-(4-(2-carboxy-ethyl)-phenyl)-methylene]-6-bromo-2-indolinone (591) 3-Z-[1-(4-((4-methyl-piperazin-1-yl)-methyl)-anilino)-1-(4-(2-carboxy-ethyl)-phenyl)-methylene]-6-bromo-2-indolinone
(592) 3-Z-[1-(4-(piperazin-1-yl-methyl)-anilino)-1-(4-(2-carboxy-ethyl)-phenyl)-methylene]-6-bromo-2-indolinone
(593) 3-Z-[1-(4-(morpholin-4-yl-methyl)-anilino)-1-(4-(2-carboxy-ethyl)-phenyl)-methylene]-6-bromo-2-indolinone
(594) 3-Z-[1-(4-(thiomorpholin-4-yl-methyl)-anilino)-1-(4-(2-carboxy-ethyl)-phenyl)-methylene]-6-bromo-2-indolinone
(595) 3-Z-[1-(4-(imidazol-1-yl-methyl)-anilino)-1-(4-(2-carboxy-ethyl)-phenyl)-methylene]-6-bromo-2-indolinone
(596) 3-Z-[1-(4-dimethylaminomethyl-anilino)-1-(3-(2-carboxy-ethyl)-phenyl)-methylene]-6-bromo-2-indolinone
(597) 3-Z-[1-(4-(N-(2-dimethylamino-ethyl)-N-methylsulphonyl-amino)-anilino)-1-(3-(2-carboxy-ethyl)-phenyl)-methylene]-6-bromo-2-indolinone
(598) 3-Z-[1-(4-(N-(dimethylamino-methylcarbonyl)-N-methyl-amino)-anilino)-1-(3-(2-carboxy-ethyl)-phenyl)-methylene]-6-bromo-2-indolinone
(599) 3-Z-[1-(4-(N-(2-dimethylamino-ethyl)-N-acetyl-amino)-anilino)-1-(3-(2-carboxy-ethyl)-phenyl)-methylene]-6-bromo-2-indolinone
(600) 3-Z-[1-(4-(N-(2-methylamino-ethyl)-N-acetyl-amino)-anilino)-1-(3-(2-carboxy-ethyl)-phenyl)-methylene]-6-bromo-2-indolinone
(601) 3-Z-[1-(4-(N-(3-dimethylamino-propyl)-N-acetyl-amino)-anilino)-1-(3-(2-carboxy-ethyl)-phenyl)-methylene]-6-bromo-2-indolinone
(602) 3-Z-[1-(4-(N-(3-methylamino-propyl)-N-acetyl-amino)-anilino)-1-(3-(2-carboxy-ethyl)-phenyl)-methylene]-6-bromo-2-indolinone
(603) 3-Z-[1-(4-(3-dimethylamino-propyl)-anilino)-1-(3-(2-carboxy-ethyl)-phenyl)-methylene]-6-bromo-2-indolinone
(604) 3-Z-[1-(4-ethylaminomethyl-anilino)-1-(3-(2-carboxy-ethyl)-phenyl)-methylene]-6-bromo-2-indolinone
(605) 3-Z-[1-(4-methylaminomethyl-anilino)-1-(3-(2-carboxy-ethyl)-phenyl)-methylene]-6-bromo-2-indolinone
(606) 3-Z-[1-(4-(N-(4-methyl-piperazin-1-yl-methylcarbonyl)-N-methyl-amino)-anilino)-1-(3-(2-carboxy-ethyl)-phenyl)-methylene]-6-bromo-2-indolinone
(607) 3-Z-[1-(4-(4-methyl-piperazin-1-yl-carbonyl)-anilino)-1-(3-(2-carboxy-ethyl)-phenyl)-methylene]-6-bromo-2-indolinone
(608) 3-Z-[1-(4-(N-(3-dimethylamino-propyl)-N-methylsulphonyl-amino)-anilino)-1-(3-(2-carboxy-ethyl)-phenyl)-methylene]-6-bromo-2-indolinone
(609) 3-Z-[1-(4-(N-(2-dimethylamino-ethyl)-N-propylsulphonyl-amino)-anilino)-1-(3-(2-carboxy-ethyl)-phenyl)-methylene]-6-bromo-2-indolinone
(610) 3-Z-[1-(4-aminomethyl-anilino)-1-(3-(2-carboxy-ethyl)-phenyl)-methylene]-6-bromo-2-indolinone
(611) 3-Z-[1-(3-(dimethylamino-methyl)-anilino)-1-(3-(2-carboxy-ethyl)-phenyl)-methylene]-6-bromo-2-indolinone
(612) 3-Z-[1-(3-(methylamino-methyl)-anilino)-1-(3-(2-carboxy-ethyl)-phenyl)-methylene]-6-bromo-2-indolinone
(613) 3-Z-[1-(3-(2-dimethylamino-ethyl)-anilino)-1-(3-(2-carboxy-ethyl)-phenyl)-methylene]-6-bromo-2-indolinone
(614) 3-Z-[1-(3-(3-dimethylamino-propyl)-anilino)-1-(3-(2-carboxy-ethyl)-phenyl)-methylene]-6-bromo-2-indolinone
(615) 3-Z-[1-(4-(2-dimethylamino-ethyl)-anilino)-1-(3-(2-carboxy-ethyl)-phenyl)-methylene]-6-bromo-2-indolinone
(616) 3-Z-[1-(4-(N-(dimethylamino-carbonylmethyl)-N-methylsulphonyl-amino)-anilino)-1-(3-(2-carboxy-ethyl)-phenyl)-methylene]-6-bromo-2-indolinone
(617) 3-Z-[1-(4-(N-methyl-N-methylsulphonyl-amino)-anilino)-1-(3-(2-carboxy-ethyl)-phenyl)-methylene]-6-bromo-2-indolinone
(618) 3-Z-[1-(4-(N-methyl-N-acetyl-amino)-anilino)-1-(3-(2-carboxy-ethyl)-phenyl)-methylene]-6-bromo-2-indolinone
(619) 3-Z-[1-(4-(1-methyl-imidazol-2-yl)-anilino)-1-(3-(2-carboxy-ethyl)-phenyl)-methylene]-6-bromo-2-indolinone
(620) 3-Z-[1-(4-(N—(N-(2-dimethylamino-ethyl)-N-methyl-amino-methylcarbonyl)-N-methyl-amino)-anilino)-1-(3-(2-carboxy-ethyl)-phenyl)-methylene]-6-bromo-2-indolinone
(621) 3-Z-[1-(4-(2-diethylamino-ethyl-sulphonyl)-anilino)-1-(3-(2-carboxy-ethyl)-phenyl)-methylene]-6-bromo-2-indolinone
(622) 3-Z-[1-(4-(N-(2-dimethylamino-ethyl-carbonyl)-N-methyl-amino)-anilino)-1-(3-(2-carboxy-ethyl)-phenyl)-methylene]-6-bromo-2-indolinone
(623) 3-Z-[1-(4-(N-(2-dimethylamino-ethyl)-N-methyl-amino-methyl)-anilino)-1-(3-(2-carboxy-ethyl)-phenyl)-methylene]-6-bromo-2-indolinone
(624) 3-Z-[1-(4-(2-dimethylamino-ethoxy)-anilino)-1-(3-(2-carboxy-ethyl)-phenyl)-methylene]-6-bromo-2-indolinone
(625) 3-Z-[1-(4-(N-(4-dimethylamino-butyl-carbonyl)-N-methyl-amino)-anilino)-1-(3-(2-carboxy-ethyl)-phenyl)-methylene]-6-bromo-2-indolinone
(626) 3-Z-[1-(4-(N-(3-dimethylamino-propyl-carbonyl)-N-methyl-amino)-anilino)-1-(3-(2-carboxy-ethyl)-phenyl)-methylene]-6-bromo-2-indolinone
(627) 3-Z-[1-(4-(methylethylamino-methyl)-anilino)-1-(3-(2-carboxy-ethyl)-phenyl)-methylene]-6-bromo-2-indolinone
(628) 3-Z-[1-(4-(methylpropylamino-methyl)-anilino)-1-(3-(2-carboxy-ethyl)-phenyl)-methylene]-6-bromo-2-indolinone
(629) 3-Z-[1-(4-(methylbenzylamino-methyl)-anilino)-1-(3-(2-carboxy-ethyl)-phenyl)-methylene]-6-bromo-2-indolinone
(630) 3-Z-[1-(4-(diethylamino-methyl)-anilino)-1-(3-(2-carboxy-ethyl)-phenyl)-methylene]-6-bromo-2-indolinone
(631) 3-Z-[1-(4-(N-(2-dimethylamino-ethyl)-N-methyl-amino-methyl)-anilino)-1-(3-(2-carboxy-ethyl)-phenyl)-methylene]-6-bromo-2-indolinone
(632) 3-Z-[1-(4-(piperidin-1-yl-methyl)-anilino)-1-(3-(2-carboxy-ethyl)-phenyl)-methylene]-6-bromo-2-indolinone
(633) 3-Z-[1-(4-(pyrrolidin-1-yl-methyl)-anilino)-1-(3-(2-carboxy-ethyl)-phenyl)-methylene]-6-bromo-2-indolinone
(634) 3-Z-[1-(4-(azetidin-1-yl-methyl)-anilino)-1-(3-(2-carboxy-ethyl)-phenyl)-methylene]-6-bromo-2-indolinone
(635) 3-Z-[1-(4-((4-methyl-piperazin-1-yl)-methyl)-anilino)-1-(3-(2-carboxy-ethyl)-phenyl)-methylene]-6-bromo-2-indolinone
(636) 3-Z-[1-(4-(piperazin-1-yl-methyl)-anilino)-1-(3-(2-carboxy-ethyl)-phenyl)-methylene]-6-bromo-2-indolinone
(637) 3-Z-[1-(4-(morpholin-4-yl-methyl)-anilino)-1-(3-(2-carboxy-ethyl)-phenyl)-methylene]-6-bromo-2-indolinone
(638) 3-Z-[1-(4-(thiomorpholin-4-yl-methyl)-anilino)-1-(3-(2-carboxy-ethyl)-phenyl)-methylene]-6-bromo-2-indolinone (639) 3-Z-[1-(4-(imidazol-1-yl-methyl)-anilino)-1-(3-(2-carboxy-ethyl)-phenyl)-methylene]-6-bromo-2-indolinone
(640) 3-Z-[1-(4-dimethylaminomethyl-anilino)-1-(4-carboxymethylamino-phenyl)-methylene]-6-fluoro-2-indolinone
(641) 3-Z-[1-(4-dimethylaminomethyl-anilino)-1-(3-carboxymethylamino-phenyl)-methylene]-6-fluoro-2-indolinone
(642) 3-Z-[1-(4-dimethylaminomethyl-anilino)-1-(4-(N-methyl-carboxymethylamino)-phenyl)-methylene]-6-fluoro-2-indolinone
(643) 3-Z-[1-(4-dimethylaminomethyl-anilino)-1-(3-(N-methyl-carboxymethylamino)-phenyl)-methylene]-6-fluoro-2-indolinone
(644) 3-Z-[1-(4-dimethylaminomethyl-anilino)-1-(4-carboxymethoxy-phenyl)-methylene]-6-chloro-2-indolinone
(645) 3-Z-[1-(4-dimethylaminomethyl-anilino)-1-(3-carboxymethoxy-phenyl)-methylene]-6-chloro-2-indolinone
(646) 3-Z-[1-(4-dimethylaminomethyl-anilino)-1-(4-carboxymethylamino-phenyl)-methylene]-6-chloro-2-indolinone
(647) 3-Z-[1-(4-dimethylaminomethyl-anilino)-1-(3-carboxymethylamino-phenyl)-methylene]-6-chloro-2-indolinone
(648) 3-Z-[1-(4-dimethylaminomethyl-anilino)-1-(4-(N-methyl-carboxymethylamino)-phenyl)-methylene]-6-chloro-2-indolinone
(649) 3-Z-[1-(4-dimethylaminomethyl-anilino)-1-(3-(N-methyl-carboxymethylamino)-phenyl)-methylene]-6-chloro-2-indolinone
(650) 3-Z-[1-(4-dimethylaminomethyl-anilino)-1-(4-carboxymethoxy-phenyl)-methylene]-6-bromo-2-indolinone
(651) 3-Z-[1-(4-dimethylaminomethyl-anilino)-1-(3-carboxymethoxy-phenyl)-methylene]-6-bromo-2-indolinone
(652) 3-Z-[1-(4-dimethylaminomethyl-anilino)-1-(4-carboxymethylamino-phenyl)-methylene]-6-bromo-2-indolinone
(653) 3-Z-[1-(4-dimethylaminomethyl-anilino)-1-(3-carboxymethylamino-phenyl)-methylene]-6-bromo-2-indolinone
(654) 3-Z-[1-(4-dimethylaminomethyl-anilino)-1-(4-(N-methyl-carboxymethylamino)-phenyl)-methylene]-6-bromo-2-indolinone
(655) 3-Z-[1-(4-dimethylaminomethyl-anilino)-1-(3-(N-methyl-carboxymethylamino)-phenyl)-methylene]-6-bromo-2-indolinone In the above Tables
Me denotes methyl,
Et denotes ethyl,
Pr denotes propyl,
nPr denotes n-propyl,
iPr denotes isopropyl,
nBu denotes n-butyl,
tBu denotes tert.-butyl and
Bn denotes benzyl.

The invention claimed is:
1. Compounds of general formula

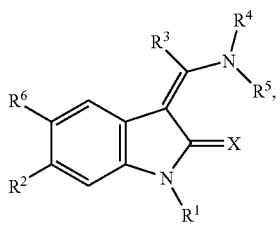

(I)

wherein

X denotes an oxygen or sulphur atom, $R^1$ denotes a hydrogen atom, a $C_{1-4}$-alkoxy-carbonyl, $C_{1-3}$-alkyl-carbonyl, aminomethyl, $C_{1-3}$-alkylaminomethyl, di-($C_{1-3}$-alkyl)-aminomethyl or a 5- to 7-membered cycloalkyleneiminomethyl group, $R^2$ denotes a fluorine, chlorine or bromine atom or a cyano group, $R^3$ denotes a phenyl group or a phenyl group mono- or disubstituted by a fluorine, chlorine, bromine or iodine atom, by a trifluoromethyl, $C_{1-3}$-alkyl or $C_{1-3}$-alkoxy group, while in the case of disubstitution the substituents may be identical or different and the abovementioned unsubstituted as well as the mono- and disubstituted phenyl group may additionally be substituted by a fluorine, chlorine, bromine or iodine atom, by a $C_{1-3}$-alkyl, $C_{1-4}$-alkoxy, $C_{1-4}$-alkoxy-carbonyl, $C_{1-4}$-alkyloxy-carbonylamino, aminocarbonyl, $C_{1-3}$-alkylamino-carbonyl, di-($C_{1-3}$-alkyl)-aminocarbonyl, benzyloxy, carboxy, cyano, trifluoromethyl, nitro, amino, $C_{4-7}$-cycloalkylamino, $C_{1-3}$-alkyl-carbonyl-amino, N—($C_{1-3}$-alkyl)-N—($C_{1-3}$-alkyl-carbonyl)-amino, phenyl-carbonylamino, N—($C_{1-3}$-alkyl)-N-(phenyl-carbonyl)-amino, benzylcarbonylamino, N—($C_{1-3}$-alkyl)-N-(benzylcarbonyl)-amino, hydroxy, $C_{1-3}$-alkylsulphonylamino, N—($C_{1-3}$-alkyl)-$C_{1-3}$-alkylsulphonylamino, phenylsulphonylamino, N—($C_{1-3}$-alkyl)-phenylsulphonylamino, phenyl-$C_{1-3}$-alkyl-sulphonylamino, N—($C_{1-3}$-alkyl)-N-(phenyl-$C_{1-3}$-alkyl-sulphonyl)-amino, $C_{1-3}$-alkylamino or di-($C_{1-3}$-alkyl)-amino group, by a $C_{1-3}$-alkyl group which is substituted by a hydroxy, cyano, carboxy, $C_{1-4}$-alkoxy, $C_{1-4}$-alkoxy-carbonyl, aminocarbonyl, ($C_{1-3}$-alkylamino)-carbonyl, di-($C_{1-3}$-alkyl)-aminocarbonyl, amino, $C_{1-3}$-alkylamino, [di-($C_{1-3}$-alkyl)-amino], N—($C_{1-4}$-alkoxy-carbonyl)-amino, N—($C_{1-4}$-alkoxy-carbonyl)-N—($C_{1-3}$-alkyl)-amino, phenylamino, diphenylamino, N-phenyl-N—($C_{1-3}$-alkyl)-amino, benzylamino, dibenzylamino, N-benzyl-N—($C_{1-3}$-alkyl)-amino, heteroarylamino, N-heteroaryl-N—($C_{1-3}$-alkyl)-amino, $C_{1-4}$-alkyl-sulphonylamino, N—($C_{1-3}$-alkyl)-$C_{1-4}$-alkylsulphonylamino, phenyl-sulphonylamino, N—($C_{1-3}$-alkyl)-phenylsulphonylamino, phenyl-$C_{1-3}$-alkyl-sulphonylamino, N—($C_{1-3}$-alkyl)-N-(phenyl-$C_{1-3}$-alkyl-sulphonyl)-amino, benzylcarbonylamino, N—($C_{1-3}$-alkyl)-N-(benzylcarbonyl)-amino, phenylcarbonylamino, N—($C_{1-3}$-alkyl)-N-(phenylcarbonyl)-amino, 4-($C_{1-3}$-alkyl)-piperazin-1-yl-carbonyl, ($C_{1-6}$-alkyl-carbonyl)-amino, N—($C_{1-3}$-alkyl)-N—($C_{1-6}$-alkyl-carbonyl)-amino, ($C_{3-7}$-cycloalkyl-carbonyl)-amino, N—($C_{1-3}$-alkyl)-N—($C_{3-7}$-cycloalkyl-carbonyl)-amino, ($C_{3-7}$-cycloalkyl-$C_{1-3}$-alkyl-carbonyl)-amino, N—($C_{1-3}$-alkyl)-N—($C_{3-7}$-cycloalkyl-$C_{1-3}$-alkyl-carbonyl)-amino, ($C_{1-4}$-alkoxy-$C_{1-3}$-alkyl-carbonyl)-amino, N—($C_{1-3}$-alkyl)-N—($C_{1-4}$-alkoxy-$C_{1-3}$-alkyl-carbonyl)-amino, (heteroaryl-carbonyl)-amino, N—($C_{1-3}$-alkyl)-N-(heteroaryl-carbonyl)-amino, ($C_{3-7}$-cycloalkyl-sulphonyl)-amino, N—($C_{1-3}$-alkyl)-N—($C_{3-7}$-cycloalkyl-sulphonyl)-amino, ($C_{3-7}$-cycloalkyl-$C_{1-3}$-alkyl-sulphonyl)-amino, N—($C_{1-3}$-alkyl)-N—($C_{3-7}$-cycloalkyl-$C_{1-3}$-alkyl-sulphonyl)-amino, ($C_{1-4}$-alkoxy-$C_{1-3}$-alkyl-sulphonyl)-amino, N—($C_{1-3}$-alkyl)-N—($C_{1-4}$-alkoxy-$C_{1-3}$-alkyl-sulphonyl)-amino, (heteroaryl-sulphonyl)-amino, N—($C_{1-3}$-alkyl)-N-(heteroaryl-sulphonyl)-amino, tetrazolyl or heteroaryl group,
by a carboxy-$C_{2-3}$-alkenyl, aminocarbonyl-$C_{2-3}$-alkenyl, ($C_{1-3}$-alkylamino)-carbonyl-$C_{2-3}$-alkenyl, di-($C_{1-3}$-alkyl)-amino-carbonyl-$C_{2-3}$-alkenyl or $C_{1-4}$-alkoxy-carbonyl-$C_{2-3}$-alkenyl group,
by a heteroaryl group or
by a cycloalkyleneimino or cycloalkyleneimino-$C_{1-3}$-alkyl group with in each case 5 to 7 ring members, wherein in each case a methylene group linked to the imino group is replaced by a carbonyl or sulphonyl group or the two methylene groups linked to the imino group are each replaced by a carbonyl group or a —$CH_2$—$CH_2$— group linked to the imino group is replaced by the group —O—CO—, while the carbonyl group of the —O—CO— group is linked to the imino group and a phenyl ring may be fused to the 5- to 7-membered cycloalkyleneimino group via two adjacent carbon atoms, or
by a cycloalkyleneimino, cycloalkyleneiminocarbonyl, cycloalkyleneiminosulphonyl, cycloalkyleneimino-$C_{1-3}$-alkyl, cycloalkyleneiminocarbonyl-$C_{1-3}$-alkyl or cycloalkyleneiminosulphonyl-$C_{1-3}$-alkyl group with 4 to 7 ring members in each case, while
in each case the methylene group in the 4 position of a 6- or 7-membered cycloalkyleneimino group may be substituted by a carboxy, $C_{1-4}$-alkoxy-carbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or
may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl)- group,
while the substituents may be identical or different,
$R^4$ denotes a phenyl group substituted by the group $R_9$ which may additionally be mono- or disubstituted by fluorine, chlorine, bromine or iodine atoms, by $C_{1-5}$-alkyl, trifluoromethyl, hydroxy, $C_{1-4}$-alkoxy, benzyloxy, carboxy, $C_{1-4}$-alkoxy-carbonyl, amino, $C_{1-3}$-alkylamino, di-($C_{1-3}$-alkyl)-amino, acetylamino, $C_{1-3}$-alkylsulphonylamino, aminocarbonyl, $C_{1-3}$-alkyl-aminocarbonyl, di-($C_{1-3}$-alkyl)-aminocarbonyl, aminosulphonyl, $C_{1-3}$-alkyl-aminosulphonyl, di-($C_{1-3}$-alkyl)-aminosulphonyl, nitro or cyano groups, while the substituents may be identical or different and wherein
$R_9$ denotes a hydrogen, fluorine, chlorine, bromine or iodine atom,
a cyano, nitro, amino, $C_{1-5}$-alkyl, $C_{3-7}$-cycloalkyl, trifluoromethyl, phenyl, tetrazolyl or heteroaryl group,
a $C_{1-3}$-alkyl-sulphonyl, amino-$C_{1-3}$-alkyl-sulphonyl, ($C_{1-3}$-alkylamino)-$C_{1-3}$-alkylsulphonyl or di-($C_{1-3}$-alkyl)-amino-$C_{1-3}$-alkylsulphonyl group,
a $C_{1-4}$-alkoxy group, a ω-$C_{1-3}$-alkoxy-$C_{2-3}$-alkoxy, phenyl-$C_{1-3}$-alkoxy, ω-amino-$C_{2-3}$-alkoxy, ω-($C_{1-3}$-alkylamino)-$C_{2-3}$-alkoxy, ω-[di-($C_{1-3}$-alkyl)-amino]-$C_{2-3}$-alkoxy, ω-(phenyl-$C_{1-3}$-alkylamino)-$C_{2-3}$-alkoxy, ω-[N—($C_{1-3}$-alkyl)-phenyl-$C_{1-3}$-alkyl-amino]-$C_{2-3}$-alkoxy, ω-($C_{5-7}$-cycloalkyleneimino)-$C_{2-3}$-alkoxy or $C_{1-3}$-alkylmercapto group,
a carboxy or $C_{1-4}$-alkoxy-carbonyl group, aminocarbonyl, $C_{1-4}$-alkylamino-carbonyl, N—($C_{1-5}$-alkyl)-$C_{1-3}$-alkylaminocarbonyl, $C_{3-7}$-cycloalkylamino-carbonyl, N—($C_{1-5}$-alkyl)-$C_{3-7}$-cycloalkylaminocarbonyl, (phenyl-$C_{1-3}$-alkyl)-amino-carbonyl, N—($C_{1-3}$-alkyl)-phenyl-$C_{1-3}$-alkylamino-carbonyl group,
a $C_{1-3}$-alkylaminocarbonyl or N—($C_{1-3}$-alkyl)-$C_{1-3}$-alkylaminocarbonyl group, wherein one or two alkyl moieties are substituted independently of one another by a nitro, cyano, carbamoyl, N—($C_{1-3}$-alkyl)-carbamoyl, di-N—($C_{1-3}$-alkyl)-carbamoyl, carboxy or $C_{1-4}$-alkoxycarbonyl group or in the 2 or 3 position by an amino, ($C_{1-3}$-alkyl)-amino, di-($C_{1-3}$-alkyl)-amino, ($C_{1-4}$-alkoxy-carbonyl)-amino, N—($C_{1-4}$-alkoxy-carbonyl)-N—($C_{1-3}$-alkyl)-amino, piperazino, N—($C_{1-3}$-alkyl)-piperazino, a 4- to 7-membered cycloalkyleneimino group, a hydroxy or methoxy group,
a 4- to 7-membered cycloalkyleneiminocarbonyl group wherein
the cycloalkylene moiety may be fused to a phenyl ring via two adjacent ring atoms or may be bridged to a methylene or ethylene group via two non-adjacent ring atoms or
one or two hydrogen atoms in each case may be replaced by a $C_{1-3}$-alkyl group and/or
in each case the methylene group in the 4 position of a 6- or 7-membered cyclo-alkyleneiminocarbonyl group may be substituted by a carboxy, $C_{1-4}$-alkoxy-carbonyl, aminocarbonyl, $C_{1-3}$-alkylaminocarbonyl, di-($C_{1-3}$-alkyl)-aminocarbonyl, di-($C_{1-3}$-alkyl)-amino-$C_{1-3}$-alkyl, di-($C_{1-3}$-alkyl)-amino, phenyl-$C_{1-3}$-alkylamino or N—($C_{1-3}$-alkyl)-phenyl-$C_{1-3}$-alkylamino group, a hydroxy or methoxy group or
replaced by an oxygen or sulphur atom, by a sulphinyl, sulphonyl or —NH group or by a nitrogen atom, the by a $C_{1-3}$-alkyl, phenyl, $C_{1-3}$-alkyl-carbonyl, $C_{1-4}$-alkoxy-carbonyl, di-($C_{1-3}$-alkyl)-amino-$C_{1-3}$-alkyl, ω-hydroxy-$C_{2-3}$-alkyl or benzoyl group,
a 4- to 7-membered cycloalkyleneimino group wherein
a methylene group linked to the imino group by a carbonyl or sulphonyl group may be replaced or
the cycloalkylene moiety may be fused to a phenyl ring or
one or two hydrogen atoms in each case may be replaced by a $C_{1-3}$-alkyl group and/or
in each case the methylene group in the 4 position of a 6- or 7-membered cyclo-alkyleneimino group may be substituted by a carboxy, $C_{1-4}$-alkoxy-carbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or
replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group,
a $C_{1-4}$-alkyl group substituted by the group $R_{10}$, where denotes a $C_{3-7}$-cycloalkyl group,
while the methylene group in the 4 position of a 6- or 7-membered cycloalkyl group may be substituted by an amino, $C_{1-3}$-alkylamino or di-($C_{1-3}$-alkyl)-amino group or replaced by a —NH or —N($C_{1-3}$-alkyl) group or
in a 5- to 7-membered cycloalkyl group a —$(CH_2)_2$ group may be replaced by a —CO—NH group, a —$(CH_2)_3$ group may be replaced by a —NH—CO—NH or —CO—NH—CO group or a —$(CH_2)_4$ group may be replaced by a —NH—CO—NH—CO group, while in each case a hydrogen atom bonded to a nitrogen atom may be replaced by a $C_{1-3}$-alkyl group,
a phenyl, triazolyl or heteroaryl group,
a hydroxy or $C_{1-4}$-alkoxy group, an amino, $C_{1-7}$-alkylamino, di-($C_{1-7}$-alkyl)-amino, phenylamino, N-phenyl-N—($C_{1-3}$-alkyl)-amino, N-(phenyl-$C_{1-3}$-alkyl)-amino, N—($C_{1-3}$-alkyl)-N-(phenyl-$C_{1-3}$-alkyl)-amino or di-(phenyl-$C_{1-3}$-alkyl)-amino group, a ω-hydroxy-$C_{2-3}$-alkyl-amino, N—($C_{1-3}$-alkyl)-(ω-hydroxy-$C_{2-3}$-alkyl)-amino, di-(ω-hydroxy-$C_{2-3}$-alkyl)-amino or di-(ω-($C_{1-3}$-alkoxy)-$C_{2-3}$-alkyl)-amino- group, a $C_{1-3}$-alkyl-carbonylamino-$C_{2-3}$-alkyl-amino or $C_{1-3}$-alkyl-carbonyl-amino-$C_{2-3}$-alkyl-N—($C_{1-3}$-alkyl)-amino group, a $C_{1-4}$-alkyloxy-carbonyl-amino, N—($C_{1-4}$-alkyloxy-carbonyl)-N—($C_{1-3}$-alkyl)-amino or N-{ω-[N—($C_{1-4}$-alkoxy-carbonyl)-amino]-($C_{1-4}$-alkyl)}-N—($C_{1-3}$-alkyl)-amino group, a $C_{1-3}$-alkylsulphonylamino, N—($C_{1-3}$-alkyl)-$C_{1-3}$-alkylsulphonylamino, $C_{1-3}$-alkyl-sulphonylamino-$C_{2-3}$-alkyl-amino or $C_{1-3}$-alkylsulphonylamino-$C_{2-3}$-alkyl-N—($C_{1-3}$-alkyl)-amino group, a hydroxycarbonyl-$C_{1-3}$-alkylamino or N—($C_{1-3}$-alkyl)-hydroxycarbonyl-$C_{1-3}$-alkyl-amino group, an N-(ω-amino-$C_{2-3}$-alkyl)-N—($C_{1-3}$-alkyl)-amino, N-(ω-$C_{1-3}$-alkylamino-$C_{2-3}$-alkyl)-N—($C_{1-3}$-alkyl)-amino, N-[ω-di-($C_{1-3}$-alkyl)-amino-$C_{2-3}$-alkyl]-N—($C_{1-3}$-alkyl)-amino, N-(ω-$C_{1-3}$-alkoxy-$C_{2-3}$-alkoxy-$C_{1-3}$-alkyl)-amino or N-(ω-$C_{1-3}$-alkoxy-$C_{2-3}$-alkoxy-$C_{1-3}$-alkyl)-N—($C_{1-3}$-alkyl)-amino group, a guanidino group wherein one or two hydrogen atoms may each be replaced by a $C_{1-3}$-alkyl group, a $C_{4-7}$-cycloalkylamino, $C_{4-7}$-cycloalkyl-$C_{1-3}$-alkylamino or $C_{4-7}$-cycloalkenylamino group wherein position 1 of the ring does not participate in the double bond and the abovementioned groups may each additionally be substituted at the aminonitrogen atom by a $C_{5-7}$-cycloalkyl, $C_{2-4}$-alkenyl or $C_{1-4}$-alkyl group may, a 4- to 7-membered cycloalkyleneimino group wherein
the cycloalkylene moiety may be fused with a phenyl group or with an oxazolo, imidazolo, thiazolo, pyridino, pyrazino or pyrimidino group optionally substituted by a fluorine, chlorine, bromine or iodine atom or by a nitro, $C_{1-3}$-alkyl, $C_{1-3}$-alkoxy or amino group and/or one or two hydrogen atoms may each be replaced by a $C_{1-3}$-alkyl, $C_{1-4}$-alkoxy-carbonyl, amino, $C_{1-3}$-alkylamino or di-($C_{1-3}$-alkyl)-amino group $C_{5-7}$-cycloalkyl or phenyl group and/or the methylene group in position 3 of a 5-membered cycloalkyleneimino group may be substituted by a hydroxy, hydroxy-$C_{1-3}$-alkyl, $C_{1-4}$-alkoxy or $C_{1-3}$-alkoxy-$C_{1-3}$-alkyl group, in each case the methylene group in position 3 or 4 of a 6- or 7-membered cycloalkyleneimino group may be substituted by a hydroxy, hydroxy-$C_{1-3}$-alkyl, $C_{1-4}$-alkoxy, $C_{1-4}$-alkoxy-$C_{1-3}$-alkyl, carboxy, $C_{1-4}$-alkoxy-carbonyl, amino-carbonyl, $C_{1-3}$-alkylaminocarbonyl, di-($C_{1-3}$-alkyl)-aminocarbonyl, $C_{1-3}$-alkylamino, di-($C_{1-3}$-alkyl)-amino, N-(phenyl-$C_{1-3}$-alkyl)-amino or N—($C_{1-3}$-alkyl)-N-(phenyl-$C_{1-3}$-alkyl)-amino group or may be replaced by an oxygen or sulphur atom, by a sulphinyl, sulphonyl, —NH, —N($C_{1-3}$-alkyl-), —N(phenyl), —N(phenyl-$C_{1-3}$-alkyl-), —N($C_{1-3}$-alkyl-carbonyl-), —N($C_{1-4}$-hydroxy-carbonyl-), —N($C_{1-4}$-alkoxy-carbonyl-), —N(benzoyl-) or —N(phenyl-$C_{1-3}$-alkyl-carbonyl-) group, while a methylene group linked to an imino-nitrogen atom of the cyclo-alkyleneimino group may be replaced by a carbonyl or sulphonyl group or in a 5- to 7-membered monocyclic cycloalkyleneimino group or a cyclo-alkyleneimino group fused to a phenyl group the two methylene groups linked to the imino-nitrogen atom may each be replaced by a carbonyl group, and all the dialkylamino groups contained in the group may also be present in quaternised form, for example as the N-methyl-(N,N-dialkyl)-ammonium group, the counter-ion preferably being selected from among iodide, chloride, bromide, methylsulphonate, para-toluenesulphonate, or trifluoroacetate, or $R_9$ denotes a $C_{1-4}$-alkyl group which is substituted by a carboxy, $C_{1-4}$-alkoxy-carbonyl, aminocarbonyl, $C_{1-3}$-alkylaminocarbonyl, di-($C_{1-3}$-alkyl)-aminocarbonyl, N-[amino-$C_{1-3}$-alkyl]-aminocarbonyl, N-[($C_{1-3}$-alkyl)-amino-$C_{1-3}$-alkyl]-aminocarbonyl, N-[di-($C_{1-3}$-alkyl)-amino-$C_{1-3}$-alkyl]-aminocarbonyl, N-[amino-$C_{1-3}$-alkyl]-N—($C_{1-3}$-alkyl)-aminocarbonyl, N-[($C_{1-3}$-alkyl)-amino-$C_{1-3}$-alkyl]-N—($C_{1-3}$-alkyl)-aminocarbonyl, N—($C_{3-7}$-cycloalkyl)-N—($C_{1-3}$-alkyl)-amino or N-[di-($C_{1-3}$-alkyl)-amino-$C_{1-3}$-alkyl]-N—($C_{1-3}$-alkyl)-aminocarbonyl group or by a 4- to 7-membered cycloalkyleneiminocarbonyl group, while in the above mentioned cycloalkyleneimino groups one or two hydrogen atoms may each be replaced by a $C_{1-3}$-alkyl, carboxy, $C_{1-4}$-alkoxy-carbonyl, aminocarbonyl, $C_{1-3}$-alkylaminocarbonyl or di-($C_{1-3}$-alkyl)-aminocarbonyl group or one or two hydrogen atoms, which are bonded to a carbon atom not adjacent to the imino group, may be replaced by an amino, $C_{1-3}$-alkylamino, di-($C_{1-3}$-alkyl)-amino, phenyl-$C_{1-3}$-alkylamino or N—($C_{1-3}$-alkyl)-phenyl-$C_{1-3}$-alkylamino group and/or the methylene group in the 4 position of a 6- or 7-membered cycloalkyleneimino group may be replaced by one of the groups —S, —SO, —$SO_2$, —NH, —N($C_{1-3}$-alkyl), —N(phenyl), —N($C_{1-3}$-alkyl-carbonyl), —N($C_{1-4}$-alkoxy-carbonyl), —N(benzoyl) or —O—, an N—($C_{1-3}$-alkyl)-$C_{1-3}$-alkyl-carbonyl-amino group which is additionally substituted in the alkyl moiety by a carboxy or $C_{1-4}$-alkoxy-carbonyl group, or a group of formula

wherein
$R^7$ denotes a hydrogen atom, a $C_{1-4}$-alkyl or $C_{3-7}$-cycloalkyl group, a $C_{1-3}$-alkyl group terminally substituted by a phenyl, heteroaryl, trifluoromethyl, aminocarbonyl, $C_{1-4}$-alkylamino-carbonyl, di-($C_{1-4}$-alkyl)-amino-carbonyl, $C_{1-3}$-alkyl-carbonyl, $C_{1-3}$-alkyl-sulphonylamino, N—($C_{1-3}$-alkyl)-$C_{1-3}$-alkyl-sulphonylamino, $C_{1-3}$-alkyl-aminosulphonyl or di-($C_{1-3}$-alkyl)-aminosulphonyl group, a $C_{2-3}$-alkyl group terminally substituted by a hydroxy or $C_{1-3}$-alkoxy group, a $C_{1-4}$-alkyl-carbonyl, benzylcarbonyl, heteroarylcarbonyl, heteroaryl-$C_{1-3}$-alkyl-carbonyl, cycloalkyleneimino-$C_{1-3}$-alkyl-carbonyl with 5 to 7 ring atoms in the cycloalkyleneimino moiety, $C_{1-3}$-alkoxy-$C_{1-3}$-alkyl-carbonyl, amino-$C_{1-3}$-alkylcarbonyl, ($C_{1-3}$-alkyl)-amino-$C_{1-3}$-alkyl-carbonyl, di-($C_{1-3}$-alkyl)-amino-carbonyl-$C_{1-3}$-alkyl, $C_{1-4}$-alkylsulphonyl, phenylsulphonyl, heteroarylsulphonyl, heteroaryl-$C_{1-3}$-alkyl-sulphonyl or benzylsulphonyl group or a phenylcarbonyl group optionally substituted in the phenyl moiety by one or two methoxy groups and $R^8$ denotes a $C_{1-3}$-alkyl, di-($C_{1-3}$-alkyl)-amino-$C_{1-3}$-alkyl-amino-carbonyl or 1-($C_{1-3}$-alkyl)-piperidin-4-yl-aminocarbonyl group, a $C_{1-4}$-alkyl-carbonyl group terminally substituted by a (ω-alkoxy-$C_{2-3}$-alkyl)-amino, $C_{1-3}$-alkyl-carbonyl-amino or N-[di-($C_{1-3}$-alkyl)-amino-$C_{1-3}$-alkyl]-N—($C_{1-3}$-alkyl)-amino group or a $C_{2-4}$-alkyl, carbonyl, $C_{1-4}$-alkyl-carbonyl or carbonyl-$C_{1-3}$-alkyl group terminally substituted by one of the groups described under $R^{10}$, while $R^{10}$ additionally also denotes a $C_{5-7}$-cycloalkyloxy group wherein the methylene group may be substituted in the 4 position by a —NH or —N($C_{1-3}$-alkyl)- group, a 5- to 7-membered cycloalkyleneimino-amino group, while the methylene group in the 4 position of a 6- or 7-membered cyclo-alkyleneimino group may be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl)- group, or may denote an N-(heteroaryl-$C_{1-3}$-alkyl)-amino group, $R^5$ denotes a hydrogen atom or a $C_{1-3}$-alkyl group and $R^6$ denotes a hydrogen atom or a nitro group, while the unsubstituted, mono- or disubstituted phenyl groups contained in the above definitions, whether singly bonded or fused on, may additionally be substituted by one or two fluorine, chlorine, bromine or iodine atoms or by one or two $C_{1-5}$-alkyl, $C_{1-4}$-alkoxy, benzyloxy, carboxy, cyano, $C_{1-4}$-alkoxy-carbonyl, aminocarbonyl, $C_{1-4}$-alkylamino-carbonyl, di-($C_{1-4}$-alkyl)-amino-carbonyl, aminosulphonyl, $C_{1-3}$-alkyl-aminosulphonyl, di-($C_{1-3}$-alkyl)-aminosulphonyl, trifluoromethyl, nitro, amino, hydroxy, $C_{1-3}$-alkylsulphonylamino, $C_{1-3}$-alkylamino or di-($C_{1-3}$-alkyl)-amino groups, while the substituents may be identical or different, the abovementioned alkyl groups including straight-chain and branched alkyl groups, wherein additionally one to 3 hydrogen atoms may be replaced by fluorine atoms, while, unless otherwise stated, the expression a heteroaryl group refers to a monocyclic 5- or 6-membered heteroaryl group optionally substituted in the carbon skeleton by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl or phenyl-$C_{1-3}$-alkyl group or an oxygen or sulphur atom and additionally contains a nitrogen atom or an imino group optionally substituted by a $C_{1-3}$-alkyl or phenyl-$C_{1-3}$-alkyl group and two nitrogen atoms, and moreover a phenyl ring may be fused to the abovementioned monocyclic heterocyclic groups via two adjacent carbon atoms and the bonding takes place via a nitrogen atom or via a carbon atom of the heterocyclic moiety or a fused-on phenyl ring, and additionally any carboxy, amino or imino group present may be substituted by a group which can be cleaved in vivo, or may be present in the form of a prodrug, the tautomers, enantiomers, diastereomers, mixtures thereof and the salts thereof, with the exception of the compounds (Z)-3-[1-(4-piperidinomethyl-phenylamino)-1-phenyl-methylidene]-6-chloro-2-indolinone and (Z)-3-[1-(4-piperidinomethyl-phenylamino)-1-phenyl-methylidene]-6-bromo-2-indolinone.

2. Compounds of general formula (I) according to claim 1 wherein

X denotes an oxygen or sulphur atom, $R^1$ denotes a hydrogen atom, a $C_{1-4}$-alkoxy-carbonyl, $C_{1-3}$-alkyl-carbonyl, aminomethyl, $C_{1-3}$-alkylaminomethyl, di-($C_{1-3}$-alkyl)-aminomethyl or a 5- to 7-membered cycloalkyleneiminomethyl group, $R^2$ denotes a fluorine, chlorine or bromine atom or a cyano group, $R^3$ denotes a phenyl group or a phenyl group mono- or disubstituted by a fluorine, chlorine, bromine or iodine atom, by a trifluoromethyl, $C_{1-3}$-alkyl or $C_{1-3}$-alkoxy group, while in the case of disubstitution the substituents may be identical or different and the abovementioned unsubstituted as well as the mono- and disubstituted phenyl group may additionally be substituted by a fluorine, chlorine, bromine or iodine atom, by a $C_{1-3}$-alkyl, $C_{1-4}$-alkoxy, benzyloxy, carboxy, cyano, trifluoromethyl, nitro, amino, $C_{1-3}$-alkyl-carbonyl-amino, $C_{1-4}$-alkyloxy-carbonylamino, N—($C_{1-3}$-alkyl)-N—($C_{1-3}$-alkyl-carbonyl)-amino, phenyl-carbonylamino, N—($C_{1-3}$-alkyl)-N-(phenyl-carbonyl)-amino, benzyl-carbonylamino, N—($C_{1-3}$-alkyl)-N-(benzyl-carbonyl)-amino, hydroxy, $C_{1-3}$-alkylsulphonylamino, N—($C_{1-3}$-alkyl)-N—($C_{1-3}$-alkylsulphonyl)-amino, phenylsulphonylamino, N—($C_{1-3}$-alkyl)-N-(phenylsulphonyl)-amino, benzyl-sulphonylamino, N—($C_{1-3}$-alkyl)-N-(benzylsulphonyl)-amino, $C_{1-3}$-alkylamino or di-($C_{1-3}$-alkyl)-amino group, by a hydroxy-$C_{1-3}$-alkyl, cyano-$C_{1-3}$-alkyl, carboxy-$C_{1-3}$-alkyl, $C_{1-4}$-alkoxy-$C_{1-3}$-alkyl, amino-$C_{1-3}$-alkyl, $C_{1-3}$-alkylamino-$C_{1-3}$-alkyl, [di-($C_{1-3}$-alkyl)-amino]-$C_{1-3}$-alkyl, benzylamino-$C_{1-3}$-alkyl, dibenzylamino-$C_{1-3}$-alkyl, N-benzyl-N—($C_{1-3}$-alkyl)-amino-$C_{1-3}$-alkyl, benzylcarbonylamino-$C_{1-3}$-alkyl, N—($C_{1-3}$-alkyl)-N-(benzylcarbonyl)-amino-$C_{1-3}$-alkyl, phenylcarbonylamino-$C_{1-3}$-alkyl, N—($C_{1-3}$-alkyl)-N-(phenylcarbonyl)-amino-$C_{1-3}$-alkyl, phenylamino-$C_{1-3}$-alkyl, diphenylamino-$C_{1-3}$-alkyl, N-phenyl-N—($C_{1-3}$-alkyl)-amino-$C_{1-3}$-alkyl, heteroarylamino-$C_{1-3}$-alkyl, N-heteroaryl-N—($C_{1-3}$-alkyl)-amino-$C_{1-3}$-alkyl, $C_{1-4}$-alkyl-sulphonylamino-$C_{1-3}$-alkyl, N—($C_{1-3}$-alkyl)-N—($C_{1-4}$-alkyl-sulphonyl)-amino-$C_{1-3}$-alkyl, phenyl-sulphonylamino-$C_{1-3}$-alkyl, N—($C_{1-3}$-alkyl)-N-(phenyl-sulphonyl)-amino-$C_{1-3}$-alkyl, benzyl-sulphonyl-amino-$C_{1-3}$-alkyl, N—($C_{1-3}$-alkyl)-N-(benzyl-sulphonyl)-amino-$C_{1-3}$-alkyl, $C_{1-4}$-alkoxy-carbonyl-$C_{1-3}$-alkyl, N—($C_{1-4}$-alkoxy-carbonyl)-amino-$C_{1-3}$-alkyl, N—($C_{1-3}$-alkyl)-N—($C_{1-4}$-alkoxy-carbonyl)-amino-$C_{1-3}$-alkyl, aminocarbonyl-$C_{1-3}$-alkyl, ($C_{1-3}$-alkyl-amino)-carbonyl-$C_{1-3}$-alkyl, di-($C_{1-3}$-alkyl)-aminocarbonyl-$C_{1-3}$-alkyl, ($C_{1-6}$-alkyl-carbonyl)-amino-$C_{1-3}$-alkyl, N—($C_{1-3}$-alkyl)-N—($C_{1-6}$-alkyl-carbonyl)-amino-$C_{1-3}$-alkyl, ($C_{3-7}$-cycloalkyl-carbonyl)-amino-$C_{1-3}$-alkyl, N—($C_{1-3}$-alkyl)-N—($C_{3-7}$-cycloalkyl-carbonyl)-amino-$C_{1-3}$-alkyl, ($C_{3-7}$-cycloalkyl-$C_{1-3}$-alkyl-carbonyl)-amino-$C_{1-3}$-alkyl, N—($C_{1-3}$-alkyl)-N—($C_{3-7}$-cycloalkyl-$C_{1-3}$-alkyl-carbonyl)-amino-$C_{1-3}$-alkyl, ($C_{1-4}$-alkoxy-$C_{1-3}$-alkyl-carbonyl)-amino-$C_{1-3}$-alkyl, N—($C_{1-3}$-alkyl)-N—($C_{1-4}$-alkoxy-$C_{1-3}$-alkyl-carbonyl)-amino-$C_{1-3}$-alkyl, (heteroaryl-carbonyl)-amino-$C_{1-3}$-alkyl, N—($C_{1-3}$-alkyl)- N-(heteroaryl-carbonyl)-amino-$C_{1-3}$-alkyl, 4-($C_{1-3}$-alkyl)-piperazin-1-yl-carbonyl-($C_{1-3}$-alkyl), tetrazolyl-$C_{1-3}$-alkyl or heteroaryl-$C_{1-3}$-alkyl group, by a carboxy-$C_{2-3}$-alkenyl, aminocarbonyl-$C_{2-3}$-alkenyl, ($C_{1-3}$-alkylamino)-carbonyl-$C_{2-3}$-alkenyl, di-($C_{1-3}$-alkylamino)-carbonyl-$C_{2-3}$-alkenyl or $C_{1-4}$-alkoxy-carbonyl-$C_{2-3}$-alkenyl group or by a cycloalkyleneimino or cycloalkyleneimino-$C_{1-3}$-alkyl group each with 5 to 7 ring members, wherein in each case one or two methylene groups adjacent to the nitrogen atom may be replaced by a carbonyl or sulphonyl group or a —$CH_2$—$CH_2$— group linked to the imino group may be replaced by the group —O—CO—, while the carbonyl group of the —O—CO— group is linked to the imino group, while the substituents may be identical or different, $R^4$ denotes a phenyl group which is substituted in the carbon skeleton by a fluorine, chlorine, bromine or iodine atom, by a $C_{1-3}$-alkyl, $C_{1-4}$-alkoxy, cyano, nitro, carboxy or trifluoromethyl group, by a ω-amino-$C_{2-3}$-alkoxy, ω-[($C_{1-3}$-alkyl)-amino]-$C_{2-3}$-alkoxy, ω-[di-($C_{1-3}$-alkyl)-amino]-$C_{2-3}$-alkoxy, $C_{1-3}$-alkyl-sulphonyl, ($C_{1-3}$-alkyl)-amino-$C_{1-3}$-alkyl-sulphonyl, amino-$C_{1-3}$-alkyl-sulphonyl, di-($C_{1-3}$-alkyl)-amino-$C_{1-3}$-alkyl-sulphonyl, 4-($C_{1-3}$-alkyl)-piperazino or heteroaryl group, by a $C_{1-3}$-alkyl group which is terminally substituted by a carboxy, $C_{1-4}$-alkoxy-carbonyl, amino, $C_{1-3}$-alkylamino, di-($C_{1-3}$-alkyl)-amino, N—($C_{1-3}$-alkyl)-N-(ω-amino-$C_{2-3}$-alkyl)-amino, N-benzyl-N—($C_{1-3}$-alkyl)-amino, N-[ω-(di-($C_{1-3}$-alkyl)-amino)-$C_{2-3}$-alkyl]-N—($C_{1-3}$-alkyl)-amino, N-[di-($C_{1-3}$-alkyl)-amino-$C_{1-3}$-alkyl]-N—($C_{1-3}$-alkyl)-amino-carbonyl, N-(ω-hydroxy-$C_{2-3}$-alkyl)-N—($C_{1-3}$-alkyl)-amino, di-(ω-hydroxy-$C_{2-3}$-alkyl)-amino, N-(ω-$C_{1-3}$-alkoxy-$C_{2-3}$-alkoxy-$C_{1-3}$-alkyl)-N—($C_{1-3}$-alkyl)-amino, N—($C_{1-4}$-alkoxy-carbonyl)-amino, N—($C_{1-4}$-alkoxy-carbonyl)-N—($C_{1-3}$-alkyl)-amino, N-{ω-[N—($C_{1-4}$-alkoxy-carbonyl)-amino]-($C_{1-4}$-alkyl)}-N—($C_{1-3}$-alkyl)-amino, heteroaryl, triazolyl or by a 5- to 7-membered cycloalkyleneimino or cycloalkyleneiminocarbonyl group, while in the abovementioned cycloalkyleneimino groups one or two hydrogen atoms may each be replaced by a $C_{1-3}$-alkyl, $C_{1-4}$-alkoxy-carbonyl, amino, $C_{1-3}$-alkylamino or di-($C_{1-3}$-alkyl)-amino group and/or the methylene group in the 4 position of a 6- or 7-membered cyclo-alkyleneimino group may be replaced by one of the groups NH, —N($C_{1-3}$-alkyl), —N($C_{1-4}$-alkoxy-carbonyl) or —O—, by a carbonyl group which is substituted by a $C_{1-3}$-alkoxy, N-[amino-$C_{1-3}$-alkyl]-amino, N-[($C_{1-3}$-alkyl)-amino-$C_{1-3}$-alkyl]-amino, N-[di-($C_{1-3}$-alkyl)-amino-$C_{1-3}$-alkyl]-amino, N-[amino-$C_{1-3}$-alkyl]-N—($C_{1-3}$-alkyl)-amino, N-[($C_{1-3}$-alkyl)-amino-$C_{1-3}$-alkyl]-N—($C_{1-3}$-alkyl)-amino, N-[di-($C_{1-3}$-alkyl)-amino-$C_{1-3}$-alkyl]-N—($C_{1-3}$-alkyl)-amino, N—($C_{3-7}$-cycloalkyl)-N—($C_{1-3}$-alkyl)-amino or 5- to 7-membered cycloalkyleneimino group, while the methylene group in the 4 position of a 6- or 7-membered cycloalkylene group may be replaced by a —NH, —N($C_{1-3}$-alkyl) or N($C_{1-4}$-alkyloxy-carbonyl)- group, or by a group of formula

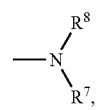

wherein $R^7$ denotes a hydrogen atom or a $C_{1-4}$-alkyl, $C_{1-4}$-alkyl-carbonyl, benzyl-carbonyl, heteroarylcarbonyl, cycloalkyleneimino-$C_{1-3}$-alkyl-carbonyl with 5 to 7 ring atoms in the cycloalkyleneimino moiety, $C_{1-3}$-alkoxy-$C_{1-3}$-alkyl-carbonyl, amino-$C_{1-3}$-alkyl-carbonyl, ($C_{1-3}$-alkyl)-amino-$C_{1-3}$-alkyl-carbonyl, di-($C_{1-3}$-alkyl)-amino-carbonyl-$C_{1-3}$-alkyl, $C_{1-4}$-alkylsulphonyl, phenylsulphonyl, heteroarylsulphonyl or benzylsulphonyl group or a phenylcarbonyl group optionally substituted in the phenyl moiety by one or two methoxy groups and $R^8$ denotes a $C_{1-3}$-alkyl group, a $C_{2-4}$-alkyl group terminally substituted by an amino, ($C_{1-3}$-alkyl)-amino, di-($C_{1-3}$-alkyl)-amino or N-benzyl-N—($C_{1-3}$-alkyl)-amino group, an amino-carbonyl-$C_{1-3}$-alkyl, ($C_{1-3}$-alkyl)-amino-carbonyl-$C_{1-3}$-alkyl or di-($C_{1-3}$-alkyl)-amino-carbonyl-$C_{1-3}$-alkyl group, a di-($C_{1-3}$-alkyl)-amino-$C_{1-3}$-alkyl-amino-carbonyl, 4-($C_{1-3}$-alkyl)-piperazin-1-yl-carbonyl, 4-($C_{1-3}$-alkyl)-piperazin-1-yl-aminocarbonyl, 1-($C_{1-3}$-alkyl)-piperidin-4-yl-aminocarbonyl, 1-($C_{1-3}$-alkyl)-piperidin-4-yl-oxy-carbonyl or (pyridinyl-$C_{1-3}$-alkyl)-aminocarbonyl group or a $C_{1-4}$-alkyl-carbonyl group terminally substituted by a hydroxy, $C_{1-4}$-alkyloxy, amino, ($C_{1-3}$-alkyl)-amino, di-($C_{1-3}$-alkyl)-amino, (ω-hydroxy-$C_{2-3}$-alkyl)-amino, di-(ω-hydroxy-$C_{2-3}$-alkyl)-amino, (ω-alkoxy-$C_{2-3}$-alkyl)-amino, di-(ω-alkoxy-$C_{2-3}$-alkyl)-amino, $C_{1-3}$-alkyl-carbonyl-amino, N-benzyl-N—($C_{1-3}$-alkyl)-amino, N-[di-($C_{1-3}$-alkyl)-amino-$C_{1-3}$-alkyl]-N—($C_{1-3}$-alkyl)-amino, 1-($C_{1-3}$-alkyl)-piperidin-4-yl or heteroaryl group or by a 5- to 7-membered cycloalkyleneimino group, while the cycloalkylene group may be substituted by a $C_{1-3}$-alkyl group and/or
one or two methylene groups linked to the imino group may be replaced by a carbonyl group and/or
the methylene group in the 4 position of a 6- or 7-membered cycloalkylimino group may be replaced by an —NH, —N($C_{1-3}$-alkyl), —N(benzyl), —N($C_{1-4}$-alkoxy-carbonyl) or —O— and/or
a phenyl ring may be fused via two adjacent carbon atoms of the cycloalkyleneimino group,
while a 2- or 3-linked pyrrolyl group may additionally be substituted at the nitrogen atom by a $C_{1-3}$-alkyl group,
$R^5$ denotes a hydrogen atom or a $C_{1-3}$-alkyl group and
$R^6$ denotes a hydrogen atom or a nitro group,
while the unsubstituted, mono- or disubstituted phenyl groups containedin the above definitions may additionally be substituted by a fluorine, chlorine, bromine or iodine atom or by a $C_{1-3}$-alkyl, $C_{1-3}$-alkoxy, benzyloxy, carboxy, cyano, trifluoromethyl, nitro, amino, hydroxy, $C_{1-3}$-alkylsulphonylamino, $C_{1-3}$-alkylamino or di-($C_{1-3}$-alkyl)-amino group or by two methyl groups,
the abovementioned alkyl groups including straight-chain and branched alkyl groups, wherein additionally one to 3 hydrogen atoms may be replaced by fluorine atoms, while, unless otherwise stated, the expression a heteroaryl group refers to a monocyclic 5- or 6-membered heteroaryl group optionally substituted in the carbon skeleton by a $C_{1-3}$-alkyl group, wherein
the 6-membered heteroaryl group contains one, two or three nitrogen atoms and
the 5-membered heteroaryl group contains an imino group optionally substituted by a $C_{1-3}$-alkyl or phenyl-$C_{1-3}$-alkyl group, an oxygen or sulphur atom or
an imino group optionally substituted by a $C_{1-3}$-alkyl, amino-$C_{1-3}$-alkyl, [($C_{1-3}$-alkyl)-amino]-$C_{1-3}$-alkyl, [di-($C_{1-3}$-alkyl)-amino]-$C_{1-3}$-alkyl or phenyl-$C_{1-3}$-alkyl group or an oxygen or sulphur atom and additionally contains a nitrogen atom or
an imino group optionally substituted by a $C_{1-3}$-alkyl or phenyl-$C_{1-3}$-alkyl group and two nitrogen atoms,
and moreover a phenyl ring may be fused to the abovementioned monocyclic heterocyclic groups via two adjacent carbon atoms and the bonding takes place via a nitrogen atom or via a carbon atom of the heterocyclic moiety or a fused-on phenyl ring,
and additionally any carboxy, amino or imino group present may be substituted by a group which can be cleaved in vivo,
the tautomers, enantiomers, diastereomers, mixtures thereof and the salts thereof,
with the exception of the compounds
(Z)-3-[1-(4-piperidinomethyl-phenylamino)-1-phenyl-methylidene]-6-chloro-2-indolinone and
(Z)-3-[1-(4-piperidinomethyl-phenylamino)-1-phenyl-methyl idene]-6-bromo-2-indolinone.

3. Compounds of general formula (I) according to claim 1 wherein
X denotes an oxygen or sulphur atom,
$R^1$ denotes a hydrogen atom, a $C_{1-4}$-alkoxy-carbonyl, $C_{1-3}$-alkyl-carbonyl, aminomethyl, $C_{1-3}$-alkylaminomethyl, di-($C_{1-3}$-alkyl)-aminomethyl or a 5- to 7-membered cycloalkyleneiminomethyl group,
$R^2$ denotes a fluorine, chlorine or bromine atom or a cyano group,
$R^3$ denotes a phenyl group or
a phenyl group mono- or disubstituted by a fluorine, chlorine, bromine or iodine atom, by a trifluoromethyl, $C_{1-3}$-alkyl or $C_{1-3}$-alkoxy group, while in the case of disubstitution the substituents may be identical or different and the abovementioned unsubstituted as well as the mono- and disubstituted phenyl group may additionally be substituted
by a fluorine, chlorine, bromine or iodine atom,
by a $C_{1-3}$-alkyl, $C_{1-4}$-alkoxy, benzyloxy, carboxy, cyano, trifluoromethyl, nitro, amino, $C_{1-3}$-alkyl-carbonyl-amino, $C_{1-4}$-alkyloxy-carbonylamino, hydroxy, $C_{1-3}$-alkylsulphonylamino, $C_{1-3}$-alkylamino or di-($C_{1-3}$-alkyl)-amino group,
by a hydroxy-$C_{1-3}$-alkyl, cyano-$C_{1-3}$-alkyl, carboxy-$C_{1-3}$-alkyl, $C_{1-4}$-alkoxy-$C_{1-3}$-alkyl, amino-$C_{1-3}$-alkyl, $C_{1-3}$-alkylamino-$C_{1-3}$-alkyl, [di-($C_{1-3}$-alkyl)-amino]-$C_{1-3}$-alkyl, benzylamino-$C_{1-3}$-alkyl, dibenzylamino-$C_{1-3}$-alkyl, N-benzyl-N—($C_{1-3}$-alkyl)-amino-$C_{1-3}$-alkyl, benzylcarbonylamino-$C_{1-3}$-alkyl, phenylcarbonylamino-$C_{1-3}$-alkyl, phenylamino-$C_{1-3}$-alkyl, diphenylamino-$C_{1-3}$-alkyl, N-phenyl-N—($C_{1-3}$-alkyl)-amino-$C_{1-3}$-alkyl, heteroarylamino-$C_{1-3}$-alkyl, N-heteroaryl-N—($C_{1-3}$-alkyl)-amino-$C_{1-3}$-alkyl, $C_{1-4}$-alkyl-sulphonylamino-$C_{1-3}$-alkyl, phenyl-sulphonylamino-$C_{1-3}$-alkyl, benzyl-sulphonylamino-$C_{1-3}$-alkyl, $C_{1-4}$-alkoxy-carbonyl-$C_{1-3}$-alkyl, N—($C_{1-4}$-alkoxy-carbonyl)-amino-$C_{1-3}$-alkyl, aminocarbonyl-$C_{1-3}$-alkyl, ($C_{1-3}$-alkylamino)-carbonyl-$C_{1-3}$-alkyl, di-($C_{1-3}$-alkyl)-aminocarbonyl-$C_{1-3}$-alkyl, ($C_{1-6}$-alkyl-carbonyl)-amino-$C_{1-3}$-alkyl, N—($C_{1-3}$-alkyl)-N—($C_{1-6}$-alkyl-carbonyl)-amino-$C_{1-3}$-alkyl, ($C_{3-7}$-cycloalkyl-carbonyl)-amino-$C_{1-3}$-alkyl, N—($C_{1-3}$-alkyl)-N—($C_{3-7}$-cycloalkyl-carbonyl)-amino-$C_{1-3}$-alkyl, ($C_{3-7}$-cycloalkyl-$C_{1-3}$-alkyl-carbonyl)-amino-$C_{1-3}$-alkyl, N—($C_{1-3}$-alkyl)-N—($C_{3-7}$-cycloalkyl-$C_{1-3}$-alkyl-carbonyl)-amino-$C_{1-3}$-alkyl, ($C_{1-4}$-alkoxy-$C_{1-3}$-alkyl-carbonyl)-amino-$C_{1-3}$-alkyl, N—($C_{1-3}$-alkyl)-N—($C_{1-4}$-alkoxy-$C_{1-3}$-alkyl-carbonyl)-amino-$C_{1-3}$-alkyl, (heteroaryl-carbonyl)-amino-$C_{1-3}$-alkyl, N—($C_{1-3}$-alkyl)-N-(heteroaryl-carbonyl)-amino-$C_{1-3}$-alkyl, 4-($C_{1-3}$-alkyl)-piperazin-1-yl-carbonyl-($C_{1-3}$-alkyl), tetrazolyl-$C_{1-3}$-alkyl or imidazoyl-$C_{1-3}$-alkyl group,
by a carboxy-$C_{2-3}$-alkenyl, aminocarbonyl-$C_{2-3}$-alkenyl or $C_{1-4}$-alkoxy-carbonyl-$C_{2-3}$-alkenyl group or
by a 5- to 7-membered cycloalkyleneimino group wherein one or two methylene groups adjacent to the nitrogen atom may be replaced by a carbonyl group or a —$CH_2$—$CH_2$— group linked to the imino group may be replaced by the group —O—CO—, while the carbonyl group of the —O—CO— group is linked to the imino group, while the substituents may be identical or different,
$R^4$ denotes a phenyl group which may be substituted in the carbon skeleton
by a fluorine, chlorine, bromine or iodine atom, by a $C_{1-3}$-alkyl, $C_{1-3}$-alkoxy, cyano, nitro, carboxy or trifluoromethyl group,
by a ω-[di-($C_{1-3}$-alkyl)-amino]-$C_{2-3}$-alkoxy, $C_{1-3}$-alkyl-sulphonyl, di-($C_{1-3}$-alkyl)-amino-$C_{1-3}$-alkyl-sulphonyl, 4-($C_{1-3}$-alkyl)-piperazino, imidazolyl, $C_{1-3}$-alkyl-imidazolyl or [di-($C_{1-3}$-alkyl)-amino]-$C_{1-3}$-alkyl-imidazolyl group,
by a $C_{1-3}$-alkyl group which is terminally substituted by a carboxy, $C_{1-4}$-alkoxy-carbonyl, amino, $C_{1-3}$-alkylamino, di-($C_{1-3}$-alkyl)-amino, N—($C_{1-3}$-alkyl)-N-

(ω-amino-$C_{2-3}$-alkyl)-amino, N-benzyl-N—($C_{1-3}$-alkyl)-amino, N-[ω-(di-($C_{1-3}$-alkyl)-amino)-$C_{2-3}$-alkyl]-N—($C_{1-3}$-alkyl)-amino, N-[di-($C_{1-3}$-alkyl)-amino-$C_{1-3}$-alkyl]-N—($C_{1-3}$-alkyl)-amino-carbonyl, N-(ω-hydroxy-$C_{2-3}$-alkyl)-N—($C_{1-3}$-alkyl)-amino, di-(ω-hydroxy-$C_{2-3}$-alkyl)-amino, N-(ω-$C_{1-3}$-alkoxy-$C_{2-3}$-alkoxy-$C_{1-3}$-alkyl)-N—($C_{1-3}$-alkyl)-amino, N—($C_{1-4}$-alkoxy-carbonyl)-amino, N—($C_{1-4}$-alkoxy-carbonyl)-N—($C_{1-3}$-alkyl)-amino, N-{ω-[N—($C_{1-4}$-alkoxy-carbonyl)-amino]-($C_{1-4}$-alkyl)}-N—($C_{1-3}$-alkyl)-amino, pyridinyl, triazolyl, pyrrolidino, piperidino, di-($C_{1-3}$-alkyl)-piperidino, [di-($C_{1-3}$-alkyl)-amino]-piperidino, piperazino, morpholino, ($C_{1-3}$-alkyl)-piperazino, ($C_{1-3}$-alkyl)-piperazin-1-yl-carbonyl or 4-($C_{1-4}$-alkoxy-carbonyl)-piperazino group, by a carbonyl group which is substituted by a $C_{1-4}$-alkoxy, N-[di-($C_{1-3}$-alkyl)-amino-$C_{1-3}$-alkyl]-amino, N-[di-($C_{1-3}$-alkyl)-amino-$C_{1-3}$-alkyl]-N—($C_{1-3}$-alkyl)-amino, N—($C_{3-7}$-cycloalkyl)-N—($C_{1-3}$-alkyl)-amino, piperidino, piperazino, 4-($C_{1-4}$-alkyloxy-carbonyl)-piperazino or 4-($C_{1-3}$-alkyl)-piperazino group, or by a group of formula

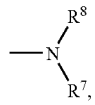

wherein $R^7$ denotes a hydrogen atom or a $C_{1-3}$-alkyl, $C_{1-3}$-alkyl-carbonyl, benzyl-carbonyl, pyridinylcarbonyl, furanylcarbonyl, pyrrolidino-$C_{1-3}$-alkyl-carbonyl, $C_{1-3}$-alkoxy-$C_{1-3}$-alkyl-carbonyl, di-($C_{1-3}$-alkyl)-amino-carbonyl-$C_{1-3}$-alkyl, $C_{1-4}$-alkylsulphonyl or benzylsulphonyl group or a phenylcarbonyl group optionally substituted in the phenyl moiety by one or two methoxy groups and $R^8$ denotes a $C_{1-3}$-alkyl, di-($C_{1-3}$-alkyl)-amino-$C_{1-4}$-alkyl-amino-carbonyl or di-($C_{1-3}$-alkyl)-amino-carbonyl-$C_{1-3}$-alkyl group, a $C_{2-3}$-alkyl group terminally substituted by a di-($C_{1-3}$-alkyl)-amino or N-benzyl-N—($C_{1-3}$-alkyl)-amino group, a 4-($C_{1-3}$-alkyl)-piperazin-1-yl-carbonyl, 4-($C_{1-3}$-alkyl)-piperazin-1-yl-aminocarbonyl, 1-($C_{1-3}$-alkyl)-piperidin-4-yl-aminocarbonyl, 1-($C_{1-3}$-alkyl)-piperidin-4-yl-oxy-carbonyl or (pyridinyl-$C_{1-3}$-alkyl)-aminocarbonyl group or a $C_{1-4}$-alkyl-carbonyl group terminally substituted by a hydroxy, amino, di-($C_{1-3}$-alkyl)-amino, di-(ω(ω-hydroxy-$C_{2-3}$-alkyl)-amino, $C_{1-3}$-alkyl-carbonyl-amino, N-benzyl-N—($C_{1-3}$-alkyl)-amino, N-[di-($C_{1-3}$-alkyl)-amino-$C_{1-3}$-alkyl]-N—($C_{1-3}$-alkyl)-amino, imidazolyl, piperazino, 4-($C_{1-3}$-alkyl)-piperazin-1-yl, 4-benzyl-piperazin-1-yl, 4-($C_{1-4}$-alkoxy-carbonyl)-piperazin-1-yl, 4-($C_{1-3}$-alkyl)-homopiperazin-1-yl, morpholino, pyrrolidino, piperidino, 1-($C_{1-3}$-alkyl)-piperidin-4-yl, 4-($C_{1-3}$-alkyl)-piperidin-1-yl or phthalimido group, while a 2- or 3-linked pyrrolyl group may additionally be substituted at the nitrogen atom by a $C_{1-3}$-alkyl group, $R^5$ denotes a hydrogen atom or a $C_{1-3}$-alkyl group and $R^6$ denotes a hydrogen atom or a nitro group, while the unsubstituted, mono- or disubstituted phenyl groups contained in the above definitions may additionally be substituted by a fluorine, chlorine, bromine or iodine atom or by a $C_{1-3}$-alkyl, $C_{1-3}$-alkoxy, benzyloxy, carboxy, cyano, trifluoromethyl, nitro, amino, hydroxy, $C_{1-3}$-alkylsulphonylamino, $C_{1-3}$-alkylamino or di-($C_{1-3}$-alkyl)-amino group or by two methyl groups, the abovementioned alkyl groups including straight-chain and branched alkyl groups, wherein additionally one to 3 hydrogen atoms may be replaced by fluorine atoms, while, unless otherwise stated, the expression a heteroaryl group refers to a monocyclic 5- or 6-membered heteroaryl group optionally substituted in the carbon skeleton by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two nitrogen atoms, and moreover a phenyl ring may be fused to the abovementioned monocyclic heterocyclic groups via two adjacent carbon atoms and the bonding takes place via a nitrogen atom or via a carbon atom of the heterocyclic moiety or a fused-on phenyl ring, and additionally any carboxy, amino or imino group present may be substituted by a group which can be cleaved in vivo, the tautomers, enantiomers, diastereomers, mixtures thereof and the salts thereof, with the exception of the compounds (Z)-3-[1-(4-piperidinomethyl-phenylamino)-1-phenyl-methylidene]-6-chloro-2-indolinone and (Z)-3-[1-(4-piperidinomethyl-phenylamino)-1-phenyl-methylidene]-6-bromo-2-indolinone.

4. Compounds of general formula I according to claim 1, wherein $R^1$, $R^2$, $R^3$, $R^5$, $R^6$ and X are defined as in claim 3 and $R^4$ denotes a phenyl group which may be substituted in the carbon skeleton by a fluorine, chlorine, bromine or iodine atom, by a $C_{1-3}$-alkyl, $C_{1-3}$-alkoxy, cyano, nitro, carboxy or trifluoromethyl group, by a ω-[di-($C_{1-3}$-alkyl)-amino]-$C_{2-3}$-alkoxy, $C_{1-3}$-alkylsulphonyl, di-($C_{1-3}$-alkyl)-amino-$C_{1-3}$-alkyl-sulphonyl, 4-($C_{1-3}$-alkyl)-piperazino, imidazolyl, $C_{1-3}$-alkyl-imidazolyl or [di-($C_{1-3}$-alkyl)-amino]-$C_{1-3}$-alkyl-imidazolyl group, by a carbonyl group which is substituted by a $C_{1-4}$-alkoxy, N-[di-($C_{1-3}$-alkyl)-amino-$C_{1-3}$-alkyl]-amino, N-[di-($C_{1-3}$-alkyl)-amino-$C_{1-3}$-alkyl]-N—$C_{1-3}$-alkyl-amino, N—($C_{3-7}$-cycloalkyl)-N—($C_{1-3}$-alkyl)-amino, piperidino, piperazino, 4-($C_{1-4}$-alkyloxy-carbonyl)-piperazino or 4-($C_{1-3}$-alkyl)-piperazino group, or by a group of formula

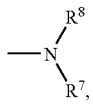

wherein
$R^7$ denotes a hydrogen atom or a $C_{1-3}$-alkyl, $C_{1-3}$-alkyl-carbonyl, benzyl-carbonyl, pyridinylcarbonyl, furanylcarbonyl, pyrrolidino-$C_{1-3}$-alkyl-carbonyl, $C_{1-3}$-alkoxy-$C_{1-3}$-alkyl-carbonyl, di-($C_{1-3}$-alkyl)-amino-carbonyl-$C_{1-3}$-alkyl, $C_{1-4}$-alkylsulphonyl or benzylsulphonyl group or a phenylcarbonyl group optionally substituted in the phenyl moiety by one or two methoxy groups and $R^8$ denotes a $C_{1-3}$-alkyl, di-($C_{1-3}$-alkyl)-amino-$C_{1-3}$-alkyl-amino-carbonyl or di-($C_{1-3}$-alkyl)-amino-carbonyl-$C_{1-3}$-alkyl group, a $C_{2-3}$-alkyl group terminally substituted by a di-($C_{1-3}$-alkyl)-amino or N-benzyl-N—($C_{1-3}$-alkyl)-amino group, a 4-($C_{1-3}$-alkyl)-piperazin-1-yl-carbonyl, 4-($C_{1-3}$-alkyl)-piperazin-1-yl-aminocarbonyl, 1-($C_{1-3}$-alkyl)-piperidin-4-yl-aminocarbonyl, 1-($C_{1-3}$-alkyl)-piperidin-4-yl-oxy-carbonyl or (pyridinyl-$C_{1-3}$-alkyl)-aminocarbonyl group or a $C_{1-4}$-alkyl-carbonyl group terminally substituted by a hydroxy, amino, di-($C_{1-3}$-alkyl)-amino, di-(ω-hydroxy-$C_{2-3}$-alkyl)-amino, $C_{1-3}$-alkyl-carbonyl-amino, N-benzyl-N—($C_{1-3}$-alkyl)-amino, N-[di-($C_{1-3}$-alkyl)-amino-$C_{1-3}$-alkyl]-N—($C_{1-3}$-alkyl)-amino, imidazolyl, piperazino, 4-($C_{1-3}$-alkyl)-piperazin-1-yl, 4-benzyl-piperazin-1-yl, 4-($C_{1-4}$-alkoxy-carbonyl)-piperazin-1-yl, 4-($C_{1-3}$-alkyl)-homopiperazin-1-yl, morpholino, pyrrolidino, piperidino, 1-($C_{1-3}$-alkyl)-piperidin-4-yl, 4-($C_{1-3}$-alkyl)-piperidin-1-yl or phthalimido group, while a 2- or 3-linked pyrrolyl group may additionally be substituted at the nitrogen atom by a $C_{1-3}$-alkyl group, while the unsubstituted, mono- or disubstituted phenyl groups containedin the above definitions may additionally be substituted by a fluorine, chlorine, bromine or iodine atom or by a $C_{1-3}$-alkyl, $C_{1-3}$-alkoxy, benzyloxy, carboxy, cyano, trifluoromethyl, nitro, amino, hydroxy, $C_{1-3}$-alkylsulphonylamino, $C_{1-3}$-alkylamino or di-($C_{1-3}$-alkyl)-amino group or by two methyl groups, the abovementioned alkyl groups including straight-chain and branched alkyl groups, wherein additionally one to 3 hydrogen atoms may be replaced by fluorine atoms, while, unless otherwise stated, the expression a heteroaryl group refers to a monocyclic 5- or 6-membered heteroaryl group optionally substituted in the carbon skeleton by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two nitrogen atoms, and moreover a phenyl ring may be fused to the abovementioned monocyclic heterocyclic groups via two adjacent carbon atoms and the bonding takes place via a nitrogen atom or via a carbon atom of the heterocyclic moiety or a fused-on phenyl ring, and additionally any carboxy, amino or imino group present may be substituted by a group which can be cleavedin vivo, the tautomers, enantiomers, diastereomers, mixtures thereof and the salts thereof.

5. Compounds of general formula I according to claim 3, wherein $R^1$, $R^2$, $R^4$, $R^5$, $R^6$ and X are defined as in claim 3 and $R^3$ denotes a phenyl group or a phenyl group mono- or disubstituted by a fluorine, chlorine, bromine or iodine atom, by a trifluoromethyl, $C_{1-3}$-alkyl or $C_{1-3}$-alkoxy group, while in the case of disubstitution the substituents may be identical or different and the abovementioned unsubstituted as well as the mono- and disubstituted phenyl group may additionally be substituted by a fluorine, chlorine, bromine or iodine atom, by a $C_{1-3}$-alkyl, $C_{1-4}$-alkoxy, benzyloxy, carboxy, cyano, trifluoromethyl, nitro, amino, $C_{1-3}$-alkyl-carbonyl-amino, $C_{1-4}$-alkyloxy-carbonylamino, hydroxy, $C_{1-3}$-alkylsulphonylamino, $C_{1-3}$-alkylamino or di-($C_{1-3}$-alkyl)-amino group, by a hydroxy-$C_{1-3}$-alkyl, cyano-$C_{1-3}$-alkyl, carboxy-$C_{1-3}$-alkyl, $C_{1-4}$-alkoxy-$C_{1-3}$-alkyl, amino-$C_{1-3}$-alkyl, $C_{1-3}$-alkylamino-$C_{1-3}$-alkyl, [di-($C_{1-3}$-alkyl)-amino]-$C_{1-3}$-alkyl, benzylamino-$C_{1-3}$-alkyl, dibenzylamino-$C_{1-3}$-alkyl, N-benzyl-N—($C_{1-3}$-alkyl)-amino-$C_{1-3}$-alkyl, benzylcarbonylamino-$C_{1-3}$-alkyl, phenylcarbonylamino-$C_{1-3}$-alkyl, phenylamino-$C_{1-3}$-alkyl, diphenylamino-$C_{1-3}$-alkyl, N-phenyl-N—($C_{1-3}$-alkyl)-amino-$C_{1-3}$-alkyl, heteroarylamino-$C_{1-3}$-alkyl, N-heteroaryl-N—($C_{1-3}$-alkyl)-amino-$C_{1-3}$-alkyl, $C_{1-4}$-alkyl-sulphonylamino-$C_{1-3}$-alkyl, phenyl-sulphonylamino-$C_{1-3}$-alkyl, benzyl-sulphonylamino-$C_{1-3}$-alkyl, $C_{1-4}$-alkoxy-carbonyl-$C_{1-3}$-alkyl, N—($C_{1-4}$-alkoxy-carbonyl)-amino-$C_{1-3}$-alkyl, aminocarbonyl-$C_{1-3}$-alkyl, ($C_{1-3}$-alkylamino)-carbonyl-$C_{1-3}$-alkyl, di-($C_{1-3}$-alkyl)-aminocarbonyl-$C_{1-3}$-alkyl, ($C_{1-6}$-alkyl-carbonyl)-amino-$C_{1-3}$-alkyl, N—($C_{1-3}$-alkyl)-N—($C_{1-6}$-alkyl-carbonyl)-amino-$C_{1-3}$-alkyl, ($C_{3-7}$-cycloalkyl-carbonyl)-amino-$C_{1-3}$-alkyl, N—($C_{1-3}$-alkyl)-N—($C_{3-7}$-cycloalkyl-carbonyl)-amino-$C_{1-3}$-alkyl, ($C_{3-7}$-cycloalkyl-$C_{1-3}$-alkyl-carbonyl)-amino-$C_{1-3}$-alkyl, N—($C_{1-3}$-alkyl)-N—($C_{3-7}$-cycloalkyl-$C_{1-3}$-alkyl-carbonyl)-amino-$C_{1-3}$-alkyl, ($C_{1-4}$-alkoxy-$C_{1-3}$-alkyl-carbonyl)-amino-$C_{1-3}$-alkyl, N—($C_{1-3}$-alkyl)-N—($C_{1-4}$-alkoxy-$C_{1-3}$-alkyl-carbonyl)-amino-$C_{1-3}$-alkyl, (heteroaryl-carbonyl)-amino-$C_{1-3}$-alkyl, N—($C_{1-3}$-alkyl)-N-(heteroaryl- carbonyl)-amino-$C_{1-3}$-alkyl, 4-($C_{1-3}$-alkyl)-piperazin-1-yl-carbonyl-($C_{1-3}$-alkyl), tetrazolyl-$C_{1-3}$-alkyl or imidazoyl-$C_{1-3}$-alkyl group, by a carboxy-$C_{2-3}$-alkenyl, aminocarbonyl-$C_{2-3}$-alkenyl or $C_{1-4}$-alkoxy-carbonyl-$C_{2-3}$-alkenyl group or by a 5- to 7-membered cycloalkyleneimino group wherein one or two methylene groups adjacent to the nitrogen atom may be replaced by a carbonyl group or a $CH_2$—$CH_2$— group linked to the imino group may be replaced by the group —O—CO—, while the carbonyl group of the —O—CO— group is linked to the imino group, while the substituents may be identical or different, and the unsubstituted, mono- or disubstituted phenyl groups containedin the above definitions may additionally be substituted by a fluorine, chlorine, bromine or iodine atom or by a $C_{1-3}$-alkyl, $C_{1-3}$-alkoxy, benzyloxy, carboxy, cyano, trifluoromethyl, nitro, amino, hydroxy, $C_{1-3}$-alkylsulphonylamino, $C_{1-3}$-alkylamino or di-($C_{1-3}$-alkyl)-amino group or by two methyl groups, the abovementioned alkyl groups including straight-chain and branched alkyl groups, wherein additionally one to 3 hydrogen atoms may be replaced by fluorine atoms, while, unless otherwise stated, the expression a heteroaryl group refers to a monocyclic 5- or 6-membered heteroaryl group optionally substituted in the carbon skeleton by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two nitrogen atoms, and moreover a phenyl ring may be fused to the abovementioned monocyclic heterocyclic groups via two adjacent carbon atoms and the bonding takes place via a nitrogen atom or via a carbon atom of the heterocyclic moiety or a fused-on phenyl ring, and additionally any carboxy, amino or imino group present may be substituted by a group which can be cleavedin vivo, the tautomers, enantiomers, diastereomers, mixtures thereof and the salts thereof.

6. Compounds of general formula I according to claim 1, wherein

X denotes an oxygen or sulphur atom, $R^1$ denotes a hydrogen atom, a $C_{1-4}$-alkoxy-carbonyl, $C_{1-3}$-alkyl-carbonyl, aminomethyl, $C_{1-3}$-alkylaminomethyl, di-($C_{1-3}$-alkyl)-aminomethyl or a 5- to 7-membered cycloalkyleneiminomethyl group, $R^2$ denotes a fluorine, chlorine or bromine atom or a cyano group, $R^3$ denotes a phenyl group or a phenyl group mono- or disubstituted by a fluorine, chlorine, bromine or iodine atom, by a trifluoromethyl, $C_{1-3}$-alkyl or $C_{1-3}$-alkoxy group, while in the case of disubstitution the substituents may be identical or different and the abovementioned unsubstituted as well as the mono- and disubstituted phenyl group may additionally be substituted by a $C_{1-3}$-alkyl-carbonyl-amino, $C_{1-4}$-alkyloxy-carbonylamino, benzyloxy or hydroxy group, by a hydroxy-$C_{1-3}$-alkyl, carboxy-$C_{1-3}$-alkyl, $C_{1-4}$-alkoxy-$C_{1-3}$-alkyl, cyano-$C_{1-3}$-alkyl, benzylamino-$C_{1-3}$-alkyl, dibenzylamino-$C_{1-3}$-alkyl, N-benzyl-N—($C_{1-3}$-alkyl)-amino-$C_{1-3}$-alkyl, $C_{1-4}$-alkoxy-$C_{1-3}$-alkyl-carbonylamino-$C_{1-3}$-alkyl, $C_{3-7}$-cycloalkyl-carbonylamino-$C_{1-3}$-alkyl, $C_{3-7}$-cycloalkyl-$C_{1-3}$-alkyl-carbonylamino-$C_{1-3}$-alkyl, benzylcarbonylamino-$C_{1-3}$-alkyl, phenylcarbonylamino-$C_{1-3}$-alkyl, heteroaryl-carbonylamino-$C_{1-3}$-alkyl, phenylamino-$C_{1-3}$-alkyl, diphenylamino-$C_{1-3}$-alkyl, N-phenyl-N—($C_{1-3}$-alkyl)-amino-$C_{1-3}$-alkyl, heteroarylamino-$C_{1-3}$-alkyl, N-heteroaryl-N—($C_{1-3}$-alkyl)-amino-$C_{1-3}$-alkyl, $C_{1-4}$-alkyl-sulphonylamino-$C_{1-3}$-alkyl, phenyl-sulphonylamino-$C_{1-3}$-alkyl, benzyl-sulphonylamino-$C_{1-3}$-alkyl, $C_{1-4}$-alkoxy-carbonyl-$C_{1-3}$-alkyl, N—($C_{1-4}$-alkoxy-carbonyl)-amino-$C_{1-3}$-alkyl, aminocarbonyl-$C_{1-3}$-alkyl, ($C_{1-3}$-alkylamino)-carbonyl-$C_{1-3}$-alkyl, di-($C_{1-3}$-alkyl)-aminocarbonyl-$C_{1-3}$-alkyl, 4-($C_{1-3}$-alkyl)-piperazin-1-yl-carbonyl-($C_{1-3}$-alkyl) or tetrazolyl-$C_{1-3}$-alkyl group, by an aminocarbonyl-$C_{2-3}$-alkenyl or $C_{1-4}$-alkoxy-carbonyl-$C_{2-3}$-alkenyl group or by a 5- to 7-membered cycloalkyleneimino groups, wherein one or two methylene groups adjacent to the nitrogen atom may be replaced by a carbonyl group or a $CH_2$—$CH_2$— group linked to the imino group may be replaced by the group —O—CO—, while the carbonyl group of the O—CO— group is linked to the imino group, while the substituents may be identical or different, $R^4$ denotes a phenyl group which may be substituted by a fluorine, chlorine, bromine or iodine atom, by a $C_{1-3}$-alkyl, $C_{1-3}$-alkoxy, cyano, nitro, carboxy or trifluoromethyl group, by a ω-[di-($C_{1-3}$-alkyl)-amino]-$C_{2-3}$-alkoxy, $C_{1-3}$-alkyl-sulphonyl, di-($C_{1-3}$-alkyl)-amino-$C_{1-3}$-alkyl-sulphonyl, 4-($C_{1-3}$-alkyl)-piperazino, imidazolyl, $C_{1-3}$-alkylimidazolyl or [di-($C_{1-3}$-alkyl)-amino]-$C_{1-3}$-alkyl-imidazolyl group, by a $C_{1-3}$-alkyl group which is terminally substituted by a carboxy, $C_{1-3}$-alkoxy-carbonyl, amino, $C_{1-3}$-alkylamino, di-($C_{1-3}$-alkyl)-amino, N—($C_{1-3}$-alkyl)-N-(ω-amino-$C_{2-3}$-alkyl)-amino, N-benzyl-N—($C_{1-3}$-alkyl)-amino, N-[ω-(di-($C_{1-3}$-alkyl)-amino)-$C_{2-3}$-alkyl]-N—($C_{1-3}$-alkyl)-amino, N-[di-($C_{1-3}$-alkyl)-amino-$C_{1-3}$-alkyl]-N—($C_{1-3}$-alkyl)-amino-carbonyl, N-(ω-hydroxy-$C_{2-3}$-alkyl)-N—($C_{1-3}$-alkyl)-amino, di-(ω-hydroxy-$C_{2-3}$-alkyl)-amino, N-(ω-$C_{1-3}$-alkoxy-$C_{2-3}$-alkoxy-$C_{1-3}$-alkyl)-N—($C_{1-3}$-alkyl)-amino, N—($C_{1-4}$-alkoxy-carbonyl)-amino, N—($C_{1-4}$-alkoxy-carbonyl)-N—($C_{1-3}$-alkyl)-amino, N-{ω-[N—($C_{1-4}$-alkoxy-carbonyl)-amino]-($C_{1-3}$-alkyl)}-N—($C_{1-3}$-alkyl)-amino, pyridinyl, triazolyl, pyrrolidino, piperidino, di-($C_{1-3}$-alkyl)-piperidino, [di-($C_{1-3}$-alkyl)-amino]-piperidino, piperazino, morpholino, ($C_{1-3}$-alkyl)-piperazino, 4-($C_{1-3}$-alkyl)-piperazino-carbonyl or 4-($C_{1-4}$-alkoxy-carbonyl)-piperazino group, by a carbonyl group which is substituted by a $C_{1-3}$-alkoxy, N-[di-($C_{1-3}$-alkyl)-amino-$C_{1-3}$-alkyl]-amino, N-[di-($C_{1-3}$-alkyl)-amino-$C_{1-3}$-alkyl]-N—($C_{1-3}$-alkyl)-amino, N—($C_{3-7}$-cycloalkyl)-N—($C_{1-3}$-alkyl)-amino, piperidino, piperazino, 4-($C_{1-4}$-alkyloxy-carbonyl)-piperazino or ($C_{1-3}$-alkyl)-piperazino group, or by a group of formula

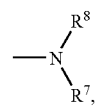

wherein
- $R^7$ denotes a hydrogen atom, a $C_{1-3}$-alkyl, $C_{1-3}$-alkyl-carbonyl, benzyl-carbonyl, pyridinylcarbonyl, furanylcarbonyl, pyrrolidino-$C_{1-3}$-alkyl-carbonyl, $C_{1-3}$-alkoxy-$C_{1-3}$-alkyl-carbonyl, di-($C_{1-3}$-alkyl)-amino-carbonyl-$C_{1-3}$-alkyl, $C_{1-4}$-alkylsulphonyl or benzylsulphonyl group or a phenylcarbonyl group optionally substituted in the phenyl moiety by one or two methoxy groups and
- $R^8$ denotes a $C_{1-3}$-alkyl, ω-[di-($C_{1-3}$-alkyl)-amino]-$C_{2-3}$-alkyl, di-($C_{1-3}$-alkyl)-amino-carbonyl-$C_{1-3}$-alkyl, di-($C_{1-3}$-alkyl)-amino-$C_{1-3}$-alkyl-aminocarbonyl or ω-[N-benzyl-N—($C_{1-3}$-alkyl)-amino]-$C_{2-3}$-alkyl group or
  - a 4-($C_{1-3}$-alkyl)-piperazin-1-yl-carbonyl, 4-($C_{1-3}$-alkyl)-piperazin-1-yl-aminocarbonyl, 1-($C_{1-3}$-alkyl)-piperidin-4-yl-aminocarbonyl, 1-($C_{1-3}$-alkyl)-piperidin-4-yl-oxy-carbonyl or (pyridinyl-$C_{1-3}$-alkyl)-aminocarbonyl group or
  - a $C_{1-3}$-alkyl-carbonyl group terminally substituted by a hydroxy, amino, di-($C_{1-3}$-alkyl)-amino, di-(ω-hydroxy-$C_{2-3}$-alkyl)-amino, $C_{1-3}$-alkyl-carbonyl-amino, N-benzyl-N—($C_{1-3}$-alkyl)-amino, N-[di-($C_{1-3}$-alkyl)-amino-$C_{1-3}$-alkyl]-N—($C_{1-3}$-alkyl)-amino, imidazolyl, piperazino, 4-($C_{1-3}$-alkyl)-piperazin-1-yl, 4-benzyl-piperazin-1-yl, 4-($C_{1-4}$-alkoxy-carbonyl)-piperazin-1-yl, 4-($C_{1-3}$-alkyl)-homopiperazin-1-yl, morpholino, pyrrolidino, piperidino-, 1-($C_{1-3}$-alkyl)-piperidin-4-yl, 4-($C_{1-3}$-alkyl)-piperidin-1-yl or phthalimido group,
- $R^5$ denotes a hydrogen atom or a $C_{1-3}$-alkyl group and
- $R^6$ denotes a hydrogen atom or a nitro group, while the unsubstituted, mono- or disubstituted phenyl groups containedin the above definitions may additionally be substituted by a cyano or a methoxy group or by two methyl groups, and the abovementioned alkyl groups include straight-chain and branched alkyl groups, wherein additionally one to 3 hydrogen atoms may be replaced by fluorine atoms, while, unless otherwise stated, the expression a heteroaryl group refers to a monocyclic 5- or 6-membered heteroaryl group optionally substituted in the carbon skeleton by a $C_{1-3}$-alkyl group, wherein
- the 6-membered heteroaryl group contains one, two or three nitrogen atoms and
- the 5-membered heteroaryl group contains an imino group optionally substituted by a $C_{1-3}$-alkyl or phenyl-$C_{1-3}$-alkyl group, an oxygen or sulphur atom or
- an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl or phenyl-$C_{1-3}$-alkyl group or an oxygen or sulphur atom and additionally a nitrogen atom or
- an imino group optionally substituted by a $C_{1-3}$-alkyl or phenyl-$C_{1-3}$-alkyl group and two nitrogen atoms,
- and moreover a phenyl ring may be fused to the abovementioned monocyclic heterocyclic groups via two adjacent carbon atoms and the bonding takes place via a nitrogen atom or via a carbon atom of the heterocyclic moiety or a fused-on phenyl ring, and additionally any carboxy, amino or imino group present may be substituted by a group which can be cleavedin vivo, the tautomers, enantiomers, diastereomers, mixtures thereof and the salts thereof.

7. Compounds of general formula I according to claim 1, wherein
- X denotes an oxygen atom,
- $R^1$ denotes a hydrogen atom,
- $R^2$ denotes a fluorine, chlorine or bromine atom or a cyano group,
- $R^3$ denotes a phenyl group or a phenyl group monosubstituted by a fluorine, chlorine, bromine or iodine atom or by a $C_{1-3}$-alkoxy group, while the abovementioned unsubstituted and monosubstituted phenyl groups may additionally be substituted in the 3 or 4-position
  - by a fluorine, chlorine or bromine atom,
  - by a $C_{1-3}$-alkoxy or $C_{1-2}$-alkyl-carbonyl-amino group,
  - by a carboxy-$C_{1-3}$-alkyl, aminocarbonyl-$C_{1-3}$-alkyl, ($C_{1-2}$-alkylamino)-carbonyl-$C_{1-3}$-alkyl, di-($C_{1-2}$-alkyl)-aminocarbonyl-$C_{1-3}$-alkyl, ($C_{1-2}$-alkyl-carbonyl)-amino-$C_{1-3}$-alkyl or (phenyl-carbonyl)-amino-$C_{1-3}$-alkyl group,
  - while the substituents may be identical or different,
- $R^4$ denotes a phenyl group which is substituted
  - by a $C_{1-3}$-alkyl group terminally substituted by a di-($C_{1-2}$-alkyl)-amino group or
  - by a group of formula

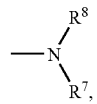

wherein
- $R^7$ denotes a $C_{1-2}$-alkyl, $C_{1-2}$-alkyl-carbonyl, di-($C_{1-2}$-alkyl)-amino-carbonyl-$C_{1-3}$-alkyl or $C_{1-3}$-alkylsulphonyl group and
- $R^8$ denotes a $C_{1-3}$-alkyl or ω-[di-($C_{1-2}$-alkyl)-amino]-$C_{2-3}$-alkyl group or
  - a $C_{1-3}$-alkyl-carbonyl group terminally substituted by a di-($C_{1-2}$-alkyl)-amino, piperazino or 4-($C_{1-3}$-alkyl)-piperazin-1-yl group,
- $R^5$ denotes a hydrogen atom and
- $R^6$ denotes a hydrogen atom, while the abovementioned alkyl groups include straight-chain and branched alkyl groups, wherein additionally one to 3 hydrogen atoms may be replaced by fluorine atoms, while additionally any carboxy, amino or imino group present may be substituted by a group which can be cleavedin vivo, the tautomers, enantiomers, diastereomers, mixtures thereof and the salts thereof.

8. Compounds of general formula I according to claim 1, wherein
X, $R^1$, $R^2$, $R^3$, $R^5$ and $R^6$ are defined as in claim 7 and
$R^4$ denotes a phenyl group which is substituted
by a group of formula

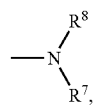

wherein
- $R^7$ denotes a $C_{1-2}$-alkyl, $C_{1-2}$-alkyl-carbonyl, di-($C_{1-2}$-alkyl)-amino-carbonyl-$C_{1-3}$-alkyl or $C_{1-3}$-alkylsulphonyl group and
- $R^8$ denotes a $C_{1-3}$-alkyl or ω-[di-($C_{1-2}$-alkyl)-amino]-$C_{2-3}$-alkyl group or a $C_{1-3}$-alkyl-carbonyl group terminally substituted by a di-($C_{1-2}$-alkyl)-amino, piperazino or 4-($C_{1-3}$-alkyl)-piperazin-1-yl group, the abovementioned alkyl groups including straight-chain and branched alkyl groups, wherein additionally one to 3 hydrogen atoms may be replaced by fluorine atoms, while additionally any carboxy, amino or imino group present may be substituted by a group which can be cleaved in vivo, the tautomers, enantiomers, diastereomers, mixtures thereof and the salts thereof.

9. Compounds of general formula I according to claim 1, wherein

X, $R^1$, $R^2$, $R^4$, $R^5$ and $R^6$ are defined as in claim 7 and $R^3$ denotes a phenyl group or a phenyl group monosubstituted by a fluorine, chlorine or bromine atom or by a $C_{1-3}$-alkoxy group, while the abovementioned unsubstituted and monosubstituted phenyl groups are additionally substituted in the 3- or 4-position by a fluorine, chlorine or bromine atom, by a $C_{1-3}$-alkoxy or $C_{1-2}$-alkyl-carbonyl-amino group or by a carboxy-$C_{1-3}$-alkyl, aminocarbonyl-$C_{1-3}$-alkyl, ($C_{1-2}$-alkylamino)-carbonyl-$C_{1-3}$-alkyl, di-($C_{1-2}$-alkyl)-aminocarbonyl-$C_{1-3}$-alkyl, ($C_{1-2}$-alkyl-carbonyl)-amino-$C_{1-3}$-alkyl or (phenyl-carbonyl)-amino-$C_{1-3}$-alkyl group, while the substituents may be identical or different, the abovementioned alkyl groups including straight-chain and branched alkyl groups, wherein additionally one to 3 hydrogen atoms may be replaced by fluorine atoms, while additionally any carboxy, amino or imino group present may be substituted by a group which can be cleaved in vivo, the tautomers, enantiomers, diastereomers, mixtures thereof and the salts thereof.

10. Compounds of general formula I according to claim 1, wherein

X denotes an oxygen atom, $R^1$ denotes a hydrogen atom, $R^2$ denotes a bromine atom, $R^3$ denotes a phenyl group, $R^4$ denotes a phenyl group which is substituted in the 4-position by a $C_{1-3}$-alkyl group terminally substituted by a $C_{1-3}$-alkylamino, di-($C_{1-3}$-alkyl)-amino, N-[ω-(di-($C_{1-3}$-alkyl)-amino)-$C_{2-3}$-alkyl]-N—($C_{1-3}$-alkyl)-amino or N—($C_{1-4}$-alkyloxy-carbonyl)-N—($C_{1-3}$-alkyl)-amino group, by a 1-($C_{1-3}$-alkyl)-imidazol-2-yl or 4-($C_{1-3}$-alkyl)-piperazin-1-yl-carbonyl group or by a group of formula

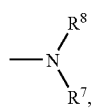

wherein $R^7$ denotes a $C_{1-3}$-alkyl, $C_{1-3}$-alkyl-carbonyl, $C_{1-3}$-alkyl-sulphonyl or benzylsulphonyl group and $R^8$ denotes a CO-[di-($C_{1-3}$-alkyl)-amino]-$C_{2-3}$-alkyl, CO-[di-($C_{1-3}$-alkyl)-amino]-$C_{1-4}$-alkyl-carbonyl, CO-[4-($C_{1-3}$-alkyl)-piperazin-1-yl]-$C_{1-3}$-alkylcarbonyl or ω-{N-[di-($C_{1-3}$-alkyl)-amino-$C_{2-3}$-alkyl]-N—($C_{1-3}$-alkyl)-amino}-$C_{1-3}$-alkyl-carbonyl group, $R^5$ denotes a hydrogen atom and $R^6$ denotes a hydrogen atom, the abovementioned alkyl groups including straight-chain and branched alkyl groups, wherein additionally one to 3 hydrogen atoms may be replaced by fluorine atoms, the tautomers, enantiomers, diastereomers, mixtures thereof and the salts thereof.

11. Compounds of general formula I according to claim 1, wherein

X denotes an oxygen atom, $R^1$ denotes a hydrogen atom, $R^2$ denotes a fluorine atom, $R^3$ denotes a phenyl group which is optionally substituted in the 3- or 4-position by a fluorine or iodine atom or by a cyano-$C_{1-3}$-alkyl, amino-$C_{1-3}$-alkyl, $C_{1-3}$-alkylamino-$C_{1-3}$-alkyl, $C_{1-5}$-alkyl-carbonylamino-$C_{1-3}$-alkyl, $C_{1-4}$-alkyloxy-carbonyl-amino-$C_{1-3}$-alkyl, $C_{1-4}$-alkyloxy-$C_{1-3}$-alkyl-carbonyl-amino-$C_{1-3}$-alkyl, $C_{3-7}$-cycloalkyl-carbonyl-amino-$C_{1-3}$-alkyl, $C_{3-7}$-cycloalkyl-$C_{1-3}$-alkyl-carbonyl-amino-$C_{1-3}$-alkyl, N-(phenyl-carbonyl)-amino-$C_{1-3}$-alkyl, N-(benzyl-carbonyl)-amino-$C_{1-3}$-alkyl, heteroaryl-carbonyl-amino-$C_{1-3}$-alkyl, N—($C_{1-3}$-alkylsulphonyl)-amino-$C_{1-3}$-alkyl, N-(phenylsulphonyl)-amino-$C_{1-3}$-alkyl, N-(benzylsulphonyl)-amino-$C_{1-3}$-alkyl, carboxy-$C_{1-3}$-alkyl, $C_{1-4}$-alkoxy-carbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, 4-($C_{1-3}$-alkyl)-piperazin-1-yl-carbonyl-$C_{1-3}$-alkyl, 2-(amino-carbonyl)-$C_{2-3}$-alkenyl or 2-($C_{1-3}$-alkyloxy-carbonyl)-$C_{2-3}$-alkenyl group, or a phenyl group trisubstituted in the 3-, 4- and 5-position by fluorine atoms, $R^4$ denotes a phenyl group which may be substituted in the 4-position by a $C_{1-3}$-alkyl group terminally substituted by a pyrrolidin-1-yl, piperidin-1-yl, 4-($C_{1-3}$-alkyl)-piperazin-1-yl, $C_{1-3}$-alkylamino, di-($C_{1-3}$-alkyl)-amino, N-[di-($C_{1-3}$-alkyl)-amino-$C_{2-3}$-alkyl]-N—($C_{1-3}$-alkyl)-amino or N—($C_{1-4}$-alkyloxy-carbonyl)-N—($C_{1-3}$-alkyl)-amino group, by a $C_{1-3}$-alkyl-sulphonyl, 1-($C_{1-3}$-alkyl)-imidazol-2-yl or 4-($C_{1-3}$-alkyl)-piperazin-1-yl-carbonyl group or by a group of formula

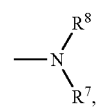

wherein $R^7$ denotes a $C_{1-3}$-alkyl, $C_{1-3}$-alkyl-carbonyl, $C_{1-3}$-alkyl-sulphonyl or benzylsulphonyl group and $R^8$ denotes a $C_{1-3}$-alkyl, ω-[di-($C_{1-3}$-alkyl)-amino]-$C_{2-3}$-alkyl, ω-[di-($C_{1-3}$-alkyl)-amino]-$C_{1-3}$-alkyl-carbonyl, di-($C_{1-3}$-alkyl)-amino-carbonyl-$C_{1-3}$-alkyl, o-[4-($C_{1-3}$-alkyl)-piperazin-1-yl]-$C_{1-3}$-alkyl-carbonyl or ω-{N-[di-($C_{1-3}$-alkyl)-amino-$C_{2-3}$-alkyl]-N—($C_{1-3}$-alkyl)-amino}-$C_{1-3}$-alkyl-carbonyl group, R⁵ denotes a hydrogen atom and
R⁶ denotes a hydrogen atom,
while the term heteroaryl group denotes a pyridinyl, furyl or thienyl group, and unsubstituted or monosubstituted phenyl groups containedin the abovementioned definitions may additionally be substituted by a methoxy group and
the above mentioned alkyl groups include straight-chain and branched alkyl groups, wherein additionally one to 3 hydrogen atoms may be replaced by fluorine atoms,
while additionally any carboxy, amino or imino group present may be substituted by a group which can be cleavedin vivo,
the tautomers, enantiomers, diastereomers, mixtures thereof and the salts thereof.

12. Compounds of general formula I according to claim 1, wherein

X denotes an oxygen atom,
$R^1$ denotes a hydrogen atom,
$R^2$ denotes a cyano group,
$R^3$ denotes a phenyl group optionally substituted by one or two methoxy groups,
$R^4$ denotes a phenyl group which is substituted in the 3- or 4-position
by a bromine atom,
by a $C_{1-3}$-alkyl group terminally substituted by a pyrrolidin-1-yl, piperidin-1-yl, 4-($C_{1-3}$-alkyl)-piperazin-1-yl-carbonyl, $C_{1-3}$-alkylamino, di-($C_{1-3}$-alkyl)-amino, N-[di-($C_{1-3}$-alkyl)-amino-$C_{1-3}$-alkyl]-N—($C_{1-3}$-alkyl)-aminocarbonyl or N—($C_{1-4}$-alkyloxy-carbonyl)-N—($C_{1-3}$-alkyl)-amino group,
by a ω-di-($C_{1-3}$-alkyl)-amino-$C_{2-3}$-alkoxy, N-(d-($C_{1-3}$-alkyl)-amino-$C_{2-3}$-alkyl)-amino-carbonyl, N-[di-($C_{1-3}$-alkyl)-amino-$C_{2-3}$-alkyl]-N—($C_{1-3}$-alkyl)-amino-carbonyl or 4-($C_{1-3}$-alkyl)-piperazin-1-yl-carbonyl group or
by a group of formula

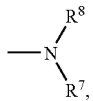

wherein
$R^7$ denotes a hydrogen atom or a $C_{1-3}$-alkyl, $C_{1-3}$-alkyl-carbonyl or $C_{1-3}$-alkylsulphonyl group and
$R^8$ denotes a ω-[di-($C_{1-3}$-alkyl)-amino]-($C_{2-3}$-alkyl), CO-[di-($C_{1-3}$-alkyl)-amino]-$C_{1-3}$-alkyl-carbonyl, ω-(piperazin-1-yl)-$C_{1-3}$-alkyl-carbonyl, ω-[4-($C_{1-3}$-alkyl)-piperazin-1-yl]-$C_{1-3}$-alkyl-carbonyl, ω-[4-($C_{1-4}$-alkyloxy-carbonyl)-piperazin-1-yl]-$C_{1-3}$-alkyl-carbonyl, CO-[4-($C_{1-3}$-alkyl)-homopiperazin-1-yl]-$C_{1-3}$-alkyl-carbonyl, ω-morpholino-$C_{1-3}$-alkyl-carbonyl or ω-{N-[di-($C_{1-3}$-alkyl)-amino-$C_{1-3}$-alkyl]-N—($C_{1-3}$-alkyl)-amino}-$C_{1-3}$-alkyl-carbonyl group,
$R^5$ denotes a hydrogen atom and
$R^6$ denotes a hydrogen atom,
the above mentioned alkyl groups including straight-chain and branched alkyl groups, wherein additionally one to 3 hydrogen atoms may be replaced by fluorine atoms, while additionally any carboxy, amino or imino group present may be substituted by a group which can be cleavedin vivo,
their stereoisomers and their salts.

13. Compounds of general formula I according to claim 1, wherein

X denotes an oxygen or sulphur atom,
$R^1$ denotes a hydrogen atom,
$R^2$ denotes a chlorine atom,
$R^3$ denotes a phenyl group which is optionally monosubstituted in the 3- or 4-position
by a chlorine or iodine atom,
by a cyano, hydroxy, benzyloxy, amino or nitro group
or by an aminomethyl, acetylamino, phenylcarbonylamino-$C_{1-3}$-alkyl, $C_{1-3}$-alkylsulphonylamino-$C_{1-3}$-alkyl, phenylsulphonylamino-$C_{1-3}$-alkyl, acetyl-aminomethyl, imidazol-1-yl-methyl, 2-oxo-pyrrolidin-1-yl, 2-carboxy-ethyl, 2-methoxycarbonyl-ethyl, 2-aminocarbonyl-ethyl, 2-(methylaminocarbonyl)-ethyl or 2-methoxycarbonyl-ethenyl group,
or a 3-hydroxy-4-nitro-phenyl, 4-amino-3-nitrophenyl or 3,4-dimethoxyphenyl group,
$R^4$ denotes a phenyl group which is substituted in the 3-position by a carboxy, carboxy-$C_{1-3}$-alkyl, $C_{1-4}$-alkoxycarbonyl, $C_{1-4}$-alkoxy-carbonyl-$C_{1-3}$-alkyl, dimethylamino-$C_{1-3}$-alkyl or pyridin-4-yl-$C_{1-3}$-alkyl group or is substituted in the 4-position
by a carboxy, ω-[di-($C_{1-3}$-alkyl)-amino]-$C_{2-3}$-alkoxy, ethoxycarbonyl, piperidin-1-yl-carbonyl, 4-($C_{1-4}$-alkyloxy-carbonyl)-piperazin-1-yl-carbonyl, N—($C_{3-7}$-cycloalkyl)-N—($C_{1-3}$-alkyl)-amino-carbonyl or N-[di-($C_{1-3}$-alkyl)-amino-$C_{1-3}$-alkyl]-N—($C_{1-3}$-alkyl)-aminocarbonyl group,
by a [di-($C_{1-3}$-alkyl)-amino]-$C_{1-3}$-alkylsulphonyl group,
by a $C_{1-3}$-alkyl group terminally substituted by a carboxy, $C_{1-4}$-alkyloxy-carbonyl, amino, $C_{1-3}$-alkylamino, di-($C_{1-3}$-alkyl)-amino, N-benzyl-N—($C_{1-3}$-alkyl)-amino, N-(2-hydroxyethyl)-N—($C_{1-3}$-alkyl)-amino, Di-(2-hydroxyethyl)-amino, triazolyl, N-(methoxyethoxyethyl)-N—($C_{1-3}$-alkyl)-amino, N-(amino-$C_{1-3}$-alkyl)-N—($C_{1-3}$-alkyl)-amino, N-[di-($C_{1-3}$-alkyl)-amino-$C_{1-3}$-alkyl]-N—($C_{1-3}$-alkyl)-amino, N-[di-($C_{1-3}$-alkyl)-amino-$C_{1-3}$-alkyl]-N—($C_{1-3}$-alkyl)-amino-carbonyl, N—($C_{1-4}$-alkyloxy-carbonyl-amino-$C_{1-3}$-alkyl)-N—($C_{1-3}$-alkyl)-amino, N—($C_{1-4}$-alkyloxy-carbonyl)-amino or N—($C_{1-4}$-alkyloxy-carbonyl)-N—($C_{1-3}$-alkyl)-amino group,
by a 1-methyl-imidazol-2-yl, 5-methyl-1H-imidazol-4-yl, 1-[di-($C_{1-3}$-alkyl)-amino-$C_{1-3}$-alkyl]-imidazol-2-yl, 4-methyl-piperazin-1-yl, piperazinylcarbonyl or 4-methyl-piperazin-1-yl-carbonyl group or
by a group of formula

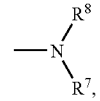

wherein
$R^7$ denotes a hydrogen atom or a $C_{1-3}$-alkyl, $C_{1-3}$-alkyl-carbonyl, di-($C_{1-3}$-alkyl)-amino-carbonyl-$C_{1-3}$-alkyl, benzylcarbonyl, pyridinylcarbonyl, furanylcarbonyl, methoxymethylcarbonyl, $C_{1-4}$-alkylsulphonyl or benzylsulphonyl group or a phenylcarbonyl group optionally substituted in the phenyl moiety by one or two methoxy groups and $R^8$ denotes a $C_{1-3}$-alkyl, ω-[di-($C_{1-3}$-alkyl)-amino]-$C_{2-3}$-alkyl, ω-[N-benzyl-N—($C_{1-3}$-alkyl)-amino]-$C_{2-3}$-alkyl, N-[di-($C_{1-3}$-alkyl)-amino-$C_{1-3}$-alkyl]-amino-carbonyl, (pyridinyl-$C_{1-3}$-alkyl)-amino-carbonyl, 1-($C_{1-3}$-alkyl)-piperidin-4-yl-amino-carbonyl, 1-($C_{1-3}$-alkyl)-piperidin-4-yl-oxy-carbonyl, 4-($C_{1-3}$-alkyl)-piperazin-1-yl-amino-carbonyl, 4-($C_{1-3}$-alkyl)-piperazin-1-yl-carbonyl or di-($C_{1-3}$-alkyl)-aminocarbonyl-$C_{1-3}$-alkyl group or a $C_{1-4}$-alkyl-carbonyl group terminally substituted by a hydroxy, amino, di-($C_{1-3}$-alkyl)-amino, N-benzyl-N—($C_{1-3}$-alkyl)-amino, di-(2-hydroxyethyl)-amino, acetylamino, N-[di-($C_{1-3}$-alkyl)-amino-$C_{1-3}$-alkyl]-N—($C_{1-3}$-alkyl)-amino, imidazol-1-yl, piperazin-1-yl, 4-($C_{1-3}$-alkyl)-piperazin-1-yl, 4-benzyl-piperazin-1-yl, 4-($C_{1-4}$-alkyloxy-carbonyl)-piperazin-1-yl, 4-($C_{1-3}$-alkyl)-homopiperazin-1-yl, morpholin-4-yl, pyrrolidin-1-yl, piperidin-1-yl, 1-($C_{1-3}$-alkyl)-piperidin-4-yl or phthalimido group, $R^5$ denotes a hydrogen atom and $R^6$ denotes a hydrogen atom or a nitro group, while the unsubstituted or monosubstituted phenyl groups mentioned in the above definitions may additionally be substituted by a methoxy or a cyano group or by two methyl groups, the above mentioned alkyl groups including straight-chain and branched alkyl groups, wherein additionally one to 3 hydrogen atoms may be replaced by fluorine atoms, while additionally any carboxy, amino or imino group present may be substituted by a group which can be cleaved in vivo, the tautomers, enantiomers, diastereomers, mixtures thereof and the salts thereof.

14. The following compounds of general formula I according to claim 1:

(a) 3-Z-[1-(4-(N-(2-dimethylamino-ethyl)-N-methylsulphonyl-amino)-anilino)-1-phenyl-methylene]-6-chloro-2-indolinone, (b) 3-Z-[1-(4-(N-(4-methyl-piperazin-1-yl-methylcarbonyl)-N-methyl-amino)-anilino)-1-phenyl-methylene]-6-chloro-2-indolinone, (c) 3-Z-[1-(4-(N-(3-dimethylamino-propyl)-N-acetyl-amino)-anilino)-1-phenyl-methylene]-6-chloro-2-indolinone, (d) 3-Z-[1-(4-(N-(4-ethyl-piperazin-1-yl-methylcarbonyl)-N-methyl-amino)-anilino)-1-phenyl-methylene]-6-chloro-2-indolinone, (e) 3-Z-[1-(4-(N-(2-dimethylamino-ethyl)-N-acetyl-amino)-anilino)-1-(3,4-dimethoxy-phenyl)-methylene]-6-chloro-2-indolinone, (f) 3-Z-[1-(4-(N-(4-methyl-piperazin-1-yl-methylcarbonyl)-N-methyl-amino)-anilino)-1-(3,4-dimethoxy-phenyl)-methylene]-6-chloro-2-indolinone, (g) 3-Z-[1-(4-(N-(3-dimethylamino-propyl)-N-acetyl-amino)-anilino)-1-phenyl-methylene]-6-bromo-2-indolinone, (h) 3-Z-[1-(4-(N-(4-methyl-piperazin-1-yl-methylcarbonyl)-N-methyl-amino)-anilino)-1-phenyl-methylene]-6-bromo-2-indolinone, (i) 3-Z-[1-(4-(N-(3-dimethylamino-propyl)-N-acetyl-amino)-anilino)-1-phenyl-methylene]-6-cyano-2-indolinone, (j) 3-Z-[1-(4-(N-(4-methyl-piperazin-1-yl-methylcarbonyl)-N-methyl-amino)-anilino)-1-phenyl-methylene]-6-cyano-2-indolinone, (k) 3-Z-[1-(4-(N-(4-ethyl-piperazin-1-yl-methylcarbonyl)-N-methyl-amino)-anilino)-1-phenyl-methylene]-6-cyano-2-indolinone, (l) 3-Z-[1-(4-(N-(dimethylamino-methylcarbonyl)-N-methyl-amino)-anilino)-1-phenyl-methylene]-6-fluoro-2-indolinone, (m) 3-Z-[1-(4-(N-(2-dimethylamino-ethyl)-N-acetyl-amino)-anilino)-1-phenyl-methylene]-6-fluoro-2-indolinone, (n) 3-Z-[1-(4-(N-(4-methyl-piperazin-1-yl-methylcarbonyl)-N-methyl-amino)-anilino)-1-phenyl-methylene]-6-fluoro-2-indolinone, (o) 3-Z-[1-(4-(dimethylaminomethyl)-anilino)-1-(3-fluoro-phenyl)-methylene]-6-fluoro-2-indolinone, (p) 3-Z-[1-(4-(N-(3-dimethylamino-propyl)-N-acetyl-amino)-anilino)-1-(3-fluoro-phenyl)-methylene]-6-fluoro-2-indolinone, (q) 3-Z-[1-(4-(N-(4-methyl-piperazin-1-yl-methylcarbonyl)-N-methyl-amino)-anilino)-1-(3-fluoro-phenyl)-methylene]-6-fluoro-2-indolinone, (r) 3-Z-[1-(4-dimethylaminomethyl-anilino)-1-(4-(2-carbamoyl-ethyl)-phenyl)-methylene]-6-fluoro-2-indolinone, (s) 3-Z-[1-(4-(N-(piperazin-1-yl-methylcarbonyl)-N-methyl-amino)-anilino)-1-phenyl-methylene]-6-chloro-2-indolinone, (t) 3-Z-[1-(4-dimethylaminomethyl-anilino)-1-(3-(2-carboxy-ethyl)-phenyl)-methylene]-6-chloro-2-indolinone, (u) 3-Z-[1-(4-dimethylaminomethyl-anilino)-1-(4-(2-carboxy-ethyl)-phenyl)-methylene]-6-fluoro-2-indolinone, (v) 3-Z-[1-(4-dimethylaminomethyl-anilino)-1-(3-(2-carboxy-ethyl)-phenyl)-methylene]-6-fluoro-2-indolinone, (w) 3-Z-[1-(4-(N-(4-methyl-piperazin-1-yl-methylcarbonyl)-N-methyl-amino)-anilino)-1-(4-carboxymethyl-phenyl)-methylene]-6-fluoro-2-indolinone, (x) 3-Z-[1-(4-dimethylaminomethyl-anilino)-1-(4-(2-methylcarbamoyl-ethyl)-phenyl)-methylene]-6-fluoro-2-indolinone, (y) 3-Z-[1-(4-dimethylaminomethyl-anilino)-1-(3-(2-carbamoyl-ethyl)-phenyl)-methylene]-6-fluoro-2-indolinone, (z) 3-Z-[1-(4-dimethylaminomethyl-anilino)-1-(3-(2-dimethylcarbamoyl-ethyl)-phenyl)-methylene]-6-fluoro-2-indolinone, (aa) 3-Z-[1-(4-(N-(2-dimethylamino-ethyl)-N-methylsulphonyl-amino)-anilino)-1-(4-dimethylcarbamoylmethyl-phenyl)-methylene]-6-fluoro-2-indolinone, (ab) 3-Z-[1-(4-(N-methyl-N-acetyl-amino)-anilino)-1-(4-(2-methylcarbamoyl-ethyl)-phenyl)-methylene]-6-fluoro-2-indolinone, (ac) 3-Z-[1-(4-(N-(4-methyl-piperazin-1-yl-methylcarbonyl)-N-methyl-amino)-anilino)-1-(4-acetylamino-phenyl)-methylene]-6-chloro-2-indolinone, (ad) 3-Z-[1-(4-dimethylaminomethyl-anilino)-1-(4-acetylaminomethyl-phenyl)-methylene]-6-chloro-2-indolinone, (ae) 3-Z-[1-(4-dimethylaminomethyl-anilino)-1-(3-acetylaminomethyl-phenyl)-methylene]-6-fluoro-2-indolinone, (af) 3-Z-[1-(4-dimethylaminomethyl-anilino)-1-(3-benzoylaminomethyl-phenyl)-methylene]-6-fluoro-2-indolinone and (ag) 3-Z-[1-(4-dimethylaminomethyl-anilino)-1-(3-(2-acetylamino-ethyl)-phenyl)-methylene]-6-fluoro-2-indolinone (ah) 3-Z-[1-(4-(N-(2-dimethylamino-ethylcarbonyl)-N-methyl-amino)-anilino)-1-(4-(2-carboxy-ethyl)-phenyl)-methylene]-6-fluoro-2-indolinone, (ai) 3-Z-[1-(4-(pyrrolidin-1-yl-methyl)-anilino)-1-(4-(2-carboxy-ethyl)-phenyl)-methylene]-6-fluoro-2-indolinone and (aj) 3-Z-[1-(4-dimethylaminomethyl-anilino)-1-(4-(2-carboxy-ethyl)-phenyl)-methylene]-6-chloro-2-indolinone (ak) 3-Z-[1-(4-diethylaminomethyl-anilino)-1-(4-(2-carboxy-ethyl)-phenyl)-methylene]-6-fluoro-2-indolinone (al) 3-Z-[1-(4-(2-dimethylamino-ethyl))-anilino)-1-(4-(2-carboxy-ethyl)-phenyl)-methylene]-6-chloro-2-indolinone (am) 3-Z-[1-(4-(pyrrolidin-1-yl-methyl)-anilino)-1-(4-(2-carboxy-ethyl)-phenyl)-methylene]-6-chloro-2-indolinone (an) 3-Z-[1-(4-(pyrrolidin-1-yl-methyl)-anilino)-1-(4-(2-carboxy-ethyl)-phenyl)-methylene]-6-bromo-2-indolinone (ap) 3-Z-[1-(4-(dimethylaminomethyl)-anilino)-1-(4-(2-carboxy-ethyl)-phenyl)-methylene]-6-bromo-2-indolinone while additionally any carboxy, amino or imino group present may be substituted by a group which can be cleaved in vivo, and the salts thereof.

15. Physiologically acceptable salts of the compounds according to any one of claims 1 to 14.

16. Pharmaceutical compositions containing a compound oto any one of claims 1 to 14, or a physiologically acceptable salt thereof with one more inert carriers and/or diluents.

17. Process for preparing the compounds according to claim 1, wherein a. a compound of general formula

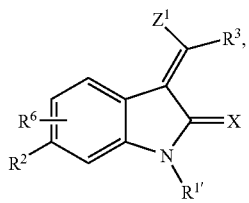

(V)

wherein the groups $Z^1$ and $R^3$ may optionally change positions,

X, $R^2$, $R^3$ and $R^6$ are defined as in claim 1, $R^{1'}$ has the meanings given for $R^1$ hereinbefore or denotes a protective group for the nitrogen atom of the lactam group, while $R^1$ may also denote a bond to a solid phase, optionally formed via a spacer, and $Z^1$ denotes a halogen atom, a hydroxy, alkoxy or arylalkoxy group, e.g. a chlorine or bromine atom, a methoxy, ethoxy or benzyloxy group, is reacted with an amine of general formula

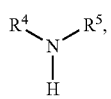

(VI)

wherein $R^4$ and $R^5$ are as hereinbefore defined, and if necessary any protective group used for the nitrogen atom of the lactam group is subsequently cleaved or any protective group used is subsequently cleaved from a solid phase, b. in order to prepare a compound of general formula I wherein $R^4$ contains the group $R^8$ where $R^8$ denotes a $C_{1-4}$-alkyl-carbonyl group terminally substituted by a hydroxy, $C_{1-3}$-alkyoxyl group, amino, ($C_{1-3}$-alkyl)-amino, di-($C_{1-3}$-alkyl)-amino, (ω-hydroxy-$C_{2-3}$-alkyl)-amino, di-(ω-hydroxy-$C_{2-3}$-alkyl)-amino, (ω-alkoxy-$C_{2-3}$-alkyl)-amino, di-(ω-alkoxy-$C_{2-3}$-alkyl)-amino, $C_{1-3}$-alkyl-carbonyl-amino, N-benzyl-N—$C_{1-3}$-alkyl-amino, N-[di-($C_{1-3}$-alkyl)-amino-$C_{1-3}$-alkyl]-N—$C_{1-3}$-alkyl-amino, 1-($C_{1-3}$-alkyl)-piperidin-4-yl- group or by a 5-to 7-membered cycloalkyleneimino group, while the cycloalkylene group may be substituted by a $C_{1-3}$-alkyl group and/or one or two methylene groups linked to the imino group may be replaced by a carbonyl group and/or the methylene group in the 4 position of a 6- or 7-membered cycloalkylimino group may be replaced by an NH, —N($C_{1-3}$-alkyl), —N(benzyl), —N($C_{1-4}$-alkoxy-carbonyl) or —O— and/or a phenyl ring may be fused on via two adjacent carbon atoms of the cycloalkyleneimino group:

a compound of general formula

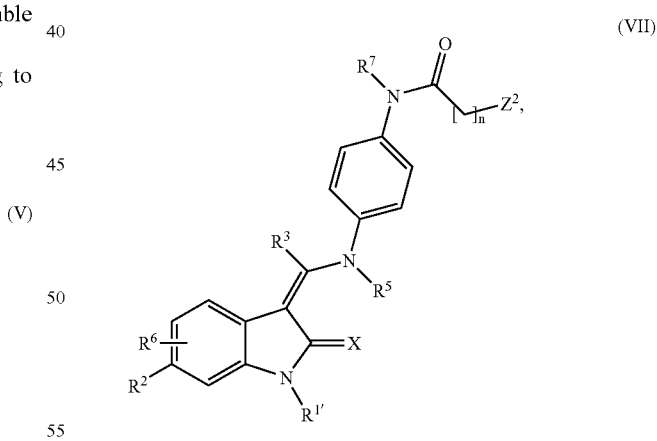

(VII)

wherein $R^2$, $R^3$, and $R^5$, $R^6$, $R^7$ and X are defined as in claim 1, $R^{1'}$ has the meanings given for $R^1$ hereinbefore or denotes a protective group for the nitrogen atom of the lactam group, while $R^{1'}$ may also denote a bond to a solid phase optionally formed via a spacer, n denotes the number 1, 2, 3 or 4 and $Z^2$ denotes a leaving group, for example a halogen atom or an alkyl or arylsulphonyloxy group such as the chlorine, bromine or iodine atom or the methylsulphonyloxy, ethylsulphonyloxy, p-toluenesulphonyloxy, or trifluoromethanesulphonyloxy group, is reacted with a hydroxide base such as sodium or potassium hydroxide or a compound of general formula $$H\text{—}R^{8'} \qquad (VIII),$$

wherein $R^{8'}$ denotes a $C_{1-3}$-alkyloxy, amino, $(C_{1-3}$-alkyl)-amino, di-$(C_{1-3}$-alkyl)-amino, ($\omega$-hydroxy-$C_{2-3}$-alkyl)-amino, di-($\omega$-hydroxy-$C_{2-3}$-alkyl)-amino, ($\omega$-alkoxy-$C_{2-3}$-alkyl)-amino, di-($\omega$-alkoxy-$C_{2-3}$-alkyl)-amino, $C_{1-3}$-alkyl-carbonyl-amino, N-benzyl-N—$C_{1-3}$-alkyl-amino, N-[di-$(C_{1-3}$-alkyl)-amino-$C_{1-3}$-alkyl]-N—$C_{1-3}$-alkyl-amino or a 5- to 7-membered cycloalkyleneimino group, while the cycloalkylene group may be substituted by a $C_{1-3}$-alkyl group and/or one or two methylene groups linked to the imino group may be replaced by a carbonyl group and/or the methylene group in the 4 position of a 6- or 7-membered cycloalkylimino group may be replaced by a —NH, —N($C_{1-3}$-alkyl), —N(benzyl), —N($C_{1-4}$-alkoxy-carbonyl) or —O— and/or a phenyl ring may be fused on via two adjacent carbon atoms of the cycloalkyleneimino group, and if necessary any protective group used for the nitrogen atom of the lactam group is subsequently cleaved or any protective group used is subsequently cleaved from a solid phase, c. in order to prepare a compound of general formula I wherein $R^3$ denotes a phenyl group substituted by a carboxy-$C_{2-3}$-alkenyl, aminocarbonyl-$C_{2-3}$-alkenyl, ($C_{1-3}$-alkyl-amino)-carbonyl-$C_{2-3}$-alkenyl, di-($C_{1-3}$-alkylamino)-carbonyl-$C_{2-3}$-alkenyl or $C_{1-4}$-alkoxy-carbonyl-$C_{2-3}$-alkenyl group, a compound of general formula

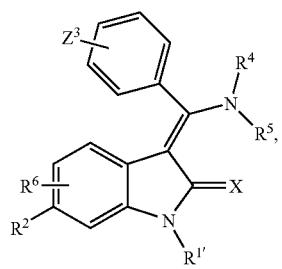

(IX)

wherein $R^2$, $R^4$, and $R^5$, $R^6$ and X are defined as in claim 1, $R^{1'}$ has the meanings given for $R^1$ hereinbefore or denotes a protective group for the nitrogen atom of the lactam group, while $R^{1'}$ may also denote a bond to a solid phase optionally formed via a spacer, and $Z^3$ denotes a leaving group, for example a halogen atom or an alkyl or arylsulphonyloxy group such as the chlorine, bromine or iodine atom or the methylsulphonyloxy, ethylsulphonyloxy, p-toluenesulphonyloxy or trifluoromethanesulphonyloxy group, is reacted with an alkene of general formula

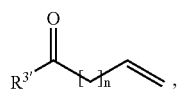

(X)

wherein $R^{3'}$ denotes an amino, ($C_{1-3}$-alkylamino), di-($C_{1-3}$-alkylamino) or $C_{1-4}$-alkoxy- group and n is the number 0 or 1, d. in order to prepare a compound of general formula I wherein $R^3$ denotes a phenyl group substituted by a carboxy-$C_{1-3}$-alkyl, $C_{1-4}$-alkoxy-carbonyl-$C_{1-3}$-alkyl, amino-carbonyl-$C_{1-3}$-alkyl, ($C_{1-3}$-alkylamino)-carbonyl-$C_{1-3}$-alkyl, di-($C_{1-3}$-alkyl)-aminocarbonyl-$C_{1-3}$-alkyl or 4-($C_{1-3}$-alkyl)-piperazin-1-yl-carbonyl-($C_{1-3}$-alkyl) group, a compound of general formula

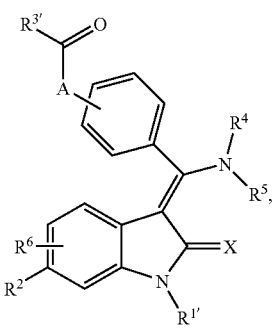

(XI)

wherein $R^2$, $R^4$, and $R^5$, $R^6$ and X are defined as in claim 1, $R^{1'}$ has the meanings given for $R^1$ hereinbefore or denotes a protective group for the nitrogen atom of the lactam group, while $R^{1'}$ may also denote a bond to a solid phase optionally formed via a spacer, A denotes a $C_{2-3}$-alkenyl group and $R^{3'}$ denotes a hydroxy, $C_{1-4}$-alkoxy, amino, ($C_{1-3}$-alkylamino), di-($C_{1-3}$-alkyl)-amino or 4-($C_{1-3}$-alkyl)-piperazin-1-yl group, is hydrogenated and subsequently any protective group which may be used for the nitrogen atom of the lactam group is cleaved or is cleaved from a solid phase as described in process (a) described hereinbefore, and then an alkoxycarbonyl group is optionally converted by hydrolysis into a corresponding carboxy compound, or an amino or alkylamino group is converted by reductive alkylation into a corresponding alkylamino or dialkylamino compound, or a dialkylamino group is converted by alkylation into a corresponding trialkylammonium compound, or an amino or alkylamino group is converted by acylation or sulphonation into a corresponding acyl or sulphonyl compound, or a carboxy group is converted by esterification or amidation into a corresponding ester or aminocarbonyl compound, or a cycloalkyleneimino group wherein a methylene group is replaced by a sulphur atom is converted by oxidation into a corresponding sulphinyl or sulphonyl compound, or a nitro group is converted by reduction into a corresponding amino compound, or a cyano group is converted by reduction into a corresponding aminomethyl compound, or an arylalkyloxy group is converted using acid into a corresponding hydroxy compound, or an alkoxycarbonyl group is converted by saponification into a corresponding carboxy compound, or a phenyl group substituted by an amino, alkylamino, aminoalkyl or N-alkyl-amino group is converted by reaction with a corresponding cyanate, isocyanate or carbamoylhalide into a corresponding urea compound of general formula I, or a carbonyl group is converted by reaction with phosphorus pentasulphide into a corresponding thiocarbonyl compound, or a phenyl group substituted by an amino, alkylamino, aminoalkyl or N-alkyl-amino group is converted by reaction with a corresponding compound which transfers the amidino group or by reaction with a corresponding nitrile into a corresponding guanidino compound of general formula I.

18. Compounds of general formula (I) according to claim 1 wherein the form of the prodrug may be converted in vivo into a carboxy group or may be converted in vivo into an imino or amino group.

* * * * *